(12) United States Patent
Bogdan et al.

(10) Patent No.: US 9,969,693 B2
(45) Date of Patent: *May 15, 2018

(54) 6-HETEROARYLOXY- OR 6-ARYLOXY-QUINOLINE-2-CARBOXAMIDES AND METHOD OF USE

(71) Applicant: AbbVie Inc., North Chicago, IL (US)

(72) Inventors: Andrew Bogdan, Evanston, IL (US); Marlon D. Cowart, Round Lake Beach, IL (US); David A. DeGoey, Salem, WI (US); Tammie K. Jinkerson, Herington, KS (US); John R. Koenig, Chicago, IL (US); Michael E. Kort, Lake Bluff, IL (US); Bo Liu, Waukegan, IL (US); Mark A. Matulenko, Libertyville, IL (US); Derek W. Nelson, Highland Park, IL (US); Meena V. Patel, Green Oaks, IL (US); Hillary Peltier, Evanston, IL (US); Marc J. Scanio, Libertyville, IL (US); Brian D. Wakefield, Vernon Hills, IL (US)

(73) Assignee: AbbVie Inc., North Chicago, IL (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/239,554

(22) Filed: Aug. 17, 2016

(65) Prior Publication Data

US 2016/0355482 A1  Dec. 8, 2016
US 2017/0226062 A9  Aug. 10, 2017

Related U.S. Application Data

(63) Continuation of application No. 14/613,579, filed on Feb. 4, 2015, now Pat. No. 9,452,986.

(60) Provisional application No. 61/936,397, filed on Feb. 6, 2014.

(51) Int. Cl.

| | | |
|---|---|---|
| C07D 215/48 | (2006.01) |
| C07D 401/12 | (2006.01) |
| C07D 409/14 | (2006.01) |
| C07D 487/08 | (2006.01) |
| C07D 401/14 | (2006.01) |
| C07D 487/04 | (2006.01) |
| C07D 405/14 | (2006.01) |
| C07D 417/14 | (2006.01) |
| C07D 471/04 | (2006.01) |

(52) U.S. Cl.
CPC ......... *C07D 215/48* (2013.01); *C07D 401/12* (2013.01); *C07D 401/14* (2013.01); *C07D 405/14* (2013.01); *C07D 409/14* (2013.01); *C07D 417/14* (2013.01); *C07D 471/04* (2013.01); *C07D 487/04* (2013.01); *C07D 487/08* (2013.01)

(58) Field of Classification Search
CPC .. C07D 215/48; C07D 401/12; C07D 401/14; C07D 409/14; C07D 487/08; C07D 487/04; C07D 405/14; C07D 471/14; C07D 471/04
See application file for complete search history.

(56) References Cited

U.S. PATENT DOCUMENTS

| | | | |
|---|---|---|---|
| 7,534,891 B2 | 5/2009 | McArthur et al. | |
| 9,452,986 B2 * | 9/2016 | Bogdan ............... | C07D 215/48 |

FOREIGN PATENT DOCUMENTS

| | | |
|---|---|---|
| WO | 2005014558 A1 | 2/2005 |
| WO | 2006124744 A1 | 11/2006 |
| WO | 2007003419 A1 | 1/2007 |
| WO | 2007127183 A1 | 11/2007 |
| WO | 2010137351 A1 | 12/2010 |
| WO | 2014120815 A1 | 8/2014 |

OTHER PUBLICATIONS

Beneng, K. et al., "Sodium Channel $Na_v1.7$ Immunoreactivity in Painful Human Dental Pulp and Burning Mouth Syndrome," BMC Neurosci. (2010), 11:71 (7 pages).
Cummins, T.R. et al., "Voltage-Gated Sodium Channel Blockers for the Treatment of Neuropathic Pain," Expert Rev Neurother (2007), 7(11): 1597-1612.
Dib-Hajj, S.D. et al. "Sodium Channels in Normal and Pathological Pain," Annu Rev Neurosci (2010) 33: 325-347.
Dib-Hajj, S.D. et al., "Gain-of-Function Mutation in $Na_v1.7$ in Familial Erythromelalgia Induces Bursting of Sensory Neurons," Brain (2005), 128(8): 1847-1854.
Dib-Hajj, S.D. et al., "The $Na_v1.7$ Sodium Channel: From Molecule to Man," Nat Rev Neurosci (2013), 14(1): 49-62.
Dixon, W.J. "Efficient Analysis of Experimental Observations," Ann Rev Pharmacol Toxicol (1980), 20: 441-462.
Eliel, E.L. "Stereochemistry of Organic Compounds" John Wiley & Sons, Inc., New York, 1994 (pp. 119-120).

(Continued)

*Primary Examiner* — D Margaret M Seaman

(57) ABSTRACT

Compounds of formula (I)

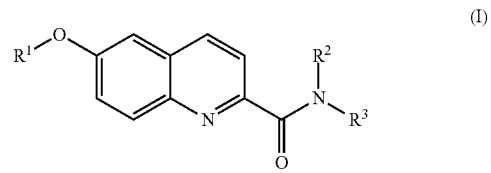

and pharmaceutically acceptable salts, esters, amides, or radiolabelled forms thereof, wherein $R^1$, $R^2$, and $R^3$ are as defined in the specification, are useful in treating conditions or disorders prevented by or ameliorated by voltage-gated sodium channels, e.g., $Na_v$ 1.7 and/or $Na_v$ 1.8. Methods for making the compounds are disclosed. Also disclosed are pharmaceutical compositions of compounds of formula (I), and methods for using such compounds and compositions.

11 Claims, No Drawings

(56) References Cited

OTHER PUBLICATIONS

Faber, C.G. et al., "Gain-of-Function $Na_v1.8$ Mutations in Painful Neuropathy," Proc Natl Acad Sci USA (2012), 109(47): 19444-19449.
Faber, C.G. et al., "Gain of Function $Na_v1.7$ Mutations in Idiopathic Small Fiber Neuropathy," Ann Neurol (2012) 71(1): 26-39.
Furniss, B.S., Editor, "Vogel's Textbook of Practical Organic Chemistry", 5th Ed, 1989, Longman Scientific & Technical, Wiley, UK.
Goldin, A.L. et al., "Nomenclature of Voltage-Gated Sodium Channels," Neuron (2000), 28(2): 365-368.
Green, Editor, "Protective Groups in Organic Synthesis," 3rd Ed., 1999, John Wiley & Sons, Inc. (52 pages).
Hargus, N.J. et al. "Voltage-Gated $Na^+$Channels in Neuropathic Pain," Expert Opin Invest Drugs (2007), 16(5): 635-646.
Hong, S. et al., "Early Painful Diabetic Neuropathy Is Associated With Differential Changes in Tetrodotoxin-Sensitive and -Resistant Sodium Channels in Dorsal Root Ganglion Neurons in the Rat," Journal of Biological Chemistry (2004), 279(28): 29341-29350.
International Search Report & Written Opinion for PCT/US2015/014380 dated Mar. 31, 2015 (10 pages).
IUPAC 1974 Recommendations for Section E, Fundamental Stereochemistry, in Pure & Appl. Chem., 45:13-30, Pergamon Press, 1976.
Kim, S.H. et al., "An Experimental Model for Peripheral Neuropathy Produced by Segmental Spinal Nerve Litigation in the Rat," (1992), Pain 50(3): 355-363.
Liu, M. et al., "The Roles of Sodium Channels in Nociception: Implications for Mechanisms of Neuropathic Pain," Pain Med (2011), 12(Suppl. S3): S93-99.
Malfait, A-M. et al., "Towards a Mechanism-Based Approach to Pain Management in Osteoarthritis," Nat Rev Rheumatol (2013) 9(11): 654-664.
McGowan, E. et al., "A Peripherally Acting $Na_v1.7$ Sodium Channel Blocker Reverses Hyperalgesia and Allodynia on Rat Models of Inflammatory and Neuropathic Pain," Anesth Analg (2009), 109(3): 951-958.
Minett, M.S. et al., "Distinct $Na_v1.7$-Dependent Pain Sensations Require Different Sets of Sensory and Sympathetic Neurons," Nat Commun (2012), 3:791 (9 pages).
Momin, A. et al., "Sensory Neuron Voltage-Gated Sodium Channels as Analgesic Drug Targets," Curr Opin Neurobiol (2008), 18(4): 383-388.
Nassar, M.A. et al., "Neuropathic Pain Develops Normally in Mice Lacking Both $Na_v1.7$ and $Na_v1.8$," Mol Pain (2005), 1:24 (9 pages).
Nassar, M.A. et al., "Nociceptor-Specific Gene Deletion Reveals a Major Role for $Na_v1.7$ (PN1) in Acute and Inflammatory Pain," PNAS USA (2004), 101(34): 12706-12711.
Persson, A.K. et al., "$Na_v1.7$ Accumulates and Co-Localizes With Phosphorylated ERK1/2 Within Transected Axons in Early Experimental Neuromas," Exp Neurol (2011) 230(2): 273-279.
Prescott, Editor, "Methods in Cell Biology," vol. XIV, Academic Press, New York, N. Y., (1976), p. 33 et seq.
Reimann, F. et al., "Pain Perception Is Altered by a Nucleotide Polymorphism in SCN9A," PNAS (2010), 107(11): 5148-5153.
Rodriguez-Sarmiento et al., "Selective naphthalene H3 receptor inverse agonists with reduced potential to induce phospholipidosis and their quinoline analogs," Bioorganic & Medicinal Chemistry Letters, 19(15): 4495-4500 (2009).
Rush, A.M. et al., "Multiple Sodium Channels and Their Roles in Electrogenesis Within Dorsal Root Ganglion Neurons," J Physiol (2007), 579(pt 1): 1-14.
Schuelert, N. et al., "Involvement of $Na_v1.8$ Sodium Ion Channels in the Transduction of Mechanical Pain in a Rodent Model of Osteoarthritis," Arthritis Research & Therapy (2012), 14:R5 (9 pages).
Shields, S.D. et al., "Sodium Channel Nav1.7 is Essential for Lowering Heat Pain Threshold after Burn Injury," Journal of Neuroscience (2012) 32(32): 10819-10832.
Staunton, C.A. et al., "Ion Channels and Osteoarthritic Pain: Potential for Novel Analgesics," Current Pain and Headache Reports (2013) 17: 378 (9 pages).
Strickland, I.T. et al., "Changes in the Expression of $Na_v1.7$, $Na_v1.8$ and $Na_v1.9$ in a Distinct Population of Dorsal Root Ganglia Innervating the Rat Knee Joint in a Model of Chronic Inflammatory Joint Pain," Eur J Pain (2008), 12(5): 564-572.
Waxman, S.G. "Polymorphisms in Ion Channel Genes: Emerging Roles in Pain," Brain (2010), 133(9): 2515-2518.
Waxman, S.G. "Neuroscience: Channelopathies Have Many Faces," Nature (2011) 472(7342): 173-174.

* cited by examiner

6-HETEROARYLOXY- OR 6-ARYLOXY-QUINOLINE-2-CARBOXAMIDES AND METHOD OF USE

CROSS REFERENCE TO RELATED APPLICATIONS

This application is a continuation of U.S. patent application Ser. No. 14/613,579, filed on Feb. 4, 2015, which claims priority to U.S. Provisional Patent Application Ser. No. 61/936,397, filed Feb. 6, 2014, both of which are incorporated herein by reference in their entirety.

BACKGROUND OF THE INVENTION

Technical Field

The invention relates to 6-heteroaryloxy- or 6-aryloxy-quinoline-2-carboxamides that are sodium channel (e.g., $Na_v 1.7$ and $Na_v 1.8$) blockers, useful in treating diseases and conditions mediated and modulated by the voltage-gated sodium channels. Additionally, the invention relates to compositions containing compounds of the invention and processes of their preparation.

Description of Related Technology

The voltage-gated sodium channels (VGSCs, $Na_v 1.x$) contribute to the initiation and propagation of action potentials in excitable tissues such as nerve and muscle by modulating the influx of sodium ions. $Na_v 1.7$, one of nine sodium channel isoforms, is preferentially expressed in the peripheral nervous system where it acts as a threshold channel for action potential firing in neurons (Cummins T R, et al. Expert Rev Neurother 2007; 7:1597-1612. Rush A M, et al. J Physiol 2007; 579:1-14.). A wealth of evidence connects abnormal activity of sodium channels in the peripheral nervous system to the pathophysiology of chronic pain (Goldin A L, et al. Neuron 2000; 28:365-368. Dib-Hajj S D, et al. Annu Rev Neurosci 2010; 33:325-347.). Polymorphisms in SCN9A, the gene that encodes $Na_v 1.7$, cause human pain disorders arising from either gain-of-function or loss-of-function mutations of the channel. Clinically, VGSC blockers have proven useful in the management of pain, but their utility is often limited by incomplete efficacy and poor tolerability. Local anesthetics (e.g., lidocaine), anti-arrhythmic agents (e.g., mexilitene), and anti-convulsants (e.g., lamotrigine) are all relatively weak ($IC_{50}$ values in the high micromolar range), non-selective (versus $Na_v 1.x$ subtypes and other ion channels) VGSC blocking agents identified without prior knowledge of their molecular targets.

The VGSCs are integral plasma membrane proteins composed of a large (260 kDa) α-subunit and one or more smaller β-subunits (Hargus N J et al. Expert Opin Invest Drugs 2007; 16:635-646). Nine α-subunits ($Na_v 1.1$-$Na_v 1.9$) and four β-subunits (β1-β4) have been identified in mammals. The various VGSC subtypes exhibit diverse functional properties and distinct expression patterns, suggesting differential involvement in transmission of specific signals. $Na_v 1.7$, $Na_v 1.8$ and $Na_v 1.9$ are expressed predominantly in the peripheral nervous system in humans and rodents (Waxman S G Brain 2010; 133:2515-2518). The biophysical characteristics of $Na_v 1.7$ suggest a role in initiation of action potentials, while $Na_v 1.8$ is a major contributor to the upstroke of action potentials in sensory neurons. $Na_v 1.9$ produces a persistent current that is involved in setting the resting membrane potential.

The $Na_v 1.7$ isoform is expressed in both small and large diameter DRG neurons, as well as in sympathetic neurons, and in peripheral axonal termini of neurons processing pain. $Na_v 1.7$ is up-regulated in preclinical models of inflammatory and neuropathic pain, including diabetic neuropathy (Dib-Hajj S D, et al. Nat Rev Neurosci. 2013; 14:49-62. Hong S, et al. Journal of Biological Chemistry. 2004; 279:29341-29350. Persson A K, et al. Exp Neurol. 2011; 230:273-279.). $Na_v 1.7$ has been shown to accumulate in painful neuromas, such as those in amputees with phantom limb pain, and in painful dental pulp (Beneng K, et al. BMC Neurosci. 2010; 11:71. Dib-Hajj S D, et al. Nat Rev Neurosci. 2013; 14:49-62). Rare human genetic conditions involving single-nucleotide polymorphisms in SCN9A, the gene encoding for $Na_v 1.7$ highlight its importance in pain pathways. Bi-allelic gain-of-function mutations (enhancing channel activity and increasing the excitability of DRG neurons) produce severe pain syndromes with dominant genetic inheritance. Mutations that hyperpolarize activation voltage dependence (i.e., facilitate channel opening and increase the excitability of DRG neurons) result in inherited erythromelalgia (IEM), a condition characterized by excruciating burning pain, attacks of edema, increased skin temperature and flushing of the skin affecting the distal extremities. Similarly, polymorphisms that impair inactivation of the channel and enhance persistent current lead to paroxysmal extreme pain disorder (PEPD), a condition wherein episodic severe perineal, perioccular and paramandibular pain is accompanied by autonomic manifestations such as skin flushing usually in the lower body (Waxman S G Nature 2011472:173-174. Dib-Hajj S D, et al. Brain 2005; 128: 1847-1854.). By contrast, bi-allelic loss-of-function mutations preventing the production of functional $Na_v 1.7$ channels produced channelopathy-associated congenital insensitivity to pain (CIP). CIP patients do not perceive or understand pain even when confronted with extreme pain stimuli such as bone fractures, surgery, dental extractions, burns, and childbirth.

The role of $Na_v 1.7$ in pain has been confirmed in knockout studies. Global deletion of $Na_v 1.7$ in knockout mice causes a disruption of normal eating behavior due to a deficit in olfaction, resulting in lethality shortly after birth (Nassar M A, et al. Proc Natl Acad Sci USA 2004; 101: 12706-12711). A conditional $Na_v 1.7$ knockout in $Na_v 1.8$-expressing DRG neurons abrogated inflammation-induced pain and diminished responses to mechanical insult, but neuropathic pain development was not affected (Nassar M A, et al. Mol Pain 2005; 1:24-31). However, ablation of $Na_v 1.7$ in both sensory and sympathetic neurons recapitulated the pain-free phenotype seen in CIP patients, abolishing inflammatory and neuropathic pain without causing any overt autonomic dysfunction (Minett M S, et al. Nat Commun 2012; 3:791). $Na_v 1.7$-deficient sensory neurons also failed to release substance P in the spinal cord or to display synaptic potentiation in the dorsal horn of the spinal cord in response to electrical stimulation of the sciatic nerve (Minett M S, et al. Nat Commun 2012; 3:791).

The level of preclinical validation for the $Na_v 1.8$ isoform as a target for pain is also compelling. Complementary to $Na_v 1.7$ in its biophysical and functional profile, one $Na_v 1.8$ isoform is expressed in nociceptive trigeminal neurons, in the vast majority of DRG neurons, and in peripheral free nerve endings (Shields S D, et al. Pain 2012; 32:10819-10832). An evaluation of $Na_v 1.8$-null mice demonstrated that this channel carries the majority of current underlying the upstroke of action potential in nociceptive neurons. Knockout studies further implicate $Na_v 1.8$ in visceral, cold, and inflammatory pain, but not in neuropathic pain. However, assessment of $Na_v$ 1.8 antisense oligonucleotides, also suggested involvement of $Na_v$ 1.8 in the development and maintenance of neuropathic pain, in addition to confirming the relevance of the channel in inflammatory pain (Momin A, et al. Curr Opin Neurobiol 2008; 18:383-388. Rush A M, et al. J Physiol 2007; 579:1-14. Liu M et al. Pain Med 12 Suppl 2011; 3:S93-99.). Human gain-of-function mutations in $Na_v$ 1.8 were recently identified in patients with SFN who were all negative for mutations in $Na_v$ 1.7 (Faber C G, et al. Proc Natl Acad Sci USA. 2012; 109:19444-19449).

While the literature offers preclinical validation for $Na_v$ 1.7 and $Na_v$ 1.8 as pain targets, multiple challenges confront the discovery and development of small molecule blockers. The potency needed for efficacy, the levels of selectivity versus the various isoforms required for acceptable therapeutic index, and the relevance of state- and use-dependent activity are not well understood. Although compounds and mechanisms exist that are used clinically to treat pain, there is need for new compounds that can effectively treat different types of pain. Pain of various types (e.g., inflammatory pain, post-surgical pain, osteoarthritis pain, knee pain, lower back pain, neuropathic pain) afflicts virtually all humans and animals at one time or another, and a substantial number of medical disorders and conditions produce some sort of pain as a prominent concern requiring treatment. As such, it would be particularly beneficial to identify new compounds for treating the various types of pain.

SUMMARY

The invention is directed to 6-heteroaryloxy- or 6-aryloxy-quinoline-2-carboxamides having a structure of formula (I):

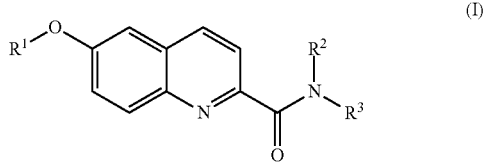

(I)

or a pharmaceutically acceptable salt, ester, amide, or radiolabelled form thereof, wherein:

$R^1$ is selected from the group consisting of phenyl and monocyclic 5- or 6-membered heteroaryl, wherein the phenyl or 5- or 6-membered heteroaryl is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, halogen, cyano, —$NO_2$, —$OR^{1a}$, —$OC(O)R^{1a}$, —$OC(O)N(R^b)(R^{3a})$, —$SR^{1a}$, —$S(O)R^{2a}$, —$S(O)_2R^{2a}$, —$S(O)_2N(R^b)(R^{3a})$, —$C(O)R^{1a}$, —$C(O)OR^{1a}$, —$C(O)N(R^b)(R^{3a})$, —$N(R^b)(R^{3a})$, —$N(R^a)C(O)R^{1a}$, —$N(R^a)C(O)O(R^{1a})$, —$N(R^a)C(O)N(R^b)(R^{3a})$, —$(CR^{4a}R^{5a})_m$—$NO_2$, —$N(R^b)S(O)_2(R^{2a})$, —$(CR^{4a}R^{5a})_m$—$OR^{1a}$, —$(CR^{4a}R^{5a})_m$—$OC(O)R^{1a}$, —$(CR^{4a}R^{5a})_m$—$OC(O)N(R^b)(R^{3a})$, —$(CR^{4a}R^{5a})_m$—$SR^{1a}$, —$(CR^{4a}R^{5a})_m$—$S(O)R^{2a}$, —$(CR^{4a}R^{5a})_m$—$S(O)_2R^{2a}$, —$(CR^{4a}R^{5a})_m$—$S(O)_2N(R^b)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^a)(R^{3a})$, —$(CR^{4a}R^{5a})_m$—$N(R^b)(R^{3a})$, —$(CR^{4a}R^{5a})_m$—$N(R^a)C(O)R^{1a}$, —$(CR^{4a}R^{5a})_m$—$N(R^a)C(O)O(R^{1a})$, —$(CR^{4a}R^{5a})_m$—$N(R^a)C(O)N(R^b)(R^{3a})$, —$(CR^{4a}R^{5a})_m$—$N(R^b)S(O)_2(R^{2a})$, cyano-$C_1$-$C_6$-alkyl, and halo-$C_1$-$C_6$-alkyl;

$R^a$ and $R^b$, at each occurrence, are each independently hydrogen, $C_1$-$C_6$-alkyl, or halo-$C_1$-$C_6$-alkyl;

$R^{1a}$ and $R^{3a}$, at each occurrence, are each independently hydrogen, $C_1$-$C_6$-alkyl, or halo-$C_1$-$C_6$-alkyl;

$R^{2a}$, at each occurrence, is independently $C_1$-$C_6$-alkyl or halo-$C_1$-$C_6$-alkyl;

$R^{4a}$ and $R^{5a}$, at each occurrence, are each independently hydrogen, halogen, $C_1$-$C_6$-alkyl, or halo-$C_1$-$C_6$-alkyl;

m, at each occurrence, is independently 1, 2, 3, 4, or 5;

$R^2$ is selected from the group consisting of hydrogen, $C_1$-$C_6$-alkyl, $C_1$-$C_6$-alkoxy-$C_1$-$C_6$-alkyl, and -$G^2$;

$R^3$ is selected from the group consisting of hydrogen, $C_1$-$C_6$-alkyl, $C_2$-$C_6$-alkenyl, $C_2$-$C_6$-alkynyl, —$(CR^{4b}R^{5b})_n$—$NO_2$, —$(CR^{4b}R^{5b})_n$—$OR^{1b}$, —CH[($CR^{4b}R^{5b})_n$—$OR^{1b}$]$_2$, —$(CR^{4b}R^{5b})_n$—$OC(O)R^{1b}$, —$(CR^{4b}R^{5b})_n$—$OC(O)N(R^b)(R^{3b})$, —$(CR^{4b}R^{5b})_n$—$SR^{1b}$, —$(CR^{4b}R^{5b})_n$—$S(O)_2R^{2b}$, —$(CR^{4b}R^{5b})_n$—$S(O)_2N(R^b)(R^{3b})$, —$(CR^{4b}R^{5b})_n$—$C(O)R^{1b}$, —$(CR^{4b}R^{5b})_n$—$C(O)OR^{1b}$, —$(CR^{4b}R^{5b})_n$—$C(O)N(R^b)(R^{3b})$, —$(CR^{4b}R^{5b})_n$—$C(O)N(R^b)(—(CR^{4b}R^{5b})_n$—$OR^{1b})$, —$(CR^{4b}R^{5b})_n$—$C(O)N(R^b)(G^4)$, —$(CR^{4b}R^{5b})_n$—$C(O)N(R^b)(G^3)$, —$(CR^{4b}R^{5b})_n$—$C(O)G^4$, —$(CR^{4b}R^{5b})_n$—$N(R^b)(R^{3b})$, —$(CR^{4b}R^{5b})_n$—$N(R^b)(G^3)$, —$(CR^{4b}R^{5b})_n$—$N(R^a)C(O)R^{1b}$, —$(CR^{4b}R^{5b})_n$—$N(R^b)S(O)_2R^{2b}$, —$S(O)_2R^{2b}$, —$(CR^{4b}R^{5b})_n$—$N(R^a)C(O)O(R^{1b})$, —$(CR^{4b}R^{5b})_n$—$N(R^a)C(O)N(R^a)C(O)N(R^b)(R^{3b})$, —$G^2$, —$(CR^{4b}R^{5b})_n$—$G^4$, -$G^2$-$G^6$, -$G^1$, —$(CR^{4b}R^{5b})_n$-$G^3$, —CH[C(O)N(R^b)(R^{3b})][—(CR^{4b}R^{5b})_n$-$G^3$], cyano-$C_1$-$C_6$-alkyl, and halo-$C_1$-$C_6$-alkyl;

$R^{1b}$ and $R^{3b}$, at each occurrence, are each independently hydrogen, $C_1$-$C_6$-alkyl, or halo-$C_1$-$C_6$-alkyl;

$R^{2b}$, at each occurrence, is independently $C_1$-$C_6$-alkyl or halo-$C_1$-$C_6$-alkyl;

$R^{4b}$ and $R^{5b}$, at each occurrence, are each independently hydrogen, halogen, $C_1$-$C_6$-alkyl, or halo-$C_1$-$C_6$-alkyl;

n, at each occurrence, is independently 1, 2, 3, 4, or 5;

$G^1$ and $G^3$ are each independently aryl or heteroaryl; wherein $G^1$ and $G^3$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, —$N(R^c)_2$, —$N(R^c)C(O)R^c$, —$OR^c$, —$C(O)R^c$, —$C(O)OR^c$, —$C(O)N(R^c)_2$, —$SO_2R^d$, and —$SO_2N(R^c)_2$;

$G^2$, $G^4$ and $G^6$ are each independently 3-6-membered-cycloalkyl, 3-6-membered-cycloalkenyl, or 4-10-membered-heterocycle; wherein $G^2$, $G^4$ and $G^6$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, benzyl, cyano, halo-$C_1$-$C_6$-alkyl, hydroxy-$C_1$-$C_6$-alkyl, halogen, nitro, oxo, —$N(R^c)_2$, —$N(R^c)C(O)R^c$, —$OR^c$, —$C(O)R^c$, —$C(O)OR^c$, —$C(O)N(R^c)_2$, —$SO_2R^d$, —$SO_2N(R^c)_2$, and phenyl, wherein phenyl and the phenyl ring of benzyl are optionally substituted with 1, 2, 3, or 4 $C_1$-$C_6$-alkyl, halogen, or $C_1$-$C_6$-alkoxy;

$R^c$ at each occurrence, is independently hydrogen, $C_1$-$C_6$-alkyl, aryl, aryl-$C_1$-$C_6$-alkyl, cycloalkyl, cycloalkyl-$C_1$-$C_6$-alkyl, or halo-$C_1$-$C_6$-alkyl; wherein said aryl, the aryl of aryl-$C_1$-$C_6$-alkyl, the cycloalkyl, and the cycloalkyl of cycloalkyl-$C_1$-$C_6$-alkyl are independently unsubstituted or substituted with 1, 2 3, 4, or 5 substituents independently selected from the group consisting of $C_1$-$C_6$-alkyl, halo-$C_1$-$C_6$-alkyl, and halogen;

$R^d$ is $C_1$-$C_6$-alkyl or halo-$C_1$-$C_6$-alkyl; or $R^2$, $R^3$ and the nitrogen atom to which they are attached form a 4-8-membered-monocyclic heterocycle, 6-11-membered-bicyclic heterocycle, 10-12-membered-tricyclic heterocycle, 7-11-membered-spirocyclic heterocycle or 8-11-membered-bicyclic heteroaryl comprised of a monocyclic heterocycle fused to a monocyclic heteroaryl, wherein said 4-8-membered monocyclic heterocycle, said 6-11-membered-bicyclic heterocycle, said, 10-12-membered-tricyclic heterocycle, said 7-11-membered-spirocyclic heterocycle and said 8-11-membered-bicyclic heteroaryl are unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, halogen, cyano, —$NO_2$, —$OR^{1c}$, —O—$(CR^{4c}R^{5c})_p$—$OR^{1c}$, —$OG^{13}$, —$OC(O)R^{1c}$, —$OC(O)N(R^b)$ $(R^{3c})$, —$SR^{1c}$, —$S(O)R^{2c}$, —$S(O)_2R^{2c}$, —$S(O)_2G^{13}$, —$S(O)_2G^{14}$, —$S(O)_2N(R^b)(R^{3c})$, —$S(O)_2$—$(CR^{4c}R^{5c})_pC(O)OR^{1c}$, —$S(O)_2$—$(CR^{4c}R^{5c})_p$-$G^{14}$, —$C(O)R^{1c}$, —$C(O)G^{14}$, —$C(O)OR^{1c}$, —$C(O)N(R^b)(R^{3c})$, —$N(R^b)(R^{3c})$, —$N(R^a)C(O)R^{1c}$, —$N(R^a)C(O)G^{14}$, —$N(R^a)C(O)O(R^{1c})$, —$N(R^a)C(O)N(R^b)(R^{3c})$, —$(CR^{4c}R^{5c})_p$—$NO_2$, —$N(R^b)S(O)_2(R^{2c})$, —$N(R^b)S(O)_2(G^{13})$, —$(CR^{4c}R^{5c})_p$—$OR^{1c}$, —$(CR^{4c}R^{5c})_p$—O—$(CR^{4c}R^{5c})_p$—$OR^{1c}$, —$(CR^{4c}R^{5c})_p$—$OC(O)R^{1c}$, —$(CR^{4c}R^{5c})_p$—$OC(O)N(R^b)(R^{3c})$, —$(CR^{4c}R^{5c})_p$—$SR^{1c}$, —$(CR^{4c}R^{5c})_p$—$S(O)R^{2c}$, —$(CR^{4c}R^{5c})_p$—$S(O)_2R^{2c}$, —$(CR^{4c}R^{5c})_p$—$S(O)_2N(R^b)(R^{3c})$, —$(CR^{4c}R^{5c})_p$—$C(O)R^{1c}$, —$(CR^{4c}R^{5c})_p$—$C(O)OR^{1c}$, —$(CR^{4c}R^{5c})_p$—$C(O)N(R^a)(R^{3c})$, —$(CR^{4c}R^{5c})_p$—$N(R^b)(R^{3c})$, —$(CR^{4c}R^{5c})_p$—$N(R^a)C(O)R^{1c}$, —$(CR^{4c}R^{5c})_p$—$N(R^a)C(O)O(R^{1c})$, —$(CR^{4c}R^{5c})_p$—$N(R^a)C(O)O(CH_2G^{13})$, —$(CR^{4c}R^{5c})_p$—$N(R^a)C(O)N(R^b)(R^{3c})$, —$(CR^{4c}R^{5c})_p$—$N(R^b)S(O)_2(R^{2c})$, -$G^{11}$, —$(CR^{4c}R^{5c})_p$-$G^{13}$, —$(CR^{4c}R^{5c})_p$—$OG^{13}$, -$G^{12}$, —$(CR^{4c}R^{5c})_p$-$G^{14}$, cyano-$C_1$-$C_6$-alkyl, oxo, $C^1$-$C^6$-alkoxyimino and halo-$C_1$-$C_6$-alkyl;

$R^{1c}$ and $R^{3c}$, at each occurrence, are each independently hydrogen, $C_1$-$C_6$-alkyl, or halo-$C_1$-$C_6$-alkyl;

$R^{2c}$, at each occurrence, is independently $C_1$-$C_6$-alkyl or halo-$C_1$-$C_6$-alkyl;

$R^{4c}$ and $R^{5c}$, at each occurrence, are each independently hydrogen, halogen, $C_1$-$C_6$-alkyl, or halo-$C_1$-$C_6$-alkyl;

p, at each occurrence, is independently 1, 2, 3, 4, or 5;

$G^{11}$ and $G^{13}$ are each independently phenyl or 5-6-membered-heteroaryl; wherein $G^{11}$ and $G^{13}$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, $C_1$-$C_6$-alkoxy-$C_1$-$C_6$-alkyl, halo-$C_1$-$C_6$-alkyl, halogen, nitro, —$N(R^e)_2$, —$N(R^e)C(O)R^e$, —$OR^e$, —$C(O)R^e$, —$C(O)OR^e$, —$C(O)N(R^e)_2$, —$SO_2R^f$, and —$SO_2N(R^e)_2$;

$G^{12}$, and $G^{14}$ are each independently 3-6-membered-cycloalkyl, 3-6-membered-cycloalkenyl, or 4-10-membered-heterocycle, wherein $G^{12}$ and $G^{14}$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, benzyl, cyano, halo-$C_1$-$C_6$-alkyl, hydroxy-$C_1$-$C_6$-alkyl, halogen, nitro, oxo, —$N(R^e)_2$, —$N(R^e)C(O)R^e$, —$N(R^e)S(O)_2R^f$, —$OR^e$, —$C(O)R^e$, —$C(O)OR^e$, —$C(O)N(R^e)_2$, —$SO_2R^f$, —$SO_2N(R^e)_2$, and phenyl, wherein phenyl and the phenyl ring of benzyl are optionally substituted with $C_1$-$C_6$-alkyl, halogen, or $C_1$-$C_6$-alkoxy;

$R^e$ at each occurrence, is independently hydrogen, $C_1$-$C_6$-alkyl, aryl, aryl-$C_1$-$C_6$-alkyl, cycloalkyl, cycloalkyl-$C_1$-$C_6$-alkyl, or halo-$C_1$-$C_6$-alkyl; wherein said aryl, the aryl of aryl-$C_1$-$C_6$-alkyl, the cycloalkyl, and the cycloalkyl of cycloalkyl-$C_1$-$C_6$-alkyl are independently unsubstituted or substituted with 1, 2 3, 4, or 5 substituents independently selected from the group consisting of $C_1$-$C_6$-alkyl, halo-$C_1$-$C_6$-alkyl, and halogen; and $R^f$ is $C_1$-$C_6$-alkyl or halo-$C_1$-$C_6$-alkyl.

Another aspect of the invention relates to pharmaceutical compositions comprising compounds of the invention. Such compositions can be administered in accordance with a method of the invention, typically as part of a therapeutic regimen for treatment or prevention of conditions and disorders related to voltage-gated sodium channel (and particularly $Na_v$ 1.7 and $Na_v$ 1.8) activity.

Yet another aspect of the invention relates to a method of selectively blocking voltage-gated sodium channels (e.g., $Na_v$ 1.7 and $Na_v$ 1.8 channels). The method is useful for treating, or preventing conditions and disorders related to blocking voltage-gated sodium channels in mammals. More particularly, the method is useful for treating or preventing conditions and disorders related to pain, neuropathy, inflammation, auto-immune disease, fibrosis, chronic kidney disease, and cancer. Accordingly, the compounds and compositions of the invention are useful as a medicament for treating or preventing voltage-gated sodium channel modulated disease.

The compounds, compositions comprising the compounds, methods for making the compounds, and methods for treating or preventing conditions and disorders by administering the compounds are further described herein.

These and other objects of the invention are described in the following paragraphs.

These objects should not be deemed to narrow the scope of the invention.

DETAILED DESCRIPTION OF THE INVENTION

Compounds of formula (I) are disclosed in this invention

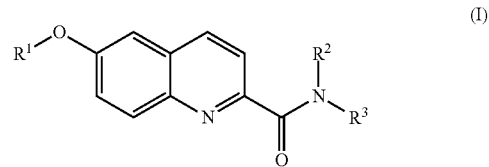

(I)

wherein $R^1$, $R^2$ and $R^3$ are as defined above in the Summary. Compositions comprising such compounds and methods for treating conditions and disorders using such compounds and compositions are also disclosed.

In various embodiments, the present invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds which can be isolated from a reaction mixture.

Definition of Terms

Certain terms as used in the specification are intended to refer to the following definitions, as detailed below.

The term "alkenyl" as used herein, means a straight or branched hydrocarbon chain containing from 2 to 10 carbons and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of from 2 to 10 carbon atoms containing at least one double bond. Representative examples of alkenylene include, but are not limited to, —CH=CH—, —CH=CH$_2$CH$_2$—, and —CH=C(CH$_3$)CH$_2$—.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxyimino" as used herein means an alkoxy group, as defined herein, appended to the parent molecular moiety through an imino group, as defined herein. Representative examples of alkoxyimino include, but are not limited to, ethoxy(imino) (i.e., CH$_3$CH$_2$O—N=) and methoxy(imino) (i.e., CH$_3$O—N=)

The term "alkyl" as used herein, means a straight or branched, saturated hydrocarbon chain containing from 1 to 10 carbon atoms. The term "lower alkyl" or "C$_1$-C$_6$-alkyl" means a straight or branched chain hydrocarbon containing from 1 to 6 carbon atoms. The term "C$_1$-C$_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" denotes a divalent group derived from a straight or branched chain hydrocarbon containing from 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "arylalkyl" as used herein, means an aryl group, as defined herein, appended to the parent molecular moiety through an alkylene group, as defined herein. Representative examples of arylalkyl include, but are not limited to, benzyl, 1-phenylethyl, 2-phenylethyl, 3-phenylpropyl, and 2-naphth-2-ylethyl.

The term "cyano" as used herein, means a —CN group.

The term "cyanoalkyl" as used herein, means a cyano group, as defined herein, appended to the parent molecular moiety through an alkylene group, as defined herein. Representative examples of cyanoalkyl include, but are not limited to, cyanomethyl, 2-cyanoethyl, and 3-cyanopropyl.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group, or a bridged monocyclic ring system in which two non-adjacent carbon atoms of the monocyclic ring are linked by an alkylene bridge containing one, two, three, or four carbon atoms. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl can be attached to the parent molecular moiety through any substitutable atom contained within the ring systems, and can be unsubstituted or substituted.

The term "cycloalkyl" or "cycloalkane" as used herein, means a monocyclic, a bicyclic, a tricyclic, or a spirocyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane.

Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$] nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system. Spirocyclic cycloalkyl is exemplified by a monocyclic or a bicyclic cycloalkyl, wherein two of the substituents on the same carbon atom of the ring, together with said carbon atom, form a 4-, 5-, or 6-membered monocyclic cycloalkyl. An example of a spirocyclic cycloalkyl is spiro[2.5]octane. The spirocyclic cycloalkyl groups of the present invention can be appended to the parent molecular moiety through any substitutable carbon atom of the groups.

The term "cycloalkylalkyl" as used herein, means a cycloalkyl group appended to the parent molecular moiety through an alkyl group, as defined herein.

The term "halo" or "halogen" as used herein, means Cl, Br, I, or F.

The term "haloalkyl" as used herein, means an alkyl group, as defined herein, in which one, two, three, four, five, six, seven or eight hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heteroaryl" as used herein, means a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heteroarylalkyl" as used herein, means a heteroaryl, as defined herein, appended to the parent molecular moiety through an alkyl group, as defined herein.

The term "heterocycle" or "heterocyclic" as used herein, means a monocyclic heterocycle, a bicyclic heterocycle, a tricyclic heterocycle, or a spirocyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), oxa-adamantane (2-oxatricyclo[3.3.1.1$^{3,7}$]decane), and octahydro-1H-4,7-epiminoisoindole. The spirocyclic heterocycles are exemplified by a monocyclic heterocycle as defined herein wherein one carbon atom of the monocyclic heterocycle is bridged by two ends of an alkylene chain. In the spirocyclic heterocycle, one or more carbon atoms in the bridging alkylene chain may be replaced with a heteroatom. Examples of spirocyclic heterocycles include, but are not limited to, 4,7-diazaspiro[2.5]octane, 2-oxa-6-azaspiro[3.3]heptane, 2,6-diazaspiro[3.3]heptane, 2-oxa-5,8-diazaspiro[3.5]nonane, 2,7-diazaspiro[3.5]nonane, 1,4-dioxa-8-azaspiro[4.5]decane, 1,6-diazaspiro[3.3]heptane, 1-azaspiro[4.4]nonane, 7-azaspiro[3.5]nonane, 1,4-dioxa-7-azaspiro[4.4]nonane, 5,8-diazaspiro[3.5]nonane, 5,8-dioxa-2-azaspiro[3.4]octane, 2-oxa-6-azaspiro[3.4]octane, 6-oxa-1-azaspiro[3.3]heptane, 6-oxa-2-azaspiro[3.4]octane, 6-oxa-2-azaspiro[3.5]nonane, and 7-oxa-2-azaspiro[3.5]nonane. The monocyclic, bicyclic, tricyclic, and spirocyclic heterocycles are connected to the parent molecular moiety through any carbon atom or any nitrogen atom contained within the rings, and can be unsubstituted or substituted.

The term "heteroatom" as used herein, means a nitrogen, oxygen, or sulfur atom.

The term "hydroxyl" or "hydroxy" as used herein, means an —OH group.

The term "hydroxyalkyl" as used herein, means at least one hydroxy group, as defined herein, is appended to the parent molecular moiety through an alkylene group, as defined herein. Representative examples of hydroxyalkyl include, but are not limited to, hydroxymethyl, 2-hydroxyethyl, 3-hydroxypropyl, and 2-ethyl-4-hydroxyheptyl.

The term "imino" as defined herein means a (=NH)— group.

The term "nitro" as used herein means a —NO$_2$ group.

The term "oxo" as used herein means (=O).

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbyl ring containing from 3 to 6 carbon ring atoms.

As used herein, the term "radiolabel" refers to a compound of the invention in which at least one of the atoms is a radioactive atom or radioactive isotope, wherein the radioactive atom or isotope spontaneously emits gamma rays or energetic particles, for example alpha particles or beta particles, or positrons. Examples of such radioactive atoms include, but are not limited to, $^3H$ (tritium), $^{14}C$, $^{11}C$, $^{15}O$, $^{18}F$, $^{35}S$, $^{123}I$, and $^{125}I$.

Compounds of the Invention

Compounds of the invention can have the formula (I) as described in the Summary.

Particular values of variable groups in compounds of formula (I) are as follows. Such values can be used where appropriate with any of the other values, definitions, claims or embodiments defined hereinbefore or hereinafter.

In one embodiment, $R^1$ is selected from the group consisting of phenyl and monocyclic 5- or 6-membered heteroaryl, wherein the phenyl or 5- or 6-membered heteroaryl is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, halogen, cyano, —$NO_2$, —$OR^{1a}$, —$OC(O)R^{1a}$, —$OC(O)N(R^b)(R^{3a})$, —$SR^{1a}$, —$S(O)R^{2a}$, —$S(O)_2R^{2a}$, —$S(O)_2N(R^b)(R^{3a})$, —$C(O)R^{1a}$, —$C(O)OR^{1a}$, —$C(O)N(R^b)(R^{3a})$, —$N(R^b)(R^{3a})$, —$N(R^a)C(O)R^{1a}$, —$N(R^a)C(O)O(R^{1a})$, —$N(R^a)C(O)N(R(R^b)(R^{3a})$, —$(CR^{4a}R^{5a})_m$—$NO_2$, —$N(R^b)S(O)_2(R^{2a})$, —$(CR^{4a}R^{5a})_m$—$OR^{1a}$, —$(CR^{4a}R^{5a})_m$—$OC(O)R^{1a}$, —$(CR^{4a}R^{5a})_m$—$OC(O)N(R^b)(R^{3a})$, —$(CR^{4a}R^{5a})_m$—$SR^{1a}$, —$(CR^{4a}R^{5a})_m$—$S(O)R^{2a}$, —$(CR^{4a}R^{5a})_m$—$S(O)_2R^{2a}$, —$(CR^{4a}R^{5a})_m$—$S(O)_2N(R^a)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^a)(R^{3a})$, —$(CR^{4a}R^{5a})_m$—$N(R^b)(R^{3a})$, —$(CR^{4a}R^{5a})_m$—$N(R^a)C(O)R^{1a}$, —$(CR^{4a}R^{5a})_m$—$N(R^a)C(O)O(R^{1a})$, —$(CR^{4a}R^{5a})_m$—$N(R^a)C(O)N(R^b)(R^{3a})$, —$(CR^{4a}R^{5a})_m$—$N(R^b)S(O)_2(R^{2a})$, cyano-$C_1$-$C_6$-alkyl, and halo-$C_1$-$C_6$-alkyl; $R^a$ and $R^b$, at each occurrence, are each independently hydrogen, $C_1$-$C_6$-alkyl, or halo-$C_1$-$C_6$-alkyl; $R^{1a}$ and $R^{3a}$, at each occurrence, are each independently hydrogen, $C_1$-$C_6$-alkyl, or halo-$C_1$-$C_6$-alkyl; $R^{2a}$, at each occurrence, is independently $C_1$-$C_6$-alkyl or halo-$C_1$-$C_6$-alkyl; $R^{4a}$ and $R^{5a}$, at each occurrence, are each independently hydrogen, halogen, $C_1$-$C_6$-alkyl, or halo-$C_1$-$C_6$-alkyl; and m, at each occurrence, is independently 1, 2, 3, 4, or 5.

In one embodiment, $R^1$ is selected from the group consisting of phenyl and monocyclic 5- or 6-membered heteroaryl, wherein the phenyl or 5- or 6-membered heteroaryl is unsubstituted or substituted with 1 or 2 substituents selected from the group consisting of $C_1$-$C_6$-alkyl, halogen, cyano, —$OR^{1a}$, —$S(O)_2R^{2a}$, —$C(O)R^{1a}$, —$(CR^{4a}R^{5a})_m$—$OR^{1a}$, and halo-$C_1$-$C_6$-alkyl; $R^a$ and $R^b$, at each occurrence, are each independently hydrogen or $C_1$-$C_6$-alkyl; $R^{1a}$ and $R^{3a}$, at each occurrence, are each independently hydrogen, $C_1$-$C_6$-alkyl, or halo-$C_1$-$C_6$-alkyl; $R^{2a}$, at each occurrence, is independently $C_1$-$C_6$-alkyl or halo-$C_1$-$C_6$-alkyl; $R^{4a}$ and $R^{5a}$, at each occurrence, are each independently hydrogen or $C_1$-$C_6$-alkyl; and m, at each occurrence, is independently 1 or 2.

In one embodiment, $R^1$ is phenyl, wherein the phenyl is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, halogen, cyano, —$NO_2$, —$OR^{1a}$, —$OC(O)R^{1a}$, —$OC(O)N(R^b)(R^{3a})$, —$SR^{1a}$, —$S(O)R^{2a}$, —$S(O)_2R^{2a}$, —$S(O)_2N(R^b)(R^{3a})$, —$C(O)R^{1a}$, —$C(O)OR^{1a}$, —$C(O)N(R^b)(R^{3a})$, —$N(R^b)(R^{3a})$, —$N(R^a)C(O)R^{1a}$, —$N(R^a)C(O)O(R^{1a})$, —$N(R^a)C(O)N(R^b)(R^{3a})$, —$(CR^{4a}R^{5a})_m$—$NO_2$, —$N(R^b)S(O)_2(R^{2a})$, —$(CR^{4a}R^{5a})_m$—$OR^{1a}$, —$(CR^{4a}R^{5a})_m$—$OC(O)R^{1a}$, —$(CR^{4a}R^{5a})_m$—$OC(O)N(R^b)(R^{3a})$, —$(CR^{4a}R^{5a})_m$—$SR^{1a}$, —$(CR^{4a}R^{5a})_m$—$S(O)R^{2a}$, —$(CR^{4a}R^{5a})_m$—$S(O)_2R^{2a}$, —$(CR^{4a}R^{5a})_m$—$S(O)_2N(R^b)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^a)(R^{3a})$, —$(CR^{4a}R^{5a})_m$—$N(R^b)(R^{3a})$, —$(CR^{4a}R^{5a})_m$—$N(R^a)C(O)R^{1a}$, —$(CR^{4a}R^{5a})_m$—$N(R^a)C(O)O(R^{1a})$, —$(CR^{4a}R^{5a})_m$—$N(R^a)C(O)N(R^b)(R^{3a})$, —$(CR^{4a}R^{5a})_m$—$N(R^b)S(O)_2(R^{2a})$, cyano-$C_1$-$C_6$-alkyl, and halo-$C_1$-$C_6$-alkyl; $R^a$ and $R^b$, at each occurrence, are each independently hydrogen, $C_1$-$C_6$-alkyl, or halo-$C_1$-$C_6$-alkyl; $R^{1a}$ and $R^{3a}$, at each occurrence, are each independently hydrogen, $C_1$-$C_6$-alkyl, or halo-$C_1$-$C_6$-alkyl; $R^{2a}$, at each occurrence, is independently $C_1$-$C_6$-alkyl or halo-$C_1$-$C_6$-alkyl; $R^{4a}$ and $R^{5a}$, at each occurrence, are each independently hydrogen, halogen, $C_1$-$C_6$-alkyl, or halo-$C_1$-$C_6$-alkyl; and m, at each occurrence, is independently 1, 2, 3, 4, or 5.

In one embodiment, $R^1$ is phenyl, wherein the phenyl is unsubstituted or substituted with 1 or 2 substituents selected from the group consisting of $C_1$-$C_6$-alkyl, halogen, cyano, —$OR^{1a}$, —$S(O)_2R^{2a}$, —$C(O)R^{1a}$, —$(CR^{4a}R^{5a})_m$—$OR^{1a}$, and halo-$C_1$-$C_6$-alkyl; $R^a$ and $R^b$, at each occurrence, are each independently hydrogen or $C_1$-$C_6$-alkyl; $R^{1a}$ and $R^{3a}$, at each occurrence, are each independently hydrogen, $C_1$-$C_6$-alkyl, or halo-$C_1$-$C_6$-alkyl; $R^{2a}$, at each occurrence, is independently $C_1$-$C_6$-alkyl or halo-$C_1$-$C_6$-alkyl; $R^{4a}$ and $R^{5a}$, at each occurrence, are each independently hydrogen or $C_1$-$C_6$-alkyl; and m, at each occurrence, is independently 1 or 2.

In one embodiment, $R^1$ is monocyclic 5- or 6-membered heteroaryl, wherein the 5- or 6-membered heteroaryl is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, halogen, cyano, —$NO_2$, —$OR^{1a}$, —$OC(O)R^{1a}$, —$OC(O)N(R^b)(R^{3a})$, —$SR^{1a}$, —$S(O)R^{2a}$, —$S(O)_2R^{2a}$, —$S(O)_2N(R^b)(R^{3a})$, —$C(O)R^{1a}$, —$C(O)OR^{1a}$, —$C(O)N(R^b)(R^{3a})$, —$N(R^b)(R^{3a})$, —$N(R^a)C(O)R^{1a}$, —$N(R^a)C(O)O(R^{1a})$, —$N(R^a)C(O)N(R^b)(R^{3a})$, —$(CR^{4a}R^{5a})_m$—$NO_2$, —$N(R^b)S(O)_2(R^{2a})$, —$(CR^{4a}R^{5a})_m$—$OR^{1a}$, —$(CR^{4a}R^{5a})_m$—$OC(O)R^{1a}$, —$(CR^{4a}R^{5a})_m$—$OC(O)N(R^b)(R^{3a})$, —$(CR^{4a}R^{5a})_m$—$SR^{1a}$, —$(CR^{4a}R^{5a})_m$—$S(O)R^{2a}$, —$(CR^{4a}R^{5a})_m$—$S(O)_2R^{2a}$, —$(CR^{4a}R^{5a})_m$—$S(O)_2N(R^b)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^a)(R^{3a})$, —$(CR^{4a}R^{5a})_m$—$N(R^b)(R^{3a})$, —$(CR^{4a}R^{5a})_m$—$N(R^a)C(O)R^{1a}$, —$(CR^{4a}R^{5a})_m$—$N(R^a)C(O)O(R^{1a})$, —$(CR^{4a}R^{5a})_m$—$N(R^a)C(O)N(R^b)(R^{3a})$, —$(CR^{4a}R^{5a})_m$—$N(R^b)S(O)_2(R^{2a})$, cyano-$C_1$-$C_6$-alkyl, and halo-$C_1$-$C_6$-alkyl; $R^a$ and $R^b$, at each occurrence, are each independently hydrogen, $C_1$-$C_6$-alkyl, or halo-$C_1$-$C_6$-alkyl; $R^{1a}$ and $R^{3a}$, at each occurrence, are each independently hydrogen, $C_1$-$C_6$-alkyl, or halo-$C_1$-$C_6$-alkyl; $R^{2a}$, at each occurrence, is independently $C_1$-$C_6$-alkyl or halo-$C_1$-$C_6$-alkyl; $R^{4a}$ and $R^{5a}$, at each occurrence, are each independently hydrogen, halogen, $C_1$-$C_6$-alkyl, or halo-$C_1$-$C_6$-alkyl; and m, at each occurrence, is independently 1, 2, 3, 4, or 5.

In one embodiment, $R^1$ is monocyclic 5- or 6-membered heteroaryl, wherein the 5- or 6-membered heteroaryl is unsubstituted or substituted with 1 or 2 substituents selected from the group consisting of $C_1$-$C_6$-alkyl, halogen, cyano, —OR$^{1a}$, —S(O)$_2$R$^{2a}$, —C(O)R$^{1a}$, —(CR$^{4a}$R$^{5a}$)$_m$—OR$^{1a}$, and halo-C$_1$-C$_6$-alkyl; R$^a$ and R$^b$, at each occurrence, are each independently hydrogen or C$_1$-C$_6$-alkyl; R$^{1a}$ and R$^{3a}$, at each occurrence, are each independently hydrogen, C$_1$-C$_6$-alkyl, or halo-C$_1$-C$_6$-alkyl; R$^{2a}$, at each occurrence, is independently C$_1$-C$_6$-alkyl or halo-C$_1$-C$_6$-alkyl; R$^{4a}$ and R$^{5a}$, at each occurrence, are each independently hydrogen or C$_1$-C$_6$-alkyl; and m, at each occurrence, is independently 1 or 2.

In one embodiment, R$^2$ is selected from the group consisting of hydrogen, C$_1$-C$_6$-alkyl, C$_1$-C$_6$-alkoxy-C$_1$-C$_6$-alkyl, and -G$^2$, wherein -G$^2$ is as defined in the Summary.

In one embodiment, R$^2$ is hydrogen.

In one embodiment, R$^2$ is C$_1$-C$_6$-alkyl.

In one embodiment, R$^2$ is selected from the group consisting of C$_1$-C$_6$-alkoxy-C$_1$-C$_6$-alkyl and -G$^2$, wherein -G$^2$ is as defined in the Summary.

In one embodiment, R$^3$ is selected from the group consisting of hydrogen, C$_1$-C$_6$-alkyl, C$_2$-C$_6$-alkenyl, C$_2$-C$_6$-alkynyl, —(CR$^{4b}$R$^{5b}$)$_n$—NO$_2$, —(CR$^{4b}$R$^{5b}$)$_n$—OR$^{1b}$, —CH[(CR$^{4b}$R$^{5b}$)$_n$—OR$^{1b}$]$_2$, —(CR$^{4b}$R$^{5b}$)$_n$—OC(O)R$^{1b}$, —(CR$^{4b}$R$^{5b}$)$_n$—OC(O)N(R$^b$)(R$^{3b}$), —(CR$^{4b}$R$^{5b}$)$_n$—SR$^{1b}$, —(CR$^{4b}$R$^{5b}$)$_n$—S(O)$_2$R$^{2b}$, —(CR$^{4b}$R$^{5b}$)$_n$—S(O)$_2$N(R$^b$)(R$^{3b}$), —(CR$^{4b}$R$^{5b}$)$_n$—C(O)R$^{1b}$, —(CR$^{4b}$R$^{5b}$)$_n$—C(O)OR$^{1b}$, —(CR$^{4b}$R$^{5b}$)$_n$—C(O)N(R$^b$)(R$^{3b}$), —(CR$^{4b}$R$^{5b}$)$_n$—C(O)N(R$^b$)(—(CR$^{4b}$R$^{5b}$)$_n$—OR$^{1b}$), —(CR$^{4b}$R$^{5b}$)$_n$—C(O)N(R$^b$)(G$^4$), —(CR$^{4b}$R$^{5b}$)$_n$—C(O)N(R$^b$)(G$^3$), —(CR$^{4b}$R$^{5b}$)$_n$—C(O)G$^4$, —(CR$^{4b}$R$^{5b}$)$_n$—N(R$^b$)(R$^{3b}$), —(CR$^{4b}$R$^{5b}$)$_n$—N(R$^b$)(G$^3$), —(CR$^{4b}$R$^{5b}$)$_n$—N(R$^a$)C(O)R$^{1b}$, —(CR$^{4b}$R$^{5b}$)$_n$—N(R$^b$)S(O)$_2$R$^{2b}$, —S(O)$_2$R$^{2b}$, —(CR$^{4b}$R$^{5b}$)$_n$—N(R$^a$)C(O)O(R$^{1b}$), —(CR$^{4b}$R$^{5b}$)$_n$—N(R$^a$)C(O)N(R$^b$)(R$^{3b}$), -G$^2$, —(CR$^{4b}$R$^{5b}$)$_n$-G$^4$, -G$^2$-G$^6$, -G$^1$, —(CR$^{4b}$R$^{5b}$)$_n$-G$^3$, —CH[C(O)N(R$^b$)(R$^{3b}$)][—(CR$^{4b}$R$^{5b}$)$_n$-G$^3$], cyano-C$_1$-C$_6$-alkyl, and halo-C$_1$-C$_6$-alkyl; R$^{1b}$ and R$^{3b}$, at each occurrence, are each independently hydrogen, C$_1$-C$_6$-alkyl, or halo-C$_1$-C$_6$-alkyl; R$^{2b}$, at each occurrence, is independently C$_1$-C$_6$-alkyl or halo-C$_1$-C$_6$-alkyl; R$^{4b}$ and R$^{5b}$, at each occurrence, are each independently hydrogen, halogen, C$_1$-C$_6$-alkyl, or halo-C$_1$-C$_6$-alkyl; n, at each occurrence, is independently 1, 2, 3, 4, or 5; G$^1$ and G$^3$ are each independently aryl or heteroaryl; wherein G$^1$ and G$^3$ are each independently unsubstituted or substituted with 1, 2, 3, 4, or 5 substituents selected from the group consisting of C$_1$-C$_6$-alkyl, C$_2$-C$_6$-alkenyl, C$_2$-C$_6$-alkynyl, cyano, halo-C$_1$-C$_6$-alkyl, halogen, nitro, —N(R$^c$)$_2$, —N(R$^c$)C(O)R$^c$, —OR$^c$, —C(O)R$^c$, —C(O)OR$^c$, —C(O)N(R$^c$)$_2$, —SO$_2$R$^d$, and —SO$_2$N(R$^c$)$_2$; G$^2$, G$^4$ and G$^6$ are each independently 3-6-membered-cycloalkyl, 3-6-membered-cycloalkenyl, or 4-10-membered-heterocycle; wherein G$^2$, G$^4$ and G$^6$ are each independently unsubstituted or substituted with 1, 2, 3, 4, or 5 substituents selected from the group consisting of C$_1$-C$_6$-alkyl, C$_2$-C$_6$-alkenyl, C$_2$-C$_6$-alkynyl, benzyl, cyano, halo-C$_1$-C$_6$-alkyl, hydroxy-C$_1$-C$_6$-alkyl, halogen, nitro, oxo, —N(R$^c$)$_2$, —N(R$^c$)C(O)R$^c$, —OR$^c$, —C(O)R$^c$, —C(O)OR$^c$, —C(O)N(R$^c$)$_2$, —SO$_2$R$^d$, —SO$_2$N(R$^c$)$_2$, and phenyl, wherein phenyl and the phenyl ring of benzyl are optionally substituted with 1, 2, 3, or 4 C$_1$-C$_6$-alkyl, halogen, or C$_1$-C$_6$-alkoxy; R$^c$ at each occurrence, is independently hydrogen, C$_1$-C$_6$-alkyl, aryl, aryl-C$_1$-C$_6$-alkyl, cycloalkyl, cycloalkyl-C$_1$-C$_6$-alkyl, or halo-C$_1$-C$_6$-alkyl; wherein said aryl, the aryl of aryl-C$_1$-C$_6$-alkyl, the cycloalkyl, and the cycloalkyl of cycloalkyl-C$_1$-C$_6$-alkyl are independently unsubstituted or substituted with 1, 2 3, 4, or 5 substituents independently selected from the group consisting of C$_1$-C$_6$-alkyl, halo-C$_1$-C$_6$-alkyl, and halogen; and R$^d$ is C$_1$-C$_6$-alkyl or halo-C$_1$-C$_6$-alkyl.

In one embodiment, R$^3$ is selected from the group consisting of hydrogen, C$_1$-C$_6$-alkyl, C$_2$-C$_6$-alkenyl, —(CR$^{4b}$R$^{5b}$)$_n$—OR$^{1b}$, —CH[(CR$^{4b}$R$^{5b}$)$_n$—OR$^{1b}$]$_2$, —(CR$^{4b}$R$^{5b}$)$_n$—S(O)$_2$R$^{2b}$, —(CR$^{4b}$R$^{5b}$)$_n$—S(O)$_2$N(R$^b$)(R$^{3b}$), —(CR$^{4b}$R$^{5b}$)$_n$—C(O)N(R$^b$)(R$^{3b}$), —(CR$^{4b}$R$^{5b}$)$_n$—C(O)N(R$^b$)(—(CR$^{4b}$R$^{5b}$)$_n$—OR$^{1b}$), —(CR$^{4b}$R$^{5b}$)$_n$—C(O)N(R$^b$)(G$^4$), —(CR$^{4b}$R$^{5b}$)$_n$—C(O)N(R$^b$)(G$^3$), —(CR$^{4b}$R$^{5b}$)$_n$—C(O)G$^4$, —(CR$^{4b}$R$^{5b}$)$_n$—N(R$^b$)(R$^{3b}$), —(CR$^{4b}$R$^{5b}$)$_n$—N(R$^b$)(G$^3$), —(CR$^{4b}$R$^{5b}$)$_n$—N(R$^a$)C(O)R$^{1b}$, —S(O)$_2$R$^{2b}$, -G$^2$, —(CR$^{4b}$R$^{5b}$)$_n$-G$^4$, -G$^2$-G$^6$, -G$^1$, —(CR$^{4b}$R$^{5b}$)$_n$-G$^3$, —CH[C(O)N(R$^b$)(R$^{3b}$)][—(CR$^{4b}$R$^{5b}$)$_n$-G$^3$], cyano-C$_1$-C$_6$-alkyl, and halo-C$_1$-C$_6$-alkyl; R$^{1b}$ and R$^{3b}$, at each occurrence, are each independently hydrogen, C$_1$-C$_6$-alkyl, or halo-C$_1$-C$_6$-alkyl; R$^{2b}$, at each occurrence, is C$_1$-C$_6$-alkyl; R$^{4b}$ and R$^{5b}$, at each occurrence, are each independently hydrogen, C$_1$-C$_6$-alkyl, or halo-C$_1$-C$_6$-alkyl; n, at each occurrence, is independently 1, 2, 3, or 4; G$^1$ and G$^3$ are each independently aryl or heteroaryl; wherein G$^1$ and G$^3$ are each independently unsubstituted or substituted with 1 or 2 substituents selected from the group consisting of C$_1$-C$_6$-alkyl and —OR$^c$; G$^2$, G$^4$ and G$^6$ are each independently 3-6-membered-cycloalkyl or 4-10-membered-heterocycle; wherein G$^2$, G$^4$ and G$^6$ are each independently unsubstituted or substituted with 1, 2 or 3 substituents selected from the group consisting of C$_1$-C$_6$-alkyl, benzyl, hydroxy-C$_1$-C$_6$-alkyl, halogen, oxo, —OR$^c$, and phenyl, wherein phenyl and the phenyl ring of benzyl are optionally substituted with 1, 2, 3, or 4 halogen, or C$_1$-C$_6$-alkoxy; and R$^c$ at each occurrence, is independently hydrogen, C$_1$-C$_6$-alkyl, aryl, or halo-C$_1$-C$_6$-alkyl; wherein said aryl, is unsubstituted or substituted with 1, 2 3, 4, or 5 substituents independently selected from the group consisting of C$_1$-C$_6$-alkyl, halo-C$_1$-C$_6$-alkyl, and halogen.

In one embodiment, R$^2$, R$^3$ and the nitrogen atom to which they are attached form a 4-8-membered-monocyclic heterocycle, 6-11-membered-bicyclic heterocycle, 10-12-membered-tricyclic heterocycle, 7-11-membered-spirocyclic heterocycle or 8-11-membered-bicyclic heteroaryl comprised of a monocyclic heterocycle fused to a monocyclic heteroaryl, wherein said 4-8-membered monocyclic heterocycle, said 6-11-membered-bicyclic heterocycle, said, 10-12-membered-tricyclic heterocycle, said 7-11-membered-spirocyclic heterocycle and said 8-11-membered-bicyclic heteroaryl are unsubstituted or substituted with 1, 2, 3, 4, or 5 substituents selected from the group consisting of C$_1$-C$_6$-alkyl, C$_2$-C$_6$-alkenyl, C$_2$-C$_6$-alkynyl, halogen, cyano, —NO$_2$, —OR$^{1c}$, —O—(CR$^{4c}$R$^{5c}$)$_p$—OR$^{1c}$, —OG$^{13}$, —OC(O)R$^{1c}$, —OC(O)N(R$^b$)(R$^{3c}$), —SR$^{1c}$, —S(O)R$^{2c}$, —S(O)$_2$R$^{2c}$, —S(O)$_2$G$^{13}$, —S(O)$_2$G$^{14}$, —S(O)$_2$N(R$^b$)(R$^{3c}$), —S(O)$_2$—(CR$^{4c}$R$^{5c}$)$_p$—C(O)OR$^{1c}$, —S(O)$_2$—(CR$^{4c}$R$^{5c}$)$_p$-G$^{14}$, —C(O)R$^{1c}$, —C(O)G$^{14}$, —C(O)OR$^c$, —C(O)N(R$^b$)(R$^{3c}$), —N(R$^b$)(R$^{3c}$), —N(R$^a$)C(O)R$^{1c}$, —N(R$^a$)C(O)G$^{14}$, —N(R$^a$)C(O)O(R$^{1c}$), —N(R$^a$)C(O)N(R$^b$)(R$^{3c}$), —(CR$^{4c}$R$^{5c}$)$_p$—NO$_2$, —N(R$^b$)S(O)$_2$(R$^{2c}$), —N(R$^b$)S(O)$_2$(G$^{13}$), —(CR$^{4c}$R$^{5c}$)$_p$—OR$^{1c}$, —(CR$^{4c}$R$^{5c}$)$_p$—O—(CR$^{4c}$R$^{5c}$)$_p$—OR$^{1c}$, —(CR$^{4c}$R$^{5c}$)$_p$—OC(O)R$^{1c}$, —(CR$^{4c}$R$^{5c}$)$_p$—OC(O)N(R$^b$)(R$^{3c}$), —(CR$^{4c}$R$^{5c}$)$_p$—SR$^{1c}$, —(CR$^{4c}$R$^{5c}$)$_p$—S(O)R$^{2c}$, —(CR$^{4c}$R$^{5c}$)$_p$—S(O)$_2$R$^{2c}$, —(CR$^{4c}$R$^{5c}$)$_p$—S(O)$_2$N(R$^b$)(R$^{3c}$), —(CR$^{4c}$R$^{5c}$)$_p$—C(O)R$^{1c}$, —(CR$^{4c}$R$^{5c}$)$_p$—C(O)OR$^{1c}$, —(CR$^{4c}$R$^{5c}$)$_p$—C(O)N(R$^a$)(R$^{3c}$), —(CR$^{4c}$R$^{5c}$)$_p$—N(R$^b$)(R$^{3c}$), —(CR$^{4c}$R$^{5c}$)$_p$—N(R$^a$)C(O)R$^{1c}$, —(CR$^{4c}$R$^{5c}$)$_p$—N(R$^a$)C(O)O(R$^{1c}$), —(CR$^{4c}$R$^{5c}$)$_p$—N(R$^a$)C(O)O(CH$_2$G$^{13}$), —(CR$^{4c}$R$^{5c}$)$_p$—N(R$^a$)C(O)N(R$^b$)(R$^{3c}$), —(CR$^{4c}$R$^{5c}$)$_p$—N(R$^b$)S(O)$_2$(R$^{2c}$), -G$^{11}$, —(CR$^{4c}$R$^{5c}$)$_p$-G$^{13}$, —(CR$^{4c}$R$^{5c}$)$_p$—OG$^{13}$, -G$^{12}$, —(CR$^{4c}$R$^{5c}$)$_p$-G$^{14}$, cyano-C$_1$-C$_6$-alkyl, oxo, C$^1$-C$^6$-alkoxyimino and halo-C$_1$-C$_6$-alkyl; R$^{1c}$ and R$^{3c}$, at each occurrence, are each independently hydrogen, C$_1$-C$_6$-alkyl, or halo-C$_1$-C$_6$-alkyl; R$^{2c}$, at each occurrence, is independently C$_1$-C$_6$-alkyl or halo-C$_1$-C$_6$-alkyl; R$^{4c}$ and R$^{5c}$, at each occurrence, are each independently hydrogen, halogen, $C_1$-$C_6$-alkyl, or halo-$C_1$-$C_6$-alkyl; p, at each occurrence, is independently 1, 2, 3, 4, or 5; $G^{11}$ and $G^{13}$ are each independently phenyl or 5-6-membered-heteroaryl; wherein $G^{11}$ and $G^{13}$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, $C_1$-$C_6$-alkoxy-$C_1$-$C_6$-alkyl, halo-$C_1$-$C_6$-alkyl, halogen, nitro, —N(R$^e$)$_2$, —N(R$^e$)C(O)R$^e$, —OR$^e$, —C(O)R$^e$, —C(O)OR$^e$, —C(O)N(R$^e$)$_2$, —SO$_2$R$^f$, and —SO$_2$N(R$^e$)$_2$; $G^{12}$, and $G^{14}$ are each independently 3-6-membered-cycloalkyl, 3-6-membered-cycloalkenyl, or 4-10-membered-heterocycle, wherein $G^{12}$ and $G^{14}$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, benzyl, cyano, halo-$C_1$-$C_6$-alkyl, hydroxy-$C_1$-$C_6$-alkyl, halogen, nitro, oxo, —N(R$^e$)$_2$, —N(R$^e$)C(O)R$^e$, —N(R$^e$)S(O)$_2$R$^f$, —OR$^e$, —C(O)R$^e$, —C(O)OR$^e$, —C(O)N(R$^e$)$_2$, —SO$_2$R$^f$, —SO$_2$N(R$^e$)$_2$, and phenyl, wherein phenyl and the phenyl ring of benzyl are optionally substituted with $C_1$-$C_6$-alkyl, halogen, or $C_1$-$C_6$-alkoxy; R$^e$ at each occurrence, is independently hydrogen, $C_1$-$C_6$-alkyl, aryl, aryl-$C_1$-$C_6$-alkyl, cycloalkyl, cycloalkyl-$C_1$-$C_6$-alkyl, or halo-$C_1$-$C_6$-alkyl; wherein said aryl, the aryl of aryl-$C_1$-$C_6$-alkyl, the cycloalkyl, and the cycloalkyl of cycloalkyl-$C_1$-$C_6$-alkyl are independently unsubstituted or substituted with 1, 2 3, 4, or 5 substituents independently selected from the group consisting of $C_1$-$C_6$-alkyl, halo-$C_1$-$C_6$-alkyl, and halogen; and R$^f$ is $C_1$-$C_6$-alkyl or halo-$C_1$-$C_6$-alkyl.

In one embodiment, R$^2$, R$^3$ and the nitrogen atom to which they are attached form a 4-8-membered-monocyclic heterocycle, 6-11-membered-bicyclic heterocycle, 10-12-membered-tricyclic heterocycle, 7-11-membered-spirocyclic heterocycle or 8-11-membered-bicyclic heteroaryl comprised of a monocyclic heterocycle fused to a monocyclic heteroaryl, wherein said 4-8-membered monocyclic heterocycle, said 6-11-membered-bicyclic heterocycle, said, 10-12-membered-tricyclic heterocycle, said 7-11-membered-spirocyclic heterocycle and said 8-11-membered-bicyclic heteroaryl are unsubstituted or substituted with 1, 2, 3 or 4 substituents selected from the group consisting of $C_1$-$C_6$-alkyl, halogen, cyano, —NO$_2$, —OR$^{1c}$, —O—(CR$^{4c}$R$^{5c}$)$_p$—OR$^{1c}$, —OG$^{13}$, —SR$^{1c}$, —S(O)$_2$R$^{2c}$, —S(O)$_2$G$^{13}$, —S(O)$_2$G$^{14}$, —S(O)$_2$N(R$^b$)(R$^{3c}$), —S(O)$_2$—(CR$^{4c}$R$^{5c}$)$_p$—C(O)OR$^{1c}$, —S(O)$_2$—(CR$^{4c}$R$^{5c}$)$_p$-G$^{14}$, —C(O)R$^{1c}$, —C(O)G$^{14}$, —C(O)OR$^{1c}$, —C(O)N(R$^b$)(R$^{3c}$), —N(R$^b$)(R$^{3c}$), —N(R$^a$)C(O)R$^{1c}$, —N(R$^a$)C(O)G$^{14}$, —N(R$^b$)S(O)$_2$(R$^{2c}$), —N(R$^b$)S(O)$_2$(G$^{13}$), —(CR$^{4c}$R$^{5c}$)$_p$—OR$^{1c}$, —(CR$^{4c}$R$^{5c}$)$_p$—O—(CR$^{4c}$R$^{5c}$)$_p$—OR$^{1c}$, —(CR$^{4c}$R$^{5c}$)$_p$—S(O)$_2$R$^{2c}$, —(CR$^{4c}$R$^{5c}$)$_p$—N(R$^b$)(R$^{3c}$), —(CR$^{4c}$R$^{5c}$)$_p$—N(R$^a$)C(O)O(CH$_2$G$^{13}$), -G$^{11}$, —(CR$^{4c}$R$^{5c}$)$_p$-G$^{13}$, —(CR$^{4c}$R$^{5c}$)$_p$—OG$^{13}$, -G$^{12}$, —(CR$^{4c}$R$^{5c}$)$_p$-G$^{14}$, cyano-$C_1$-$C_6$-alkyl, oxo, $C^1$-$C^6$-alkoxyimino and halo-$C_1$-$C_6$-alkyl; R$^{1c}$ and R$^{3c}$, at each occurrence, are each independently hydrogen, $C_1$-$C_6$-alkyl, or halo-$C_1$-$C_6$-alkyl; R$^{2c}$, at each occurrence, is independently $C_1$-$C_6$-alkyl or halo-$C_1$-$C_6$-alkyl; R$^{4c}$ and R$^{5c}$, at each occurrence, are each independently hydrogen or $C_1$-$C_6$-alkyl; p, at each occurrence, is independently 1 or 2; $G^{11}$ and $G^{13}$ are each independently phenyl or 5-6-membered-heteroaryl; wherein $G^{11}$ and $G^{13}$ are each independently unsubstituted or substituted with 1 or 2 substituents selected from the group consisting of $C_1$-$C_6$-alkyl, $C_1$-$C_6$-alkoxy-$C_1$-$C_6$-alkyl, halo-$C_1$-$C_6$-alkyl, halogen, —N(R$^e$)C(O)R$^e$, and —OR$^e$; $G^{12}$, and $G^{14}$ are each independently 3-6-membered-cycloalkyl or 4-10-membered-heterocycle, wherein $G^{12}$ and $G^{14}$ are each independently unsubstituted or substituted with 1 or 2 substituents selected from the group consisting of $C_1$-$C_6$-alkyl, halogen, oxo, and —N(R$^e$)S(O)$_2$R$^f$; R$^e$ at each occurrence, is independently hydrogen or $C_1$-$C_6$-alkyl; and R$^f$ is $C_1$-$C_6$-alkyl or halo-$C_1$-$C_6$-alkyl.

In one embodiment, R$^2$, R$^3$ and the nitrogen atom to which they are attached form a 4-8-membered-monocyclic heterocycle is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, halogen, cyano, —NO$_2$, —OR$^{1c}$, —O—(CR$^{4c}$R$^{5c}$)$_p$—OR$^{1c}$, —OG$^{13}$, —OC(O)R$^{1c}$, —OC(O)N(R$^b$)(R$^{3c}$), —SR$^{1c}$, —S(O)R$^{2c}$, —S(O)$_2$R$^{2c}$, —S(O)$_2$G$^{13}$, —S(O)$_2$G$^{14}$, —S(O)$_2$N(R$^b$)(R$^{3c}$), —S(O)$_2$—(CR$^{4c}$R$^{5c}$)$_p$—C(O)OR$^{1c}$, —S(O)$_2$—(CR$^{4c}$R$^{5c}$)$_p$-G$^{14}$, —C(O)R$^{1c}$, —C(O)G$^{14}$, —C(O)OR$^{1c}$, —C(O)N(R$^b$)(R$^{3c}$), —N(R$^b$)(R$^{3c}$), —N(R$^a$)C(O)R$^{1c}$, —N(R$^a$)C(O)G$^{14}$, —N(R$^a$)C(O)O(R$^{1c}$), —N(R$^a$)C(O)N(R$^b$)(R$^{3c}$), —(CR$^{4c}$R$^{5c}$)$_p$—NO$_2$, —N(R$^b$)S(O)$_2$(R$^{2c}$), —N(R$^b$)S(O)$_2$(G$^{13}$), —(CR$^{4c}$R$^{5c}$)$_p$—OR$^{1c}$, —(CR$^{4c}$R$^{5c}$)$_p$—O—(CR$^{4c}$R$^{5c}$)$_p$—OR$^{1c}$, —(CR$^{4c}$R$^{5c}$)$_p$—OC(O)R$^{1c}$, —(CR$^{4c}$R$^{5c}$)$_p$—OC(O)N(R$^b$)(R$^{3c}$), —(CR$^{4c}$R$^{5c}$)$_p$—SR$^{1c}$, —(CR$^{4c}$R$^{5c}$)$_p$—S(O)R$^{2c}$, —(CR$^{4c}$R$^{5c}$)$_p$—S(O)$_2$R$^{2c}$, —(CR$^{4c}$R$^{5c}$)$_p$—S(O)$_2$N(R$^b$)(R$^{3c}$), —(CR$^{4c}$R$^{5c}$)$_p$—C(O)R$^{1c}$, —(CR$^{4c}$R$^{5c}$)$_p$—C(O)OR$^{1c}$, —(CR$^{4c}$R$^{5c}$)$_p$—C(O)N(R$^a$)(R$^{3c}$), —(CR$^{4c}$R$^{5c}$)$_p$—N(R$^b$)(R$^{3c}$), —(CR$^{4c}$R$^{5c}$)$_p$—N(R$^a$)C(O)R$^{1c}$, —(CR$^{4c}$R$^{5c}$)$_p$—N(R$^a$)C(O)O(R$^{1c}$), —(CR$^{4c}$R$^{5c}$)$_p$—N(R$^a$)C(O)O(CH$_2$G$^{13}$), —(CR$^{4c}$R$^{5c}$)$_p$—N(R$^a$)C(O)N(R$^b$)(R$^{3c}$), —(CR$^{4c}$R$^{5c}$)$_p$—N(R$^b$)S(O)$_2$(R$^{2c}$), -G$^{11}$, —(CR$^{4c}$R$^{5c}$)$_p$-G$^{13}$, —(CR$^{4c}$R$^{5c}$)$_p$—OG$^{13}$, -G$^{12}$, —(CR$^{4c}$R$^{5c}$)$_p$-G$^{14}$, cyano-$C_1$-$C_6$-alkyl, oxo, $C^1$-$C^6$-alkoxyimino and halo-$C_1$-$C_6$-alkyl; R$^{1c}$ and R$^{3c}$, at each occurrence, are each independently hydrogen, $C_1$-$C_6$-alkyl, or halo-$C_1$-$C_6$-alkyl; R$^{2c}$, at each occurrence, is independently $C_1$-$C_6$-alkyl or halo-$C_1$-$C_6$-alkyl; R$^{4c}$ and R$^{5c}$, at each occurrence, are each independently hydrogen, halogen, $C_1$-$C_6$-alkyl, or halo-$C_1$-$C_6$-alkyl; p, at each occurrence, is independently 1, 2, 3, 4, or 5; $G^{11}$ and $G^{13}$ are each independently phenyl or 5-6-membered-heteroaryl; wherein $G^{11}$ and $G^{13}$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, $C_1$-$C_6$-alkoxy-$C_1$-$C_6$-alkyl, halo-$C_1$-$C_6$-alkyl, halogen, nitro, —N(R$^e$)$_2$, —N(R$^e$)C(O)R$^e$, —OR$^e$, —C(O)R$^e$, —C(O)OR$^e$, —C(O)N(R$^e$)$_2$, —SO$_2$R$^f$, and —SO$_2$N(R$^e$)$_2$; $G^{12}$, and $G^{14}$ are each independently 3-6-membered-cycloalkyl, 3-6-membered-cycloalkenyl, or 4-10-membered-heterocycle, wherein $G^{12}$ and $G^{14}$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, benzyl, cyano, halo-$C_1$-$C_6$-alkyl, hydroxy-$C_1$-$C_6$-alkyl, halogen, nitro, oxo, —N(R$^e$)$_2$, —N(R$^e$)C(O)R$^e$, —N(R$^e$)S(O)$_2$R$^f$, —OR$^e$, —C(O)R$^e$, —C(O)OR$^e$, —C(O)N(R$^e$)$_2$, —SO$_2$R$^f$, —SO$_2$N(R$^e$)$_2$, and phenyl, wherein phenyl and the phenyl ring of benzyl are optionally substituted with $C_1$-$C_6$-alkyl, halogen, or $C_1$-$C_6$-alkoxy; R$^e$ at each occurrence, is independently hydrogen, $C_1$-$C_6$-alkyl, aryl, aryl-$C_1$-$C_6$-alkyl, cycloalkyl, cycloalkyl-$C_1$-$C_6$-alkyl, or halo-$C_1$-$C_6$-alkyl; wherein said aryl, the aryl of aryl-$C_1$-$C_6$-alkyl, the cycloalkyl, and the cycloalkyl of cycloalkyl-$C_1$-$C_6$-alkyl are independently unsubstituted or substituted with 1, 2 3, 4, or 5 substituents independently selected from the group consisting of $C_1$-$C_6$-alkyl, halo-$C_1$-$C_6$-alkyl, and halogen; and R$^f$ is $C_1$-$C_6$-alkyl or halo-$C_1$-$C_6$-alkyl.

In one embodiment, R$^2$, R$^3$ and the nitrogen atom to which they are attached form a 4-8-membered-monocyclic heterocycle is unsubstituted or substituted with 1, 2, 3 or 4, substituents selected from the group consisting of $C_1$-$C_6$-alkyl, halogen, cyano, —$OR^{1c}$, —O—$(CR^{4c}R^{5c})_p$—$OR^{1c}$, —$OG^{13}$, —$SR^{1c}$, —$S(O)_2R^{2c}$, —$S(O)_2G^{13}$, —$S(O)_2G^{14}$, —$S(O)_2N(R^b)(R^{3c})$, —$S(O)_2$—$(CR^{4c}R^{5c})_p$—$C(O)OR^{1c}$, —$S(O)_2$—$(CR^{4c}R^{5c})_p$-$G^{14}$, —$C(O)R^{1c}$, —$C(O)G^{14}$, —$C(O)OR^c$, —$C(O)N(R^b)(R^{3c})$, —$N(R^b)(R^{3c})$, —$N(R^a)C(O)R^{1c}$, —$N(R^a)C(O)G^{14}$, —$N(R^b)S(O)_2(R^{2c})$, —$N(R^b)S(O)_2(G^{13})$, —$(CR^{4c}R^{5c})_p$—$OR^{1c}$, —$(CR^{4c}R^{5c})_p$—O—$(CR^{4c}R^{5c})_p$—$OR^{1c}$, —$(CR^{4c}R^{5c})_p$—$S(O)_2R^{2c}$, —$(CR^{4c}R^{5c})_p$—$N(R^b)(R^{3c})$, —$(CR^{4c}R^{5c})_p$—$N(R^a)C(O)O(CH_2G^{13})$, -$G^{11}$, —$(CR^{4c}R^{5c})_p$-$G^{13}$, —$(CR^{4c}R^{5c})_p$—$OG^{13}$, -$G^{12}$, —$(CR^{4c}R^{5c})_p$-$G^{14}$, cyano-$C_1$-$C_6$-alkyl, oxo, $C^1$-$C^6$-alkoxyimino and halo-$C_1$-$C_6$-alkyl; $R^{1c}$ and $R^{3c}$, at each occurrence, are each independently hydrogen, $C_1$-$C_6$-alkyl, or halo-$C_1$-$C_6$-alkyl; $R^{2c}$, at each occurrence, is independently $C_1$-$C_6$-alkyl or halo-$C_1$-$C_6$-alkyl; $R^{4c}$ and $R^{5c}$, at each occurrence, are each independently hydrogen or $C_1$-$C_6$-alkyl; p, at each occurrence, is independently 1 or 2; $G^{11}$ and $G^{13}$ are each independently phenyl or 5-6-membered-heteroaryl; wherein $G^{11}$ and $G^{13}$ are each independently unsubstituted or substituted with 1 or 2 substituents selected from the group consisting of $C_1$-$C_6$-alkyl, $C_1$-$C_6$-alkoxy-$C_1$-$C_6$-alkyl, halo-$C_1$-$C_6$-alkyl, halogen, —$N(R^e)C(O)R^e$, and —$OR^e$; $G^{12}$, and $G^{14}$ are each independently 3-6-membered-cycloalkyl or 4-10-membered-heterocycle, wherein $G^{12}$ and $G^{14}$ are each independently unsubstituted or substituted with 1 or 2 substituents selected from the group consisting of $C_1$-$C_6$-alkyl, halogen, oxo, and —$N(R^e)S(O)_2R^f$; $R^e$ at each occurrence, is independently hydrogen or $C_1$-$C_6$-alkyl; and $R^f$ is $C_1$-$C_6$-alkyl or halo-$C_1$-$C_6$-alkyl.

In one embodiment, $R^2$, $R^3$ and the nitrogen atom to which they are attached form a 6-11-membered-bicyclic heterocycle, wherein said 6-11-membered-bicyclic heterocycle, is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, halogen, cyano, —$NO_2$, —$OR^{1c}$, —O—$(CR^{4c}R^{5c})_p$—$OR^{1c}$, —$OG^{13}$, —OC(O)$R^{1c}$, —OC(O)N($R^b$)($R^{3c}$), —$SR^{1c}$, —$S(O)R^{2c}$, —$S(O)_2R^{2c}$, —$S(O)_2G^{13}$, —$S(O)_2G^{14}$, —$S(O)_2N(R^b)(R^{3c})$, —$S(O)_2$—$(CR^{4c}R^{5c})_p$—$C(O)OR^{1c}$, —$S(O)_2$—$(CR^{4c}R^{5c})_p$-$G^{14}$, —$C(O)R^{1c}$, —$C(O)G^{14}$, —$C(O)OR^{1c}$, —$C(O)N(R^b)(R^{3c})$, —$N(R^b)(R^{3c})$, —$N(R^a)C(O)R^{1c}$, —$N(R^a)C(O)G^{14}$, —$N(R^a)C(O)O(R^{1c})$, —$N(R^a)C(O)N(R^b)(R^{3c})$, —$(CR^{4c}R^{5c})_p$—$NO_2$, —$N(R^b)S(O)_2(R^{2c})$, —$N(R^b)S(O)_2(G^{13})$, —$(CR^{4c}R^{5c})_p$—$OR^{1c}$, —$(CR^{4c}R^{5c})_p$—O—$(CR^{4c}R^{5c})_p$—$OR^{1c}$, —$(CR^{4c}R^{5c})_p$—$OC(O)R^{1c}$, —$(CR^{4c}R^{5c})_p$—$OC(O)N(R^b)(R^{3c})$, —$(CR^{4c}R^{5c})_p$—$SR^{1c}$, —$(CR^{4c}R^{5c})_p$—$S(O)R^{2c}$, —$(CR^{4c}R^{5c})_p$—$S(O)_2R^{2c}$, —$(CR^{4c}R^{5c})_p$—$S(O)_2N(R^b)(R^{3c})$, —$(CR^{4c}R^{5c})_p$—$C(O)R^{1c}$, —$(CR^{4c}R^{5c})_p$—$C(O)OR^{1c}$, —$(CR^{4c}R^{5c})_p$—$C(O)N(R^a)(R^{3c})$, —$(CR^{4c}R^{5c})_p$—$N(R^b)(R^{3c})$, —$(CR^{4c}R^{5c})_p$—$N(R^a)C(O)R^{1c}$, —$(CR^{4c}R^{5c})_p$—$N(R^a)C(O)O(R^{1c})$, —$(CR^{4c}R^{5c})_p$—$N(R^a)C(O)O(CH_2G^{13})$, —$(CR^{4c}R^{5c})_p$—$N(R^a)C(O)N(R^b)(R^{3c})$, —$(CR^{4c}R^{5c})_p$—$N(R^b)S(O)_2(R^{2c})$, -$G^{11}$, —$(CR^{4c}R^{5c})_p$-$G^{13}$, —$(CR^{4c}R^{5c})_p$—$OG^{13}$, -$G^{12}$, —$(CR^{4c}R^{5c})_p$-$G^{14}$ cyano-$C_1$-$C_6$-alkyl, oxo, $C^1$-$C^6$-alkoxyimino and halo-$C_1$-$C_6$-alkyl; $R^{1c}$ and $R^{3c}$, at each occurrence, are each independently hydrogen, $C_1$-$C_6$-alkyl, or halo-$C_1$-$C_6$-alkyl; $R^{2c}$, at each occurrence, is independently $C_1$-$C_6$-alkyl or halo-$C_1$-$C_6$-alkyl; $R^{4c}$ and $R^{5c}$, at each occurrence, are each independently hydrogen, halogen, $C_1$-$C_6$-alkyl, or halo-$C_1$-$C_6$-alkyl; p, at each occurrence, is independently 1, 2, 3, 4, or 5; $G^{11}$ and $G^{13}$ are each independently phenyl or 5-6-membered-heteroaryl; wherein $G^{11}$ and $G^{13}$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, $C_1$-$C_6$-alkoxy-$C_1$-$C_6$-alkyl, halo-$C_1$-$C_6$-alkyl, halogen, nitro, —$N(R^e)_2$, —$N(R^e)C(O)R^e$, —$OR^e$, —$C(O)R^e$, —$C(O)OR^e$, —$C(O)N(R^e)_2$, —$SO_2R^f$, and —$SO_2N(R^e)_2$; $G^{12}$, and $G^{14}$ are each independently 3-6-membered-cycloalkyl, 3-6-membered-cycloalkenyl, or 4-10-membered-heterocycle, wherein $G^{12}$ and $G^{14}$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, benzyl, cyano, halo-$C_1$-$C_6$-alkyl, hydroxy-$C_1$-$C_6$-alkyl, halogen, nitro, oxo, —$N(R^e)_2$, —$N(R^e)C(O)R^e$, —$N(R^e)S(O)_2R^f$, —$OR^e$, —$C(O)R^e$, —$C(O)OR^e$, —$C(O)N(R^e)_2$, —$SO_2R^f$, —$SO_2N(R^e)_2$, and phenyl, wherein phenyl and the phenyl ring of benzyl are optionally substituted with $C_1$-$C_6$-alkyl, halogen, or $C_1$-$C_6$-alkoxy; $R^e$ at each occurrence, is independently hydrogen, $C_1$-$C_6$-alkyl, aryl, aryl-$C_1$-$C_6$-alkyl, cycloalkyl, cycloalkyl-$C_1$-$C_6$-alkyl, or halo-$C_1$-$C_6$-alkyl; wherein said aryl, the aryl of aryl-$C_1$-$C_6$-alkyl, the cycloalkyl, and the cycloalkyl of cycloalkyl-$C_1$-$C_6$-alkyl are independently unsubstituted or substituted with 1, 2 3, 4, or 5 substituents independently selected from the group consisting of $C_1$-$C_6$-alkyl, halo-$C_1$-$C_6$-alkyl, and halogen; and $R^f$ is $C_1$-$C_6$-alkyl or halo-$C_1$-$C_6$-alkyl.

In one embodiment, $R^2$, $R^3$ and the nitrogen atom to which they are attached form a 6-11-membered-bicyclic heterocycle, wherein said 6-11-membered-bicyclic heterocycle, is unsubstituted or substituted with 1, 2, 3 or 4, substituents selected from the group consisting of $C_1$-$C_6$-alkyl, halogen, cyano, —$OR^{1c}$, —O—$(CR^{4c}R^{5c})_p$—$OR^{1c}$, —$OG^{13}$, —$SR^{1c}$, —$S(O)R^{2c}$, —$S(O)_2R^{2c}$, —$S(O)_2G^{13}$, —$S(O)_2G^{14}$, —$S(O)_2N(R^b)(R^{3c})$, —$S(O)_2$—$(CR^{4c}R^{5c})_p$C(O)$OR^{1c}$, —$S(O)_2$—$(CR^{4c}R^{5c})_p$-$G^{14}$, —$C(O)R^{1c}$, —$C(O)G^{14}$, —$C(O)OR^{1c}$, —$C(O)N(R^b)(R^{3c})$, —$N(R^b)(R^{3c})$, —$N(R^a)C(O)R^{1c}$, —$N(R^a)C(O)G^{14}$, —$N(R^b)S(O)_2(R^{2c})$, —$N(R^b)S(O)_2(G^{13})$, —$(CR^{4c}R^{5c})_p$—$OR^{1c}$, —$(CR^{4c}R^{5c})_p$—O—$(CR^{4c}R^{5c})_p$—$OR^{1c}$, —$(CR^{4c}R^{5c})_p$—$S(O)_2R^{2c}$, —$(CR^{4c}R^{5c})_p$—$N(R^b)(R^{3c})$, —$(CR^{4c}R^{5c})_p$—$N(R^a)C(O)O(CH_2G^{13})$, -$G^{11}$, —$(CR^{4c}R^{5c})_p$-$G^{13}$, —$(CR^{4c}R^{5c})_p$—$OG^{13}$, -$G^{12}$, —$(CR^{4c}R^{5c})_p$-$G^{14}$, cyano-$C_1$-$C_6$-alkyl, oxo, $C^1$-$C^6$-alkoxyimino and halo-$C_1$-$C_6$-alkyl; $R^{1c}$ and $R^{3c}$, at each occurrence, are each independently hydrogen, $C_1$-$C_6$-alkyl, or halo-$C_1$-$C_6$-alkyl; $R^{2c}$, at each occurrence, is independently $C_1$-$C_6$-alkyl or halo-$C_1$-$C_6$-alkyl; $R^{4c}$ and $R^{5c}$, at each occurrence, are each independently hydrogen or $C_1$-$C_6$-alkyl; p, at each occurrence, is independently 1 or 2; $G^{11}$ and $G^{13}$ are each independently phenyl or 5-6-membered-heteroaryl; wherein $G^{11}$ and $G^{13}$ are each independently unsubstituted or substituted with 1 or 2 substituents selected from the group consisting of $C_1$-$C_6$-alkyl, $C_1$-$C_6$-alkoxy-$C_1$-$C_6$-alkyl, halo-$C_1$-$C_6$-alkyl, halogen, —$N(R^e)C(O)R^e$, and —$OR^e$; $G^{12}$ and $G^{14}$ are each independently 3-6-membered-cycloalkyl or 4-10-membered-heterocycle, wherein $G^{12}$ and $G^{14}$ are each independently unsubstituted or substituted with 1 or 2 substituents selected from the group consisting of $C_1$-$C_6$-alkyl, halogen, oxo, and —$N(R^e)S(O)_2R^f$; $R^e$ at each occurrence, is independently hydrogen or $C_1$-$C_6$-alkyl; and $R^f$ is $C_1$-$C_6$-alkyl or halo-$C_1$-$C_6$-alkyl.

In one embodiment, $R^2$, $R^3$ and the nitrogen atom to which they are attached form a 10-12-membered-tricyclic heterocycle or 7-11-membered-spirocyclic heterocycle, wherein said 10-12-membered-tricyclic heterocycle and said 7-11-membered-spirocyclic heterocycle are unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, halogen, cyano, —$NO_2$, —$OR^{1c}$, —O—$(CR^{4c}R^{5c})_p$—$OR^{1c}$, —$OG^{13}$, —OC(O)$R^{1c}$, —OC(O)N($R^b$)

($R^{3c}$), —$SR^{1c}$, —$S(O)R^{2c}$, —$S(O)_2R^{2c}$, —$S(O)_2G^{13}$, —$S(O)_2G^{14}$, —$S(O)_2N(R^b)(R^{3c})$, —$S(O)_2$—$(CR^{4c}R^{5c})_p$—$C(O)OR^{1c}$, —$S(O)_2$—$(CR^{4c}R^{5c})_p$-$G^{14}$, —$C(O)R^{1c}$, —$C(O)G^{14}$, —$C(O)OR^{1c}$, —$C(O)N(R^b)(R^{3c})$, —$N(R^b)(R^{3c})$, —$N(R^a)C(O)R^{1c}$, —$N(R^a)C(O)G^{14}$, —$N(R^a)C(O)O(R^c)$, —$N(R^a)C(O)N(R^b)(R^{3c})$, —$(CR^{4c}R^{5c})_p$—$NO_2$, —$N(R^b)S(O)_2(R^{2c})$, —$N(R^b)S(O)_2(G^{13})$, —$(CR^{4c}R^{5c})_p$—$OR^{1c}$, —$CR^{4c}R^{5c})_p$—$O$—$(CR^{4c}R^{5c})_p$—$OR^{1c}$, —$(CR^{4c}R^{5c})_p$—$OC(O)R^{1c}$, —$(CR^{4c}R^{5c})_p$—$OC(O)N(R^b)(R^{3c})$, —$(CR^{4c}R^{5c})_p$—$SR^{1c}$, —$(CR^{4c}R^{5c})_p$—$S(O)R^{2c}$, —$(CR^{4c}R^{5c})_p$—$S(O)_2R^{2c}$, —$(CR^{4c}R^{5c})_p$—$S(O)_2N(R^b)(R^{3c})$, —$(CR^{4c}R^{5c})_p$—$C(O)R^{1c}$, —$(CR^{4c}R^{5c})_p$—$C(O)OR^{1c}$, —$(CR^{4c}R^{5c})_p$—$C(O)N(R^a)(R^{3c})$, —$(CR^{4c}R^{5c})_p$—$N(R^b)(R^{3c})$, —$(CR^{4c}R^{5c})_p$—$N(R^a)C(O)R^{1c}$, —$(CR^{4c}R^{5c})_p$—$N(R^a)C(O)O(R^{1c})$, —$(CR^{4c}R^{5c})_p$—$N(R^a)C(O)O(CH_2G^{13})$, —$(CR^{4c}R^{5c})_p$—$N(R^a)C(O)N(R^b)(R^{3c})$, —$(CR^{4c}R^{5c})_p$—$N(R^b)S(O)_2(R^{2c})$, -$G^{11}$, —$(CR^{4c}R^{5c})_p$-$G^{13}$, —$(CR^{4c}R^{5c})_p$—$OG^{13}$, -$G^{12}$, —$(CR^{4c}R^{5c})_p$-$G^{14}$, cyano-$C_1$-$C_6$-alkyl, oxo, $C^1$-$C^6$-alkoxyimino and halo-$C_1$-$C_6$-alkyl; $R^{1c}$ and $R^{3c}$, at each occurrence, are each independently hydrogen, $C_1$-$C_6$-alkyl, or halo-$C_1$-$C_6$-alkyl; $R^{2c}$, at each occurrence, is independently $C_1$-$C_6$-alkyl or halo-$C_1$-$C_6$-alkyl; $R^{4c}$ and $R^{5c}$, at each occurrence, are each independently hydrogen, halogen, $C_1$-$C_6$-alkyl, or halo-$C_1$-$C_6$-alkyl; p, at each occurrence, is independently 1, 2, 3, 4, or 5; $G^{11}$ and $G^{13}$ are each independently phenyl or 5-6-membered-heteroaryl; wherein $G^{11}$ and $G^{13}$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, $C_1$-$C_6$-alkoxy-$C_1$-$C_6$-alkyl, halo-$C_1$-$C_6$-alkyl, halogen, nitro, —$N(R^e)_2$, —$N(R^e)C(O)R^e$, —$OR^e$, —$C(O)R^e$, —$C(O)OR^e$, —$C(O)N(R^e)_2$, —$SO_2R^f$, and —$SO_2N(R^e)_2$; $G^{12}$, and $G^{14}$ are each independently 3-6-membered-cycloalkyl, 3-6-membered-cycloalkenyl, or 4-10-membered-heterocycle, wherein $G^{12}$ and $G^{14}$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, benzyl, cyano, halo-$C_1$-$C_6$-alkyl, hydroxy-$C_1$-$C_6$-alkyl, halogen, nitro, oxo, —$N(R^e)_2$, —$N(R^e)C(O)R^e$, —$N(R^e)S(O)_2R^f$, —$OR^e$, —$C(O)R^e$, —$C(O)OR^e$, —$C(O)N(R^e)_2$, —$SO_2R^f$, —$SO_2N(R^e)_2$, and phenyl, wherein phenyl and the phenyl ring of benzyl are optionally substituted with $C_1$-$C_6$-alkyl, halogen, or $C_1$-$C_6$-alkoxy; $R^e$ at each occurrence, is independently hydrogen, $C_1$-$C_6$-alkyl, aryl, aryl-$C_1$-$C_6$-alkyl, cycloalkyl, cycloalkyl-$C_1$-$C_6$-alkyl, or halo-$C_1$-$C_6$-alkyl; wherein said aryl, the aryl of aryl-$C_1$-$C_6$-alkyl, the cycloalkyl, and the cycloalkyl of cycloalkyl-$C_1$-$C_6$-alkyl are independently unsubstituted or substituted with 1, 2 3, 4, or 5 substituents independently selected from the group consisting of $C_1$-$C_6$-alkyl, halo-$C_1$-$C_6$-alkyl, and halogen; and $R^f$ is $C_1$-$C_6$-alkyl or halo-$C_1$-$C_6$-alkyl.

In one embodiment, $R^2$, $R^3$ and the nitrogen atom to which they are attached form a 10-12-membered-tricyclic heterocycle or 7-11-membered-spirocyclic heterocycle, wherein said 10-12-membered-tricyclic heterocycle and said 7-11-membered-spirocyclic heterocycle are unsubstituted or substituted with 1, 2, 3 or 4 substituents selected from the group consisting of $C_1$-$C_6$-alkyl, halogen, cyano, —$OR^{1c}$, —$O$—$(CR^{4c}R^{5c})_p$—$OR^{1c}$, —$OG^{13}$, —$SR^{1c}$, —$S(O)R^{2c}$, —$S(O)_2G^{13}$, —$S(O)_2G^{14}$, —$S(O)_2N(R^b)(R^{3c})$, —$S(O)_2$—$(CR^{4c}R^{5c})_p$$C(O)OR^{1c}$, —$S(O)_2$—$(CR^{4c}R^{5c})_p$-$G^{14}$, —$C(O)R^{1c}$, —$C(O)G^{14}$, —$C(O)OR^{1c}$, —$C(O)N(R^b)(R^{3c})$, —$N(R^b)(R^{3c})$, —$N(R^a)C(O)R^{1c}$, —$N(R^a)C(O)G^{14}$, —$N(R^b)S(O)_2(R^{2c})$, —$N(R^b)S(O)_2(G^{13})$, —$(CR^{4c}R^{5c})_p$—$OR^{1c}$, —$(CR^{4c}R^{5c})_p$—$O$—$(CR^{4c}R^{5c})_p$—$OR^{1c}$, —$(CR^{4c}R^{5c})_p$—$S(O)_2R^{2c}$, —$(CR^{4c}R^{5c})_p$—$N(R^b)(R^{3c})$, —$(CR^{4c}R^{5c})_p$—$N$
($R^a$)$C(O)O(CH_2G^{13})$, -$G^{11}$, —$(CR^{4c}R^{5c})_p$-$G^{13}$, —$(CR^{4c}R^{5c})_p$—$OG^{13}$, -$G^{12}$, —$(CR^{4c}R^{5c})_p$-$G^{14}$, cyano-$C_1$-$C_6$-alkyl, oxo, $C^1$-$C^6$-alkoxyimino and halo-$C_1$-$C_6$-alkyl; $R^{1c}$ and $R^{3c}$, at each occurrence, are each independently hydrogen, $C_1$-$C_6$-alkyl, or halo-$C_1$-$C_6$-alkyl; $R^{2c}$, at each occurrence, is independently $C_1$-$C_6$-alkyl or halo-$C_1$-$C_6$-alkyl; $R^{4c}$ and $R^{5c}$, at each occurrence, are each independently hydrogen or $C_1$-$C_6$-alkyl; p, at each occurrence, is independently 1 or 2; $G^{11}$ and $G^{13}$ are each independently phenyl or 5-6-membered-heteroaryl; wherein $G^{11}$ and $G^{13}$ are each independently unsubstituted or substituted with 1 or 2 substituents selected from the group consisting of $C_1$-$C_6$-alkyl, $C_1$-$C_6$-alkoxy-$C_1$-$C_6$-alkyl, halo-$C_1$-$C_6$-alkyl, halogen, —$N(R^e)C(O)R^e$, and —$OR^e$; $G^{12}$, and $G^{14}$ are each independently 3-6-membered-cycloalkyl or 4-10-membered-heterocycle, wherein $G^{12}$ and $G^{14}$ are each independently unsubstituted or substituted with 1 or 2 substituents selected from the group consisting of $C_1$-$C_6$-alkyl, halogen, oxo, and —$N(R^e)S(O)_2R^f$; $R^e$ at each occurrence, is independently hydrogen or $C_1$-$C_6$-alkyl; and $R^f$ is $C_1$-$C_6$-alkyl or halo-$C_1$-$C_6$-alkyl.

In one embodiment, $R^2$, $R^3$ and the nitrogen atom to which they are attached form an 8-11-membered-bicyclic heteroaryl comprised of a monocyclic heterocycle fused to a monocyclic heteroaryl, wherein 8-11-membered-bicyclic heteroaryl is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, halogen, cyano, —$NO_2$, —$OR^{1c}$, —$O$—$(CR^{4c}R^{5c})_p$—$OR^{1c}$, —$OG^{13}$, —$OC(O)R^{1c}$, —$OC(O)N(R^b)(R^{3c})$, —$SR^{1c}$, —$S(O)R^{2c}$, —$S(O)_2R^{2c}$, —$S(O)_2G^{13}$, —$S(O)_2G^{14}$, —$S(O)_2N(R^b)(R^{3c})$, —$S(O)_2$—$(CR^{4c}R^{5c})_p$—$C(O)OR^{1c}$, —$S(O)_2$—$(CR^{4c}R^{5c})_p$-$G^{14}$, —$C(O)R^{1c}$, —$C(O)G^{14}$, —$C(O)OR^{1c}$, —$C(O)N(R^b)(R^{3c})$, —$N(R^b)(R^{3c})$, —$N(R^a)C(O)R^{1c}$, —$N(R^a)C(O)G^{14}$, —$N(R^a)C(O)O(R^{1c})$, —$N(R^a)C(O)N(R^b)(R^{3c})$, —$(CR^{4c}R^{5c})_p$—$NO_2$, —$N(R^b)S(O)_2(R^{2c})$, —$N(R^b)S(O)_2(G^{13})$, —$(CR^{4c}R^{5c})_p$—$OR^{1c}$, —$(CR^{4c}R^{5c})_p$—$O$—$(CR^{4c}R^{5c})_p$—$OR^{1c}$, —$(CR^{4c}R^{5c})_p$—$OC(O)R^{1c}$, —$(CR^{4c}R^{5c})_p$—$OC(O)N(R^b)(R^{3c})$, —$(CR^{4c}R^{5c})_p$—$SR^{1c}$, —$(CR^{4c}R^{5c})_p$—$S(O)R^{2c}$, —$(CR^{4c}R^{5c})_p$—$S(O)_2R^{2c}$, —$(CR^{4c}R^{5c})_p$—$S(O)_2N(R^b)(R^{3c})$, —$(CR^{4c}R^{5c})_p$—$C(O)R^{1c}$, —$(CR^{4c}R^{5c})_p$—$C(O)OR^{1c}$, —$(CR^{4c}R^{5c})_p$—$C(O)N(R^a)(R^{3c})$, —$(CR^{4c}R^{5c})_p$—$N(R^b)(R^{3c})$, —$(CR^{4c}R^{5c})_p$—$N(R^a)C(O)R^{1c}$, —$(CR^{4c}R^{5c})_p$—$N(R^a)C(O)O(R^{1c})$, —$(CR^{4c}R^{5c})_p$—$N(R^a)C(O)O(CH_2G^{13})$, —$(CR^{4c}R^{5c})_p$—$N(R^a)C(O)N(R^b)(R^{3c})$, —$(CR^{4c}R^{5c})_p$—$N(R^b)S(O)_2(R^{2c})$, -$G^{11}$, —$(CR^{4c}R^{5c})_p$-$G^{13}$, —$(CR^{4c}R^{5c})_p$—$OG^{13}$, -$G^{12}$, —$(CR^{4c}R^{5c})_p$-$G^{14}$, cyano-$C_1$-$C_6$-alkyl, oxo, $C^1$-$C^6$-alkoxyimino and halo-$C_1$-$C_6$-alkyl; $R^{1c}$ and $R^{3c}$, at each occurrence, are each independently hydrogen, $C_1$-$C_6$-alkyl, or halo-$C_1$-$C_6$-alkyl; $R^{2c}$, at each occurrence, is independently $C_1$-$C_6$-alkyl or halo-$C_1$-$C_6$-alkyl; $R^{4c}$ and $R^{5c}$, at each occurrence, are each independently hydrogen, halogen, $C_1$-$C_6$-alkyl, or halo-$C_1$-$C_6$-alkyl; p, at each occurrence, is independently 1, 2, 3, 4, or 5; $G^{11}$ and $G^{13}$ are each independently phenyl or 5-6-membered-heteroaryl; wherein $G^{11}$ and $G^{13}$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, $C_1$-$C_6$-alkoxy-$C_1$-$C_6$-alkyl, halo-$C_1$-$C_6$-alkyl, halogen, nitro, —$N(R^e)_2$, —$N(R^e)C(O)R^e$, —$OR^e$, —$C(O)R^e$, —$C(O)OR^e$, —$C(O)N(R^e)_2$, —$SO_2R^f$, and —$SO_2N(R^e)_2$; $G^{12}$, and $G^{14}$ are each independently 3-6-membered-cycloalkyl, 3-6-membered-cycloalkenyl, or 4-10-membered-heterocycle, wherein $G^{12}$ and $G^{14}$ are each independently unsubstituted or substituted with 1, 2, 3, 4, or 5 substituents selected from the group consisting of $C_1$-$C_6$-alkyl, $C_2$-$C_6$- alkenyl, $C_2$-$C_6$-alkynyl, benzyl, cyano, halo-$C_1$-$C_6$-alkyl, hydroxy-$C_1$-$C_6$-alkyl, halogen, nitro, oxo, —N(R$^e$)$_2$, —N(R$^e$)C(O)R$^e$, —N(R$^e$)S(O)$_2$R$^f$, —OR$^e$, —C(O)R$^e$, —C(O)OR$^e$, —C(O)N(R$^e$)$_2$, —SO$_2$R$^f$, —SO$_2$N(R$^e$)$_2$, and phenyl, wherein phenyl and the phenyl ring of benzyl are optionally substituted with $C_1$-$C_6$-alkyl, halogen, or $C_1$-$C_6$-alkoxy; R$^e$ at each occurrence, is independently hydrogen, $C_1$-$C_6$-alkyl, aryl, aryl-$C_1$-$C_6$-alkyl, cycloalkyl, cycloalkyl-$C_1$-$C_6$-alkyl, or halo-$C_1$-$C_6$-alkyl; wherein said aryl, the aryl of aryl-$C_1$-$C_6$-alkyl, the cycloalkyl, and the cycloalkyl of cycloalkyl-$C_1$-$C_6$-alkyl are independently unsubstituted or substituted with 1, 2 3, 4, or 5 substituents independently selected from the group consisting of $C_1$-$C_6$-alkyl, halo-$C_1$-$C_6$-alkyl, and halogen; and R$^f$ is $C_1$-$C_6$-alkyl or halo-$C_1$-$C_6$-alkyl.

In one embodiment, R$^2$, R$^3$ and the nitrogen atom to which they are attached form an 8-11-membered-bicyclic heteroaryl comprised of a monocyclic heterocycle fused to a monocyclic heteroaryl, wherein 8-11-membered-bicyclic heteroaryl is unsubstituted or substituted with 1, 2, 3 or 4 substituents selected from the group consisting of $C_1$-$C_6$-alkyl, halogen, cyano, —OR$^{1c}$, —O—(CR$^{4c}$R$^{5c}$)$_p$—OR$^{1c}$, —OG$^{13}$, —SR$^{1c}$, —S(O)$_2$R$^{2c}$, —S(O)$_2$G$^{13}$, —S(O)$_2$G$^{14}$, —S(O)$_2$N(R$^b$)(R$^{3c}$), —S(O)$_2$—(CR$^{4c}$R$^{5c}$)$_p$—C(O)OR$^{1c}$, —S(O)$_2$—(CR$^{4c}$R$^{5c}$)$_p$-G$^{14}$, —C(O)R$^{1c}$, —C(O)G$^{14}$, —C(O)OR$^{1c}$, —C(O)N(R$^b$)(R$^{3c}$), —N(R$^b$)(R$^{3c}$), —N(R$^a$)C(O)R$^{1c}$, —N(R$^a$)C(O)G$^{14}$, —N(R$^b$)S(O)$_2$(R$^{2c}$), —N(R$^b$)S(O)$_2$(G$^{13}$), —(CR$^{4c}$R$^{5c}$)$_p$—OR$^{1c}$, —(CR$^{4c}$R$^{5c}$)$_p$—O—(CR$^{4c}$R$^{5c}$)$_p$—OR$^{1c}$, —(CR$^{4c}$R$^{5c}$)$_p$—S(O)$_2$R$^{2c}$, —(CR$^{4c}$R$^{5c}$)$_p$—N(R$^b$)(R$^{3c}$), —(CR$^{4c}$R$^{5c}$)$_p$—N(R$^a$)C(O)O(CH$_2$G$^{13}$), -G$^{11}$, —(CR$^{4c}$R$^{5c}$)$_p$-G$^{13}$, —(CR$^{4c}$R$^{5c}$)$_p$—OG$^{13}$, -G$^{12}$, —(CR$^{4c}$R$^{5c}$)$_p$-G$^{14}$, cyano-$C_1$-$C_6$-alkyl, oxo, C$^1$-C$^6$-alkoxyimino and halo-$C_1$-$C_6$-alkyl; R$^{1c}$ and R$^{3c}$, at each occurrence, are each independently hydrogen, $C_1$-$C_6$-alkyl, or halo-$C_1$-$C_6$-alkyl; R$^{2c}$, at each occurrence, is independently $C_1$-$C_6$-alkyl or halo-$C_1$-$C_6$-alkyl; R$^{4c}$ and R$^{5c}$, at each occurrence, are each independently hydrogen or $C_1$-$C_6$-alkyl; p, at each occurrence, is independently 1 or 2; G$^{11}$ and G$^{13}$ are each independently phenyl or 5-6-membered-heteroaryl; wherein G$^{11}$ and G$^{13}$ are each independently unsubstituted or substituted with 1 or 2 substituents selected from the group consisting of $C_1$-$C_6$-alkyl, $C_1$-$C_6$-alkoxy-$C_1$-$C_6$-alkyl, halo-$C_1$-$C_6$-alkyl, halogen, —N(R$^e$)C(O)R$^e$, and —OR$^e$; G$^{12}$, and G$^{14}$ are each independently 3-6-membered-cycloalkyl or 4-10-membered-heterocycle, wherein G$^{12}$ and G$^{14}$ are each independently unsubstituted or substituted with 1 or 2 substituents selected from the group consisting of $C_1$-$C_6$-alkyl, halogen, oxo, and —N(R$^e$)S(O)$_2$R$^f$; R$^e$ at each occurrence, is independently hydrogen or $C_1$-$C_6$-alkyl; and R$^f$ is $C_1$-$C_6$-alkyl or halo-$C_1$-$C_6$-alkyl.

In one embodiment, R$^1$ is phenyl, wherein the phenyl is unsubstituted or substituted with 1, 2, 3, or 4 substituents selected from the group consisting of $C_1$-$C_6$-alkyl, halogen, cyano, —OR$^{1a}$, —S(O)$_2$R$^{2a}$, —S(O)$_2$N(R$^b$)(R$^{3a}$), —C(O)R$^{1a}$, —(CR$^{4a}$R$^{5a}$)$_m$—OR$^{1a}$, and halo-$C_1$-$C_6$-alkyl; R$^b$, at each occurrence, is independently hydrogen, $C_1$-$C_6$-alkyl, or halo-$C_1$-$C_6$-alkyl; R$^{1a}$ and R$^{3a}$, at each occurrence, are each independently hydrogen, $C_1$-$C_6$-alkyl, or halo-$C_1$-$C_6$-alkyl; R$^{2a}$, at each occurrence, is independently $C_1$-$C_6$-alkyl or halo-$C_1$-$C_6$-alkyl; R$^{4a}$ and R$^{5a}$, at each occurrence, are each independently hydrogen, $C_1$-$C_6$-alkyl, or halo-$C_1$-$C_6$-alkyl; and m, at each occurrence, is independently 1, 2, or 3.

In one embodiment, R$^1$ is phenyl, wherein the phenyl is unsubstituted or substituted with 1, 2, 3, or 4 substituents selected from the group consisting of $C_1$-$C_6$-alkyl, halogen, cyano, —OR$^{1a}$, —S(O)$_2$R$^{2a}$, —S(O)$_2$N(R$^b$)(R$^{3a}$), —C(O)R$^{1a}$, —(CR$^{4a}$R$^{5a}$)$_m$—OR$^{1a}$, and halo-$C_1$-$C_6$-alkyl; R$^b$, at each occurrence, is independently hydrogen, $C_1$-$C_6$-alkyl, or halo-$C_1$-$C_6$-alkyl; R$^{1a}$ and R$^{3a}$, at each occurrence, are each independently hydrogen, $C_1$-$C_6$-alkyl, or halo-$C_1$-$C_6$-alkyl; R$^{2a}$, at each occurrence, is independently $C_1$-$C_6$-alkyl or halo-$C_1$-$C_6$-alkyl; R$^{4a}$ and R$^{5a}$, at each occurrence, are each independently hydrogen, $C_1$-$C_6$-alkyl, or halo-$C_1$-$C_6$-alkyl; and m, at each occurrence, is independently 1, 2, or 3; R$^2$ is selected from the group consisting of hydrogen, $C_1$-$C_6$-alkyl, $C_1$-$C_6$-alkoxy-$C_1$-$C_6$-alkyl, and -G$^2$; R$^3$ is selected from the group consisting of hydrogen, $C_1$-$C_6$-alkyl, $C_2$-$C_6$-alkenyl, $C_2$-$C_6$-alkynyl, —(CR$^{4b}$R$^{5b}$)$_n$—OR$^{1b}$, —CH[(CR$^{4b}$R$^{5b}$)$_n$—OR$^{1b}$]$_2$, —(CR$^{4b}$R$^{5b}$)$_n$—SR$^{1b}$, —(CR$^{4b}$R$^{5b}$)$_n$—S(O)$_2$R$^{2b}$, —(CR$^{4b}$R$^{5b}$)$_n$—S(O)$_2$N(R$^b$)(R$^{3b}$), —(CR$^{4b}$R$^{5b}$)$_n$—C(O)R$^{1b}$, —(CR$^{4b}$R$^{5b}$)$_n$—C(O)OR$^{1b}$, —(CR$^{4b}$R$^{5b}$)$_n$—C(O)N(R$^b$)(R$^{3b}$), —(CR$^{4b}$R$^{5b}$)$_n$—C(O)N(R$^b$)(—(CR$^{4b}$R$^{5b}$)$_n$—OR$^{1b}$), —(CR$^{4b}$R$^{5b}$)$_n$—C(O)N(R$^b$)(G$^4$), —(CR$^{4b}$R$^{5b}$)$_n$—C(O)N(R$^b$)(G$^3$), —(CR$^{4b}$R$^{5b}$)$_n$—C(O)G$^4$, —(CR$^{4b}$R$^{5b}$)$_n$—N(R$^b$)(R$^{3b}$), —(CR$^{4b}$R$^{5b}$)$_n$—N(R$^b$)(G$^3$), —(CR$^{4b}$R$^{5b}$)$_n$—N(R$^a$)C(O)R$^{1b}$, —(CR$^{4b}$R$^{5b}$)$_n$—N(R$^b$)S(O)$_2$R$^{2b}$, —S(O)$_2$R$^{2b}$, —(CR$^{4b}$R$^{5b}$)$_n$—N(R$^a$)C(O)O(R$^{1b}$), —(CR$^{4b}$R$^{5b}$)$_n$—N(R$^a$)C(O)N(R$^b$)(R$^{3b}$), -G$^2$, —(CR$^{4b}$R$^{5b}$)$_n$-G$^4$, -G$^2$-G$^6$, -G$^1$, —(CR$^{4b}$R$^{5b}$)$_n$-G$^3$, —CH[C(O)N(R$^b$)(R$^{3b}$)][—(CR$^{4b}$R$^{5b}$)$_n$-G$^3$], cyano-$C_1$-$C_6$-alkyl, and halo-$C_1$-$C_6$-alkyl; R$^a$ and R$^b$, at each occurrence, are each independently hydrogen, $C_1$-$C_6$-alkyl, or halo-$C_1$-$C_6$-alkyl; R$^b$, at each occurrence, is independently hydrogen, $C_1$-$C_6$-alkyl, or halo-$C_1$-$C_6$-alkyl; R$^{1b}$ and R$^{3b}$, at each occurrence, are each independently hydrogen, $C_1$-$C_6$-alkyl, or halo-$C_1$-$C_6$-alkyl; R$^{2b}$, at each occurrence, is independently $C_1$-$C_6$-alkyl or halo-$C_1$-$C_6$-alkyl; R$^{4b}$ and R$^{5b}$, at each occurrence, are each independently hydrogen, $C_1$-$C_6$-alkyl, or halo-$C_1$-$C_6$-alkyl; n, at each occurrence, is independently 1, 2, 3, 4, or 5; G$^1$ and G$^3$ are each independently aryl or heteroaryl; wherein G$^1$ and G$^3$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, —N(R$^c$)$_2$, —N(R$^c$)C(O)R$^c$, —OR$^c$, —C(O)R$^c$, —C(O)OR$^c$, —C(O)N(R$^c$)$_2$, —SO$_2$R$^d$, and —SO$_2$N(R$^c$)$_2$; G$^2$, G$^4$ and G$^6$ are each independently 3-6-membered-cycloalkyl or 4-10-membered-heterocycle; wherein G$^2$, G$^4$ and G$^6$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, benzyl, cyano, halo-$C_1$-$C_6$-alkyl, hydroxy-$C_1$-$C_6$-alkyl, halogen, oxo, —N(R$^c$)$_2$, —N(R$^c$)C(O)R$^c$, —OR$^c$, —C(O)R$^c$, —C(O)OR$^c$, —C(O)N(R$^c$)$_2$, —SO$_2$R$^d$, —SO$_2$N(R$^c$)$_2$, and phenyl, wherein phenyl and the phenyl ring of benzyl are optionally substituted with 1, 2, 3, or 4 $C_1$-$C_6$-alkyl, halogen, or $C_1$-$C_6$-alkoxy; R$^c$ at each occurrence, is independently hydrogen, $C_1$-$C_6$-alkyl, aryl, or halo-$C_1$-$C_6$-alkyl; wherein said aryl is independently unsubstituted or substituted with 1, 2 3, 4, or 5 substituents independently selected from the group consisting of $C_1$-$C_6$-alkyl, halo-$C_1$-$C_6$-alkyl, and halogen; and R$^d$ is $C_1$-$C_6$-alkyl or halo-$C_1$-$C_6$-alkyl.

In one embodiment, R$^1$ is phenyl, wherein the phenyl is unsubstituted or substituted with 1, 2, 3, or 4 substituents selected from the group consisting of $C_1$-$C_6$-alkyl, halogen, cyano, —OR$^{1a}$, —S(O)$_2$R$^{2a}$, —S(O)$_2$N(R$^b$)(R$^{3a}$), —C(O)R$^{1a}$, —(CR$^{4a}$R$^{5a}$)$_m$—OR$^{1a}$, and halo-$C_1$-$C_6$-alkyl; R$^b$, at each occurrence, is independently hydrogen, $C_1$-$C_6$-alkyl, or halo-$C_1$-$C_6$-alkyl; R$^{1a}$ and R$^{3a}$, at each occurrence, are each independently hydrogen, $C_1$-$C_6$-alkyl, or halo-$C_1$-$C_6$-alkyl; R$^{2a}$, at each occurrence, is independently $C_1$-$C_6$-alkyl or halo-$C_1$-$C_6$-alkyl; R$^{4a}$ and R$^{5a}$, at each occurrence, are each independently hydrogen, $C_1$-$C_6$-alkyl, or halo-$C_1$-$C_6$-alkyl; m, at each occurrence, is independently 1, 2, or 3; R$^2$ is selected from the group consisting of hydrogen and $C_1$-$C_6$-alkyl; $R^3$ is selected from the group consisting of hydrogen, $C_1$-$C_6$-alkyl, $C_2$-$C_6$-alkenyl, —$(CR^{4b}R^{5b})_n$—$OR^{1b}$, —CH[$(CR^{4b}R^{5b})_n$—$OR^{1b}$]$_2$, —$(CR^{4b}R^{5b})_n$—$SR^{1b}$, —$(CR^{4b}R^{5b})_n$—$S(O)_2R^{2b}$, —$(CR^{4b}R^{5b})_n$—$S(O)_2N(R^b)(R^{3b})$, —$(CR^{4b}R^{5b})_n$—$C(O)R^{1b}$, —$(CR^{4b}R^{5b})_n$—$C(O)OR^{1b}$, —$(CR^{4b}R^{5b})_n$—$C(O)N(R^b)(R^{3b})$, —$(CR^{4b}R^{5b})_n$—$N(R^b)(R^{3b})$, —$S(O)_2R^{2b}$, and halo-$C_1$-$C_6$-alkyl; $R^b$, at each occurrence, is independently hydrogen, $C_1$-$C_6$-alkyl, or halo-$C_1$-$C_6$-alkyl; $R^{1b}$ and $R^{3b}$, at each occurrence, are each independently hydrogen, $C_1$-$C_6$-alkyl, or halo-$C_1$-$C_6$-alkyl; $R^{2b}$, at each occurrence, is independently $C_1$-$C_6$-alkyl or halo-$C_1$-$C_6$-alkyl; $R^{4b}$ and $R^{5b}$, at each occurrence, are each independently hydrogen, $C_1$-$C_6$-alkyl, or halo-$C_1$-$C_6$-alkyl; and n, at each occurrence, is independently 1, 2, 3, or 4. In one embodiment, $R^1$ is phenyl, wherein the phenyl is unsubstituted or substituted with 1, 2, 3, or 4 substituents selected from the group consisting of $C_1$-$C_6$-alkyl, halogen, cyano, —$OR^{1a}$, —$S(O)_2R^{2a}$, —$S(O)_2N(R^b)(R^{3a})$, —$C(O)R^{1a}$, —$(CR^{4a}R^{5a})_m$—$OR^{1a}$, and halo-$C_1$-$C_6$-alkyl; $R^b$, at each occurrence, is independently hydrogen, $C_1$-$C_6$-alkyl, or halo-$C_1$-$C_6$-alkyl; $R^{1a}$ and $R^{3a}$, at each occurrence, are each independently hydrogen, $C_1$-$C_6$-alkyl, or halo-$C_1$-$C_6$-alkyl; $R^{2a}$, at each occurrence, is independently $C_1$-$C_6$-alkyl or halo-$C_1$-$C_6$-alkyl; $R^{4a}$ and $R^{5a}$, at each occurrence, are each independently hydrogen, $C_1$-$C_6$-alkyl, or halo-$C_1$-$C_6$-alkyl; m, at each occurrence, is independently 1, 2, or 3; $R^2$ is selected from the group consisting of hydrogen and $C_1$-$C_6$-alkyl; $R^3$ is selected from the group consisting of -$G^1$ and —$(CR^{4b}R^{5b})_n$-$G^3$; $R^{4b}$ and $R^{5b}$, at each occurrence, are each independently hydrogen, $C_1$-$C_6$-alkyl, or halo-$C_1$-$C_6$-alkyl; n, at each occurrence, is independently 1, 2, 3, 4, or 5; $G^1$ and $G^3$ are each independently aryl or heteroaryl; wherein $G^1$ and $G^3$ are each independently unsubstituted or substituted with 1, 2, 3, 4, or 5 substituents selected from the group consisting of $C_1$-$C_6$-alkyl, $C_2$-$C_6$-alkenyl, halo-$C_1$-$C_6$-alkyl, halogen, and —$OR^c$; and $R^c$ at each occurrence, is independently $C_1$-$C_6$-alkyl, aryl, or halo-$C_1$-$C_6$-alkyl; wherein said aryl is independently unsubstituted or substituted with 1, 2 3, 4, or 5 substituents independently selected from the group consisting of $C_1$-$C_6$-alkyl, halo-$C_1$-$C_6$-alkyl, and halogen. In one embodiment, $R^1$ is phenyl, wherein the phenyl is unsubstituted or substituted with 1, 2, 3, or 4 substituents selected from the group consisting of $C_1$-$C_6$-alkyl, halogen, cyano, —$OR^{1a}$, —$S(O)_2R^{2a}$, —$S(O)_2N(R^b)(R^{3a})$, —$C(O)R^{1a}$, —$(CR^{4a}R^{5a})_m$—$OR^{1a}$, and halo-$C_1$-$C_6$-alkyl; $R^b$, at each occurrence, is independently hydrogen, $C_1$-$C_6$-alkyl, or halo-$C_1$-$C_6$-alkyl; $R^{1a}$ and $R^{3a}$, at each occurrence, are each independently hydrogen, $C_1$-$C_6$-alkyl, or halo-$C_1$-$C_6$-alkyl; $R^{2a}$, at each occurrence, is independently $C_1$-$C_6$-alkyl or halo-$C_1$-$C_6$-alkyl; $R^{4a}$ and $R^{5a}$, at each occurrence, are each independently hydrogen, $C_1$-$C_6$-alkyl, or halo-$C_1$-$C_6$-alkyl; m, at each occurrence, is independently 1, 2, or 3; $R^2$ is selected from the group consisting of hydrogen and $C_1$-$C_6$-alkyl; $R^3$ is selected from the group consisting of -$G^2$ and —$(CR^{4b}R^{5b})_n$-$G^4$; $R^{4b}$ and $R^{5b}$, at each occurrence, are each independently hydrogen, $C_1$-$C_6$-alkyl, or halo-$C_1$-$C_6$-alkyl; n is 1, 2, 3, 4, or 5; $G^2$ and $G^4$ are each independently 3-6-membered-cycloalkyl or 4-10-membered-heterocycle; wherein $G^2$ and $G^4$ are each independently unsubstituted or substituted with 1, 2, 3, 4, or 5 substituents selected from the group consisting of $C_1$-$C_6$-alkyl, $C_2$-$C_6$-alkenyl, benzyl, cyano, halo-$C_1$-$C_6$-alkyl, hydroxy-$C_1$-$C_6$-alkyl, halogen, oxo, —$OR^c$, and phenyl, wherein phenyl and the phenyl ring of benzyl are optionally substituted with 1, 2, 3, or 4 $C_1$-$C_6$-alkyl, halogen, or $C_1$-$C_6$-alkoxy; and $R^c$ at each occurrence, is independently hydrogen, $C_1$-$C_6$-alkyl or halo-$C_1$-$C_6$-alkyl.

In one embodiment, $R^1$ is phenyl, wherein the phenyl is unsubstituted or substituted with 1, 2, 3, or 4 substituents selected from the group consisting of $C_1$-$C_6$-alkyl, halogen, cyano, —$OR^{1a}$, —$S(O)_2R^{2a}$, —$S(O)_2N(R^b)(R^{3a})$, —$C(O)R^{1a}$, —$(CR^{4a}R^{5a})_m$—$OR^{1a}$, and halo-$C_1$-$C_6$-alkyl; $R^b$, at each occurrence, is independently hydrogen, $C_1$-$C_6$-alkyl, or halo-$C_1$-$C_6$-alkyl; $R^{1a}$ and $R^{3a}$, at each occurrence, are each independently hydrogen, $C_1$-$C_6$-alkyl, or halo-$C_1$-$C_6$-alkyl; $R^{2a}$, at each occurrence, is independently $C_1$-$C_6$-alkyl or halo-$C_1$-$C_6$-alkyl; $R^{4a}$ and $R^{5a}$, at each occurrence, are each independently hydrogen, $C_1$-$C_6$-alkyl, or halo-$C_1$-$C_6$-alkyl; m, at each occurrence, is independently 1, 2, or 3; $R^2$, $R^3$ and the nitrogen atom to which they are attached form a 4-8-membered-monocyclic heterocycle, 6-11-membered-bicyclic heterocycle, 10-12-membered-tricyclic heterocycle, 7-11-membered-spirocyclic heterocycle or 8-11-membered-bicyclic heteroaryl comprised of a 5-7-membered-monocyclic heterocycle fused to a 5-6-membered-monocyclic heteroaryl, wherein said 4-8-membered monocyclic heterocycle, said 6-11-membered-bicyclic heterocycle, said, 10-12-membered-tricyclic heterocycle, said 7-11-membered-spirocyclic heterocycle and said 8-11-membered-bicyclic heteroaryl are unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, halogen, cyano, —$OR^{1c}$, —O—$(CR^{4c}R^{5c})_p$—$OR^{1c}$, —$OG^{13}$, —$SR^{1c}$, —$S(O)R^{2c}$, —$S(O)_2R^{2c}$, —$S(O)_2G^{13}$, —$S(O)_2G^{14}$, —$S(O)_2N(R^b)(R^{3c})$, —$S(O)_2$—$(CR^{4c}R^{5c})_p$—$C(O)OR^{1c}$, —$S(O)_2$—$(CR^{4c}R^{5c})_p$-$G^{14}$, —$C(O)R^{1c}$, —$C(O)G^{14}$, —$C(O)OR^{1c}$, —$C(O)N(R^b)(R^{3c})$, —$N(R^b)(R^{3c})$, —$N(R^a)C(O)R^{1c}$, —$N(R^a)C(O)G^{14}$, —$N(R^a)C(O)O(R^{1c})$, —$N(R^a)C(O)N(R^b)(R^{3c})$, —$N(R^b)S(O)_2(R^{2c})$, —$N(R^b)S(O)_2(G^{13})$, —$(CR^{4c}R^{5c})_p$—$OR^{1c}$, —$(CR^{4c}R^{5c})_p$—O—$(CR^{4c}R^{5c})_p$—$OR^{1c}$, —$(CR^{4c}R^{5c})_p$—$SR^{1c}$, —$(CR^{4c}R^{5c})_p$—$S(O)R^{2c}$, —$(CR^{4c}R^{5c})_p$—$S(O)_2R^{2c}$, —$(CR^{4c}R^{5c})_p$—$S(O)_2N(R^b)(R^{3c})$, —$(CR^{4c}R^{5c})_p$—$C(O)R^{1c}$, —$(CR^{4c}R^{5c})_p$—$C(O)OR^{1c}$, —$(CR^{4c}R^{5c})_p$—$C(O)N(R^a)(R^{3c})$, —$(CR^{4c}R^{5c})_p$—$N(R^b)(R^{3c})$, —$(CR^{4c}R^{5c})_p$—$N(R^a)C(O)R^c$, —$(CR^{4c}R^{5c})_p$—$N(R^a)C(O)O(R^{1c})$, —$(CR^{4c}R^{5c})_p$—$N(R^a)C(O)O(CH_2G^{13})$, —$(CR^{4c}R^{5c})_p$—$N(R^a)C(O)N(R^b)(R^{3c})$, —$(CR^{4c}R^{5c})_p$—$N(R^b)S(O)_2(R^{2c})$, -$G^{11}$, —$(CR^{4c}R^{5c})_p$-$G^{13}$, —$(CR^{4c}R^{5c})_p$—$OG^{13}$, -$G^{12}$, —$(CR^{4c}R^{5c})_p$-$G^{14}$, cyano-$C_1$-$C_6$-alkyl, oxo, $C^1$-$C^6$-alkoxyimino and halo-$C_1$-$C_6$-alkyl; $R^a$ and $R^b$, at each occurrence, are each independently hydrogen, $C_1$-$C_6$-alkyl, or halo-$C_1$-$C_6$-alkyl; $R^{1c}$ and $R^{3c}$, at each occurrence, are each independently hydrogen, $C_1$-$C_6$-alkyl, or halo-$C_1$-$C_6$-alkyl; $R^{2c}$, at each occurrence, is independently $C_1$-$C_6$-alkyl or halo-$C_1$-$C_6$-alkyl; $R^{4c}$ and $R^{5c}$, at each occurrence, are each independently hydrogen, $C_1$-$C_6$-alkyl, or halo-$C_1$-$C_6$-alkyl; p, at each occurrence, is independently 1, 2, 3, 4, or 5; $G^{11}$ and $G^{13}$ are each independently phenyl or 5-6-membered-heteroaryl; wherein $G^{11}$ and $G^{13}$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, $C_1$-$C_6$-alkoxy-$C_1$-$C_6$-alkyl, halo-$C_1$-$C_6$-alkyl, halogen, —$N(R^e)C(O)R^e$, and —$OR^e$; $G^{12}$, and $G^{14}$ are each independently 3-6-membered-cycloalkyl, 3-6-membered-cycloalkenyl, or 4-10-membered-heterocycle, wherein $G^{12}$ and $G^{14}$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, benzyl, cyano, halo-$C_1$-$C_6$-alkyl, hydroxy-$C_1$-$C_6$-alkyl, halogen, oxo, —$N(R^e)C(O)R^e$, —$N(R^e)S(O)_2R^f$, —$OR^e$, —$C(O)R^e$, —$C(O)OR^e$, —C(O)N(R$^e$)$_2$, —SO$_2$R$^f$, —SO$_2$N(R$^e$)$_2$, and phenyl, wherein phenyl and the phenyl ring of benzyl are optionally substituted with C$_1$-C$_6$-alkyl, halogen, or C$_1$-C$_6$-alkoxy; R$^e$ at each occurrence, is independently hydrogen, C$_1$-C$_6$-alkyl, aryl or halo-C$_1$-C$_6$-alkyl; wherein said aryl, is independently unsubstituted or substituted with 1, 2 3, 4, or 5 substituents independently selected from the group consisting of C$_1$-C$_6$-alkyl, halo-C$_1$-C$_6$-alkyl, and halogen; and R$^f$ is C$_1$-C$_6$-alkyl or halo-C$_1$-C$_6$-alkyl.

In one embodiment, R$^1$ is phenyl, wherein the phenyl is unsubstituted or substituted with 1, 2, 3, or 4 substituents selected from the group consisting of C$_1$-C$_6$-alkyl, halogen, cyano, —OR$^{1a}$, —S(O)$_2$R$^{2a}$, —S(O)$_2$N(R$^b$)(R$^{3a}$), —C(O)R$^{1a}$, —(CR$^{4a}$R$^{5a}$)$_m$—OR$^{1a}$, and halo-C$_1$-C$_6$-alkyl; R$^b$, at each occurrence, is independently hydrogen, C$_1$-C$_6$-alkyl, or halo-C$_1$-C$_6$-alkyl; R$^{1a}$ and R$^{3a}$, at each occurrence, are each independently hydrogen, C$_1$-C$_6$-alkyl, or halo-C$_1$-C$_6$-alkyl; R$^{2a}$, at each occurrence, is independently C$_1$-C$_6$-alkyl or halo-C$_1$-C$_6$-alkyl; R$^{4a}$ and R$^{5a}$, at each occurrence, are each independently hydrogen, C$_1$-C$_6$-alkyl, or halo-C$_1$-C$_6$-alkyl; m, at each occurrence, is independently 1, 2, or 3; R$^2$, R$^3$ and the nitrogen atom to which they are attached form a 4-8-membered monocyclic heterocycle, wherein said 4-8-membered monocyclic heterocycle is unsubstituted or substituted with 1, 2, 3, 4, or 5 substituents selected from the group consisting of C$_1$-C$_6$-alkyl, halogen, cyano, —OR$^{1c}$, —S(O)$_2$R$^{2c}$, —S(O)$_2$N(R$^b$)(R$^{3c}$), —C(O)R$^{1c}$, —C(O)N(R$^b$)(R$^{3c}$), —N(R$^b$)(R$^{3c}$), —N(R$^a$)C(O)R$^{1c}$, —(CR$^{4c}$R$^{5c}$)$_p$—OR$^{1c}$, —(CR$^{4c}$R$^{5c}$)$_p$—S(O)$_2$R$^{2c}$, —(CR$^{4c}$R$^{5c}$)$_p$—N(R$^b$)(R$^{3c}$), -G$^{12}$, —(CR$^{4c}$R$^{5c}$)$_p$-G$^{14}$, oxo, and halo-C$_1$-C$_6$-alkyl; R$^a$ and R$^b$, at each occurrence, are each independently hydrogen, C$_1$-C$_6$-alkyl, or halo-C$_1$-C$_6$-alkyl; R$^{1c}$ and R$^{3c}$, at each occurrence, are each independently hydrogen, C$_1$-C$_6$-alkyl, or halo-C$_1$-C$_6$-alkyl; R$^{2c}$, at each occurrence, is independently C$_1$-C$_6$-alkyl or halo-C$_1$-C$_6$-alkyl; R$^{4c}$ and R$^{5c}$, at each occurrence, are each independently hydrogen, C$_1$-C$_6$-alkyl, or halo-C$_1$-C$_6$-alkyl; p, at each occurrence, is independently 1, 2, 3, 4, or 5; and G$^{12}$ and G$^{14}$ are each independently 3-6-membered-cycloalkyl, 3-6-membered-cycloalkenyl, or 4-10-membered-heterocycle, wherein G$^{12}$ and G$^{14}$ are each independently unsubstituted or substituted with 1, 2, 3, 4, or 5 substituents selected from the group consisting of C$_1$-C$_6$-alkyl, cyano, halo-C$_1$-C$_6$-alkyl, halogen, and oxo.

In one embodiment, R$^1$ is selected from the group consisting of 4-cyanophenyl and 4-acetylphenyl; R$^2$, R$^3$ and the nitrogen atom to which they are attached form an azetidine, pyrrolidine or piperazine, wherein said azetidine, pyrrolidine or piperazine is unsubstituted or substituted with 1, 2, or 3 substituents selected from the group consisting of C$_1$-C$_6$-alkyl, halogen, —OR$^{1c}$, —(CR$^{4c}$R$^{5c}$)$_p$—OR$^{1c}$, -G$^{12}$, and halo-C$_1$-C$_6$-alkyl; R$^{1c}$, at each occurrence, is each independently hydrogen, C$_1$-C$_6$-alkyl, or halo-C$_1$-C$_6$-alkyl; R$^{4c}$ and R$^{5c}$, at each occurrence, are each hydrogen or C$_1$-C$_6$-alkyl; p, at each occurrence, is independently 1, 2, or 3; and G$^{12}$, at each occurrence, is each independently 5-6-membered-heterocycle, wherein G$^{12}$ is each independently unsubstituted or substituted with 1 or 2 substituents selected from the group consisting of C$_1$-C$_6$-alkyl, halogen, or oxo.

In one embodiment, R$^1$ is phenyl, wherein the phenyl is unsubstituted or substituted with 1, 2, 3, or 4 substituents selected from the group consisting of C$_1$-C$_6$-alkyl, halogen, cyano, —OR$^{1a}$, —S(O)$_2$R$^{2a}$, —S(O)$_2$N(R$^b$)(R$^{3a}$), —C(O)R$^{1a}$, —(CR$^{4a}$R$^{5a}$)$_m$—OR$^{1a}$, and halo-C$_1$-C$_6$-alkyl; R$^b$, at each occurrence, is independently hydrogen, C$_1$-C$_6$-alkyl, or halo-C$_1$-C$_6$-alkyl; R$^{1a}$ and R$^{3a}$, at each occurrence, are each independently hydrogen, C$_1$-C$_6$-alkyl, or halo-C$_1$-C$_6$-alkyl; R$^{2a}$, at each occurrence, is independently C$_1$-C$_6$-alkyl or halo-C$_1$-C$_6$-alkyl; R$^{4a}$ and R$^{5a}$, at each occurrence, are each independently hydrogen, C$_1$-C$_6$-alkyl, or halo-C$_1$-C$_6$-alkyl; m, at each occurrence, is independently 1, 2, or 3; R$^2$, R$^3$ and the nitrogen atom to which they are attached form a 6-11-membered-bicyclic heterocycle, 10-12-membered-tricyclic heterocycle, or 7-11-membered-spirocyclic heterocycle, wherein said 6-11-membered-bicyclic heterocycle, said, 10-12-membered-tricyclic heterocycle, and said 7-11-membered-spirocyclic heterocycle are unsubstituted or substituted with 1, 2, 3, 4, or 5 substituents selected from the group consisting of C$_1$-C$_6$-alkyl, halogen, cyano, —OR$^{1c}$, —S(O)$_2$R$^{2c}$, —S(O)$_2$G$^{13}$, —S(O)$_2$G$^{14}$, —S(O)$_2$N(R$^b$)(R$^{3c}$), —S(O)$_2$—(CR$^{4c}$R$^{5c}$)$_p$—C(O)OR$^{1c}$, —S(O)$_2$—(CR$^{4c}$R$^{5c}$)$_p$-G$^{14}$, —C(O)R$^{1c}$, —C(O)G$^{14}$, —C(O)OR$^{1c}$, —C(O)N(R$^b$)(R$^{3c}$), —N(R$^b$)(R$^{3c}$), —N(R$^a$)C(O)R$^{1c}$, —N(R$^a$)C(O)G$^{14}$, —N(R$^b$)S(O)$_2$(R$^{2c}$), —N(R$^b$)S(O)$_2$(G$^{13}$), —(CR$^{4c}$R$^{5c}$)$_p$—OR$^{1c}$, —(CR$^{4c}$R$^{5c}$)$_p$—O—(CR$^{4c}$R$^{5c}$)$_p$—OR$^{1c}$, —(CR$^{4c}$R$^{5c}$)$_p$—S(O)$_2$R$^{2c}$, —(CR$^{4c}$R$^{5c}$)$_p$—N(R$^b$)(R$^{3c}$), —(CR$^{4c}$R$^{5c}$)$_p$—N(R$^a$)C(O)O(CH$_2$G$^{13}$), -G$^{11}$, —(CR$^{4c}$R$^{5c}$)$_p$-G$^{13}$, —(CR$^{4c}$R$^{5c}$)$_p$-OG$^{13}$, -G$^{12}$, —(CR$^{4c}$R$^{5c}$)$_p$-G$^{14}$, cyano-C$_1$-C$_6$-alkyl, oxo, C$^1$-C$^6$-alkoxyimino and halo-C$_1$-C$_6$-alkyl; R$^a$ and R$^b$, at each occurrence, are each independently hydrogen, C$_1$-C$_6$-alkyl, or halo-C$_1$-C$_6$-alkyl; R$^{1c}$ and R$^{3c}$, at each occurrence, are each independently hydrogen, C$_1$-C$_6$-alkyl, or halo-C$_1$-C$_6$-alkyl; R$^{2c}$, at each occurrence, is independently C$_1$-C$_6$-alkyl or halo-C$_1$-C$_6$-alkyl; R$^{4c}$ and R$^{5c}$, at each occurrence, are each independently hydrogen, C$_1$-C$_6$-alkyl, or halo-C$_1$-C$_6$-alkyl; p, at each occurrence, is independently 1, 2, 3, 4, or 5; G$^{11}$ and G$^{13}$ are each independently phenyl or 5-6-membered-heteroaryl; wherein G$^{11}$ and G$^{13}$ are each independently unsubstituted or substituted with 1, 2, 3, 4, or 5 substituents selected from the group consisting of C$_1$-C$_6$-alkyl, C$_1$-C$_6$-alkoxy-C$_1$-C$_6$-alkyl, halo-C$_1$-C$_6$-alkyl, halogen, —N(R$^e$)C(O)R$^e$, and —OR$^e$; G$^{12}$, and G$^{14}$ are each independently 3-6-membered-cycloalkyl or 4-10-membered-heterocycle, wherein G$^{12}$ and G$^{14}$ are each independently unsubstituted or substituted with 1, 2, 3, 4, or 5 substituents selected from the group consisting of C$_1$-C$_6$-alkyl, halo-C$_1$-C$_6$-alkyl, hydroxy-C$_1$-C$_6$-alkyl, halogen, oxo, —N(R$^e$)S(O)$_2$R$^e$, and —OR$^e$; and R$^e$ at each occurrence, is independently hydrogen, C$_1$-C$_6$-alkyl, aryl or halo-C$_1$-C$_6$-alkyl; wherein said aryl, is independently unsubstituted or substituted with 1, 2 3, 4, or 5 substituents independently selected from the group consisting of C$_1$-C$_6$-alkyl, halo-C$_1$-C$_6$-alkyl, and halogen.

In one embodiment, R$^1$ is phenyl, wherein the phenyl is unsubstituted or substituted with 1, 2, 3, or 4 substituents selected from the group consisting of C$_1$-C$_6$-alkyl, halogen, cyano, —OR$^{1a}$, —S(O)$_2$R$^{2a}$, —S(O)$_2$N(R$^b$)(R$^{3a}$), —C(O)R$^{1a}$, —(CR$^{4a}$R$^{5a}$)$_m$—OR$^{1a}$, and halo-C$_1$-C$_6$-alkyl; R$^b$, at each occurrence, is independently hydrogen, C$_1$-C$_6$-alkyl, or halo-C$_1$-C$_6$-alkyl; R$^{1a}$ and R$^{3a}$, at each occurrence, are each independently hydrogen, C$_1$-C$_6$-alkyl, or halo-C$_1$-C$_6$-alkyl; R$^{2a}$, at each occurrence, is independently C$_1$-C$_6$-alkyl or halo-C$_1$-C$_6$-alkyl; R$^{4a}$ and R$^{5a}$, at each occurrence, are each independently hydrogen, C$_1$-C$_6$-alkyl, or halo-C$_1$-C$_6$-alkyl; m, at each occurrence, is independently 1, 2, or 3; R$^2$, R$^3$ and the nitrogen atom to which they are attached form a 8-11-membered-bicyclic heteroaryl comprised of a 5-7-membered-monocyclic heterocycle fused to a 5-6-membered-monocyclic heteroaryl, wherein said 8-11-membered-bicyclic heteroaryl is unsubstituted or substituted with 1, 2, 3, 4, or 5 substituents selected from the group consisting of C$_1$-C$_6$-alkyl, halogen, cyano, —OR$^{1c}$, —S(O)$_2$R$^{2c}$, —S(O)$_2$G$^{13}$, —S(O)$_2$G$^{14}$, —S(O)$_2$N(R$^b$)(R$^{3c}$), —S(O)$_2$—

$(CR^{4c}R^{5c})_pC(O)OR^{1c}$, $-S(O)_2-(CR^{4c}R^{5c})_p-G^{14}$, $-C(O)R^{1c}$, $-C(O)G^{14}$, $-C(O)OR^{1c}$, $-C(O)N(R^b)(R^{3c})$, $-N(R^b)(R^{3c})$, $-N(R^a)C(O)R^{1c}$, $-N(R^a)C(O)G^{14}$, $-N(R^b)S(O)_2(R^{2c})$, $-N(R^b)S(O)_2(G^{13})$, $-(CR^{4c}R^{5c})_p-OR^{1c}$, $-(CR^{4c}R^{5c})_p-O-(CR^{4c}R^{5c})_p-OR^{1c}$, $-(CR^{4c}R^{5c})_p-S(O)_2R^{2c}$, $-(CR^{4c}R^{5c})_p-N(R^b)(R^{3c})$, $-(CR^{4c}R^{5c})_p-N(R^a)C(O)O(CH_2G^{13})$, $-G^{11}$, $-(CR^{4c}R^{5c})_p-G^{13}$, $-(CR^{4c}R^{5c})_p-OG^{13}$, $-G^{12}$, $-(CR^{4c}R^{5c})_p-G^{14}$, cyano-$C_1$-$C_6$-alkyl, oxo, $C^1$-$C^6$-alkoxyimino and halo-$C_1$-$C_6$-alkyl; $R^a$ and $R^b$, at each occurrence, are each independently hydrogen, $C_1$-$C_6$-alkyl, or halo-$C_1$-$C_6$-alkyl; $R^{1c}$ and $R^{3c}$, at each occurrence, are each independently hydrogen, $C_1$-$C_6$-alkyl, or halo-$C_1$-$C_6$-alkyl; $R^{2c}$, at each occurrence, is independently $C_1$-$C_6$-alkyl or halo-$C_1$-$C_6$-alkyl; $R^{4c}$ and $R^{5c}$, at each occurrence, are each independently hydrogen, $C_1$-$C_6$-alkyl, or halo-$C_1$-$C_6$-alkyl; p, at each occurrence, is independently 1, 2, 3, 4, or 5; $G^{11}$ and $G^{13}$ are each independently phenyl or 5-6-membered-heteroaryl; wherein $G^{11}$ and $G^{13}$ are each independently unsubstituted or substituted with 1, 2, 3, 4, or 5 substituents selected from the group consisting of $C_1$-$C_6$-alkyl, $C_1$-$C_6$-alkoxy-$C_1$-$C_6$-alkyl, halo-$C_1$-$C_6$-alkyl, halogen, $-N(R^e)C(O)R^e$, and $-OR^e$; $G^{12}$, and $G^{14}$ are each independently 3-6-membered-cycloalkyl or 4-10-membered-heterocycle, wherein $G^{12}$ and $G^{14}$ are each independently unsubstituted or substituted with 1, 2, 3, 4, or 5 substituents selected from the group consisting of $C_1$-$C_6$-alkyl, halo-$C_1$-$C_6$-alkyl, hydroxy-$C_1$-$C_6$-alkyl, halogen, oxo, $-N(R^e)S(O)_2R^f$, and $-OR^e$; $R^e$ at each occurrence, is independently hydrogen, $C_1$-$C_6$-alkyl, aryl or halo-$C_1$-$C_6$-alkyl; wherein said aryl, is independently unsubstituted or substituted with 1, 2 3, 4, or 5 substituents independently selected from the group consisting of $C_1$-$C_6$-alkyl, halo-$C_1$-$C_6$-alkyl, and halogen; and $R^f$ is $C_1$-$C_6$-alkyl or halo-$C_1$-$C_6$-alkyl.

In one embodiment, $R^1$ is 5- or 6-membered heteroaryl, wherein the 5- or 6-membered heteroaryl is unsubstituted or substituted with 1, 2, 3, or 4 substituents selected from the group consisting of $C_1$-$C_6$-alkyl, halogen, cyano, $-OR^{1a}$, $-S(O)_2R^{2a}$, $-S(O)_2N(R^b)(R^{3a})$, $-C(O)R^{1a}$, $-(CR^{4a}R^{5a})_m-OR^{1a}$, and halo-$C_1$-$C_6$-alkyl; $R^b$, at each occurrence, is independently hydrogen, $C_1$-$C_6$-alkyl, or halo-$C_1$-$C_6$-alkyl; $R^{1a}$ and $R^{3a}$, at each occurrence, are each independently hydrogen, $C_1$-$C_6$-alkyl, or halo-$C_1$-$C_6$-alkyl; $R^{2a}$, at each occurrence, is independently $C_1$-$C_6$-alkyl or halo-$C_1$-$C_6$-alkyl; $R^{4a}$ and $R^{5a}$, at each occurrence, are each independently hydrogen, $C_1$-$C_6$-alkyl, or halo-$C_1$-$C_6$-alkyl; and m, at each occurrence, is independently 1, 2, or 3. In one embodiment, $R^1$ is 5- or 6-membered heteroaryl, wherein the 5- or 6-membered heteroaryl is unsubstituted or substituted with 1, 2, 3, or 4 substituents selected from the group consisting of $C_1$-$C_6$-alkyl, halogen, cyano, $-OR^{1a}$, $-S(O)_2R^{2a}$, $-S(O)_2N(R^b)(R^{3a})$, $-C(O)R^{1a}$, $-(CR^{4a}R^{5a})_m-OR^{1a}$, and halo-$C_1$-$C_6$-alkyl; $R^b$, at each occurrence, is independently hydrogen, $C_1$-$C_6$-alkyl, or halo-$C_1$-$C_6$-alkyl; $R^{1a}$ and $R^{3a}$, at each occurrence, are each independently hydrogen, $C_1$-$C_6$-alkyl, or halo-$C_1$-$C_6$-alkyl; $R^{2a}$, at each occurrence, is independently $C_1$-$C_6$-alkyl or halo-$C_1$-$C_6$-alkyl; $R^{4a}$ and $R^{5a}$, at each occurrence, are each independently hydrogen, $C_1$-$C_6$-alkyl, or halo-$C_1$-$C_6$-alkyl; m, at each occurrence, is independently 1, 2, or 3; $R^2$ is selected from the group consisting of hydrogen, $C_1$-$C_6$-alkyl, $C_1$-$C_6$-alkoxy-$C_1$-$C_6$-alkyl, and -$G^2$; $R^3$ is selected from the group consisting of hydrogen, $C_1$-$C_6$-alkyl, $C_2$-$C_6$-alkenyl, $C_2$-$C_6$-alkynyl, $-(CR^{4b}R^{5b})_n-OR^{1b}$, $-CH[(CR^{4b}R^{5b})_n-OR^{1b}]_2$, $-(CR^{4b}R^{5b})_n-SR^{1b}$, $-(CR^{4b}R^{5b})_n-S(O)_2R^{2b}$, $-(CR^{4b}R^{5b})_n-S(O)_2N(R^b)(R^{3b})$, $-(CR^{4b}R^{5b})_n-C(O)R^{1b}$, $-(CR^{4b}R^{5b})_n-C(O)OR^{1b}$, $-(CR^{4b}R^{5b})_n-C(O)N(R^b)(R^{3b})$, $-(CR^{4b}R^{5b})_n-C(O)N(R^b)(-(CR^{4b}R^{5b})_n-OR^{1b})$, $-(CR^{4b}R^{5b})_n-N(R^b)(R^{3b})$, $-(CR^{4b}R^{5b})_n-N(R^a)C(O)R^{1b}$, $-(CR^{4b}R^{5b})_n-N(R^b)S(O)_2R^{2b}$, $-S(O)_2R^{2b}$, $-(CR^{4b}R^{5b})_n-N(R^a)C(O)O(R^{1b})$, $-(CR^{4b}R^{5b})_n-N(R^a)C(O)N(R^b)(R^{3b})$, -$G^2$, $-(CR^{4b}R^{5b})_n-G^4$, - $G^2$-$G^6$, -$G^1$, $-(CR^{4b}R^{5b})_n-G^3$, $-CH[C(O)N(R^b)(R^{3b})][-(CR^{4b}R^{5b})_n-G^3]$, cyano-$C_1$-$C_6$-alkyl, and halo-$C_1$-$C_6$-alkyl; $R^a$ and $R^b$, at each occurrence, are each independently hydrogen, $C_1$-$C_6$-alkyl, or halo-$C_1$-$C_6$-alkyl; $R^{1b}$ and $R^{3b}$, at each occurrence, are each independently hydrogen, $C_1$-$C_6$-alkyl, or halo-$C_1$-$C_6$-alkyl; $R^{2b}$, at each occurrence, is independently $C_1$-$C_6$-alkyl or halo-$C_1$-$C_6$-alkyl; $R^{4b}$ and $R^{5b}$, at each occurrence, are each independently hydrogen, $C_1$-$C_6$-alkyl, or halo-$C_1$-$C_6$-alkyl; n, at each occurrence, is independently 1, 2, 3, 4, or 5; $G^1$ and $G^3$ are each independently aryl or heteroaryl; wherein $G^1$ and $G^3$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, $-N(R^c)_2$, $-N(R^c)C(O)R^c$, $-OR^c$, $-C(O)R^c$, $-C(O)OR^c$, $-C(O)N(R^c)_2$, $-SO_2R^d$, and $-SO_2N(R^c)_2$; $G^2$, $G^4$ and $G^6$ are each independently 3-6-membered-cycloalkyl or 4-10-membered-heterocycle; wherein $G^2$, $G^4$ and $G^6$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, benzyl, cyano, halo-$C_1$-$C_6$-alkyl, hydroxy-$C_1$-$C_6$-alkyl, halogen, oxo, $-N(R^c)_2$, $-N(R^c)C(O)R^c$, $-OR^c$, $-C(O)R^c$, $-C(O)OR^c$, $-C(O)N(R^c)_2$, $-SO_2R^d$, $-SO_2N(R^c)_2$, and phenyl, wherein phenyl and the phenyl ring of benzyl are optionally substituted with 1, 2, 3, or 4 $C_1$-$C_6$-alkyl, halogen, or $C_1$-$C_6$-alkoxy; R at each occurrence, is independently hydrogen, $C_1$-$C_6$-alkyl, aryl, or halo-$C_1$-$C_6$-alkyl; wherein said aryl is independently unsubstituted or substituted with 1, 2 3, 4, or 5 substituents independently selected from the group consisting of $C_1$-$C_6$-alkyl, halo-$C_1$-$C_6$-alkyl, and halogen; and $R^d$ is $C_1$-$C_6$-alkyl or halo-$C_1$-$C_6$-alkyl. In one embodiment, $R^1$ is 5- or 6-membered heteroaryl, wherein the 5- or 6-membered heteroaryl is unsubstituted or substituted with 1, 2, 3, or 4 substituents selected from the group consisting of $C_1$-$C_6$-alkyl, halogen, cyano, $-OR^{1a}$, $-S(O)_2R^{2a}$, $-S(O)_2N(R^b)(R^{3a})$, $-C(O)R^{1a}$, $-(CR^{4a}R^{5a})_m-OR^{1a}$, and halo-$C_1$-$C_6$-alkyl; $R^b$, at each occurrence, is independently hydrogen, $C_1$-$C_6$-alkyl, or halo-$C_1$-$C_6$-alkyl; $R^{1a}$ and $R^{3a}$, at each occurrence, are each independently hydrogen, $C_1$-$C_6$-alkyl, or halo-$C_1$-$C_6$-alkyl; $R^{2a}$, at each occurrence, is independently $C_1$-$C_6$-alkyl or halo-$C_1$-$C_6$-alkyl; $R^{4a}$ and $R^{5a}$, at each occurrence, are each independently hydrogen, $C_1$-$C_6$-alkyl, or halo-$C_1$-$C_6$-alkyl; m, at each occurrence, is independently 1, 2, or 3; $R^2$ is selected from the group consisting of hydrogen, $C_1$-$C_6$-alkyl, and $C_1$-$C_6$-alkoxy-$C_1$-$C_6$-alkyl; $R^3$ is selected from the group consisting of hydrogen, $C_1$-$C_6$-alkyl, $C_2$-$C_6$-alkenyl, $C_2$-$C_6$-alkynyl, $-(CR^{4b}R^{5b})_n-OR^{1b}$, $-CH[(CR^{4b}R^{5b})_n-OR^{1b}]_2$, $-(CR^{4b}R^{5b})_n-SR^{1b}$, $-(CR^{4b}R^{5b})_n-S(O)_2R^{2b}$, $-(CR^{4b}R^{5b})_n-S(O)_2N(R^b)(R^{3b})$, $-(CR^{4b}R^{5b})_n-C(O)R^{1b}$, $-(CR^{4b}R^{5b})_n-C(O)OR^{1b}$, $-(CR^{4b}R^{5b})_n-C(O)N(R(R^b)(R^{3b})$, $-(CR^{4b}R^{5b})_n-C(O)N(R^b)(-(CR^{4b}R^{5b})_n-OR^{1b})$, $-(CR^{4b}R^{5b})_n-N(R^b)(R^{3b})$, $-(CR^{4b}R^{5b})_n-N(R^a)C(O)R^{1b}$, $-(CR^{4b}R^{5b})_n-N(R^b)S(O)_2R^{2b}$, $-S(O)_2R^{2b}$, $-(CR^{4b}R^{5b})_n-N(R^a)C(O)O(R^{1b})$, $-(CR^{4b}R^{5b})_n-N(R^a)C(O)N(R^b)(R^{3b})$, cyano-$C_1$-$C_6$-alkyl, and halo-$C_1$-$C_6$-alkyl; $R^a$ and $R^b$, at each occurrence, are each independently hydrogen, $C_1$-$C_6$-alkyl, or halo-$C_1$-$C_6$-alkyl; $R^{1b}$ and $R^{3b}$, at each occurrence, are each independently hydrogen, $C_1$-$C_6$-alkyl, or halo-$C_1$-$C_6$-alkyl; $R^{2b}$, at each occurrence, is independently $C_1$-$C_6$-alkyl or halo-$C_1$-$C_6$-alkyl; $R^{4b}$ and $R^{5b}$, at each occurrence, are each independently hydrogen, $C_1$-$C_6$-alkyl, or halo-$C_1$-$C_6$-alkyl; and n, at each occurrence, is independently 1, 2, 3, 4, or 5.

In one embodiment, $R^1$ is selected from the group consisting of 5-(trifluoromethyl)pyridin-2-yl, 5-(difluoromethyl)pyridin-2-yl, and 6-(trifluoromethyl)pyridin-3-yl; $R^2$ is hydrogen; $R^3$ is selected from the group consisting of —$(CR^{4b}R^{5b})_n$—$OR^{1b}$, —$(CR^{4b}R^{5b})_n$—$C(O)N(R^b)(R^{3b})$, and halo-$C_1$-$C_6$-alkyl; $R^b$ is hydrogen, $C_1$-$C_6$-alkyl, or halo-$C_1$-$C_6$-alkyl; $R^{1b}$ and $R^{3b}$, at each occurrence, are each independently hydrogen or $C_1$-$C_6$-alkyl; $R^{4b}$ and $R^{5b}$, at each occurrence, are each independently hydrogen or $C_1$-$C_6$-alkyl; and n, at each occurrence, is independently 1, 2, 3 or 4. In one embodiment, $R^1$ is 5- or 6-membered heteroaryl, wherein the 5- or 6-membered heteroaryl is unsubstituted or substituted with 1, 2, 3, or 4 substituents selected from the group consisting of $C_1$-$C_6$-alkyl, halogen, cyano, —$OR^{1a}$, —$S(O)_2R^{2a}$, —$S(O)_2N(R^b)(R^{3a})$, —$C(O)R^{1a}$, —$(CR^{4a}R^{5a})_m$—$OR^{1a}$, and halo-$C_1$-$C_6$-alkyl; $R^b$, at each occurrence, is independently hydrogen, $C_1$-$C_6$-alkyl, or halo-$C_1$-$C_6$-alkyl; $R^{1a}$ and $R^{3a}$, at each occurrence, are each independently hydrogen, $C_1$-$C_6$-alkyl, or halo-$C_1$-$C_6$-alkyl; $R^{2a}$, at each occurrence, is independently $C_1$-$C_6$-alkyl or halo-$C_1$-$C_6$-alkyl; $R^{4a}$ and $R^{5a}$, at each occurrence, are each independently hydrogen, $C_1$-$C_6$-alkyl, or halo-$C_1$-$C_6$-alkyl; m, at each occurrence, is independently 1, 2, or 3; $R^2$ is selected from the group consisting of hydrogen and $C_1$-$C_6$-alkyl; $R^3$ is selected from the group consisting of —$(CR^{4b}R^{5b})_n$—$C(O)N(R^b)(G^3)$, —$(CR^{4b}R^{5b})_n$—$N(R^b)$(G^3)$, -$G^1$, —$(CR^{4b}R^{5b})_n$-$G^3$, and —$CH[C(O)N(R^b)(R^{3b})]$[—$(CR^{4b}R^{5b})_n$-$G^3$]; $R^b$ is hydrogen, $C_1$-$C_6$-alkyl, or halo-$C_1$-$C_6$-alkyl; $R^{3b}$ is hydrogen, $C_1$-$C_6$-alkyl, or halo-$C_1$-$C_6$-alkyl; $R^{4b}$ and $R^{5b}$, at each occurrence, are each independently hydrogen, $C_1$-$C_6$-alkyl, or halo-$C_1$-$C_6$-alkyl; n, at each occurrence, is independently 1, 2, 3, 4, or 5; $G^1$ and $G^3$ are each independently aryl or heteroaryl; wherein $G^1$ and $G^3$ are each independently unsubstituted or substituted with 1, 2, 3, 4, or 5 substituents selected from the group consisting of $C_1$-$C_6$-alkyl and —$OR^c$; and $R^c$ at each occurrence, is independently hydrogen or $C_1$-$C_6$-alkyl.

In one embodiment, $R^1$ is 5- or 6-membered heteroaryl, wherein the 5- or 6-membered heteroaryl is unsubstituted or substituted with 1, 2, 3, or 4 substituents selected from the group consisting of $C_1$-$C_6$-alkyl, halogen, cyano, —$OR^{1a}$, —$S(O)_2R^{2a}$, —$S(O)_2N(R^b)(R^{3a})$, —$C(O)R^{1a}$, —$(CR^{4a}R^{5a})_m$—$OR^{1a}$, and halo-$C_1$-$C_6$-alkyl; $R^b$, at each occurrence, is independently hydrogen, $C_1$-$C_6$-alkyl, or halo-$C_1$-$C_6$-alkyl; $R^{1a}$ and $R^{3a}$, at each occurrence, are each independently hydrogen, $C_1$-$C_6$-alkyl, or halo-$C_1$-$C_6$-alkyl; $R^{2a}$, at each occurrence, is independently $C_1$-$C_6$-alkyl or halo-$C_1$-$C_6$-alkyl; $R^{4a}$ and $R^{5a}$, at each occurrence, are each independently hydrogen, $C_1$-$C_6$-alkyl, or halo-$C_1$-$C_6$-alkyl; m, at each occurrence, is independently 1, 2, or 3; $R^2$ is selected from the group consisting of hydrogen, $C_1$-$C_6$-alkyl, and -$G^2$; $R^3$ is selected from the group consisting of —$(CR^{4b}R^{5b})_n$—$C(O)N(R^b)(G^4)$, —$(CR^{4b}R^{5b})_n$—$C(O)G^4$, -$G^2$, and —$(CR^{4b}R^{5b})_n$-$G^4$, -$G^2$-$G^6$; $R^b$ is hydrogen, $C_1$-$C_6$-alkyl, or halo-$C_1$-$C_6$-alkyl; $R^{4b}$ and $R^{5b}$, at each occurrence, are each independently hydrogen, $C_1$-$C_6$-alkyl, or halo-$C_1$-$C_6$-alkyl; n, at each occurrence, is independently 1, 2, 3, 4, or 5; $G^2$, $G^4$ and $G^6$ are each independently 3-6-membered-cycloalkyl or 4-10-membered-heterocycle; wherein $G^2$, $G^4$ and $G^6$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, benzyl, cyano, halo-$C_1$-$C_6$-alkyl, hydroxy-$C_1$-$C_6$-alkyl, halogen, oxo, —OR, and phenyl, wherein phenyl and the phenyl ring of benzyl are optionally substituted with 1, 2, 3, or 4 $C_1$-$C_6$-alkyl, halogen, or $C_1$-$C_6$-alkoxy; and $R^c$ at each occurrence, is independently hydrogen, $C_1$-$C_6$-alkyl, or halo-$C_1$-$C_6$-alkyl.

In one embodiment, $R^1$ is selected from the group consisting of 5-(trifluoromethyl)pyridin-2-yl, 5-(difluoromethyl)pyridin-2-yl, and 6-(trifluoromethyl)pyridin-3-yl; $R^2$ is selected from the group consisting of hydrogen and $C_1$-$C_6$-alkyl; $R^3$ is -$G^2$; and $G^2$ is a 4-6-membered-cycloalkyl or 4-6-membered-heterocycle; wherein $G^2$ is unsubstituted or substituted with 1, 2, or 3 substituents selected from the group consisting of $C_1$-$C_6$-alkyl, halogen, and oxo.

In one embodiment, $R^1$ is 5- or 6-membered heteroaryl, wherein the 5- or 6-membered heteroaryl is unsubstituted or substituted with 1, 2, 3, or 4 substituents selected from the group consisting of $C_1$-$C_6$-alkyl, halogen, cyano, —$OR^{1a}$, —$S(O)_2R^{2a}$, —$S(O)_2N(R^b)(R^{3a})$, —$C(O)R^{1a}$, —$(CR^{4a}R^{5a})_m$—$OR^{1a}$, and halo-$C_1$-$C_6$-alkyl; $R^b$, at each occurrence, is independently hydrogen, $C_1$-$C_6$-alkyl, or halo-$C_1$-$C_6$-alkyl; $R^{1a}$ and $R^{3a}$, at each occurrence, are each independently hydrogen, $C_1$-$C_6$-alkyl, or halo-$C_1$-$C_6$-alkyl; $R^{2a}$, at each occurrence, is independently $C_1$-$C_6$-alkyl or halo-$C_1$-$C_6$-alkyl; $R^{4a}$ and $R^{5a}$, at each occurrence, are each independently hydrogen, $C_1$-$C_6$-alkyl, or halo-$C_1$-$C_6$-alkyl; m, at each occurrence, is independently 1, 2, or 3; $R^2$, $R^3$ and the nitrogen atom to which they are attached form a 4-8-membered-monocyclic heterocycle, 6-11-membered-bicyclic heterocycle, 10-12-membered-tricyclic heterocycle, 7-11-membered-spirocyclic heterocycle or 8-11-membered-bicyclic heteroaryl comprised of a 5-7-membered-monocyclic heterocycle fused to a 5-6-membered-monocyclic heteroaryl, wherein said 4-8-membered monocyclic heterocycle, said 6-11-membered-bicyclic heterocycle, said 10-12-membered-tricyclic heterocycle, said 7-11-membered-spirocyclic heterocycle and said 8-11-membered-bicyclic heteroaryl are unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, halogen, cyano, —$OR^{1c}$, —O—$(CR^{4c}R^{5c})_p$—$OR^{1c}$, —$OG^{13}$, —$OC(O)R^{1c}$, —$OC(O)N(R^b)(R^{3c})$, —$SR^{1c}$, —$S(O)R^{2c}$, —$S(O)_2R^{2c}$, —$S(O)_2G^{13}$, —$S(O)_2G^{14}$, —$S(O)_2N(R^b)(R^{3c})$, —$S(O)_2$—$(CR^{4c}R^{5c})_p$—$C(O)OR^{1c}$, —$S(O)_2$—$(CR^{4c}R^{5c})_p$-$G^{14}$, —$C(O)R^{1c}$, —$C(O)G^{14}$, —$C(O)OR^{1c}$, —$C(O)N(R^b)(R^{3c})$, —$N(R^b)(R^{3c})$, —$N(R^a)C(O)R^{1c}$, —$N(R^a)C(O)G^{14}$, —$N(R^a)C(O)O(R^{1c})$, —$N(R^a)C(O)N(R^b)(R^{3c})$, —$N(R^b)S(O)_2(R^{2c})$, —$N(R^b)S(O)_2(G^{13})$, —$(CR^{4c}R^{5c})_p$—$OR^{1c}$, —$(CR^{4c}R^{5c})_p$—O—$(CR^{4c}R^{5c})_p$—$OR^{1c}$, —$(CR^{4c}R^{5c})_p$—$OC(O)R^{1c}$, —$(CR^{4c}R^{5c})_p$—$OC(O)N(R^b)(R^{3c})$, —$(CR^{4c}R^{5c})_p$—$SR^{1c}$, —$(CR^{4c}R^{5c})_p$—$S(O)R^{2c}$, —$(CR^{4c}R^{5c})_p$—$S(O)_2R^{2c}$, —$(CR^{4c}R^{5c})_p$—$S(O)_2N(R^b)(R^{3c})$, —$(CR^{4c}R^{5c})_p$—$C(O)R^{1c}$, —$(CR^{4c}R^{5c})_p$—$C(O)OR^{1c}$, —$(CR^{4c}R^{5c})_p$—$C(O)N(R^a)(R^{3c})$, —$(CR^{4c}R^{5c})_p$—$N(R^b)(R^{3c})$, —$(CR^{4c}R^{5c})_p$—$N(R^a)C(O)R^{1c}$, —$(CR^{4c}R^{5c})_p$—$N(R^a)C(O)O(R^{1c})$, —$(CR^{4c}R^{5c})_p$—$N(R^a)C(O)O(CH_2G^{13})$, —$(CR^{4c}R^{5c})_p$—$N(R^a)C(O)N(R^b)(R^{3c})$, —$(CR^{4c}R^{5c})_p$—$N(R^b)S(O)_2(R^{2c})$, -$G^{11}$, —$(CR^{4c}R^{5c})_p$-$G^{13}$, —$(CR^{4c}R^{5c})_p$—$OG^{13}$, -$G^{12}$, —$(CR^{4c}R^{5c})_p$-$G^{14}$, cyano-$C_1$-$C_6$-alkyl, oxo, $C^1$-$C^6$-alkoxyimino and halo-$C_1$-$C_6$-alkyl; $R^a$ and $R^b$, at each occurrence, are each independently hydrogen, $C_1$-$C_6$-alkyl, or halo-$C_1$-$C_6$-alkyl; $R^{1c}$ and $R^{3c}$, at each occurrence, are each independently hydrogen, $C_1$-$C_6$-alkyl, or halo-$C_1$-$C_6$-alkyl; $R^{2c}$, at each occurrence, is independently $C_1$-$C_6$-alkyl or halo-$C_1$-$C_6$-alkyl; $R^{4c}$ and $R^{5c}$, at each occurrence, are each independently hydrogen, $C_1$-$C_6$-alkyl, or halo-$C_1$-

$C_6$-alkyl; p, at each occurrence, is independently 1, 2, 3, 4, or 5; $G^{11}$ and $G^{13}$ are each independently phenyl or 5-6-membered-heteroaryl; wherein $G^{11}$ and $G^{13}$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, $C_1$-$C_6$-alkoxy-$C_1$-$C_6$-alkyl, halo-$C_1$-$C_6$-alkyl, halogen, —N(R$^e$)C(O)R$^e$, and —OR$^e$; $G^{12}$, and $G^{14}$ are each independently 3-6-membered-cycloalkyl, 3-6-membered-cycloalkenyl, or 4-10-membered-heterocycle, wherein $G^{12}$ and $G^{14}$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, benzyl, cyano, halo-$C_1$-$C_6$-alkyl, hydroxy-$C_1$-$C_6$-alkyl, halogen, oxo, —N(R$^e$)C(O)R$^e$, —N(R$^e$)S(O)$_2$R$^f$, —OR$^e$, —C(O)R$^e$, —C(O)OR$^e$, —C(O)N(R$^e$)$_2$, —SO$_2$R$^f$, —SO$_2$N(R$^e$)$_2$, and phenyl, wherein phenyl and the phenyl ring of benzyl are optionally substituted with $C_1$-$C_6$-alkyl, halogen, or $C_1$-$C_6$-alkoxy; R$^e$ at each occurrence, is independently hydrogen, $C_1$-$C_6$-alkyl, aryl, or halo-$C_1$-$C_6$-alkyl; wherein said aryl is independently unsubstituted or substituted with 1, 2 3, 4, or 5 substituents independently selected from the group consisting of $C_1$-$C_6$-alkyl, halo-$C_1$-$C_6$-alkyl, and halogen; and R$^f$ is $C_1$-$C_6$-alkyl or halo-$C_1$-$C_6$-alkyl.

In one embodiment, $R^1$ is 5- or 6-membered heteroaryl, wherein the 5- or 6-membered heteroaryl is unsubstituted or substituted with 1, 2, 3, or 4 substituents selected from the group consisting of $C_1$-$C_6$-alkyl, halogen, cyano, —OR$^{1a}$, —S(O)$_2$R$^{2a}$, —S(O)$_2$N(R$^b$)(R$^{3a}$), —C(O)R$^{1a}$, —(CR$^{4a}$R$^{5a}$)$_m$—OR$^{1a}$, and halo-$C_1$-$C_6$-alkyl; R$^b$, at each occurrence, is independently hydrogen, $C_1$-$C_6$-alkyl, or halo-$C_1$-$C_6$-alkyl; R$^{1a}$ and R$^{3a}$, at each occurrence, are each independently hydrogen, $C_1$-$C_6$-alkyl, or halo-$C_1$-$C_6$-alkyl; R$^{2a}$, at each occurrence, is independently $C_1$-$C_6$-alkyl or halo-$C_1$-$C_6$-alkyl; R$^{4a}$ and R$^{5a}$, at each occurrence, are each independently hydrogen, $C_1$-$C_6$-alkyl, or halo-$C_1$-$C_6$-alkyl; m, at each occurrence, is independently 1, 2, or 3; $R^2$, $R^3$ and the nitrogen atom to which they are attached form a 4-8-membered-monocyclic heterocycle, wherein said 4-8-membered monocyclic heterocycle is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, halogen, cyano, —OR$^{1c}$, —O—(CR$^{4c}$R$^{5c}$)$_p$—OR$^{1c}$, —OG$^{13}$, —SR$^{1c}$, —S(O)R$^{2c}$, —S(O)$_2$R$^{2c}$, —S(O)$_2$G$^{13}$, —S(O)$_2$G$^{14}$, —S(O)$_2$N(R$^b$)(R$^{3c}$), —S(O)$_2$—(CR$^{4c}$R$^{5c}$)$_p$—C(O)OR$^{1c}$, —S(O)$_2$—(CR$^{4c}$R$^{5c}$)$_p$-G$^{14}$, —C(O)R$^{1c}$, —C(O)G$^{14}$, —C(O)OR$^{1c}$, —C(O)N(R$^b$)(R$^{3c}$), —N(R$^b$)(R$^{3c}$), —N(R$^a$)C(O)R$^{1c}$, —N(R$^a$)C(O)G$^{14}$, —N(R$^a$)C(O)O(R$^{1c}$), —N(R$^a$)C(O)N(R$^b$)(R$^{3c}$), —N(R$^b$)S(O)$_2$(R$^{2c}$), —N(R$^b$)S(O)$_2$(G$^{13}$), —(CR$^{4c}$R$^{5c}$)$_p$—OR$^{1c}$, —(CR$^{4c}$R$^{5c}$)$_p$—O—(CR$^{4c}$R$^{5c}$)$_p$—OR$^{1c}$, —(CR$^{4c}$R$^{5c}$)$_p$—S(O)R$^{2c}$, —(CR$^{4c}$R$^{5c}$)$_p$—S(O)$_2$R$^{2c}$, —(CR$^{4c}$R$^{5c}$)$_p$—S(O)$_2$N(R$^b$)(R$^{3c}$), —(CR$^{4c}$R$^{5c}$)$_p$—C(O)R$^{1c}$, —(CR$^{4c}$R$^{5c}$)$_p$—C(O)N(R$^a$)(R$^{3c}$), —(CR$^{4c}$R$^{5c}$)$_p$—N(R$^b$)(R$^{3c}$), —(CR$^{4c}$R$^{5c}$)$_p$—N(R$^a$)C(O)R$^{1c}$, —(CR$^{4c}$R$^{5c}$)$_p$—N(R$^a$)C(O)O(R$^{1c}$), —(CR$^{4c}$R$^{5c}$)$_p$—N(R$^a$)C(O)O(CH$_2$G$^{13}$), —(CR$^{4c}$R$^{5c}$)$_p$—N(R$^a$)C(O)N(R$^b$)(R$^{3c}$), —(CR$^{4c}$R$^{5c}$)$_p$—N(R$^b$)S(O)$_2$(R$^{2c}$), -G$^{11}$, —(CR$^{4c}$R$^{5c}$)$_p$-G$^{13}$, —(CR$^{4c}$R$^{5c}$)$_p$—OG$^{13}$, -G$^{12}$, —(CR$^{4c}$R$^{5c}$)$_p$-G$^{14}$, cyano-$C_1$-$C_6$-alkyl, oxo, $C^1$-$C^6$-alkoxyimino and halo-$C_1$-$C_6$-alkyl; R$^a$ and R$^b$, at each occurrence, are each independently hydrogen, $C_1$-$C_6$-alkyl, or halo-$C_1$-$C_6$-alkyl; R$^{1c}$ and R$^{3c}$, at each occurrence, are each independently hydrogen, $C_1$-$C_6$-alkyl, or halo-$C_1$-$C_6$-alkyl; R$^{2c}$, at each occurrence, is independently $C_1$-$C_6$-alkyl or halo-$C_1$-$C_6$-alkyl; R$^{4c}$ and R$^{5c}$, at each occurrence, are each independently hydrogen, $C_1$-$C_6$-alkyl, or halo-$C_1$-$C_6$-alkyl; p, at each occurrence, is independently 1, 2, 3, 4, or 5; $G^{11}$ and $G^{13}$ are each independently phenyl or 5-6-membered-heteroaryl; wherein $G^{11}$ and $G^{13}$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, $C_1$-$C_6$-alkoxy-$C_1$-$C_6$-alkyl, halo-$C_1$-$C_6$-alkyl, halogen, —N(R$^e$)C(O)R$^e$, and —OR$^e$; $G^{12}$, and $G^{14}$ are each independently 3-6-membered-cycloalkyl, 3-6-membered-cycloalkenyl, or 4-10-membered-heterocycle, wherein $G^{12}$ and $G^{14}$ are each independently unsubstituted or substituted with 1, 2, 3, 4, or 5 substituents selected from the group consisting of $C_1$-$C_6$-alkyl, $C_2$-$C_6$-alkenyl, cyano, halo-$C_1$-$C_6$-alkyl, hydroxy-$C_1$-$C_6$-alkyl, halogen, oxo, —N(R$^e$)C(O)R$^e$, —N(R$^e$)S(O)$_2$R$^f$, —OR$^e$, —C(O)R$^e$, —C(O)N(R$^e$)$_2$, —SO$_2$R$^f$, —SO$_2$N(R$^e$)$_2$; R$^e$ at each occurrence, is independently hydrogen, $C_1$-$C_6$-alkyl, or halo-$C_1$-$C_6$-alkyl; and R$^f$ is $C_1$-$C_6$-alkyl or halo-$C_1$-$C_6$-alkyl.

In one embodiment, $R^1$ is selected from the group consisting of 5-(trifluoromethyl)pyridin-2-yl, 5-(difluoromethyl)pyridin-2-yl, and 6-(trifluoromethyl)pyridin-3-yl; $R^2$, $R^3$ and the nitrogen atom to which they are attached form an azetidine, pyrrolidine or piperazine, wherein said azetidine, pyrrolidine or piperazine is unsubstituted or substituted with 1, 2, or 3 substituents selected from the group consisting of $C_1$-$C_6$-alkyl, halogen, —OR$^c$, —(CR$^{4c}$R$^{5c}$)$_p$—OR$^{1c}$, -G$^{12}$, and halo-$C_1$-$C_6$-alkyl; R$^{1c}$, at each occurrence, is independently hydrogen, $C_1$-$C_6$-alkyl, or halo-$C_1$-$C_6$-alkyl; R$^{4c}$ and R$^{5c}$, at each occurrence, are each independently hydrogen or $C_1$-$C_6$-alkyl; p, at each occurrence, is independently 1, 2, or 3; and $G^{12}$, at each occurrence, is each independently 5-6-membered-heterocycle, wherein $G^{12}$ is each independently unsubstituted or substituted with 1 or 2 substituents selected from the group consisting of $C_1$-$C_6$-alkyl, halogen, or oxo.

In one embodiment, $R^1$ is 5- or 6-membered heteroaryl, wherein the 5- or 6-membered heteroaryl is unsubstituted or substituted with 1, 2, 3, or 4 substituents selected from the group consisting of $C_1$-$C_6$-alkyl, halogen, cyano, —OR$^{1a}$, —S(O)$_2$R$^{2a}$, —S(O)$_2$N(R$^b$)(R$^{3a}$), —C(O)R$^{1a}$, —(CR$^{4a}$R$^{5a}$)$_m$—OR$^{1a}$, and halo-$C_1$-$C_6$-alkyl; R$^b$, at each occurrence, is independently hydrogen, $C_1$-$C_6$-alkyl, or halo-$C_1$-$C_6$-alkyl; R$^{1a}$ and R$^{3a}$, at each occurrence, are each independently hydrogen, $C_1$-$C_6$-alkyl, or halo-$C_1$-$C_6$-alkyl; R$^{2a}$, at each occurrence, is independently $C_1$-$C_6$-alkyl or halo-$C_1$-$C_6$-alkyl; R$^{4a}$ and R$^{5a}$, at each occurrence, are each independently hydrogen, $C_1$-$C_6$-alkyl, or halo-$C_1$-$C_6$-alkyl; m, at each occurrence, is independently 1, 2, or 3; $R^2$, $R^3$ and the nitrogen atom to which they are attached form a 6-11-membered-bicyclic heterocycle, 10-12-membered-tricyclic heterocycle, or 7-11-membered-spirocyclic heterocycle, wherein said 6-11-membered-bicyclic heterocycle, said 10-12-membered-tricyclic heterocycle, or said 7-11-membered-spirocyclic heterocycle are unsubstituted or substituted with 1, 2, 3, or 4 substituents selected from the group consisting of $C_1$-$C_6$-alkyl, halogen, —OR$^{1c}$, —N(R$^b$)(R$^{3c}$), —(CR$^{4c}$R$^{5c}$)$_p$—OR$^{1c}$, oxo, and halo-$C_1$-$C_6$-alkyl; R$^b$, at each occurrence, is independently hydrogen, $C_1$-$C_6$-alkyl, or halo-$C_1$-$C_6$-alkyl; R$^{1c}$ and R$^{3c}$, at each occurrence, are each independently hydrogen or $C_1$-$C_6$-alkyl; R$^{4c}$ and R$^{5c}$, at each occurrence, are each independently hydrogen or $C_1$-$C_6$-alkyl; and p, at each occurrence, is independently 1, 2, 3, or 4.

In one embodiment, $R^1$ is 5- or 6-membered heteroaryl, wherein the 5- or 6-membered heteroaryl is unsubstituted or substituted with 1, 2, 3, or 4 substituents selected from the group consisting of $C_1$-$C_6$-alkyl, halogen, cyano, —OR$^{1a}$, —S(O)$_2$R$^{2a}$, —S(O)$_2$N(R$^b$)(R$^{3a}$), —C(O)R$^{1a}$, —(CR$^{4a}$R$^{5a}$)$_m$—OR$^{1a}$, and halo-$C_1$-$C_6$-alkyl; R$^b$, at each occurrence, is independently hydrogen, $C_1$-$C_6$-alkyl, or halo-$C_1$-$C_6$-alkyl; $R^{1a}$ and $R^{3a}$, at each occurrence, are each independently hydrogen, $C_1$-$C_6$-alkyl, or halo-$C_1$-$C_6$-alkyl; $R^{2a}$, at each occurrence, is independently $C_1$-$C_6$-alkyl or halo-$C_1$-$C_6$-alkyl; $R^{4a}$ and $R^{5a}$, at each occurrence, are each independently hydrogen, $C_1$-$C_6$-alkyl, or halo-$C_1$-$C_6$-alkyl; m, at each occurrence, is independently 1, 2, or 3; $R^2$, $R^3$ and the nitrogen atom to which they are attached form a 8-11-membered-bicyclic heteroaryl comprised of a 5-7-membered-monocyclic heterocycle fused to a 5-6-membered-monocyclic heteroaryl, wherein said 8-11-membered-bicyclic heteroaryl are unsubstituted or substituted with 1, 2, or 3 substituents selected from the group consisting of $C_1$-$C_6$-alkyl, halogen, cyano, —$OR^{1c}$, —$S(O)_2R^{2c}$, —$(CR^{4c}R^{5c})_p$—$OR^{1c}$, oxo, and halo-$C_1$-$C_6$-alkyl; $R^{1c}$, at each occurrence, is independently hydrogen, $C_1$-$C_6$-alkyl, or halo-$C_1$-$C_6$-alkyl; $R^{2c}$, at each occurrence, is independently $C_1$-$C_6$-alkyl or halo-$C_1$-$C_6$-alkyl; $R^{4c}$ and $R^{5c}$, at each occurrence, are each independently hydrogen and $C_1$-$C_6$-alkyl; and p, at each occurrence, is independently 1, 2, 3, or 4.

Specific embodiments contemplated as part of the invention also include, but are not limited to, compounds of formula (I), as defined, for example:

piperazin-1-yl(6-{[5-(trifluoromethyl)pyridin-2-yl]oxy}quinolin-2-yl)methanone;
N-(1,1-dioxidotetrahydrothiophen-3-yl)-6-{[5-(trifluoromethyl)pyridin-2-yl]oxy}quinoline-2-carboxamide;
(1 S,4S)-2,5-diazabicyclo[2.2.1]hept-2-yl(6-{[5-(trifluoromethyl)pyridin-2-yl]oxy}quinolin-2-yl)methanone;
N-[(3S)-1,1-dioxidotetrahydrothiophen-3-yl]-6-{[5-(trifluoromethyl)pyridin-2-yl]oxy}quinoline-2-carboxamide;
N-[(3R)-1,1-dioxidotetrahydrothiophen-3-yl]-6-{[5-(trifluoromethyl)pyridin-2-yl]oxy}quinoline-2-carboxamide;
[3-(morpholin-4-yl)azetidin-1-yl](6-{[5-(trifluoromethyl)pyridin-2-yl]oxy}quinolin-2-yl)methanone;
1-(4-{[2-(piperazin-1-ylcarbonyl)quinolin-6-yl]oxy}phenyl)ethanone;
(3-aminoazetidin-1-yl)(6-{[5-(trifluoromethyl)pyridin-2-yl]oxy}quinolin-2-yl)methanone;
[cis-3,4-dihydroxypyrrolidin-1-yl](6-{[5-(trifluoromethyl)pyridin-2-yl]oxy}quinolin-2-yl)methanone;
pyrrolidin-1-yl(6-{[5-(trifluoromethyl)pyridin-2-yl]oxy}quinolin-2-yl)methanone;
[4-(morpholin-4-yl)piperidin-1-yl](6-{[5-(trifluoromethyl)pyridin-2-yl]oxy}quinolin-2-yl)methanone;
[(3R)-3-methylpiperazin-1-yl](6-{[5-(trifluoromethyl)pyridin-2-yl]oxy}quinolin-2-yl)methanone;
[(3 S)-3-methylpiperazin-1-yl](6-{[5-(trifluoromethyl)pyridin-2-yl]oxy}quinolin-2-yl)methanone;
(6-{[5-(difluoromethyl)pyridin-2-yl]oxy}quinolin-2-yl)(piperazin-1-yl)methanone;
N-(1,1-dioxidotetrahydro-2H-thiopyran-4-yl)-6-{[5-(trifluoromethyl)pyridin-2-yl]oxy}quinoline-2-carboxamide;
[(3R)-3-ethylpiperazin-1-yl](6-{[5-(trifluoromethyl)pyridin-2-yl]oxy}quinolin-2-yl)methanone;
[(3R)-3-(hydroxymethyl)piperazin-1-yl](6-{[5-(trifluoromethyl)pyridin-2-yl]oxy}quinolin-2-yl)methanone;
(3-hydroxyazetidin-1-yl)(6-{[5-(trifluoromethyl)pyridin-2-yl]oxy}quinolin-2-yl)methanone;
piperazin-1-yl(6-{[6-(trifluoromethyl)pyridin-3-yl]oxy}quinolin-2-yl)methanone;
[3-(trifluoromethyl)piperazin-1-yl](6-{[5-(trifluoromethyl)pyridin-2-yl]oxy}quinolin-2-yl)methanone;
N-[2-(morpholin-4-yl)ethyl]-6-{[5-(trifluoromethyl)pyridin-2-yl]oxy}quinoline-2-carboxamide;
N-(2-methoxy ethyl)-6-{[5-(trifluoromethyl)pyridin-2-yl]oxy}quinoline-2-carboxamide;
N-(4,4-difluorocyclohexyl)-6-{[5-(trifluoromethyl)pyridin-2-yl]oxy}quinoline-2-carboxamide;
N-[(3S,4S)-4-hydroxy-1,1-dioxidotetrahydrothiophen-3-yl]-6-{[5-(trifluoromethyl)pyridin-2-yl]oxy}quinoline-2-carboxamide;
[2-(difluoromethyl)piperazin-1-yl](6-{[5-(trifluoromethyl)pyridin-2-yl]oxy}quinolin-2-yl)methanone;
N-[(3R,4S)-4-hydroxy-1,1-dioxidotetrahydrothiophen-3-yl]-6-{[5-(trifluoromethyl)pyridin-2-yl]oxy}quinoline-2-carboxamide;
(8aS)-2-[(6-{[5-(trifluoromethyl)pyridin-2-yl]oxy}quinolin-2-yl)carbonyl]hexahydropyrrolo[1,2-a]pyrazin-4(1H)-one;
[4-(2-hydroxyethyl)piperazin-1-yl](6-{[5-(trifluoromethyl)pyridin-2-yl]oxy}quinolin-2-yl)methanone;
[3-(methylsulfonyl)azetidin-1-yl](6-{[5-(trifluoromethyl)pyridin-2-yl]oxy}quinolin-2-yl)methanone;
N-(2-hydroxy-2-methylpropyl)-6-{[5-(trifluoromethyl)pyridin-2-yl]oxy}quinoline-2-carboxamide;
[(3R)-3-(methoxymethyl)piperazin-1-yl](6-{[5-(trifluoromethyl)pyridin-2-yl]oxy}quinolin-2-yl)methanone;
N-(1-oxidotetrahydro-2H-thiopyran-4-yl)-6-{[5-(trifluoromethyl)pyridin-2-yl]oxy}quinoline-2-carboxamide;
N-[2-(dimethylamino)-2-oxoethyl]-6-{[5-(trifluoromethyl)pyridin-2-yl]oxy}quinoline-2-carboxamide;
N-(cis-3-hydroxycyclobutyl)-6-{[5-(trifluoromethyl)pyridin-2-yl]oxy}quinoline-2-carboxamide;
(3-fluoropyrrolidin-1-yl)(6-{[5-(trifluoromethyl)pyridin-2-yl]oxy}quinolin-2-yl)methanone;
meso-[(1R,5S,6s)-6-amino-3-azabicyclo[3.1.0]hex-3-yl](6-{[5-(trifluoromethyl)pyridin-2-yl]oxy}quinolin-2-yl)methanone;
N-(oxetan-2-ylmethyl)-6-{[5-(trifluoromethyl)pyridin-2-yl]oxy}quinoline-2-carboxamide;
N-[(2R)-2-hydroxypropyl]-6-{[5-(trifluoromethyl)pyridin-2-yl]oxy}quinoline-2-carboxamide;
4,7-diazaspiro[2.5]oct-7-yl(6-{[5-(trifluoromethyl)pyridin-2-yl]oxy}quinolin-2-yl)methanone;
N-(2-oxopiperidin-4-yl)-6-{[5-(trifluoromethyl)pyridin-2-yl]oxy}quinoline-2-carboxamide;
N-(cis-3-methoxycyclobutyl)-6-{[5-(trifluoromethyl)pyridin-2-yl]oxy}quinoline-2-carboxamide;
N-[2-(dimethylamino)-2-oxoethyl]-6-{[6-(trifluoromethyl)pyridin-3-yl]oxy}quinoline-2-carboxamide;
(6-{[5-(difluoromethyl)pyridin-2-yl]oxy}quinolin-2-yl)[(3S)-3-methylpiperazin-1-yl]methanone;
N-[2-oxo-2-(pyrrolidin-1-yl)ethyl]-6-{[5-(trifluoromethyl)pyridin-2-yl]oxy}quinoline-2-carboxamide;
N-(1-ethyl-5-oxopyrrolidin-3-yl)-6-{[5-(trifluoromethyl)pyridin-2-yl]oxy}quinoline-2-carboxamide;
6-{[5-(difluoromethyl)pyridin-2-yl]oxy}-N-(1-ethyl-5-oxopyrrolidin-3-yl)quinoline-2-carboxamide;
(4-cyclobutylpiperazin-1-yl)(6-{[5-(trifluoromethyl)pyridin-2-yl]oxy}quinolin-2-yl)methanone;
N-(3-methyloxetan-3-yl)-6-{[5-(trifluoromethyl)pyridin-2-yl]oxy}quinoline-2-carboxamide;
meso-[(1R,5S,6s)-6-amino-3-azabicyclo[3.1.0]hex-3-yl](6-{[5-(difluoromethyl)pyridin-2-yl]oxy}quinolin-2-yl)methanone;
[(2S,4S)-4-fluoro-2-(hydroxymethyl)pyrrolidin-1-yl](6-{[5-(trifluoromethyl)pyridin-2-yl]oxy}quinolin-2-yl)methanone;
[(3S)-3-fluoropyrrolidin-1-yl](6-{[5-(trifluoromethyl)pyridin-2-yl]oxy}quinolin-2-yl)methanone;
[(3R)-3-fluoropyrrolidin-1-yl](6-{[5-(trifluoromethyl)pyridin-2-yl]oxy}quinolin-2-yl)methanone;

[(8aS)-7,7-difluorohexahydropyrrolo[1,2-a]pyrazin-2(1H)-yl](6-{[5-(trifluoromethyl)pyridin-2-yl]oxy}quinolin-2-yl)methanone;
N-[1-(4-fluorophenyl)-5-oxopyrrolidin-3-yl]-6-{[5-(trifluoromethyl)pyridin-2-yl]oxy}quinoline-2-carboxamide;
(6-{[5-(difluoromethyl)pyridin-2-yl]oxy}quinolin-2-yl)[(3R)-3-ethylpiperazin-1-yl]methanone;
N-(2-methoxy ethyl)-6-{[6-(trifluoromethyl)pyridin-3-yl]oxy}quinoline-2-carboxamide;
(6-{[5-(difluoromethoxy)pyridin-2-yl]oxy}quinolin-2-yl)(piperazin-1-yl)methanone;
N-[(3R)-5-oxopyrrolidin-3-yl]-6-{[5-(trifluoromethyl)pyridin-2-yl]oxy}quinoline-2-carboxamide;
N-(3,3-difluorocyclobutyl)-6-{[5-(trifluoromethyl)pyridin-2-yl]oxy}quinoline-2-carboxamide;
[3-(methoxymethyl)azetidin-1-yl](6-{[5-(trifluoromethyl)pyridin-2-yl]oxy}quinolin-2-yl)methanone;
N-ethyl-N-(1-ethyl-2-oxopiperidin-4-yl)-6-{[5-(trifluoromethyl)pyridin-2-yl]oxy}quinoline-2-carboxamide;
[(3R)-3-methylpiperazin-1-yl](6-{[6-(trifluoromethyl)pyridin-3-yl]oxy}quinolin-2-yl)methanone;
[(3R)-3-(methoxymethyl)piperazin-1-yl](6-{[6-(trifluoromethyl)pyridin-3-yl]oxy}quinolin-2-yl)methanone;
[(3S)-3-(methoxymethyl)piperazin-1-yl](6-{[6-(trifluoromethyl)pyridin-3-yl]oxy}quinolin-2-yl)methanone;
N-[3-(methylsulfonyl)propyl]-6-{[5-(trifluoromethyl)pyridin-2-yl]oxy}quinoline-2-carboxamide;
(3-aminoazetidin-1-yl)(6-{[6-(trifluoromethyl)pyridin-3-yl]oxy}quinolin-2-yl)methanone;
(6-{[5-(difluoromethyl)pyridin-2-yl]oxy}quinolin-2-yl)(3,5-dimethylpiperazin-1-yl)methanone;
(6-{[5-(difluoromethyl)pyridin-2-yl]oxy}quinolin-2-yl)[(3R)-3-methylpiperazin-1-yl]methanone;
(6-{[5-(difluoromethyl)pyridin-2-yl]oxy}quinolin-2-yl)[(3S)-3-(methoxymethyl)piperazin-1-yl]methanone;
{3-[(3R)-3-fluoropyrrolidin-1-yl]azetidin-1-yl}(6-{[5-(trifluoromethyl)pyridin-2-yl]oxy}quinolin-2-yl)methanone;
(6-{[5-(difluoromethyl)pyridin-2-yl]oxy}quinolin-2-yl)[(3R)-3-(methoxymethyl)piperazin-1-yl]methanone;
[(2S*)-2-(difluoromethyl)piperazin-1-yl](6-{[5-(trifluoromethyl)pyridin-2-yl]oxy}quinolin-2-yl)methanone;
N-[(3R*)-1-methyl-5-oxopyrrolidin-3-yl]-6-{[5-(trifluoromethyl)pyridin-2-yl]oxy}quinoline-2-carboxamide;
N-[(3S*) 1-methyl-5-oxopyrrolidin-3-yl]-6-{[5-(trifluoromethyl)pyridin-2-yl]oxy}quinoline-2-carboxamide;
N-(3,3,3-trifluoro-2-hydroxypropyl)-6-{[5-(trifluoromethyl)pyridin-2-yl]oxy}quinoline-2-carboxamide;
morpholin-4-yl[6-(pyridin-2-yloxy)quinolin-2-yl]methanone;
(4-methylpiperazin-1-yl)[6-(pyridin-2-yloxy) quinolin-2-yl]methanone;
[3-(3-methyl-1,2,4-oxadiazol-5-yl)piperidin-1-yl][6-(pyridin-2-yloxy)quinolin-2-yl]methanone;
N-[2-(piperidin-1-yl)ethyl]-6-(pyridin-2-yloxy)quinoline-2-carboxamide;
6-(pyridin-2-yloxy)-N-(1,2,4-thiadiazol-5-yl)quinoline-2-carboxamide;
4-({2-[(4-methylpiperazin-1-yl)carbonyl]quinolin-6-yl}oxy)benzonitrile;
6-(4-cyanophenoxy)-N-[2-(piperidin-1-yl)ethyl]quinoline-2-carboxamide;
4-{[2-(morpholin-4-ylcarbonyl)quinolin-6-yl]oxy}benzonitrile;
6-(4-cyanophenoxy)-N-(1H-indazol-6-yl)quinoline-2-carboxamide;
6-(4-cyanophenoxy)-N-[3-(dimethylamino)propyl]quinoline-2-carboxamide;
6-(4-cyanophenoxy)-N-[2-(morpholin-4-yl)ethyl]quinoline-2-carboxamide;
6-(4-cyanophenoxy)-N-[3-(morpholin-4-yl)propyl]quinoline-2-carboxamide;
6-(4-cyanophenoxy)-N-(1,3-thiazol-2-yl)quinoline-2-carboxamide;
6-(4-cyanophenoxy)-N-(pyridin-3-ylmethyl)quinoline-2-carboxamide;
6-(4-cyanophenoxy)-N-[(3S)-2-oxotetrahydrofuran-3-yl]quinoline-2-carboxamide;
6-(4-cyanophenoxy)-N-[(2R)-1-hydroxy-3-methylbutan-2-yl]quinoline-2-carboxamide;
6-(4-cyanophenoxy)-N-(2-thienylmethyl)quinoline-2-carboxamide;
6-(4-cyanophenoxy)-N-[2-(2-thienyl)ethyl]quinoline-2-carboxamide;
6-(4-cyanophenoxy)-N-(2-furylmethyl)quinoline-2-carboxamide;
6-(4-cyanophenoxy)-N-(1-hydroxy-3-methylbutan-2-yl)quinoline-2-carboxamide;
6-(4-cyanophenoxy)-N-[2-(pyrrolidin-1-yl)ethyl]quinoline-2-carboxamide;
6-(4-cyanophenoxy)-N-(pyridin-2-ylmethyl)quinoline-2-carboxamide;
6-(4-cyanophenoxy)-N-(pyridin-4-ylmethyl)quinoline-2-carboxamide;
6-(4-cyanophenoxy)-N-[(5-methyl-2-furyl)methyl]quinoline-2-carboxamide,
6-(4-cyanophenoxy)-N-[3-(piperidin-1-yl)propyl]quinoline-2-carboxamide;
6-(4-cyanophenoxy)-N-(4-phenoxyphenyl)quinoline-2-carboxamide;
6-(4-cyanophenoxy)-N-[3-(trifluoromethoxy)benzyl]quinoline-2-carboxamide;
6-(4-cyanophenoxy)-N-(4-methylbenzyl)quinoline-2-carboxamide;
N-(1,3-benzodioxol-5-ylmethyl)-6-(4-cyanophenoxy)quinoline-2-carboxamide;
6-(4-cyanophenoxy)-N-(2,3-dimethoxybenzyl)quinoline-2-carboxamide;
4-{[2-(azepan-1-ylcarbonyl)quinolin-6-yl]oxy}benzonitrile;
6-(4-cyanophenoxy)-N-(2-methoxy ethyl)-N-propylquinoline-2-carboxamide;
6-(4-cyanophenoxy)-N-(2-ethoxyethyl)quinoline-2-carboxamide;
N-(1-benzylpyrrolidin-3-yl)-6-(4-cyanophenoxy)quinoline-2-carboxamide;
4-[(2-{[3-(trifluoromethyl)piperidin-1-yl]carbonyl}quinolin-6-yl)oxy]benzonitrile;
4-{[2-(2, 3-dihydro-1H-indol-1-ylcarbonyl) quinolin-6-yl]oxy}benzonitrile;
4-{[2-(piperazin-1-ylcarbonyl)quinolin-6-yl]oxy}benzonitrile;
6-(4-cyanophenoxy)-N-[(3R)-2-oxotetrahydrofuran-3-yl]quinoline-2-carboxamide;
6-(4-cyanophenoxy)-N-(tetrahydrofuran-3-yl)quinoline-2-carboxamide;
6-(4-cyanophenoxy)-N-(methylsulfonyl)quinoline-2-carboxamide;
6-(4-cyanophenoxy)-N-(tetrahydro-2H-pyran-3-yl)quinoline-2-carboxamide;
6-(4-cyanophenoxy)-N-[(3R)-tetrahydrofuran-3-yl]quinoline-2-carboxamide;
6-(4-cyanophenoxy)-N-[(3S)-tetrahydrofuran-3-yl]quinoline-2-carboxamide;

6-(4-cyanophenoxy)-N-[(1R,2S)-2-hydroxycyclohexyl]quinoline-2-carboxamide;
6-(4-cyanophenoxy)-N-[(1S,2S)-2-hydroxycyclohexyl]quinoline-2-carboxamide;
6-(4-cyanophenoxy)-N-[(1S,2S)-2-hydroxycyclopentyl]quinoline-2-carboxamide;
6-(4-cyanophenoxy)-N-(2-hydroxy-2-methylpropyl)quinoline-2-carboxamide;
6-(4-cyanophenoxy)-N-[1-(hydroxymethyl)cyclopropyl]quinoline-2-carboxamide;
6-(4-cyanophenoxy)-N-(1-hydroxy-2-methylpropan-2-yl)quinoline-2-carboxamide;
6-(4-cyanophenoxy)-N-(trans-4-hydroxycyclohexyl) quinoline-2-carboxamide;
6-(4-cyanophenoxy)-N-(1,3-dihydroxypropan-2-yl)quinoline-2-carboxamide;
6-(4-cyanophenoxy)-N-(1-hydroxypropan-2-yl)quinoline-2-carboxamide;
6-(4-cyanophenoxy)-N-(2-hydroxypropyl)quinoline-2-carboxamide;
6-(4-cyanophenoxy)-N-[(1S,3R)-3-hydroxycyclohexyl]quinoline-2-carboxamide;
6-(4-cyanophenoxy)-N-[(1S,3R)-3-hydroxycyclopentyl]quinoline-2-carboxamide;
6-(4-cyanophenoxy)-N-[(1R,2S)-2-hydroxycyclopentyl]quinoline-2-carboxamide;
6-(4-cyanophenoxy)-N-[(1S,3S)-3-hydroxycyclohexyl]quinoline-2-carboxamide;
6-(4-cyanophenoxy)-N-(cis-4-hydroxycyclohexyl)quinoline-2-carboxamide;
6-(4-cyanophenoxy)-N-(3-hydroxybutan-2-yl)quinoline-2-carboxamide,
6-(4-cyanophenoxy)-N-(2-hydroxy-3-methylbutyl)quinoline-2-carboxamide;
6-(4-cyanophenoxy)-N-(1,1-dioxidotetrahydrothiophen-3-yl)quinoline-2-carboxamide;
4-({2-[(3-oxopiperazin-1-yl)carbonyl]quinolin-6-yl}oxy)benzonitrile;
4-[(2-{[4-(morpholin-4-yl)piperidin-1-yl]carbonyl}quinolin-6-yl)oxy]benzonitrile;
6-(4-cyanophenoxy)-N-[(4R)-6-fluoro-3,4-dihydro-2H-chromen-4-yl]quinoline-2-carboxamide;
4-({2-[(4-tert-butylpiperazin-1-yl)carbonyl]quinolin-6-yl}oxy)benzonitrile;
6-(4-cyanophenoxy)-N-[(4R)-6-fluoro-2,2-dimethyl-3,4-dihydro-2H-chromen-4-yl]quinoline-2-carboxamide;
4-[(2-{[(3S)-3-isopropylpiperazin-1-yl]carbonyl}quinolin-6-yl)oxy]benzonitrile;
6-(4-cyanophenoxy)-N-(1-methyl-2-oxopyrrolidin-3-yl)quinoline-2-carboxamide;
6-(4-cyanophenoxy)-N-(1,3-oxazol-2-ylmethyl)quinoline-2-carboxamide;
6-(4-cyanophenoxy)-N-[2-(methylamino)-2-oxoethyl]quinoline-2-carboxamide;
N-(2-amino-2-oxoethyl)-6-(4-cyanophenoxy)quinoline-2-carboxamide;
6-(4-cyanophenoxy)-N-(2-sulfamoylethyl)quinoline-2-carboxamide;
4-({2-[(1,1-dioxidothiomorpholin-4-yl)carbonyl]quinolin-6-yl}oxy)benzonitrile;
N-(tetrahydrofuran-3-yl)-6-{[5-(trifluoromethyl)pyridin-2-yl]oxy}quinoline-2-carboxamide;
N-(2-amino-2-oxoethyl)-6-{[5-(trifluoromethyl)pyridin-2-yl]oxy}quinoline-2-carboxamide;
N-(pyridin-2-ylmethyl)-6-{[5-(trifluoromethyl)pyridin-2-yl]oxy}quinoline-2-carboxamide;
piperazin-1-yl(6-{[4-(trifluoromethyl)pyridin-2-yl]oxy}quinolin-2-yl)methanone;
piperazin-1-yl(6-{[6-(trifluoromethyl)pyridin-2-yl]oxy}quinolin-2-yl)methanone;
6-{[3-chloro-5-(trifluoromethyl)pyridin-2-yl]oxy}-N-(1,1-dioxidotetrahydrothiophen-3-yl)quinoline-2-carboxamide;
N-(1,1-dioxidotetrahydrothiophen-3-yl)-6-{[5-(trifluoromethyl)pyrimidin-2-yl]oxy}quinoline-2-carboxamide;
2-oxa-6-azaspiro[3.3]hept-6-yl(6-{[5-(trifluoromethyl)pyridin-2-yl]oxy}quinolin-2-yl)methanone;
2,6-diazaspiro[3.3]hept-2-yl(6-{[5-(trifluoromethyl)pyridin-2-yl]oxy}quinolin-2-yl)methanone;
6-[(5-cyanopyridin-2-yl)oxy]-N-(1,1-dioxidotetrahydrothiophen-3-yl)quinoline-2-carboxamide;
6-(4-cyanophenoxy)-N-[(3S)-1,1-dioxidotetrahydrothiophen-3-yl]quinoline-2-carboxamide;
6-(4-cyanophenoxy)-N-[(3R)-1,1-dioxidotetrahydrothiophen-3-yl]quinoline-2-carboxamide;
N-(1,1-dioxidotetrahydrothiophen-3-yl)-6-[(5-methylpyrimidin-2-yl)oxy]quinoline-2-carboxamide;
6-[(4,6-dimethylpyrimidin-2-yl)oxy]-N-(1,1-dioxidotetrahydrothiophen-3-yl)quinoline-2-carboxamide;
N-(1,1-dioxidotetrahydrothiophen-3-yl)-6-[(4-methylpyrimidin-2-yl)oxy]quinoline-2-carboxamide;
(3aR,6aS)-hexahydropyrrolo[3,4-c]pyrrol-2(1H)-yl(6-{[5-(trifluoromethyl)pyridin-2-yl]oxy}quinolin-2-yl)methanone;
6-[(6-chloropyridazin-3-yl)oxy]-N-(1,1-dioxidotetrahydrothiophen-3-yl)quinoline-2-carboxamide;
(3aR,6aR)-5-[(6-{[5-(trifluoromethyl)pyridin-2-yl]oxy}quinolin-2-yl)carbonyl]hexahydropyrrolo[3,4-c]pyrrol-1(2H)-one;
(3aR,4R,7S,7aS)-octahydro-1H-4,7-epiminoisoindol-8-yl (6-{[5-(trifluoromethyl)pyridin-2-yl]oxy}quinolin-2-yl)methanone;
N-(1,1-dioxidotetrahydrothiophen-3-yl)-6-{[6-(trifluoromethyl)pyridazin-3-yl]oxy}quinoline-2-carboxamide;
8-[(6-{[5-(trifluoromethyl)pyridin-2-yl]oxy}quinolin-2-yl)carbonyl]hexahydro-2H-pyrazino[1,2-a]pyrazin-1(6H)-one;
5,6-dihydro[1,2,4]triazolo[4,3-a]pyrazin-7(8H)-yl(6-{[5-(trifluoromethyl)pyridin-2-yl]oxy}quinolin-2-yl)methanone;
8-[(6-{[5-(trifluoromethyl)pyridin-2-yl]oxy}quinolin-2-yl)carbonyl]tetrahydro-2H-pyrazino[1,2-a]pyrazine-1,4(3H,6H)-dione;
4-[(6-{[5-(trifluoromethyl)pyridin-2-yl]oxy}quinolin-2-yl)carbonyl]piperazin-2-one;
5,6-dihydroimidazo[1,5-a]pyrazin-7(8H)-yl(6-{[5-(trifluoromethyl)pyridin-2-yl]oxy}quinolin-2-yl)methanone;
N-[2-(pyrrolidin-1-yl)ethyl]-6-{[5-(trifluoromethyl)pyridin-2-yl]oxy}quinoline-2-carboxamide;
N-[2-(piperidin-1-yl)ethyl]-6-{[5-(trifluoromethyl)pyridin-2-yl]oxy}quinoline-2-carboxamide;
[4-(methylsulfonyl)piperazin-1-yl](6-{[5-(trifluoromethyl)pyridin-2-yl]oxy}quinolin-2-yl)methanone;
[4-(isopropylsulfonyl)piperazin-1-yl](6-{[5-(trifluoromethyl)pyridin-2-yl]oxy}quinolin-2-yl)methanone;
[4-(phenylsulfonyl)piperazin-1-yl](6-{[5-(trifluoromethyl)pyridin-2-yl]oxy}quinolin-2-yl)methanone;
[(2R,4S)-2-(2,5-difluorophenyl)-4-fluoropyrrolidin-1-yl](6-{[5-(trifluoromethyl)pyridin-2-yl]oxy}quinolin-2-yl)methanone;
[(2R,4R)-2-(2,5-difluorophenyl)-4-fluoropyrrolidin-1-yl](6-{[5-(trifluoromethyl)pyridin-2-yl]oxy}quinolin-2-yl)methanone;

[4-(2,2,2-trifluoroethyl)piperazin-1-yl](6-{[5-(trifluoromethyl)pyridin-2-yl]oxy}quinolin-2-yl)methanone;
[4-(pyridin-2-yl)piperazin-1-yl](6-{[5-(trifluoromethyl)pyridin-2-yl]oxy}quinolin-2-yl)methanone;
[4-(pyridin-3-ylsulfonyl)piperazin-1-yl](6-{[5-(trifluoromethyl)pyridin-2-yl]oxy}quinolin-2-yl)methanone;
[4-(piperidin-1-ylsulfonyl)piperazin-1-yl](6-{[5-(trifluoromethyl)pyridin-2-yl]oxy}quinolin-2-yl)methanone;
[4-(morpholin-4-ylsulfonyl)piperazin-1-yl](6-{[5-(trifluoromethyl)pyridin-2-yl]oxy}quinolin-2-yl)methanone;
methyl 4-[(6-{[5-(trifluoromethyl)pyridin-2-yl]oxy}quinolin-2-yl)carbonyl]piperazine-1-carboxylate;
N,N-dimethyl-4-[(6-{[5-(trifluoromethyl)pyridin-2-yl]oxy}quinolin-2-yl)carbonyl]piperazine-1-carboxamide;
5-methyl-8-[(6-{[5-(trifluoromethyl)pyridin-2-yl]oxy}quinolin-2-yl)carbonyl]-2-oxa-5,8-diazaspiro[3.5]nonan-6-one;
2-[(6-{[5-(trifluoromethyl)pyridin-2-yl]oxy}quinolin-2-yl)carbonyl]hexahydroimidazo[1,5-a]pyrazin-3(2H)-one;
(3,3-difluoro-4-hydroxypiperidin-1-yl)(6-{[5-(trifluoromethyl)pyridin-2-yl]oxy}quinolin-2-yl)methanone;
[cis-3-fluoro-4-hydroxypiperidin-1-yl](6-{[5-(trifluoromethyl)pyridin-2-yl]oxy}quinolin-2-yl)methanone;
[cis-4-fluoro-3-hydroxypiperidin-1-yl](6-{[5-(trifluoromethyl)pyridin-2-yl]oxy}quinolin-2-yl)methanone;
(4,4-difluoro-3-hydroxypiperidin-1-yl)(6-{[5-(trifluoromethyl)pyridin-2-yl]oxy}quinolin-2-yl)methanone;
[trans-3-ethyl-2-(hydroxymethyl)azetidin-1-yl](6-{[5-(trifluoromethyl)pyridin-2-yl]oxy}quinolin-2-yl)methanone;
[trans-3-fluoro-4-hydroxypiperidin-1-yl](6-{[5-(trifluoromethyl)pyridin-2-yl]oxy}quinolin-2-yl)methanone;
[trans-4-fluoro-3-hydroxypiperidin-1-yl](6-{[5-(trifluoromethyl)pyridin-2-yl]oxy}quinolin-2-yl)methanone;
(6-{[5-(trifluoromethyl)pyridin-2-yl]oxy}quinolin-2-yl)[(2R)-2,3,3-trimethylazetidin-1-yl]methanone;
(3-hydroxy-3-methylazetidin-1-yl)(6-{[5-(trifluoromethyl)pyridin-2-yl]oxy}quinolin-2-yl)methanone;
[3-(methoxymethyl)-3-methylazetidin-1-yl](6-{[5-(trifluoromethyl)pyridin-2-yl]oxy}quinolin-2-yl)methanone;
(3-methyl-3-phenoxyazetidin-1-yl)(6-{[5-(trifluoromethyl)pyridin-2-yl]oxy}quinolin-2-yl)methanone;
(3-phenoxyazetidin-1-yl)(6-{[5-(trifluoromethyl)pyridin-2-yl]oxy}quinolin-2-yl)methanone;
[3-(1H-imidazol-1-yl)azetidin-1-yl](6-{[5-(trifluoromethyl)pyridin-2-yl]oxy}quinolin-2-yl)methanone;
[3-(4-chlorophenoxy)azetidin-1-yl](6-{[5-(trifluoromethyl)pyridin-2-yl]oxy}quinolin-2-yl)methanone;
[3-(1H-1,2,4-triazol-1-yl)azetidin-1-yl](6-{[5-(trifluoromethyl)pyridin-2-yl]oxy}quinolin-2-yl)methanone;
(6-{[5-(trifluoromethyl)pyridin-2-yl]oxy}quinolin-2-yl)[(2S)-2,3,3-trimethylazetidin-1-yl]methanone;
[3-(4-bromophenoxy)azetidin-1-yl](6-{[5-(trifluoromethyl)pyridin-2-yl]oxy}quinolin-2-yl)methanone;
[3-(hydroxymethyl)-3-methylazetidin-1-yl](6-{[5-(trifluoromethyl)pyridin-2-yl]oxy}quinolin-2-yl)methanone;
3-phenyl-4-[(6-{[5-(trifluoromethyl)pyridin-2-yl]oxy}quinolin-2-yl)carbonyl]piperazin-2-one;
{6-[4-(2-hydroxypropan-2-yl)phenoxy]quinolin-2-yl}(piperazin-1-yl)methanone;
6-{[5-(trifluoromethyl)pyridin-2-yl]oxy}quinoline-2-carboxamide;
(4-methylpiperazin-1-yl)(6-{[5-(trifluoromethyl)pyridin-2-yl]oxy}quinolin-2-yl)methanone;
(8S,9aS)-8-hydroxy-2-[(6-{[5-(trifluoromethyl)pyridin-2-yl]oxy}quinolin-2-yl)carbonyl]octahydro-5H-pyrrolo[1,2-a][1,4]diazepin-5-one;
(1S,6R)-3,8-diazabicyclo[4.2.0]oct-3-yl(6-{[5-(trifluoromethyl)pyridin-2-yl]oxy}quinolin-2-yl)methanone;
{6-[4-(methylsulfonyl)phenoxy]quinolin-2-yl}(piperazin-1-yl)methanone;
piperazin-1-yl(6-{4-[(trifluoromethyl)sulfonyl]phenoxy}quinolin-2-yl)methanone;
N-(azetidin-3-yl)-6-{[5-(trifluoromethyl)pyridin-2-yl]oxy}quinoline-2-carboxamide;
[3-(pyridin-3-yl)azetidin-1-yl](6-{[5-(trifluoromethyl)pyridin-2-yl]oxy}quinolin-2-yl)methanone;
1-{4-[(6-{[5-(trifluoromethyl)pyridin-2-yl]oxy}quinolin-2-yl)carbonyl]piperazin-1-yl}ethanone;
1,4-diazepan-1-yl(6-{[5-(trifluoromethyl)pyridin-2-yl]oxy}quinolin-2-yl)methanone;
2,5-dihydro-1H-pyrrol-1-yl(6-{[5-(trifluoromethyl)pyridin-2-yl]oxy}quinolin-2-yl)methanone;
thiomorpholin-4-yl(6-{[5-(trifluoromethyl)pyridin-2-yl]oxy}quinolin-2-yl)methanone;
3,4-dihydro-2,7-naphthyridin-2(1H)-yl(6-{[5-(trifluoromethyl)pyridin-2-yl]oxy}quinolin-2-yl)methanone;
[(2R,4S)-2-(2,5-difluorophenyl)-4-hydroxypyrrolidin-1-yl](6-{[5-(trifluoromethyl)pyridin-2-yl]oxy}quinolin-2-yl)methanone;
{2-[4-(trifluoromethyl)phenyl]pyrrolidin-1-yl}(6-{[5-(trifluoromethyl)pyridin-2-yl]oxy}quinolin-2-yl)methanone;
N-{(2R,3S)-2-phenyl-1-[(6-{[5-(trifluoromethyl)pyridin-2-yl]oxy}quinolin-2-yl)carbonyl]pyrrolidin-3-yl}-4-(trifluoromethyl)benzenesulfonamide;
1-(6-{[2-(piperazin-1-ylcarbonyl)quinolin-6-yl]oxy}pyridin-3-yl)ethanone;
(1,1-dioxidothiomorpholin-4-yl)(6-{[5-(trifluoromethyl)pyridin-2-yl]oxy}quinolin-2-yl)methanone;
(4-tert-butylpiperazin-1-yl)(6-{[5-(trifluoromethyl)pyridin-2-yl]oxy}quinolin-2-yl)methanone;
{6-[(5-fluoropyridin-2-yl)oxy]quinolin-2-yl}(piperazin-1-yl)methanone;
N-[(3aS,4R,6aR)-2-benzyloctahydrocyclopenta[c]pyrrol-4-yl]-6-{[5-(trifluoromethyl)pyridin-2-yl]oxy}quinoline-2-carboxamide;
(4-isopropylpiperazin-1-yl)(6-{[5-(trifluoromethyl)pyridin-2-yl]oxy}quinolin-2-yl)methanone;
2,7-diazaspiro[3.5]non-2-yl(6-{[5-(trifluoromethyl)pyridin-2-yl]oxy}quinolin-2-yl)methanone;
tetrahydropyrimidin-1(2H)-yl(6-{[5-(trifluoromethyl)pyridin-2-yl]oxy}quinolin-2-yl)methanone;
[(2S)-2-(hydroxymethyl)piperazin-1-yl](6-{[5-(trifluoromethyl)pyridin-2-yl]oxy}quinolin-2-yl)methanone;
N-methyl-4-[(6-{[5-(trifluoromethyl)pyridin-2-yl]oxy}quinolin-2-yl)carbonyl]piperazine-1-sulfonamide;
N-ethyl-4-[(6-{[5-(trifluoromethyl)pyridin-2-yl]oxy}quinolin-2-yl)carbonyl]piperazine-1-sulfonamide;
[(2S)-2-(hydroxymethyl)pyrrolidin-1-yl](6-{[5-(trifluoromethyl)pyridin-2-yl]oxy}quinolin-2-yl)methanone;
azepan-1-yl(6-{[5-(trifluoromethyl)pyridin-2-yl]oxy}quinolin-2-yl)methanone;
N-methyl-1-[(6-{[5-(trifluoromethyl)pyridin-2-yl]oxy}quinolin-2-yl)carbonyl]-L-prolinamide;
1,4-dioxa-8-azaspiro[4.5]dec-8-yl(6-{[5-(trifluoromethyl)pyridin-2-yl]oxy}quinolin-2-yl)methanone;
(1R,4R)-2,5-diazabicyclo[2.2.1]hept-2-yl(6-{[5-(trifluoromethyl)pyridin-2-yl]oxy}quinolin-2-yl)methanone;
piperazin-1-yl[6-(pyrimidin-2-yloxy)quinolin-2-yl]methanone;
[(2R)-2-(hydroxymethyl)piperazin-1-yl](6-{[5-(trifluoromethyl)pyridin-2-yl]oxy}quinolin-2-yl)methanone;
{6-[(5-fluoropyrimidin-2-yl)oxy]quinolin-2-yl}(piperazin-1-yl)methanone;

piperazin-1-yl(6-{[5-(trifluoromethyl)pyrazin-2-yl]oxy}quinolin-2-yl)methanone;
piperazin-1-yl(6-{[6-(trifluoromethyl)pyridazin-3-yl]oxy}quinolin-2-yl)methanone;
piperazin-1-yl(6-{[5-(trifluoromethyl)pyrimidin-2-yl]oxy}quinolin-2-yl)methanone;
[(3aR,4S,6aS)-4-aminohexahydrocyclopenta[c]pyrrol-2(1H)-yl](6-{[5-(trifluoromethyl)pyridin-2-yl]oxy}quinolin-2-yl)methanone;
piperazin-1-yl {6-[4-(trifluoromethyl)phenoxy]quinolin-2-yl}methanone;
(6-{[3-fluoro-5-(trifluoromethyl)pyridin-2-yl]oxy}quinolin-2-yl)(piperazin-1-yl)methanone;
N-[2-(methylsulfonyl)ethyl]-6-{[5-(trifluoromethyl)pyridin-2-yl]oxy}quinoline-2-carboxamide;
[4-(oxetan-3-yl)piperazin-1-yl](6-{[5-(trifluoromethyl)pyridin-2-yl]oxy}quinolin-2-yl)methanone;
3,4-dihydroisoquinolin-2(1H)-yl(6-{[5-(trifluoromethyl)pyridin-2-yl]oxy}quinolin-2-yl)methanone;
[4-(methylsulfonyl)piperidin-1-yl](6-{[5-(trifluoromethyl)pyridin-2-yl]oxy}quinolin-2-yl)methanone;
(4-hydroxy-4-methylpiperidin-1-yl)(6-{[5-(trifluoromethyl)pyridin-2-yl]oxy}quinolin-2-yl)methanone;
(4-hydroxypiperidin-1-yl)(6-{[5-(trifluoromethyl)pyridin-2-yl]oxy}quinolin-2-yl)methanone;
[(1R,4R,6R)-6-(hydroxymethyl)-2-azabicyclo[2.2.1]hept-2-yl](6-{[5-(trifluoromethyl)pyridin-2-yl]oxy}quinolin-2-yl)methanone;
[(1R,4R,6S)-6-(hydroxymethyl)-2-azabicyclo[2.2.1]hept-2-yl](6-{[5-(trifluoromethyl)pyridin-2-yl]oxy}quinolin-2-yl)methanone;
N-[(3aR,4R,6aS)-2-benzyloctahydrocyclopenta[c]pyrrol-4-yl]-6-{[5-(trifluoromethyl)pyridin-2-yl]oxy}quinoline-2-carboxamide;
(4-methyl-1,4-diazepan-1-yl)(6-{[5-(trifluoromethyl)pyridin-2-yl]oxy}quinolin-2-yl)methanone;
(4-cyclopropylpiperazin-1-yl)(6-{[5-(trifluoromethyl)pyridin-2-yl]oxy}quinolin-2-yl)methanone;
(4-phenylpiperazin-1-yl)(6-{[5-(trifluoromethyl)pyridin-2-yl]oxy}quinolin-2-yl)methanone;
[(3R)-3-isopropylpiperazin-1-yl](6-{[5-(trifluoromethyl)pyridin-2-yl]oxy}quinolin-2-yl)methanone;
N-(piperidin-4-yl)-6-{[5-(trifluoromethyl)pyridin-2-yl]oxy}quinoline-2-carboxamide;
[4-(hydroxymethyl)piperidin-1-yl](6-{[5-(trifluoromethyl)pyridin-2-yl]oxy}quinolin-2-yl)methanone;
[3-(hydroxymethyl)pyrrolidin-1-yl](6-{[5-(trifluoromethyl)pyridin-2-yl]oxy}quinolin-2-yl)methanone;
N-(8-azabicyclo[3.2.1]oct-3-yl)-6-{[5-(trifluoromethyl)pyridin-2-yl]oxy}quinoline-2-carboxamide;
[4-(pyrazin-2-yl)piperazin-1-yl](6-{[5-(trifluoromethyl)pyridin-2-yl]oxy}quinolin-2-yl)methanone;
[4-(pyridin-3-yl)piperazin-1-yl](6-{[5-(trifluoromethyl)pyridin-2-yl]oxy}quinolin-2-yl)methanone;
[4-(pyrimidin-2-yl)piperazin-1-yl](6-{[5-(trifluoromethyl)pyridin-2-yl]oxy}quinolin-2-yl)methanone;
[4-(pyridazin-3-yl)piperazin-1-yl](6-{[5-(trifluoromethyl)pyridin-2-yl]oxy}quinolin-2-yl)methanone;
[4-(5-chloropyridin-2-yl)piperazin-1-yl](6-{[5-(trifluoromethyl)pyridin-2-yl]oxy}quinolin-2-yl)methanone;
[(3S)-3-ethylpiperazin-1-yl](6-{[5-(trifluoromethyl)pyridin-2-yl]oxy}quinolin-2-yl)methanone;
[(3S)-3-isopropylpiperazin-1-yl](6-{[5-(trifluoromethyl)pyridin-2-yl]oxy}quinolin-2-yl)methanone;
{6-[4-(1-hydroxyethyl)phenoxy]quinolin-2-yl}(piperazin-1-yl)methanone;
[(3S)-3-(hydroxymethyl)piperazin-1-yl](6-{[5-(trifluoromethyl)pyridin-2-yl]oxy}quinolin-2-yl)methanone;
isopropyl 4-[(6-{[5-(trifluoromethyl)pyridin-2-yl]oxy}quinolin-2-yl)carbonyl]piperazine-1-carboxylate;
(1S,5S)-3,6-diazabicyclo[3.2.0]hept-3-yl(6-{[5-(trifluoromethyl)pyridin-2-yl]oxy}quinolin-2-yl)methanone;
1,6-diazaspiro[3.3]hept-1-yl(6-{[5-(trifluoromethyl)pyridin-2-yl]oxy}quinolin-2-yl)methanone;
(3aS,6aS)-hexahydropyrrolo[3,4-b]pyrrol-5 (1H)-yl(6-{[5-(trifluoromethyl)pyridin-2-yl]oxy}quinolin-2-yl)methanone;
N-(morpholin-4-yl)-6-{[5-(trifluoromethyl)pyridin-2-yl]oxy}quinoline-2-carboxamide;
[(3R)-3-hydroxypyrrolidin-1-yl](6-{[5-(trifluoromethyl)pyridin-2-yl]oxy}quinolin-2-yl)methanone;
[(3S)-3-hydroxypyrrolidin-1-yl](6-{[5-(trifluoromethyl)pyridin-2-yl]oxy}quinolin-2-yl)methanone;
(4-hydroxyazepan-1-yl)(6-{[5-(trifluoromethyl)pyridin-2-yl]oxy}quinolin-2-yl)methanone;
N-(4-hydroxy-1,1-dioxidotetrahydrothiophen-3-yl)-6-{[5-(trifluoromethyl)pyridin-2-yl]oxy}quinoline-2-carboxamide;
{4-[(3-methyloxetan-3-yl)methyl]piperazin-1-yl}(6-{[5-(trifluoromethyl)pyridin-2-yl]oxy}quinolin-2-yl)methanone;
[3-(methylsulfonyl)pyrrolidin-1-yl](6-{[5-(trifluoromethyl)pyridin-2-yl]oxy}quinolin-2-yl)methanone;
2-[(6-{[5-(trifluoromethyl)pyridin-2-yl]oxy}quinolin-2-yl)carbonyl]hexahydropyrrolo[1,2-a]pyrazin-6(2H)-one;
ethyl 4-[(6-{[5-(trifluoromethyl)pyridin-2-yl]oxy}quinolin-2-yl)carbonyl]piperazine-1-carboxylate;
cyclopropyl{4-[(6-{[5-(trifluoromethyl)pyridin-2-yl]oxy}quinolin-2-yl)carbonyl]piperazin-1-yl}methanone;
(4-cyclohexylpiperazin-1-yl)(6-{[5-(trifluoromethyl)pyridin-2-yl]oxy}quinolin-2-yl)methanone;
(3-fluoro-4-hydroxypyrrolidin-1-yl)(6-{[5-(trifluoromethyl)pyridin-2-yl]oxy}quinolin-2-yl)methanone;
isobutyl 4-[(6-{[5-(trifluoromethyl)pyridin-2-yl]oxy}quinolin-2-yl)carbonyl]piperazine-1-carboxylate;
(4-ethylpiperazin-1-yl)(6-{[5-(trifluoromethyl)pyridin-2-yl]oxy}quinolin-2-yl)methanone;
(6-{[3-bromo-5-(trifluoromethyl)pyridin-2-yl]oxy}quinolin-2-yl)(piperazin-1-yl)methanone;
morpholin-4-yl(6-{[5-(trifluoromethyl)pyridin-2-yl]oxy}quinolin-2-yl)methanone;
piperidin-1-yl(6-{[5-(trifluoromethyl)pyridin-2-yl]oxy}quinolin-2-yl)methanone;
[4-(2,2-difluoroethyl)piperazin-1-yl](6-{[5-(trifluoromethyl)pyridin-2-yl]oxy}quinolin-2-yl)methanone;
morpholin-4-yl {4-[(6-{[5-(trifluoromethyl)pyridin-2-yl]oxy}quinolin-2-yl)carbonyl]piperazin-1-yl}methanone;
[(2S,4R)-4-hydroxy-2-(hydroxymethyl)pyrrolidin-1-yl](6-{[5-(trifluoromethyl)pyridin-2-yl]oxy}quinolin-2-yl)methanone;
[(3R)-3-fluoropyrrolidin-1-yl](6-{[5-(trifluoromethoxy)pyridin-2-yl]oxy}quinolin-2-yl)methanone;
N-(trans-3-hydroxycyclobutyl)-6-{[5-(trifluoromethyl)pyridin-2-yl]oxy}quinoline-2-carboxamide;
[trans-3,4-dihydroxypyrrolidin-1-yl](6-{[5-(trifluoromethyl)pyridin-2-yl]oxy}quinolin-2-yl)methanone;
[(2R,3S)-3-hydroxy-2-(hydroxymethyl)pyrrolidin-1-yl](6-{[5-(trifluoromethyl)pyridin-2-yl]oxy}quinolin-2-yl)methanone;
[trans-3-hydroxy-4-methoxypyrrolidin-1-yl](6-{[5-(trifluoromethyl)pyridin-2-yl]oxy}quinolin-2-yl)methanone;
[trans-3-hydroxy-4-methylpyrrolidin-1-yl](6-{[5-(trifluoromethyl)pyridin-2-yl]oxy}quinolin-2-yl)methanone;

[cis-3,5-bis(hydroxymethyl)piperidin-1-yl](6-{[5-(trifluoromethyl)pyridin-2-yl]oxy}quinolin-2-yl)methanone;
[4-(pyridin-2-ylmethyl)piperazin-1-yl](6-{[5-(trifluoromethyl)pyridin-2-yl]oxy}quinolin-2-yl)methanone;
3,3-dimethyl-1-{4-[(6-{[5-(trifluoromethyl)pyridin-2-yl]oxy}quinolin-2-yl)carbonyl]piperazin-1-yl}butan-1-one;
[(3R)-3-aminopyrrolidin-1-yl](6-{[5-(trifluoromethyl)pyridin-2-yl]oxy}quinolin-2-yl)methanone;
(6-{[5-(trifluoromethyl)pyridin-2-yl]oxy}quinolin-2-yl)[4-(3,3,3-trifluoropropyl)piperazin-1-yl]methanone;
(3,3-difluoropiperidin-1-yl)(6-{[5-(trifluoromethyl)pyridin-2-yl]oxy}quinolin-2-yl)methanone;
[(5S,7S)-7-hydroxy-1-azaspiro[4.4]non-1-yl](6-{[5-(trifluoromethyl)pyridin-2-yl]oxy}quinolin-2-yl)methanone;
[3-(azetidin-1-yl)pyrrolidin-1-yl](6-{[5-(trifluoromethyl)pyridin-2-yl]oxy}quinolin-2-yl)methanone;
[4-(1,3-oxazol-4-ylmethyl)piperazin-1-yl](6-{[5-(trifluoromethyl)pyridin-2-yl]oxy}quinolin-2-yl)methanone;
[3-(morpholin-4-yl)pyrrolidin-1-yl](6-{[5-(trifluoromethyl)pyridin-2-yl]oxy}quinolin-2-yl)methanone;
N-(2-sulfamoylethyl)-6-{[5-(trifluoromethyl)pyridin-2-yl]oxy}quinoline-2-carboxamide;
(4-fluoropiperidin-1-yl)(6-{[5-(trifluoromethyl)pyridin-2-yl]oxy}quinolin-2-yl)methanone;
[(3R)-3-(piperidin-1-yl)pyrrolidin-1-yl](6-{[5-(trifluoromethyl)pyridin-2-yl]oxy}quinolin-2-yl)methanone;
piperazin-1-yl(6-{[5-(trifluoromethyl)-1,3,4-thiadiazol-2-yl]oxy}quinolin-2-yl)methanone;
N-isopropyl-4-[(6-{[5-(trifluoromethyl)pyridin-2-yl]oxy}quinolin-2-yl)carbonyl]piperazine-2-carboxamide;
N-methyl-4-[(6-{[5-(trifluoromethyl)pyridin-2-yl]oxy}quinolin-2-yl)carbonyl]piperazine-2-carboxamide;
rac-[(3R,4S)-3,4-dihydroxy-2,5-dimethylpyrrolidin-1-yl](6-{[5-(trifluoromethyl)pyridin-2-yl]oxy}quinolin-2-yl)methanone;
[cis-3,4-dimethoxypyrrolidin-1-yl](6-{[5-(trifluoromethyl)pyridin-2-yl]oxy}quinolin-2-yl)methanone;
(3S)-1-[(6-{[5-(trifluoromethyl)pyridin-2-yl]oxy}quinolin-2-yl)carbonyl]piperidine-3-carboxamide;
N-(2-hydroxyethyl)-6-{[5-(trifluoromethyl)pyridin-2-yl]oxy}quinoline-2-carboxamide;
N-(tetrahydro-2H-pyran-4-yl)-6-{[5-(trifluoromethyl)pyridin-2-yl]oxy}quinoline-2-carboxamide;
6-{[2-(piperazin-1-ylcarbonyl)quinolin-6-yl]oxy}nicotinonitrile;
7-[(6-{[5-(trifluoromethyl)pyridin-2-yl]oxy}quinolin-2-yl)carbonyl]hexahydro[1,3]oxazolo[3,4-a]pyrazin-3-one;
(4,4-difluoropiperidin-1-yl)(6-{[5-(trifluoromethyl)pyridin-2-yl]oxy}quinolin-2-yl)methanone;
N-[(3R)-pyrrolidin-3-yl]-6-{[5-(trifluoromethyl)pyridin-2-yl]oxy}quinoline-2-carboxamide;
(6-{[5-(trifluoromethyl)pyridin-2-yl]oxy}quinolin-2-yl) {4-[(3,3,3-trifluoropropyl)sulfonyl]piperazin-1-yl}methanone;
(8aR)-7-[(6-{[5-(trifluoromethyl)pyridin-2-yl]oxy}quinolin-2-yl)carbonyl]hexahydro[1,3]oxazolo[3,4-a]pyrazin-3-one;
N-(3-hydroxy-3-methylbutyl)-6-{[5-(trifluoromethyl)pyridin-2-yl]oxy}quinoline-2-carboxamide;
N-[(2R)-pyrrolidin-2-ylmethyl]-6-{[5-(trifluoromethyl)pyridin-2-yl]oxy}quinoline-2-carboxamide;
N-[(1-hydroxycyclobutyl)methyl]-6-{[5-(trifluoromethyl)pyridin-2-yl]oxy}quinoline-2-carboxamide;
N-[2-(2-oxopyrrolidin-1-yl)ethyl]-6-{[5-(trifluoromethyl)pyridin-2-yl]oxy}quinoline-2-carboxamide;
N-(2-aminoethyl)-6-{[5-(trifluoromethyl)pyridin-2-yl]oxy}quinoline-2-carboxamide;
[2-(hydroxymethyl)morpholin-4-yl](6-{[5-(trifluoromethyl)pyridin-2-yl]oxy}quinolin-2-yl)methanone;
[2-(fluoromethyl)morpholin-4-yl](6-{[5-(trifluoromethyl)pyridin-2-yl]oxy}quinolin-2-yl)methanone;
(1-hydroxy-7-azaspiro[3.5]non-7-yl)(6-{[5-(trifluoromethyl)pyridin-2-yl]oxy}quinolin-2-yl)methanone;
6-[(6-{[5-(trifluoromethyl)pyridin-2-yl]oxy}quinolin-2-yl)carbonyl]-5,6,7,8-tetrahydropyrido[4,3-d]pyrimidin-4(3H)-one;
4-[(6-{[5-(trifluoromethyl)pyridin-2-yl]oxy}quinolin-2-yl)carbonyl]-1,4-diazepan-2-one;
N-(2,2,2-trifluoroethyl)-6-{[5-(trifluoromethyl)pyridin-2-yl]oxy}quinoline-2-carboxamide;
(2-hydroxy-6-azaspiro[3.4]oct-6-yl)(6-{[5-(trifluoromethyl)pyridin-2-yl]oxy}quinolin-2-yl)methanone;
N-(2-fluoroethyl)-6-{[5-(trifluoromethyl)pyridin-2-yl]oxy}quinoline-2-carboxamide;
N-(2,2-difluoroethyl)-6-{[5-(trifluoromethyl)pyridin-2-yl]oxy}quinoline-2-carboxamide;
[(3S,4S)-3-hydroxy-4-(methylsulfanyl)pyrrolidin-1-yl](6-{[5-(trifluoromethyl)pyridin-2-yl]oxy}quinolin-2-yl)methanone;
N-(1,1-dioxidotetrahydro-2H-thiopyran-3-yl)-6-{[5-(trifluoromethyl)pyridin-2-yl]oxy}quinoline-2-carboxamide;
[cis-3,4-dihydroxypiperidin-1-yl](6-{[5-(trifluoromethyl)pyridin-2-yl]oxy}quinolin-2-yl)methanone;
[trans-3-hydroxy-4-(methylsulfonyl)pyrrolidin-1-yl](6-{[5-(trifluoromethyl)pyridin-2-yl]oxy}quinolin-2-yl)methanone;
1,4-dioxa-7-azaspiro[4.4]non-7-yl(6-{[5-(trifluoromethyl)pyridin-2-yl]oxy}quinolin-2-yl)methanone;
[4-(methoxyimino)piperidin-1-yl](6-{[5-(trifluoromethyl)pyridin-2-yl]oxy}quinolin-2-yl)methanone;
(2-hydroxy-7-azaspiro[3.5]non-7-yl)(6-{[5-(trifluoromethyl)pyridin-2-yl]oxy}quinolin-2-yl)methanone;
6-{[5-(trifluoromethyl)pyridin-2-yl]oxy}-N-(3,3,3-trifluoropropyl)quinoline-2-carboxamide;
[(7S,8aR)-7-fluorohexahydropyrrolo[1,2-a]pyrazin-2(1H)-yl](6-{[5-(trifluoromethyl)pyridin-2-yl]oxy}quinolin-2-yl)methanone;
[(3R,7S,8aR)-7-fluoro-3-methylhexahydropyrrolo[1,2-a]pyrazin-2(1H)-yl](6-{[5-(trifluoromethyl)pyridin-2-yl]oxy}quinolin-2-yl)methanone;
[(3R,8aR)-7,7-difluoro-3-methylhexahydropyrrolo[1,2-a]pyrazin-2(1H)-yl](6-{[5-(trifluoromethyl)pyridin-2-yl]oxy}quinolin-2-yl)methanone;
[(7S,8aS)-7-fluorohexahydropyrrolo[1,2-a]pyrazin-2(1H)-yl](6-{[5-(trifluoromethyl)pyridin-2-yl]oxy}quinolin-2-yl)methanone;
1,4,6,7-tetrahydro-5H-imidazo[4,5-c]pyridin-5-yl(6-{[5-(trifluoromethyl)pyridin-2-yl]oxy}quinolin-2-yl)methanone;
N-[(4-benzylmorpholin-3-yl)methyl]-6-{[5-(trifluoromethyl)pyridin-2-yl]oxy}quinoline-2-carboxamide;
N-[(4-hydroxytetrahydro-2H-pyran-4-yl)methyl]-6-{[5-(trifluoromethyl)pyridin-2-yl]oxy}quinoline-2-carboxamide;
N-[(2S)-pyrrolidin-2-ylmethyl]-6-{[5-(trifluoromethyl)pyridin-2-yl]oxy}quinoline-2-carboxamide;
N-[2-(3,3-dimethylazetidin-1-yl)ethyl]-6-{[5-(trifluoromethyl)pyridin-2-yl]oxy}quinoline-2-carboxamide;
N-[2-(thiomorpholin-4-yl)ethyl]-6-{[5-(trifluoromethyl)pyridin-2-yl]oxy}quinoline-2-carboxamide;
N-allyl-N-methyl-6-{[5-(trifluoromethyl)pyridin-2-yl]oxy}quinoline-2-carboxamide;
1-[(6-{[5-(trifluoromethyl)pyridin-2-yl]oxy}quinolin-2-yl)carbonyl]azetidine-3-carbonitrile;

[cis-3-hydroxy-4-(methoxymethoxy)pyrrolidin-1-yl](6-{[5-(trifluoromethyl)pyridin-2-yl]oxy}quinolin-2-yl)methanone;
N-[(1-hydroxycyclopropyl)methyl]-6-{[5-(trifluoromethyl)pyridin-2-yl]oxy}quinoline-2-carboxamide;
1-[(6-{[5-(trifluoromethyl)pyridin-2-yl]oxy}quinolin-2-yl)carbonyl]azetidin-3-one;
N-(4-hydroxytetrahydrofuran-3-yl)-6-{[5-(trifluoromethyl)pyridin-2-yl]oxy}quinoline-2-carboxamide;
5-{[2-(piperazin-1-ylcarbonyl)quinolin-6-yl]oxy}pyrazine-2-carbonitrile;
[cis-2,2-dimethyltetrahydro-5H-[1,3]dioxolo[4,5-c]pyrrol-5-yl](6-{[5-(trifluoromethyl)pyridin-2-yl]oxy}quinolin-2-yl)methanone;
{2-[(dimethylamino)methyl]morpholin-4-yl}(6-{[5-(trifluoromethyl)pyridin-2-yl]oxy}quinolin-2-yl)methanone;
1-[(6-{[5-(trifluoromethyl)pyridin-2-yl]oxy}quinolin-2-yl)carbonyl]piperidin-4-one;
N,N-di(tetrahydro-2H-pyran-4-yl)-6-{[5-(trifluoromethyl)pyridin-2-yl]oxy}quinoline-2-carboxamide;
{4-[(1S,4S)-2-oxa-5-azabicyclo[2.2.1]hept-5-yl]piperidin-1-yl}(6-{[5-(trifluoromethyl)pyridin-2-yl]oxy}quinolin-2-yl)methanone;
{4-[(1R,4R)-2-oxa-5-azabicyclo[2.2.1]hept-5-yl]piperidin-1-yl}(6-{[5-(trifluoromethyl)pyridin-2-yl]oxy}quinolin-2-yl)methanone;
N,N-bis(2-methoxyethyl)-6-{[5-(trifluoromethyl)pyridin-2-yl]oxy}quinoline-2-carboxamide;
N-[1-(hydroxymethyl)cyclopropyl]-6-{[5-(trifluoromethyl)pyridin-2-yl]oxy}quinoline-2-carboxamide;
[4-(tetrahydrofuran-3-ylsulfonyl)piperazin-1-yl](6-{[5-(trifluoromethyl)pyridin-2-yl]oxy}quinolin-2-yl)methanone;
methyl ({4-[(6-{[5-(trifluoromethyl)pyridin-2-yl]oxy}quinolin-2-yl)carbonyl]piperazin-1-yl}sulfonyl)acetate;
[4-(tetrahydro-2H-pyran-4-ylsulfonyl)piperazin-1-yl](6-{[5-(trifluoromethyl)pyridin-2-yl]oxy}quinolin-2-yl)methanone;
(4-{[1-(2-methoxyethyl)-1H-pyrazol-4-yl]sulfonyl}piperazin-1-yl)(6-{[5-(trifluoromethyl)pyridin-2-yl]oxy}quinolin-2-yl)methanone;
{4-[(tetrahydrofuran-3-ylmethyl)sulfonyl]piperazin-1-yl}(6-{[5-(trifluoromethyl)pyridin-2-yl]oxy}quinolin-2-yl)methanone;
{4-[(1,1-dioxidotetrahydrothiophen-3-yl)sulfonyl]piperazin-1-yl}(6-{[5-(trifluoromethyl)pyridin-2-yl]oxy}quinolin-2-yl)methanone;
{4-[(1-methyl-1H-pyrazol-4-yl)sulfonyl]piperazin-1-yl}(6-{[5-(trifluoromethyl)pyridin-2-yl]oxy}quinolin-2-yl)methanone;
N-[4-methyl-5-({4-[(6-{[5-(trifluoromethyl)pyridin-2-yl]oxy}quinolin-2-yl)carbonyl]piperazin-1-yl}sulfonyl)-1,3-thiazol-2-yl]acetamide
N-[5-({4-[(6-{[5-(trifluoromethyl)pyridin-2-yl]oxy}quinolin-2-yl)carbonyl]piperazin-1-yl}sulfonyl)-1,3-thiazol-2-yl]acetamide
{4-[(1,5-dimethyl-1H-pyrazol-4-yl)sulfonyl]piperazin-1-yl}(6-{[5-(trifluoromethyl)pyridin-2-yl]oxy}quinolin-2-yl)methanone;
N-[(3S)-tetrahydrofuran-3-yl]-6-{[5-(trifluoromethyl)pyridin-2-yl]oxy}quinoline-2-carboxamide;
N-(2-methoxyethyl)-N-methyl-6-{[5-(trifluoromethyl)pyridin-2-yl]oxy}quinoline-2-carboxamide;
N-[(3R)-tetrahydrofuran-3-yl]-6-{[5-(trifluoromethyl)pyridin-2-yl]oxy}quinoline-2-carboxamide;
N-[(2S)-tetrahydrofuran-2-ylmethyl]-6-{[5-(trifluoromethyl)pyridin-2-yl]oxy}quinoline-2-carboxamide;
[(3R,5R)-3,5-dihydroxypiperidin-1-yl](6-{[5-(trifluoromethyl)pyridin-2-yl]oxy}quinolin-2-yl)methanone;
(3-methoxyazetidin-1-yl)(6-{[5-(trifluoromethyl)pyridin-2-yl]oxy}quinolin-2-yl)methanone;
N-(trans-3-methoxycyclobutyl)-6-{[5-(trifluoromethyl)pyridin-2-yl]oxy}quinoline-2-carboxamide;
N-(4-hydroxy-1,1-dioxidotetrahydrothiophen-3-yl)-N-methyl-6-{[5-(trifluoromethyl)pyridin-2-yl]oxy}quinoline-2-carboxamide;
N-(oxetan-3-yl)-6-{[5-(trifluoromethyl)pyridin-2-yl]oxy}quinoline-2-carboxamide;
N-(tetrahydro-2H-thiopyran-4-yl)-6-{[5-(trifluoromethyl)pyridin-2-yl]oxy}quinoline-2-carboxamide;
N-[(1S,2R)-2-hydroxycyclopentyl]-6-{[5-(trifluoromethyl)pyridin-2-yl]oxy}quinoline-2-carboxamide;
4-[(6-{[5-(trifluoromethyl)pyridin-2-yl]oxy}quinolin-2-yl)carbonyl]piperazine-2-carboxamide;
(4-aminopiperidin-1-yl)(6-{[5-(trifluoromethyl)pyridin-2-yl]oxy}quinolin-2-yl)methanone;
(3,3-difluoropyrrolidin-1-yl)(6-{[5-(trifluoromethyl)pyridin-2-yl]oxy}quinolin-2-yl)methanone;
(3,3-dimethylpyrrolidin-1-yl)(6-{[5-(trifluoromethyl)pyridin-2-yl]oxy}quinolin-2-yl)methanone;
(6-fluoro-1,4-diazepan-1-yl)(6-{[5-(trifluoromethyl)pyridin-2-yl]oxy}quinolin-2-yl)methanone;
(6-hydroxy-1,4-diazepan-1-yl)(6-{[5-(trifluoromethyl)pyridin-2-yl]oxy}quinolin-2-yl)methanone;
N-{1-[(6-{[5-(trifluoromethyl)pyridin-2-yl]oxy}quinolin-2-yl)carbonyl]piperidin-4-yl}methanesulfonamide;
N-[(2R)-tetrahydrofuran-2-ylmethyl]-6-{[5-(trifluoromethyl)pyridin-2-yl]oxy}quinoline-2-carboxamide;
N-[(2S)-2-hydroxypropyl]-6-{[5-(trifluoromethyl)pyridin-2-yl]oxy}quinoline-2-carboxamide;
N-methyl-N-(tetrahydro-2H-pyran-4-yl)-6-{[5-(trifluoromethyl)pyridin-2-yl]oxy}quinoline-2-carboxamide;
N-[(3-hydroxy oxetan-3-yl)methyl]-6-{[5-(trifluoromethyl)pyridin-2-yl]oxy}quinoline-2-carboxamide;
N-[2-(dimethylamino)-2-oxoethyl]-N-methyl-6-{[5-(trifluoromethyl)pyridin-2-yl]oxy}quinoline-2-carboxamide;
(6-{[5-(trifluoromethyl)pyridin-2-yl]oxy}quinolin-2-yl)[3-(trifluoromethyl)pyrrolidin-1-yl]methanone;
(3,4-difluoropyrrolidin-1-yl)(6-{[5-(trifluoromethyl)pyridin-2-yl]oxy}quinolin-2-yl)methanone;
N-(6-oxopiperidin-3-yl)-6-{[5-(trifluoromethyl)pyridin-2-yl]oxy}quinoline-2-carboxamide;
(6,6-difluoro-1,4-diazepan-1-yl)(6-{[5-(trifluoromethyl)pyridin-2-yl]oxy}quinolin-2-yl)methanone;
5,8-diazaspiro[3.5]non-8-yl(6-{[5-(trifluoromethyl)pyridin-2-yl]oxy}quinolin-2-yl)methanone;
N-(1,1-dioxidotetrahydrothiophen-3-yl)-N-methyl-6-{[5-(trifluoromethyl)pyridin-2-yl]oxy}quinoline-2-carboxamide;
N-(tetrahydrothiophen-3-yl)-6-{[5-(trifluoromethyl)pyridin-2-yl]oxy}quinoline-2-carboxamide;
N-[2-(2-oxoimidazolidin-1-yl)ethyl]-6-{[5-(trifluoromethyl)pyridin-2-yl]oxy}quinoline-2-carboxamide;
N-[2-(pyridin-2-ylamino)ethyl]-6-{[5-(trifluoromethyl)pyridin-2-yl]oxy}quinoline-2-carboxamide;
N-[2-(1H-imidazol-1-yl)ethyl]-6-{[5-(trifluoromethyl)pyridin-2-yl]oxy}quinoline-2-carboxamide;
N-(azetidin-2-ylmethyl)-6-{[5-(trifluoromethyl)pyridin-2-yl]oxy}quinoline-2-carboxamide;
N-[(3R,4R)-4-hydroxy-1,1-dioxidotetrahydrothiophen-3-yl]-6-{[5-(trifluoromethyl)pyridin-2-yl]oxy}quinoline-2-carboxamide;
N-(3-hydroxy-3-methylcyclobutyl)-6-{[5-(trifluoromethyl)pyridin-2-yl]oxy}quinoline-2-carboxamide;

[3-(2-methoxyethoxy)azetidin-1-yl](6-{[5-(trifluoromethyl)pyridin-2-yl]oxy}quinolin-2-yl)methanone;
N-{1-[(6-{[5-(trifluoromethyl)pyridin-2-yl]oxy}quinolin-2-yl)carbonyl]azetidin-3-yl}methanesulfonamide;
(6-{[5-(difluoromethyl)pyridin-2-yl]oxy}quinolin-2-yl)[3-(morpholin-4-yl)azetidin-1-yl]methanone;
[2-(difluoromethyl)piperazin-1-yl](6-{[5-(difluoromethyl)pyridin-2-yl]oxy}quinolin-2-yl)methanone;
piperazin-1-yl(6-{[5-(trifluoromethoxy)pyridin-2-yl]oxy}quinolin-2-yl)methanone;
N-(3-oxocyclobutyl)-6-{[5-(trifluoromethyl)pyridin-2-yl]oxy}quinoline-2-carboxamide;
N-[3-(morpholin-4-yl)cyclobutyl]-6-{[5-(trifluoromethyl)pyridin-2-yl]oxy}quinoline-2-carboxamide;
6-{[5-(difluoromethyl)pyridin-2-yl]oxy}-N-(2-hydroxy-2-methylpropyl)quinoline-2-carboxamide;
(6-{[5-(difluoromethyl)pyridin-2-yl]oxy}quinolin-2-yl)[4-(morpholin-4-yl)piperidin-1-yl]methanone;
6-{[5-(difluoromethyl)pyridin-2-yl]oxy}-N-(2,2,2-trifluoroethyl)quinoline-2-carboxamide;
N-(4,4-difluorocyclohexyl)-6-{[5-(difluoromethyl)pyridin-2-yl]oxy}quinoline-2-carboxamide;
N-{(3R)-1-[(6-{[5-(trifluoromethyl)pyridin-2-yl]oxy}quinolin-2-yl)carbonyl]pyrrolidin-3-yl}acetamide;
N-{(3R)-1-[(6-{[5-(trifluoromethyl)pyridin-2-yl]oxy}quinolin-2-yl)carbonyl]pyrrolidin-3-yl}cyclopropanecarboxamide;
(6-{[5-(difluoromethyl)pyridin-2-yl]oxy}quinolin-2-yl)[(3R)-3-(hydroxymethyl)piperazin-1-yl]methanone;
6-{[5-(difluoromethyl)pyridin-2-yl]oxy}-N-[2-(dimethylamino)-2-oxoethyl]quinoline-2-carboxamide;
N-{2-[(2-methoxyethyl)amino]-2-oxoethyl}-N-methyl-6-{[5-(trifluoromethyl)pyridin-2-yl]oxy}quinoline-2-carboxamide;
N-[2-(morpholin-4-yl)-2-oxoethyl]-6-{[5-(trifluoromethyl)pyridin-2-yl]oxy}quinoline-2-carboxamide;
N-[3-(morpholin-4-yl)-3-oxopropyl]-6-{[5-(trifluoromethyl)pyridin-2-yl]oxy}quinoline-2-carboxamide;
N-[3-oxo-3-(pyrrolidin-1-yl)propyl]-6-{[5-(trifluoromethyl)pyridin-2-yl]oxy}quinoline-2-carboxamide;
N-[2-(diethylamino)-2-oxoethyl]-6-{[5-(trifluoromethyl)pyridin-2-yl]oxy}quinoline-2-carboxamide;
N-[2-oxo-2-(piperidin-1-yl)ethyl]-6-{[5-(trifluoromethyl)pyridin-2-yl]oxy}quinoline-2-carboxamide;
N-(1-methyl-5-oxopyrrolidin-3-yl)-6-{[5-(trifluoromethyl)pyridin-2-yl]oxy}quinoline-2-carboxamide;
N-[3-oxo-3-(piperidin-1-yl)propyl]-6-{[5-(trifluoromethyl)pyridin-2-yl]oxy}quinoline-2-carboxamide;
1-methyl-4-[(6-{[5-(trifluoromethyl)pyridin-2-yl]oxy}quinolin-2-yl)carbonyl]piperazin-2-one;
N,N-dimethyl-1-[(6-{[5-(trifluoromethyl)pyridin-2-yl]oxy}quinolin-2-yl)carbonyl]-L-prolinamide;
N-[2-(cyclopropylamino)-2-oxoethyl]-N-methyl-6-{[5-(trifluoromethyl)pyridin-2-yl]oxy}quinoline-2-carboxamide;
N-[3-(diethylamino)-3-oxopropyl]-6-{[5-(trifluoromethyl)pyridin-2-yl]oxy}quinoline-2-carboxamide;
N-[2-(isopropylamino)-2-oxoethyl]-N-methyl-6-{[5-(trifluoromethyl)pyridin-2-yl]oxy}quinoline-2-carboxamide;
1-[(6-{[5-(difluoromethyl)pyridin-2-yl]oxy}quinolin-2-yl)carbonyl]-N-methyl-L-prolinamide;
6-{[5-(difluoromethyl)pyridin-2-yl]oxy}-N-[2-oxo-2-(pyrrolidin-1-yl)ethyl]quinoline-2-carboxamide;
6-{[5-(difluoromethyl)pyridin-2-yl]oxy}-N-{2-[(2-methoxyethyl)amino]-2-oxoethyl}-N-methylquinoline-2-carboxamide;
6-{[5-(difluoromethyl)pyridin-2-yl]oxy}-N-[2-(morpholin-4-yl)-2-oxoethyl]quinoline-2-carboxamide;
6-{[5-(difluoromethyl)pyridin-2-yl]oxy}-N-[3-(morpholin-4-yl)-3-oxopropyl]quinoline-2-carboxamide;
6-{[5-(difluoromethyl)pyridin-2-yl]oxy}-N-[3-oxo-3-(pyrrolidin-1-yl)propyl]quinoline-2-carboxamide;
N-[2-(diethylamino)-2-oxoethyl]-6-{[5-(difluoromethyl)pyridin-2-yl]oxy}quinoline-2-carboxamide;
6-{[5-(difluoromethyl)pyridin-2-yl]oxy}-N-(1-methyl-5-oxopyrrolidin-3-yl)quinoline-2-carboxamide;
6-{[5-(difluoromethyl)pyridin-2-yl]oxy}-N-[3-oxo-3-(piperidin-1-yl)propyl]quinoline-2-carboxamide;
4-[(6-{[5-(difluoromethyl)pyridin-2-yl]oxy}quinolin-2-yl)carbonyl]-1-methylpiperazin-2-one;
1-[(6-{[5-(difluoromethyl)pyridin-2-yl]oxy}quinolin-2-yl)carbonyl]-N,N-dimethyl-L-prolinamide;
N-[2-(cyclopropylamino)-2-oxoethyl]-6-{[5-(difluoromethyl)pyridin-2-yl]oxy}-N-methylquinoline-2-carboxamide;
N-[3-(diethylamino)-3-oxopropyl]-6-{[5-(difluoromethyl)pyridin-2-yl]oxy}quinoline-2-carboxamide;
6-{[5-(difluoromethyl)pyridin-2-yl]oxy}-N-[2-(isopropylamino)-2-oxoethyl]-N-methylquinoline-2-carboxamide;
N-[2-(2-oxopiperazin-1-yl)ethyl]-6-{[5-(trifluoromethyl)pyridin-2-yl]oxy}quinoline-2-carboxamide;
N-(azetidin-3-ylmethyl)-6-{[5-(trifluoromethyl)pyridin-2-yl]oxy}quinoline-2-carboxamide;
N-(2-hydroxy-2-methylpropyl)-6-{[6-(trifluoromethyl)pyridin-3-yl]oxy}quinoline-2-carboxamide;
4-{4-[(6-{[5-(trifluoromethyl)pyridin-2-yl]oxy}quinolin-2-yl)carbonyl]piperazin-1-yl}butanenitrile;
3-{4-[(6-{[5-(trifluoromethyl)pyridin-2-yl]oxy}quinolin-2-yl)carbonyl]piperazin-1-yl}propanenitrile;
1-[(6-{[5-(trifluoromethyl)pyridin-2-yl]oxy}quinolin-2-yl)carbonyl]piperidine-4-carbonitrile;
6-{[5-(difluoromethyl)pyridin-2-yl]oxy}-N-(oxetan-3-yl)quinoline-2-carboxamide;
5,8-dioxa-2-azaspiro[3.4]oct-2-yl(6-{[5-(trifluoromethyl)pyridin-2-yl]oxy}quinolin-2-yl)methanone;
6-{[5-(difluoromethyl)pyridin-2-yl]oxy}-N-[(3S,4S)-4-hydroxy-1,1-dioxidotetrahydrothiophen-3-yl]quinoline-2-carboxamide;
tetrahydro-5H-[1,3]dioxolo[4,5-c]pyrrol-5-yl(6-{[5-(trifluoromethyl)pyridin-2-yl]oxy}quinolin-2-yl)methanone;
(6-{[5-(difluoromethyl)pyridin-2-yl]oxy}quinolin-2-yl)[3-(methylsulfonyl)azetidin-1-yl]methanone;
N-methyl-N-(oxetan-3-yl)-6-{[5-(trifluoromethyl)pyridin-2-yl]oxy}quinoline-2-carboxamide;
6-{[5-(difluoromethyl)pyridin-2-yl]oxy}-N-(1-oxidotetrahydro-2H-thiopyran-4-yl)quinoline-2-carboxamide;
N-(oxetan-3-ylmethyl)-6-{[5-(trifluoromethyl)pyridin-2-yl]oxy}quinoline-2-carboxamide;
4-[(6-{[5-(trifluoromethyl)pyridin-2-yl]oxy}quinolin-2-yl)carbonyl]piperazine-2-carbonitrile;
6-(4-cyanophenoxy)-N-(2-oxopiperidin-4-yl)quinoline-2-carboxamide;
N-(3,3-difluorocyclopentyl)-6-{[5-(trifluoromethyl)pyridin-2-yl]oxy}quinoline-2-carboxamide;
N-(3,3-difluorocyclopentyl)-6-{[5-(difluoromethyl)pyridin-2-yl]oxy}quinoline-2-carboxamide;
[3-fluoro-3-(methoxy methyl)pyrrolidin-1-yl](6-{[5-(trifluoromethyl)pyridin-2-yl]oxy}quinolin-2-yl)methanone;
[3-(ethoxymethyl)-3-fluoropyrrolidin-1-yl](6-{[5-(trifluoromethyl)pyridin-2-yl]oxy}quinolin-2-yl)methanone;
{3-fluoro-3-[(pyridin-4-yloxy)methyl]pyrrolidin-1-yl}(6-{[5-(trifluoromethyl)pyridin-2-yl]oxy}quinolin-2-yl)methanone;

{3-fluoro-3-[(pyridin-3-yloxy)methyl]pyrrolidin-1-yl}(6-{[5-(trifluoromethyl)pyridin-2-yl]oxy}quinolin-2-yl)methanone;

[3-fluoro-3-(phenoxymethyl)pyrrolidin-1-yl](6-{[5-(trifluoromethyl)pyridin-2-yl]oxy}quinolin-2-yl)methanone;

benzyl ({4-fluoro-1-[(6-{[5-(trifluoromethyl)pyridin-2-yl]oxy}quinolin-2-yl)carbonyl]pyrrolidin-3-yl}methyl)carbamate;

{3-fluoro-3-[(2-methoxyethoxy)methyl]pyrrolidin-1-yl}(6-{[5-(trifluoromethyl)pyridin-2-yl]oxy}quinolin-2-yl)methanone;

2-oxa-6-azaspiro[3.4]oct-6-yl(6-{[5-(trifluoromethyl)pyridin-2-yl]oxy}quinolin-2-yl)methanone;

[(2R,4S)-4-fluoro-2-(hydroxymethyl)pyrrolidin-1-yl](6-{[5-(trifluoromethyl)pyridin-2-yl]oxy}quinolin-2-yl)methanone;

[(2R)-4,4-difluoro-2-(hydroxymethyl)pyrrolidin-1-yl](6-{[5-(trifluoromethyl)pyridin-2-yl]oxy}quinolin-2-yl)methanone;

[(2S)-4,4-difluoro-2-(hydroxymethyl)pyrrolidin-1-yl](6-{[5-(trifluoromethyl)pyridin-2-yl]oxy}quinolin-2-yl)methanone;

1-(3-methoxyphenyl)-4-[(6-{[5-(trifluoromethyl)pyridin-2-yl]oxy}quinolin-2-yl)carbonyl]piperazin-2-one;

N-(thietan-3-yl)-6-{[5-(trifluoromethyl)pyridin-2-yl]oxy}quinoline-2-carboxamide;

N-{3-[(2-methylphenyl)amino]-3-oxopropyl}-6-{[5-(trifluoromethyl)pyridin-2-yl]oxy}quinoline-2-carboxamide;

N-[(2S)-1-(dimethylamino)-1-oxo-3-phenylpropan-2-yl]-6-{[5-(trifluoromethyl)pyridin-2-yl]oxy}quinoline-2-carboxamide;

N-[1-(2-methoxyphenyl)-5-oxopyrrolidin-3-yl]-6-{[5-(trifluoromethyl)pyridin-2-yl]oxy}quinoline-2-carboxamide;

N-(1-oxidothietan-3-yl)-6-{[5-(trifluoromethyl)pyridin-2-yl]oxy}quinoline-2-carboxamide;

N-(1,1-dioxidothietan-3-yl)-6-{[5-(trifluoromethyl)pyridin-2-yl]oxy}quinoline-2-carboxamide;

6-oxa-1-azaspiro[3.3]hept-1-yl(6-{[5-(trifluoromethyl)pyridin-2-yl]oxy}quinolin-2-yl)methanone;

1-{1-[(6-{[5-(trifluoromethyl)pyridin-2-yl]oxy}quinolin-2-yl)carbonyl]azetidin-3-yl}ethanone;

(3-fluoroazetidin-1-yl)(6-{[5-(trifluoromethyl)pyridin-2-yl]oxy}quinolin-2-yl)methanone;

(3,3-difluoroazetidin-1-yl)(6-{[5-(trifluoromethyl)pyridin-2-yl]oxy}quinolin-2-yl)methanone;

(4R)-4-fluoro-N,N-dimethyl-1-[(6-{[5-(trifluoromethyl)pyridin-2-yl]oxy}quinolin-2-yl)carbonyl]-L-prolinamide;

[4-(1,3-oxazol-2-ylmethyl)piperazin-1-yl](6-{[5-(trifluoromethyl)pyridin-2-yl]oxy}quinolin-2-yl)methanone;

N-(4,4-difluorocyclohexyl)-6-{[6-(trifluoromethyl)pyridin-3-yl]oxy}quinoline-2-carboxamide;

N-[(4S)-2-oxopiperidin-4-yl]-6-{[5-(trifluoromethyl)pyridin-2-yl]oxy}quinoline-2-carboxamide;

N-[2-oxo-2-(pyrrolidin-1-yl)ethyl]-6-{[6-(trifluoromethyl)pyridin-3-yl]oxy}quinoline-2-carboxamide;

N-{2-[(2-methoxyethyl)amino]-2-oxoethyl}-N-methyl-6-{[6-(trifluoromethyl)pyridin-3-yl]oxy}quinoline-2-carboxamide;

N-[3-(morpholin-4-yl)-3-oxopropyl]-6-{[6-(trifluoromethyl)pyridin-3-yl]oxy}quinoline-2-carboxamide;

N-[3-oxo-3-(pyrrolidin-1-yl)propyl]-6-{[6-(trifluoromethyl)pyridin-3-yl]oxy}quinoline-2-carboxamide;

N-[2-(diethylamino)-2-oxoethyl]-6-{[6-(trifluoromethyl)pyridin-3-yl]oxy}quinoline-2-carboxamide;

N-[2-oxo-2-(piperidin-1-yl)ethyl]-6-{[6-(trifluoromethyl)pyridin-3-yl]oxy}quinoline-2-carboxamide;

N-(1-methyl-5-oxopyrrolidin-3-yl)-6-{[6-(trifluoromethyl)pyridin-3-yl]oxy}quinoline-2-carboxamide;

N-[3-oxo-3-(piperidin-1-yl)propyl]-6-{[6-(trifluoromethyl)pyridin-3-yl]oxy}quinoline-2-carboxamide;

N-[(4R)-2-oxopiperidin-4-yl]-6-{[6-(trifluoromethyl)pyridin-2-yl]oxy}quinoline-2-carboxamide;

N-[2-(cyclopropylamino)-2-oxoethyl]-N-methyl-6-{[6-(trifluoromethyl)pyridin-3-yl]oxy}quinoline-2-carboxamide;

N-(1-ethyl-5-oxopyrrolidin-3-yl)-6-{[6-(trifluoromethyl)pyridin-3-yl]oxy}quinoline-2-carboxamide;

N-[3-(diethylamino)-3-oxopropyl]-6-{[6-(trifluoromethyl)pyridin-3-yl]oxy}quinoline-2-carboxamide;

N-[2-(isopropylamino)-2-oxoethyl]-N-methyl-6-{[6-(trifluoromethyl)pyridin-3-yl]oxy}quinoline-2-carboxamide;

[4-(morpholin-4-yl)piperidin-1-yl](6-{[6-(trifluoromethyl)pyridin-3-yl]oxy}quinolin-2-yl)methanone;

N-methyl-6-{[5-(trifluoromethyl)pyridin-2-yl]oxy}quinoline-2-carboxamide;

meso-[(1R,5S,6s)-6-amino-3-azabicyclo[3.1.0]hex-3-yl](6-{[6-(trifluoromethyl)pyridin-3-yl]oxy}quinolin-2-yl)methanone;

N-methyl-N-(1-methyl-2-oxopiperidin-4-yl)-6-{[5-(trifluoromethyl)pyridin-2-yl]oxy}quinoline-2-carboxamide;

N-[(3R)-2-oxotetrahydrofuran-3-yl]-6-{[5-(trifluoromethyl)pyridin-2-yl]oxy}quinoline-2-carboxamide;

{4-[(2-methyl-1,3-oxazol-4-yl)methyl]piperazin-1-yl}(6-{[5-(trifluoromethyl)pyridin-2-yl]oxy}quinolin-2-yl)methanone;

6-oxa-2-azaspiro[3.4]oct-2-yl(6-{[5-(trifluoromethyl)pyridin-2-yl]oxy}quinolin-2-yl)methanone;

6-oxa-2-azaspiro[3.5]non-2-yl(6-{[5-(trifluoromethyl)pyridin-2-yl]oxy}quinolin-2-yl)methanone;

[3-(methylsulfonyl)azetidin-1-yl](6-{[6-(trifluoromethyl)pyridin-3-yl]oxy}quinolin-2-yl)methanone;

N-(1,1-dioxidotetrahydro-2H-thiopyran-4-yl)-6-{[6-(trifluoromethyl)pyridin-3-yl]oxy}quinoline-2-carboxamide;

N-(oxetan-3-yl)-6-{[6-(trifluoromethyl)pyridin-3-yl]oxy}quinoline-2-carboxamide;

N-[(3R,4S)-4-hydroxy-1,1-dioxidotetrahydrothiophen-3-yl]-6-{[6-(trifluoromethyl)pyridin-3-yl]oxy}quinoline-2-carboxamide;

N-[(3S,4S)-4-hydroxy-1,1-dioxidotetrahydrothiophen-3-yl]-6-{[6-(trifluoromethyl)pyridin-3-yl]oxy}quinoline-2-carboxamide;

2,5-dihydro-1H-pyrrol-1-yl(6-{[6-(trifluoromethyl)pyridin-3-yl]oxy}quinolin-2-yl)methanone;

[4-(3,3-difluoroazetidin-1-yl)piperidin-1-yl](6-{[5-(trifluoromethyl)pyridin-2-yl]oxy}quinolin-2-yl)methanone;

N-(2-methoxy-2-methylpropyl)-6-{[5-(trifluoromethyl)pyridin-2-yl]oxy}quinoline-2-carboxamide;

[(8aS)-7,7-difluorohexahydropyrrolo[1,2-a]pyrazin-2(1H)-yl](6-{[5-(difluoromethyl)pyridin-2-yl]oxy}quinolin-2-yl)methanone;

[(3R)-3-ethylpiperazin-1-yl](6-{[6-(trifluoromethyl)pyridin-3-yl]oxy}quinolin-2-yl)methanone;

[(3R)-3-(hydroxymethyl)piperazin-1-yl](6-{[6-(trifluoromethyl)pyridin-3-yl]oxy}quinolin-2-yl)methanone;

[(3S)-3-(hydroxymethyl)piperazin-1-yl](6-{[6-(trifluoromethyl)pyridin-3-yl]oxy}quinolin-2-yl)methanone;

[cis-3,4-dihydroxypyrrolidin-1-yl](6-{[6-(trifluoromethyl)pyridin-3-yl]oxy}quinolin-2-yl)methanone;

N-[2-(trifluoromethoxy)ethyl]-6-{[5-(trifluoromethyl)pyridin-2-yl]oxy}quinoline-2-carboxamide;

[(3R)-3-fluoropyrrolidin-1-yl](6-{[6-(trifluoromethyl)pyridin-3-yl]oxy}quinolin-2-yl)methanone;

[(3 S)-3-methylpiperazin-1-yl](6-{[6-(trifluoromethyl)pyridin-3-yl]oxy}quinolin-2-yl)methanone;
[(3S)-3-fluoropyrrolidin-1-yl](6-{[6-(trifluoromethyl)pyridin-3-yl]oxy}quinolin-2-yl)methanone;
N-(3,3,3-trifluoro-2-hydroxypropyl)-6-{[6-(trifluoromethyl)pyridin-3-yl]oxy}quinoline-2-carboxamide;
(3,5-dimethylpiperazin-1-yl)(6-{[5-(trifluoromethyl)pyridin-2-yl]oxy}quinolin-2-yl)methanone;
[(3S)-3-ethylpiperazin-1-yl](6-{[6-(trifluoromethyl)pyridin-3-yl]oxy}quinolin-2-yl)methanone;
[3-(morpholin-4-yl) azetidin-1-yl](6-{[6-(trifluoromethyl)pyridin-3-yl]oxy}quinolin-2-yl)methanone;
N-(3,3-difluorocyclobutyl)-6-{[6-(trifluoromethyl)pyridin-3-yl]oxy}quinoline-2-carboxamide;
N-(3-oxocyclobutyl)-6-{[6-(trifluoromethyl)pyridin-3-yl]oxy}quinoline-2-carboxamide;
[3-(piperazin-1-yl)azetidin-1-yl](6-{[5-(trifluoromethyl)pyridin-2-yl]oxy}quinolin-2-yl)methanone;
4,7-diazaspiro[2.5]oct-7-yl(6-{[5-(difluoromethyl)pyridin-2-yl]oxy}quinolin-2-yl)methanone;
N-{2-[(3R)-3-hydroxypyrrolidin-1-yl]-2-oxoethyl}-6-{[5-(trifluoromethyl)pyridin-2-yl]oxy}quinoline-2-carboxamide;
N-{2-[(3S)-3-hydroxypyrrolidin-1-yl]-2-oxoethyl}-6-{[5-(trifluoromethyl)pyridin-2-yl]oxy}quinoline-2-carboxamide;
N-[2-(3-hydroxy-3-methylpyrrolidin-1-yl)-2-oxoethyl]-6-{[5-(trifluoromethyl)pyridin-2-yl]oxy}quinoline-2-carboxamide;
N-{2-[(3S,4S)-3,4-dihydroxypyrrolidin-1-yl]-2-oxoethyl}-6-{[5-(trifluoromethyl)pyridin-2-yl]oxy}quinoline-2-carboxamide;
N-{2-[(3R,4R)-3,4-dihydroxypyrrolidin-1-yl]-2-oxoethyl}-6-{[5-(trifluoromethyl)pyridin-2-yl]oxy}quinoline-2-carboxamide;
N-{2-[(2S,4R)-4-hydroxy-2-(hydroxymethyl)pyrrolidin-1-yl]-2-oxoethyl}-6-{[5-(trifluoromethyl)pyridin-2-yl]oxy}quinoline-2-carboxamide;
N-[2-(3,3-difluoropyrrolidin-1-yl)-2-oxoethyl]-6-{[5-(trifluoromethyl)pyridin-2-yl]oxy}quinoline-2-carboxamide;
N-[2-(3-hydroxyazetidin-1-yl)-2-oxoethyl]-6-{[5-(trifluoromethyl)pyridin-2-yl]oxy}quinoline-2-carboxamide;
N-[2-(3-hydroxy-3-methylazetidin-1-yl)-2-oxoethyl]-6-{[5-(trifluoromethyl)pyridin-2-yl]oxy}quinoline-2-carboxamide;
N-[2-(1,1-dioxido-1,3-thiazolidin-3-yl)-2-oxoethyl]-6-{[5-(trifluoromethyl)pyridin-2-yl]oxy}quinoline-2-carboxamide;
N-[2-(3-methoxyazetidin-1-yl)-2-oxoethyl]-6-{[5-(trifluoromethyl)pyridin-2-yl]oxy}quinoline-2-carboxamide;
N-{2-[(2R)-2-(hydroxymethyl)pyrrolidin-1-yl]-2-oxoethyl}-6-{[5-(trifluoromethyl)pyridin-2-yl]oxy}quinoline-2-carboxamide;
N-[2-(azetidin-1-yl)-2-oxoethyl]-6-{[5-(trifluoromethyl)pyridin-2-yl]oxy}quinoline-2-carboxamide;
N-[2-oxo-2-(3-oxopyrrolidin-1-yl)ethyl]-6-{[5-(trifluoromethyl)pyridin-2-yl]oxy}quinoline-2-carboxamide;
N-[2-(3-fluoropyrrolidin-1-yl)-2-oxoethyl]-6-{[5-(trifluoromethyl)pyridin-2-yl]oxy}quinoline-2-carboxamide;
N-[3-(morpholin-4-yl)cyclobutyl]-6-{[6-(trifluoromethyl)pyridin-3-yl]oxy}quinoline-2-carboxamide;
(6-{[5-(difluoromethyl)pyridin-2-yl]oxy}quinolin-2-yl)[(3R)-3-fluoropyrrolidin-1-yl]methanone;
(6-{[5-(difluoromethyl)pyridin-2-yl]oxy}quinolin-2-yl)[(3S)-3-fluoropyrrolidin-1-yl]methanone;
N-(methylsulfonyl)-6-{[5-(trifluoromethyl)pyridin-2-yl]oxy}quinoline-2-carboxamide;
N-(3-hydroxy-3-methylcyclobutyl)-6-{[6-(trifluoromethyl)pyridin-3-yl]oxy}quinoline-2-carboxamide;
N-[1-(dimethylamino)-1-oxopropan-2-yl]-6-{[5-(trifluoromethyl)pyridin-2-yl]oxy}quinoline-2-carboxamide;
N-(3,3-difluorocyclobutyl)-6-{[5-(difluoromethyl)pyridin-2-yl]oxy}quinoline-2-carboxamide;
[(3R)-3-hydroxypiperidin-1-yl](6-{[5-(trifluoromethyl)pyridin-2-yl]oxy}quinolin-2-yl)methanone;
[(3 S)-3-hydroxypiperidin-1-yl](6-{[5-(trifluoromethyl)pyridin-2-yl]oxy}quinolin-2-yl)methanone;
[(3R,4R)-4-amino-3-fluoropiperidin-1-yl](6-{[5-(trifluoromethyl)pyridin-2-yl]oxy}quinolin-2-yl)methanone;
N-[(3R,4R)-3-fluoropiperidin-4-yl]-6-{[5-(trifluoromethyl)pyridin-2-yl]oxy}quinoline-2-carboxamide;
(6-{[5-(difluoromethyl)pyridin-2-yl]oxy}quinolin-2-yl)[(3S)-3-(hydroxymethyl)piperazin-1-yl]methanone;
{3-[(3S)-3-fluoropyrrolidin-1-yl]azetidin-1-yl}(6-{[5-(trifluoromethyl)pyridin-2-yl]oxy}quinolin-2-yl)methanone;
N-(1-methyl-2-oxopyrrolidin-3-yl)-6-{[5-(trifluoromethyl)pyridin-2-yl]oxy}quinoline-2-carboxamide;
[(3R)-3-methoxypyrrolidin-1-yl](6-{[5-(trifluoromethyl)pyridin-2-yl]oxy}quinolin-2-yl)methanone;
[(3 S)-3-methoxypyrrolidin-1-yl](6-{[5-(trifluoromethyl)pyridin-2-yl]oxy}quinolin-2-yl)methanone;
N-(2-methoxypropyl)-6-{[5-(trifluoromethyl)pyridin-2-yl]oxy}quinoline-2-carboxamide;
N-[(1-methoxycyclobutyl)methyl]-6-{[5-(trifluoromethyl)pyridin-2-yl]oxy}quinoline-2-carboxamide;
6-{[5-(difluoromethyl)pyridin-2-yl]oxy}-N-(3-oxocyclobutyl)quinoline-2-carboxamide;
[(3S)-3-(methoxymethyl)piperazin-1-yl](6-{[5-(trifluoromethyl)pyridin-2-yl]oxy}quinolin-2-yl)methanone;
[3-(difluoromethyl)piperazin-1-yl](6-{[5-(trifluoromethyl)pyridin-2-yl]oxy}quinolin-2-yl)methanone;
N-(3-cyanopropyl)-6-{[5-(trifluoromethyl)pyridin-2-yl]oxy}quinoline-2-carboxamide;
N-cyclobutyl-6-{[5-(trifluoromethyl)pyridin-2-yl]oxy}quinoline-2-carboxamide;
azetidin-1-yl(6-{[5-(trifluoromethyl)pyridin-2-yl]oxy}quinolin-2-yl)methanone;
[2-(trifluoromethyl)piperazin-1-yl](6-{[5-(trifluoromethyl)pyridin-2-yl]oxy}quinolin-2-yl)methanone;
N-(3-methoxypropyl)-6-{[5-(trifluoromethyl)pyridin-2-yl]oxy}quinoline-2-carboxamide;
N-(thietan-3-ylmethyl)-6-{[5-(trifluoromethyl)pyridin-2-yl]oxy}quinoline-2-carboxamide;
N-[(1-oxidothietan-3-yl)methyl]-6-{[5-(trifluoromethyl)pyridin-2-yl]oxy}quinoline-2-carboxamide;
N-[(1,1-dioxidothietan-3-yl)methyl]-6-{[5-(trifluoromethyl)pyridin-2-yl]oxy}quinoline-2-carboxamide;
[(2R)-2-(difluoromethyl)piperazin-1-yl](6-{[5-(trifluoromethyl)pyridin-2-yl]oxy}quinolin-2-yl)methanone;
N-(3-fluorocyclobutyl)-6-{[5-(trifluoromethyl)pyridin-2-yl]oxy}quinoline-2-carboxamide;
N-[2-(2-oxo-1,3-oxazolidin-3-yl)ethyl]-6-{[5-(trifluoromethyl)pyridin-2-yl]oxy}quinoline-2-carboxamide;
N-[2-(pyridin-2-yl)ethyl]-6-{[5-(trifluoromethyl)pyridin-2-yl]oxy}quinoline-2-carboxamide;
N-[3-(pyridin-2-yl)propyl]-6-{[5-(trifluoromethyl)pyridin-2-yl]oxy}quinoline-2-carboxamide;
N-[3-(2-oxopyrrolidin-1-yl)propyl]-6-{[5-(trifluoromethyl)pyridin-2-yl]oxy}quinoline-2-carboxamide;
N-[(5-oxopyrrolidin-3-yl)methyl]-6-{[5-(trifluoromethyl)pyridin-2-yl]oxy}quinoline-2-carboxamide;
N-(3-acetamido-2-methylpropyl)-6-{[5-(trifluoromethyl)pyridin-2-yl]oxy}quinoline-2-carboxamide;

N-methyl-N-[2-(methylsulfonyl)ethyl]-6-{[5-(trifluoromethyl)pyridin-2-yl]oxy}quinoline-2-carboxamide;
N-[4-(methylsulfonyl)butyl]-6-{[5-(trifluoromethyl)pyridin-2-yl]oxy}quinoline-2-carboxamide;
N-(3-acetamidopropyl)-6-{[5-(trifluoromethyl)pyridin-2-yl]oxy}quinoline-2-carboxamide;
1-[(6-{[5-(trifluoromethyl)pyridin-2-yl]oxy}quinolin-2-yl)carbonyl]hexahydropyrrolo[1,2-a]pyrimidin-6(2H)-one;
N-[2-(1,1-dioxidothietan-3-yl)ethyl]-6-{[5-(trifluoromethyl)pyridin-2-yl]oxy}quinoline-2-carboxamide;
N-methyl-N-(2,2,2-trifluoroethyl)-6-{[5-(trifluoromethyl)pyridin-2-yl]oxy}quinoline-2-carboxamide;
6-{[5-(difluoromethyl)pyridin-2-yl]oxy}-N-(3-fluorocyclobutyl)quinoline-2-carboxamide;
[4-fluoro-4-(methoxymethyl)piperidin-1-yl](6-{[5-(trifluoromethyl)pyridin-2-yl]oxy}quinolin-2-yl)methanone;
[3-(2,2-difluoroethoxy)azetidin-1-yl](6-{[5-(trifluoromethyl)pyridin-2-yl]oxy}quinolin-2-yl)methanone;
1,1-dimethyl-4-[(6-{[5-(trifluoromethyl)pyridin-2-yl]oxy}quinolin-2-yl)carbonyl]piperazin-1-ium iodide;
{3-[(2,2,2-trifluoroethyl)amino]azetidin-1-yl}(6-{[5-(trifluoromethyl)pyridin-2-yl]oxy}quinolin-2-yl)methanone;
N-(2,2-difluoroethyl)-N-methyl-6-{[5-(trifluoromethyl)pyridin-2-yl]oxy}quinoline-2-carboxamide; and
7-oxa-2-azaspiro[3.5]non-2-yl(6-{[5-(trifluoromethyl)pyridin-2-yl]oxy}quinolin-2-yl)methanone.

Compound names are assigned by using Name 2012 naming algorithm by Advanced Chemical Development or Struct=Name naming algorithm as part of CHEMDRAW® ULTRA v. 12.0.2.1076.

Compounds of the invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

On occasion, the relative stereochemistry of an enantiomeric pair is known, however, the absolute configuration is not known. In that circumstance, the relative stereochemistry descriptor terms "R*" and "S*" are used. The terms "R*" and "S*" used herein are defined in Eliel, E. L.; Wilen, S. H. Stereochemistry of Organic Compounds; John Wiley & Sons, Inc.: New York, 1994; pp 119-120 and 1206.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutane may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention.

The present invention also includes isotopically-labeled compounds, which are identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Compounds incorporating positron-emitting isotopes are useful in medical imaging and positron-emitting tomography (PET) studies for determining the distribution of receptors. Suitable positron-emitting isotopes that can be incorporated in compounds of formula (I) are $^{11}$C, $^{13}$N, $^{15}$O, and $^{18}$F. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

Methods for Preparing Compounds of the Invention

The compounds of the invention can be better understood in connection with the following synthetic schemes and methods which illustrate a means by which the compounds can be prepared.

The compounds of this invention can be prepared by a variety of synthetic procedures. Representative procedures are shown in, but are not limited to, Schemes 1-2.

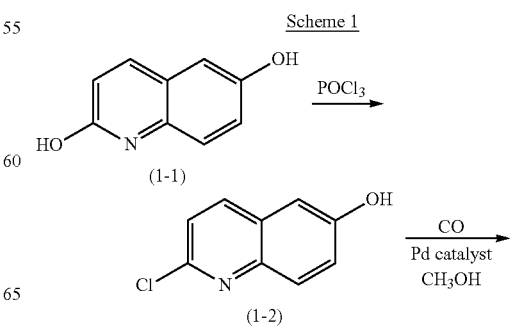

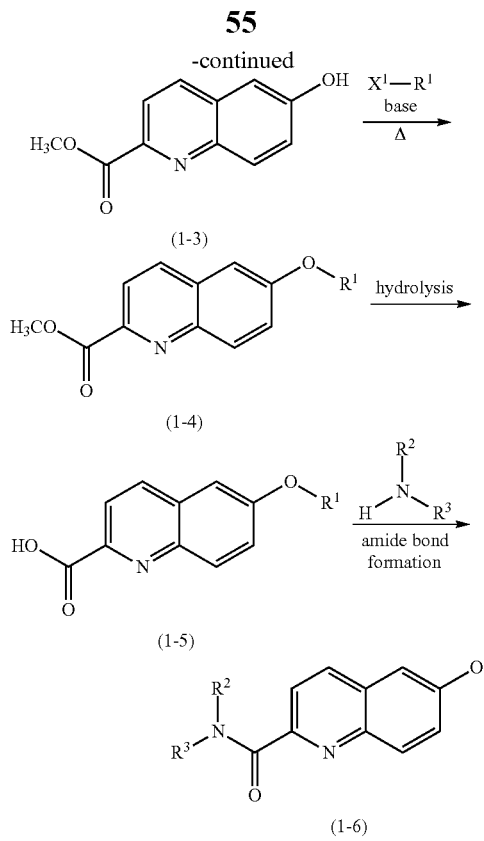

(1-3)

(1-4)

(1-5)

(1-6)

As shown in Scheme 1, compounds of formula (1-6) can be prepared in a 5-step sequence starting with quinoline-2,6-diol, (1-1). Treatment of quinoline-2,6-diol, (1-1), with phosphoryl chloride in heated N,N-dimethylformamide gives 2-chloroquinolin-6-ol, (1-2). 2-Chloroquinolin-6-ol, (1-2), can then be carbonylated with carbon monoxide (40-70 psi) in the presence of a palladium catalyst such as but not limited to [1,1'-bis(diphenylphosphino)ferrocene] dichloropalladium(II) (Pd(dppf)Cl$_2$) and a tertiary amine base such as triethyl amine in heated (90-110° C.) methanol to supply methyl 6-hydroxyquinoline-2-carboxylate, (1-3). Methyl 6-hydroxyquinoline-2-carboxylate, (1-3), can then be reacted with $X^1$—$R^1$, wherein $X^1$ is a halogen or sulfonate and $R^1$ is as described in the Summary, in the presence of a base such as cesium carbonate or potassium carbonate in a heated (60-140° C.) aprotic solvent such as N,N-dimethylformamide or N-methyl-2-pyrrolidinone to give compounds of formula (1-4). The ester of compounds of formula (1-4) can be hydrolyzed with a base such as lithium hydroxide, sodium hydroxide or potassium hydroxide in a mixture of water and tetrahydrofuran to give compounds of formula (1-5). Compounds of formula (1-5) can be reacted with amines or heterocycles, HNR$^2$R$^3$, wherein R$^2$ and R$^3$ are as described in the Summary, under amide bond forming conditions to give compounds of formula (1-6). Examples of conditions known to generate amides from a mixture of a carboxylic acid and an amine include but are not limited to adding a coupling reagent such as but not limited to N-(3-dimethylaminopropyl)-N'-ethylcarbodiimide or 1-(3-dimethylaminopropyl)-3-ethylcarbodiimide (EDC, EDAC or EDCI), 1,3-dicyclohexylcarbodiimide (DCC), bis(2-oxo-3-oxazolidinyl)phosphinic chloride (BOPCl), 2-(7-azabenzotriazol-1-yl)-N,N,N',N'-tetramethyluronium hexafluorophosphate or 1-[bis(dimethylamino)methylene]-1H-1,2,3-triazolo[4,5-b]pyridinium 3-oxid hexafluorophosphate (HATU), O-(benzotriazol-1-yl)-N,N,N',N'-tetramethyluronium tetrafluoroborate (TBTU), 2-(1H-benzo[d][1,2,3]triazol-1-yl)-1,1,3,3-tetramethylisouronium hexafluorophosphate(V) (HBTU), and 2,4,6-tripropyl-1,3,5,2,4,6-trioxatriphosphinane 2,4,6-trioxide (T3P®). The coupling reagents may be added as a solid, a solution, or as the reagent bound to a solid support resin. In addition to the coupling reagents, auxiliary-coupling reagents may facilitate the coupling reaction. Auxiliary coupling reagents that are often used in the coupling reactions include but are not limited to (dimethylamino)pyridine (DMAP), 1-hydroxy-7-azabenzotriazole (HOAT) and 1-hydroxybenzotriazole (HOBT). The reaction may be carried out optionally in the presence of a base such as triethylamine or diisopropylethylamine. The coupling reaction may be carried out in solvents such as but not limited to tetrahydrofuran, N,N-dimethylformamide, N,N-dimethylacetamide, dimethyl sulfoxide, dichloromethane, and ethyl acetate. The compounds of formula (1-6) are representative of compounds of formula (I). Compounds of formula (1-6) can be further transformed using the methodologies described in the Examples to give additional compounds of formula (I).

Scheme 2

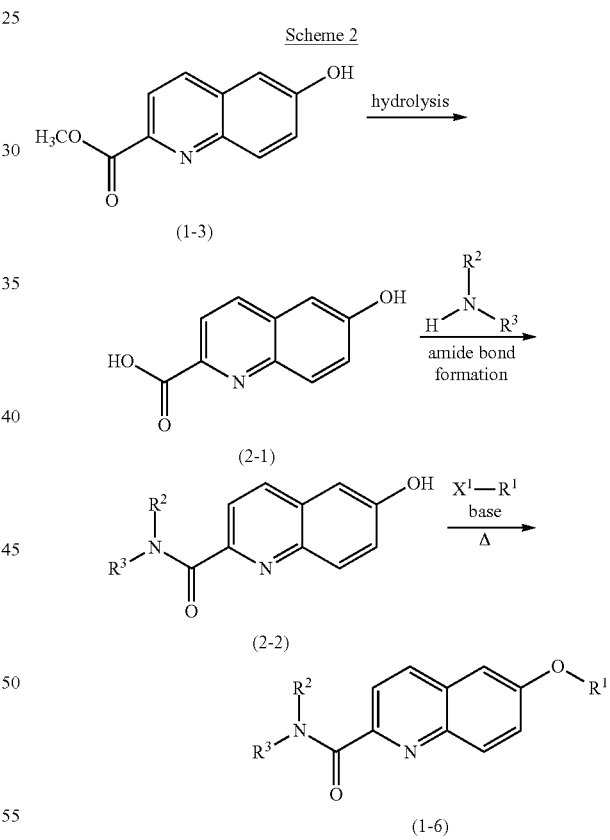

As shown in Scheme 2, compounds of formula (1-6) can also be prepared in an alternative sequence starting with methyl 6-hydroxyquinoline-2-carboxylate, (1-3). Methyl 6-hydroxyquinoline-2-carboxylate, (1-3), can be hydrolyzed at or near ambient temperature with a base such as lithium hydroxide, sodium hydroxide or potassium hydroxide in a mixture of water and tetrahydrofuran to give 6-hydroxyquinoline-2-carboxylic acid, (2-1). 6-Hydroxyquinoline-2-carboxylic acid, (2-1), can be reacted with amines or heterocycles, HNR$^2$R$^3$, wherein R$^2$ and R$^3$ are as described in the Summary, under amide bond forming conditions to give compounds of formula (2-2). Examples of conditions known to generate amides from a mixture of a carboxylic acid and an amine are described in Scheme 1 for the conversion of compounds of formula (1-5) to compounds of formula (1-6). Compounds of formula (2-2), can then be reacted with $X^1$—$R^1$, wherein $X^1$ is a halogen or sulfonate and $R^1$ is as described in the Summary, in the presence of a base such as cesium carbonate or potassium carbonate in a heated (60-140° C.) aprotic solvent such as N,N-dimethylformamide or N-methyl-2-pyrrolidinone to give compounds of formula (1-6). The compounds of formula (1-6) are representative of compounds of formula (I). Compounds of formula (1-6) can be further transformed using the methodologies described in the Examples to give additional compounds of formula (I).

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, reversed phase C8- or C18-bonded silica, alumina, or silica derivatized with alkylsilane groups using elution with water, organic solvents, or solvent combinations with or without the addition buffers or other additives such as trifluoroacetic acid or ammonium acetate, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England. Basic amine containing compounds purified using chromatography in the presence of additives such as trifluoroacetic acid, may be isolated as salts.

Many of the compounds of the invention have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, trifluoroacetic acid or glutamic acid, and the like.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis (4$^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection, for topical administration, or for rectal administration.

The term "pharmaceutically acceptable carrier", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally", as used herein, refers to modes of administration which include intravenous, intramuscular, intraperitoneal, intrasternal, subcutaneous, intraarticular injection and infusion.

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Ophthalmic formulations, eye ointments, powders and solutions are contemplated as being within the scope of this invention. Aqueous liquid compositions comprising compounds of the invention also are contemplated.

The compounds of the invention can be used in the form of pharmaceutically acceptable salts or esters, or amides derived from inorganic or organic acids. The term "pharmaceutically acceptable salts and esters and amides", as used herein, refer to carboxylate salts, amino acid addition salts, zwitterions, and esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid. An example of a suitable salt is a hydrochloride salt.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Preferred salts of the compounds of the invention are the tartrate and hydrochloride salts.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulfuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, and piperazine.

The term "pharmaceutically acceptable ester", as used herein, refers to esters of compounds of the invention which hydrolyze in vivo and include those that break down readily in the human body to leave the parent compound or a salt thereof. Examples of pharmaceutically acceptable, nontoxic esters of the invention include $C_1$-to-$C_6$-alkyl esters and $C_5$-to-$C_7$-cycloalkyl esters, although $C_1$-to-$C_4$-alkyl esters are preferred. Esters of the compounds of formula (I) may be prepared according to conventional methods. For example, such esters may be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also may be prepared by reaction of the compound with an acid such as hydrochloric acid and an alcohol such as methanol or ethanol.

The term "pharmaceutically acceptable amide", as used herein, refers to non-toxic amides of the invention derived from ammonia, primary $C_1$-to-$C_6$-alkyl amines and secondary $C_1$-to-$C_6$-dialkyl amines. In the case of secondary amines, the amine may also be in the form of a 5- or 6-membered heterocycle containing one nitrogen atom. Amides derived from ammonia, $C_1$-to-$C_3$-alkyl primary amides and $C_1$-to-$C_2$-dialkyl secondary amides are preferred. Amides of the compounds of formula (I) may be prepared according to conventional methods. Pharmaceutically acceptable amides are prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also may be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The invention contemplates pharmaceutically active compounds either chemically synthesized or formed by in vivo biotransformation to compounds of formula (I).

Methods of the Invention

The compounds and compositions of the invention are useful for treating and preventing certain diseases and disorders in humans and animals. As an important consequence of the ability of the compounds of the invention to modulate the effects of voltage-gated sodium channels (e.g., $Na_v 1.7$ and $Na_v 1.8$) in cells, the compounds described in the invention can affect physiological processes in humans and animals. In this way, the compounds and compositions described in the invention are useful for treating and preventing diseases and disorders modulated by voltage-gated sodium channels, e.g., $Na_v 1.7$ and $Na_v 1.8$. Typically, treatment or prevention of such diseases and disorders can be effected by selectively modulating voltage-gated sodium channels, e.g., $Na_v 1.7$ and $Na_v 1.8$, in a mammal, by administering a compound or composition of the invention, either alone or in combination with another active agent as part of a therapeutic regimen.

The terms "treat," "treating," and "treatment" are readily understood by a physician of ordinary skill and, with respect to treatment of a particular condition, can include ameliorating, suppressing, eradicating, preventing, reducing the risk of, and/or delaying the onset of the disease being treated.

The term "subject" includes animals such as mammals, including primates (e.g., humans), cows, sheep, goats, horses, dogs, cats, rabbits, rats, mice and the like. The methods of treatment are particularly suitable for use with a human subject, but may be used with other animal subjects, particularly mammals.

One embodiment of the present invention provides a method of treating pain in a subject in need thereof. The method comprises administering to the subject, including a mammal, such as a human, a therapeutically effective amount of a compound of formula (I), or a pharmaceutically acceptable salt thereof. Conditions related to pain include, for example, acute pain, chronic pain, neuropathic pain, nociceptive pain, allodynia, inflammatory pain, inflammatory hyperalgesia, post herpetic neuralgia, post-operative pain, post-stroke pain, neuropathies, neuralgia, diabetic neuropathy, HIV-related neuropathy, nerve injury, rheumatoid arthritic pain, osteoarthritic pain, burns, back pain, eye pain, visceral pain, cancer pain, dental pain, headache, migraine, carpal tunnel syndrome, knee pain, fibromyalgia, neuritis, sciatica, pelvic hypersensitivity, pelvic pain, menstrual pain.

Pain generally can be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain include neuropathic pain (e.g., painful diabetic neuropathy, postherpetic neuralgia), carpal tunnel syndrome, back pain, headache, cancer pain, arthritic pain and chronic post-surgical pain. In one embodiment, the condition related to pain is chronic pain. In another embodiment, the condition related to pain is acute pain.

Pain also can be divided into a number of different subtypes according to differing pathophysiology, including neuropathic, nociceptive, and inflammatory pain. Some types of pain have multiple etiologies and can be classified in more than one area, e.g., back pain and cancer pain have both nociceptive and neuropathic components.

In one embodiment, the condition related to pain is selected from the group consisting of neuropathic pain, nociceptive pain, and inflammatory pain.

In another embodiment, the condition related to pain is neuropathic pain. Neuropathic pain generally is defined as pain initiated or caused by a primary lesion or dysfunction in the nervous system and can result, for example, from trauma or disease. The term neuropathic pain encompasses many conditions with diverse etiologies including peripheral neuropathy, diabetic neuropathy, post-herpetic neuralgia, trigeminal neuralgia, back pain, cancer neuropathy, HIV-neuropathy, phantom limb pain, carpal tunnel syndrome, central post-stroke pain, and pain associated with chronic alcoholism, hypothyroidism, uremia, multiple sclerosis, spinal cord injury, Parkinson's disease, epilepsy and vitamin deficiency.

In another embodiment, the condition related to pain is nociceptive pain. Nociceptive pain is induced by tissue injury or by intense stimuli with the potential to cause injury. When a substantial injury occurs to body tissue through trauma or disease, the characteristics of nociceptor activation are altered and there is sensitization in the periphery leading to a heightened sensation of pain in the subject. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain can be chronic pain such as tumor related pain (e. g., bone pain, headache, facial pain or visceral pain) or pain associated with cancer therapy (e.g., post-chemotherapy syndrome, chronic postsurgical pain syndrome or post radiation syndrome). Cancer pain can also occur in response to chemotherapy, immunotherapy, hormonal therapy or radiotherapy. Back pain can be due to herniated or ruptured intervertebral discs or abnormalities of the lumber facet joints, sacroiliac joints, paraspinal muscles or the posterior longitudinal ligament.

In another embodiment, the condition related to pain is inflammatory pain. A common type of inflammatory pain is arthritic pain arising from rheumatoid disease (such as ankylosing spondylitis) or symptomatic osteoarthritis or degenerative joint disease. Another type of inflammatory pain is visceral pain. Visceral pain is pain associated with the viscera, which encompass the organs of the abdominal cavity including the sex organs, spleen and part of the digestive system. Pain associated with the viscera can be divided into digestive visceral pain and non-digestive visceral pain. Commonly encountered gastrointestinal disorders that cause pain include functional bowel disorder and inflammatory bowel disease. These gastrointestinal disorders include a wide range of disease states that are currently only moderately controlled, including, with respect to functional bowel disorder, gastro-esophageal reflux, dyspepsia, irritable bowel syndrome, and functional abdominal pain syndrome, and, in respect of inflammatory bowel disease, Crohn's disease, ileitis and ulcerative colitis, all of which regularly produce visceral pain. Other types of visceral pain include the pain associated with dysmenorrhea, cystitis and pancreatitis and pelvic pain.

In another embodiment, the condition related to pain results from a musculo-skeletal condition such as myalgia, fibromyalgia, spondylitis, sero-negative (non-rheumatoid) arthropathies, non-articular rheumatism, dystrophinopathy, glycogenolysis, polymyositis and pyomyositis; heart and vascular pain, including pain caused by angina, myocardial infarction, mitral stenosis, pericarditis, Raynaud's phenomenon, scleredoma and skeletal muscle ischemia; head pain, such as migraine (including migraine with aura and migraine without aura), cluster headache, tension-type headache mixed headache and headache associated with vascular disorders; and orofacial pain, including dental pain, otic pain, burning mouth syndrome, temporomandibular myofascial pain, and paroxysmal extreme pain disorder (PEPD); and inherited erythromelalgia (IEM).

In some embodiments, the methods comprise combination therapy, wherein the compound(s) and/or salt(s) of the invention is/are co-administered with a second (or even a third, fourth, etc.) compound, such as, for example, another therapeutic agent used to treat pain. The compound(s) and/or salt(s) of this invention can also be co-administered with therapeutic agents other than therapeutic agents used to treat pain. In these co-administration embodiments, the compound(s) and/or salt(s) of the invention and the second, etc. therapeutic agent(s) may be administered in a substantially simultaneous manner (e.g., or within about five minutes of each other), in a sequential manner, or both. It is contemplated that such combination therapies may include administering one therapeutic agent multiple times between the administrations of the other. The time period between the administration of each agent may range from a few seconds (or less) to several hours or days, and will depend on, for example, the properties of each composition and active ingredient (e.g., potency, solubility, bioavailability, half-life, and kinetic profile), as well as the condition of the patient. The compound(s) and/or salt(s) of this invention and the second, etc. therapeutic agent may also be administered in a single formulation.

In certain embodiments, the method comprises co-administering to the subject the compound(s) and/or salt(s) of the invention with one or more compounds selected from the group consisting of nonsteroidal anti-inflammatory drugs (NSAIDs), opioid analgesics, barbiturates, benzodiazapines, histamine antagonists, sedatives, skeletal muscle relaxants, transient receptor potential ion channel antagonists, α-adrenergics, tricyclic antidepressants, anticonvulsants, tachykinin antagonists, muscarinic antagonists, cyclooxygenase-2 selective inhibitors, neuroleptics, vanilloid receptor agonists, vanilloid receptor antagonists, β-adrenergics, local anesthetics, corticosteroids, 5-HT receptor agonists, 5-HT receptor antagonists, 5-HT$_{2A}$ receptor antagonists, cholinergic analgesics, α$_2$δ ligands (such as gabapentin or pregabalin), cannabinoid receptor ligands, metabotropic glutamate subtype 1 receptor antagonists, serotonin reuptake inhibitors, norepinephrine reuptake inhibitors, dual serotonin-noradrenaline reuptake inhibitors, Rho kinase inhibitors, inducible nitric oxide synthase inhibitors, acetylcholinesterase inhibitors, prostaglandin E$_2$ subtype 4 antagonists, leukotriene B4 antagonists, 5-lipoxygenase inhibitors, sodium channel blockers, 5-HT$_3$ antagonists, N-methyl-D-aspartic acid receptor antagonists, phosphodiesterase V inhibitors, voltage-gated calcium channel blockers (e.g., N-type and T-type), and KCNQ openers (e.g., KCNQ2/3 (K$_v$ 7.2/3)).

In one embodiment, the method comprises administering to the subject a therapeutically effective amount of a compound described herein, or a pharmaceutically acceptable salt, with or without a pharmaceutically acceptable carrier, in combination with a second therapeutic agent selected from the group consisting of acetaminophen, NSAIDs, opioid analgesics, and combinations thereof.

In one embodiment, the method comprises administering to the subject a therapeutically effective amount of a compound described herein, or a pharmaceutically acceptable salt, with or without a pharmaceutically acceptable carrier, in combination with one or more additional therapeutic agents for treating pain. In one embodiment, the additional therapeutic agent is selected from the group consisting of acetaminophen, NSAIDs (such aspirin, ibuprofen, and naproxen), and opioid analgesics. In another embodiment, the additional therapeutic agent is acetaminophen. In another embodiment, the additional therapeutic agent is an NSAID. In another embodiment, the additional therapeutic agent is an opioid analgesic.

The present invention also is directed, in part, to one or more compounds and/or salts of the invention for use in the treatment of a voltage-gated sodium channel-mediated condition, such as pain.

The present invention also is directed, in part, to one or more compounds and/or salts of the invention, and, optionally one or more additional therapeutic agents, for use as a medicament. In some embodiments, the medicament is for treating pain. In another embodiment, the medicament is for treating neuropathic pain. In another embodiment, the medicament is for treating nociceptive pain. In another embodiment, the medicament is for treating inflammatory pain.

The present invention is further directed, in part, to a use of one or more compounds and/or salts of the invention, and, optionally one or more additional therapeutic agents to prepare a medicament. In some embodiments, the medicament is for co-administration with one or more additional therapeutic agents. In some embodiments, the medicament is for treating pain. In some embodiments, the medicament is for treating neuropathic pain. In some embodiments, the medicament is for treating nociceptive pain. In some embodiments, the medicament is for treating inflammatory pain.

Compounds of the invention are particularly useful for treating and preventing a condition or disorder affecting pain.

The ability of the compounds of the invention, including, but not limited to, those specified in the examples, to treat the pain of peripheral neuropathy may be demonstrated by Faber C G, et al. Ann Neurol 2012; 72:26-39; Faber C G, et al. Proc. Natl. Acad. Sci. U.S.A. 2012; 109:19444-19449.

The ability of the compounds of the invention, including, but not limited to, those specified in the examples, to treat inflammatory and neuropathic pain may be demonstrated by McGowan E, et al. Anesth. Analg. 2009; 109:951-958.

The ability of the compounds of the invention, including, but not limited to, those specified in the examples, to treat chronic inflammatory knee pain may be demonstrated by Strickland I T, et al. European Journal of Pain 2008; 12:564-572.

The ability of the compounds of the invention, including, but not limited to, those specified in the examples, to treat osteoarthritis may be demonstrated by Schuelert N, et al. Arthritis Research & Therapy 2012; 14:R5; Malfait, A-M, et al. Nat. Rev. Rheumatol. 2013; 9:654-664; and Staunton C A, et al. Current Pain and Headache Reports 2013; 17:378.

The ability of the compounds of the invention, including, but not limited to, those specified in the examples, to treat osteoarthritis and sciatic pain may be demonstrated by Reimann F, et al. Proceedings of the National Academy of Sciences of the United States of America 2010; 107:5148-5153.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt or ester, or amide form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

For treatment or prevention of disease, the total daily dose of the compounds of this invention administered to a human or lower animal may range from about 0.0003 to about 100 mg/kg/day. For purposes of oral administration, more preferable doses can be in the range of from about 0.0003 to about 30 mg/kg/day. If desired, the effective daily dose can be divided into multiple doses for purposes of administration; consequently, single dose compositions may contain such amounts or submultiples thereof to make up the daily dose.

The compounds and processes of the invention will be better understood by reference to the following examples, which are intended as an illustration of and not a limitation upon the scope of the invention.

EXAMPLES

Abbreviations: DCI for desorption chemical ionization; DMSO for dimethyl sulfoxide; ESI for electrospray ionization; HPLC for high performance liquid chromatography; LC/MS for liquid chromatography/mass spectrometry; psi for pounds per square inch; and SFC for super critical fluid chromatography.

Example 1 piperazin-1-yl(6-{[5-(trifluoromethyl)pyridin-2-yl]oxy}quinolin-2-yl)methanone

Example 1A 2-chloroquinolin-6-ol

Phosphoryl chloride (30.0 mL, 322 mmol) was slowly added to a mixture of quinoline-2,6-diol (10.2 g, 63.2 mmol) and N,N-dimethylformamide (25 mL) at room temperature. The reaction mixture was warmed to 70° C. After 2.5 h, the reaction mixture was cooled to room temperature and then to 0° C. using an ice bath. Ice and water were slowly added to the reaction mixture which was then slowly neutralized with sodium hydroxide pellets and aqueous NaOH (1M). The pH of the reaction mixture was adjusted to >9. The mixture was extracted with ethyl acetate (3×). The combined organic extracts were dried with sodium sulfate, filtered, and concentrated. The titled compound was used in the next step without further purification.

Example 1B methyl 6-hydroxyquinoline-2-carboxylate

The product from Example 1A (0.100 g, 0.557 mmol) in methanol (10 mL) was added to [1,1'-bis(diphenylphosphino)ferrocene]dichloropalladium(II) (Pd(dppf)Cl$_2$, Heraeus) (0.020 g, 0.028 mmol) and triethylamine (0.155 mL, 1.114 mmol) in a 50 mL pressure bottle. The mixture was pressurized with carbon monoxide (60 psi), and stirred for 16 h at 100° C. The crude reaction mixture was filtered through diatomaceous earth. The filtrate was concentrated, and the residue was purified by column chromatography on silica gel using a gradient of 0-100% ethyl acetate/dichloromethane to yield 0.110 g (97%) of the titled compound. $^1$H NMR (300 MHz, DMSO-d$_6$) δ ppm 10.43 (s, 1H), 8.31 (d, J=8.3 Hz, 1H), 8.03-7.98 (m, 2H), 7.42 (dd, J=9.0, 2.7 Hz, 1H), 7.23 (d, 2.7 Hz, 1H), 3.92 (s, 3H); MS (ESI) m/z 204.0 [M+H]$^+$.

Example 1C methyl 6-{[5-(trifluoromethyl)pyridin-2-yl]oxy}quinoline-2-carboxylate 2-Fluoro-5-(trifluoromethyl)pyridine (26.7 mL, 221 mmol) was added to a mixture of the product from Example 1B (30.0 g, 148 mmol), cesium carbonate (40.6 g, 125 mmol) and N,N-dimethylformamide (300 mL) at room temperature, and the reaction mixture was heated to 70° C. After 6 h, the reaction mixture was cooled to room temperature, and water was added (400 mL). The solid was collected by filtration and washed with additional portions of water. The solid was dissolved in dichloromethane and washed with brine. The organic phase was collected, dried with Na$_2$SO$_4$, filtered and concentrated. The residue was taken up in 5 volumes of methyl tert-butyl ether and heated to 50° C. to nearly dissolve all material. To this was added 10 volumes of heptane. The mixture was removed from the heat and cooled to room temperature. The solids were collected by filtration, washed with heptane, and dried. The material was further purified by column chromatography on silica gel using a gradient of 0-20% ethyl acetate/dichloromethane to yield 46.6 g (91%) of the titled compound. $^1$H NMR (400 MHz, DMSO-d$_6$) δ ppm 8.62 (dd, J=1.7, 0.8 Hz, 1H), 8.58-8.51 (m, 1H), 8.35-8.29 (m, 1H), 8.25 (d, J=9.2 Hz, 1H), 8.15 (dd, J=8.4, 4.5 Hz, 1H), 7.94 (d, J=2.6 Hz, 1H), 7.77 (dt, J=7.2, 3.6 Hz, 1H), 7.42 (d, J=8.7 Hz, 1H), 3.98 (d, J=4.4 Hz, 3H); MS (ESI) m/z 349.0 [M+H]$^+$.

Example 1D

6-{[5-(trifluoromethyl)pyridin-2-yl]oxy}quinoline-2-carboxylic acid

Lithium hydroxide (9.61 g, 401 mmol) was added to a mixture of the product from Example 1C (46.6 g, 134 mmol), tetrahydrofuran (600 mL) and water (200 mL) at room temperature. The reaction became thick and overhead stirring was necessary. After 30 minutes, the reaction mixture was acidified with 1 M HCl (500 mL), transferred to a separatory funnel with water (500 mL) and extracted with ethyl acetate (2×500 mL). The organic phases were combined, dried with Na$_2$SO$_4$, filtered and concentrated. The solid was dried overnight under vacuum at 50° C. to yield 44.55 g (100%) of the titled compound. $^1$H NMR (400 MHz, DMSO-d$_6$) δ ppm 13.49 (br s, 1H), 8.61 (d, J=1.5 Hz, 1H), 8.53 (d, J=8.6 Hz, 1H), 8.31 (dd, J=8.7, 2.6 Hz, 1H), 8.23 (d, J=9.2 Hz, 1H), 8.14 (d, J=8.5 Hz, 1H), 7.93 (d, J=2.6 Hz, 1H), 7.76 (dd, J=9.2, 2.7 Hz, 1H), 7.41 (d, J=8.7 Hz, 1H); MS (ESI) m/z 335.1 [M+H]$^+$.

Example 1E tert-butyl 4-[(6-{[5-(trifluoromethyl)pyridin-2-yl]oxy}quinolin-2-yl)carbonyl]piperazine-1-carboxylate To a mixture of the product from Example 1D (44.55 g, 133 mmol) and tert-butyl piperazine-1-carboxylate (27.3 g, 147 mmol) in tetrahydrofuran (500 mL) at room temperature was added triethylamine (74.3 mL, 533 mmol) followed by a 15 minute addition of 2,4,6-tripropyl-1,3,5,2,4,6-trioxatriphosphinane 2,4,6-trioxide (117 mL, 200 mmol). After 15 min, water (500 mL) was added, and the mixture was stirred for 5 minutes. Then the mixture was transferred to a separatory funnel with additional water (500 mL) and ethyl acetate (1 L). The organic phase was washed with water (500 mL), 1 M HCl (200 mL), saturated aqueous NaHCO$_3$ (200 mL) and brine (200 mL). The organic phase was collected, dried with Na$_2$SO$_4$, filtered and concentrated. The residue was concentrated from diethyl ether (2×) to provide 63.6 g (95%) of the titled compound. $^1$H NMR (400 MHz, DMSO-d$_6$) δ ppm 8.58 (s, 1H), 8.49 (d, J=8.5 Hz, 1H), 8.30 (dd, J=8.7, 2.5 Hz, 1H), 8.11 (d, J=9.1 Hz, 1H), 7.89 (d, J=2.6 Hz, 1H), 7.75-7.69 (m, 2H), 7.39 (d, J=8.7 Hz, 1H), 3.74-3.66 (m, 2H), 3.54-3.45 (m, 4H), 3.42-3.35 (m, 2H), 1.42 (s, 9H); MS (ESI) m/z 502.9 [M+H]$^+$.

Example 1F piperazin-1-yl(6-{[5-(trifluoromethyl)pyridin-2-yl]oxy}quinolin-2-yl)methanone To a solution of the product from Example 1E (63.6 g, 127 mmol) in dichloromethane (300 mL) at room temperature was added trifluoroacetic acid (200 mL). The reaction mixture was stirred for 30 minutes, concentrated, taken up in dichloromethane and washed with 2.5 M NaOH. The organic phase was dried with Na$_2$SO$_4$, filtered and concentrated. The residue was concentrated from diethyl ether to provide a solid. The solid was dried in a vacuum oven at 50° C. to yield 50.65 g (99%) of the titled compound. $^1$H NMR (400 MHz, DMSO-d$_6$) δ ppm 8.60-8.56 (m, 1H), 8.47 (d, J=8.4 Hz, 1H), 8.30 (dd, J=8.7, 2.5 Hz, 1H), 8.11 (d, J=9.1 Hz, 1H), 7.88 (d, J=2.6 Hz, 1H), 7.77-7.60 (m, 2H), 7.39 (d, J=8.7 Hz, 1H), 3.72-3.55 (m, 2H), 3.44-3.31 (m, 2H), 2.86-2.74 (m, 2H), 2.73-2.61 (m, 2H); MS (ESI) m/z 403.1 [M+H]$^+$.

Example 2

N-(1,1-dioxidotetrahydrothiophen-3-yl)-6-{[5-(trifluoromethyl)pyridin-2-yl]oxy}quinoline-2-carboxamide A mixture of the product from Example 1D (1 g, 2.99 mmol), 3-aminotetrahydrothiophene 1,1-dioxide hydrochloride (0.514 g, 2.99 mmol), 1-[bis(dimethylamino)methylene]-1H-1,2,3-triazolo[4,5-b]pyridinium 3-oxid hexafluorophosphate (HATU, 1.706 g, 4.49 mmol), N,N-diisopropylethylamine (1.568 mL, 8.98 mmol), and dimethyl sulfoxide (14.96 mL) was stirred at room temperature for 4 h. Water was added, followed by saturated aqueous sodium bicarbonate. The mixture was extracted with dichloromethane (3×), dried with $Na_2SO_4$, filtered and concentrated. The residue was purified by column chromatography on silica gel using a gradient of 0-100% ethyl acetate/dichloromethane to yield 1.00 g (73%) of the titled compound. $^1$H NMR (400 MHz, DMSO-$d_6$) δ ppm 9.30 (d, J=8.1 Hz, 1H), 8.63-8.60 (m, 1H), 8.55 (d, J=8.6 Hz, 1H), 8.32 (dd, J=8.7, 2.4 Hz, 1H), 8.22 (d, J=9.2 Hz, 1H), 8.18 (d, J=8.5 Hz, 1H), 7.94 (d, J=2.5 Hz, 1H), 7.77 (dd, J=9.2, 2.6 Hz, 1H), 7.41 (d, J=8.7 Hz, 1H), 4.88-4.76 (m, 1H), 3.51 (dd, J=13.1, 7.7 Hz, 1H), 3.46-3.37 (m, 1H), 3.37-3.33 (m, 1H), 3.28-3.18 (m, 1H), 2.53-2.44 (m, 1H), 2.43-2.30 (m, 1H); MS (ESI) m/z 452.1 [M+H]$^+$.

Example 3

(1S,4S)-2,5-diazabicyclo[2.2.1]hept-2-yl(6-{[5-(trifluoromethyl)pyridin-2-yl]oxy}quinolin-2-yl)methanone Example 3A (1S,4S)-tert-butyl 5-(6-((5-(trifluoromethyl)pyridin-2-yl)oxy)quinoline-2-carbonyl)-2,5-diazabicyclo[2.2.1]heptane-2-carboxylate The product from Example 1D (800 mg, 2.39 mmol) was subjected to the conditions described in Example 2, substituting (1S,4S)-tert-butyl 2,5-diazabicyclo[2.2.1]heptane-2-carboxylate for 3-aminotetrahydrothiophene 1,1-dioxide hydrochloride to give the titled compound.

Example 3B (1S,4S)-2,5-diazabicyclo[2.2.1]hept-2-yl(6-{[5-(trifluoromethyl)pyridin-2-yl]oxy}quinolin-2-yl)methanone The product from Example 3A was then subjected to the conditions described in Example 1F to give 855 mg (85%, over two steps) of the titled compound. $^1$H NMR (400 MHz, DMSO-$d_6$, rotamers) δ ppm 8.61-8.58 (m, 1H), 8.50-8.45 (m, 1H), 8.30 (dd, J=8.7, 2.4 Hz, 1H), 8.12 (d, J=9.1 Hz, 1H), 7.94-7.83 (m, 2H), 7.74-7.69 (m, 1H), 7.39 (d, J=8.9 Hz, 1H), 4.91-4.77 (m, 1H), 3.88 (dd, J=10.4, 2.1 Hz, 0.5H), 3.68-3.59 (m, 1.5H), 3.52 (dd, J=11.1, 2.1 Hz, 1H), 3.38 (d, J=14.0, 2.8 Hz, 1H), 3.11 (d, J=9.6 Hz, 1H), 2.98-2.89 (m, 1H), 1.82-1.74 (m, 1H), 1.69-1.59 (m, 1H); MS (ESI) m/z 415.2 [M+H]$^+$.

Example 4

N-[(3S)-1,1-dioxidotetrahydrothiophen-3-yl]-6-{[5-(trifluoromethyl)pyridin-2-yl]oxy}quinoline-2-carboxamide The product from Example 2 (5.0 g, 11.07 mmol) was subjected to preparative super critical fluid chromatography (SFC) to give 2.17 g of the titled compound as a single enantiomer (first to elute, $t_R$ 4.17 minutes, >99% ee). Preparative SFC was performed on a THAR/Waters SFC 80 system running under SuperChrom™ software control. The preparative SFC system was equipped with an 8-way preparative column switcher, $CO_2$ pump, modifier pump, automated back pressure regulator (ABPR), UV detector, and 6-position fraction collector. The mobile phase comprised of supercritical $CO_2$ supplied by a Dewar of bone-dry non-certified $CO_2$ pressurized to 350 psi with a modifier of methanol at a flow rate of 80 g/min. UV detection was set to collect at a wavelength of 220 nm, the column was at ambient temperature, and the backpressure regulator was set to maintain 100 bar. The sample was dissolved in a 2:1 mixture of methanol/dichloromethane at a concentration of 50 mg/mL. The sample was loaded into the modifier stream in 1 mL (50 mg) injections. The mobile phase was held isocratically at 40% methanol:carbon dioxide. Fraction collection was time triggered. The instrument was fitted with a Chiralcel® OJ-H column with dimensions 30 mm i.d.×250 mm length with 5 μm particles.

Analytical SFC was performed on an Aurora SFC Fusion A5™ and Agilent 1100 system running under Agilent ChemStation software control. The SFC system included a 10-way column switcher, $CO_2$ pump, modifier pump, oven, and backpressure regulator. The mobile phase comprised of supercritical $CO_2$ supplied by a beverage-grade $CO_2$ cylinder with a modifier mixture of methanol at a flow rate of 3 mL/min. Oven temperature was at 35° C. and the outlet pressure at 150 bar. The mobile phase gradient started with 5% modifier and held it for 0.1 minutes at a flow rate of 1 mL/min, then the flow rate was ramped up to 3 mL/min and held for 0.4 min. The modifier was ramped from 5% to 50% over the next 8 minutes at 3 mL/min then held for 1 minute at 50% modifier (3 mL/min). The gradient was ramped down from 50% to 5% modifier over 0.5 min (3 mL/min). The instrument was fitted with a Chiralcel® OJ-H column with dimensions of 4.6 mm i.d.×150 mm length with 5 m particles.

$^1$H NMR (400 MHz, DMSO-$d_6$) δ ppm 9.30 (d, J=8.1 Hz, 1H), 8.63-8.60 (m, 1H), 8.55 (d, J=8.6 Hz, 1H), 8.32 (dd, J=8.7, 2.4 Hz, 1H), 8.22 (d, J=9.2 Hz, 1H), 8.18 (d, J=8.5 Hz, 1H), 7.94 (d, J=2.5 Hz, 1H), 7.77 (dd, J=9.2, 2.6 Hz, 1H), 7.41 (d, J=8.7 Hz, 1H), 4.88-4.76 (m, 1H), 3.51 (dd, J=13.1, 7.7 Hz, 1H), 3.46-3.37 (m, 1H), 3.37-3.33 (m, 1H), 3.28-3.18 (m, 1H), 2.53-2.44 (m, 1H), 2.43-2.30 (m, 1H); MS (ESI) m/z 452.1 [M+H]$^+$.

Example 5

N-[(3R)-1,1-dioxidotetrahydrothiophen-3-yl]-6-{[5-(trifluoromethyl)pyridin-2-yl]oxy}quinoline-2-carboxamide The product from Example 2 (5.0 g, 11.07 mmol) was subjected to preparative SFC to give 2.14 g of the titled compound as a single enantiomer (second to elute, $t_R$ 6.78 minutes, >99% ee). Preparative SFC was performed on a THAR/Waters SFC 80 system running under SuperChrom™ software control. The preparative SFC system was equipped with an 8-way preparative column switcher, $CO_2$ pump, modifier pump, automated back pressure regulator (ABPR), UV detector, and 6-position fraction collector. The mobile phase comprised of supercritical $CO_2$ supplied by a Dewar of bone-dry non-certified $CO_2$ pressurized to 350 psi with a modifier of methanol at a flow rate of 80 g/min. UV detection was set to collect at a wavelength of 220 nm, the column was at ambient temperature, and the backpressure regulator was set to maintain 100 bar. The sample was dissolved in a 2:1 mixture of methanol/dichloromethane at a concentration of 50 mg/mL. The sample was loaded into the modifier stream in 1 mL (50 mg) injections. The mobile phase was held isocratically at 40% methanol:carbon dioxide. Fraction collection was time triggered. The instrument was fitted with a Chiralcel® OJ-H column with dimensions 30 mm i.d.×250 mm length with 5 μm particles.

Analytical SFC was performed on an Aurora SFC Fusion A5™ and Agilent 1100 system running under Agilent ChemStation software control. The SFC system included a 10-way column switcher, $CO_2$ pump, modifier pump, oven, and backpressure regulator. The mobile phase comprised of supercritical $CO_2$ supplied by a beverage-grade $CO_2$ cylinder with a modifier mixture of methanol at a flow rate of 3 mL/min. Oven temperature was at 35° C. and the outlet pressure at 150 bar. The mobile phase gradient started with 5% modifier and held it for 0.1 minutes at a flow rate of 1 mL/min, then the flow rate was ramped up to 3 mL/min and held for 0.4 min. The modifier was ramped from 5% to 50% over the next 8 minutes at 3 mL/min then held for 1 minute at 50% modifier (3 mL/min). The gradient was ramped down from 50% to 5% modifier over 0.5 min (3 mL/min). The instrument was fitted with a Chiralcel® OJ-H column with dimensions of 4.6 mm i.d.×150 mm length with 5 μm particles.

$^1$H NMR (400 MHz, DMSO-$d_6$) δ ppm 9.30 (d, J=8.1 Hz, 1H), 8.63-8.60 (m, 1H), 8.55 (d, J=8.6 Hz, 1H), 8.32 (dd, J=8.7, 2.4 Hz, 1H), 8.22 (d, J=9.2 Hz, 1H), 8.18 (d, J=8.5 Hz, 1H), 7.94 (d, J=2.5 Hz, 1H), 7.77 (dd, J=9.2, 2.6 Hz, 1H), 7.41 (d, J=8.7 Hz, 1H), 4.88-4.76 (m, 1H), 3.51 (dd, J=13.1, 7.7 Hz, 1H), 3.46-3.37 (m, 1H), 3.37-3.33 (m, 1H), 3.28-3.18 (m, 1H), 2.53-2.44 (m, 1H), 2.43-2.30 (m, 1H). MS (ESI) m/z 452.1 [M+H]$^+$.

Example 6

[3-(morpholin-4-yl)azetidin-1-yl](6-{[5-(trifluoromethyl)pyridin-2-yl]oxy}quinolin-2-yl)methanone The product from Example 1D (1.00 g, 2.99 mmol) was subjected to the conditions described in Example 2, substituting 4-(azetidin-3-yl)morpholine hydrochloride for 3-aminotetrahydrothiophene 1,1-dioxide hydrochloride and purifying the material by column chromatography on silica gel using a gradient of 0-5% methanol/ethyl acetate, to give 720 mg (53%) of the titled compound. $^1$H NMR (400 MHz, DMSO-$d_6$) δ ppm 8.61-8.57 (m, 1H), 8.48 (d, J=8.6 Hz, 1H), 8.30 (dd, J=8.7, 2.6 Hz, 1H), 8.17 (d, J=9.1 Hz, 1H), 8.04 (d, J=8.6 Hz, 1H), 7.89 (d, J=2.6 Hz, 1H), 7.72 (dd, J=9.1, 2.7 Hz, 1H), 7.39 (d, J=8.7 Hz, 1H), 4.77 (dd, J=10.6, 7.0 Hz, 1H), 4.56 (dd, J=10.7, 4.9 Hz, 1H), 4.15 (dd, J=10.1, 7.5 Hz, 1H), 3.96 (dd, J=10.5, 4.8 Hz, 1H), 3.65-3.58 (m, 4H), 3.24-3.16 (m, 1H), 2.37 (br s, 4H); MS (ESI) m/z 459.0 [M+H]$^+$.

Example 7

1-(4-{[2-(piperazin-1-ylcarbonyl)quinolin-6-yl]oxy}phenyl)ethanone

Example 7A 6-hydroxyquinoline-2-carboxylic acid

Lithium hydroxide (3.61 g, 151 mmol) was added to a mixture of the product from Example 1B (10.2 g, 50.2 mmol), tetrahydrofuran (200 mL) and water (70 mL) at room temperature. After 30 minutes, tetrahydrofuran was distilled off, and the reaction mixture was acidified with 1 M HCl to pH ~1. A yellow solid precipitate was collected by filtration and washed with water. The solid was dried overnight under vacuum at 50° C. to give the titled compound (9.4 g, 99%).

Example 7B tert-butyl 4-(6-hydroxyquinoline-2-carbonyl)piperazine-1-carboxylate

A mixture of the product from Example 7A (4 g, 21.15 mmol), tert-butyl piperazine-1-carboxylate (3.94 g, 21.15 mmol), O-(benzotriazol-1-yl)-N,N,N',N'-tetramethyluronium tetrafluoroborate (8.15 g, 25.4 mmol), N,N-diisopropylethylamine (9.41 mL, 52.9 mmol), and N,N-dimethylformamide (30 mL) was stirred at room temperature for 18 h. The reaction mixture was poured into brine, and the resultant white precipitate was collected by filtration and washed with water. The solid was dried overnight under vacuum at 50° C. to give the titled compound (6 g, 79%).

Example 7C tert-butyl 4-{[6-(4-acetylphenoxy)quinolin-2-yl]carbonyl}piperazine-1-carboxylate A mixture of tert-butyl 4-(6-hydroxyquinoline-2-carbonyl)piperazine-1-carboxylate (1 g, 2.80 mmol), 1-(4-fluorophenyl)ethanone (0.42 mL, 4.20 mmol), and $K_2CO_3$ (0.77 g, 5.60 mmol) in N,N-dimethylformamide (15 mL) was heated at 120° C. for 16 h. The reaction mixture was cooled to room temperature, poured into brine and extracted with ethyl acetate. The organic layer was washed with brine (3×100 mL), dried with $MgSO_4$ and concentrated. The crude material was purified by column chromatography on silica gel using a gradient of 0-100% heptane/ethyl acetate to give the titled compound (0.93 mg, 70%).

Example 7D 1-(4-{[2-(piperazin-1-ylcarbonyl)quinolin-6-yl]oxy}phenyl)ethanone

The product from Example 7C (100 mg, 0.210 mmol) was subjected to the conditions described in Example 1F, substituting tert-butyl 4-{[6-(4-acetylphenoxy)quinolin-2-yl]carbonyl}piperazine-1-carboxylate for tert-butyl 4-[(6-{[5-(trifluoromethyl)pyridin-2-yl]oxy}quinolin-2-yl)carbonyl]piperazine-1-carboxylate to give the titled compound (74.2 mg, 94%). $^1$H NMR (300 MHz, DMSO-$d_6$) δ ppm 2.57 (s, 3H), 2.61-2.72 (m, 2H), 2.78 (dd, J=14.2, 9.4 Hz, 2H), 3.33-3.41 (m, 2H), 3.53-3.72 (m, 2H), 7.13-7.25 (m, 2H), 7.52-7.74 (m, 3H), 7.94-8.17 (m, 3H), 8.44 (d, J=8.4 Hz, 1H); MS (DCI) m/z 376.0 [M+H]$^+$.

Example 8

(3-aminoazetidin-1-yl)(6-{[5-(trifluoromethyl)pyridin-2-yl]oxy}quinolin-2-yl)methanone Example 8A tert-butyl {1-[(6-{[5-(trifluoromethyl)pyridin-2-yl]oxy}quinolin-2-yl)carbonyl]azetidin-3-yl}carbamate The product from Example 1D (1.10 g, 3.29 mmol) was subjected to the conditions described in Example 2, substituting tert-butyl azetidin-3-ylcarbamate for 3-aminotetrahydrothiophene 1,1-dioxide hydrochloride.

Example 8B (3-aminoazetidin-1-yl)(6-{[5-(trifluoromethyl)pyridin-2-yl]oxy}quinolin-2-yl)methanone The product from Example 8A was then subjected to the conditions described in Example 1F to give 434 mg (32%, over two steps) of the titled compound. $^1$H NMR (400 MHz, DMSO-$d_6$) δ ppm 8.61-8.58 (m, 1H), 8.48 (d, J=8.6 Hz, 1H), 8.31 (dd, J=8.7, 2.5 Hz, 1H), 8.14 (d, J=9.1 Hz, 1H), 8.04 (d, J=8.6 Hz, 1H), 7.89 (d, J=2.6 Hz, 1H), 7.72 (dd, J=9.1, 2.6 Hz, 1H), 7.40 (d, J=8.7 Hz, 1H), 4.90-4.84 (m, 1H), 4.36-4.25 (m, 2H), 3.83-3.71 (m, 2H), 2.21 (br s, 2H); MS (ESI) m/z 389.1 [M+H]$^+$.

Example 9

[cis-3,4-dihydroxypyrrolidin-1-yl](6-{[5-(trifluoromethyl)pyridin-2-yl]oxy}quinolin-2-yl)methanone

Example 9A 2,5-dihydro-1H-pyrrol-1-yl(6-{[5-(trifluoromethyl)pyridin-2-yl]oxy}quinolin-2-yl)methanone A mixture of the compound from Example 1D (75 mg, 0.224 mmol), 2,5-dihydro-1H-pyrrole (16 mg, 0.224 mmol), diisopropylethylamine (0.2 mL, 1.122 mmol), and O-(benzotriazol-1-yl)-N,N,N',N'-tetramethyluronium tetrafluoroborate (TBTU, 87 mg, 0.269 mmol) in N,N-dimethylacetamide (1.5 mL) was stirred overnight at room temperature. After this time, the mixture was diluted with ethyl acetate (20 mL) and washed with water (3×5 mL). The organic layer was dried over Na$_2$SO$_4$ and concentrated in vacuo. The residue was purified by silica gel chromatography (0 to 5% methanol-ethyl acetate, eluant) to afford the titled compound, 64 mg (74%). $^1$H NMR (300 MHz, DMSO-$d_6$) δ ppm 8.59 (m, 1H), 8.49 (d, J=8.6 Hz, 1H), 8.31 (m, 1H), 8.17 (d, J=8.9 Hz, 1H), 7.90-7.93 (m, 2H), 7.73 (m, 1H), 7.40 (d, J=8.6 Hz, 1H), 5.93-6.01 (m, 2H), 4.66-4.69 (m, 2H), 4.38-4.41 (m, 2H); MS (ESI$^+$) m/z 386.1 [M+H]$^+$.

Example 9B

[cis-3,4-dihydroxypyrrolidin-1-yl](6-{[5-(trifluoromethyl)pyridin-2-yl]oxy}quinolin-2-yl)methanone A mixture of the product from Example 9A (38 mg, 0.099 mmol) in acetonitrile (4 mL) and t-butanol (1 mL) was treated with N-methylmorpholine-N-oxide (50% weight solution in water; 0.03 mL, 0.145 mmol) and then osmium tetroxide (2.5% weight solution in t-butanol; 0.06 mL, 4.78 µmol). The mixture stirred overnight at room temperature. After this time, the reaction mixture was treated with solid sodium sulfite (230 mg) and stirred vigorously at room temperature for 1 h. The mixture was then filtered through a pad of sodium sulfite, and the filtrate was concentrated in vacuo. The residue was chromatographed on silica gel (0 to 10% methanol-ethyl acetate, eluant) to afford the titled compound (26 mg, 63%). $^1$H NMR (300 MHz, DMSO-$d_6$) δ ppm 8.60 (m, 1H), 8.47 (d, J=8.6 Hz, 1H), 8.31 (m, 1H), 8.13 (d, J=9.2 Hz, 1H), 7.89 (d, J=2.4 Hz, 1H), 7.85 (d, J=8.6 Hz, 1H), 7.73 (m, 1H), 7.40 (d, J=8.9 Hz, 1H), 4.96-5.01 (m, 2H), 4.05-4.14 (m, 2H), 3.90 (m, 1H), 3.61-3.69 (m, 2H), 3.45 (m, 1H); MS (ESI$^+$) m/z 420.1 [M+H]$^+$.

Example 10 pyrrolidin-1-yl(6-{[5-(trifluoromethyl)pyridin-2-yl]oxy}quinolin-2-yl)methanone

The product from Example 1D (500 mg, 1.496 mmol) was subjected to the conditions described in Example 2, substituting pyrrolidine for 3-aminotetrahydrothiophene 1,1-dioxide hydrochloride to give 552 mg (93%) of the titled compound. $^1$H NMR (400 MHz, DMSO-$d_6$) δ ppm 8.60-8.57 (m, 1H), 8.46 (d, J=8.5 Hz, 1H), 8.30 (dd, J=8.7, 2.6 Hz, 1H), 8.13 (d, J=9.1 Hz, 1H), 7.88 (d, J=2.6 Hz, 1H), 7.83 (d, J=8.5 Hz, 1H), 7.71 (dd, J=9.1, 2.7 Hz, 1H), 7.39 (d, J=8.7 Hz, 1H), 3.76-3.69 (m, 2H), 3.61-3.54 (m, 2H), 1.93-1.85 (m, 4H); MS (ESI) m/z 388.1 [M+H]$^+$.

Example 11

[4-(morpholin-4-yl)piperidin-1-yl](6-{[5-(trifluoromethyl)pyridin-2-yl]oxy}quinolin-2-yl)methanone A mixture of the product from Example 1D (0.1 g, 0.299 mmol), 4-(piperidin-4-yl)morpholine (0.05 g, 0.299 mmol), O-(benzotriazol-1-yl)-N,N,N',N'-tetramethyluronium tetrafluoroborate (0.144 g, 0.23 mmol), N,N-diisopropylethylamine (0.16 mL, 0.89 mmol), and N,N-dimethylformamide (1 mL) was stirred at room temperature for 18 h. The reaction mixture was poured into brine and extracted with ethyl acetate. The organic layer was washed with brine (3×100 mL), dried with MgSO$_4$ and concentrated. The crude material was purified by column chromatography on silica gel using 10% ethanol in ethyl acetate as eluent to give the titled compound (0.122 g, 84%). $^1$H NMR (500 MHz, DMSO-$d_6$) δ ppm 1.44 (qd, J=12.2, 4.2 Hz, 2H), 1.73 (d, J=12.2 Hz, 1H), 1.92 (d, J=12.3 Hz, 1H), 2.48-2.56 (m, 4H), 2.90 (td, J=12.8, 2.7 Hz, 1H), 3.08 (dd, J=18.4, 7.0 Hz, 1H), 3.57 (t, J=4.4 Hz, 4H), 3.73 (d, J=14.4 Hz, 1H), 4.53 (d, J=12.9 Hz, 1H), 7.39 (d, J=8.7 Hz, 1H), 7.61-7.78 (m, 2H), 7.89 (d, J=2.6 Hz, 1H), 8.11 (d, J=9.1 Hz, 1H), 8.30 (dd, J=8.7, 2.5 Hz, 1H), 8.47 (d, J=8.4 Hz, 1H), 8.53-8.64 (m, 1H); MS (DCI) m/z 487.0 [M+H]$^+$.

Example 12

[(3R)-3-methylpiperazin-1-yl](6-{[5-(trifluoromethyl)pyridin-2-yl]oxy}quinolin-2-yl)methanone

Example 12A tert-butyl (2R)-2-methyl-4-[(6-{[5-(trifluoromethyl)pyridin-2-yl]oxy}quinolin-2-yl)carbonyl]piperazine-1-carboxylate The product from Example 1D (200 mg, 0.56 mmol) was subjected to the conditions described in Example 11, substituting (R)-tert-butyl 2-methylpiperazine-1-carboxylate for 4-(piperidin-4-yl)morpholine to give the titled compound (242 mg, 74%).

Example 12B

[(3R)-3-methylpiperazin-1-yl](6-{[5-(trifluoromethyl)pyridin-2-yl]oxy}quinolin-2-yl)methanone The product from Example 12A (200 mg, 0.38 mmol) was subjected to the conditions described in Example 1F, to give the titled compound (104 mg, 64.5%). $^1$H NMR (400 MHz, DMSO-d$_6$) δ ppm 0.78-1.11 (m, 3H), 2.57-2.91 (m, 4H), 2.93-3.14 (m, 1H), 3.57 (d, J=11.2 Hz, 1H), 4.38 (d, J=11.3 Hz, 1H), 7.38 (dt, J=11.6, 5.8 Hz, 1H), 7.63-7.78 (m, 2H), 7.88 (d, J=2.6 Hz, 1H), 8.10 (d, J=9.1 Hz, 1H), 8.30 (dd, J=8.7, 2.5 Hz, 1H), 8.47 (d, J=8.3 Hz, 1H), 8.59 (dd, J=1.7, 0.8 Hz, 1H); MS (DCI) m/z 417.0 [M+H]$^+$.

Example 13

[(3S)-3-methylpiperazin-1-yl](6-{[5-(trifluoromethyl)pyridin-2-yl]oxy}quinolin-2-yl)methanone Example 13A tert-butyl (2S)-2-methyl-4-[(6-{[5-(trifluoromethyl)pyridin-2-yl]oxy}quinolin-2-yl)carbonyl]piperazine-1-carboxylate The product from Example 1D (200 mg, 0.59 mmol) was subjected to the conditions described in Example 11, substituting (S)-tert-butyl 2-methylpiperazine-1-carboxylate for 4-(piperidin-4-yl)morpholine to give the titled compound (232 mg, 75%).

Example 13B

[(3S)-3-methylpiperazin-1-yl](6-{[5-(trifluoromethyl)pyridin-2-yl]oxy}quinolin-2-yl)methanone The product from Example 13A (200 mg, 0.38 mmol) was subjected to the conditions described in Example 1F, substituting tert-butyl (2S)-2-methyl-4-[(6-{[5-(trifluoromethyl)pyridin-2-yl]oxy}quinolin-2-yl)carbonyl]piperazine-1-carboxylate for tert-butyl 4-[(6-{[5-(trifluoromethyl)pyridin-2-yl]oxy}quinolin-2-yl)carbonyl]piperazine-1-carboxylate to give the titled compound (106 mg, 73%). $^1$H NMR (400 MHz, DMSO-d$_6$) δ ppm 0.78-1.11 (m, 3H), 2.57-2.91 (m, 4H), 2.93-3.14 (m, 1H), 3.57 (d, J=11.2 Hz, 1H), 4.38 (d, J=11.3 Hz, 1H), 7.38 (dt, J=11.6, 5.8 Hz, 1H), 7.63-7.78 (m, 2H), 7.88 (d, J=2.6 Hz, 1H), 8.10 (d, J=9.1 Hz, 1H), 8.30 (dd, J=8.7, 2.5 Hz, 1H), 8.47 (d, J=8.3 Hz, 1H), 8.59 (dd, J=1.7, 0.8 Hz, 1H); MS (DCI) m/z 417.0 [M+H]$^+$.

Example 14

(6-{[5-(difluoromethyl)pyridin-2-yl]oxy}quinolin-2-yl)(piperazin-1-yl)methanone

Example 14A

6-{[5-(difluoromethyl)pyridin-2-yl]oxy}quinoline-2-carboxylic acid

To a mixture of the product from Example 1B (72.1 g, 355 mmol) and cesium carbonate (127 g, 390 mmol) in N-methyl-2-pyrrolidinone (1000 mL) at room temperature was added 2-chloro-5-(difluoromethyl)pyridine (42.3 mL, 355 mmol). The reaction mixture was heated to 130° C. for 62 h. The crude product was a 1:1 mixture of ester and the corresponding carboxylic acid. The reaction mixture was cooled to room temperature and tetrahydrofuran (400 mL) was added followed by lithium hydroxide hydrate (14 g, 334 mmol) in water. After 1 h, the reaction was acidified with 1 M HCl (pH ~1), and the mixture was extracted with ethyl acetate (4000 mL total). The organic phases were combined and concentrated. The residue was triturated with diethyl ether (800 mL). The solid was pulverized by stirring, collected by filtration, and dried to yield 65.1 g of the titled compound. A second crop of material was collected from the mother liquor. The second crop was taken up in tetrahydrofuran (300 mL) and water (200 mL) and treated with LiOH (8.0 g). After 30 minutes, the reaction mixture was processed in a similar manner as described above to yield 11.7 g of titled compound. All of the remaining acidic aqueous layers were combined and extracted with 1:1 tetrahydrofuran/diethyl ether (3×400 mL). The combined organic layers were dried with Na$_2$SO$_4$, filtered and concentrated. The residue was processed in a similar manner as described above to yield 5.91 g of titled compound. A combined total of 82.7 g (74%) of titled compound was obtained. $^1$H NMR (400 MHz, DMSO-d$_6$) δ ppm 13.27 (s, 1H), 8.53 (d, J=8.5 Hz, 1H), 8.42 (d, J=1.6 Hz, 1H), 8.23 (d, J=9.2 Hz, 1H), 8.14 (dd, J=8.5, 3.2 Hz, 2H), 7.89 (d, J=2.6 Hz, 1H), 7.73 (dd, J=9.2, 2.6 Hz, 1H), 7.34 (d, J=8.5 Hz, 1H), 7.14 (t, J=55.3 Hz, 1H).

Example 14B tert-butyl 4-[(6-{[5-(difluoromethyl)pyridin-2-yl]oxy}quinolin-2-yl)carbonyl]piperazine-1-carboxylate To a mixture of the product from Example 14A (20.52 g, 64.9 mmol) and tert-butyl piperazine-1-carboxylate (13.29 g, 71.4 mmol) in tetrahydrofuran (400 mL) at room temperature was added triethylamine (36.2 mL, 260 mmol) followed by 2,4,6-tripropyl-1,3,5,2,4,6-trioxatriphosphinane 2,4,6-trioxide [T3P®] (56.8 mL, 97 mmol). After 15 minutes, water was added and stirring was continued for 15 minutes. The crude product was extracted with ethyl acetate (3×300 mL). The organic phases were combined, washed with saturated aqueous NaHCO$_3$ (1×200 mL) and brine (1×200 mL), dried with Na$_2$SO$_4$, filtered and concentrated. The residue was taken up in 300 mL of diethyl ether and stirred overnight to pulverize. The solid was collected by filtration and dried to yield 26.0 g (83%) of the titled compound. $^1$H NMR (400 MHz, DMSO-d$_6$) δ ppm 8.48 (d, J=8.5 Hz, 1H), 8.38 (d, J=1.7 Hz, 1H), 8.15-8.08 (m, 2H), 7.85 (d, J=2.6 Hz, 1H), 7.72 (d, J=8.5 Hz, 1H), 7.69 (dd, J=9.1, 2.7 Hz, 1H), 7.32 (d, J=8.6 Hz, 1H), 7.12 (t, J=55.3 Hz, 1H), 3.74-3.66 (m, 2H), 3.54-3.44 (m, 4H), 3.42-3.36 (m, 2H), 1.41 (s, 9H); MS (ESI) m/z 484.9 [M+H]$^+$.

Example 14C (6-{[5-(difluoromethyl)pyridin-2-yl]oxy}quinolin-2-yl)(piperazin-1-yl)methanone Trifluoroacetic acid (30 mL) was added to a solution of the product from Example 14B (26.0 g, 53.6 mmol) in dichloromethane (30 mL) at room temperature. The reaction mixture was stirred for 30 minutes and concentrated. Water (100 mL) was added followed by 2.5 M NaOH (100 mL). The aqueous mixture was extracted with ethyl acetate (2×200 mL). The organic phases were combined, dried with Na$_2$SO$_4$, filtered and concentrated. The solid was dried in a vacuum oven at 50° C. to yield 18.3 g (89%) of the titled compound. $^1$H NMR (400 MHz, DMSO-d$_6$) δ ppm 8.47 (d, J=8.4 Hz, 1H), 8.40 (d, J=1.6 Hz, 1H), 8.17-8.04 (m, 2H), 7.85 (d, J=2.6 Hz, 1H), 7.68 (dd, J=8.9, 2.5 Hz, 2H), 7.32 (d, J=8.6 Hz, 1H), 7.13 (t, J=55.3 Hz, 1H), 3.68-3.58 (m, 2H), 3.39-3.30 (m, 2H), 2.84-2.75 (m, 2H), 2.70-2.62 (m, 2H); MS (ESI) m/z 385.1 [M+H]⁺.

Example 15

N-(1,1-dioxidotetrahydro-2H-thiopyran-4-yl)-6-{[5-(trifluoromethyl)pyridin-2-yl]oxy}quinoline-2-carboxamide The titled compound was prepared using the reaction conditions described for Example 9A, substituting 4-aminotetrahydro-2H-thiopyran 1,1-dioxide for 2,5-dihydro-1H-pyrrole. $^1$H NMR (300 MHz, DMSO-$d_6$) δ ppm 9.03 (d, J=8.5 Hz, 1H), 8.62 (s, 1H), 8.53 (d, J=8.9 Hz, 1H), 8.32 (m, 1H), 8.23 (d, J=9.1 Hz, 1H), 8.16 (d, J=8.5 Hz, 1H), 7.92 (d, J=2.7 Hz, 1H), 7.77 (m, 1H), 7.41 (d, J=8.9 Hz, 1H), 4.30 (m, 1H), 3.39-3.42 (m, 2H), 3.11-3.15 (m, 2H), 2.25-2.32 (m, 2H), 2.12-2.19 (m, 2H); MS (ESI⁺) m/z 466.1 [M+H]⁺.

Example 16

[(3R)-3-ethylpiperazin-1-yl](6-{[5-(trifluoromethyl)pyridin-2-yl]oxy}quinolin-2-yl)methanone

Example 16A tert-butyl (2R)-2-ethyl-4-[(6-{[5-(trifluoromethyl)pyridin-2-yl]oxy}quinolin-2-yl)carbonyl]piperazine-1-carboxylate The product from Example 1D (200 mg, 0.59 mmol) was subjected to the conditions described in Example 11, substituting (R)-tert-butyl 2-ethylpiperazine-1-carboxylate for 4-(piperidin-4-yl)morpholine to give the titled compound (238 mg, 67.5%).

Example 16B

[(3R)-3-ethylpiperazin-1-yl](6-{[5-(trifluoromethyl)pyridin-2-yl]oxy}quinolin-2-yl)methanone The product from Example 16A (200 mg, 0.38 mmol) was subjected to the conditions described in Example 1F, substituting tert-butyl (2R)-2-ethyl-4-[(6-{[5-(trifluoromethyl)pyridin-2-yl]oxy}quinolin-2-yl)carbonyl]piperazine-1-carboxylate for tert-butyl 4-[(6-{[5-(trifluoromethyl)pyridin-2-yl]oxy}quinolin-2-yl)carbonyl]piperazine-1-carboxylate to give the titled compound (145 mg, 85%). $^1$H NMR (500 MHz, DMSO-$d_6$, rotamers) δ ppm 0.74 (t, J=7.5 Hz, 1.5H), 0.95 (t, J=7.5 Hz, 1.5H), 1.08-1.33 (m, 1H), 1.35-1.49 (m, 1H), 2.52-2.95 (m, 4H), 2.95-3.12 (m, 1H), 3.58 (d, J=13.1 Hz, 0.56H), 3.73 (d, J=12.1 Hz, 0.54H), 4.41 (dt, J=24.4, 10.6 Hz, 1H), 7.40 (dd, J=8.7, 3.7 Hz, 1H), 7.63-7.77 (m, 2H), 7.89 (t, J=2.1 Hz, 1H), 8.10 (dd, J=9.1, 4.6 Hz, 1H), 8.31 (d, J=8.6 Hz, 1H), 8.48 (d, J=8.4 Hz, 1H), 8.59 (s, 1H); MS (DCI) m/z 431 [M+H]⁺.

Example 17

[(3R)-3-(hydroxymethyl)piperazin-1-yl](6-{[5-(trifluoromethyl)pyridin-2-yl]oxy}quinolin-2-yl)methanone

Example 17A tert-butyl (2R)-2-(hydroxymethyl)-4-[(6-{[5-(trifluoromethyl)pyridin-2-yl]oxy}quinolin-2-yl)carbonyl]piperazine-1-carboxylate The product from Example 1D (400 mg, 1.19 mmol) was subjected to the conditions described in Example 11, substituting (R)-tert-butyl 2-(hydroxymethyl)piperazine-1-carboxylate for 4-(piperidin-4-yl)morpholine to give the titled compound (285 mg, 44.7%).

Example 17B

[(3R)-3-(hydroxymethyl)piperazin-1-yl](6-{[5-(trifluoromethyl)pyridin-2-yl]oxy}quinolin-2-yl)methanone The product from Example 17A (250 mg, 0.46 mmol) was subjected to the conditions described in Example 1F, substituting tert-butyl (2R)-2-(hydroxymethyl)-4-[(6-{[5-(trifluoromethyl)pyridin-2-yl]oxy}quinolin-2-yl)carbonyl]piperazine-1-carboxylate for tert-butyl 4-[(6-{[5-(trifluoromethyl)pyridin-2-yl]oxy}quinolin-2-yl)carbonyl]piperazine-1-carboxylate to give the titled compound (163 mg, 80%). $^1$H NMR (400 MHz, DMSO-$d_6$, rotamers) δ ppm 2.53-3.18 (m, 8H), 3.65 (dd, J=41.9, 12.3 Hz, 1H), 4.27-4.61 (m, 1.5H), 4.76 (t, J=5.1 Hz, 0.5H), 7.39 (d, J=8.1 Hz, 1H), 7.70 (ddd, J=10.4, 6.3, 1.9 Hz, 2H), 7.89 (d, J=2.6 Hz, 1H), 8.11 (d, J=9.1 Hz, 1H), 8.30 (dd, J=8.7, 2.5 Hz, 1H), 8.47 (d, J=8.5 Hz, 1H), 8.61 (d, J=17.7 Hz, 1H); MS (DCI) m/z 433 [M+H]⁺.

Example 18

(3-hydroxyazetidin-1-yl)(6-{[5-(trifluoromethyl)pyridin-2-yl]oxy}quinolin-2-yl)methanone The titled compound was prepared using the reaction conditions described for Example 9A, substituting azetidin-3-ol hydrochloride for 2,5-dihydro-1H-pyrrole. $^1$H NMR (300 MHz, DMSO-$d_6$) δ ppm 8.59 (s, 1H), 8.48 (d, J=8.5 Hz, 1H), 8.30 (m, 1H), 8.16 (d, J=9.1 Hz, 1H), 8.05 (d, J=8.6 Hz, 1H), 7.89 (d, J=2.5 Hz, 1H), 7.73 (m, 1H), 7.40 (d, J=8.6 Hz, 1H), 5.76 (m, 1H), 4.91 (m, 1H), 4.56 (m, 1H), 4.47 (m, 1H), 4.34 (m, 1H), 3.86 (m, 1H); MS (ESI⁺) m/z 390.1 [M+H]⁺.

Example 19 piperazin-1-yl(6-{[6-(trifluoromethyl)pyridin-3-yl]oxy}quinolin-2-yl)methanone

Example 19A methyl 6-{[6-(trifluoromethyl)pyridin-3-yl]oxy}quinoline-2-carboxylate 5-Fluoro-2-(trifluoromethyl)pyridine (1.00 g, 6.06 mmol) was added to a mixture of the product from Example 1B (1.119 g, 5.51 mmol), cesium carbonate (1.974 g, 6.06 mmol) and N,N-dimethylformamide (25 mL) at room temperature, and the reaction mixture was heated to 90° C. After 90 minutes, the reaction mixture was cooled to room temperature, and water was added (150 mL). The solid was collected by filtration washing with additional portions of water. The solid was dried in a vacuum oven at 50° C. overnight to yield 1.726 g (90%) of the titled compound. $^1$H NMR (300 MHz, DMSO-$d_6$) δ ppm 8.73 (d, J=2.8 Hz, 1H), 8.52 (d, J=8.2 Hz, 1H), 8.26-8.28 (m, 1H), 8.14 (d, J=8.5 Hz, 1H), 7.99 (d, J=8.9 Hz, 1H), 7.78-7.84 (m, 3H), 3.97 (s, 3H); MS (ESI) m/z 349.0 [M+H]+.

Example 19B

6-{[6-(trifluoromethyl)pyridin-3-yl]oxy}quinoline-2-carboxylic acid

Lithium hydroxide (202.6 mg, 8.46 mmol) was added to a mixture of the product from Example 19A (1.00 g, 2.87 mmol), tetrahydrofuran (15 mL) and water (5 mL) at room temperature. After 30 minutes, the reaction was acidified with 1 M HCl (10 mL), transferred to a separatory funnel with water (25 mL) and extracted with ethyl acetate (2×50 mL). The organic phases were combined, dried with Na$_2$SO$_4$, filtered and concentrated. The solid was dried overnight under vacuum at 50° C. to yield 956 mg (100%) of the titled compound. $^1$H NMR (400 MHz, DMSO-d$_6$) δ ppm 8.71 (d, J=2.4 Hz, 1H), 8.47 (d, J=8.6 Hz, 1H), 8.27 (d, J=9.8 Hz, 1H), 8.13 (d, J=8.6 Hz, 1H), 7.98 (d, J=8.5 Hz, 1H), 7.74-7.81 (m, 3H); MS (ESI) m/z 335.1 [M+H]+.

Example 19C tert-butyl 4-[(6-{[6-(trifluoromethyl)pyridin-3-yl]oxy}quinolin-2-yl)carbonyl]piperazine-1-carboxylate To a mixture of the product from Example 19B (371 mg, 1.00 mmol) and O-(benzotriazol-1-yl)-N,N,N',N'-tetramethyluronium tetrafluoroborate (TBTU, 146.7 mg, 1.49 mmol) in N,N-dimethylformamide (5 mL) at room temperature was added triethylamine (0.3 mL, 2.15 mmol) followed by tert-butyl piperazine-1-carboxylate (378.8 mg, 2.03 mmol). After 3 h, water (50 mL) was added, and the mixture was transferred to a separatory funnel and extracted with ethyl acetate (3×50 mL). The organic phase was washed with brine (35 mL). The organic phase was collected, dried with MgSO$_4$, filtered and concentrated. The residue was purified by silica gel chromatography using a mobile phase of 50% ethyl acetate/dichloromethane, R$_f$=0.40) to yield 489.3 mg (97%) of the titled compound. $^1$H NMR (400 MHz, DMSO-d$_6$) δ ppm 8.70 (d, J=2.8 Hz, 1H), 8.47 (d, J=8.5 Hz, 1H), 8.15 (d, J=8.9 Hz, 1H), 7.97 (d, J=8.5 Hz, 1H), 7.71-7.78 (m, 4H), 3.68-3.71 (m, 2H), 3.47-3.49 (m, 4H), 3.37-3.40 (m, 2H), 1.42 (s, 9H); MS (ESI) m/z 503.1 [M+H]+.

Example 19D piperazin-1-yl(6-{[6-(trifluoromethyl)pyridin-3-yl]oxy}quinolin-2-yl)methanone To a solution of the product from Example 19C (486.2 mg, 0.97 mmol) in dichloromethane (5 mL) at room temperature was added trifluoroacetic acid (1 mL). The reaction mixture was stirred for 2 h, concentrated, taken up in 1 M NaOH (50 mL) and extracted with dichloromethane (3×50 mL). The organic phase was dried with Na$_2$SO$_4$, filtered and concentrated to yield 376.6 mg (97%) of the titled compound. $^1$H NMR (400 MHz, DMSO-d$_6$) δ ppm 8.69 (d, J=2.4 Hz, 1H), 8.46 (d, J=8.6 Hz, 1H), 8.46 (d, J=8.6 Hz, 1H), 8.14 (d, J=8.9 Hz, 1H), 7.96 (d, J=8.5 Hz, 1H), 7.72-7.78 (m, 3H), 7.67 (d, J=8.5 Hz, 1H), 3.33-3.36 (m, 2H), 3.62-3.64 (m, 2H), 2.79-2.81 (m, 2H), 2.67-2.69 (m, 2H); MS (ESI) m/z 403.1 [M+H]+.

Example 20

[3-(trifluoromethyl)piperazin-1-yl](6-{[5-(trifluoromethyl)pyridin-2-yl]oxy}quinolin-2-yl)methanone To a mixture of the product from Example 1D (107.9 mg, 0.323 mmol) and O-(benzotriazol-1-yl)-N,N,N',N'-tetramethyluronium tetrafluoroborate (TBTU, 156.4 mg, 0.487 mmol) in dimethyl sulfoxide (1 mL) at room temperature was added triethylamine (0.1 mL, 0.72 mmol) followed by 2-(trifluoromethyl)piperazine (79.5 mg, 0.518 mmol). After 3 h, the mixture was diluted with methanol (1 mL) and purified by reverse phase preparative HPLC on a Waters Nova-Pak® HR C18 6 μm 60 Å Prep-Pak® cartridge column (40 mm×100 mm) using a gradient of 10% to 100% acetonitrile in 10 mM aqueous ammonium acetate over 12 minutes at a flow rate of 70 mL/minute to yield 104.3 mg (69%) of the titled compound. $^1$H NMR (400 MHz, DMSO-d$_6$) δ ppm 1:1 mixture of rotamers 8.57-5-61 (m, 1H), 8.50 (dd, J=8.5, 4.6 Hz, 1H), 8.31 (dd, J=8.5, 2.4 Hz, 1H), 8.10 (t, J=9.0 Hz, 1H), 7.90 (t, J=2.7 Hz, 1H), 7.70-7.78 (m, 2H), 7.40 (dd, J=8.5, 3.7 Hz, 1H), 4.36 (dd, J=12.5, 3.1 Hz, 0.5H), 4.11-4.14 (m, 0.5H), 4.02 (dd, J=13.3, 2.3 Hz, 0.5H), 3.03-3.64 (m, 4H), 2.67-2.90 (m, 1.5H); MS (ESI) m/z 471.1 [M+H]+.

Example 21

N-[2-(morpholin-4-yl)ethyl]-6-{[5-(trifluoromethyl)pyridin-2-yl]oxy}quinoline-2-carboxamide The product from Example 1D (106.2 mg, 0.318 mmol) was subjected to the conditions described in Example 20, substituting 2-morpholinoethanamine for 2-(trifluoromethyl)piperazine, to give the titled compound (110.7 mg, 78%). $^1$H NMR (400 MHz, DMSO-d$_6$) δ ppm 8.90 (t, J=6.0 Hz, 1H), 8.60-8.61 (m, 1H), 8.53 (d, J=8.2 Hz, 1H), 8.31 (dd, J=8.7, 2.6 Hz, 1H), 8.17-8.20 (m, 2H), 7.93 (d, J=2.8 Hz, 1H), 7.76 (dd, J=9.2, 2.8 Hz, 1H), 7.41 (d, J=8.9 Hz, 1H), 3.59-3.62 (m, 4H), 3.51 (q, J=6.7 Hz, 2H), 2.55 (t, J=6.7 Hz, 2H), 2.45-2.47 (m, 4H); MS (ESI) m/z 447.1 [M+H]+.

Example 22

N-(2-methoxyethyl)-6-{[5-(trifluoromethyl)pyridin-2-yl]oxy}quinoline-2-carboxamide The product from Example 1D (101.6 mg, 0.304 mmol) was subjected to the conditions described in Example 20, substituting 2-methoxyethanamine for 2-(trifluoromethyl)piperazine, to give the titled compound (62.6 mg, 53%). $^1$H NMR (400 MHz, DMSO-d$_6$) δ ppm 8.90 (t, J=6.0 Hz, 1H), 8.60-8.61 (m, 1H), 8.53 (d, J=4.9 Hz, 1H), 8.60-8.61 (m, 1H), 8.54 (d, J=8.5 Hz, 1H), 8.31 (dd, J=8.7, 2.6 Hz, 1H), 8.17-8.22 (m, 2H), 7.93 (d, J=2.8 Hz, 1H), 7.76 (dd, J=9.2, 2.8 Hz, 1H), 7.42 (d, J=8.9 Hz, 1H), 3.53-3.58 (m, 4H), 3.31 (s, 3H); MS (ESI) m/z 392.1 [M+H]+.

Example 23

N-(4,4-difluorocyclohexyl)-6-{[5-(trifluoromethyl)pyridin-2-yl]oxy}quinoline-2-carboxamide The product from Example 1D (200 mg, 0.59 mmol) was subjected to the conditions described in Example 1E, substituting 4,4-difluorocyclohexanamine hydrochloride for tert-butyl piperazine-1-carboxylate to give the titled compound (72 mg, 53.3%). $^1$H NMR (400 MHz, DMSO-d$_6$) δ ppm 1.71-2.22 (m, 8H), 4.07 (d, J=8.4 Hz, 1H), 7.40 (d, J=8.7 Hz, 1H), 7.76 (dd, J=9.1, 2.7 Hz, 1H), 7.92 (d, J=2.6 Hz, 1H), 8.19 (dd, J=23.9, 8.8 Hz, 2H), 8.32 (dd, J=8.7, 2.5 Hz, 1H), 8.53 (d, J=8.5 Hz, 1H), 8.81 (d, J=8.4 Hz, 1H); MS (DCI) m/z 452 [M+H]$^+$.

Example 24

N-[(3S,4S)-4-hydroxy-1,1-dioxidotetrahydrothiophen-3-yl]-6-{[5-(trifluoromethyl)pyridin-2-yl]oxy}quinoline-2-carboxamide The titled compound was prepared using the reaction conditions described for Example 9A, substituting (3S,4S)-3-amino-4-hydroxytetrahydrothiophene 1,1-dioxide for 2,5-dihydro-1H-pyrrole. $^1$H NMR (300 MHz, DMSO-d$_6$) δ ppm 8.88 (d, J=8.3 Hz, 1H), 8.62 (m, 1H), 8.58 (d, J=8.5 Hz, 1H), 8.34 (m, 1H), 8.22 (m, 1H), 8.20 (m, 1H), 7.96 (d, J=2.7 Hz, 1H), 7.78 (m, 1H), 7.41 (d, J=8.8 Hz, 1H), 6.30 (br, 1H), 4.80 (m, 1H), 4.63 (m, 1H), 3.39-3.59 (m, 4H); MS (ESI$^+$) m/z 468.1 [M+H]$^+$.

Example 25

[2-(difluoromethyl)piperazin-1-yl](6-{[5-(trifluoromethyl)pyridin-2-yl]oxy}quinolin-2-yl)methanone Example 25A tert-butyl 3-(difluoromethyl)-4-[(6-{[5-(trifluoromethyl)pyridin-2-yl]oxy}quinolin-2-yl)carbonyl]piperazine-1-carboxylate The product from Example 1D (500 mg, 1.496 mmol) was subjected to the conditions described in Example 2, substituting tert-butyl 3-(difluoromethyl)piperazine-1-carboxylate for 3-aminotetrahydrothiophene 1,1-dioxide hydrochloride.

Example 25B

[2-(difluoromethyl)piperazin-1-yl](6-{[5-(trifluoromethyl)pyridin-2-yl]oxy}quinolin-2-yl)methanone The product from Example 25A was then subjected to the conditions described in Example 1F to give 350 mg (51%, over two steps) of the titled compound. $^1$H NMR (500 MHz, DMSO-d$_6$, rotamers) δ ppm 8.59 (s, 1H), 8.50 (d, J=8.5 Hz, 1H), 8.30 (dd, J=8.7, 2.5 Hz, 1H), 8.12 (t, J=8.9 Hz, 1H), 7.90 (d, J=2.6 Hz, 1H), 7.74-7.71 (m, 1H), 7.69 (dd, J=8.5, 7.0 Hz, 1H), 7.40 (dd, J=8.7, 3.7 Hz, 1H), 6.55 (tdd, J=57.0, 37.5, 6.7 Hz, 1H), 4.82-4.74 (m, 0.5H), 4.43-4.34 (m, 0.5H), 4.35-4.27 (m, 0.5H), 3.56 (d, J=13.3 Hz, 0.5H), 3.39-3.34 (m, 0.5H), 3.16 (d, J=13.1 Hz, 0.5H), 3.09-2.93 (m, 2H), 2.87-2.77 (m, 1H), 2.76-2.68 (m, 0.5H), 2.63-2.55 (m, 1.5H); MS (ESI) m/z 453.1 [M+H]$^+$.

Example 26

N-[(3R,4S)-4-hydroxy-1,1-dioxidotetrahydrothiophen-3-yl]-6-{[5-(trifluoromethyl)pyridin-2-yl]oxy}quinoline-2-carboxamide The titled compound was prepared using the reaction conditions described for Example 9A, substituting (3R,4S)-3-amino-4-hydroxytetrahydrothiophene 1,1-dioxide for 2,5-dihydro-1H-pyrrole. $^1$H NMR (300 MHz, DMSO-d$_6$) δ ppm 8.88 (d, J=8.3 Hz, 1H), 8.61 (m, 1H), 8.58 (d, J=8.2 Hz, 1H), 8.32 (m, 1H), 8.22 (m, 1H), 8.20 (m, 1H), 7.95 (d, J=2.7 Hz, 1H), 7.78 (m, 1H), 7.41 (d, J=8.8 Hz, 1H), 6.30 (br, 1H), 4.80 (m, 1H), 4.63 (m, 1H), 3.39-3.59 (m, 4H); MS (ESI$^+$) m/z 468.1 [M+H]$^+$.

Example 27

(8aS)-2-[(6-{[5-(trifluoromethyl)pyridin-2-yl]oxy}quinolin-2-yl)carbonyl]hexahydropyrrolo[1,2-a]pyrazin-4(1H)-one A mixture of the product from Example 1D (100 mg, 0.299 mmol) and 1-[bis(dimethylamino)methylene]-1H-1,2,3-triazolo[4,5-b]pyridinium 3-oxid hexafluorophosphate (HATU, 148 mg, 0.389 mmol) in N,N-dimethylformamide (1.5 mL) was stirred at ambient temperature for 10 minutes, and then (S)-hexahydropyrrolo[1,2-a]pyrazin-4(1H)-one hydrochloride (53 mg, 0.3 mmol) and (N,N-diisopropylethylamine (0.16 mL, 0.9 mmol) were added. The mixture was stirred at room temperature for another 2 h, CH$_2$Cl$_2$ (20 mL) and saturated aqueous NaHCO$_3$ (10 mL) were added to the reaction mixture. The water layer was extracted with CH$_2$Cl$_2$. The combined organic fractions were dried over MgSO$_4$, filtered and concentrated under reduced pressure. The residue was dissolved in methanol, filtered using a syringe filter, and purified by preparative HPLC on a Phenomenex® Luna® C8(2) 5 μm 100 Å AXIA™ column (30 mm×75 mm). A gradient of acetonitrile (A) and 10 mM ammonium acetate in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). Samples were injected in 1.5 mL dimethyl sulfoxide:methanol (1:1). A custom purification system was used, consisting of the following modules: Waters LC4000 preparative pump; Waters 996 diode-array detector; Waters 717+ autosampler; Waters SAT/IN module, Alltech Varex III evaporative light-scattering detector; Gilson 506C interface box; and two Gilson FC204 fraction collectors. The system was controlled using Waters Millennium32 software, automated using an AbbVie developed Visual Basic application for fraction collector control and fraction tracking. Fractions were collected based upon UV signal threshold and selected fractions subsequently analyzed by flow injection analysis mass spectrometry using positive APCI ionization on a Finnigan LCQ using 70:30 methanol: 10 mM NH$_4$OH(aqueous) at a flow rate of 0.8 mL/min. Loop-injection mass spectra were acquired using a Finnigan LCQ running LCQ Navigator 1.2 software and a Gilson 215 liquid handler for fraction injection controlled by an AbbVie developed Visual Basic application. The desired fractions were collected and concentrated to yield 93 mg (68%) of the titled compound. $^1$H NMR (400 MHz, DMSO-d$_6$) δ ppm 1.29-1.63 (m, 1H) 1.67-2.03 (m, 3H) 2.85-3.22 (m, 1H) 3.33-3.55 (m, 2H) 3.62-4.13 (m, 2H) 4.24-4.42 (m, 1H) 4.54-4.89 (m, 1H) 7.40 (d, J=8.85 Hz, 1H) 7.69-7.81 (m, 2H) 7.91 (d, J=2.75 Hz, 1H) 8.09-8.18 (m, 1H) 8.25-8.35 (m, J=8.85, 2.14 Hz, 1H) 8.45-8.54 (m, J=8.55, 3.36 Hz, 1H) 8.59 (s, 1H); MS (ESI) m/z 457.0 [M+H]$^+$.

Example 28

[4-(2-hydroxyethyl)piperazin-1-yl](6-{[5-(trifluoromethyl)pyridin-2-yl]oxy}quinolin-2-yl)methanone The product from Example 1D (105.2 mg, 0.315 mmol) was subjected to the conditions described in Example 20, substituting 2-(piperazin-1-yl)ethanol for 2-(trifluoromethyl)piperazine, to give the titled compound (105.8 mg, 75%). $^1$H NMR (400 MHz, DMSO-d$_6$) δ ppm 8.58-8.59 (m, 1H), 8.48 (d, J=8.2 Hz, 1H), 8.30 (dd, J=8.6, 2.4 Hz, 1H), 8.11 (d, J=9.2 Hz, 1H), 7.89 (d, J=2.8 Hz, 1H), 7.65-7.75 (m, 2H), 7.39 (d, J=8.9 Hz, 1H), 4.43 (br s, 1H), 3.70-3.72 (m, 2H), 3.52 (t, J=6.1 Hz, 2H), 3.44-3.46 (m, 2H), 2.53-2.56 (m, 2H), 2.42-2.46 (m, 6H); MS (ESI) m/z 447.1 [M+H]$^+$.

Example 29

[3-(methylsulfonyl)azetidin-1-yl](6-{[5-(trifluoromethyl)pyridin-2-yl]oxy}quinolin-2-yl)methanone The titled compound was prepared using the reaction conditions described for Example 9A, substituting 3-(methylsulfonyl)azetidine hydrochloride for 2,5-dihydro-1H-pyrrole. $^1$H NMR (300 MHz, DMSO-d$_6$) δ ppm 8.60 (m, 1H), 8.52 (d, J=8.2 Hz, 1H), 8.31 (m, 1H), 8.22 (d, J=9.2 Hz, 1H), 8.09 (d, J=8.5 Hz, 1H), 7.92 (d, J=2.5 Hz, 1H), 7.75 (m, 1H), 7.41 (d, J=8.6 Hz, 1H), 4.97-5.12 (m, 2H), 4.44 (m, 2H), 4.33 (m, 1H), 3.10 (s, 3H); MS (ESI$^+$) m/z 452.0.

Example 30

N-(2-hydroxy-2-methylpropyl)-6-{[5-(trifluoromethyl)pyridin-2-yl]oxy}quinoline-2-carboxamide The product from Example 1D (200 mg, 0.59 mmol) was subjected to the conditions described in Example 11, substituting 1-amino-2-methylpropan-2-ol for 4-(piperidin-4-yl)morpholine to give the titled compound (205 mg, 85%). $^1$H NMR (500 MHz, DMSO-d$_6$) δ ppm 1.17 (d, J=6.1 Hz, 6H), 3.37 (t, J=7.3 Hz, 2H), 4.78 (s, 1H), 7.41 (d, J=8.7 Hz, 1H), 7.76 (dd, J=9.1, 2.6 Hz, 1H), 7.94 (d, J=2.6 Hz, 1H), 8.22 (dd, J=8.8, 4.6 Hz, 2H), 8.32 (dd, J=8.7, 2.5 Hz, 1H), 8.56 (d, J=8.5 Hz, 1H), 8.61-8.71 (m, 2H); MS (DCI) m/z 406 [M+H]$^+$.

Example 31

[(3R)-3-(methoxymethyl)piperazin-1-yl](6-{[5-(trifluoromethyl)pyridin-2-yl]oxy}quinolin-2-yl)methanone Example 31A tert-butyl (2R)-2-(methoxymethyl)-4-[(6-{[5-(trifluoromethyl)pyridin-2-yl]oxy}quinolin-2-yl)carbonyl]piperazine-1-carboxylate The product from Example 17A (65 mg, 0.12 mmol) in toluene (0.8 mL) was treated with sodium hydroxide (9.76 mg, 0.12 mmol), tetrabutylammonium hydrogen sulfate (4.14 mg, 0.012 mmol) and dimethyl sulfate (0.023 mL, 0.244 mmol), and the reaction mixture was stirred at room temperature overnight. The reaction mixture was partitioned between ethyl acetate and water. The organic layer was washed with brine, dried (MgSO$_4$) and concentrated in vacuo to give the titled compound (60 mg, 90%).

Example 31B

[(3R)-3-(methoxymethyl)piperazin-1-yl](6-{[5-(trifluoromethyl)pyridin-2-yl]oxy}quinolin-2-yl)methanone The product from Example 31A (55 mg, 0.1 mmol) was subjected to the conditions described in Example 1F, substituting tert-butyl (2R)-2-(methoxymethyl)-4-[(6-{[5-(trifluoromethyl)pyridin-2-yl]oxy}quinolin-2-yl)carbonyl]piperazine-1-carboxylate for tert-butyl 4-[(6-{[5-(trifluoromethyl)pyridin-2-yl]oxy}quinolin-2-yl)carbonyl]piperazine-1-carboxylate to give the titled compound (40 mg, 89%). $^1$H NMR (400 MHz, DMSO-d$_6$) δ ppm 2.54-3.23 (m, 8H), 3.33 (s, 3H), 3.52-3.74 (m, 1H), 4.27-4.51 (m, 1H), 7.39 (dd, J=8.7, 3.7 Hz, 1H), 7.62-7.77 (m, 2H), 7.89 (t, J=2.1 Hz, 1H), 8.10 (dd, J=9.1, 1.9 Hz, 1H), 8.30 (dd, J=8.7, 2.1 Hz, 1H), 8.47 (d, J=8.5 Hz, 1H), 8.61 (d, J=20.2 Hz, 1H); MS (DCI) m/z 447 [M+H]$^+$.

Example 32

N-(1-oxidotetrahydro-2H-thiopyran-4-yl)-6-{[5-(trifluoromethyl)pyridin-2-yl]oxy}quinoline-2-carboxamide Example 32A N-(tetrahydro-2H-thiopyran-4-yl)-6-{[5-(trifluoromethyl)pyridin-2-yl]oxy}quinoline-2-carboxamide The titled compound was prepared using the reaction conditions described for Example 9A, substituting tetrahydro-2H-thiopyran-4-amine for 2,5-dihydro-1H-pyrrole. $^1$H NMR (300 MHz, DMSO-d$_6$) δ ppm 8.79 (d, J=8.6 Hz, 1H), 8.61 (m, 1H), 8.52 (d, J=8.5 Hz, 1H), 8.31 (m, 1H), 8.23 (d, J=9.2 Hz, 1H), 8.16 (d, J=8.5 Hz, 1H), 7.92 (d, J=2.8 Hz, 1H), 7.75 (m, 1H), 7.40 (d, J=8.9 Hz, 1H), 3.91 (m, 1H), 2.67-2.81 (m, 4H), 2.13 (m, 2H), 1.83 (m, 2H); MS (ESI$^+$) m/z 434.1 [M+H]$^+$.

Example 32B

N-(1-oxidotetrahydro-2H-thiopyran-4-yl)-6-{[5-(trifluoromethyl)pyridin-2-yl]oxy}quinoline-2-carboxamide A mixture of the product from Example 32A (0.415 g, 0.957 mmol) in ethanol (11 mL) was cooled to −20° and was then treated with magnesium 2-carboperoxybenzoate hexahydrate (MMPP; 0.474 g, 0.766 mmol). The reaction mixture was stirred at −20° for 2.5 h and was then quenched with saturated aqueous sodium bicarbonate solution (10 mL). The mixture was extracted with ethyl acetate (5×20 mL), then the combined extracts were concentrated in vacuo. The residue was taken up in ethyl acetate (~3 mL), causing precipitation of a solid. This solid was collected by filtration and air-dried to afford the titled compound (mixture of diastereomers; 0.233 g, 0.518 mmol, 54% yield). $^1$H NMR (300 MHz, DMSO-d$_6$) δ ppm 8.82-9.03 (m, 1H), 8.62 (m, 1H), 8.53 (m, 1H), 8.32 (m, 1H), 8.23 (m, 1H), 8.16 (m, 1H), 7.92 (m, 1H), 7.75-7.77 (m, 1H), 7.40 (m, 1H), 4.06-4.31 (m, 1H), 3.41 and 3.12 (2 m, 1H), 2.97 and 2.83 (2 m, 3H), 1.84-2.41 (m, 4H); MS (ESI$^+$) m/z 450.1 [M+H]$^+$.

Example 33

N-[2-(dimethylamino)-2-oxoethyl]-6-{[5-(trifluoromethyl)pyridin-2-yl]oxy}quinoline-2-carboxamide The product from Example 1D (29.67 g, 89.00 mmol) was subjected to the conditions described in Example 2, substituting 2-amino-N,N-dimethylacetamide for 3-aminotetrahydrothiophene 1,1-dioxide hydrochloride, to give the titled compound (22.20 g, 60%). 1H NMR (400 MHz, DMSO-d$_6$)

δ ppm 8.95 (t, J=5.1 Hz, 1H), 8.68-8.50 (m, 2H), 8.32 (dd, J=8.7, 2.6 Hz, 1H), 8.21 (dd, J=8.8, 2.9 Hz, 2H), 7.95 (d, J=2.6 Hz, 1H), 7.78 (dd, J=9.1, 2.7 Hz, 1H), 7.41 (d, J=8.7 Hz, 1H), 4.25 (d, J=5.1 Hz, 2H), 3.04 (s, 3H), 2.91 (s, 3H); MS (ESI+) m/z 419.0 [M+H]+.

Example 34

N-(cis-3-hydroxycyclobutyl)-6-{[5-(trifluoromethyl)pyridin-2-yl]oxy}quinoline-2-carboxamide The product from Example 1D (625 mg, 1.86 mmol) was subjected to the conditions described in Example 1E, substituting (cis)-3-aminocyclobutanol hydrochloride for tert-butyl piperazine-1-carboxylate to give the titled compound (280 mg, 37%). $^1$H NMR (500 MHz, DMSO-d$_6$) δ ppm 2.07 (ddd, J=17.3, 8.8, 2.8 Hz, 2H), 2.61 (ddd, J=9.4, 7.1, 2.9 Hz, 2H), 3.81-3.94 (m, 1H), 3.94-4.08 (m, 1H), 5.10 (d, J=6.0 Hz, 1H), 7.41 (d, J=8.7 Hz, 1H), 7.76 (dd, J=9.1, 2.6 Hz, 1H), 7.92 (d, J=2.5 Hz, 1H), 8.14 (d, J=8.5 Hz, 1H), 8.23 (d, J=9.1 Hz, 1H), 8.31 (dd, J=8.7, 2.4 Hz, 1H), 8.52 (d, J=8.5 Hz, 1H), 8.61 (s, 1H), 8.92 (d, J=8.0 Hz, 1H); MS (DCI) m/z 404 [M+H]+.

Example 35

(3-fluoropyrrolidin-1-yl)(6-{[5-(trifluoromethyl)pyridin-2-yl]oxy}quinolin-2-yl)methanone The product from Example 1D (100 mg, 0.299 mmol) was subjected to the conditions described in Example 2, substituting 3-fluoropyrrolidine hydrochloride for 3-aminotetrahydrothiophene 1,1-dioxide hydrochloride to give 105 mg (85%) of the titled compound. $^1$H NMR (500 MHz, DMSO-d$_6$, rotamers) δ ppm 8.61-8.58 (m, 1H), 8.49 (d, J=8.6 Hz, 1H), 8.30 (dd, J=8.7, 2.4 Hz, 1H), 8.15 (dd, J=9.0, 6.6 Hz, 1H), 7.93-7.87 (m, 2H), 7.73 (dd, J=9.1, 2.3 Hz, 1H), 7.40 (d, J=8.7 Hz, 1H), 5.49-5.32 (m, 1H), 4.14-3.71 (m, 3.5H), 3.67-3.57 (m, 0.5H), 2.28-2.05 (m, 2H); MS (ESI) m/z 406.1 [M+H]+.

Example 36 meso-[(1R,5S,6s)-6-amino-3-azabicyclo[3.1.0]hex-3-yl](6-{[5-(trifluoromethyl)pyridin-2-yl]oxy}quinolin-2-yl)methanone

Example 36A meso-tert-butyl {(1R,5S,6s)-3-[(6-{[5-(trifluoromethyl)pyridin-2-yl]oxy}quinolin-2-yl)carbonyl]-3-azabicyclo[3.1.0]hex-6-yl}carbamate The product from Example 1D (258 mg, 0.772 mmol) was subjected to the conditions described in Example 2, substituting tert-butyl (1R,5S,6s)-3-azabicyclo[3.1.0]hexan-6-ylcarbamate for 3-aminotetrahydrothiophene 1,1-dioxide hydrochloride, to give the titled compound (339 mg, 85%).

Example 36B meso-[(1R,5S,6s)-6-amino-3-azabicyclo[3.1.0]hex-3-yl](6-{[5-(trifluoromethyl)pyridin-2-yl]oxy}quinolin-2-yl)methanone The protected from Example 36A was dissolved in dichloromethane (4 mL) under an atmosphere of nitrogen. A solution of 4 N hydrochloric acid (4 mL) was added and the mixture was stirred at room temperature for two hours. The volatiles were removed under reduced pressure, and the crude material was diluted in dichloromethane. The organic layer was washed with 1 N NaOH and dried over sodium sulfate. The solvents were removed under reduced pressure, and the residue was triturated with heptane to afford the titled compound (125 mg, 26%). $^1$H NMR (500 MHz, CDCl$_3$) δ ppm 8.43 (s, 1H), 8.15 (dd, J=18.7, 8.8 Hz, 2H), 7.96 (dd, J=8.6, 2.3 Hz, 1H), 7.88 (d, J=8.5 Hz, 1H), 7.60 (d, J=2.4 Hz, 1H), 7.55 (dd, J=9.1, 2.4 Hz, 1H), 7.13 (d, J=8.6 Hz, 1H), 4.13 (dd, J=12.0, 8.3 Hz, 2H), 4.04 (d, J=11.9 Hz, 1H), 3.69 (d, J=12.3 Hz, 1H), 2.34 (s, 1H), 1.92 (s, 2H); MS (ESI) m/z 415.0 [M+H]+.

Example 37

N-(oxetan-2-ylmethyl)-6-{[5-(trifluoromethyl)pyridin-2-yl]oxy}quinoline-2-carboxamide The product from Example 1D (100.9 mg, 0.302 mmol) was subjected to the conditions described in Example 20, substituting oxetan-2-ylmethanamine for 2-(trifluoromethyl)piperazine, to give the titled compound (79.1 mg, 65%). $^1$H NMR (400 MHz, DMSO-d$_6$) δ ppm 8.95 (t, J=6.1 Hz, 1H), 8.61-8.62 (m, 1H), 8.55 (d, J=8.6 Hz, 1H), 8.31 (dd, J=8.7, 2.6 Hz, 1H), 8.18-8.23 (m, 2H), 7.94 (d, J=2.4 Hz, 1H), 7.76 (dd, J=9.2, 2.4 Hz, 1H), 7.41 (d, J=8.9 Hz, 1H), 4.89-4.95 (m, 1H), 4.44-4.57 (m, 2H), 3.59-3.72 (m, 2H), 2.62-2.70 (m, 2H), 2.42-2.50 (m, 1H); MS (ESI) m/z 404.1 [M+H]+.

Example 38

N-[(2R)-2-hydroxypropyl]-6-{[5-(trifluoromethyl)pyridin-2-yl]oxy}quinoline-2-carboxamide The product from Example 1D (107.4 mg, 0.321 mmol) was subjected to the conditions described in Example 20, substituting (R)-1-aminopropan-2-ol for 2-(trifluoromethyl)piperazine, to give the titled compound (80.1 mg, 64%). $^1$H NMR (400 MHz, DMSO-d$_6$) δ ppm 8.76 (t, J=6.0 Hz, 1H), 8.61-8.62 (m, 1H), 8.55 (d, J=8.5 Hz, 1H), 8.31 (dd, J=8.7, 2.6 Hz, 1H), 8.18-8.22 (m, 2H), 7.93 (d, J=2.8 Hz, 1H), 7.76 (dd, J=9.0, 2.6 Hz, 1H), 7.41 (d, J=8.9 Hz, 1H), 4.91 (br s, 1H), 3.83-3.91 (m, 1H), 3.40-3.47 (m, 1H), 3.23-3.30 (m, 1H), 1.12 (d, J=6.1 Hz, 3H); MS (ESI) m/z 392.1 [M+H]+.

Example 39

4,7-diazaspiro[2.5]oct-7-yl(6-{[5-(trifluoromethyl)pyridin-2-yl]oxy}quinolin-2-yl)methanone The product from Example 1D (181 mg, 0.540 mmol) was subjected to the conditions described in Example 2, substituting 4,7-diazaspiro[2.5]octane dihydrochloride for 3-aminotetrahydrothiophene 1,1-dioxide hydrochloride, to give the titled compound (192 mg, 83%). $^1$H NMR (500 MHz, CDCl$_3$) δ ppm 8.44 (bs, 1H), 8.23 (t, J=7.9 Hz, 1H), 8.15 (dd, J=25.0, 9.1 Hz, 1H), 7.98 (dd, J=8.6, 2.5 Hz, 1H), 7.76 (dd, J=8.4, 4.8 Hz, 1H), 7.63 (dd, J=5.7, 2.5 Hz, 1H), 7.61-7.53 (m, 1H), 7.15 (dd, J=8.6, 3.6 Hz, 1H), 3.88 (t, J=4.9 Hz, 1H), 3.76-3.68 (m, 2H), 3.54 (s, 1H), 3.13 (t, J=5.0 Hz, 1H), 3.02 (t, J=4.8 Hz, 1H), 0.80-0.69 (m, 2H), 0.69-0.63 (m, 1H), 0.54-0.49 (m, 1H); MS (ESI) m/z 429.1 [M+H]+.

Example 40

N-(2-oxopiperidin-4-yl)-6-{[5-(trifluoromethyl)pyridin-2-yl]oxy}quinoline-2-carboxamide The product from Example 1D (100 mg, 0.299 mmol) was subjected to the conditions described in Example 2, substituting 4-aminopiperidin-2-one 2,2,2-trifluoroacetate for 3-aminotetrahydrothiophene 1,1-dioxide hydrochloride and collecting the product by filtration after the addition of water to give 122 mg (93%) of the titled compound. $^1$H NMR (500 MHz, DMSO-$d_6$) δ ppm 8.89 (d, J=8.1 Hz, 1H), 8.63-8.60 (m, 1H), 8.54 (d, J=8.6 Hz, 1H), 8.31 (dd, J=8.7, 2.5 Hz, 1H), 8.23 (d, J=9.1 Hz, 1H), 8.17 (d, J=8.5 Hz, 1H), 7.93 (d, J=2.6 Hz, 1H), 7.76 (dd, J=9.1, 2.6 Hz, 1H), 7.60 (s, 1H), 7.40 (d, J=8.8 Hz, 1H), 4.34-4.24 (m, 1H), 3.26-3.20 (m, 2H), 2.55-2.42 (m, 2H), 2.04-1.96 (m, 1H), 1.95-1.83 (m, 1H); MS (ESI) m/z 431.0 [M+H]$^+$.

Example 41

N-(cis-3-methoxycyclobutyl)-6-{[5-(trifluoromethyl)pyridin-2-yl]oxy}quinoline-2-carboxamide The titled compound was prepared using the reaction conditions described for Example 9A, substituting cis-3-methoxycyclobutanamine hydrochloride for 2,5-dihydro-1H-pyrrole. $^1$H NMR (300 MHz, DMSO-$d_6$) δ ppm 9.05 (d, J=8.2 Hz, 1H), 8.61 (m, 1H), 8.52 (d, J=8.3 Hz, 1H), 8.31 (m, 1H), 8.22 (d, J=9.1 Hz, 1H), 8.13 (d, J=8.6 Hz, 1H), 7.91 (d, J=2.5 Hz, 1H), 7.76 (m, 1H), 7.40 (d, J=8.8 Hz, 1H), 4.11 (m, 1H), 3.66 (m, 1H), 3.17 (s, 3H), 2.58-2.67 (m, 2H), 2.09-2.17 (m, 2H); MS (ESI$^+$) m/z 418.1 [M+H]$^+$.

Example 42

N-[2-(dimethylamino)-2-oxoethyl]-6-{[6-(trifluoromethyl)pyridin-3-yl]oxy}quinoline-2-carboxamide The product from Example 19B (144 mg, 0.431 mmol) was subjected to the conditions described in Example 2, substituting 2-amino-N,N-dimethylacetamide hydrochloride for 3-aminotetrahydrothiophene 1,1-dioxide hydrochloride, to give the titled compound (75 mg, 42%). $^1$H NMR (400 MHz, DMSO-$d_6$) δ ppm 8.93 (t, J=5.1 Hz, 1H), 8.72 (d, J=2.7 Hz, 1H), 8.54 (d, J=8.5 Hz, 1H), 8.21 (dd, J=20.0, 8.7 Hz, 2H), 7.98 (d, J=8.6 Hz, 1H), 7.85-7.76 (m, 3H), 4.24 (d, J=5.1 Hz, 2H), 3.03 (s, 3H), 2.91 (s, 3H); MS (ESI) m/z 419.0 [M+H]$^+$.

Example 43

(6-{[5-(difluoromethyl)pyridin-2-yl]oxy}quinolin-2-yl)[(3S)-3-methylpiperazin-1-yl]methanone

Example 43A tert-butyl (2S)-4-[(6-{[5-(difluoromethyl)pyridin-2-yl]oxy}quinolin-2-yl)carbonyl]-2-methylpiperazine-1-carboxylate The product from Example 14A (200 mg, 0.632 mmol) was subjected to the conditions described in Example 14B, substituting (S)-tert-butyl 2-methylpiperazine-1-carboxylate for tert-butyl piperazine-1-carboxylate to give 155 mg (49%) of the titled compound.

Example 43B (6-{[5-(difluoromethyl)pyridin-2-yl]oxy}quinolin-2-yl)[(3S)-3-methylpiperazin-1-yl]methanone The product from Example 43A (130 mg, 0.26 mmol) was subjected to the conditions described in Example 14C to give 100 mg (96%) of the titled compound. $^1$H NMR (400 MHz, DMSO-$d_6$) δ ppm 0.69-1.13 (m, 3H), 2.30-2.46 (m, 1H), 2.55-3.13 (m, 5H), 3.47-3.67 (m, 1H), 4.29-4.50 (m, 1H), 7.12 (t, J=55.3 Hz, 1H), 7.32 (dd, J=8.6, 2.3 Hz, 1H), 7.57-7.74 (m, 2H), 7.84 (d, J=2.5 Hz, 1H), 8.11 (dd, J=15.5, 8.9 Hz, 2H), 8.39 (d, J=1.2 Hz, 1H), 8.46 (d, J=8.5 Hz, 1H); MS (DCI) m/z 399 [M+H]$^+$.

Example 44

N-[2-oxo-2-(pyrrolidin-1-yl)ethyl]-6-{[5-(trifluoromethyl)pyridin-2-yl]oxy}quinoline-2-carboxamide The product from Example 1D (600 mg, 1.79 mmol) was subjected to the conditions described in Example 2, substituting 2-amino-1-(pyrrolidin-1-yl)ethanone hydrochloride for 3-aminotetrahydrothiophene 1,1-dioxide hydrochloride to give 560 mg (70%) of the titled compound. $^1$H NMR (500 MHz, DMSO-$d_6$) δ 8.95 (t, J=5.2 Hz, 1H), 8.64-8.59 (m, 1H), 8.56 (d, J=8.5 Hz, 1H), 8.31 (dd, J=8.8, 2.6 Hz, 1H), 8.20 (dd, J=8.8, 4.1 Hz, 2H), 7.95 (d, J=2.6 Hz, 1H), 7.77 (dd, J=9.2, 2.6 Hz, 1H), 7.41 (d, J=8.7 Hz, 1H), 4.17 (d, J=5.1 Hz, 2H), 3.49 (t, J=6.8 Hz, 2H), 3.37 (t, J=6.9 Hz, 2H), 1.93 (p, J=6.8 Hz, 2H), 1.81 (p, J=6.9 Hz, 2H); MS (ESI) m/z 445.0 [M+H]$^+$.

Example 45

N-(1-ethyl-5-oxopyrrolidin-3-yl)-6-{[5-(trifluoromethyl)pyridin-2-yl]oxy}quinoline-2-carboxamide The product from Example 1D (398 mg, 1.19 mmol) was subjected to the conditions described in Example 2, substituting 4-amino-1-ethylpyrrolidin-2-one hydrochloride for 3-aminotetrahydrothiophene 1,1-dioxide hydrochloride, to give the titled compound (394 mg, 75%). $^1$H NMR (500 MHz, CDCl$_3$) δ ppm 8.47-8.39 (m, 2H), 8.29 (s, 2H), 8.19 (d, J=9.1 Hz, 1H), 7.99 (d, J=8.6, 2.5 Hz, 1H), 7.67 (d, J=2.5 Hz, 1H), 7.61 (dd, J=9.1, 2.5 Hz, 1H), 7.16 (d, J=8.6 Hz, 1H), 4.88-4.78 (m, 1H), 3.90 (dd, J=10.4, 6.8 Hz, 1H), 3.50-3.35 (m, 3H), 2.95 (dd, J=17.1, 8.3 Hz, 1H), 2.55 (dd, J=17.1, 4.6 Hz, 1H), 1.17 (t, J=7.2 Hz, 3H); MS (ESI) m/z 445.0 [M+H]$^+$.

Example 46

6-{[5-(difluoromethyl)pyridin-2-yl]oxy}-N-(1-ethyl-5-oxopyrrolidin-3-yl)quinoline-2-carboxamide The product from Example 14A (553 mg, 1.75 mmol) was subjected to the conditions described in Example 2, substituting 4-amino-1-ethylpyrrolidin-2-one hydrochloride for 3-aminotetrahydrothiophene 1,1-dioxide hydrochloride, to give the titled compound (651 mg, 87%). $^1$H NMR (400 MHz, CDCl$_3$) δ ppm 8.50-8.43 (m, 1H), 8.29 (s, 3H), 8.20 (d, J=9.1 Hz, 1H), 7.94 (d, J=8.6, 2.4 Hz, 1H), 7.66 (d, J=2.5 Hz, 1H), 7.62 (dd, J=9.0, 2.6 Hz, 1H), 7.15 (d, J=8.5 Hz, 1H), 4.89-4.77 (m, 1H), 3.90 (dd, J=10.4, 6.8 Hz, 1H), 3.51-3.34 (m, 3H), 2.94 (dd, J=17.1, 8.3 Hz, 1H), 2.56 (dd, J=17.1, 4.7 Hz, 1H), 1.75 (bs, 1H), 1.17 (t, J=7.2 Hz, 3H); MS (ESI) m/z 427.1 [M+H]+.

Example 47

(4-cyclobutylpiperazin-1-yl)(6-{[5-(trifluoromethyl) pyridin-2-yl]oxy}quinolin-2-yl)methanone To a mixture of the product from Example 1D (102.7 mg, 0.307 mmol) and O-(benzotriazol-1-yl)-N,N,N',N'-tetramethyluronium tetrafluoroborate (TBTU, 157.1 mg, 0.489 mmol) in dimethyl sulfoxide (1 mL) at room temperature was added triethylamine (0.1 mL, 0.72 mmol) followed by 1-cyclobutylpiperazine (79.4 mg, 0.566 mmol). After 3 h, the mixture was diluted with methanol (1 mL) and purified by reverse phase preparative HPLC on a Phenomenex® Luna® C8(2) 5 um 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield 173.9 mg (83%) of the titled compound as a trifluoroacetic acid salt. $^1$H NMR (400 MHz, DMSO-$d_6$) δ ppm 10.15 (br s, 1H), 8.58-8.59 (m, 1H), 8.53 (d, J=8.5 Hz, 1H), 8.32 (dd, J=8.7, 2.6 Hz, 1H), 8.12 (d, J=9.2 Hz, 1H), 7.92 (d, J=2.4 Hz, 1H), 7.80 (d, J=8.5 Hz, 1H), 7.75 (d, J=9.2, 2.7 Hz, 1H), 7.41 (d, J=8.9 Hz, 1H), 4.71-7.68 (m, 1H), 4.28-4.30 (m, 1H), 3.75-3.78 (m, 1H), 3.48-3.54 (m, 2H), 3.34-3.36 (m, 1H), 3.22-3.27 (m, 1H), 3.00-3.03 (m, 2H), 2.20-2.23 (m, 4H), 1.71-1.82 (m, 2H); MS (ESI) m/z 457.1 [M+H]+.

Example 48

N-(3-methyloxetan-3-yl)-6-{[5-(trifluoromethyl) pyridin-2-yl]oxy}quinoline-2-carboxamide The titled compound was prepared using the reaction conditions described for Example 9A, substituting 3-methyloxetan-3-amine for 2,5-dihydro-1H-pyrrole. $^1$H NMR (300 MHz, DMSO-$d_6$) δ ppm 9.40 (s, 1H), 8.62 (s, 1H), 8.52 (d, J=8.6 Hz, 1H), 8.31 (m, 1H), 8.21 (d, J=9.2 Hz, 1H), 8.14 (d, J=8.5 Hz, 1H), 7.93 (d, J=2.7 Hz, 1H), 7.77 (m, 1H), 7.41 (d, J=8.5 Hz, 1H), 4.82 (d, J=6.4 Hz, 2H), 4.42 (d, J=6.4 Hz, 2H), 1.67 (s, 3H); MS (ESI+) m/z 404.1 [M+H]+.

Example 49 meso-[(1R,5S,6s)-6-amino-3-azabicyclo[3.1.0]hex-3-yl](6-{[5-(difluoromethyl)pyridin-2-yl] oxy}quinolin-2-yl)methanone

Example 49A meso-tert-butyl {(1R,5S,6s)-3-[(6-{[5-(difluoromethyl)pyridin-2-yl]oxy}quinolin-2-yl)carbonyl]-3-azabicyclo[3.1.0]hex-6-yl}carbamate The product from Example 14A (511 mg, 1.62 mmol) was subjected to the conditions described in Example 2, substituting meso-tert-butyl (1R,5S,6s)-3-azabicyclo[3.1.0]hexan-6-ylcarbamate for 3-aminotetrahydrothiophene 1,1-dioxide hydrochloride, to give the titled compound (686 mg, 90%).

Example 49B meso-[(1R,5S,6s)-6-amino-3-azabicyclo[3.1.0]hex-3-yl](6-{[5-(difluoromethyl)pyridin-2-yl] oxy}quinolin-2-yl)methanone The product from Example 49A was dissolved in dichloromethane (4 mL) under an atmosphere of nitrogen. A solution of 4 N hydrochloric acid (4 mL) was added, and the mixture was stirred at room temperature for two hours. The volatiles were removed under reduced pressure, and the crude material was diluted in dichloromethane. The organic layer was washed with 1 N NaOH and dried over sodium sulfate. The solvents were removed under reduced pressure, and the residue was triturated with heptane to afford the titled compound (307 mg, 56%). $^1$H NMR (400 MHz, CDCl$_3$) δ ppm 8.30 (d, J=2.2 Hz, 1H), 8.16 (dd, J=15.2, 8.8 Hz, 2H), 7.99-7.84 (m, 2H), 7.60 (d, J=2.6 Hz, 1H), 7.56 (dd, J=9.0, 2.6 Hz, 1H), 7.12 (d, J=8.5 Hz, 1H), 6.68 (t, J=55.9 Hz, 1H), 4.28-3.99 (m, 3H), 3.71 (dd, J=12.2, 2.8 Hz, 1H), 2.88-2.06 (m, 2H), 2.28-2.21 (m, 1H); MS (ESI) m/z 397.0 [M+H]+.

Example 50

[(2S,4S)-4-fluoro-2-(hydroxymethyl)pyrrolidin-1-yl] (6-{[5-(trifluoromethyl)pyridin-2-yl]oxy}quinolin-2-yl)methanone The product from Example 1D (800 mg, 2.39 mmol) was subjected to the conditions described in Example 2, substituting [(2S,4S)-4fluoropyrrolidin-2-yl]methanol hydrochloride for 3-aminotetrahydrothiophene 1,1-dioxide hydrochloride to give 885 mg (83%) of the titled compound. $^1$H NMR (400 MHz, DMSO-$d_6$, rotamers) δ ppm 8.61-8.57 (m, 1H), 8.48 (d, J=8.6 Hz, 1H), 8.30 (dd, J=8.7, 2.5 Hz, 1H), 8.16 (t, J=9.6 Hz, 1H), 7.91-7.80 (m, 2H), 7.72 (dd, J=9.1, 2.6 Hz, 1H), 7.40 (d, J=8.8 Hz, 1H), 5.52-5.25 (m, 1H), 4.96 (dd, J=6.2, 5.3 Hz, 0.5H), 4.83-4.72 (m, 1H), 4.41 (td, J=8.8, 4.6 Hz, 0.5H), 4.27 (dd, J=25.3, 13.7 Hz, 0.5H), 4.12-3.88 (m, 1.5H), 3.80 (dd, J=27.3, 14.9 Hz, 0.5H), 3.48-3.34 (m, 1H), 3.30-3.21 (m, 0.5H), 2.43-2.09 (m, 2H); MS (ESI) m/z 436.0 [M+H]+.

Example 51

[(3S)-3-fluoropyrrolidin-1-yl](6-{[5-(trifluoromethyl)pyridin-2-yl]oxy}quinolin-2-yl)methanone The product from Example 1D (1.0 g, 2.99 mmol) was subjected to the conditions described in Example 2, substituting (S)-3-fluoropyrrolidine hydrochloride for 3-aminotetrahydrothiophene 1,1-dioxide hydrochloride to give 1.18 g (96%) of the titled compound. $^1$H NMR (500 MHz, DMSO-$d_6$, rotamers) δ ppm 8.61-8.58 (m, 1H), 8.49 (d, J=8.6 Hz, 1H), 8.30 (dd, J=8.7, 2.4 Hz, 1H), 8.15 (dd, J=9.0, 6.6 Hz, 1H), 7.93-7.87 (m, 2H), 7.73 (dd, J=9.1, 2.3 Hz, 1H), 7.40 (d, J=8.7 Hz, 1H), 5.49-5.32 (m, 1H), 4.14-3.71 (m, 3.5H), 3.67-3.57 (m, 0.5H), 2.28-2.05 (m, 2H); MS (ESI) m/z 406.1 [M+H]+.

Example 52

[(3R)-3-fluoropyrrolidin-1-yl](6-{[5-(trifluoromethyl)pyridin-2-yl]oxy}quinolin-2-yl)methanone A mixture of the product from Example 1D (1.0 g, 2.99 mmol), (R)-3-fluoropyrrolidine hydrochloride (0.376 g, 2.99 mmol), 1-[bis(dimethylamino)methylene]-1H-1,2,3-triazolo[4,5-b]pyridinium 3-oxid hexafluorophosphate (HATU, 1.706 g, 4.49 mmol), N,N-diisopropylethylamine (1.568 mL, 8.98 mmol), and dimethyl sulfoxide (14.96 mL) was stirred at room temperature for 16 hours. Water was added, followed by saturated aqueous sodium bicarbonate. The crude product was extracted with dichloromethane (3×), dried with sodium sulfate, decanted, and concentrated. The compound was purified by chromatography on silica gel (0-100% ethyl acetate/heptanes) to give 1.12 g (91%) of the titled compound. $^1$H NMR (500 MHz, DMSO-$d_6$, rotamers) δ ppm 8.61-8.58 (m, 1H), 8.49 (d, J=8.6 Hz, 1H), 8.30 (dd, J=8.7, 2.4 Hz, 1H), 8.15 (dd, J=9.0, 6.6 Hz, 1H), 7.93-7.87 (m, 2H), 7.73 (dd, J=9.1, 2.3 Hz, 1H), 7.40 (d, J=8.7 Hz, 1H), 5.49-5.32 (m, 1H), 4.14-3.71 (m, 3.5H), 3.67-3.57 (m, 0.5H), 2.28-2.05 (m, 2H); MS (ESI) m/z 406.1 [M+H]$^+$.

Example 53

[(8aS)-7,7-difluorohexahydropyrrolo[1,2-a]pyrazin-2(1H)-yl](6-{[5-(trifluoromethyl)pyridin-2-yl]oxy}quinolin-2-yl)methanone The product from Example 1D (100 mg, 0.299 mmol) was subjected to the conditions described in Example 27, substituting (S)-7,7-difluorooctahydropyrrolo[1,2-a]pyrazine dihydrochloride (91 mg, 0.389 mmol) for (S)-hexahydropyrrolo[1,2-a]pyrazin-4(1H)-one hydrochloride, to give the titled compound (123 mg, 86%). $^1$H NMR (400 MHz, DMSO-$d_6$) δ ppm 1.77-2.10 (m, 1H) 2.17-2.49 (m, 3H) 2.53-2.67 (m, 1H) 2.70-2.92 (m, 1H) 2.98-3.30 (m, 2H) 3.38-3.49 (m, 1H) 3.84 (dd, J=65.61, 12.82 Hz, 1H) 4.64 (dd, J=60.73, 12.82 Hz, 1H) 7.39 (d, J=8.85 Hz, 1H) 7.66-7.75 (m, 2H) 7.89 (d, J=1.83 Hz, 1H) 8.12 (dd, J=9.16, 1.83 Hz, 1H) 8.31 (dd, J=8.85, 2.44 Hz, 1H) 8.49 (d, J=7.93 Hz, 1H) 8.58 (s, 1H); MS (ESI) m/z 479.0 [M+H]$^+$.

Example 54

N-[1-(4-fluorophenyl)-5-oxopyrrolidin-3-yl]-6-{[5-(trifluoromethyl)pyridin-2-yl]oxy}quinoline-2-carboxamide The product from Example 1D (100 mg, 0.299 mmol) was subjected to the conditions described in Example 27, substituting 4-amino-1-(4-fluorophenyl)pyrrolidin-2-one hydrochloride (69.0 mg, 0.299 mmol for (S)-hexahydropyrrolo[1,2-a]pyrazin-4(1H)-one hydrochloride, to give the titled compound (110 mg, 72.0%). $^1$H NMR (400 MHz, DMSO-$d_6$) δ ppm 2.82 (dd, J=17.09, 5.49 Hz, 1H) 2.98 (dd, J=17.09, 8.85 Hz, 1H) 3.93 (dd, J=9.92, 4.73 Hz, 1H) 4.23 (dd, J=10.07, 7.63 Hz, 1H) 4.77-4.88 (m, 1H) 7.23 (t, J=8.85 Hz, 2H) 7.41 (d, J=8.54 Hz, 1H) 7.70-7.81 (m, 3H) 7.93 (d, J=2.75 Hz, 1H) 8.18 (d, J=8.54 Hz, 1H) 8.22 (d, J=9.16 Hz, 1H) 8.31 (dd, J=8.54, 2.44 Hz, 1H) 8.54 (d, J=8.54 Hz, 1H) 8.61 (s, 1H) 9.44 (d, J=7.32 Hz, 1H); MS (ESI) m/z 511 [M+H]$^+$.

Example 55

(6-{[5-(difluoromethyl)pyridin-2-yl]oxy}quinolin-2-yl)[(3R)-3-ethylpiperazin-1-yl]methanone Example 55A tert-butyl (2R)-4-[(6-{[5-(difluoromethyl)pyridin-2-yl]oxy}quinolin-2-yl)carbonyl]-2-ethylpiperazine-1-carboxylate The product from Example 14A (300 mg, 0.95 mmol) was subjected to the conditions described in Example 14B, substituting (R)-tert-butyl 2-ethylpiperazine-1-carboxylate for tert-butyl piperazine-1-carboxylate to give the titled compound (470 mg, 97%).

Example 55B (6-{[5-(difluoromethyl)pyridin-2-yl]oxy}quinolin-2-yl)[(3R)-3-ethylpiperazin-1-yl]methanone The product from Example 55A (455 mg, 0.88 mmol) was subjected to the conditions described in Example 14C, to give the titled compound (320 mg, 87%). $^1$H NMR (400 MHz, DMSO-$d_6$, rotamers) δ ppm 0.74 (t, J=7.5 Hz, 1.5H), 0.95 (t, J=7.5 Hz, 1.5H), 1.06-1.32 (m, 1H), 1.32-1.57 (m, 1H), 2.35 (s, 1H), 2.56-2.94 (m, 3H), 2.94-3.15 (m, 1H), 3.65 (dd, J=58.1, 12.6 Hz, 1H), 4.40 (dd, J=26.1, 11.1 Hz, 1H), 7.12 (t, J=55.3 Hz, 1H), 7.32 (dd, J=8.6, 2.6 Hz, 1H), 7.68 (ddd, J=8.3, 6.3, 2.1 Hz, 2H), 7.84 (d, J=2.2 Hz, 1H), 8.01-8.22 (m, 2H), 8.39 (s, 1H), 8.46 (d, J=8.5 Hz, 1H); MS (DCI) m/z 413 [M+H]$^+$.

Example 56

N-(2-methoxyethyl)-6-{[6-(trifluoromethyl)pyridin-3-yl]oxy}quinoline-2-carboxamide The product from Example 19B (99.9 mg, 0.299 mmol) was subjected to the conditions described in Example 20, substituting 2-methoxyethanamine for 2-(trifluoromethyl)piperazine, to give the titled compound (66.4 mg, 57%). $^1$H NMR (400 MHz, DMSO-$d_6$) δ ppm 8.85 (t, J=4.9 Hz, 1H), 8.71 (d, J=2.8 Hz, 1H), 8.52 (d, J=8.6 Hz, 1H), 8.24 (d, J=9.2 Hz, 1H), 8.17 (d, J=8.5 Hz, 1H), 7.98 (d, J=8.9 Hz, 1H), 7.76-7.82 (m, 3H), 3.52-3.58 (m, 4H), 3.30 (s, 3H); MS (ESI) m/z 392.1 [M+H]$^+$.

Example 57

(6-{[5-(difluoromethoxy)pyridin-2-yl]oxy}quinolin-2-yl)(piperazin-1-yl)methanone Example 57A tert-butyl 4-[(6-{[5-(difluoromethoxy)pyridin-2-yl]oxy}quinolin-2-yl)carbonyl]piperazine-1-carboxylate The product from Example 7B (400 mg, 1.11 mmol) was subjected to the conditions described in Example 7C, substituting 2-chloro-5-(difluoromethoxy)pyridine for 1-(4-fluorophenyl)ethanone at 140° C. to give the titled compound (135 mg, 24%).

Example 57B (6-{[5-(difluoromethoxy)pyridin-2-yl]oxy}quinolin-2-yl)(piperazin-1-yl)methanone The product from Example 57A (114 mg, 0.22 mmol) was subjected to the conditions described in Example 1F, to give the titled compound (76 mg, 83%). $^1$H NMR (400 MHz, DMSO-$d_6$) δ ppm 2.66 (dd, J=16.6, 11.8 Hz, 2H), 2.74-2.85 (m, 2H), 3.34 (d, J=14.0 Hz, 2H), 3.55-3.70 (m, 2H), 7.01-7.49 (m, 2H), 7.57-7.70 (m, 2H), 7.77 (d, J=2.6 Hz, 1H), 7.84 (dd, J=8.9, 3.0 Hz, 1H), 8.09 (dd, J=12.0, 6.0 Hz, 2H), 8.44 (d, J=8.5 Hz, 1H); MS (DCI) m/z 401 [M+H]$^+$.

Example 58

N-[(3R)-5-oxopyrrolidin-3-yl]-6-{[5-(trifluoromethyl)pyridin-2-yl]oxy}quinoline-2-carboxamide The product from Example 1D (100 mg, 0.299 mmol) was subjected to the conditions described in Example 27, substituting (R)-4-aminopyrrolidin-2-one (35.9 mg, 0.359 mmol) for (S)-hexahydropyrrolo[1,2-a]pyrazin-4(1H)-one hydrochloride, to give the titled compound (72 mg, 57.8% yield). $^1$H NMR (400 MHz, DMSO-$d_6$) δ ppm 2.44-2.58 (m, 2H) 3.26-3.32 (m, 1H) 3.61 (dd, J=9.31, 8.09 Hz, 1H) 4.66-4.78 (m, 1H) 7.41 (d, J=8.85 Hz, 1H) 7.70 (s, 1H) 7.76 (dd, J=9.16, 2.75 Hz, 1H) 7.93 (d, J=2.75 Hz, 1H) 8.16 (d, J=8.54 Hz, 1H) 8.23 (d, J=9.16 Hz, 1H) 8.32 (dd, J=8.54, 2.44 Hz, 1H) 8.54 (d, J=8.54 Hz, 1H) 8.62 (s, 1H) 9.19 (d, J=7.63 Hz, 1H); MS (ESI) m/z 417.0 [M+H]$^+$.

Example 59

N-(3,3-difluorocyclobutyl)-6-{[5-(trifluoromethyl)pyridin-2-yl]oxy}quinoline-2-carboxamide The product from Example 1D (200 mg, 0.59 mmol) was subjected to the conditions described in Example 1E, substituting 3,3-difluorocyclobutanamine hydrochloride for 4 tert-butyl piperazine-1-carboxylate to give the titled compound (136 mg, 53.7%). $^1$H NMR (400 MHz, DMSO-$d_6$) δ ppm 2.85-3.12 (m, 4H), 4.29-4.52 (m, 1H), 7.41 (d, J=8.7 Hz, 1H), 7.77 (dd, J=9.1, 2.6 Hz, 1H), 7.93 (d, J=2.6 Hz, 1H), 8.16 (d, J=8.5 Hz, 1H), 8.23 (d, J=9.1 Hz, 1H), 8.32 (dd, J=8.7, 2.5 Hz, 1H), 8.54 (d, J=8.6 Hz, 1H), 8.62 (d, J=1.3 Hz, 1H), 9.41 (d, J=7.5 Hz, 1H); MS (DCI) m/z 424 [M+H]$^+$.

Example 60

[3-(methoxymethyl)azetidin-1-yl](6-{[5-(trifluoromethyl)pyridin-2-yl]oxy}quinolin-2-yl)methanone The titled compound was prepared using the reaction conditions described for Example 9A, substituting 3-(methoxymethyl)azetidine 2,2,2-trifluoroacetate for 2,5-dihydro-1H-pyrrole. $^1$H NMR (300 MHz, DMSO-$d_6$) δ ppm 8.60 (m, 1H), 8.48 (d, J=8.8 Hz, 1H), 8.31 (m, 1H), 8.15 (d, J=9.2 Hz, 1H), 8.05 (d, J=8.5 Hz, 1H), 7.89 (d, J=2.8 Hz, 1H), 7.72 (m, 1H), 7.40 (d, J=8.6 Hz, 1H), 4.80 (t, J=8.9 Hz, 1H), 4.47 (m, 1H), 4.18 (t, J=9.3 Hz, 1H), 3.85 (m, 1H), 3.55 (d, J=6.4 Hz, 2H), 3.31 (s, 3H), 2.93 (m, 1H); MS (ESI$^+$) m/z 418.1 [M+H]$^+$.

Example 61

N-ethyl-N-(1-ethyl-2-oxopiperidin-4-yl)-6-{[5-(trifluoromethyl)pyridin-2-yl]oxy}quinoline-2-carboxamide Sodium hydride (0.102 g, 2.56 mmol, 60% dispersion in mineral oil) was added to a mixture of N-(2-oxopiperidin-4-yl)-6-{[5-(trifluoromethyl)pyridin-2-yl]oxy}quinoline-2-carboxamide (the product from Example 40) (0.5 g, 1.162 mmol), and N,N-dimethylformamide (5.81 mL) at 0° C., and the reaction mixture was stirred for 30 minutes at 0° C. Iodoethane (0.207 mL, 2.56 mmol) was added. The reaction mixture was allowed to warm to room temperature and was stirred at room temperature overnight. The reaction mixture was cooled to 0° C. using an ice bath. Water and saturated aqueous sodium bicarbonate were added slowly. The mixture was extracted with dichloromethane (3×), dried with Na$_2$SO$_4$, filtered and concentrated. The residue was purified by column chromatography on silica gel using a gradient of 0-100% ethyl acetate/heptanes to yield 280 mg (49%) of the titled compound. $^1$H NMR (400 MHz, CDCl$_3$, rotamers) δ ppm 8.44 (s, 1H), 8.33-8.25 (m, 0.5H), 8.25-8.10 (m, 2H), 8.01-7.94 (m, 1H), 7.76-7.65 (m, 1H), 7.64-7.54 (m, 1.5H), 7.15 (d, J=8.6 Hz, 1H), 4.69-4.32 (m, 1H), 3.71 (q, J=7.0 Hz, 1H), 3.59-3.35 (m, 4H), 3.35-3.09 (m, 1H), 2.95-2.72 (m, 1H), 2.69-2.47 (m, 0.5H), 2.39-2.17 (m, 1H), 2.12-1.99 (m, 0.5H), 1.38 (t, J=7.0 Hz, 1H), 1.28-1.12 (m, 5H), 1.06 (t, J=7.1 Hz, 1H); MS (ESI) m/z 487.0 [M+H]$^+$.

Example 62

[(3R)-3-methylpiperazin-1-yl](6-{[6-(trifluoromethyl)pyridin-3-yl]oxy}quinolin-2-yl)methanone

Example 62A tert-butyl (2R)-2-methyl-4-[(6-{[6-(trifluoromethyl)pyridin-3-yl]oxy}quinolin-2-yl)carbonyl]piperazine-1-carboxylate The titled compound was prepared using the reaction conditions described for Example 1E, substituting 6-{[6-(trifluoromethyl)pyridin-3-yl]oxy}quinoline-2-carboxylic acid for 6-{[5-(trifluoromethyl)pyridin-2-yl]oxy}quinoline-2-carboxylic acid and (R)-tert-butyl 2-methylpiperazine-1-carboxylate for tert-butyl piperazine-1-carboxylate (254 mg, 82%).

Example 62B

[(3R)-3-methylpiperazin-1-yl](6-{[6-(trifluoromethyl)pyridin-3-yl]oxy}quinolin-2-yl)methanone The product from Example 62A (234 mg, 0.45 mmol) was subjected to the conditions described in Example 19D to give the titled compound (0.187 g, 99%). $^1$H NMR (400 MHz, DMSO-$d_6$, rotamers) δ ppm 0.84 (d, J=5.7 Hz, 1.5H), 1.05 (d, J=6.2 Hz, 1.5H), 2.56-2.91 (m, 4H), 2.93-3.12 (m, 1H), 3.57 (d, J=10.8 Hz, 1H), 4.38 (d, J=12.4 Hz, 1H), 7.63-7.84 (m, 4H), 7.96 (t, J=7.9 Hz, 1H), 8.14 (d, J=9.1 Hz, 1H), 8.45 (d, J=8.5 Hz, 1H), 8.70 (s, 1H); MS (DCI) m/z 417 [M+H]$^+$.

Example 63

[(3R)-3-(methoxymethyl)piperazin-1-yl](6-{[6-(trifluoromethyl)pyridin-3-yl]oxy}quinolin-2-yl)methanone

Example 63A tert-butyl (2R)-2-(hydroxymethyl)-4-[(6-{[6-(trifluoromethyl)pyridin-3-yl]oxy}quinolin-2-yl)carbonyl]piperazine-1-carboxylate The titled compound was prepared using the conditions described in Example 1E, substituting 6-{[6-(trifluoromethyl)pyridin-3-yl]oxy}quinoline-2-carboxylic acid (300 mg, 0.898 mmol) for 6-{[5-(trifluoromethyl)pyridin-2-yl]oxy}quinoline-2-carboxylic acid and (R)-tert-butyl 2-(hydroxymethyl)piperazine-1-carboxylate for tert-butyl piperazine-1-carboxylate (402 mg, 84%).

Example 63B tert-butyl (2R)-2-(methoxymethyl)-4-[(6-{[6-(trifluoromethyl)pyridin-3-yl]oxy}quinolin-2-yl)carbonyl]piperazine-1-carboxylate The titled compound was prepared using the conditions described in Example 31A, substituting (R)-tert-butyl 2-(hydroxymethyl)-4-(6-((6-(trifluoromethyl)pyridin-3-yl)oxy)quinoline-2-carbonyl)piperazine-1-carboxylate (323 mg, 0.607 mmol) for tert-butyl (2R)-2-(hydroxymethyl)-4-[(6-{[5-(trifluoromethyl)pyridin-2-yl]oxy}quinolin-2-yl)carbonyl]piperazine-1-carboxylate (225 mg, 68%).

Example 63C

[(3R)-3-(methoxymethyl)piperazin-1-yl](6-{[6-(trifluoromethyl)pyridin-3-yl]oxy}quinolin-2-yl)methanone The product from Example 63B (210 mg, 0.38 mmol) was subjected to the conditions described in Example 19D, to give the titled compound (155 mg, 90%). $^1$H NMR (400 MHz, DMSO-d$_6$, rotamers) δ ppm 2.55-3.24 (m, 8H), 3.33 (dd, J=12.0, 5.0 Hz, 3H), 3.51-3.73 (m, 1H), 4.24-4.39 (m, 0.5H), 4.39-4.53 (m, 0.5H), 7.59-7.85 (m, 4H), 7.97 (d, J=8.7 Hz, 1H), 8.07-8.20 (m, 1H), 8.46 (d, J=8.5 Hz, 1H), 8.64-8.76 (m, 1H); MS (DCI) m/z 447 [M+H]$^+$.

Example 64

[(3S)-3-(methoxymethyl)piperazin-1-yl](6-{[6-(trifluoromethyl)pyridin-3-yl]oxy}quinolin-2-yl)methanone

Example 64A tert-butyl (2S)-2-(hydroxymethyl)-4-[(6-{[6-(trifluoromethyl)pyridin-3-yl]oxy}quinolin-2-yl)carbonyl]piperazine-1-carboxylate The titled compound was prepared using the conditions described in Example 1E, substituting 6-{[6-(trifluoromethyl)pyridin-3-yl]oxy}quinoline-2-carboxylic acid (300 mg, 0.898 mmol) for 6-{[5-(trifluoromethyl)pyridin-2-yl]oxy}quinoline-2-carboxylic acid and (S)-tert-butyl 2-(hydroxymethyl)piperazine-1-carboxylate for tert-butyl piperazine-1-carboxylate (422 mg, 79%).

Example 64B tert-butyl (2S)-2-(methoxymethyl)-4-[(6-{[6-(trifluoromethyl)pyridin-3-yl]oxy}quinolin-2-yl)carbonyl]piperazine-1-carboxylate The titled compound was prepared using the conditions described in Example 31A, substituting (S)-tert-butyl 2-(hydroxymethyl)-4-(6-((6-(trifluoromethyl)pyridin-3-yl)oxy)quinoline-2-carbonyl)piperazine-1-carboxylate (345 mg, 0.648 mmol) for tert-butyl (2R)-2-(hydroxymethyl)-4-[(6-{[5-(trifluoromethyl)pyridin-2-yl]oxy}quinolin-2-yl)carbonyl]piperazine-1-carboxylate (226 mg, 64%)

Example 64C

[(3S)-3-(methoxymethyl)piperazin-1-yl](6-{[6-(trifluoromethyl)pyridin-3-yl]oxy}quinolin-2-yl)methanone The product from Example 64B (210 mg, 0.38 mmol) was subjected to the conditions described in Example 1F, to give the titled compound (152 mg, 89%). $^1$H NMR (400 MHz, DMSO-d$_6$, rotamers) δ ppm 2.55-3.24 (m, 8H), 3.33 (dd, J=12.0, 5.0 Hz, 3H), 3.51-3.73 (m, 1H), 4.24-4.39 (m, 0.5H), 4.39-4.53 (m, 0.5H), 7.59-7.85 (m, 4H), 7.97 (d, J=8.7 Hz, 1H), 8.07-8.20 (m, 1H), 8.46 (d, J=8.5 Hz, 1H), 8.64-8.76 (m, 1H); MS (DCI) m/z 447 [M+H]$^+$.

Example 65

N-[3-(methylsulfonyl)propyl]-6-{[5-(trifluoromethyl)pyridin-2-yl]oxy}quinoline-2-carboxamide The titled compound was prepared using the reaction conditions described for Example 9A, substituting 3-(methylsulfonyl)propan-1-amine (prepared according to WO2007127183, Example 308) for 2,5-dihydro-1H-pyrrole. $^1$H NMR (300 MHz, DMSO-d$_6$) δ ppm 9.12 (t, J=6.1 Hz, 1H), 8.61 (s, 1H), 8.54 (d, J=8.5 Hz, 1H), 8.31 (m, 1H), 8.20 (d, J=9.1 Hz, 1H), 8.18 (d, J=8.5 Hz, 1H), 7.93 (d, J=2.5 Hz, 1H), 7.77 (m, 1H), 7.41 (d, J=8.9 Hz, 1H), 3.50 (q, J=6.7 Hz, 2H), 3.19 (m, 2H), 2.99 (s, 3H), 2.03 (m, 2H); MS (ESI$^+$) m/z 454.1 [M+H]$^+$.

Example 66

(3-aminoazetidin-1-yl)(6-{[6-(trifluoromethyl)pyridin-3-yl]oxy}quinolin-2-yl)methanone

Example 66A tert-butyl {1-[(6-{[6-(trifluoromethyl)pyridin-3-yl]oxy}quinolin-2-yl)carbonyl]azetidin-3-yl}carbamate To a mixture of the product from Example 19B (461.3 mg, 1.380 mmol) and O-(benzotriazol-1-yl)-N,N,N',N'-tetramethyluronium tetrafluoroborate (TBTU, 576.0 mg, 1.794 mmol) in dimethyl sulfoxide (3 mL) at room temperature was added triethylamine (0.5 mL, 3.59 mmol) followed tert-butyl azetidin-3-ylcarbamate (383.9 mg, 1.615 mmol). After 17 h, a precipitate had formed. The reaction mixture was diluted with methanol (3 mL) and the precipitate was isolated by filtration, washed with additional methanol (3×2 mL) and dried to yield 383.4 mg (57%) of the titled compound.

Example 66B (3-aminoazetidin-1-yl)(6-{[6-(trifluoromethyl)pyridin-3-yl]oxy}quinolin-2-yl)methanone The product from Example 66A (357.2 mg, 0.731 mmol) was subjected to the conditions described in Example 19D to give the titled compound (246.0 mg, 87%). $^1$H NMR (400 MHz, DMSO-d$_6$) δ ppm 8.70 (d, J=2.8 Hz, 1H), 8.46 (d, J=8.5 Hz, 1H), 8.17 (d, J=8.9 Hz, 1H), 8.03 (d, J=8.5 Hz, 1H), 7.97 (d, J=8.9 Hz, 1H), 7.73-7.80 (m, 3H), 4.85-4.89 (m, 1H), 4.26-4.34 (m, 2H), 3.72-3.83 (m, 2H); MS (ESI) m/z 389.1 [M+H]$^+$.

Example 67

(6-{[5-(difluoromethyl)pyridin-2-yl]oxy}quinolin-2-yl)(3,5-dimethylpiperazin-1-yl)methanone

Example 67A tert-butyl 4-[(6-{[5-(difluoromethyl)pyridin-2-yl]oxy}quinolin-2-yl)carbonyl]-2,6-dimethylpiperazine-1-carboxylate The product from Example 14A (350 mg, 1.1 mmol) was subjected to the conditions described in Example 14B, substituting tert-butyl 2,6,dimethylpiperazine-1-carboxylate for tert-butyl piperazine-1-carboxylate to give the titled compound (406 mg, 72%).

Example 67B (6-{[5-(difluoromethyl)pyridin-2-yl]oxy}quinolin-2-yl)(3,5-dimethylpiperazin-1-yl)methanone The product from Example 67A (310 mg, 0.58 mmol) was subjected to the conditions described in Example 14C, to give the titled compound (235 mg, 93%). $^1$H NMR (400 MHz, DMSO-$d_6$) δ ppm 0.84 (d, J=6.2 Hz, 3H), 1.06 (d, J=6.3 Hz, 3H), 2.35 (dd, J=12.3, 10.8 Hz, 2H), 2.64 (dd, J=12.3, 10.8 Hz, 1H), 2.68-2.88 (m, 2H), 3.58 (d, J=11.9 Hz, 1H), 4.44 (dd, J=12.4, 1.1 Hz, 1H), 7.12 (t, J=55.3 Hz, 1H), 7.32 (d, J=8.5 Hz, 1H), 7.61-7.72 (m, 2H), 7.85 (d, J=2.6 Hz, 1H), 8.01-8.20 (m, 2H), 8.39 (d, J=1.6 Hz, 1H), 8.46 (d, J=8.4 Hz, 1H); MS (DCI) m/z 413 [M+H]$^+$.

Example 68

(6-{[5-(difluoromethyl)pyridin-2-yl]oxy}quinolin-2-yl)[(3R)-3-methylpiperazin-1-yl]methanone

Example 68A tert-butyl (2R)-4-[(6-{[5-(difluoromethyl)pyridin-2-yl]oxy}quinolin-2-yl)carbonyl]-2-methylpiperazine-1-carboxylate The titled compound was prepared using the conditions described in Example 14B, substituting (R)-tert-butyl 2-methylpiperazine-1-carboxylate for tert-butyl piperazine-1-carboxylate (269 mg, 53%).

Example 68B (6-{[5-(difluoromethyl)pyridin-2-yl]oxy}quinolin-2-yl)[(3R)-3-methylpiperazin-1-yl]methanone The product from Example 68A (250 mg, 0.5 mmol) was subjected to the conditions described in Example 14C, to give the titled compound (172 mg, 86%). $^1$H NMR (500 MHz, DMSO-$d_6$, rotamers) δ ppm 0.84 (d, J=5.9 Hz, 1.5H), 1.05 (d, J=6.3 Hz, 1.5H), 2.27-2.40 (m, 1H), 2.40-2.49 (m, 0.5H), 2.56-2.91 (m, 3.5H), 2.91-3.12 (m, 1H), 3.50-3.65 (m, 1H), 4.40 (t, J=11.8 Hz, 1H), 7.12 (t, J=55.3 Hz, 1H), 7.32 (dd, J=8.6, 3.1 Hz, 1H), 7.58-7.73 (m, 2H), 7.85 (d, J=2.3 Hz, 1H), 8.11 (dd, J=19.1, 8.8 Hz, 2H), 8.39 (d, J=1.0 Hz, 1H), 8.46 (d, J=8.5 Hz, 1H); MS (DCI) m/z 399 [M+H]$^+$.

Example 69

(6-{[5-(difluoromethyl)pyridin-2-yl]oxy}quinolin-2-yl)[(3S)-3-(methoxymethyl)piperazin-1-yl]methanone

Example 69A tert-butyl (2S)-4-[(6-{[5-(difluoromethyl)pyridin-2-yl]oxy}quinolin-2-yl)carbonyl]-2-(hydroxymethyl)piperazine-1-carboxylate The titled compound was prepared using the conditions described in Example 14B, substituting (S)-tert-butyl 2-(hydroxymethyl)piperazine-1-carboxylate for tert-butyl piperazine-1-carboxylate (592 mg, 73%).

Example 69B tert-butyl (2S)-4-[(6-{[5-(difluoromethyl)pyridin-2-yl]oxy}quinolin-2-yl)carbonyl]-2-(methoxymethyl)piperazine-1-carboxylate The product from Example 69A (263 mg, 0.511 mmol) was subjected to the conditions described in Example 31A, to give the titled compound (209 mg, 77%).

Example 69C (6-{[5-(difluoromethyl)pyridin-2-yl]oxy}quinolin-2-yl)[(3S)-3-(methoxymethyl)piperazin-1-yl]methanone The product from Example 69B (180 mg, 0.34 mmol) was subjected to the conditions described in Example 14C, to give the titled compound (99 mg, 68%). $^1$H NMR (400 MHz, DMSO-$d_6$, rotamers) δ ppm 2.33-3.21 (m, 10H), 3.53-3.74 (m, 1H), 4.27-4.39 (m, 0.5H), 4.41-4.54 (m, 0.5H), 7.12 (t, J=55.4 Hz, 1H), 7.32 (dd, J=8.6, 3.4 Hz, 1H), 7.62-7.73 (m, 2H), 7.81-7.88 (m, 1H), 8.11 (ddd, J=10.9, 8.9, 1.5 Hz, 2H), 8.39 (s, 1H), 8.47 (d, J=8.6 Hz, 1H); MS (DCI) m/z 429 [M+H]$^+$.

Example 70

{3-[(3R)-3-fluoropyrrolidin-1-yl]azetidin-1-yl}(6-{[5-(trifluoromethyl)pyridin-2-yl]oxy}quinolin-2-yl)methanone The product from Example 1D (7.65 g, 22.88 mmol) was subjected to the conditions described in Example 2, substituting azetidine-3-one hydrochloric acid for 3-aminotetrahydrothiophene 1,1-dioxide hydrochloride to give 2.73 g (31%) of 1-[(6-{[5-(trifluoromethyl)pyridin-2-yl]oxy}quinolin-2-yl)carbonyl]azetidin-3-one. A mixture of 1-[(6-{[5-(trifluoromethyl)pyridin-2-yl]oxy}quinolin-2-yl)carbonyl]azetidin-3-one (0.2 g, 0.516 mmol), (R)-3-fluoropyrrolidine hydrochloride (0.065 g, 0.516 mmol), acetic acid (0.059 mL, 1.033 mmol), and methanol (3.97 mL) was stirred at room temperature for 45 minutes. Sodium cyanoborohydride on resin (0.5 g, 1.09 mmol, 2.17 mmol/g) was added. The reaction mixture was stirred at room temperature for 16 h. The resin was removed by filtration and washed with methanol. The filtrate was concentrated. The residue was dissolved in methanol, filtered using a syringe filter, and purified by preparative HPLC on a Phenomenex® Luna® C8(2) 5 um 100 Å AXIA™ column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). Samples were injected in 1.5 mL dimethyl sulfoxide:methanol (1:1). A custom purification system was used, consisting of the following modules: Waters LC4000 preparative pump; Waters 996 diode-array detector; Waters 717+ autosampler; Waters SAT/IN module, Alltech Varex III evaporative light-scattering detector; Gilson 506C interface box; and two Gilson FC204 fraction collectors. The system was controlled using Waters Millennium32 software, automated using an AbbVie developed Visual Basic application for fraction collector control and fraction tracking. Fractions were collected based upon UV signal threshold and selected fractions subsequently analyzed by flow injection analysis mass spectrometry using positive APCI ionization on a Finnigan LCQ using 70:30 methanol: 10 mM $NH_4OH$(aqueous) at a flow rate of 0.8 mL/min. Loop-injection mass spectra were acquired using a Finnigan LCQ running LCQ Navigator 1.2 software and a Gilson 215 liquid handler for fraction injection controlled by an AbbVie developed Visual Basic application. The desired fractions were then combined and treated with saturated aqueous sodium bicarbonate. The desired material was extracted with dichloromethane (3×), dried with $Na_2SO_4$, filtered and concentrated to yield 89 mg (37%) of the titled compound. $^1$H NMR (400 MHz, DMSO-$d_6$, rotamers) δ ppm 8.61-8.57 (m, 1H), 8.48 (d, J=8.6 Hz, 1H), 8.30 (dd, J=8.7, 2.6 Hz, 1H), 8.18 (dd, J=9.1, 2.7 Hz, 1H), 8.04 (d, J=8.6 Hz, 1H), 7.89 (d, J=2.6 Hz, 1H), 7.72 (dd, J=9.1, 2.6 Hz, 1H), 7.39 (d, J=8.7 Hz, 1H), 5.33-5.28 (m, 0.5H), 5.19-5.14 (m, 0.5H), 4.83-4.76 (m, 1H), 4.60-4.53 (m, 1H), 4.19 (dd, J=10.1, 7.3 Hz, 1H), 4.02-3.94 (m, 1H), 3.47-3.40 (m, 1H), 2.94-2.79 (m, 2H), 2.71 (dd, J=11.5, 4.9 Hz, 0.5H), 2.63 (dd, J=11.5, 4.9 Hz, 0.5H), 2.44-2.35 (m, 1H), 2.24-2.06 (m, 1H), 1.99-1.82 (m, 1H); MS (ESI) m/z 461.1 [M+H]$^+$.

Example 71

(6-{[5-(difluoromethyl)pyridin-2-yl]oxy}quinolin-2-yl)[(3R)-3-(methoxymethyl)piperazin-1-yl]methanone Example 71A tert-butyl (2R)-4-[(6-{[5-(difluoromethyl)pyridin-2-yl]oxy}quinolin-2-yl)carbonyl]-2-(hydroxymethyl)piperazine-1-carboxylate The titled compound was prepared using the conditions described in Example 14B, substituting (R)-tert-butyl 2-(hydroxymethyl)piperazine-1-carboxylate for tert-butyl piperazine-1-carboxylate (780 mg, 96%).

Example 71B tert-butyl (2R)-4-[(6-{[5-(difluoromethyl)pyridin-2-yl]oxy}quinolin-2-yl)carbonyl]-2-(methoxymethyl)piperazine-1-carboxylate The product from Example 71A (215 mg, 0.418 mmol) was subjected to the conditions described in Example 31A, to give the titled compound (86 mg, 39%).

Example 71C

The product from Example 71B (80 mg, 0.15 mmol) was subjected to the conditions described in Example 14C, to give the titled compound (53 mg, 82%). $^1$H NMR (400 MHz, DMSO-$d_6$, rotamers) δ ppm 2.33-3.21 (m, 10H), 3.53-3.74 (m, 1H), 4.27-4.39 (m, 0.5H), 4.41-4.54 (m, 0.5H), 7.12 (t, J=55.4 Hz, 1H), 7.32 (dd, J=8.6, 3.4 Hz, 1H), 7.62-7.73 (m, 2H), 7.81-7.88 (m, 1H), 8.11 (ddd, J=10.9, 8.9, 1.5 Hz, 2H), 8.39 (s, 1H), 8.47 (d, J=8.6 Hz, 1H); MS (DCI) m/z 429 [M+H]$^+$.

Example 72

[(2S*)-2-(difluoromethyl)piperazin-1-yl](6-{[5-(trifluoromethyl)pyridin-2-yl]oxy}quinolin-2-yl)methanone The product from Example 25B (1.39 g, 3.07 mmol) was subjected to preparative super critical fluid chromatography (SFC) to give 589 mg of the titled compound as a single enantiomer (second to elute, $t_R$=5.28 minutes, >99% ee). Preparative SFC was performed on a THAR/Waters SFC 80 system running under SuperChrom software control. The preparative SFC system was equipped with an 8-way preparative column switcher, $CO_2$ pump, modifier pump, automated back pressure regulator (ABPR), UV detector, and 6-position fraction collector. The mobile phase comprised of supercritical $CO_2$ supplied by a Dewar of bone-dry non-certified $CO_2$ pressurized to 350 psi with a modifier of methanol buffered with 0.3% diethylamine at a flow rate of 70 g/minute. UV detection was set to collect at a wavelength of 220 nm, the column was at ambient temperature, and the backpressure regulator was set to maintain 100 bar. The sample was dissolved in methanol at a concentration of 40 mg/mL. The sample was loaded into the modifier stream in 1.5 mL (40 mg) injections. The mobile phase was held isocratically at 30% methanol:$CO_2$. Fraction collection was time triggered. The instrument was fitted with a CHIRAL-CEL® OZ-H column with dimensions 21 mm i.d.×250 mm length with 5 μm particles.

Analytical SFC was performed on an Aurora A5 SFC Fusion and Agilent 1100 system running under Agilent Chemstation software control. The SFC system included a 10-way column switcher, $CO_2$ pump, modifier pump, oven, and backpressure regulator. The mobile phase comprised of supercritical $CO_2$ supplied by a beverage-grade $CO_2$ cylinder with a modifier mixture of methanol buffered with 0.1% diethylamine at a flow rate of 3 mL/minute. Oven temperature was at 35° C. and the outlet pressure at 150 bar. The mobile phase gradient started with 5% modifier and held it for 0.1 minutes at a flow rate of 1 mL/minute, then the flow rate was ramped up to 3 mL/minute and held for 0.4 minutes. The modifier was ramped from 5% to 50% over the next 8 minutes at 3 mL/minute then held for 1 minute at 50% modifier (3 mL/minute). The gradient was ramped down from 50% to 5% modifier over 0.5 minutes (3 mL/minute). The instrument was fitted with a CHIRALCEL® OZ-H column with dimensions of 4.6 mm i.d.×150 mm length with 5 μm particles.

This was the second compound to elute from the SFC purification. It is an enantiopure sample, but the absolute stereochemistry was not determined. $^1$H NMR (500 MHz, DMSO-$d_6$, rotamers) δ ppm 8.59 (s, 1H), 8.50 (d, J=8.5 Hz, 1H), 8.30 (dd, J=8.7, 2.5 Hz, 1H), 8.12 (t, J=8.9 Hz, 1H), 7.90 (d, J=2.6 Hz, 1H), 7.74-7.71 (m, 1H), 7.69 (dd, J=8.5, 7.0 Hz, 1H), 7.40 (dd, J=8.7, 3.7 Hz, 1H), 6.55 (tdd, J=57.0, 37.5, 6.7 Hz, 1H), 4.82-4.74 (m, 0.5H), 4.43-4.34 (m, 0.5H), 4.35-4.27 (m, 0.5H), 3.56 (d, J=13.3 Hz, 0.5H), 3.39-3.34 (m, 0.5H), 3.16 (d, J=13.1 Hz, 0.5H), 3.09-2.93 (m, 2H), 2.87-2.77 (m, 1H), 2.76-2.68 (m, 0.5H), 2.63-2.55 (m, 1.5H); MS (ESI) m/z 453.1 [M+H]$^+$.

Example 73

N-[(3R*)-1-methyl-5-oxopyrrolidin-3-yl]-6-{[5-(trifluoromethyl)pyridin-2-yl]oxy}quinoline-2-carboxamide The product from Example 1D (500 mg, 1.5 mmol) was subjected to the conditions described in Example 27, substituting 4-amino-1-methylpyrrolidin-2-one hydrochloride (225 mg, 1.496 mmol) for (S)-hexahydropyrrolo[1,2-a]pyrazin-4(1H)-one hydrochloride, to give N-[(3R)-1-methyl-5-oxopyrrolidin-3-yl]-6-{[5-(trifluoromethyl)pyridin-2-yl]oxy}quinoline-2-carboxamide (460 mg, 71.5% yield), which subjected to chiral SFC separation (CHIRALCEL® OJ-H, 5-50% methanol:carbon dioxide, 10 minutes at flow rate 3 mL/minute, 150 bar) to yield the titled compound (first to elute, $t_R$=3.42 minutes, >99% ee) (206 mg, 44.8%). It is an enantiopure sample, but the absolute stereochemistry was not determined $^1$H NMR (400 MHz, DMSO-d$_6$) δ ppm 2.52-2.72 (m, 2H) 2.77 (s, 3H) 3.41 (dd, J=10.07, 4.88 Hz, 1H) 3.73 (dd, J=9.92, 7.78 Hz, 1H) 4.60-4.71 (m, 1H) 7.40 (d, J=8.85 Hz, 1H) 7.76 (dd, J=9.16, 2.44 Hz, 1H) 7.93 (d, J=2.44 Hz, 1H) 8.16 (d, J=8.54 Hz, 1H) 8.22 (d, J=9.16 Hz, 1H) 8.31 (dd, J=8.70, 2.29 Hz, 1H) 8.53 (d, J=8.54 Hz, 1H) 8.61 (s, 1H) 9.24 (d, J=7.32 Hz, 1H); MS (ESI) m/z 431.0 [M+H]$^+$.

Example 74

N-[(3S*)-1-methyl-5-oxopyrrolidin-3-yl]-6-{[5-(trifluoromethyl)pyridin-2-yl]oxy}quinoline-2-carboxamide The titled compound was obtained (second to elute, $t_R$=4.77 minutes, >99% ee) (203 mg, 44.1% yield) from chiral SFC separation described in Example 73. It is an enantiopure sample, but the absolute stereochemistry undetermined. $^1$H NMR (400 MHz, DMSO-d$_6$) δ ppm 2.53-2.72 (m, 2H) 2.77 (s, 3H) 3.41-3.47 (m, 1H) 3.73 (dd, J=9.92, 7.78 Hz, 1H) 4.60-4.73 (m, 1H) 7.40 (d, J=8.85 Hz, 1H) 7.76 (dd, J=9.16, 2.75 Hz, 1H) 7.92 (d, J=2.75 Hz, 1H) 8.16 (d, J=8.54 Hz, 1H) 8.23 (d, J=9.16 Hz, 1H) 8.31 (dd, J=8.85, 2.44 Hz, 1H) 8.54 (d, J=8.54 Hz, 1H) 8.61 (s, 1H) 9.25 (d, J=7.32 Hz, 1H); MS (ESI) m/z 431.0 [M+H]$^+$.

The compounds in the table below were prepared using methodologies described in the above Schemes and Examples. Compounds containing a basic nitrogen moiety that were purified by reverse phase HPLC using an eluent buffered with trifluoroacetic acid were isolated as the corresponding trifluoroacetic acid salt.

| Example Number | Name | $^1$H NMR | MS |
|---|---|---|---|
| Example 75 | N-(3,3,3-trifluoro-2-hydroxypropyl)-6-{[5-(trifluoromethyl)pyridin-2-yl]oxy}quinoline-2-carboxamide | $^1$H NMR (400 MHz, DMSO-d$_6$) δ ppm 9.01 (t, J = 6.0 Hz, 1H), 8.61 (d, J = 2.4 Hz, 1H), 8.56 (d, J = 8.6 Hz, 1H), 8.32 (dd, J = 8.7, 2.6 Hz, 1H), 8.24-8.17 (m, 2H), 7.94 (d, J = 2.6 Hz, 1H), 7.77 (dd, J = 9.1, 2.6 Hz, 1H), 7.41 (d, J = 8.7 Hz, 1H), 6.56 (bs, 1H), 4.38-4.29 (m, 1H), 3.78-3.66 (m, 1H), 3.59-3.48 (m, 1H). | MS (ESI) m/z 397.0 [M + H]$^+$ |
| Example 76 | morpholin-4-yl[6-(pyridin-2-yloxy)quinolin-2-yl]methanone | $^1$H NMR (300 MHz, DMSO-d$_6$) δ ppm 8.58 (d, J = 8.6 Hz, 1H), 8.17-8.09 (m, 2H), 7.87 (dd, J = 9.0, 2.4 Hz, 1H), 7.83-7.74 (m, 2H), 7.62-7.53 (m, 1H), 6.59-6.51 (m, 1H), 6.40 (td, J = 6.7, 1.3 Hz, 1H), 3.73 (s, 4H), 3.63-3.55 (m, 2H), 3.53-3.46 (m, 2H). | MS (ESI) m/z 336.1 [M + H]$^+$ |
| Example 77 | (4-methylpiperazin-1-yl)[6-(pyridin-2-yloxy)quinolin-2-yl]methanone | $^1$H NMR (300 MHz, DMSO-d$_6$) δ ppm 8.56 (d, J = 8.6 Hz, 1H), 8.16-8.09 (m, 2H), 7.86 (dd, J = 9.0, 2.4 Hz, 1H), 7.84-7.78 (m, 1H), 7.73 (d, J = 8.5 Hz, 1H), 7.62-7.53 (m, 1H), 6.55 (d, J = 8.4 Hz, 1H), 6.40 (td, J = 6.7, 1.3 Hz, 1H), 3.76-3.67 (m, 2H), 3.48-3.37 (m, 2H), 2.47-2.38 (m, 2H), 2.36-2.28 (m, 2H), 2.22 (s, 3H). | MS (ESI) m/z 349.1 [M + H]$^+$ |
| Example 78 | [3-(3-methyl-1,2,4-oxadiazol-5-yl)piperidin-1-yl][6-(pyridin-2-yloxy)quinolin-2-yl]methanone | $^1$H NMR (300 MHz, DMSO-d$_6$, rotamers) δ ppm 8.58 (dd, J = 8.5, 5.4 Hz, 1H), 8.16-8.07 (m, 2H), 7.90-7.79 (m, 2H), 7.74 (dd, J = 8.5, 1.9 Hz, 1H), 7.62-7.54 (m, 1H), 6.55 (d, J = 9.2 Hz, 1H), 6.43-6.36 (m, 1H), 4.74-4.61 (m, 0.5H), 4.14-3.94 (m, 1H), 3.74-3.60 (m, 1H), 3.51-3.33 (m, 2H), 3.28-3.16 (m, 0.5H), 2.37 (s, 1H), 2.25 (s, 2H), 2.23-2.15 (m, 1H), 2.02-1.60 (m, 3H). | MS (ESI) m/z 416.2 [M + H]$^+$ |
| Example 79 | N-[2-(piperidin-1-yl)ethyl]-6-(pyridin-2-yloxy)quinoline-2-carboxamide | $^1$H NMR (300 MHz, DMSO-d$_6$) δ ppm 8.90 (t, J = 5.6 Hz, 1H), 8.63 (d, J = 8.6 Hz, 1H), 8.25-8.16 (m, 3H), 7.92 (dd, J = 9.0, 2.3 Hz, 1H), 7.86-7.81 (m, 1H), 7.62-7.54 (m, 1H), 6.58-6.53 (m, 1H), 6.40 (td, J = 6.7, 1.2 Hz, 1H), 3.49 (q, J = 6.6 Hz, 2H), 2.47-2.33 (m, 6H), 1.59-1.47 (m, 4H), 1.47-1.37 (m, 2H). | MS (ESI) m/z 377.1 [M + H]$^+$ |
| Example 80 | 6-(pyridin-2-yloxy)-N-(1,2,4-thiadiazol-5-yl)quinoline-2-carboxamide | $^1$H NMR (300 MHz, DMSO-d$_6$) δ ppm 13.56 (s, 1H), 8.73 (d, J = 8.7 Hz, 1H), 8.60 (s, 1H), 8.34 (d, J = 8.6 Hz, 2H), 8.25 (d, J = 2.3 Hz, 1H), 7.99 (dd, J = 9.0, 2.4 Hz, 1H), 7.88-7.83 (m, 1H), 7.63-7.56 (m, 1H), 6.60-6.54 (m, 1H), 6.42 (td, J = 6.7, 1.3 Hz, 1H). | MS (ESI) m/z 350.2 [M + H]$^+$ |

-continued

| Example Number | Name | ¹H NMR | MS |
|---|---|---|---|
| Example 81 | 4-({2-[(4-methylpiperazin-1-yl)carbonyl]quinolin-6-yl}oxy)benzonitrile | ¹H NMR (300 MHz, DMSO-$d_6$) δ ppm 8.46 (d, J = 8.4 Hz, 1H), 8.12 (d, J = 9.1 Hz, 1H), 7.93-7.87 (m, 2H), 7.73 (d, J = 2.7 Hz, 1H), 7.70-7.63 (m, 2H), 7.29-7.23 (m, 2H), 3.75-3.67 (m, 2H), 3.48-3.40 (m, 2H), 2.46-2.38 (m, 2H), 2.34-2.27 (m, 2H), 2.21 (s, 3H). | MS (ESI) m/z 373.1 [M + H]⁺ |
| Example 82 | 6-(4-cyanophenoxy)-N-[2-(piperidin-1-yl)ethyl]quinoline-2-carboxamide | ¹H NMR (300 MHz, DMSO-$d_6$) δ ppm 8.89-8.81 (m, 1H), 8.51 (d, J = 8.4 Hz, 1H), 8.21-8.13 (m, 2H), 7.96-7.88 (m, 2H), 7.76-7.67 (m, 2H), 7.33-7.26 (m, 2H), 3.47 (dd, J = 12.8, 6.6 Hz, 2H), 2.54-2.46 (m, 2H), 2.45-2.38 (m, 4H), 1.59-1.47 (m, 4H), 1.46-1.34 (m, 2H). | MS (ESI) m/z 401.1 [M + H]⁺ |
| Example 83 | 4-{[2-(morpholin-4-ylcarbonyl)quinolin-6-yl]oxy}benzonitrile | ¹H NMR (300 MHz, DMSO-$d_6$) δ ppm 8.47 (d, J = 8.5 Hz, 1H), 8.13 (d, J = 9.1 Hz, 1H), 7.94-7.88 (m, 2H), 7.75-7.64 (m, 3H), 7.30-7.23 (m, 2H), 3.72 (s, 4H), 3.63-3.55 (m, 2H), 3.54-3.47 (m, 2H). | MS (ESI) m/z 360.1 [M + H]⁺ |
| Example 84 | 6-(4-cyanophenoxy)-N-(1H-indazol-6-yl)quinoline-2-carboxamide | ¹H NMR (400 MHz, DMSO-$d_6$/$D_2O$, 90° C.) δ ppm 8.55 (d, J = 8.5 Hz, 1H), 8.39-8.32 (m, 1H), 8.30 (d, J = 1.5 Hz, 1H), 8.27 (d, J = 8.4 Hz, 1H), 8.02 (s, 1H), 7.89-7.83 (m, 2H), 7.77 (d, J = 8.6 Hz, 1H), 7.73-7.67 (m, 2H), 7.50 (dd, J = 8.6, 1.8 Hz, 1H), 7.32-7.26 (m, 2H). | MS (APCI) m/z 406.1 [M + H]⁺ |
| Example 85 | 6-(4-cyanophenoxy)-N-[3-(dimethylamino)propyl]quinoline-2-carboxamide | ¹H NMR (400 MHz, DMSO-$d_6$/$D_2O$, 90° C.) δ ppm 8.48 (d, J = 8.5 Hz, 1H), 8.22 (d, J = 8.7 Hz, 1H), 8.15 (d, J = 8.5 Hz, 1H), 7.91-7.80 (m, 2H), 7.71-7.61 (m, 2H), 7.31-7.21 (m, 2H), 3.49 (t, J = 6.8 Hz, 2H), 3.19-3.12 (m, 2H), 2.83 (s, 6H), 2.08-1.92 (m, 2H). | MS (APCI) m/z 375.0 [M + H]⁺ |
| Example 86 | 6-(4-cyanophenoxy)-N-[2-(morpholin-4-yl)ethyl]quinoline-2-carboxamide | ¹H NMR (400 MHz, DMSO-$d_6$/$D_2O$, 90° C.) δ ppm 8.49 (d, J = 8.6 Hz, 1H), 8.28-8.18 (m, 1H), 8.16 (d, J = 8.5 Hz, 1H), 7.91-7.80 (m, 2H), 7.67 (m, 2H), 7.32-7.21 (m, 2H), 3.91-3.82 (m, 4H), 3.80 (t, J = 6.2 Hz, 2H), 3.42 (t, J = 6.2 Hz, 2H), 3.39-3.32 (m, 4H). | MS (APCI) m/z 403.1 [M + H]⁺ |
| Example 87 | 6-(4-cyanophenoxy)-N-[3-(morpholin-4-yl)propyl]quinoline-2-carboxamide | ¹H NMR (400 MHz, DMSO-$d_6$/$D_2O$, 90° C.) δ ppm 8.48 (d, J = 8.6 Hz, 1H), 8.22 (d, J = 8.7 Hz, 1H), 8.15 (d, J = 8.5 Hz, 1H), 7.91-7.80 (m, 2H), 7.72-7.60 (m, 2H), 7.31-7.21 (m, 2H), 3.86 (s, 4H), 3.51 (t, J = 6.7 Hz, 2H), 3.26-3.15 (m, 6H), 2.13-1.99 (m, 2H). | MS (APCI) m/z 417.1 [M + H]⁺ |
| Example 88 | 6-(4-cyanophenoxy)-N-(1,3-thiazol-2-yl)quinoline-2-carboxamide | ¹H NMR (400 MHz, DMSO-$d_6$/$D_2O$, 90° C.) δ ppm 8.57 (d, J = 8.6 Hz, 1H), 8.35 (d, J = 10.0 Hz, 1H), 8.25 (d, J = 8.5 Hz, 1H), 7.90-7.82 (m, 2H), 7.71 (dd, J = 4.9, 2.3 Hz, 2H), 7.58 (d, J = 3.5 Hz, 1H), 7.33 (d, J = 3.5 Hz, 1H), 7.31-7.24 (m, 2H). | MS (APCI) m/z 372.9 [M + H]⁺ |
| Example 89 | 6-(4-cyanophenoxy)-N-(pyridin-3-ylmethyl)quinoline-2-carboxamide | ¹H NMR (400 MHz, DMSO-$d_6$/$D_2O$, 90° C.) δ ppm 8.78-8.67 (m, 1H), 8.67-8.56 (m, 1H), 8.48 (d, J = 8.6 Hz, 1H), 8.23 (d, J = 8.8 Hz, 1H), 8.20-8.10 (m, 2H), 7.90-7.79 (m, 2H), 7.73-7.60 (m, 3H), 7.32-7.21 (m, 2H), 4.71 (s, 2H) | MS (APCI) m/z 381.0 [M + H]⁺ |
| Example 90 | 6-(4-cyanophenoxy)-N-[(3S)-2-oxotetrahydrofuran-3-yl]quinoline-2-carboxamide | ¹H NMR (400 MHz, DMSO-$d_6$/$D_2O$, 90° C.) δ ppm 8.49 (d, J = 8.6 Hz, 1H), 8.23 (d, J = 10.0 Hz, 1H), 8.14 (d, J = 8.5 Hz, 1H), 7.85 (d, J = 8.8 Hz, 2H), 7.73-7.61 (m, 2H), 7.27 (d, J = 8.8 Hz, 2H), 4.84 (t, J = 10.0 Hz, 1H), 4.46 (dt, J = 8.8, 4.5 Hz, 1H), 4.34 (dt, J = 15.9, 7.9 Hz, 1H), 2.64-2.42 (m, 2H). | MS (APCI) m/z 373.9 [M + H]⁺ |
| Example 91 | 6-(4-cyanophenoxy)-N-[(2R)-1-hydroxy-3-methylbutan-2-yl]quinoline-2-carboxamide | ¹H NMR (400 MHz, DMSO-$d_6$/$D_2O$, 90° C.) δ ppm 8.48 (d, J = 8.6 Hz, 1H), 8.22 (d, J = 9.0 Hz, 1H), 8.16 (d, J = 8.5 Hz, 1H), 7.90-7.79 (m, 2H), 7.71-7.59 (m, 2H), 7.31-7.21 (m, 2H), 3.92-3.79 (m, 1H), 3.64 (dd, J = 13.5, 5.0 Hz, 2H), 2.14-1.96 (m, 1H), 0.97 (m, 6H). | MS (APCI) m/z 376.0 [M + H]⁺ |
| Example 92 | 6-(4-cyanophenoxy)-N-(2-thienylmethyl)quinoline-2-carboxamide | ¹H NMR (400 MHz, DMSO-$d_6$/$D_2O$, 90° C.) δ ppm 8.48 (d, J = 8.5 Hz, 1H), 8.21 (d, J = 8.9 Hz, 1H), 8.16 (d, J = 8.5 Hz, 1H), 7.90-7.81 (m, 2H), 7.71-7.58 (m, 2H), 7.34 (dd, J = 5.1, 1.2 Hz, 1H), 7.32-7.21 (m, 2H), 7.09 (d, J = 3.4 Hz, 1H), 7.03-6.92 (m, 1H), 4.76 (s, 2H). | MS (APCI) m/z 385.9 [M + H]⁺ |

-continued

| Example Number | Name | ¹H NMR | MS |
|---|---|---|---|
| Example 93 | 6-(4-cyanophenoxy)-N-[2-(2-thienyl)ethyl]quinoline-2-carboxamide | ¹H NMR (400 MHz, DMSO-$d_6$/$D_2O$, 90° C.) δ ppm 8.46 (d, J = 8.6 Hz, 1H), 8.19 (d, J = 9.0 Hz, 1H), 8.14 (d, J = 8.5 Hz, 1H), 7.87-7.79 (m, 2H), 7.70-7.61 (m, 2H), 7.31-7.21 (m, 3H), 6.99-6.91 (m, 2H), 3.67 (t, J = 7.1 Hz, 2H), 3.17 (t, J = 7.1 Hz, 2H). | MS (APCI) m/z 400.0 [M + H]⁺ |
| Example 94 | 6-(4-cyanophenoxy)-N-(2-furylmethyl)quinoline-2-carboxamide | ¹H NMR (400 MHz, DMSO-$d_6$/$D_2O$, 90° C.) δ ppm 8.47 (d, J = 8.6 Hz, 1H), 8.22 (d, J = 8.9 Hz, 1H), 8.15 (d, J = 8.5 Hz, 1H), 7.89-7.81 (m, 2H), 7.69-7.60 (m, 2H), 7.54-7.49 (m, 1H), 7.29-7.22 (m, 2H), 6.41-6.37 (m, 1H), 6.35-6.32 (m, 1H), 4.60 (s, 2H). | MS (APCI) m/z 369.9 [M + H]⁺ |
| Example 95 | 6-(4-cyanophenoxy)-N-(1-hydroxy-3-methylbutan-2-yl)quinoline-2-carboxamide | ¹H NMR (400 MHz, DMSO-$d_6$/$D_2O$, 90° C.) δ ppm 8.48 (d, J = 8.5 Hz, 1H), 8.22 (d, J = 9.0 Hz, 1H), 8.16 (d, J = 8.5 Hz, 1H), 7.84 (d, J = 8.9 Hz, 2H), 7.70-7.61 (m, 2H), 7.26 (d, J = 8.8 Hz, 2H), 3.90-3.79 (m, 1H), 3.70-3.56 (m, 2H), 2.10-1.96 (m, 1H), 1.04-0.93 (m, 6H). | MS (APCI) m/z 376.0 [M + H]⁺ |
| Example 96 | 6-(4-cyanophenoxy)-N-[2-(pyrrolidin-1-yl)ethyl]quinoline-2-carboxamide | ¹H NMR (400 MHz, DMSO-$d_6$/$D_2O$, 90° C.) δ ppm 8.49 (d, J = 8.6 Hz, 1H), 8.22 (d, J = 9.0 Hz, 1H), 8.16 (d, J = 8.5 Hz, 1H), 7.89-7.81 (m, 2H), 7.71-7.64 (m, 2H), 7.30-7.23 (m, 2H), 3.77 (t, J = 6.1 Hz, 2H), 3.73-3.53 (m, 2H), 3.44 (t, J = 6.1 Hz, 2H), 3.22-3.00 (m, 2H), 2.13-1.85 (m, 4H). | MS (APCI) m/z 387.0 [M + H]⁺ |
| Example 97 | 6-(4-cyanophenoxy)-N-(pyridin-2-ylmethyl)quinoline-2-carboxamide | ¹H NMR (400 MHz, DMSO-$d_6$/$D_2O$, 90° C.) δ ppm 8.59 (d, J = 4.9 Hz, 1H), 8.49 (d, J = 8.5 Hz, 1H), 8.24 (d, J = 8.7 Hz, 1H), 8.17 (d, J = 8.5 Hz, 1H), 7.95 (dt, J = 7.7, 1.7 Hz, 1H), 7.89-7.79 (m, 2H), 7.71-7.62 (m, 2H), 7.56 (d, J = 7.7 Hz, 1H), 7.49-7.41 (m, 1H), 7.31-7.21 (m, 2H), 4.77 (s, 2H). | MS (APCI) m/z 381.0 [M + H]⁺ |
| Example 98 | 6-(4-cyanophenoxy)-N-(pyridin-4-ylmethyl)quinoline-2-carboxamide | ¹H NMR (400 MHz, DMSO-$d_6$/$D_2O$, 90° C.) δ ppm 8.75-8.65 (m, 2H), 8.50 (d, J = 8.6 Hz, 1H), 8.25 (d, J = 8.7 Hz, 1H), 8.15 (d, J = 8.5 Hz, 1H), 7.91-7.82 (m, 2H), 7.79 (d, J = 6.0 Hz, 2H), 7.71-7.64 (m, 2H), 7.32-7.22 (m, 2H), 4.78 (s, 2H). | MS (APCI) m/z 381.0 [M + H]⁺ |
| Example 99 | 6-(4-cyanophenoxy)-N-[(5-methyl-2-furyl)methyl]quinoline-2-carboxamide | ¹H NMR (400 MHz, DMSO-$d_6$/$D_2O$, 90° C.) δ ppm 8.47 (d, J = 8.6 Hz, 1H), 8.22 (d, J = 8.9 Hz, 1H), 8.15 (d, J = 8.5 Hz, 1H), 7.88-7.78 (m, 2H), 7.70-7.60 (m, 2H), 7.30-7.22 (m, 2H), 6.20 (d, J = 3.1 Hz, 1H), 6.03-5.95 (m, 1H), 4.53 (s, 2H), 2.24 (s, 3H). | MS (APCI) m/z 384.0 [M + H]⁺ |
| Example 100 | 6-(4-cyanophenoxy)-N-[3-(piperidin-1-yl)propyl]quinoline-2-carboxamide | ¹H NMR (400 MHz, DMSO-$d_6$/$D_2O$, 90° C.) δ ppm 8.48 (d, J = 8.6 Hz, 1H), 8.22 (d, J = 8.7 Hz, 1H), 8.15 (d, J = 8.5 Hz, 1H), 7.91-7.80 (m, 2H), 7.72-7.60 (m, 2H), 7.31-7.21 (m, 2H), 3.55-3.39 (m, 4H), 3.20-3.08 (m, 2H), 3.06-2.74 (m, 2H), 2.12-1.95 (m, 2H), 1.94-1.55 (m, 6H). | MS (APCI) m/z 415.1 [M + H]⁺ |
| Example 101 | 6-(4-cyanophenoxy)-N-(4-phenoxyphenyl)quinoline-2-carboxamide | ¹H NMR (400 MHz, DMSO-$d_6$/$D_2O$, 90° C.) δ ppm 8.53 (d, J = 8.5 Hz, 1H), 8.33 (d, J = 9.8 Hz, 1H), 8.24 (d, J = 8.5 Hz, 1H), 7.92-7.82 (m, 4H), 7.72-7.66 (m, 2H), 7.43-7.36 (m, 2H), 7.32-7.26 (m, 2H), 7.14 (t, J = 7.4 Hz, 1H), 7.09-6.97 (m, 4H). | MS (APCI) m/z 458.1 [M + H]⁺ |
| Example 102 | 6-(4-cyanophenoxy)-N-[3-(trifluoromethoxy)benzyl]quinoline-2-carboxamide | ¹H NMR (400 MHz, DMSO-$d_6$/$D_2O$, 90° C.) δ ppm 8.48 (d, J = 8.5 Hz, 1H), 8.22 (d, J = 8.9 Hz, 1H), 8.15 (d, J = 8.5 Hz, 1H), 7.84 (d, J = 8.8 Hz, 2H), 7.69-7.62 (m, 2H), 7.51-7.38 (m, 2H), 7.33 (s, 1H), 7.26 (d, J = 8.8 Hz, 2H), 7.20 (d, J = 7.8 Hz, 1H), 4.64 (s, 2H). | MS (APCI) m/z 464.0 [M + H]⁺ |
| Example 103 | 6-(4-cyanophenoxy)-N-(4-methylbenzyl)quinoline-2-carboxamide | ¹H NMR (400 MHz, DMSO-$d_6$/$D_2O$, 90° C.) δ ppm 9.10-9.02 (m, 1H), 8.47 (d, J = 8.6 Hz, 1H), 8.21 (d, J = 9.0 Hz, 1H), 8.16 (d, J = 8.5 Hz, 1H), 7.84 (d, J = 8.8 Hz, 2H), 7.68-7.60 (m, 2H), 7.27 (t, J = 7.7 Hz, 4H), 7.14 (d, J = 7.9 Hz, 2H), 4.55 (s, 2H), 2.28 (s, 3H). | MS (APCI) m/z 394.0 [M + H]⁺ |

| Example Number | Name | ¹H NMR | MS |
|---|---|---|---|
| Example 104 | N-(1,3-benzodioxol-5-ylmethyl)-6-(4-cyanophenoxy)quinoline-2-carboxamide | ¹H NMR (400 MHz, DMSO-$d_6$/$D_2O$, 90° C.) δ ppm 8.47 (d, J = 8.6 Hz, 1H), 8.21 (d, J = 8.9 Hz, 1H), 8.15 (d, J = 8.5 Hz, 1H), 7.87-7.81 (m, 2H), 7.68-7.61 (m, 2H), 7.26 (d, J = 8.8 Hz, 2H), 6.94 (s, 1H), 6.90-6.85 (m, 1H), 6.83 (d, J = 7.9 Hz, 1H), 5.94 (s, 2H), 4.50 (s, 2H). | MS (APCI) m/z 424.1 [M + H]⁺ |
| Example 105 | 6-(4-cyanophenoxy)-N-(2,3-dimethoxybenzyl)quinoline-2-carboxamide | ¹H NMR (400 MHz, DMSO-$d_6$/$D_2O$, 90° C.) δ ppm 8.95-8.87 (m, 1H), 8.48 (d, J = 8.6 Hz, 1H), 8.21 (d, J = 9.0 Hz, 1H), 8.16 (d, J = 8.5 Hz, 1H), 7.87-7.81 (m, 2H), 7.69-7.61 (m, 2H), 7.30-7.22 (m, 2H), 7.06-6.90 (m, 3H), 4.62 (s, 2H), 3.85 (s, 3H), 3.82 (s, 3H). | MS (APCI) m/z 440.1 [M + H]⁺ |
| Example 106 | 4-{[2-(azepan-1-ylcarbonyl)quinolin-6-yl]oxy}benzonitrile | ¹H NMR (400 MHz, DMSO-$d_6$/$D_2O$, 90° C.) δ ppm 8.40 (d, J = 8.6 Hz, 1H), 8.10 (d, J = 9.1 Hz, 1H), 7.86-7.79 (m, 2H), 7.65 (d, J = 2.6 Hz, 1H), 7.63-7.56 (m, 2H), 7.27-7.20 (m, 2H), 3.71-3.61 (m, 2H), 3.49-3.41 (m, 2H), 1.85-1.73 (m, 2H), 1.69-1.58 (m, 6H). | MS (APCI) m/z 372.0 [M + H]⁺ |
| Example 107 | 6-(4-cyanophenoxy)-N-(2-methoxyethyl)-N-propylquinoline-2-carboxamide | ¹H NMR (400 MHz, DMSO-$d_6$/$D_2O$, 90° C.) δ ppm 8.39 (d, J = 8.5 Hz, 1H), 8.11 (d, J = 9.1 Hz, 1H), 7.87-7.80 (m, 2H), 7.67-7.57 (m, 3H), 7.29-7.20 (m, 2H), 3.71-3.07 (m, 9H), 1.78-1.46 (m, 2H), 1.05-0.55 (m, 3H). | MS (APCI) m/z 390.0 [M + H]⁺ |
| Example 108 | 6-(4-cyanophenoxy)-N-(2-ethoxyethyl)quinoline-2-carboxamide | ¹H NMR (400 MHz, DMSO-$d_6$/$D_2O$, 90° C.) δ ppm 8.47 (d, J = 8.5 Hz, 1H), 8.21 (d, J = 8.8 Hz, 1H), 8.15 (d, J = 8.5 Hz, 1H), 7.84 (d, J = 8.8 Hz, 2H), 7.69-7.62 (m, 2H), 7.26 (d, J = 8.8 Hz, 2H), 3.64-3.48 (m, 6H), 1.15 (t, J = 7.0 Hz, 3H). | MS (APCI) m/z 362.0 [M + H]⁺ |
| Example 109 | N-(1-benzylpyrrolidin-3-yl)-6-(4-cyanophenoxy)quinoline-2-carboxamide | ¹H NMR (400 MHz, DMSO-$d_6$/$D_2O$, 90° C.) δ ppm 8.48 (d, J = 8.6 Hz, 1H), 8.23 (d, J = 10.1 Hz, 1H), 8.12 (d, J = 8.5 Hz, 1H), 7.87-7.80 (m, 2H), 7.69-7.63 (m, 2H), 7.58-7.44 (m, 4H), 7.29-7.23 (m, 2H), 4.81-4.70 (m, 1H), 4.45 (s, 2H), 3.74-3.56 (m, 2H), 3.51-3.34 (m, 2H), 2.63-2.53 (m, 1H), 2.28-2.13 (m, 1H). | MS (APCI) m/z 449.1 [M + H]⁺ |
| Example 110 | 4-[(2-{[3-(trifluoromethyl)piperidin-1-yl]carbonyl}quinolin-6-yl)oxy]benzonitrile | ¹H NMR (400 MHz, DMSO-$d_6$/$D_2O$, 90° C.) δ ppm 8.43 (d, J = 8.5 Hz, 1H), 8.11 (d, J = 9.0 Hz, 1H), 7.87-7.81 (m, 2H), 7.72-7.58 (m, 3H), 7.28-7.22 (m, 2H), 4.78-3.49 (m, 2H), 3.22-2.95 (m, 2H), 2.76-2.54 (m, 1H), 2.11-1.97 (m, 1H), 1.97-1.47 (m, 3H). | MS (APCI) m/z 426.1 [M + H]⁺ |
| Example 111 | 4-{[2-(2,3-dihydro-1H-indol-1-ylcarbonyl)quinolin-6-yl]oxy}benzonitrile | ¹H NMR (400 MHz, DMSO-$d_6$/$D_2O$, 90° C.) δ ppm 8.48 (d, J = 8.5 Hz, 1H), 8.17 (d, J = 9.0 Hz, 1H), 7.85 (d, J = 8.8 Hz, 3H), 7.69 (d, J = 2.6 Hz, 1H), 7.64 (dd, J = 9.1, 2.8 Hz, 1H), 7.31 (d, J = 7.5 Hz, 1H), 7.27 (d, J = 8.8 Hz, 2H), 7.19 (s, 1H), 7.13-7.05 (m, 1H), 4.31 (t, J = 8.3 Hz, 2H), 3.16 (t, J = 8.3 Hz, 3H). | MS (APCI) m/z 392.0 [M + H]⁺ |
| Example 112 | 4-{[2-(piperazin-1-ylcarbonyl)quinolin-6-yl]oxy}benzonitrile | ¹H NMR (300 MHz, DMSO-$d_6$) δ ppm 8.45 (d, J = 8.5 Hz, 1H), 8.12 (d, J = 9.1 Hz, 1H), 7.94-7.87 (m, 2H), 7.73 (d, J = 2.6 Hz, 1H), 7.69-7.62 (m, 2H), 7.30-7.22 (m, 2H), 3.66-3.57 (m, 2H), 3.36-3.32 (m, 2H), 2.83-2.75 (m, 2H), 2.71-2.62 (m, 2H). | MS (ESI) m/z 359.4 [M + H]⁺ |
| Example 113 | 6-(4-cyanophenoxy)-N-[(3R)-2-oxotetrahydrofuran-3-yl]quinoline-2-carboxamide | ¹H NMR (501 MHz, DMSO-$d_6$) δ ppm 9.46 (d, J = 8.5 Hz, 1H), 8.53 (d, J = 8.6 Hz, 1H), 8.22 (d, J = 9.0 Hz, 1H), 8.15 (d, J = 8.5 Hz, 1H), 7.94-7.90 (m, 2H), 7.76-7.70 (m, 2H), 7.33-7.28 (m, 2H), 4.91 (dd, J = 18.7, 10.0 Hz, 1H), 4.48-4.40 (m, 1H), 4.35-4.27 (m, 1H), 2.53-2.46 (m, 2H). | MS (ESI) m/z 374.1 [M + H]⁺ |
| Example 114 | 6-(4-cyanophenoxy)-N-(tetrahydrofuran-3-yl)quinoline-2-carboxamide | ¹H NMR (400 MHz, DMSO-$d_6$) δ ppm 8.86 (d, J = 7.3 Hz, 1H), 8.51 (d, J = 8.5 Hz, 1H), 8.24 (d, J = 9.1 Hz, 1H), 8.13 (d, J = 8.5 Hz, 1H), 7.95-7.89 (m, 2H), 7.75-7.67 (m, 2H), 7.33-7.26 (m, 2H), 4.61-4.49 (m, 1H), 3.96-3.83 (m, 3H), 3.79-3.64 (m, 2H), 2.30-2.15 (m, 1H), 2.11-2.00 (m, 1H). | MS (ESI) m/z 360.1 [M + H]⁺ |
| Example 115 | 6-(4-cyanophenoxy)-N-(methylsulfonyl)quinoline-2-carboxamide | ¹H NMR (300 MHz, DMSO-$d_6$) δ ppm 11.92 (s, 1H), 8.46 (d, J = 8.6 Hz, 1H), 8.24 (d, J = 8.9 Hz, 1H), 8.11 (d, J = 8.5 Hz, 1H), 7.95-7.88 (m, 2H), 7.74-7.65 (m, 2H), 7.33-7.26 (m, 2H), 3.21 (s, 3H). | MS (ESI) m/z 368.0 [M + H]⁺ |

| Example Number | Name | ¹H NMR | MS |
|---|---|---|---|
| Example 116 | 6-(4-cyanophenoxy)-N-(tetrahydro-2H-pyran-3-yl)quinoline-2-carboxamide | ¹H NMR (400 MHz, DMSO-d$_6$) δ ppm 8.65 (d, J = 8.5 Hz, 1H), 8.51 (d, J = 8.5 Hz, 1H), 8.24 (d, J = 9.1 Hz, 1H), 8.15 (d, J = 8.5 Hz, 1H), 7.98-7.86 (m, 2H), 7.78-7.64 (m, 2H), 7.36-7.23 (m, 2H), 4.10-3.92 (m, 1H), 3.80 (dd, J = 10.8, 3.0 Hz, 1H), 3.76-3.69 (m, 1H), 3.50-3.37 (m, 2H), 2.03-1.87 (m, 1H), 1.86-1.67 (m, 2H), 1.67-1.50 (m, 1H). | MS (ESI) m/z 374.1 [M + H]⁺ |
| Example 117 | 6-(4-cyanophenoxy)-N-[(3R)-tetrahydrofuran-3-yl]quinoline-2-carboxamide | ¹H NMR (400 MHz, DMSO-d$_6$) δ ppm 8.85 (d, J = 7.3 Hz, 1H), 8.51 (d, J = 8.5 Hz, 1H), 8.24 (d, J = 9.1 Hz, 1H), 8.13 (d, J = 8.5 Hz, 1H), 7.98-7.86 (m, 2H), 7.78-7.64 (m, 2H), 7.35-7.23 (m, 2H), 4.63-4.47 (m, 1H), 3.96-3.85 (m, 2H), 3.75 (td, J = 8.2, 6.1 Hz, 1H), 3.69 (dd, J = 8.9, 4.5 Hz, 1H), 2.31-2.14 (m, 1H), 2.10-2.00 (m, 1H). | MS (ESI) m/z 360.1 [M + H]⁺ |
| Example 118 | 6-(4-cyanophenoxy)-N-[(3S)-tetrahydrofuran-3-yl]quinoline-2-carboxamide | ¹H NMR (400 MHz, DMSO-d$_6$) δ ppm 8.85 (d, J = 7.3 Hz, 1H), 8.51 (d, J = 8.5 Hz, 1H), 8.24 (d, J = 9.1 Hz, 1H), 8.13 (d, J = 8.5 Hz, 1H), 7.98-7.86 (m, 2H), 7.78-7.64 (m, 2H), 7.35-7.23 (m, 2H), 4.63-4.47 (m, 1H), 3.96-3.85 (m, 2H), 3.75 (td, J = 8.2, 6.1 Hz, 1H), 3.69 (dd, J = 8.9, 4.5 Hz, 1H), 2.31-2.14 (m, 1H), 2.10-2.00 (m, 1H). | MS (ESI) m/z 360.1 [M + H]⁺ |
| Example 119 | 6-(4-cyanophenoxy)-N-[(1R,2S)-2-hydroxycyclohexyl]quinoline-2-carboxamide | 1H NMR (500 MHz, DMSO-d$_6$/D$_2$O) δ ppm 8.55-8.49 (m, 2H), 8.24 (d, J = 9.1 Hz, 1H), 8.18 (d, J = 8.5 Hz, 1H), 7.94-7.88 (m, 2H), 7.76-7.66 (m, 2H), 7.33-7.25 (m, 2H), 3.97-3.85 (m, 2H), 1.82-1.50 (m, 6H), 1.42-1.31 (m, 2H). | MS (APCI) m/z 388.0 [M + H]⁺ |
| Example 120 | 6-(4-cyanophenoxy)-N-[(1S,2S)-2-hydroxycyclohexyl]quinoline-2-carboxamide | ¹H NMR (500 MHz, DMSO-d$_6$/D$_2$O) δ ppm 8.62 (d, J = 8.3 Hz, 1H), 8.51 (d, J = 8.6 Hz, 1H), 8.27 (d, J = 9.0 Hz, 1H), 8.16 (d, J = 8.6 Hz, 1H), 7.93-7.88 (m, 2H), 7.75-7.66 (m, 2H), 7.32-7.25 (m, 2H), 3.72-3.61 (m, 1H), 3.58-3.48 (m, 1H), 2.01-1.90 (m, 2H), 1.72-1.60 (m, 2H), 1.43-1.33 (m, 1H), 1.33-1.20 (m, 3H). | MS (APCI) m/z 388.0 [M + H]⁺ |
| Example 121 | 6-(4-cyanophenoxy)-N-[(1S,2S)-2-hydroxycyclopentyl]quinoline-2-carboxamide | ¹H NMR (500 MHz, DMSO-d$_6$/D$_2$O) δ ppm 8.51 (d, J = 8.6 Hz, 1H), 8.27 (d, J = 9.0 Hz, 1H), 8.15 (d, J = 8.5 Hz, 1H), 7.91 (d, J = 8.8 Hz, 2H), 7.75-7.66 (m, 2H), 7.29 (d, J = 8.8 Hz, 2H), 4.16-4.01 (m, 2H), 2.12-2.02 (m, 1H), 1.97-1.89 (m, 1H), 1.76-1.67 (m, 2H), 1.64-1.48 (m, 2H). | MS (APCI) m/z 374.0 [M + H]⁺ |
| Example 122 | 6-(4-cyanophenoxy)-N-(2-hydroxy-2-methylpropyl)quinoline-2-carboxamide | ¹H NMR (500 MHz, DMSO-d$_6$/D$_2$O) δ ppm 8.54 (d, J = 8.6 Hz, 1H), 8.26 (d, J = 9.1 Hz, 1H), 8.19 (d, J = 8.5 Hz, 1H), 7.94-7.87 (m, 2H), 7.74 (d, J = 2.7 Hz, 1H), 7.71 (dd, J = 9.1, 2.7 Hz, 1H), 7.32-7.26 (m, 2H), 3.38 (s, 2H), 1.17 (s, 6H). | MS (APCI) m/z 362.0 [M + H]⁺ |
| Example 123 | 6-(4-cyanophenoxy)-N-[1-(hydroxymethyl)cyclopropyl]quinoline-2-carboxamide | ¹H NMR (500 MHz, DMSO-d$_6$/D$_2$O) δ ppm 8.51 (d, J = 8.5 Hz, 1H), 8.25 (d, J = 8.9 Hz, 1H), 8.14 (d, J = 8.5 Hz, 1H), 7.95-7.87 (m, 2H), 7.74-7.66 (m, 2H), 7.32-7.24 (m, 2H), 3.57 (s, 2H), 0.85 (s, 4H). | MS (APCI) m/z 360.0 [M + H]⁺ |
| Example 124 | 6-(4-cyanophenoxy)-N-(1-hydroxy-2-methylpropan-2-yl)quinoline-2-carboxamide | ¹H NMR (500 MHz, DMSO-d$_6$/D$_2$O) δ ppm 8.52 (d, J = 8.6 Hz, 1H), 8.22 (d, J = 9.0 Hz, 1H), 8.16 (d, J = 8.5 Hz, 1H), 7.95-7.88 (m, 2H), 7.73-7.67 (m, 2H), 7.32-7.25 (m, 2H), 3.54 (s, 2H), 1.41 (s, 6H). | MS (APCI) m/z 362.0 [M + H]⁺ |
| Example 125 | 6-(4-cyanophenoxy)-N-(trans-4-hydroxycyclohexyl)quinoline-2-carboxamide | ¹H NMR (500 MHz, DMSO-d$_6$/D$_2$O) δ ppm 8.50 (d, J = 8.6 Hz, 1H), 8.26 (d, J = 9.0 Hz, 1H), 8.14 (d, J = 8.5 Hz, 1H), 7.95-7.86 (m, 2H), 7.75-7.62 (m, 2H), 7.28 (d, J = 8.8 Hz, 2H), 3.84-3.77 (m, 1H), 3.52-3.40 (m, 1H), 1.95-1.80 (m, 4H), 1.59-1.44 (m, 2H), 1.37-1.22 (m, 2H). | MS (APCI) m/z 388.0 [M + H]⁺ |
| Example 126 | 6-(4-cyanophenoxy)-N-(1,3-dihydroxypropan-2-yl)quinoline-2-carboxamide | ¹H NMR (500 MHz, DMSO-d$_6$/D$_2$O) δ ppm 8.53 (d, J = 8.6 Hz, 1H), 8.25 (d, J = 9.0 Hz, 1H), 8.18 (d, J = 8.5 Hz, 1H), 7.94-7.88 (m, 2H), 7.76-7.67 (m, 2H), 7.32-7.26 (m, 2H), 4.08-3.99 (m, 1H), 3.69-3.55 (m, 4H). | MS (APCI) m/z 364.0 [M + H]⁺ |

| Example Number | Name | ¹H NMR | MS |
|---|---|---|---|
| Example 127 | 6-(4-cyanophenoxy)-N-(1-hydroxypropan-2-yl)quinoline-2-carboxamide | ¹H NMR (500 MHz, DMSO-$d_6$/$D_2O$) δ ppm 8.52 (d, J = 8.6 Hz, 1H), 8.26 (d, J = 9.0 Hz, 1H), 8.16 (d, J = 8.5 Hz, 1H), 7.94-7.87 (m, 2H), 7.75-7.66 (m, 2H), 7.33-7.25 (m, 2H), 4.17-4.04 (m, 1H), 3.60-3.46 (m, 2H), 1.23 (d, J = 6.7 Hz, 3H). | MS (APCI) m/z 348.0 [M + H]⁺ |
| Example 128 | 6-(4-cyanophenoxy)-N-(2-hydroxypropyl)quinoline-2-carboxamide | ¹H NMR (500 MHz, DMSO-$d_6$/$D_2O$) δ ppm 8.52 (d, J = 8.5 Hz, 1H), 8.25 (d, J = 9.1 Hz, 1H), 8.17 (d, J = 8.5 Hz, 1H), 7.94-7.88 (m, 2H), 7.72 (dd, J = 11.8, 5.8 Hz, 2H), 7.33-7.26 (m, 2H), 3.91-3.83 (m, 1H), 3.43 (dd, J = 13.2, 4.8 Hz, 1H), 3.29 (dd, J = 13.2, 7.0 Hz, 1H), 1.12 (d, J = 6.2 Hz, 3H). | MS (APCI) m/z 348.0 [M + H]⁺ |
| Example 129 | 6-(4-cyanophenoxy)-N-[(1S,3R)-3-hydroxycyclohexyl]quinoline-2-carboxamide | ¹H NMR (500 MHz, DMSO-$d_6$/$D_2O$) δ ppm 8.51 (d, J = 8.5 Hz, 1H), 8.25 (d, J = 9.0 Hz, 1H), 8.15 (d, J = 8.5 Hz, 1H), 7.91 (d, J = 8.8 Hz, 2H), 7.74-7.67 (m, 2H), 7.28 (d, J = 8.8 Hz, 2H), 4.00-3.84 (m, 1H), 3.65-3.51 (m, 1H), 2.08-1.97 (m, 1H), 1.85-1.71 (m, 3H), 1.52-1.36 (m, 2H), 1.36-1.25 (m, 1H), 1.25-1.14 (m, 1H) | MS (APCI) m/z 388.0 [M + H]⁺ |
| Example 130 | 6-(4-cyanophenoxy)-N-[(1S,3R)-3-hydroxycyclopentyl]quinoline-2-carboxamide | ¹H NMR (500 MHz, DMSO-$d_6$/$D_2O$) δ ppm 8.51 (d, J = 8.5 Hz, 1H), 8.21 (d, J = 9.1 Hz, 1H), 8.15 (d, J = 8.5 Hz, 1H), 7.93-7.88 (m, 2H), 7.75-7.66 (m, 2H), 7.32-7.24 (m, 2H), 4.45-4.38 (m, 1H), 4.28-4.21 (m, 1H), 2.15-2.07 (m, 1H), 2.06-1.94 (m, 1H), 1.84-1.69 (m, 3H), 1.68-1.61 (m, 1H). | MS (APCI) m/z 374.0 [M + H]⁺ |
| Example 131 | 6-(4-cyanophenoxy)-N-[(1R,2S)-2-hydroxycyclopentyl]quinoline-2-carboxamide | ¹H NMR (500 MHz, DMSO-$d_6$/$D_2O$) δ ppm 8.52 (d, J = 7.3 Hz, 1H), 8.23 (d, J = 9.1 Hz, 1H), 8.18 (d, J = 8.5 Hz, 1H), 7.94-7.88 (m, 2H), 7.75-7.67 (m, 2H), 7.32-7.26 (m, 2H), 4.14-4.08 (m, 2H), 2.06-1.96 (m, 1H), 1.95-1.76 (m, 2H), 1.72-1.51 (m, 3H). | MS (APCI) m/z 374.0 [M + H]⁺ |
| Example 132 | 6-(4-cyanophenoxy)-N-[(1S,3S)-3-hydroxycyclohexyl]quinoline-2-carboxamide | ¹H NMR (500 MHz, DMSO-$d_6$/$D_2O$) δ ppm 8.51 (d, J = 8.6 Hz, 1H), 8.27 (d, J = 9.1 Hz, 1H), 8.15 (d, J = 8.5 Hz, 1H), 7.94-7.88 (m, 2H), 7.75-7.66 (m, 2H), 7.33-7.22 (m, 2H), 4.32-4.21 (m, 1H), 4.01 (s, 1H), 1.87-1.77 (m, 2H), 1.77-1.68 (m, 2H), 1.63-1.36 (m, 4H) | MS (APCI) m/z 388.0 [M + H]⁺ |
| Example 133 | 6-(4-cyanophenoxy)-N-(cis-4-hydroxycyclohexyl)quinoline-2-carboxamide | ¹H NMR (500 MHz, DMSO-$d_6$/$D_2O$) δ ppm 8.51 (d, J = 8.6 Hz, 1H), 8.28 (d, J = 9.0 Hz, 1H), 8.15 (d, J = 8.5 Hz, 1H), 7.94-7.88 (m, 2H), 7.74-7.68 (m, 2H), 7.31-7.26 (m, 2H), 3.89 (t, J = 9.4 Hz, 1H), 3.81-3.76 (m, 1H), 1.89-1.77 (m, 2H), 1.73-1.53 (m, 6H). | MS (APCI) m/z 388.0 [M + H]⁺ |
| Example 134 | 6-(4-cyanophenoxy)-N-(3-hydroxybutan-2-yl)quinoline-2-carboxamide | ¹H NMR (500 MHz, DMSO-$d_6$/$D_2O$, 90° C.) δ ppm 8.52 (d, J = 8.5 Hz, 1H), 8.26 (d, J = 9.1 Hz, 1H), 8.17 (d, J = 8.5 Hz, 1H), 7.94-7.88 (m, 2H), 7.74-7.68 (m, 2H), 7.32-7.24 (m, 2H), 4.01-3.88 (m, 1H), 3.82-3.76 (m, 1H), 1.19 (d, J = 6.7 Hz, 3H), 1.13 (d, J = 6.4 Hz, 3H). | MS (APCI) m/z 362.0 [M + H]⁺ |
| Example 135 | 6-(4-cyanophenoxy)-N-(2-hydroxy-3-methylbutyl)quinoline-2-carboxamide | ¹H NMR (500 MHz, DMSO-$d_6$/$D_2O$) δ ppm 8.53 (d, J = 8.6 Hz, 1H), 8.24 (d, J = 9.1 Hz, 1H), 8.17 (d, J = 8.5 Hz, 1H), 7.91 (dd, J = 9.1, 2.3 Hz, 2H), 7.79-7.66 (m, 2H), 7.34-7.24 (m, 2H), 3.57 (dd, J = 13.4, 3.9 Hz, 1H), 3.50-3.41 (m, 1H), 3.26 (dd, J = 13.4, 7.9 Hz, 1H), 1.77-1.57 (m, 1H), 0.99-0.85 (m, 6H). | MS (APCI) m/z 376.0 [M + H]⁺ |
| Example 136 | 6-(4-cyanophenoxy)-N-(1,1-dioxidotetrahydrothiophen-3-yl)quinoline-2-carboxamide | ¹H NMR (300 MHz, DMSO-$d_6$) δ ppm 9.28 (d, J = 8.2 Hz, 1H), 8.52 (d, J = 8.3 Hz, 1H), 8.23 (d, J = 8.9 Hz, 1H), 8.15 (d, J = 8.5 Hz, 1H), 8.00-7.84 (m, 2H), 7.80-7.64 (m, 2H), 7.38-7.22 (m, 2H), 4.90-4.71 (m, 1H), 3.55-3.15 (m, 4H), 2.48-2.25 (m, 2H). | MS (ESI) m/z 408.1 [M + H]⁺ |
| Example 137 | 4-({2-[(3-oxopiperazin-1-yl)carbonyl]quinolin-6-yl}oxy)benzonitrile | ¹H NMR (300 MHz, DMSO-$d_6$) δ ppm 8.48 (d, J = 8.5 Hz, 1H), 8.22-8.07 (m, 2H), 7.99-7.82 (m, 2H), 7.79-7.73 (m, 2H), 7.68 (dd, J = 9.1, 2.7 Hz, 1H), 7.36-7.19 (m, 2H), 4.26-4.12 (m, 2H), 3.95-3.81 (m, 1H), 3.81-3.66 (m, 1H), 3.36-3.26 (m, 2H). | MS (ESI) m/z 373.1 [M + H]⁺ |

| Example Number | Name | ¹H NMR | MS |
|---|---|---|---|
| Example 138 | 4-[(2-{[4-(morpholin-4-yl)piperidin-1-yl]carbonyl}quinolin-6-yl)oxy]benzonitrile | ¹H NMR (300 MHz, DMSO-d₆) δ ppm 8.45 (d, J = 8.4 Hz, 1H), 8.12 (d, J = 9.1 Hz, 1H), 7.94-7.86 (m, 2H), 7.73 (d, J = 2.7 Hz, 1H), 7.70-7.62 (m, 2H), 7.31-7.22 (m, 2H), 4.52 (d, J = 12.3 Hz, 1H), 3.73 (d, J = 13.8 Hz, 1H), 3.61-3.51 (m, 4H), 3.15-3.01 (m, 1H), 2.98-2.83 (m, 1H), 2.49-2.41 (m, 5H), 1.92 (d, J = 12.3 Hz, 1H), 1.73 (d, J = 12.0 Hz, 1H), 1.43 (qd, J = 11.9, 4.0 Hz, 2H). | MS (ESI) m/z 443.1 [M + H]⁺ |
| Example 139 | 6-(4-cyanophenoxy)-N-[(4R)-6-fluoro-3,4-dihydro-2H-chromen-4-yl]quinoline-2-carboxamide | ¹H NMR (300 MHz, DMSO-d₆) δ ppm 9.26 (d, J = 8.8 Hz, 1H), 8.54 (d, J = 8.5 Hz, 1H), 8.21 (dd, J = 8.8, 3.4 Hz, 2H), 8.00-7.84 (m, 2H), 7.75 (d, J = 2.7 Hz, 1H), 7.69 (dd, J = 9.1, 2.7 Hz, 1H), 7.32-7.25 (m, 2H), 7.07-6.94 (m, 2H), 6.84 (dd, J = 8.9, 4.9 Hz, 1H), 5.45-5.27 (m, 1H), 4.44-4.16 (m, 2H), 2.33-2.07 (m, 2H). | MS (ESI) m/z 440.0 [M + H]⁺ |
| Example 140 | 4-({2-[(4-tert-butylpiperazin-1-yl)carbonyl]quinolin-6-yl}oxy)benzonitrile | ¹H NMR (300 MHz, DMSO-d₆) δ ppm 8.45 (d, J = 8.4 Hz, 1H), 8.13 (d, J = 9.1 Hz, 1H), 7.93-7.87 (m, 2H), 7.73 (d, J = 2.7 Hz, 1H), 7.71-7.62 (m, 2H), 7.30-7.22 (m, 2H), 3.71-3.62 (m, 2H), 3.45-3.37 (m, 2H), 2.65-2.55 (m, 2H), 2.48-2.45 (m, 2H), 1.02 (s, 9H). | MS (ESI) m/z 415.0 [M + H]⁺ |
| Example 141 | 6-(4-cyanophenoxy)-N-[(4R)-6-fluoro-2,2-dimethyl-3,4-dihydro-2H-chromen-4-yl]quinoline-2-carboxamide | ¹H NMR (300 MHz, DMSO-d₆) δ ppm 9.26 (d, J = 9.0 Hz, 1H), 8.55 (d, J = 8.4 Hz, 1H), 8.21 (t, J = 9.1 Hz, 2H), 7.96-7.86 (m, 2H), 7.79-7.64 (m, 2H), 7.33-7.25 (m, 2H), 7.00 (td, J = 8.5, 3.1 Hz, 1H), 6.93 (dd, J = 9.4, 3.1 Hz, 1H), 6.80 (dd, J = 8.9, 4.9 Hz, 1H), 5.44-5.30 (m, 1H), 2.26-2.14 (m, 1H), 2.09 (dd, J = 13.1, 6.7 Hz, 1H), 1.43 (s, 3H), 1.32 (s, 3H). | MS (ESI) m/z 467.9 [M + H]⁺ |
| Example 142 | 4-[(2-{[(3S)-3-isopropylpiperazin-1-yl]carbonyl}quinolin-6-yl)oxy]benzonitrile | ¹H NMR (300 MHz, DMSO-d₆, rotamers) δ ppm 8.45 (d, J = 8.5 Hz, 1H), 8.11 (dd, J = 9.1, 3.3 Hz, 1H), 7.99-7.82 (m, 2H), 7.79-7.58 (m, 3H), 7.36-7.18 (m, 2H), 4.41 (dd, J = 25.9, 12.3 Hz, 1H), 3.81 (d, J = 12.3 Hz, 0.5H), 3.55 (d, J = 13.2 Hz, 0.5H), 3.16-2.95 (m, 1H), 2.89-2.54 (m, 3H), 2.47-2.19 (m, 2H), 1.71-1.56 (m, 0.5H), 1.55-1.40 (m, 0.5H), 0.96 (d, J = 6.8 Hz, 3H), 0.82 (d, J = 6.8 Hz, 1.5H), 0.70 (d, J = 6.8 Hz, 1.5H). | MS (ESI) m/z 401.1 [M + H]⁺ |
| Example 143 | 6-(4-cyanophenoxy)-N-(1-methyl-2-oxopyrrolidin-3-yl)quinoline-2-carboxamide | ¹H NMR (300 MHz, DMSO-d₆) δ ppm 9.15 (d, J = 8.4 Hz, 1H), 8.53 (d, J = 8.4 Hz, 1H), 8.21 (d, J = 9.0 Hz, 1H), 8.15 (d, J = 8.5 Hz, 1H), 8.00-7.84 (m, 2H), 7.81-7.64 (m, 2H), 7.39-7.23 (m, 2H), 4.64 (q, J = 9.1 Hz, 1H), 3.41-3.33 (m, 2H), 2.80 (s, 3H), 2.45-2.30 (m, 1H), 2.18-2.03 (m, 1H). | MS (ESI) m/z 387.1 [M + H]⁺ |
| Example 144 | 6-(4-cyanophenoxy)-N-(1,3-oxazol-2-ylmethyl)quinoline-2-carboxamide | ¹H NMR (300 MHz, DMSO-d₆) δ ppm 9.51 (t, J = 6.1 Hz, 1H), 8.53 (d, J = 8.7 Hz, 1H), 8.22 (d, J = 9.0 Hz, 1H), 8.16 (d, J = 8.5 Hz, 1H), 8.05 (d, J = 0.7 Hz, 1H), 8.00-7.84 (m, 2H), 7.82-7.65 (m, 2H), 7.39-7.23 (m, 2H), 7.17 (d, J = 0.7 Hz, 1H), 4.68 (d, J = 6.1 Hz, 2H). | MS (ESI) m/z 371.0 [M + H]⁺ |
| Example 145 | 6-(4-cyanophenoxy)-N-[2-(methylamino)-2-oxoethyl]quinoline-2-carboxamide | ¹H NMR (400 MHz, DMSO-d₆) δ ppm 9.05 (t, J = 5.9 Hz, 1H), 8.52 (d, J = 8.5 Hz, 1H), 8.22 (d, J = 9.1 Hz, 1H), 8.16 (d, J = 8.5 Hz, 1H), 7.98-7.86 (m, 3H), 7.80-7.66 (m, 2H), 7.36-7.24 (m, 2H), 3.97 (d, J = 5.9 Hz, 2H), 2.62 (d, J = 4.6 Hz, 3H). | MS (ESI) m/z 360.9 [M + H]⁺ |
| Example 146 | N-(2-amino-2-oxoethyl)-6-(4-cyanophenoxy)quinoline-2-carboxamide | ¹H NMR (300 MHz, DMSO-d₆) δ ppm 8.95 (t, J = 5.8 Hz, 1H), 8.53 (d, J = 8.5 Hz, 1H), 8.22 (d, J = 9.1 Hz, 1H), 8.16 (d, J = 8.5 Hz, 1H), 8.00-7.84 (m, 2H), 7.81-7.64 (m, 2H), 7.48 (s, 1H), 7.38-7.22 (m, 2H), 7.13 (s, 1H), 3.96 (d, J = 5.8 Hz, 2H). | MS (ESI) m/z 347.0 [M + H]⁺ |
| Example 147 | 6-(4-cyanophenoxy)-N-(2-sulfamoylethyl)quinoline-2-carboxamide | ¹H NMR (300 MHz, DMSO-d₆) δ ppm 9.15 (t, J = 6.1 Hz, 1H), 8.52 (d, J = 8.5 Hz, 1H), 8.25-8.09 (m, 2H), 8.00-7.84 (m, 2H), 7.81-7.63 (m, 2H), 7.38-7.22 (m, 2H), 7.00 (s, 2H), 3.79 (dd, J = 13.7, 6.3 Hz, 2H), 3.35-3.27 (m, 2H). | MS (ESI) m/z 397.1 [M + H]⁺ |

| Example Number | Name | ¹H NMR | MS |
|---|---|---|---|
| Example 148 | 4-({2-[(1,1-dioxidothiomorpholin-4-yl)carbonyl]quinolin-6-yl}oxy)benzonitrile | ¹H NMR (300 MHz, DMSO-$d_6$) δ ppm 8.50 (d, J = 8.4 Hz, 1H), 8.16 (d, J = 9.0 Hz, 1H), 7.94-7.87 (m, 2H), 7.82 (d, J = 8.5 Hz, 1H), 7.74 (d, J = 2.7 Hz, 1H), 7.68 (dd, J = 9.1, 2.7 Hz, 1H), 7.31-7.22 (m, 2H), 4.15-4.07 (m, 2H), 3.96-3.88 (m, 2H), 3.39-3.27 (m, 4H). | MS (ESI) m/z 408.1 [M + H]⁺ |
| Example 149 | N-(tetrahydrofuran-3-yl)-6-{[5-(trifluoromethyl)pyridin-2-yl]oxy}quinoline-2-carboxamide | ¹H NMR (300 MHz, DMSO-$d_6$) δ ppm 8.86 (d, J = 7.3 Hz, 1H), 8.65-8.57 (m, 1H), 8.53 (d, J = 8.4 Hz, 1H), 8.31 (dd, J = 8.7, 2.5 Hz, 1H), 8.23 (d, J = 9.2 Hz, 1H), 8.16 (d, J = 8.5 Hz, 1H), 7.92 (d, J = 2.6 Hz, 1H), 7.76 (dd, J = 9.2, 2.7 Hz, 1H), 7.40 (d, J = 8.7 Hz, 1H), 4.63-4.48 (m, 1H), 3.99-3.85 (m, 2H), 3.77 (dt, = J 8.2, 4.1 Hz, 1H), 3.70 (dd, J = 8.8, 4.5 Hz, 1H), 2.31-2.16 (m, 1H), 2.13-1.96 (m, 1H). | MS (ESI⁺) m/z 404 (M + H)⁺ |
| Example 150 | N-(2-amino-2-oxoethyl)-6-{[5-(trifluoromethyl)pyridin-2-yl]oxy}quinoline-2-carboxamide | ¹H NMR (300 MHz, DMSO-$d_6$) δ ppm 8.96 (t, J = 5.7 Hz, 1H), 8.65-8.60 (m, 1H), 8.55 (d, J = 8.5 Hz, 1H), 8.31 (dd, J = 8.5, 2.7 Hz, 1H), 8.21 (d, J = 6.7 Hz, 1H), 8.18 (d, J = 6.1 Hz, 1H), 7.94 (d, J = 2.6 Hz, 1H), 7.77 (dd, J = 9.1, 2.7 Hz, 1H), 7.49 (s, 1H), 7.41 (d, J = 8.7 Hz, 1H), 7.14 (s, 1H), 3.97 (d, J = 5.8 Hz, 2H). | MS (ESI⁺) m/z 391 (M + H)⁺, 389 (M − H)+ |
| Example 151 | N-(pyridin-2-ylmethyl)-6-{[5-(trifluoromethyl)pyridin-2-yl]oxy}quinoline-2-carboxamide | ¹H NMR (300 MHz, DMSO-$d_6$) δ ppm 9.52 (t, J = 6.1 Hz, 1H), 8.65-8.51 (m, 3H), 8.36-8.27 (m, 1H), 8.21 (dd, J = 8.8, 4.6 Hz, 2H), 7.95 (d, J = 2.6 Hz, 1H), 7.83-7.71 (m, 2H), 7.46-7.35 (m, 2H), 7.33-7.23 (m, 1H), 4.70 (d, J = 6.1 Hz, 2H) | MS (ESI+) m/z 425 (M + H)⁺ |
| Example 152 | piperazin-1-yl(6-{[4-(trifluoromethyl)pyridin-2-yl]oxy}quinolin-2-yl)methanone | ¹H NMR (300 MHz, DMSCW₆) δ ppm 8.46 (d, J = 8.4 Hz, 1H), 8.42 (d, J = 5.3 Hz, 1H), 8.10 (d, J = 9.1 Hz, 1H), 7.86 (d, J = 2.6 Hz, 1H), 7.73-7.64 (m, 2H), 7.62 (s, 1H), 7.58-7.52 (m, 1H), 3.68-3.58 (m, 2H), 3.39-3.32 (m, 2H), 2.84-2.76 (m, 2H), 2.71-2.64 (m, 2H) | MS (ESI⁺) m/z 403 (M + H)⁺ |
| Example 153 | piperazin-1-yl(6-{[6-(trifluoromethyl)pyridin-2-yl]oxy}quinolin-2-yl)methanone | ¹H NMR (300 MHz, DMSO-$d_6$) δ ppm 8.46 (d, J = 8.3 Hz, 1H), 8.23-8.14 (m, 1H), 8.10 (d, J = 9.1 Hz, 1H), 7.86 (d, J = 2.6 Hz, 1H), 7.74-7.64 (m, 3H), 7.48 (d, J = 8.3 Hz, 1H), 3.68-3.58 (m, 2H), 3.39-3.33 (m, 2H), 2.84-2.75 (m, 2H), 2.71-2.63 (m, 2H), 2.45 (s, 1H) | MS (ESI⁺) m/z 403 (M + H)⁺ |
| Example 154 | 6-{[3-chloro-5-(trifluoromethyl)pyridin-2-yl]oxy}-N-(1,1-dioxidotetrahydrothiophen-3-yl)quinoline-2-carboxamide | ¹H NMR (300 MHz, DMSO-$d_6$) δ ppm 9.30 (d, J = 8.1 Hz, 1H), 8.67-8.63 (m, 1H), 8.59-8.51 (m, 2H), 8.23 (d, J = 9.2 Hz, 1H), 8.19 (d, J = 8.5 Hz, 1H), 7.99 (d, J = 2.6 Hz, 1H), 7.82 (dd, J = 9.2, 2.7 Hz, 1H), 4.90-4.73 (m, 1H), 3.56-3.33 (m, 3H), 3.26-3.17 (m, 1H), 2.47-2.24 (m, 2H). | MS (ESI) m/z 486.1 [M + H]⁺ |
| Example 155 | N-(1,1-dioxidotetrahydrothiophen-3-yl)-6-{[5-(trifluoromethyl)pyrimidin-2-yl]oxy}quinoline-2-carboxamide | ¹H NMR (300 MHz, DMSO-$d_6$) δ ppm 9.31 (d, J = 8.2 Hz, 1H), 9.19-9.15 (m, 2H), 8.56 (d, J = 8.5 Hz, 1H), 8.23 (d, J = 9.2 Hz, 1H), 8.19 (d, J = 8.5 Hz, 1H), 8.03 (d, J = 2.6 Hz, 1H), 7.85 (dd, J = 9.2, 2.7 Hz, 1H), 4.91-4.72 (m, 1H), 3.57-3.33 (m, 3H), 3.27-3.15 (m, 1H), 2.46-2.23 (m, 2H). | MS (ESI) m/z 453.1 [M + H]⁺ |
| Example 156 | 2-oxa-6-azaspiro[3.3]hept-6-yl(6-{[5-(trifluoromethyl)pyridin-2-yl]oxy}quinolin-2-yl)methanone | ¹H NMR (300 MHz, DMSO-$d_6$) δ ppm 8.62-8.58 (m, 1H), 8.48 (d, J = 8.6 Hz, 1H), 8.31 (dd, J = 8.7, 2.5 Hz, 1H), 8.17 (d, J = 9.1 Hz, 1H), 8.04 (d, J = 8.6 Hz, 1H), 7.89 (d, J = 2.6 Hz, 1H), 7.74 (dd, J = 9.1, 2.7 Hz, 1H), 7.40 (d, J = 8.8 Hz, 1H), 4.93 (s, 2H), 4.74 (s, 4H), 4.31 (s, 2H). | MS (ESI) m/z 416.1 [M + H]⁺ |
| Example 157 | 2,6-diazaspiro[3.3]hept-2-yl(6-{[5-(trifluoromethyl)pyridin-2-yl]oxy}quinolin-2-yl)methanone | ¹H NMR (300 MHz, DMSO-$d_6$) δ ppm 8.62-8.57 (m, 1H), 8.47 (d, J = 8.4 Hz, 1H), 8.30 (dd, J = 8.8, 2.7 Hz, 1H), 8.17 (d, J = 9.1 Hz, 1H), 8.04 (d, J = 8.6 Hz, 1H), 7.89 (d, J = 2.6 Hz, 1H), 7.73 (dd, J = 9.1, 2.7 Hz, 1H), 7.40 (d, J = 8.6 Hz, 1H), 4.82 (s, 2H), 4.20 (s, 2H), 3.62 (s, 4H). | MS (ESI) m/z 415.2 [M + H]⁺ |
| Example 158 | 6-[(5-cyanopyridin-2-yl)oxy]-N-(1,1-dioxidotetrahydrothiophen-3-yl)quinoline-2-carboxamide | ¹H NMR (500 MHz, DMSO-$d_6$) δ ppm 9.32 (d, J = 8.1 Hz, 1H), 8.68 (d, J = 2.2 Hz, 1H), 8.55 (d, J = 8.5 Hz, 1H), 8.39 (dd, J = 8.7, 2.3 Hz, 1H), 8.22 (d, J = 9.1 Hz, 1H), 8.18 (d, J = 8.5 Hz, 1H), 7.93 (d, J = 2.6 Hz, 1H), 7.76 (dd, J = 9.1, 2.6 Hz, 1H), 7.40 (d, J = 8.7 Hz, 1H), 4.87-4.75 (m, 1H), 3.51 (dd, J = 13.1, 7.7 Hz, | MS (ESI) m/z 409.1 [M + H]⁺ |

| Example Number | Name | ¹H NMR | MS |
|---|---|---|---|
| | | 1H), 3.44-3.40 (m, 1H), 3.33-3.30 (m, 1H), 3.30-3.17 (m, 1H), 2.49-2.44 (m, 1H), 2.42-2.31 (m, 1H). | |
| Example 159 | 6-(4-cyanophenoxy)-N-[(3S)-1,1-dioxidotetrahydrothiophen-3-yl]quinoline-2-carboxamide | ¹H NMR (300 MHz, DMSO-$d_6$) δ ppm 9.28 (d, J = 8.2 Hz, 1H), 8.52 (d, J = 8.5 Hz, 1H), 8.23 (d, J = 8.8 Hz, 1H), 8.15 (d, J = 8.5 Hz, 1H), 7.96-7.87 (m, 2H), 7.78-7.68 (m, 2H), 7.35-7.27 (m, 2H), 4.89-4.72 (m, 1H), 3.56-3.46 (m, 1H), 3.46-3.35 (m, 1H), 3.28-3.14 (m, 2H), 2.48-2.41 (m, 1H), 2.41-2.24 (m, 1H). | MS (ESI) m/z 408.2 [M + H]⁺ |
| Example 160 | 6-(4-cyanophenoxy)-N-[(3R)-1,1-dioxidotetrahydrothiophen-3-yl]quinoline-2-carboxamide | ¹H NMR (300 MHz, DMSO-$d_6$) δ ppm 9.28 (d, J = 8.2 Hz, 1H), 8.52 (d, J = 8.5 Hz, 1H), 8.23 (d, J = 8.8 Hz, 1H), 8.15 (d, J = 8.5 Hz, 1H), 7.96-7.87 (m, 2H), 7.78-7.68 (m, 2H), 7.35-7.27 (m, 2H), 4.89-4.72 (m, 1H), 3.56-3.46 (m, 1H), 3.46-3.35 (m, 1H), 3.28-3.14 (m, 2H), 2.48-2.41 (m, 1H), 2.41-2.24 (m, 1H). | MS (ESI) m/z 408.2 [M + H]⁺ |
| Example 161 | N-(1,1-dioxidotetrahydrothiophen-3-yl)-6-[(5-methylpyrimidin-2-yl)oxy]quinoline-2-carboxamide | ¹H NMR (300 MHz, DMSO-$d_6$) δ ppm 9.29 (d, J = 8.2 Hz, 1H), 8.58-8.48 (m, 3H), 8.18 (t, J = 8.4 Hz, 2H), 7.89 (d, J = 2.6 Hz, 1H), 7.74 (dd, J = 9.2, 2.7 Hz, 1H), 4.88-4.73 (m, 1H), 3.51 (dd, J = 13.2, 7.7 Hz, 1H), 3.47-3.35 (m, 2H), 3.27-3.16 (m, 1H), 2.48-2.29 (m, 2H), 2.25 (s, 3H). | MS (ESI) m/z 399.2 [M + H]⁺ |
| Example 162 | 6-[(4,6-dimethylpyrimidin-2-yl)oxy]-N-(1,1-dioxidotetrahydrothiophen-3-yl)quinoline-2-carboxamide | ¹H NMR (300 MHz, DMSO-$d_6$) δ ppm 9.28 (d, J = 8.2 Hz, 1H), 8.54 (d, J = 8.5 Hz, 1H), 8.17 (dd, J = 8.8, 6.0 Hz, 2H), 7.88 (d, J = 2.6 Hz, 1H), 7.73 (dd, J = 9.2, 2.6 Hz, 1H), 7.09 (s, 1H), 4.89-4.72 (m, 1H), 3.51 (dd, J = 13.1, 7.7 Hz, 1H), 3.47-3.34 (m, 2H), 3.27-3.18 (m, 1H), 2.48-2.37 (m, 2H), 2.35 (s, 6H). | MS (ESI) m/z 413.1 [M + H]⁺ |
| Example 163 | N-(1,1-dioxidotetrahydrothiophen-3-yl)-6-[(4-methylpyrimidin-2-yl)oxy]quinoline-2-carboxamide | ¹H NMR (400 MHz, DMSO-$d_6$) δ ppm 9.30 (d, J = 8.2 Hz, 1H), 8.54 (d, J = 8.6 Hz, 1H), 8.49 (d, J = 5.0 Hz, 1H), 8.18 (dd, J = 12.3, 8.8 Hz, 2H), 7.90 (d, J = 2.6 Hz, 1H), 7.75 (dd, J = 9.1, 2.6 Hz, 1H), 7.21 (d, J = 5.0 Hz, 1H), 4.88-4.74 (m, 1H), 3.51 (dd, J = 13.2, 7.7 Hz, 1H), 3.45-3.39 (m, 1H), 3.32-3.17 (m, 2H), 2.49-2.44 (m, 1H), 2.42 (s, 3H), 2.40-2.31 (m, 1H). | MS (ESI) m/z 399.1 [M + H]⁺ |
| Example 164 | (3aR,6aS)-hexahydropyrrolo[3,4-c]pyrrol-2(1H)-yl(6-{[5-(trifluoromethyl)pyridin-2-yl]oxy}quinolin-2-yl)methanone | ¹H NMR (300 MHz, DMSO-$d_6$, rotamers) δ ppm 8.62-8.56 (m, 1H), 8.46 (d, J = 8.4 Hz, 1H), 8.33-8.26 (m, 1H), 8.14 (t, J = 9.1 Hz, 1H), 7.88 (d, J = 2.5 Hz, 1H), 7.81 (t, J = 8.7 Hz, 1H), 7.74-7.65 (m, 1H), 7.39 (d, J = 8.8 Hz, 1H), 4.16-3.71 (m, 2.5H), 3.57-3.38 (m, 2.5H), 3.15-3.07 (m, 0.5H), 3.06-2.98 (m, 0.5H), 2.96-2.61 (m, 4H). | MS (ESI) m/z 429.2 [M + H]⁺ |
| Example 165 | 6-[(6-chloropyridazin-3-yl)oxy]-N-(1,1-dioxidotetrahydrothiophen-3-yl)quinoline-2-carboxamide | ¹H NMR (500 MHz, DMSO-$d_6$) δ ppm 9.32 (d, J = 8.1 Hz, 1H), 8.55 (d, J = 8.5 Hz, 1H), 8.23 (d, J = 9.2 Hz, 1H), 8.18 (d, J = 8.5 Hz, 1H), 8.03 (d, J = 9.2 Hz, 1H), 7.95 (d, J = 2.7 Hz, 1H), 7.82 (dd, J = 9.2, 2.7 Hz, 1H), 7.75 (d, J = 9.3 Hz, 1H), 4.86-4.76 (m, 1H), 3.51 (dd, J = 13.2, 7.7 Hz, 1H), 3.46-3.38 (m, 1H), 3.32 (dd, J = 13.2, 8.8 Hz, 1H), 3.27-3.19 (m, 1H), 2.52-2.45 (m, 1H), 2.42-2.31 (m, 1H). | MS (ESI) m/z 419.1 [M + H]⁺ |
| Example 166 | (3aR,6aR)-5-[(6-{[5-(trifluoromethyl)pyridin-2-yl]oxy}quinolin-2-yl)carbonyl]hexahydropyrrolo[3,4-c]pyrrol-1(2H)-one | ¹H NMR (500 MHz, DMSO-$d_6$) δ ppm 8.62-8.55 (m, 1H), 8.47 (dd, J = 8.5, 4.3 Hz, 1H), 8.29 (dd, J = 8.7, 2.5 Hz, 1H), 8.15 (dd, J = 9.1, 2.4 Hz, 1H), 7.89 (dd, J = 5.9, 2.6 Hz, 1H), 7.83 (dd, J = 8.5, 4.5 Hz, 1H), 7.79 (s, 1H), 7.72 (td, J = 8.9, 2.6 Hz, 1H), 7.39 (d, J = 8.8 Hz, 1H), 4.1 1 (dd, J = 12.0, 8.8 Hz, 0.5H), 4.06-3.93 (m, 1.5H), 3.90 (d, J = 11.4 Hz, 0.5H), 3.74 (dd, J = 12.6, 8.2 Hz, 0.5H), 3.57-3.45 (m, 2H), 3.16 (d, J = 10.2 Hz, 0.5H), 3.13-2.97 (m, 2.5H). | MS (ESI) m/z 443.1 [M + H]⁺ |
| Example 167 | (3aR,4R,7S,7aS)-octahydro-1H-4,7-epiminoisoindol-8-yl(6-{[5-(trifluoromethyl)pyridin-2-yl]oxy} | ¹H NMR (500 MHz, DMSO-$d_6$) δ ppm 8.58 (s, 1H), 8.50 (d, J = 8.5 Hz, 0.3H), 8.45 (d, J = 8.5 Hz, 0.7H), 8.32-8.26 (m, 1H), 8.13 (dd, J = 16.1, 9.1 Hz, 1H), 7.93-7.86 (m, 1H), 7.76 (d, J = 8.6 Hz, 1H), 7.70 (dd, J = 9.1, 2.6 Hz, 1H), 7.43-7.36 (m, 1H), 4.00-3.92 (m, 1.5H), | MS (ESI) m/z 455.2 [M + H]⁺ |

| Example Number | Name | ¹H NMR | MS |
|---|---|---|---|
| | yl]oxy}quinolin-2-yl)methanone | 3.33-3.18 (m, 3H), 2.42-2.31 (m, 1.5H), 1.90-1.65 (m, 1H), 1.61-1.39 (m, 2.5H), 1.36-1.10 (m, 2.5H). | |
| Example 168 | N-(1,1-dioxidotetrahydrothiophen-3-yl)-6-{[6-(trifluoromethyl)pyridazin-3-yl]oxy}quinoline-2-carboxamide | ¹H NMR (400 MHz, DMSO-d₆) δ ppm 9.33 (d, J = 8.1 Hz, 1H), 8.58 (d, J = 8.6 Hz, 1H), 8.38 (d, J = 9.2 Hz, 1H), 8.26 (d, J = 9.2 Hz, 1H), 8.20 (d, J = 8.5 Hz, 1H), 8.04 (d, J = 2.6 Hz, 1H), 7.92 (d, J = 9.2 Hz, 1H), 7.88 (dd, J = 9.2, 2.6 Hz, 1H), 4.88-4.73 (m, 1H), 3.52 (dd, J = 13.2, 7.7 Hz, 1H), 3.46-3.38 (m, 1H), 3.37-3.30 (m, 1H), 3.29-3.18 (m, 1H), 2.53-2.44 (m, 1H), 2.44-2.30 (m, 1H). | MS (ESI) m/z 453.0 [M + H]⁺ |
| Example 169 | 8-[(6-{[5-(trifluoromethyl)pyridin-2-yl]oxy}quinolin-2-yl)carbonyl]hexahydro-2H-pyrazino[1,2-a]pyrazin-1(6H)-one | ¹H NMR (400 MHz, DMSO-d₆, rotamers) δ ppm 2.13-2.36 (m, 1H), 2.39-2.54 (m, 1H), 2.60-3.16 (m, 6H), 3.33 (m, 1H), 3.76 (d, J = 14.1 Hz, 0.44H), 4.04 (dd, J = 21.4, 9.8 Hz, 0.6H), 4.44-4.62 (m, 0.6H), 4.93 (d, J = 12.3 Hz, 0.4H), 7.40 (dd, J = 8.7, 3.2 Hz, 1H), 7.64-7.97 (m, 4H), 8.11 (dd, J = 9.1, 4.8 Hz, 1H), 8.30 (dt, J = 8.7, 3.1 Hz, 1H), 8.42-8.54 (m, 1H), 8.54-8.67 (m, 1H) | DCI m/z 472.0 [M + H]⁺ |
| Example 170 | 5,6-dihydro[1,2,4]triazolo[4,3-a]pyrazin-7(8H)-yl(6-{[5-(trifluoromethyl)pyridin-2-yl]oxy}quinolin-2-yl)methanone | ¹H NMR (400 MHz, DMSO-d₆) δ ppm 4.01 (dd, J = 8.6, 3.3 Hz, 1H), 4.11-4.30 (m, 3H), 5.08 (d, J = 13.3 Hz, 2H), 7.41 (d, J = 8.7 Hz, 1H), 7.75 (dd, J = 9.1, 2.6 Hz, 1H), 7.79-7.87 (m, 1H), 7.92 (d, J = 2.6 Hz, 1H), 8.16 (d, J = 9.1 Hz, 1H), 8.31 (dd, J = 8.7, 2.5 Hz, 1H), 8.46-8.69 (m, 3H) | DCI m/z 441.0 [M + H]⁺ |
| Example 171 | 8-[(6-{[5-(trifluoromethyl)pyridin-2-yl]oxy}quinolin-2-yl)carbonyl]tetrahydro-2H-pyrazino[1,2-a]pyrazine-1,4(3H,6H)-dione | ¹H NMR (400 MHz, DMSO-d₆ rotamers) δ ppm 2.92 (m, 2H), 3.10-3.24 (m, 1H), 3.72-4.05 (m, 2.5H), 4.21 (ddd, J = 16.4, 15.9, 11.1 Hz, 2H), 4.47 (m, 0.58), 4.57 (d, J = 12.6 Hz, 0.56H), 4.91 (dd, J = 13.0, 1.9 Hz, 0.46H), 7.40 (dd, J = 8.7, 3.9 Hz, 1H), 7.66-7.84 (m, 2H), 7.92 (dd, J = 7.1, 2.6 Hz, 1H), 8.12 (dd, J = 9.1, 5.4 Hz, 1H), 8.19-8.43 (m, 2H), 8.52 (t, J = 8.3 Hz, 1H), 8.61 (d, J = 9.6 Hz, 1H) | DCI m/z 486.0 [M + H]⁺ |
| Example 172 | 4-[(6-{[5-(trifluoromethyl)pyridin-2-yl]oxy}quinolin-2-yl)carbonyl]piperazin-2-one | ¹H NMR (400 MHz, DMSO-d₆, rotamers) δ ppm, 3.34 (m, 2H), 3.69-3.80 (m, 1H), 3.89 (t, J = 5.4 Hz, 1H), 4.21 (d, J = 5.7 Hz, 2H), 7.40 (d, J = 8.7 Hz, 1H), 7.67-7.84 (m, 2H), 7.90 (d, J = 2.2 Hz, 1H), 8.08-8.20 (m, 2H), 8.30 (dd, J = 8.7, 2.2 Hz, 1H), 8.46-8.63 (m, 2H) | DCI m/z 417.0 [M + H]⁺ |
| Example 173 | 5,6-dihydroimidazo[1,5-a]pyrazin-7(8H)-yl(6-{[5-(trifluoromethyl)pyridin-2-yl]oxy}quinolin-2-yl)methanone | ¹H NMR (300 MHz, DMSO-d₆, rotamers) δ ppm 3.85-4.26 (m, 4H), 4.90 (d, J = 17.4 Hz, 2H), 6.75 (d, J = 63.7 Hz, 1H), 7.41 (d, J = 8.7 Hz, 1H), 7.47-7.85 (m, 3H), 7.92 (d, J = 2.6 Hz, 1H), 8.15 (d, J = 9.1 Hz, 1H), 8.32 (dd, J = 8.8, 2.6 Hz, 1H), 8.42-8.73 (m, 2H) | DCI m/z 440.0 [M + H]⁺ |
| Example 174 | N-[2-(pyrrolidin-1-yl)ethyl]-6-{[5-(trifluoromethyl)pyridin-2-yl]oxy}quinoline-2-carboxamide | ¹H NMR (500 MHz, DMSO-d₆) δ ppm 1.71 (t, J = 8.6 Hz, 4H), 2.42 (s, 4H), 2.65 (t, J = 6.7 Hz, 2H), 3.50 (q, J = 6.5 Hz, 2H), 7.41 (d, J = 8.7 Hz, 1H), 7.76 (dd, J = 9.1, 2.6 Hz, 1H), 7.93 (d, J = 2.6 Hz, 1H), 8.19 (dd, J = 8.8, 5.1 Hz, 2H), 8.32 (dd, J = 8.7, 2.5 Hz, 1H), 8.54 (d, J = 8.6 Hz, 1H), 8.61 (s, 1H), 8.88 (t, J = 5.9 Hz, 1H) | DCI m/z 431.0 [M + H]⁺ |
| Example 175 | N-[2-(piperidin-1-yl)ethyl]-6-{[5-(trifluoromethyl)pyridin-2-yl]oxy}quinoline-2-carboxamide | ¹H NMR (500 MHz, DMSO-d₆) δ ppm 1.35-1.63 (m, 6H), 2.42 (s, 4H), 2.47-2.61 (m, 2H), 3.48 (dd, J = 12.9, 6.5 Hz, 2H), 7.41 (d, J = 8.7 Hz, 1H), 7.66-7.79 (m, 1H), 7.93 (d, J = 2.6 Hz, 1H), 8.18 (d, J = 8.7 Hz, 2H), 8.32 (dd, J = 8.7, 2.5 Hz, 1H), 8.47-8.64 (m, 2H), 8.88 (t, J = 5.7 Hz, 1H) | DCI m/z 445.0 [M + H]⁺ |
| Example 176 | [4-(methylsulfonyl)piperazin-1-yl](6-{[5-(trifluoromethyl)pyridin-2-yl]oxy}quinolin-2-yl)methanone | ¹H NMR (300 MHz, DMSO-d₆) δ ppm 8.65-8.56 (m, 1H), 8.51 (d, J = 8.3 Hz, 1H), 8.38-8.23 (m, 1H), 8.13 (d, J = 9.1 Hz, 1H), 7.90 (d, J = 2.6 Hz, 1H), 7.81-7.66 (m, 2H), 7.40 (d, J = 8.7 Hz, 1H), 3.90-3.76 (m, 2H), 3.70-3.56 (m, 2H), 3.29-3.25 (m, 2H), 3.23-3.11 (m, 2H), 2.94 (s, 3H). | MS (ESI) m/z 481.0 [M + H]⁺ |

| Example Number | Name | ¹H NMR | MS |
| --- | --- | --- | --- |
| Example 177 | [4-(isopropylsulfonyl)piper-azin-1-yl](6-{[5-(trifluoromethyl)pyr-idin-2-yl]oxy}quinolin-2-yl)methanone | ¹H NMR (300 MHz, DMSO-$d_6$) δ ppm 8.65-8.56 (m, 1H), 8.50 (d, J = 8.6 Hz, 1H), 8.30 (dd, J = 8.6, 2.5 Hz, 1H), 8.12 (d, J = 9.1 Hz, 1H), 7.90 (d, J = 2.6 Hz, 1H), 7.82-7.65 (m, 2H), 7.39 (d, J = 8.7 Hz, 1H), 3.85-3.70 (m, 2H), 3.63-3.49 (m, 2H), 3.45-3.40 (m, 2H), 3.34-3.30 (m, 2H), 1.25 (d, J = 6.8 Hz, 6H). | MS (ESI) m/z 509.0 [M + H]⁺ |
| Example 178 | [4-(phenylsulfonyl)piper-azin-1-yl](6-{[5-(trifluoromethyl)pyr-idin-2-yl]oxy}quinolin-2-yl)methanone | ¹H NMR (300 MHz, DMSO-$d_6$) δ ppm 8.61-8.54 (m, 1H), 8.45 (d, J = 8.4 Hz, 1H), 8.30 (dd, J = 8.7, 2.6 Hz, 1H), 8.05 (d, J = 9.2 Hz, 1H), 7.87 (d, J = 2.6 Hz, 1H), 7.80-7.74 (m, 3H), 7.73-7.64 (m, 4H), 7.38 (d, J = 8.7 Hz, 1H), 3.85-3.75 (m, 2H), 3.65-3.56 (m, 2H), 3.10-3.03 (m, 2H), 3.01-2.91 (m, 2H). | MS (ESI) m/z 543.1 [M + H]⁺ |
| Example 179 | [(2R,4S)-2-(2,5-difluorophenyl)-4-fluoropyrrolidin-1-yl](6-{[5-(trifluoromethyl)pyr-idin-2-yl]oxy}quinolin-2-yl)methanone | ¹H NMR (300 MHz, DMSO-$d_6$, rotamers) δ ppm 2.05-2.38 (m, 1H), 2.64-2.90 (m, 1H), 3.90-4.57 (m, 2H), 5.47 (dt, J = 34.0, 27.1 Hz, 1.5H), 5.93-6.11 (m, 0.4H), 6.70-7.00 (m, 1H), 7.07-7.53 (m, 3H), 7.64-7.83 (m, 1.5H), 7.91 (t, J = 5.2 Hz, 1H), 8.04 (d, J = 9.0 Hz, 1H), 8.20 (d, J = 9.0 Hz, 1H), 8.31 (dt, J = 8.8, 3.1 Hz, 0.4H), 8.50 (d, J = 8.4 Hz, 1H), 8.61 (dd, J = 1.6, 0.7 Hz, 1H) | DCI m/z 518.0 [M + H]⁺ |
| Example 180 | [(2R,4R)-2-(2,5-difluorophenyl)-4-fluoropyrrolidin-1-yl](6-{[5-(trifluoromethyl)pyr-idin-2-yl]oxy}quinolin-2-yl)methanone | ¹H NMR (300 MHz, DMSO-$d_6$, rotamers) δ ppm 2.05-2.38 (m, 1H), 2.64-2.90 (m, 1H), 3.90-4.57 (m, 2H), 5.47 (dt, J = 34.0, 27.1 Hz, 1.5H), 5.93-6.11 (m, 0.4H), 6.70-7.00 (m, 1H), 7.07-7.53 (m, 3H), 7.64-7.83 (m, 1.5H), 7.91 (t, J = 5.2 Hz, 1H), 8.04 (d, J = 9.0 Hz, 1H), 8.20 (d, J = 9.0 Hz, 1H), 8.31 (dt, J = 8.8, 3.1 Hz, 0.4H), 8.50 (d, J = 8.4 Hz, 1H), 8.61 (dd, J = 1.6, 0.7 Hz, 1H) | DCI m/z 518.0 [M + H]⁺ |
| Example 181 | [4-(2,2,2-trifluoroethyl)piper-azin-1-yl](6-{[5-(trifluoromethyl)pyr-idin-2-yl]oxy}quinolin-2-yl)methanone | ¹H NMR (300 MHz, DMSO-$d_6$) δ ppm 8.60-8.56 (m, 1H), 8.48 (d, J = 8.3 Hz, 1H), 8.33-8.25 (m, 1H), 8.10 (d, J = 9.1 Hz, 1H), 7.89 (d, J = 2.6 Hz, 1H), 7.74-7.66 (m, 2H), 7.39 (d, J = 8.6 Hz, 1H), 3.77-3.67 (m, 2H), 3.51-3.45 (m, 2H), 3.25-3.16 (m, 2H), 2.79-2.71 (m, 2H), 2.70-2.60 (m, 2H). | MS (ESI) m/z 485.1 [M + H]⁺ |
| Example 182 | [4-(pyridin-2-yl)piperazin-1-yl](6-{[5-(trifluoromethyl)pyr-idin-2-yl]oxy}quinolin-2-yl)methanone | ¹H NMR (400 MHz, DMSO-$d_6$) δ ppm 8.64-8.56 (m, 1H), 8.50 (d, J = 8.3 Hz, 1H), 8.30 (dd, J = 8.8, 2.4 Hz, 1H), 8.19-8.08 (m, 2H), 7.90 (d, J = 2.6 Hz, 1H), 7.75 (d, J = 8.5 Hz, 1H), 7.72 (dd, J = 9.1, 2.7 Hz, 1H), 7.63-7.50 (m, 1H), 7.40 (d, J = 8.8 Hz, 1H), 6.86 (d, J = 8.6 Hz, 1H), 6.73-6.62 (m, 1H), 3.89-3.77 (m, 2H), 3.72-3.64 (m, 2H), 3.64-3.58 (m, 2H), 3.58-3.51 (m, 2H). | MS (ESI) m/z 480.1 [M + H]⁺ |
| Example 183 | [4-(pyridin-3-ylsulfonyl)piperazin-1-yl](6-{[5-(trifluoromethyl)pyr-idin-2-yl]oxy}quinolin-2-yl)methanone | ¹H NMR (400 MHz, DMSO-$d_6$) δ ppm 8.96-8.90 (m, 2H), 8.61-8.56 (m, 1H), 8.45 (d, J = 8.5 Hz, 1H), 8.30 (dd, J = 8.7, 2.5 Hz, 1H), 8.21-8.15 (m, 1H), 8.07 (d, J = 9.1 Hz, 1H), 7.87 (d, J = 2.6 Hz, 1H), 7.75-7.65 (m, 3H), 7.38 (d, J = 8.7 Hz, 1H), 3.88-3.74 (m, 2H), 3.68-3.57 (m, 2H), 3.21-3.10 (m, 2H), 3.10-3.00 (m, 2H). | MS (ESI) m/z 544.1 [M + H]⁺ |
| Example 184 | [4-(piperidin-1-ylsulfonyl)piperazin-1-yl](6-{[5-(trifluoromethyl)pyr-idin-2-yl]oxy}quinolin-2-yl)methanone | ¹H NMR (400 MHz, DMSO-$d_6$) δ ppm 8.61-8.56 (m, 1H), 8.50 (d, J = 8.5 Hz, 1H), 8.30 (dd, J = 8.7, 2.5 Hz, 1H), 8.12 (d, J = 9.1 Hz, 1H), 7.90 (d, J = 2.6 Hz, 1H), 7.77-7.70 (m, 2H), 7.39 (d, J = 8.7 Hz, 1H), 3.82-3.72 (m, 2H), 3.60-3.53 (m, 2H), 3.30-3.26 (m, 2H), 3.23-3.13 (m, 6H), 1.58-1.46 (m, 6H). | MS (ESI) m/z 550.1 [M + H]⁺ |
| Example 185 | [4-(morpholin-4-ylsulfonyl)piperazin-1-yl](6-{[5-(trifluoromethyl)pyr-idin-2-yl]oxy}quinolin-2-yl)methanone | ¹H NMR (400 MHz, DMSO-$d_6$) δ ppm 8.61-8.56 (m, 1H), 8.50 (d, J = 8.5 Hz, 1H), 8.30 (dd, J = 8.7, 2.5 Hz, 1H), 8.12 (d, J = 9.1 Hz, 1H), 7.90 (d, J = 2.6 Hz, 1H), 7.77-7.70 (m, 2H), 7.39 (d, J = 8.7 Hz, 1H), 3.82-3.74 (m, 2H), 3.66-3.53 (m, 6H), 3.40-3.34 (m, 2H), 3.28-3.22 (m, 2H), 3.19-3.12 (m, 4H). | MS (ESI) m/z 552.1 [M + H]⁺ |

| Example Number | Name | ¹H NMR | MS |
|---|---|---|---|
| Example 186 | methyl 4-[(6-{5-(trifluoromethyl)pyridin-2-yl]oxy}quinolin-2-yl)carbonyl]piperazine-1-carboxylate | ¹H NMR (400 MHz, DMSO-d₆) δ ppm 8.61-8.57 (m, 1H), 8.49 (d, J = 8.5 Hz, 1H), 8.30 (dd, J = 8.7, 2.5 Hz, 1H), 8.11 (d, J = 9.1 Hz, 1H), 7.89 (d, J = 2.6 Hz, 1H), 7.76-7.69 (m, 2H), 7.39 (d, J = 8.7 Hz, 1H), 3.76-3.67 (m, 2H), 3.63 (s, 3H), 3.57-3.48 (m, 4H), 3.47-3.38 (m, 2H). | MS (ESI) m/z 461.1 [M + H]⁺ |
| Example 187 | N,N-dimethyl-4-[(6-{[5-(trifluoromethyl)pyridin-2-yl]oxy}quinolin-2-yl)carbonyl]piperazine-1-carboxamide | ¹H NMR (400 MHz, DMSO-d₆/D₂O, 90° C.) δ ppm 8.53 (s, 1H), 8.46 (d, J = 8.5 Hz, 1H), 8.22 (dd, J = 8.7, 2.5 Hz, 1H), 8.12 (d, J = 9.1 Hz, 1H), 7.82 (d, J = 2.6 Hz, 1H), 7.75-7.62 (m, 2H), 7.33 (d, J = 8.7 Hz, 1H), 3.71 (s, 4H), 3.24 (s, 4H), 2.79 (s, 6H). | MS (APCI) m/z 474.2 [M + H]⁺ |
| Example 188 | 5-methyl-8-[(6-{[5-(trifluoromethyl)pyridin-2-yl]oxy}quinolin-2-yl)carbonyl]-2-oxa-5,8-diazaspiro[3.5]nonan-6-one | ¹H NMR (400 MHz, DMSO-d₆/D₂O, 90° C.) δ ppm 8.58-8.40 (m, 2H), 8.23 (dd, J = 8.7, 2.5 Hz, 1H), 8.13 (t, J = 10.5 Hz, 1H), 7.83 (dd, J = 16.3, 5.4 Hz, 2H), 7.76-7.60 (m, 1H), 7.34 (t, J = 7.8 Hz, 1H), 4.89 (d, J = 7.0 Hz, 2H), 4.58 (d, J = 7.4 Hz, 2H), 4.33 (d, J = 9.1 Hz, 4H), 3.17 (s, 3H). | MS (APCI) m/z 473.2 [M + H]⁺ |
| Example 189 | 2-[(6-{[5-(trifluoromethyl)pyridin-2-yl]oxy}quinolin-2-yl)carbonyl]hexahydro-imidazo[1,5-a]pyrazin-3(2H)-one | ¹H NMR (400 MHz, DMSO-d₆/D₂O, 90° C.) δ ppm 8.53 (s, 1H), 8.46 (d, J = 8.5 Hz, 1H), 8.23 (dd, J = 8.7, 2.5 Hz, 1H), 8.13 (d, J = 9.1 Hz, 1H), 7.82 (d, J = 2.6 Hz, 1H), 7.76-7.64 (m, 2H), 7.33 (d, J = 8.7 Hz, 1H), 4.81-3.38 (m, 4H), 3.17-2.65 (m, 4H). | MS (APCI) m/z 458.2 [M + H]⁺ |
| Example 190 | (3,3-difluoro-4-hydroxypiperidin-1-yl)(6-{[5-(trifluoromethyl)pyridin-2-yl]oxy}quinolin-2-yl)methanone | ¹H NMR (400 MHz, DMSO-d₆/D₂O, 90° C.) δ ppm 8.58-8.42 (m, 2H), 8.28-8.18 (m, 1H), 8.18-8.07 (m, 1H), 7.84 (dd, J = 8.9, 2.1 Hz, 1H), 7.75-7.64 (m, 2H), 7.35 (dd, J = 9.3, 4.6 Hz, 1H), 4.19-3.43 (m, 5H), 2.07-1.83 (m, 1H), 1.83-1.69 (m, 1H). | MS (APCI) m/z 454.2 [M + H]⁺ |
| Example 191 | [cis-3-fluoro-4-hydroxypiperidin-1-yl](6-{[5-(trifluoromethyl)pyridin-2-yl]oxy}quinolin-2-yl)methanone | ¹H NMR (400 MHz, DMSO-d₆/D₂O, 90° C.) δ ppm 8.57-8.40 (m, 2H), 8.28-8.17 (m, 1H), 8.16-8.06 (m, 1H), 7.82 (d, J = 2.6 Hz, 1H), 7.74-7.59 (m, 2H), 7.33 (d, J = 8.7 Hz, 1H), 4.93-3.39 (m, 6H), 2.07-1.64 (m, 2H) | MS (APCI) m/z 436.1 [M + H]⁺ |
| Example 192 | [cis-4-fluoro-3-hydroxypiperidin-1-yl](6-{[5-(trifluoromethyl)pyridin-2-yl]oxy}quinolin-2-yl)methanone | ¹H NMR (400 MHz, DMSO-d₆/D₂O, 90° C.) δ ppm 8.50 (dt, J = 29.0, 7.8 Hz, 2H), 8.27-8.19 (m, 1H), 8.19-8.06 (m, 1H), 7.82 (d, J = 2.6 Hz, 1H), 7.73-7.63 (m, 2H), 7.33 (d, J = 8.7 Hz, 1H), 4.93-4.72 (m, 1H), 4.14-3.90 (m, 1H), 3.90-3.43 (m, 4H), 2.32-1.71 (m, 2H). | MS (APCI) m/z 436.1 [M + H]⁺ |
| Example 193 | (4,4-difluoro-3-hydroxypiperidin-1-yl)(6-{[5-(trifluoromethyl)pyridin-2-yl]oxy}quinolin-2-yl)methanone | ¹H NMR (400 MHz, DMSO-d₆/D₂O, 90° C.) δ ppm 8.53 (s, 1H), 8.47 (d, J = 8.5 Hz, 1H), 8.22 (dd, J = 8.7, 2.5 Hz, 1H), 8.12 (d, J = 9.1 Hz, 1H), 7.83 (d, J = 2.6 Hz, 1H), 7.77-7.63 (m, 2H), 7.33 (d, J = 8.7 Hz, 1H), 4.26-3.52 (m, 5H), 2.25 (ddd, J = 30.3, 13.6, 7.0 Hz, 1H), 2.02 (s, 1H). | MS (APCI) m/z 454.1 [M + H]⁺ |
| Example 194 | [(2S,3R)-3-ethyl-2-(hydroxymethyl)azetidin-1-yl](6-{[5-(trifluoromethyl)pyridin-2-yl]oxy}quinolin-2-yl)methanone | ¹H NMR (400 MHz, DMSO-d₆/D₂O, 90° C.) δ ppm 8.62-8.39 (m, 2H), 8.27-8.05 (m, 2H), 8.05-7.94 (m, 1H), 7.93-7.74 (m, 1H), 7.70 (ddd, J = 11.8, 6.8, 2.3 Hz, 1H), 7.41-7.28 (m, 1H), 5.17-3.45 (m, 5H), 3.14-2.65 (m, 1H), 1.86-1.47 (m, 2H), 1.16-0.78 (m, 3H). | MS (APCI) m/z 432.2 [M + H]⁺ |
| Example 195 | [trans-3-fluoro-4-hydroxypiperidin-1-yl](6-{[5-(trifluoromethyl)pyridin-2-yl]oxy}quinolin-2-yl)methanone | ¹H NMR (400 MHz, DMSO-d₆/D₂O, 90° C.) δ ppm 8.57-8.50 (m, 1H), 8.50-8.40 (m, 1H), 8.27-8.18 (m, 1H), 8.12 (dd, J = 9.0, 4.9 Hz, 1H), 7.82 (d, J = 2.6 Hz, 1H), 7.68 (dd, J = 12.9, 5.7 Hz, 2H), 7.38-7.28 (m, 1H), 4.82-4.24 (m, 1H), 4.10-3.37 (m, 5H), 2.07-1.88 (m, 1H), 1.85-1.48 (m, 1H). | MS (APCI) m/z 436.1 [M + H]⁺ |
| Example 196 | [trans-4-fluoro-3-hydroxypiperidin-1-yl](6-{[5-(trifluoromethyl)pyridin-2-yl]oxy}quinolin-2-yl)methanone | ¹H NMR (400 MHz, DMSO-d₆/D₂O, 90° C.) δ ppm 8.54 (t, J = 4.0 Hz, 1H), 8.46 (d, J = 8.5 Hz, 1H), 8.27-8.18 (m, 1H), 8.18-8.07 (m, 1H), 7.83 (t, J = 3.9 Hz, 1H), 7.68 (dd, J = 9.0, 2.6 Hz, 2H), 7.34 (dd, J = 9.2, 5.0 Hz, 1H), | MS (APCI) m/z 436.1 [M + H]⁺ |

| Example Number | Name | ¹H NMR | MS |
|---|---|---|---|
| | yl]oxy}quinolin-2-yl)methanone | 4.70-4.44 (m, 1H), 4.41-3.35 (m, 4H), 3.26-3.16 (m, 1H), 2.40-1.65 (m, 2H). | |
| Example 197 | (6-{[5-(trifluoromethyl)pyridin-2-yl]oxy}quinolin-2-yl)[(2R)-2,3,3-trimethylazetidin-1-yl]methanone | ¹H NMR (400 MHz, DMSO-$d_6$/$D_2O$, 90° C.) δ ppm 8.49 (ddd, J = 41.4, 8.3, 5.9 Hz, 2H), 8.27-8.19 (m, 1H), 8.19-8.08 (m, 1H), 8.03-7.91 (m, 1H), 7.85-7.77 (m, 1H), 7.73-7.62 (m, 1H), 7.34 (t, J = 6.9 Hz, 1H), 4.76-3.96 (m, 2H), 3.95-3.55 (m, 1H), 1.47-1.08 (m, 9H). | MS (APCI) m/z 416.1 [M + H]⁺ |
| Example 198 | (3-hydroxy-3-methylazetidin-1-yl)(6-{[5-(trifluoromethyl)pyridin-2-yl]oxy}quinolin-2-yl)methanone | ¹H NMR (400 MHz, DMSO-$d_6$/$D_2O$, 90° C.) δ ppm 8.58-8.40 (m, 2H), 8.23 (dd, J = 8.7, 2.5 Hz, 1H), 8.15 (d, J = 9.1 Hz, 1H), 8.03 (d, J = 8.6 Hz, 1H), 7.81 (d, J = 2.6 Hz, 1H), 7.68 (dd, J = 9.1, 2.6 Hz, 1H), 7.33 (d, J = 8.6 Hz, 1H), 4.62-4.29 (m, 2H), 4.24-3.96 (m, 2H), 1.47 (s, 3H). | MS (APCI) m/z 404.1 [M + H]⁺ |
| Example 199 | [3-(methoxymethyl)-3-methylazetidin-1-yl](6-{[5-(trifluoromethyl)pyridin-2-yl]oxy}quinolin-2-yl)methanone | ¹H NMR (400 MHz, DMSO-$d_6$/$D_2O$, 90° C.) δ ppm 8.58-8.39 (m, 2H), 8.22 (dd, J = 8.7, 2.5 Hz, 1H), 8.15 (d, J = 9.1 Hz, 1H), 8.03 (d, J = 8.6 Hz, 1H), 7.81 (d, J = 2.6 Hz, 1H), 7.68 (dd, J = 9.1, 2.6 Hz, 1H), 7.33 (d, J = 8.7 Hz, 1H), 4.61-4.50 (m, 1H), 4.35 (d, J = 9.8 Hz, 1H), 4.04-3.93 (m, 1H), 3.76 (d, J = 9.9 Hz, 1H), 3.42 (s, 2H), 3.35 (s, 3H), 1.30 (s, 3H). | MS (APCI) m/z 432.2 [M + H]⁺ |
| Example 200 | (3-methyl-3-phenoxyazetidin-1-yl)(6-{[5-(trifluoromethyl)pyridin-2-yl]oxy}quinolin-2-yl)methanone | ¹H NMR (400 MHz, DMSO-$d_6$/$D_2O$, 90° C.) δ ppm 8.54 (s, 1H), 8.47 (d, J = 8.6 Hz, 1H), 8.23 (dd, J = 8.7, 2.5 Hz, 1H), 8.19 (d, J = 9.1 Hz, 1H), 8.05 (d, J = 8.5 Hz, 1H), 7.82 (d, J = 2.6 Hz, 1H), 7.69 (dd, J = 9.1, 2.6 Hz, 1H), 7.33 (t, J = 8.0 Hz, 3H), 7.01 (t, J = 7.4 Hz, 1H), 6.87 (d, J = 7.8 Hz, 2H), 4.90 (d, J = 9.6 Hz, 2H), 4.32 (d, J = 10.5 Hz, 2H), 1.71 (s, 3H). | MS (APCI) m/z 480.1 [M + H]⁺ |
| Example 201 | (3-phenoxyazetidin-1-yl)(6-{[5-(trifluoromethyl)pyridin-2-yl]oxy}quinolin-2-yl)methanone | ¹H NMR (400 MHz, DMSO-$d_6$/$D_2O$, 90° C.) δ ppm 8.58-8.42 (m, 2H), 8.22 (d, J = 8.8, 2.3 Hz, 1H), 8.17 (d, J = 9.1 Hz, 1H), 8.05 (d, J = 8.6 Hz, 1H), 7.82 (d, J = 2.5 Hz, 1H), 7.68 (dd, J = 9.1, 2.6 Hz, 1H), 7.40-7.27 (m, 3H), 7.01 (t, J = 7.4 Hz, 1H), 6.90 (d, J = 8.4 Hz, 2H), 5.18 (s, 2H), 4.66 (d, J = 30.9 Hz, 2H), 4.12 (s, 1H). | MS (APCI) m/z 466.2 [M + H]⁺ |
| Example 202 | [3-(1H-imidazol-1-yl)azetidin-1-yl](6-{[5-(trifluoromethyl)pyridin-2-yl]oxy}quinolin-2-yl)methanone | ¹H NMR (400 MHz, DMSO-$d_6$/$D_2O$, 90° C.) δ ppm 9.23 (s, 1H), 8.57-8.45 (m, 2H), 8.24 (dd, J = 8.7, 2.4 Hz, 1H), 8.17 (d, J = 9.2 Hz, 1H), 8.10 (d, J = 8.6 Hz, 1H), 7.99 (s, 1H), 7.84 (d, J = 2.6 Hz, 1H), 7.76-7.62 (m, 2H), 7.34 (d, J = 8.7 Hz, 1H), 5.59-5.46 (m, 1H), 4.92 (dd, J = 243.8, 109.1 Hz, 4H). | MS (APCI) m/z 440.1 [M + H]⁺ |
| Example 203 | [3-(4-chlorophenoxy)azetidin-1-yl](6-{[5-(trifluoromethyl)pyridin-2-yl]oxy}quinolin-2-yl)methanone | H NMR (400 MHz, DMSO-$d_6$/$D_2O$, 90° C.) δ ppm 8.58-8.42 (m, 2H), 8.23 (dd, J = 8.7, 2.4 Hz, 1H), 8.17 (d, J = 9.1 Hz, 1H), 8.05 (d, J = 8.5 Hz, 1H), 7.82 (d, J = 2.6 Hz, 1H), 7.68 (dd, J = 9.1, 2.6 Hz, 1H), 7.40-7.28 (m, 3H), 6.99-6.88 (m, 2H), 5.17 (s, 2H), 4.66 (d, J = 25.1 Hz, 2H), 4.12 (s, 1H). | MS (APCI) m/z 500.1 [M + H]⁺ |
| Example 204 | [3-(1H-1,2,4-triazol-1-yl)azetidin-1-yl](6-{[5-(trifluoromethyl)pyridin-2-yl]oxy}quinolin-2-yl)methanone | ¹H NMR (400 MHz, DMSO-$d_6$/$D_2O$, 90° C.) δ ppm 8.67-8.58 (m, 1H), 8.58-8.39 (m, 2H), 8.23 (dd, J = 8.7, 2.4 Hz, 1H), 8.19-8.02 (m, 3H), 7.82 (dd, J = 7.1, 2.6 Hz, 1H), 7.67 (ddd, J = 12.3, 7.5, 4.2 Hz, 1H), 7.33 (d, J = 8.7 Hz, 1H), 5.54 (tdd, J = 10.3, 6.5, 3.4 Hz, 1H), 5.34-4.87 (m, 2H), 4.87-4.58 (m, 1H), 4.57-4.38 (m, 1H). | MS (APCI) m/z 441.2 [M + H]⁺ |
| Example 205 | (6-{[5-(trifluoromethyl)pyridin-2-yl]oxy}quinolin-2-yl)[(2S)-2,3,3-trimethylazetidin-1-yl]methanone | ¹H NMR (400 MHz, DMSO-$d_6$, 90° C.) δ ppm 8.58-8.39 (m, 2H), 8.22 (dd, J = 8.7, 2.6 Hz, 1H), 8.14 (d, J = 9.1 Hz, 1H), 7.98 (s, 1H), 7.81 (d, J = 2.6 Hz, 1H), 7.73-7.62 (m, 1H), 7.33 (d, J = 8.8 Hz, 1H), 4.76-3.40 (m, 3H), 1.45-1.14 (m, 9H). | MS (APCI) m/z 416.1 [M + H]⁺ |

-continued

| Example Number | Name | ¹H NMR | MS |
|---|---|---|---|
| Example 206 | [3-(4-bromophenoxy)azetidin-1-yl](6-{5-(trifluoromethyl)pyridin-2-yl]oxy}quinolin-2-yl)methanone | ¹H NMR (400 MHz, DMSO-$d_6$/$D_2O$, 90° C.) δ ppm 8.58-8.42 (m, 2H), 8.23 (dd, J = 8.6, 2.4 Hz, 1H), 8.17 (d, J = 9.1 Hz, 1H), 8.05 (d, J = 8.6 Hz, 1H), 7.82 (d, J = 2.6 Hz, 1H), 7.68 (dd, J = 9.1, 2.6 Hz, 1H), 7.47 (d, J = 8.9 Hz, 2H), 7.33 (d, J = 8.6 Hz, 1H), 6.89 (d, J = 8.9 Hz, 2H), 5.17 (s, 2H), 4.65 (d, J = 32.2 Hz, 2H), 4.12 (s, 1H). | MS (APCI) m/z 544.0 [M + H]⁺ |
| Example 207 | [3-(hydroxymethyl)-3-methylazetidin-1-yl](6-{5-(trifluoromethyl)pyridin-2-yl]oxy}quinolin-2-yl)methanone | ¹H NMR (400 MHz, DMSO-$d_6$/$D_2O$, 90° C.) δ ppm 8.58-8.39 (m, 2H), 8.22 (dd, J = 8.7, 2.5 Hz, 1H), 8.14 (d, J = 9.1 Hz, 1H), 8.03 (dd, J = 8.5, 4.1 Hz, 1H), 7.81 (d, J = 2.6 Hz, 1H), 7.68 (dd, J = 9.1, 2.6 Hz, 1H), 7.38-7.28 (m, 1H), 4.60-4.38 (m, 1H), 4.31 (d, J = 9.9 Hz, 1H), 4.00 (dd, J = 10.3, 5.4 Hz, 1H), 3.93-3.60 (m, 1H), 3.47 (s, 2H), 1.28 (s, 3H). | MS (APCI) m/z 418.1 [M + H]⁺ |
| Example 208 | 3-phenyl-4-[(6-{5-(trifluoromethyl)pyridin-2-yl]oxy}quinolin-2-yl)carbonyl]piperazin-2-one | ¹H NMR (400 MHz, DMSO-$d_6$) δ ppm 8.57-8.41 (m, 2H), 8.22 (dd, J = 8.7, 2.5 Hz, 2H), 7.86-7.06 (m, 11H), 6.05 (s, 1H), 4.40-3.42 (m, 3H). | MS (APCI) m/z 493.2 [M + H]⁺ |
| Example 209 | (6-[4-(2-hydroxypropan-2-yl)phenoxy]quinolin-2-yl}(piperazin-1-yl)methanone | ¹H NMR (300 MHz, DMSO-$d_6$) δ ppm 1.45 (s, 6H), 2.62-2.70 (m, 2H), 2.75-2.84 (m, 2H), 3.34 (dd, J = 9.1, 4.2 Hz, 2H), 3.52-3.69 (m, 2H), 5.03 (s, 1H), 7.01-7.13 (m, 2H), 7.44 (d, J = 2.7 Hz, 1H), 7.48-7.69 (m, 4H), 8.05 (d, J = 9.2 Hz, 1H), 8.38 (d, J = 8.4 Hz, 1H) | DCI m/z 392.0 [M + H]⁺ |
| Example 210 | 6-{[5-(trifluoromethyl)pyridin-2-yl]oxy}quinoline-2-carboxamide | ¹H NMR (400 MHz, DMSO-$d_6$) δ ppm 7.40 (d, J = 8.7 Hz, 1H), 7.68-7.85 (m, 2H), 7.92 (d, J = 2.5 Hz, 1H), 8.18 (dd, J = 8.8, 4.0 Hz, 2H), 8.24-8.38 (m, 2H), 8.52 (d, J = 8.6 Hz, 1H), 8.61 (s, 1H) | DCI m/z 334.0 [M + H]⁺ |
| Example 211 | (4-methylpiperazin-1-yl)(6-{[5-(trifluoromethyl)pyridin-2-yl]oxy}quinolin-2-yl)methanone | ¹H NMR (300 MHz, DMSO-$d_6$) δ ppm 8.61-8.55 (m, 1H), 8.48 (d, J = 8.5 Hz, 1H), 8.30 (dd, J = 8.8, 2.6 Hz, 1H), 8.11 (d, J = 9.1 Hz, 1H), 7.89 (d, J = 2.6 Hz, 1H), 7.74-7.66 (m, 2H), 7.39 (d, J = 8.8 Hz, 1H), 3.75-3.66 (m, 2H), 3.50-3.39 (m, 2H), 2.46-2.39 (m, 2H), 2.36-2.27 (m, 2H), 2.22 (s, 3H). | MS (ESI) m/z 417.1 [M + H]⁺ |
| Example 212 | (8S,9aS)-8-hydroxy-2-[(6-{[5-(trifluoromethyl)pyridin-2-yl]oxy}quinolin-2-yl)carbonyl]octahydro-5H-pyrrolo[1,2-a][1,4]diazepin-5-one | ¹H NMR (300 MHz, DMSO-$d_6$, rotamers) δ ppm 1.33-1.58 (m, 0.58H), 1.67-1.87 (m, 0.55H), 2.13-2.44 (m, 2H), 2.53-2.66 (m, 0.3H), 2.65-3.10 (m, 1.68H), 3.10-3.4 (m, 2H), 3.32-3.40 (m, 0.4H), 3.42-3.58 (m, 0.8H), 3.73-3.94 (m, 1H), 3.97-4.38 (m, 2H), 4.49-4.76 (m, 1H), 4.95 (d, J = 3.2 Hz, 0.5H), 5.10 (dd, J = 7.4, 3.0 Hz, 0.5H), 7.28-7.50 (m, 1H), 7.67-7.80 (m, 2H), 7.90 (t, J = 2.8 Hz, 1H), 8.05-8.16 (m, 1H), 8.24-8.36 (m, 1H), 8.50 (dd, J = 8.5, 4.0 Hz, 1H), 8.54-8.65 (m, 1H) | DCI m/z 487.0 [M + H]⁺ |
| Example 213 | (1S,6R)-3,8-diazabicyclo[4.2.0]oct-3-yl(6-{[5-(trifluoromethyl)pyridin-2-yl]oxy}quinolin-2-yl)methanone | ¹H NMR (500 MHz, DMSO-$d_6$, rotamers) δ ppm 1.66-1.95 (m, 1.4H), 1.95-2.06 (m, 0.6H), 2.70 (dd, J = 25.7, 10.2 Hz, 1H), 2.93-3.17 (m, 1.4H), 3.23-3.41 (m, 3.6H), 3.66 (dt, J = 33.3, 7.6 Hz, 1H), 3.84-3.97 (m, 1H), 4.00-4.18 (m, 1H), 7.39 (dd, J = 8.7, 4.2 Hz, 1H), 7.65-7.80 (m, 2H), 7.89 (dd, J = 8.2, 2.6 Hz, 1H), 8.04-8.17 (m, 1H), 8.30 (dd, J = 8.7, 2.3 Hz, 1H), 8.46 (dt, J = 15.5, 7.7 Hz, 1H), 8.57 (d, J = 10.8 Hz, 1H) | DCI m/z 429.0 [M + H]⁺ |
| Example 214 | (6-[4-(methylsulfonyl)phenoxy]quinolin-2-yl}(piperazin-1-yl)methanone | ¹H NMR (500 MHz, DMSO-$d_6$) δ ppm 2.50 (dd, J = 7.0, 5.2 Hz, 1H), 2.62-2.73 (m, 2H), 2.75-2.84 (m, 2H), 3.23 (s, 3H), 3.33-3.46 (m, 2H), 3.55-3.68 (m, 2H), 7.24-7.38 (m, 2H), 7.62-7.71 (m, 2H), 7.75 (d, J = 2.7 Hz, 1H), 7.89-8.02 (m, 2H), 8.13 (d, J = 9.1 Hz, 1H), 8.46 (d, J = 8.5 Hz, 1H) | DCI m/z 412.0 [M + H]⁺ |
| Example 215 | piperazin-1-yl(6-{4-[(trifluoromethyl)sulfonyl]phenoxy}quinolin-2-yl)methanone | ¹H NMR (500 MHz, DMSO-$d_6$) δ ppm 2.64-2.72 (m, 2H), 2.76-2.89 (m, 2H), 3.31-3.42 (m, 2H), 3.59-3.66 (m, 2H), 7.29-7.49 (m, 2H), 7.65-7.82 (m, 2H), 7.94 (d, J = 2.7 Hz, 1H), 8.16 (dt, J = 11.8, 6.0 Hz, 3H), 8.50 (d, J = 8.5 Hz, 1H) | DCI m/z 466.0 [M + H]⁺ |

| Example Number | Name | ¹H NMR | MS |
|---|---|---|---|
| Example 216 | N-(azetidin-3-yl)-6-{[5-(trifluoromethyl)pyridin-2-yl]oxy}quinoline-2-carboxamide | ¹H NMR (400 MHz, DMSO-$d_6$) δ ppm 9.23 (d, J = 7.8 Hz, 1H), 8.64-8.58 (m, 1H), 8.53 (d, J = 8.5 Hz, 1H), 8.31 (dd, J = 8.7, 2.5 Hz, 1H), 8.24 (d, J = 9.1 Hz, 1H), 8.14 (d, J = 8.5 Hz, 1H), 7.92 (d, J = 2.6 Hz, 1H), 7.77 (dd, J = 9.1, 2.7 Hz, 1H), 7.41 (d, J = 8.7 Hz, 1H), 4.84-4.72 (m, 1H), 3.70 (t, J = 7.6 Hz, 2H), 3.61 (t, J = 7.8 Hz, 2H). | MS (ESI) m/z 389.2 [M + H]⁺ |
| Example 217 | [3-(pyridin-3-yl)azetidin-1-yl](6-{[5-(trifluoromethyl)pyridin-2-yl]oxy}quinolin-2-yl)methanone | ¹H NMR (400 MHz, DMSO-$d_6$) δ ppm 8.65-8.58 (m, 2H), 8.53-8.47 (m, 2H), 8.30 (dd, J = 8.8, 2.5 Hz, 1H), 8.17 (d, J = 9.1 Hz, 1H), 8.10 (d, J = 8.6 Hz, 1H), 7.98-7.93 (m, 1H), 7.90 (d, J = 2.6 Hz, 1H), 7.72 (dd, J = 9.1, 2.6 Hz, 1H), 7.44-7.37 (m, 2H), 5.22 (t, J = 9.6 Hz, 1H), 4.81 (dd, J = 10.3, 6.4 Hz, 1H), 4.59 (t, J = 9.6 Hz, 1H), 4.20 (dd, J = 10.2, 6.4 Hz, 1H), 4.13-4.04 (m, 1H). | MS (ESI) m/z 451.1 [M + H]⁺ |
| Example 218 | 1-{4-[(6-{[5-(trifluoromethyl)pyridin-2-yl]oxy}quinolin-2-yl)carbonyl]piperazin-1-yl}ethanone | ¹H NMR (400 MHz, DMSO-$d_6$) δ ppm 2.03 and 2.07 (2s, 3 H), 3.46-3.52 (m, 3 H) 3.54-3.62 (m, 3 H) 3.68 (d, J = 5.80 Hz, 1 H) 3.72-3.78 (m, 1 H) 7.40 (d, J = 8.54 Hz, 1 H) 7.70-7.77 (m, 2 H) 7.90 (s, 1 H) 8.12 (d, J = 8.85 Hz, 1 H) 8.31 (dd, J = 8.70, 2.59 Hz, 1 H) 8.50 (d, J = 8.54 Hz, 1 H) 8.60 (s, 1 H) | ESI m/z 445.1 [M + H]⁺ |
| Example 219 | 1,4-diazepan-1-yl(6-{[5-(trifluoromethyl)pyridin-2-yl]oxy}quinolin-2-yl)methanone | ¹H NMR (400 MHz, DMSO-$d_6$) δ ppm 8.60 (s, 1H), 8.52 (dd, J = 15.2, 6.5 Hz, 1H), 8.41-8.29 (m, 2H), 8.26 (s, 1H), 8.14 (dd, J = 9.1, 5.0 Hz, 1H), 7.92 (d, J = 2.4 Hz, 1H), 7.83-7.69 (m, 2H), 7.41 (d, J = 8.7 Hz, 1H), 7.24 (d, J = 4.9 Hz, 1H), 4.93 (s, 1H), 4.81 (s, 1H), 3.74 (t, J = 5.8 Hz, 1H), 3.08 (s, 1H), 3.02 (m, 2H). | ESI m/z 451.1 [M + H]⁺ |
| Example 220 | 2,5-dihydro-1H-pyrrol-1-yl(6-{[5-(trifluoromethyl)pyridin-2-yl]oxy}quinolin-2-yl)methanone | ¹H NMR (400 MHz, DMSO-$d_6$) δ ppm 8.60 (dd, J = 2.5, 1.3 Hz, 1H), 8.49 (d, J = 8.5 Hz, 1H), 8.31 (dd, J = 8.7, 2.6 Hz, 1H), 8.17 (d, J = 9.0 Hz, 1H), 7.95-7.88 (m, 2H), 7.73 (dd, J = 9.0, 2.6 Hz, 1H), 7.40 (d, J = 8.6 Hz, 1H), 5.99 (dt, J = 6.4, 2.1 Hz, 1H), 5.98-5.91 (m, 1H), 4.70-4.64 (m, 2H), 4.43-4.35 (m, 2H). | ESI m/z 386.1 [M + H]⁺ |
| Example 221 | thiomorpholin-4-yl(6-{[5-(trifluoromethyl)pyridin-2-yl]oxy}quinolin-2-yl)methanone | ¹H NMR (400 MHz, DMSO-$d_6$) δ ppm 8.61-8.57 (m, 1H), 8.49 (d, J = 8.4 Hz, 1H), 8.31 (dd, J = 8.7, 2.6 Hz, 1H), 8.12 (d, J = 9.0 Hz, 1H), 7.89 (d, J = 2.6 Hz, 1H), 7.75-7.68 (m, 2H), 7.39 (d, J = 8.6 Hz, 1H), 3.99 (m, 2H), 3.67 (m, 2H), 2.75 (m, 2H), 2.71-2.66 (m, 2H). | ESI m/z 420.0 [M + H]⁺ |
| Example 222 | 3,4-dihydro-2,7-naphthyridin-2(1H)-yl(6-{[5-(trifluoromethyl)pyridin-2-yl]oxy}quinolin-2-yl)methanone | ¹H NMR (500 MHz, DMSO-$d_6$) δ ppm 8.62-8.57 (m, 1H), 8.55-8.47 (m, 2H), 8.40-8.28 (m, 2H), 8.14 (dd, J = 9.1, 5.0 Hz, 1H), 7.92 (d, J = 2.5 Hz, 1H), 7.81-7.71 (m, 2H), 7.44-7.38 (m, 1H), 7.27-7.21 (m, 1H), 4.93 (s, 1H), 4.81 (s, 1H), 3.96 (t, J = 6.0 Hz, 1H), 3.74 (t, J = 5.8 Hz, 1H), 3.00-2.92 (m, 2H). | ESI m/z 451.1 [M + H]⁺ |
| Example 223 | [(2R,4S)-2-(2,5-difluorophenyl)-4-hydroxypyrrolidin-1-yl](6-{[5-(trifluoromethyl)pyridin-2-yl]oxy}quinolin-2-yl)methanone | ¹H NMR (400 MHz, DMSO-$d_6$, rotamers) δ ppm 8.63-8.58 (m, 1H), 8.49 (d, J = 8.5 Hz, 0.65H), 8.34-8.27 (m, 1H), 8.22-8.17 (m, 1H), 7.95 (d, J = 9.1 Hz, 0.35H), 7.91 (d, J = 2.6 Hz, 0.65H), 7.88 (d, J = 8.5 Hz, 0.65H), 7.77-7.72 (m, 1H), 7.68 (dd, J = 9.1, 2.6 Hz, 0.35H), 7.50 (d, J = 8.5 Hz, 0.35H), 7.40 (d, J = 8.7 Hz, 0.65H), 7.36 (d, J = 8.7 Hz, 0.35H), 7.30-7.19 (m, 1.35H), 7.17-7.09 (m, 0.65H), 6.92-6.86 (m, 0.35H), 6.83-6.77 (m, 0.65H), 6.00 (t, J = 8.0 Hz, 0.35H), 5.42 (t, J = 8.4 Hz, 0.65H), 5.27 (d, J = 3.0 Hz, 0.35H), 5.08 (d, J = 3.1 Hz, 0.65H), 4.44 (s, 0.35H), 4.34 (s, 0.65H), 4.22 (dd, J = 11.9, 3.5 Hz, 0.65H), 3.94 (dd, J = 12.5, 4.0 Hz, 0.35H), 3.86 (d, J = 12.5 Hz, 0.35H), 3.74 (d, J = 12.0 Hz, 0.65H), 2.43-2.34 (m, 1H), 2.04-1.90 (m, 1H). | MS (ESI) m/z 516.0 [M + H]⁺ |
| Example 224 | (2-[4-(trifluoromethyl)phenyl]pyrrolidin-1-yl}(6-{[5-(trifluoromethyl)pyr- | ¹H NMR (500 MHz, DMSO-$d_6$, rotamers) δ ppm 8.61-8.55 (m, 1H), 8.48 (d, J = 8.5 Hz, 0.6H), 8.29 (ddd, J = 13.7, 8.7, 2.5 Hz, 1H), 8.21 (dd, J = 18.1, 8.8 Hz, 1H), 7.90 (d, J = 2.6 Hz, 0.4H), 7.84 (d, J = 8.5 Hz, 0.6H), 7.77 (d, | MS (ESI) m/z 532.1 [M + H]⁺ |

| Example Number | Name | ¹H NMR | MS |
|---|---|---|---|
| | idin-2-yl]oxy}quinolin-2-yl)methanone | J = 9.1 Hz, 0.4H), 7.75-7.69 (m, 2H), 7.65-7.60 (m, 1H), 7.57 (d, J = 8.2 Hz, 1H), 7.49 (d, J = 8.2 Hz, 1H), 7.40 (d, J = 8.7 Hz, 0.6H), 7.35 (d, J = 8.7 Hz, 0.4H), 7.29 (d, J = 8.1 Hz, 1H), 5.95-5.85 (m, 0.4H), 5.33 (dd, J = 7.8, 5.2 Hz, 0.6H), 4.19-4.10 (m, 0.6H), 3.97-3.81 (m, 1.4H), 2.48-2.39 (m, 1H), 2.01-1.76 (m, 3H). | |
| Example 225 | N-{(2R,3S)-2-phenyl-1-[(6-{[5-(trifluoromethyl)pyridin-2-yl]oxy}quinolin-2-yl)carbonyl]pyrrolidin-3-yl}-4-(trifluoromethyl)benzenesulfonamide | ¹H NMR (500 MHz, DMSO-d₆, rotamers) δ ppm 8.76-8.68 (m, 1H), 8.59 (d, J = 13.8 Hz, 1H), 8.49 (d, J = 8.5 Hz, 0.5H), 8.33-8.27 (m, 1H), 8.19 (dd, J = 8.9, 3.1 Hz, 1H), 8.00 (d, J = 8.3 Hz, 1H), 7.97-7.89 (m, 2.5H), 7.84 (d, J = 8.5 Hz, 0.5H), 7.78 (d, J = 8.4 Hz, 1H), 7.76-7.71 (m, 1H), 7.65-7.62 (m, 1H), 7.58 (d, J = 8.5 Hz, 0.5H), 7.40 (d, J = 8.7 Hz, 0.5H), 7.36 (d, J = 8.7 Hz, 0.5H), 7.31-7.25 (m, 1H), 7.23-7.18 (m, 0.5H), 7.17 (d, J = 7.3 Hz, 1H), 7.08-6.98 (m, 1.5H), 6.87 (d, J = 6.7 Hz, 1H), 5.69 (d, J = 2.8 Hz, 0.5H), 5.13 (d, J = 3.1 Hz, 0.5H), 4.31-4.22 (m, 0.5H), 4.07-3.87 (m, 1.5H), 3.68 (d, J = 30.8 Hz, 1H), 2.12-1.98 (m, 1H), 1.90-1.73 (m, 1H). | MS (ESI) m/z 687.1 [M + H]⁺ |
| Example 226 | 1-(6-{[2-(piperazin-1-ylcarbonyl)quinolin-6-yl]oxy}pyridin-3-yl)ethanone | ¹H NMR (400 MHz, DMSO-d₆) δ ppm 2.58 (s, 3H), 2.64-2.70 (m, 2H), 2.75-2.86 (m, 2H), 3.57-3.70 (m, 2H), 7.28 (d, J = 8.5 Hz, 1H), 7.63-7.76 (m, 2H), 7.87 (d, J = 2.6 Hz, 1H), 8.10 (d, J = 9.1 Hz, 1H), 8.38 (dd, J = 8.7, 2.5 Hz, 1H), 8.47 (d, J = 8.4 Hz, 1H), 8.77 (d, J = 2.3 Hz, 1H) | DCI m/z 377.0 [M + H]⁺ |
| Example 227 | (1,1-dioxidothiomorpholin-4-yl)(6-{[5-(trifluoromethyl)pyridin-2-yl]oxy}quinolin-2-yl)methanone | ¹H NMR (400 MHz, DMSO-d₆) δ ppm 3.33 (m, 4H), 3.87-3.97 (m, 2H), 4.08-4.18 (m, 2H), 7.40 (d, J = 8.7 Hz, 1H), 7.74 (dd, J = 9.1, 2.7 Hz, 1H), 7.83 (d, J = 8.5 Hz, 1H), 7.91 (d, J = 2.6 Hz, 1H), 8.14 (d, J = 9.1 Hz, 1H), 8.31 (dd, J = 8.7, 2.6 Hz, 1H), 8.52 (d, J = 8.5 Hz, 1H), 8.59 (dd, J = 1.6, 0.8 Hz, 1H) | DCI m/z 452.0 [M + H]⁺ |
| Example 228 | (4-tert-butylpiperazin-1-yl)(6-{[5-(trifluoromethyl)pyridin-2-yl]oxy}quinolin-2-yl)methanone | ¹H NMR (400 MHz, DMSO-d₆) δ ppm 1.02 (s, 9H), 2.47 (s, 2H), 2.56-2.64 (m, 2H), 3.38-3.48 (m, 2H), 3.60-3.75 (m, 2H), 7.39 (d, J = 8.6 Hz, 1H), 7.62-7.76 (m, 2H), 7.89 (d, J = 2.6 Hz, 1H), 8.11 (d, J = 9.1 Hz, 1H), 8.30 (dd, J = 8.7, 2.5 Hz, 1H), 8.47 (d, J = 8.4 Hz, 1H), 8.59 (d, J = 1.6 Hz, 1H) | DCI m/z 459.0 [M + H]⁺ |
| Example 229 | {6-[(5-fluoropyridin-2-yl)oxy]quinolin-2-yl}(piperazin-1-yl)methanone | ¹H NMR (300 MHz, DMSO-d₆) δ ppm 8.94 (br s, 2H), 8.49 (d, J = 8.6 Hz, 1H), 8.19 (d, J = 3.1 Hz, 1H), 8.09 (d, J = 9.2 Hz, 1H), 7.89-7.94 (m, 1H), 7.75-7.77 (m, 2H), 7.67 (dd, J = 9.2, 2.8 Hz, 1H), 7.28 (dd, J = 8.9, 3.7 Hz, 1H), 3.90-3.93 (m, 2H), 3.80-3.82 (m, 2H), 3.18-3.28 (m, 4H). | MS (ESI) m/z 353.2 [M + H]⁺ |
| Example 230 | N-[(3aS,4R,6aR)-2-benzyloctahydrocyclopenta[c]pyrrol-4-yl]-6-{[5-(trifluoromethyl)pyridin-2-yl]oxy}quinoline-2-carboxamide | ¹H NMR (400 MHz, DMSO-d₆) δ ppm 1.32-1.50 (m, 1H), 1.59-1.76 (m, 1H), 1.88-2.07 (m, 2H), 2.14-2.35 (m, 2H), 2.41-2.50 (m, 1H), 2.54-2.81 (m, 3H), 3.47-3.66 (m, 2H), 4.04-4.27 (m, 1H), 7.20-7.28 (m, 1H), 7.30-7.37 (m, 4H), 7.41 (dd, J = 12.0, 5.7 Hz, 1H), 7.70-7.80 (m, 1H), 7.87-7.97 (m, 1H), 8.11-8.18 (m, 1H), 8.18-8.24 (m, 1H), 8.27-8.37 (m, 1H), 8.47-8.56 (m, 1H), 8.58-8.66 (m, 1H), 8.71 (t, J = 7.3 Hz, 1H) | DCI m/z 533.0 [M + H]⁺ |
| Example 231 | (4-isopropylpiperazin-1-yl)(6-{[5-(trifluoromethyl)pyridin-2-yl]oxy}quinolin-2-yl)methanone | ¹H NMR (500 MHz, DMSO-d₆) δ ppm 0.98 (d, J = 6.5 Hz, 6H), 2.40 (d, J = 33.9 Hz, 2H), 2.55 (s, 2H), 2.79 (dd, J = 67.3, 21.3 Hz, 1H), 3.38-3.50 (m, 2H), 3.70 (s, 2H), 7.39 (d, J = 8.7 Hz, 1H), 7.61-7.78 (m, 2H), 7.89 (d, J = 2.6 Hz, 1H), 8.11 (d, J = 9.1 Hz, 1H), 8.30 (dd, J = 8.7, 2.5 Hz, 1H), 8.48 (d, J = 8.5 Hz, 1H), 8.53-8.64 (m, 1H) | DCI m/z 445.0 [M + H]⁺ |
| Example 232 | 2,7-diazaspiro[3.5]non-2-yl(6-{[5-(trifluoromethyl)pyridin-2-yl]oxy}quinolin-2-yl)methanone | ¹H NMR (400 MHz, DMSO-d₆) δ ppm 1.49-1.80 (m, 4H), 2.65 (s, 4H), 3.82 (s, 2H), 4.42 (s, 2H), 7.40 (d, J = 8.7 Hz, 1H), 7.72 (dd, J = 9.1, 2.7 Hz, 1H), 7.89 (d, J = 2.6 Hz, 1H), 8.06 (dd, J = 8.6, 5.2 Hz, 1H), 8.18 (t, J = 7.5 Hz, 1H), 8.31 (dd, J = 8.7, 2.6 Hz, 1H), 8.48 (d, J = 8.6 Hz, 1H), 8.53-8.65 (m, 1H) | DCI m/z 443.0 [M + H]⁺ |

| Example Number | Name | ¹H NMR | MS |
|---|---|---|---|
| Example 233 | tetrahydropyrimidin-1(2H)-yl(6-{[5-(trifluoromethyl)pyridin-2-yl]oxy}quinolin-2-yl)methanone | ¹H NMR (500 MHz, DMSO-d$_6$) δ ppm 1.61 (dd, J = 34.5, 23.7 Hz, 2H), 2.80-2.95 (m, 2H), 3.48-3.90 (m, 2H), 4.44 (d, J = 88.4 Hz, 2H), 7.39 (d, J = 8.7 Hz, 1H), 7.62-7.81 (m, 2H), 7.89 (d, J = 2.6 Hz, 1H), 8.11 (t, J = 8.7 Hz, 1H), 8.30 (dd, J = 8.7, 2.5 Hz, 1H), 8.48 (d, J = 8.5 Hz, 1H), 8.59 (s, 1H) | DCI m/z 403.0 [M + H]⁺ |
| Example 234 | [(2S)-2-(hydroxymethyl)piperazin-1-yl](6-{[5-(trifluoromethyl)pyridin-2-yl]oxy}quinolin-2-yl)methanone | ¹H NMR (500 MHz, DMSO-d$_6$ rotamers) δ ppm 2.53-2.80 (m, 2.8H), 2.92 (ddd, J = 37.7, 29.2, 12.4 Hz, 2.3H), 3.16 (t, J = 13.0 Hz, 1H), 3.46-3.65 (m, 1H), 3.68-3.83 (m, 1.4H), 3.88 (t, J = 9.5 Hz, 0.4H), 4.23 (dd, J = 23.5, 19.8 Hz, 0.7H), 4.46 (s, 0.4H), 4.75 (s, 0.6H), 7.39 (d, J = 8.7 Hz, 1H), 7.57-7.75 (m, 2H), 7.87 (d, J = 2.6 Hz, 1H), 8.10 (dd, J = 12.3, 9.2 Hz, 1H), 8.30 (dd, J = 8.7, 2.4 Hz, 1H), 8.46 (t, J = 8.3 Hz, 1H), 8.59 (s, 1H) | DCI m/z 433.0 [M + H]⁺ |
| Example 235 | N-methyl-4-[(6-{[5-(trifluoromethyl)pyridin-2-yl]oxy}quinolin-2-yl)carbonyl]piperazine-1-sulfonamide | ¹H NMR (400 MHz, DMSO-d$_6$) δ ppm 8.62-8.57 (m, 1H), 8.50 (d, J = 8.5 Hz, 1H), 8.30 (dd, J = 8.7, 2.5 Hz, 1H), 8.12 (d, J = 9.1 Hz, 1H), 7.90 (d, J = 2.6 Hz, 1H), 7.77-7.70 (m, 2H), 7.39 (d, J = 8.7 Hz, 1H), 7.22 (q, J = 4.9 Hz, 1H), 3.85-3.75 (m, 2H), 3.64-3.53 (m, 2H), 3.24-3.18 (m, 2H), 3.15-3.08 (m, 2H), 2.57 (d, J = 4.9 Hz, 3H). | MS (ESI) m/z 496.0 [M + H]⁺ |
| Example 236 | N-ethyl-4-[(6-{[5-(trifluoromethyl)pyridin-2-yl]oxy}quinolin-2-yl)carbonyl]piperazine-1-sulfonamide | ¹H NMR (400 MHz, DMSO-d$_6$) δ ppm 8.61-8.57 (m, 1H), 8.50 (d, J = 8.5 Hz, 1H), 8.30 (dd, J = 8.7, 2.6 Hz, 1H), 8.12 (d, J = 9.1 Hz, 1H), 7.90 (d, J = 2.6 Hz, 1H), 7.77-7.69 (m, 2H), 7.39 (d, J = 8.7 Hz, 1H), 7.31 (t, J = 5.7 Hz, 1H), 3.84-3.76 (m, 2H), 3.62-3.52 (m, 2H), 3.22-3.14 (m, 2H), 3.13-3.05 (m, 2H), 3.01-2.92 (m, 2H), 1.08 (t, J = 7.2 Hz, 3H). | MS (ESI) m/z 509.9 [M + H]⁺ |
| Example 237 | [(2S)-2-(hydroxymethyl)pyrrolidin-1-yl](6-{[5-(trifluoromethyl)pyridin-2-yl]oxy}quinolin-2-yl)methanone | ¹H NMR (400 MHz, DMSO-d$_6$) δ ppm 8.59 (s, 1H), 8.46 (d, J = 8.6 Hz, 1H), 8.30 (dd, J = 8.8, 2.5 Hz, 1H), 8.13 (dd, J = 9.1, 3.2 Hz, 1H), 7.94-7.63 (m, 3H), 7.39 (d, J = 8.7 Hz, 1H), 4.80 (m, 1H), 4.39 (m, 1H), 3.51-3.74 (m, 3H), 3.14 (m, 1H), 1.96-1.78 (m, 4H). | ESI m/z 418.0 [M + H]⁺ |
| Example 238 | azepan-1-yl(6-{[5-(trifluoromethyl)pyridin-2-yl]oxy}quinolin-2-yl)methanone | ¹H NMR (400 MHz, DMSO-d$_6$) δ ppm 8.58 (d, J = 0.8 Hz, 1H), 8.46 (d, J = 8.5 Hz, 1H), 8.30 (dd, J = 8.7, 2.6 Hz, 1H), 8.09 (d, J = 9.1 Hz, 1H), 7.88 (d, J = 2.6 Hz, 1H), 7.76-7.61 (m, 2H), 7.39 (d, J = 8.7 Hz, 1H), 3.71-3.59 (m, 2H), 3.42 (t, J = 5.7 Hz, 2H), 1.78 (dd, J = 11.5, 5.7 Hz, 2H), 1.71-1.45 (m, 6H). | ESI m/z 416.2 [M + H]⁺ |
| Example 239 | N-methyl-1-[(6-{[5-(trifluoromethyl)pyridin-2-yl]oxy}quinolin-2-yl)carbonyl]-L-prolinamide | ¹H NMR (400 MHz, DMSO-d$_6$) δ ppm 8.60 (bs, 1H), 8.50-8.39 (m, 1H), 8.30 (dd, J = 8.7, 2.3 Hz, 1H), 8.11 (dd, J = 37.5, 9.1 Hz, 1H), 7.95-7.81 (m, 2H), 7.83-7.68 (m, 2H), 7.39 (dd, J = 8.7, 4.3 Hz, 1H), 4.98 and 4.50 (2m, 1H), 3.89 and 3.72 (2m, 2H), 2.63 and 2.40 (2d, J = 4.5 Hz, 3H), 2.29-2.11 (m, 2H), 1.90 (m, 2H). | ESI m/z 445.1 [M + H]⁺ |
| Example 240 | 1,4-dioxa-8-azaspiro[4.5]dec-8-yl(6-{[5-(trifluoromethyl)pyridin-2-yl]oxy}quinolin-2-yl)methanone | ¹H NMR (500 MHz, DMSO-d$_6$) δ ppm 8.61-8.57 (m, 1H), 8.48 (d, J = 8.4 Hz, 1H), 8.30 (dd, J = 8.7, 2.6 Hz, 1H), 8.11 (d, J = 9.0 Hz, 1H), 7.89 (d, J = 2.6 Hz, 1H), 7.74-7.68 (m, 2H), 7.39 (d, J = 8.7 Hz, 1H), 3.98-3.87 (m, 4H), 3.77 (t, J = 5.5 Hz, 2H), 3.47 (t, J = 5.3 Hz, 2H), 1.78-1.72 (m, 2H), 1.69 (t, J = 5.4 Hz, 2H). | ESI m/z 460.0 [M + H]⁺ |
| Example 241 | (1R,4R)-2,5-diazabicyclo[2.2.1]hept-2-yl(6-{[5-(trifluoromethyl)pyridin-2-yl]oxy}quinolin-2-yl)methanone | ¹H NMR (400 MHz, DMSO-d$_6$, rotamers) δ ppm 8.59 (s, 1H), 8.50-8.44 (m, 1H), 8.30 (dd, J = 8.7, 2.4 Hz, 1H), 8.12 (d, J = 9.1 Hz, 1H), 7.93-7.87 (m, 1.5H), 7.85 (d, J = 8.5 Hz, 0.5H), 7.74-7.68 (m, 1H), 7.39 (d, J = 8.6 Hz, 1H), 4.88 (s, 0.5H), 4.80 (s, 0.5H), 3.88 (dd, J = 10.4, 2.1 Hz, 0.5H), 3.69-3.58 (m, 1.5H), 3.52 (d, J = 11.1, 2.0 Hz, 1H), 3.38 (d, J = 11.1 Hz, 1H), 3.11 (d, J = 9.6 Hz, 1H), 2.95-2.89 (m, 1H), 1.81-1.73 (m, 1H), 1.68-1.57 (m, 1H). | MS (ESI) m/z 415.2 [M + H]⁺ |
| Example 242 | piperazin-1-yl[6-(pyrimidin-2- | ¹H NMR (400 MHz, DMSO-d$_6$) δ ppm 8.93 (br s, 2H), 8.69 (d, J = 4.9 Hz, 2H), 8.52 (d, | MS (ESI) |

| Example Number | Name | ¹H NMR | MS |
|---|---|---|---|
| | yloxy)quinolin-2-yl]methanone | J = 8.5 Hz, 1H), 8.11 (d, J = 9.2 Hz, 1H), 7.91 (d, J = 2.4 Hz, 1H), 7.79 (d, J = 8.2 Hz, 1H), 7.75 (dd, J = 9.0, 2.6 Hz, 1H), 7.34 (t, J = 4.7 Hz, 1H), 3.91-3.93 (m, 2H), 3.80-3.81 (m, 2H), 3.28-3.30 (m, 2H), 3.17-3.19 (m, 2H). | m/z 336.1 [M + H]⁺ |
| Example 243 | [(2R)-2-(hydroxymethyl)piper-azin-1-yl](6-{[5-(trifluoromethyl)pyr-idin-2-yl]oxy}quinolin-2-yl)methanone | ¹H NMR (500 MHz, DMSO-d₆ rotamers) δ ppm 2.53-2.80 (m, 2.8H), 2.92 (ddd, J = 37.7, 29.2, 12.4 Hz, 2.3H), 3.16 (t, J = 13.0 Hz, 1H), 3.46-3.65 (m, 1H), 3.68-3.83 (m, 1.4H), 3.88 (t, J = 9.5 Hz, 0.4H), 4.23 (dd, J = 23.5, 19.8 Hz, 0.7H), 4.46 (s, 0.4H), 4.75 (s, 0.6H), 7.39 (d, J = 8.7 Hz, 1H), 7.57-7.75 (m, 2H), 7.87 (d, J = 2.6 Hz, 1H), 8.10 (dd, J = 12.3, 9.2 Hz, 1H), 8.30 (dd, J = 8.7, 2.4 Hz, 1H), 8.46 (t, J = 8.3 Hz, 1H), 8.59 (s, 1H) | DCI m/z 433.0 [M + H]⁺ |
| Example 244 | (6-[(5-fluoropyrimidin-2-yl)oxy)quinolin-2-yl](piperazin-1-yl)methanone | ¹H NMR (300 MHz, DMSO-d₆) δ ppm 8.95 (br s, 2H), 8.79 (s, 2H), 8.51 (d, J = 8.6 Hz, 1H), 8.12 (d, J = 9.2 Hz, 1H), 7.89-7.93 (m, 1H), 7.91 (d, J = 2.8 Hz, 1H), 7.79 (d, J = 8.5 Hz, 1H), 7.75 (dd, J = 9.2, 2.8 Hz, 1H), 3.91-3.94 (m, 2H), 3.79-3.82 (m, 2H), 3.28-3.31 (m, 2H), 3.17-3.20 (m, 2H). | MS (ESI) m/z 354.2 [M + H]⁺ |
| Example 245 | piperazin-1-yl(6-{[5-(trifluoromethyl)pyrazin-2-yl]oxy}quinolin-2-yl)methanone | ¹H NMR (400 MHz, DMSO-d₆) δ ppm 8.97 (br s, 2H), 8.86 (s, 1H), 8.75 (s, 1H), 8.54 (d, J = 8.5 Hz, 1H), 8.15 (d, J = 9.2 Hz, 1H), 8.00 (d, J = 2.8 Hz, 1H), 7.80-7.84 (m, 2H), 3.91-3.93 (m, 2H), 3.79-3.81 (m, 2H), 3.28-3.31 (m, 2H), 3.17-3.20 (m, 2H). | MS (ESI) m/z 404.1 [M + H]⁺ |
| Example 246 | piperazin-1-yl(6-{[6-(trifluoromethyl)pyr-dazin-3-yl]oxy}quinolin-2-yl)methanone | ¹H NMR (400 MHz, DMSO-d₆) δ ppm 8.50 (d, J = 8.5 Hz, 1H), 8.37 (d, J = 9.2 Hz, 1H), 8.15 (d, J = 9.2 Hz, 1H), 7.99 (d, J = 2.4 Hz, 1H), 7.89 (d, J = 9.2 Hz, 1H), 7.81 (dd, J = 9.2, 2.8 Hz, 1H), 7.70 (d, J = 8.5 Hz, 1H), 3.63-3.66(m, 2H), 3.35-3.37 (m, 2H), 2.80-2.82 (m, 2H), 2.67-2.70 (m, 2H), 1.90 (s, 3H) | MS (ESI) m/z 404.1 [M + H]⁺ |
| Example 247 | piperazin-1-yl(6-{[5-(trifluoromethyl)pyri-midin-2-yl]oxy}quinolin-2-yl)methanone | ¹H NMR (400 MHz, DMSO-d₆) δ ppm 9.15 (s, 2H), 8.94 (br s, 2H), 8.54 (d, J = 8.5 Hz, 1H), 8.15 (d, J = 9.2 Hz, 1H), 7.99 (d, J = 2.4 Hz, 1H), 7.79-7.83 (m, 2H), 3.91-3.94 (m, 2H), 3.79-3.81 (m, 2H), 3.28-3.31 (m, 2H), 3.17-3.20 (m, 2H). | MS (ESI) m/z 404.1 [M + H]⁺ |
| Example 248 | [(3aR,4S,6aS)-4-aminohexahydrocyclo-penta[c]pyrrol-2(1H)-yl](6-{[5-(trifluoromethyl)pyr-idin-2-yl]oxy}quinolin-2-yl)methanone | ¹H NMR (400 MHz, DMSO-d₆) δ ppm 1.13-1.53 (m, 2H), 1.71-2.14 (m, 3H), 2.18-2.37 (m, 1H), 2.76 (qd, J = 8.5, 4.3 Hz, 1H), 2.90 (dd, J = 12.8, 6.1 Hz, 1H), 3.04 (dd, J = 11.9, 5.9 Hz, 1H), 3.41-3.52 (m, 1H), 3.53-3.77 (m, 2H), 3.85 (td, J = 11.5, 8.1 Hz, 1H), 7.39 (d, J = 8.8 Hz, 1H), 7.66-7.74 (m, 1H), 7.80 (dd, J = 8.5, 1.8 Hz, 1H), 7.89 (t, J = 2.6 Hz, 1H), 8.13 (dd, J = 9.1, 5.8 Hz, 1H), 8.30 (dd, J = 8.7, 2.6 Hz, 1H), 8.46 (dd, J = 8.5, 2.9 Hz, 1H), 8.59 (s, 1H) | DCI m/z 443.0 [M + H]⁺ |
| Example 249 | piperazin-1-yl{6-[4-(trifluoromethyl)phe-noxy]quinolin-2-yl}methanone | ¹H NMR (400 MHz, DMSO-d₆) δ ppm 2.50 (m, 2H), 2.62-2.75 (m, 2H), 2.75-2.88 (m, 2H), 3.54-3.71 (m, 2H), 7.30 (d, J = 8.6 Hz, 2H), 7.53-7.73 (m, 3H), 7.80 (d, J = 8.7 Hz, 2H), 8.04-8.20 (m, 1H), 8.36-8.54 (m, 1H) | DCI m/z 402.0 [M + H]⁺ |
| Example 250 | (6-{[3-fluoro-5-(trifluoromethyl)pyr-idin-2-yl]oxy}quinolin-2-yl)(piperazin-1-yl)methanone | ¹H NMR (400 MHz, DMSO-d₆) δ ppm 9.02 (br s, 2H), 8.50-8.54 (m, 2H), 8.41 (s, 1H), 8.15 (d, J = 9.2 Hz, 1H), 7.98 (d, J = 2.4 Hz, 1H), 7.80-7.83 (m, 2H), 3.92-3.94 (m, 2H), 3.80-3.82 (m, 2H), 3.28-3.31 (m, 2H), 3.17-3.20 (m, 2H). | MS (ESI) m/z 421.1 [M + H]⁺ |
| Example 251 | N-[2-(methylsulfonyl)ethyl]-6-{[5-(trifluoromethyl)pyr-idin-2-yl]oxy}quinoline-2-carboxamide | ¹H NMR (400 MHz, DMSO-d₆) δ ppm 9.22-9.15 (m, 1H), 8.63-8.52 (m, 2H), 8.35-8.28 (m, 1H), 8.22-8.15 (m, 2H), 7.94 (d, J = 2.6 Hz, 1H), 7.77 (dd, J = 9.1, 2.6 Hz, 1H), 7.44-7.38 (m, 1H), 3.86-3.77 (m, 2H), 3.54-3.40 (m, 2H), 3.07 (s, 3H). | ESI m/z 440.1 [M + H]⁺ |
| Example 252 | [4-(oxetan-3-yl)piperazin-1-yl](6-{[5-(trifluoromethyl)pyr-idin-2- | ¹H NMR (400 MHz, DMSO-d₆) δ ppm 8.59 (dd, J = 2.5, 1.3 Hz, 1H), 8.48 (d, J = 8.4 Hz, 1H), 8.30 (dd, J = 8.7, 2.6 Hz, 1H), 8.10 (d, J = 9.0 Hz, 1H), 7.89 (d, J = 2.6 Hz, 1H), 7.74-7.67 (m, 2H), 7.39 (d, J = 8.6 Hz, 1H), 4.55 (t, | ESI m/z 459.1 [M + H]⁺ |

| Example Number | Name | ¹H NMR | MS |
|---|---|---|---|
| | yl]oxy}quinolin-2-yl)methanone | J = 6.5 Hz, 2H), 4.45 (t, J = 6.0 Hz, 2H), 3.75 (d, J = 4.6 Hz, 2H), 3.56-3.42 (m, 3H), 2.40 (t, J = 4.8 Hz, 2H), 2.29 (t, J = 4.7 Hz, 2H). | |
| Example 253 | 3,4-dihydroisoquinolin-2(1H)-yl(6-{[5-(trifluoromethyl)pyridin-2-yl]oxy}quinolin-2-yl)methanone | ¹H NMR (400 MHz, DMSO-d₆) δ ppm 8.62-8.57 (m, 1H), 8.51 (d, J = 8.1 Hz, 1H), 8.31 (dd, J = 8.7, 2.7 Hz, 1H), 8.13 (d, J = 9.1, 2.5 Hz, 1H), 7.91 (d, J = 2.6 Hz, 1H), 7.79-7.70 (m, 2H), 7.44-7.37 (m, 1H), 7.33-7.15 (m, 4H), 4.88 and 4.73 (2s, 2H), 3.94 and 3.71 (2t, J = 5.8 Hz, 2H), 3.00-2.90 (m, 2H). | ESI m/z 450.1 [M + H]⁺ |
| Example 254 | [4-(methylsulfonyl)piperidin-1-yl](6-{[5-(trifluoromethyl)pyridin-2-yl]oxy}quinolin-2-yl)methanone | ¹H NMR (400 MHz, DMSO-d₆) δ ppm 8.61-8.57 (m, 1H), 8.49 (d, J = 8.4 Hz, 1H), 8.30 (dd, J = 8.6, 2.6 Hz, 1H), 8.12 (d, J = 9.0 Hz, 1H), 7.90 (d, J = 2.6 Hz, 1H), 7.73 (t, J = 1.3 Hz, 1H), 7.71 (d, J = 2.0 Hz, 1H), 7.39 (d, J = 8.6 Hz, 1H), 4.70 (m, 1H), 3.93 (m, 1H), 3.45 (m, 1H), 3.18 (m, 1H), 2.97 (s, 3H), 2.93 (m, 1H), 2.20 (m, 1H), 2.01 (m, 1H), 1.75-1.62 (m, 2H). | ESI m/z 480.1 [M + H]⁺ |
| Example 255 | (4-hydroxy-4-methylpiperidin-1-yl)(6-{[5-(trifluoromethyl)pyridin-2-yl]oxy}quinolin-2-yl)methanone | ¹H NMR (500 MHz, DMSO-d₆) δ ppm 8.59 (d, J = 2.5 Hz, 1H), 8.46 (d, J = 8.4 Hz, 1H), 8.30 (dd, J = 8.7, 2.6 Hz, 1H), 8.10 (d, J = 9.0 Hz, 1H), 7.88 (d, J = 2.6 Hz, 1H), 7.70 (dd, J = 9.0, 2.6 Hz, 1H), 7.66 (d, J = 8.4 Hz, 1H), 7.39 (d, J = 8.6 Hz, 1H), 4.46 (s, 1H), 4.20-4.12 (m, 1H), 3.43-3.23 (m, 3H), 2.67 (s, 3H), 1.63-1.41 (m, 4H). | ESI m/z 432.0 [M + H]⁺ |
| Example 256 | (4-hydroxypiperidin-1-yl)(6-{[5-(trifluoromethyl)pyridin-2-yl]oxy}quinolin-2-yl)methanone | ¹H NMR (400 MHz, DMSO-d₆) δ ppm 8.61-8.56 (m, 1H), 8.47 (d, J = 8.4 Hz, 1H), 8.30 (dd, J = 8.7, 2.6 Hz, 1H), 8.10 (d, J = 9.0 Hz, 1H), 7.88 (d, J = 2.6 Hz, 1H), 7.73-7.64 (m, 2H), 7.39 (d, J = 8.6 Hz, 1H), 4.80 (d, J = 4.0 Hz, 1H), 4.14-3.98 (m, 1H), 3.78 (dq, J = 8.1, 4.1 Hz, 1H), 3.64-3.54 (m, 1H), 3.24-3.13 (m, 1H), 1.91-1.81 (m, 1H), 1.79-1.69 (m, 1H), 1.52-1.35 (m, 2H). | ESI m/z 418.1 [M + H]⁺ |
| Example 257 | [(1R,4R,6R)-6-(hydroxymethyl)-2-azabicyclo[2.2.1]hept-2-yl](6-{[5-(trifluoromethyl)pyridin-2-yl]oxy}quinolin-2-yl)methanone | ¹H NMR (400 MHz, DMSO-d₆, rotamers) δ ppm 8.62-8.56 (m, 1H), 8.48-8.42 (m, 1H), 8.30 (dd, J = 8.7, 2.5 Hz, 1H), 8.22 (d, J = 9.1 Hz, 0.7H), 8.13 (d, J = 9.1 Hz, 0.3H), 7.88 (dd, J = 5.4, 2.8 Hz, 1H), 7.84 (d, J = 8.5 Hz, 1H), 7.74-7.66 (m, 1H), 7.39 (d, J = 8.7 Hz, 1H), 4.70-4.63 (m, 1.3H), 4.54 (t, J = 5.5 Hz, 0.7H), 3.80-3.71 (m, 0.3H), 3.49-3.43 (m, 0.7H), 3.26-3.10 (m, 3H), 2.61-2.53 (m, 1H), 2.42-2.29 (m, 0.7H), 2.14-2.04 (m, 0.3H), 1.64-1.49 (m, 2H), 1.31-1.22 (m, 2H). | MS (ESI) m/z 444.1 [M + H]⁺ |
| Example 258 | [(1R,4R,6S)-6-(hydroxymethyl)-2-azabicyclo[2.2.1]hept-2-yl](6-{[5-(trifluoromethyl)pyridin-2-yl]oxy}quinolin-2-yl)methanone | ¹H NMR (400 MHz, DMSO-d₆, rotamers) δ ppm 8.61-8.58 (m, 1H), 8.51 (d, J = 8.6 Hz, 0.7H), 8.48 (d, J = 8.6 Hz, 0.3H), 8.31 (dd, J = 8.7, 2.3 Hz, 1H), 8.14 (d, J = 9.1 Hz, 0.3H), 8.08 (d, J = 9.1 Hz, 0.7H), 7.93-7.88 (m, 1.3H), 7.86 (d, J = 8.5 Hz, 0.7H), 7.75 (dd, J = 9.1, 2.7 Hz, 0.7H), 7.71 (dd, J = 9.1, 2.7 Hz, 0.3H), 7.40 (dd, J = 8.7, 3.5 Hz, 1H), 5.30 (dd, J = 7.6, 4.2 Hz, 0.7H), 4.81 (s, 0.7H), 4.69 (s, 0.3H), 4.28 (dd, J = 7.3, 4.9 Hz, 0.3H), 3.89-3.81 (m, 0.3H), 3.59-3.50 (m, 0.7H), 3.44-3.33 (m, 2H), 3.01 (d, J = 12.0 Hz, 1H), 2.60-2.53 (m, 1H), 2.34-2.13 (m, 1H), 1.86-1.75 (m, 1H), 1.75-1.60 (m, 1H), 1.57 (d, J = 9.6 Hz, 1H), 0.97-0.84 (m, 1H). | MS (ESI) m/z 444.1 [M + H]⁺ |
| Example 259 | N-[(3aR,4R,6aS)-2-benzyloctahydrocyclopenta[c]pyrrol-4-yl]-6-{[5-(trifluoromethyl)pyridin-2-yl]oxy}quinoline-2-carboxamide | ¹H NMR (400 MHz, DMSO-d₆, rotamers) δ ppm 1.32-1.47 (m, 1.4H), 1.61-2.06 (m, 3.6H), 2.11-2.31 (m, 2H), 2.54-2.87 (m, 3H), 3.44-3.67 (m, 1H), 3.67-3.85 (m, 1H), 4.23-4.60 (m, 1H), 7.04-7.21 (m, 3H), 7.35-7.49 (m, 3H), 7.62-7.71 (m, 1H), 7.87-7.99 (m, 1H), 8.05 (d, J = 9.2 Hz, 1H), 8.11-8.25 (m, 1H), 8.25-8.37 (m, 1H), 8.55 (ddd, J = 15.5, 6.5, 1.8 Hz, 2H), 9.04-9.18 (m, 1H) | DCI m/z 533.0 [M + H]⁺ |
| Example 260 | (4-methyl-1,4-diazepan-1-yl)(6-{[5-(trifluoromethyl)pyridin-2- | ¹H NMR (400 MHz, DMSO-d₆) δ ppm 1.79 (dt, J = 11.4, 5.9 Hz, 1H), 1.84-2.02 (m, 1H), 2.28 (dd, J = 25.6, 6.9 Hz, 3H), 2.53-2.63 (m, 3H), 2.65-2.76 (m, 1H), 3.41-3.57 (m, 2H), | DCI m/z 431.0 [M + H]⁺ |

| Example Number | Name | ¹H NMR | MS |
|---|---|---|---|
| | yl]oxy}quinolin-2-yl)methanone | 3.71 (ddd, J = 12.4, 7.4, 4.7 Hz, 2H), 7.39 (dd, J = 8.6, 0.6 Hz, 1H), 7.61-7.77 (m, 2H), 7.88 (d, J = 2.6 Hz, 1H), 8.00-8.18 (m, 1H), 8.30 (dd, J = 8.7, 2.6 Hz, 1H), 8.47 (d, J = 8.3 Hz, 1H), 8.54-8.67 (m, 1H) | |
| Example 261 | (4-cyclopropylpiperazin-1-yl)(6-{[5-(trifluoromethyl)pyridin-2-yl]oxy}quinolin-2-yl)methanone | ¹H NMR (500 MHz, DMSO-$d_6$) δ ppm 8.58-8.59 (m, 1H), 8.48 (d, J = 8.5 Hz, 1H), 8.30 (dd, J = 8.7, 2.6 Hz, 1H), 8.11 (d, J = 9.2 Hz, 1H), 7.89 (d, J = 2.8 Hz, 1H), 7.68-7.72 (m, 2H), 7.39 (d, J = 8.5 Hz, 1H), 3.66-3.68 (m, 2H), 3.40-3.42 (m, 2H), 2.64-2.67 (m, 2H), 2.53-2.56 (m, 2H), 1.67-1.72 (m, 1H), 0.42-0.46 (m, 2H), 0.32-0.36 (m, 2H). | MS (ESI) m/z 443.1 [M + H]⁺ |
| Example 262 | (4-phenylpiperazin-1-yl)(6-{[5-(trifluoromethyl)pyridin-2-yl]oxy}quinolin-2-yl)methanone | (500 MHz, DMSO-$d_6$) δ ppm 8.50 (d, J = 8.5 Hz, 1H), 8.60 (s, 1H). 8.51 (dd, J = 8.7, 2.6 Hz, 1H), 8.14 (d, J = 9.2 Hz, 1H), 7.91 (d, J = 2.8 Hz, 1H), 7.71-7.76 (m, 2H), 7.41 (d, J = 8.5 Hz, 1H), 7.39-7.41 (m, 2H), 6.97-6.98 (m, 2H), 6.82 (t, J = 7.3 Hz, 1H), 3.86-3.88 (m, 2H), 3.64-3.66 (m, 2H), 3.28-3.30 (m, 2H), 3.16-3.18 (m, 2H). | MS (ESI) m/z 479.1 [M + H]⁺ |
| Example 263 | [(3R)-3-isopropylpiperazin-1-yl](6-{[5-(trifluoromethyl)pyridin-2-yl]oxy}quinolin-2-yl)methanone | ¹H NMR (500 MHz, DMSO-$d_6$ rotamers) δ ppm 0.77 (dd, J = 63.1, 6.8 Hz, 3H), 0.97 (d, J = 6.6 Hz, 3H), 1.56 (ddq, J = 87.5, 13.4, 6.7 Hz, 1H), 2.14-2.47 (m, 2H), 2.54-2.90 (m, 3H), 2.97-3.15 (m, 1H), 3.56 (d, J = 13.0 Hz, 0.5H), 3.82 (d, J = 12.3 Hz, 0.5H), 4.43 (dd, J = 42.0, 12.5 Hz, 1H), 7.40 (dd, J = 8.7, 4.4 Hz, 1H), 7.70 (ddd, J = 16.8, 10.8, 5.5 Hz, 2H), 7.89 (t, J = 2.6 Hz, 1H), 8.10 (dd, J = 9.1, 4.0 Hz, 1H), 8.31 (d, J = 8.7 Hz, 1H), 8.47 (dd, J = 8.5, 2.6 Hz, 1H), 8.60 (d, J = 7.0 Hz, 1H) | DCI m/z 445.0 [M + H]⁺ |
| Example 264 | N-(piperidin-4-yl)-6-{[5-(trifluoromethyl)pyridin-2-yl]oxy}quinoline-2-carboxamide | ¹H NMR (400 MHz, DMSO-$d_6$) δ ppm 8.61-8.60 (m, 2H), 8.53 (d, J = 8.5 Hz, 1H), 8.31 (dd, J = 8.7, 2.6 Hz, 1H), 8.23 (d, J = 9.1 Hz, 1H), 8.16 (d, J = 8.4 Hz, 1H), 7.92 (d, J = 2.6 Hz, 1H), 7.75 (dd, J = 9.1, 2.6 Hz, 1H), 7.40 (d, J = 8.7 Hz, 1H), 3.95-3.84 (m, 1H), 3.02-2.94 (m, 2H), 2.58-2.50 (m, 2H), 2.17-1.85 (br s, 1H) 1.83-1.75 (m, 2H), 1.59-1.50 (m, 2H) | MS (ESI) m/z 417.1 [M + H]⁺. |
| Example 265 | [4-(hydroxymethyl)piperidin-1-yl](6-{[5-(trifluoromethyl)pyridin-2-yl]oxy}quinolin-2-yl)methanone | ¹H NMR (400 MHz, DMSO-$d_6$) δ ppm 8.61-8.56 (m, 1H), 8.47 (d, J = 8.4 Hz, 1H), 8.30 (dd, J = 8.7, 2.6 Hz, 1H), 8.10 (d, J = 9.0 Hz, 1H), 7.88 (d, J = 2.6 Hz, 1H), 7.73-7.62 (m, 2H), 7.39 (d, J = 8.6 Hz, 1H), 4.60-4.47 (m, 2H), 3.74-3.65 (m, 1H), 3.17 (m, 1H), 3.06 (t, J = 11.6 Hz, 1H), 2.81 (tt, J = 55.6, 27.7 Hz, 1H), 1.91-1.49 (m, 3H), 1.31-1.01 (m, 2H) | ESI m/z 432.2 [M + H]⁺ |
| Example 266 | [3-(hydroxymethyl)pyrrolidin-1-yl](6-{[5-(trifluoromethyl)pyridin-2-yl]oxy}quinolin-2-yl)methanone | ¹H NMR (400 MHz, DMSO-$d_6$) δ ppm 8.61-8.56 (m, 1H), 8.47 (d, J = 8.4 Hz, 1H), 8.30 (dd, J = 8.7, 2.6 Hz, 1H), 8.10 (d, J = 9.0 Hz, 1H), 7.88 (d, J = 2.6 Hz, 1H), 7.73-7.62 (m, 2H), 7.39 (d, J = 8.6 Hz, 1H), 4.75 and 4.64 (2m, 1H), 3.85-3.41 (m, 6H), 2.36 (m, 1H), 1.99 (m, 1H), 1.70 (m, 1H). | ESI m/z 418.1 [M + H]⁺ |
| Example 267 | N-(8-azabicyclo[3.2.1]oct-3-yl)-6-{[5-(trifluoromethyl)pyridin-2-yl]oxy}quinoline-2-carboxamide | ¹H NMR (400 MHz, DMSO-$d_6$) δ ppm 8.64-8.59 (m, 1H), 8.52 (d, J = 8.6 Hz, 1), 8.47 (d, J = 8.6 Hz, 1H), 8.31 (dd, J = 8.7, 2.6 Hz, 1H), 8.21 (d, J = 9.2 Hz, 1H) 8.15 (d, J = 8.7 Hz, 1H), 7.91 (d, J = 2.6 Hz, 1H), 7.75 (dd, J = 9.1, 2.6 Hz, 1H), 7.40 (d, J = 8.6 Hz, 1H), 4.33-4.18 (m, 1H), 3.46 (br s, 2H), 1.85-1.58 (m, 8H) | MS (ESI) m/z 443.2 [M + H]⁺ |
| Example 268 | [4-(pyrazin-2-yl)piperazin-1-yl](6-{[5-(trifluoromethyl)pyridin-2-yl]oxy}quinolin-2-yl)methanone | ¹H NMR (500 MHz, DMSO-$d_6$) δ ppm 8.59-8.60 (m, 1H), 8.51 (d, J = 8.2 Hz, 1H), 8.35 (d, J = 1.5 Hz, 1H), 8.31 (dd, J = 9.0, 2.3 Hz, 1H), 8.11-8.15 (m, 2H), 7.91 (d, J = 2.8 Hz, 1H), 7.88 (d, J = 2.4 Hz, 1H), 7.77 (d, J = 8.5 Hz, 1H), 7.73 (dd, J = 9.0, 2.6 Hz, 1H), 7.40 (d, J = 8.5 Hz, 1H), 3.84-3.87 (m, 2H), 3.75-3.78 (m, 2H), 3.64-3.66 (m, 4H). | MS (ESI) m/z 481.0 [M + H]⁺ |
| Example 269 | [4-(pyridin-3-yl)piperazin-1-yl](6-{[5-(trifluoromethyl)pyridin-2- | ¹H NMR (400 MHz, DMSO-$d_6$) δ ppm 8.59-8.60 (m, 1H), 8.51 (d, J = 8.2 Hz, 1H), 8.34 (d, J = 2.8 Hz, 1H), 8.31 (dd, J = 8.7, 2.6 Hz, 1H), 8.03 (dd, J = 4.4, 1.4 Hz, 1H), 7.91 (d, J = 2.8 Hz, 1H), 7.71-7.77 (m, 2H), 7.35-7.41 (m, 2H), | MS (ESI) m/z 480.1 [M + H]⁺ |

-continued

| Example Number | Name | ¹H NMR | MS |
|---|---|---|---|
| | yl]oxy}quinolin-2-yl)methanone | 7.24 (dd, J = 8.5, 4.6 Hz, 1H), 3.36-3.39 (m, 2H), 3.66-3.69 (m, 2H), 3.24-3.27 (m, 2H). | |
| Example 270 | [4-(pyrimidin-2-yl)piperazin-1-yl](6-{[5-(trifluoromethyl)pyridin-2-yl]oxy}quinolin-2-yl)methanone | ¹H NMR (400 MHz, DMSO-$d_6$) δ ppm 8.59-8.60 (m, 1H), 8.51 (d, J = 8.5 Hz, 1H), 8.40 (d, J = 4.9 Hz, 2H), 8.31 (dd, J = 8.7, 2.6 Hz, 1H), 8.13 (d, 9.2 Hz, 1H), 7.91 (d, J = 2.4 Hz, 1H), 7.71-7.77 (m, 2H), 7.40 (d, J = 8.5 Hz, 1H), 6.68 (t, J = 4.7 Hz, 1H), 3.90-3.93 (m, 2H), 3.79-3.82 (m, 4H), 3.58-3.61 (m, 2H). | MS (ESI) m/z 481.1 [M + H]⁺ |
| Example 271 | [4-(pyridazin-3-yl)piperazin-1-yl](6-{[5-(trifluoromethyl)pyridin-2-yl]oxy}quinolin-2-yl)methanone | ¹H NMR (400 MHz, DMSO-$d_6$) δ ppm 8.59-8.60 (m, 2H), 8.51 (d, J = 8.5 Hz, 1H), 8.31 (dd, J = 8.7, 2.6 Hz, 1H), 8.14 (d, J = 9.2 Hz, 1H), 7.91 (d, J = 2.4 Hz, 1H), 7.47 (d, J = 8.5 Hz, 1H), 7.73 (dd, J = 9.2, 2.4 Hz, 1H), 7.39-7.44 (m, 2H), 7.27-7.29 (m, 2H), 3.86-3.88 (m, 2H), 3.77-3.80 (m, 2H), 3.66-3.68 (m, 4H). | MS (ESI) m/z 481.2 [M + H]⁺ |
| Example 272 | [4-(5-chloropyridin-2-yl)piperazin-1-yl](6-{[5-(trifluoromethyl)pyridin-2-yl]oxy}quinolin-2-yl)methanone | ¹H NMR (400 MHz, DMSO-$d_6$) δ ppm 3.49-3.59 (m, 2H), 3.63 (dd, J = 6.7, 3.2 Hz, 2H), 3.67 (dd, J = 10.8, 6.4 Hz, 2H), 3.77-3.89 (m, 2H), 6.91 (d, J = 9.1 Hz, 1H), 7.40 (d, J = 8.7 Hz, 1H), 7.64 (dd, J = 9.1, 2.7 Hz, 1H), 7.69-7.81 (m, 2H), 7.90 (d, J = 2.6 Hz, 1H), 8.06-8.22 (m, 2H), 8.26-8.40 (m, 1H), 8.50 (d, J = 8.5 Hz, 1H), 8.60 (s, 1H) | DCI m/z 514.0 [M + H]⁺ |
| Example 273 | [(3S)-3-ethylpiperazin-1-yl](6-{[5-(trifluoromethyl)pyridin-2-yl]oxy}quinolin-2-yl)methanone | ¹H NMR (400 MHz, DMSO-$d_6$ rotamers) δ ppm 0.74 (t, J = 7.5 Hz, 1.3H), 0.95 (t, J = 7.5 Hz, 1.7H), 1.08-1.34 (m, 1H), 1.34-1.54 (m, 1H), 2.50-2.94 (m, 4H), 2.94-3.15 (m, 1H), 3.65 (dd, J = 57.9, 12.5 Hz, 2H), 4.40 (dd, J = 26.3, 11.1 Hz, 1H), 7.39 (dt, J = 16.4, 8.2 Hz, 2H), 7.62-7.80 (m, 2H), 7.90 (dd, J = 12.2, 10.7 Hz, 1H), 8.10 (dd, J = 9.1, 3.5 Hz, 1H), 8.30 (dd, J = 8.7, 2.4 Hz, 1H), 8.47 (d, J = 8.5 Hz, 1H), 8.53-8.66 (m, 1H) | DCI m/z 431.0 [M + H]⁺ |
| Example 274 | [(3S)-3-isopropylpiperazin-1-yl](6-{[5-(trifluoromethyl)pyridin-2-yl]oxy}quinolin-2-yl)methanone | ¹H NMR (500 MHz, DMSO-$d_6$ rotamers) δ ppm 0.77 (dd, J = 63.1, 6.8 Hz, 3H), 0.97 (d, J = 6.6 Hz, 3H), 1.56 (ddq, J = 87.5, 13.4, 6.7 Hz, 1H), 2.14-2.47 (m, 2H), 2.54-2.90 (m, 3H), 2.97-3.15 (m, 1H), 3.56 (d, J = 13.0 Hz, 0.5H), 3.82 (d, J = 12.3 Hz, 0.5H), 4.43 (dd, J = 42.0, 12.5 Hz, 1H), 7.40 (dd, J = 8.7, 4.4 Hz, 1H), 7.70 (ddd, J = 16.8, 10.8, 5.5 Hz, 2H), 7.89 (t, J = 2.6 Hz, 1H), 8.10 (dd, J = 9.1, 4.0 Hz, 1H), 8.31 (d, J = 8.7 Hz, 1H), 8.47 (dd, J = 8.5, 2.6 Hz, 1H), 8.60 (d, J = 7.0 Hz, 1H) | DCI m/z 445.0 [M + H]⁺ |
| Example 275 | (6-[4-(1-hydroxyethyl)phenoxy]quinolin-2-yl}(piperazin-1-yl)methanone | ¹H NMR (400 MHz, DMSO-$d_6$) δ ppm 1.35 (t, J = 6.6 Hz, 3H), 2.75 (s, 2H), 2.87 (s, 2H), 3.67 (s, 2H), 4.76 (d, J = 6.3 Hz, 2H), 5.19 (s, 1H), 7.00-7.22 (m, 3H), 7.29-7.47 (m, 4H), 7.50-7.68 (m, 3H), 7.98-8.12 (m, 1H), 8.23-8.51 (m, 1H) | DCI m/z 378.0 [M + H]⁺ |
| Example 276 | [(3S)-3-(hydroxymethyl)piperazin-1-yl](6-{[5-(trifluoromethyl)pyridin-2-yl]oxy}quinolin-2-yl)methanone | ¹H NMR (400 MHz, DMSO-$d_6$ rotamers) δ ppm 2.81 (ddt, J = 39.0, 23.3, 11.0 Hz, 4), 3.02-3.29 (m, 4H), 3.72 (dd, J = 37.2, 12.5 Hz, 1H), 4.40 (d, J = 12.9 Hz, 0.5H), 4.52 (d, J = 12.8 Hz, 0.5H), 4.68 (s, 0.5H), 4.90 (s, 0.5H), 7.39 (d, J = 8.8 Hz, 1H), 7.57-7.78 (m, 2H), 7.89 (d, J = 2.5 Hz, 1H), 8.11 (d, J = 9.1 Hz, 1H), 8.31 (d, J = 8.7, 2.4 Hz, 1H), 8.48 (d, J = 8.5 Hz, 1H), 8.59 (s, 1H) | DCI m/z 433.0 [M + H]⁺ |
| Example 277 | isopropyl 4-[(6-{[5-(trifluoromethyl)pyridin-2-yl]oxy}quinolin-2-yl)carbonyl]piperazine-1-carboxylate | ¹H NMR (400 MHz, DMSO-$d_6$) δ ppm 8.59-8.60 (m, 1H). 8.49 (d, J = 8.2 Hz, 8.31 (dd, J = 8.7, 2.6 Hz, 1H), 1H), 8.12 (d, J = 9.2 Hz, 1H), 7.90 (d, J = 2.4 Hz, 7.71-7.75 (m, 2H), 1H), 7.40 (d, J = 8.5 Hz, 1H), 3.70-3.73 (m, 2H), 3.51-3.52 (m, 4H), 3.42-3.44 (m, 2H), 1.20 (d, J = 6.4 Hz, 6H). | MS (ESI) m/z 489.1 [M + H]⁺ |
| Example 278 | (1S,5S)-3,6-diazabicyclo[3.2.0]hept-3-yl(6-{[5-(trifluoromethyl)pyridin-2-yl]oxy}quinolin-2-yl)methanone | ¹H NMR (400 MHz, DMSO-$d_6$, rotamers) δ ppm 8.59 (s, 1H), 8.49 (dd, J = 8.5, 4.5 Hz, 1H), 8.30 (dd, J = 8.7, 2.4 Hz, 1H), 8.13 (dd, J = 9.1, 3.0 Hz, 1H), 7.92-7.84 (m, 2H), 7.74-7.68 (m, 1H), 7.39 (d, J = 8.7 Hz, 1H), 4.37 (dd, J = 11.4, 5.1 Hz, 1H), 4.23 (d, J = 13.0 Hz, 0.5H), 4.10 (d, J = 13.1 Hz, 0.5H), 4.00 (d, J = 12.4 Hz, 0.5H), 3.84 (d, J = 12.6 Hz, 0.5H), 3.74-3.65 (m, 1H), 3.65-3.55 (m, | MS (ESI) m/z 415.1 [M + H]⁺ |

| Example Number | Name | ¹H NMR | MS |
|---|---|---|---|
| | | 1H), 3.44 (dd, J = 13.0, 7.5 Hz, 1H), 3.27-3.24 (m, 1H), 3.22-3.12 (m, 1H), 3.11-3.03 (m, 1H). | |
| Example 279 | 1,6-diazaspiro[3.3]hept-1-yl(6-{[5-(trifluoromethyl)pyridin-2-yl]oxy}quinolin-2-yl)methanone | ¹H NMR (400 MHz, DMSO-$d_6$) δ ppm 8.62-8.57 (m, 1H), 8.53-8.48 (m, 1H), 8.31 (dd, J = 8.7, 2.4 Hz, 1H), 8.14 (d, J = 9.1 Hz, 1H), 8.09-8.02 (m, 1H), 7.91-7.88 (m, 1H), 7.76-7.70 (m, 1H), 7.40 (d, J = 8.7 Hz, 1H), 4.68-4.54 (m, 3H), 3.73 (d, J = 9.7 Hz, 2H), 3.53-3.46 (m, 2H), 2.66-2.56 (m, 2H). | MS (ESI) m/z 415.1 [M + H]⁺ |
| Example 280 | (3aS,6aS)-hexahydropyrrolo[3,4-b]pyrrol-5(1H)-yl(6-{[5-(trifluoromethyl)pyridin-2-yl]oxy}quinolin-2-yl)methanone | ¹H NMR (400 MHz, DMSO-$d_6$) δ ppm 8.60-8.56 (m, 1H), 8.46 (d, J = 8.5 Hz, 1H), 8.30 (dd, J = 8.7, 2.6 Hz, 1H), 8.15-8.09 (m, 1H), 7.88 (d, J = 2.6 Hz, 1H), 7.84-7.77 (m, 1H), 7.74-7.68 (m, 1H), 7.39 (d, J = 8.6 Hz, 1H), 3.96-3.68 (m, 3H), 3.62-3.53 (m, 1H), 3.51-3.40 (m, 1H), 2.96-2.86 (m, 1H), 2.86-2.69 (m, 2H), 1.92-1.73 (m, 1H), 1.68-1.48 (m, 1H). | MS (ESI) m/z 429.2 [M + H]⁺ |
| Example 281 | N-(morpholin-4-yl)-6-{[5-(trifluoromethyl)pyridin-2-yl]oxy}quinoline-2-carboxamide | ¹H NMR (400 MHz, DMSO-$d_6$) δ ppm 9.90 (s, 1H), 8.64-8.59 (m, 1H), 8.52 (d, J = 8.5 Hz, 1H), 8.32 (dd, J = 8.6, 2.7 Hz, 1H), 8.22 (d, J = 9.1 Hz, 1H), 8.13 (d, J = 8.4 Hz, 1H), 7.92 (d, J = 2.6 Hz, 1H), 7.79-7.72 (m, 1H), 7.41 (d, J = 8.6 Hz, 1H), 3.75-3.64 (m, 4H), 3.02-2.89 (m, 4H). | ESI m/z 419.1 [M + H]⁺ |
| Example 282 | [(3R)-3-hydroxypyrrolidin-1-yl](6-{[5-(trifluoromethyl)pyridin-2-yl]oxy}quinolin-2-yl)methanone | ¹H NMR (400 MHz, DMSO-$d_6$) δ ppm 8.59 (s, 1H), 8.47 (d, J = 8.5 Hz, 1H), 8.31 (m, 1H), 8.14 (m, 1H), 7.88-7.84 (m, 2H), 7.71 (m, 1H), 7.41 (m, 1H), 4.97 (m, 1H), 4.34 (m, 1H), 3.85-3.62 (m, 4H), 2.01-1.83 (m, 2H). | ESI m/z 404.1 [M + H]⁺ |
| Example 283 | [(3S)-3-hydroxypyrrolidin-1-yl](6-{[5-(trifluoromethyl)pyridin-2-yl]oxy}quinolin-2-yl)methanone | ¹H NMR (400 MHz, DMSO-$d_6$) δ ppm 8.60 (d, J = 3.0 Hz, 1H), 8.47 (d, J = 8.5 Hz, 1H), 8.31 (dd, J = 8.7, 2.6 Hz, 1H), 8.14 (dd, J = 9.1, 6.8 Hz, 1H), 7.92-7.82 (m, 2H), 7.72 (ddd, J = 9.0, 2.7, 1.3 Hz, 1H), 7.43-7.37 (m, 1H), 5.00 (dd, J = 31.4, 3.4 Hz, 1H), 4.40-4.28 (m, 1H), 3.91-3.76 (m, 2H), 3.71-3.56 (m, 2H), 2.01-1.80 (m, 2H). | ESI m/z 404.1 [M + H]⁺ |
| Example 284 | (4-hydroxyazepan-1-yl)(6-{[5-(trifluoromethyl)pyridin-2-yl]oxy}quinolin-2-yl)methanone | ¹H NMR (400 MHz, DMSO-$d_6$) δ ppm 8.59 (s, 1H), 8.46 (d, J = 8.6 Hz, 1H), 8.30 (dd, J = 8.7, 2.5 Hz, 1H), 8.09 (dd, J = 9.1, 3.1 Hz, 1H), 7.88 (t, J = 2.3 Hz, 1H), 7.76-7.59 (m, 2H), 7.74-7.62 (m, 2H), 7.39 (d, J = 8.8 Hz, 1H), 4.58 (dd, J = 18.3, 3.9 Hz, 1H), 3.76 (s, 1H), 3.72-3.49 (m, 2H), 3.44 (d, J = 13.9 Hz, 1H), 1.97 (d, J = 11.7 Hz, 2H), 1.87-1.53 (m, 5H). | ESI m/z 432.1 [M + H]⁺ |
| Example 285 | N-(4-hydroxy-1,1-dioxidotetrahydrothiophen-3-yl)-6-{[5-(trifluoromethyl)pyridin-2-yl]oxy}quinoline-2-carboxamide | ¹H NMR (400 MHz, DMSO-$d_6$) δ ppm 8.88 (d, J = 8.1 Hz, 1H), 8.62 (d, J = 2.4 Hz, 1H), 8.58 (d, J = 8.5 Hz, 1H), 8.32 (dd, J = 8.7, 2.6 Hz, 1H), 8.25-8.18 (m, 2H), 7.95 (d, J = 2.6 Hz, 1H), 7.78 (dd, J = 9.1, 2.6 Hz, 1H), 7.41 (d, J = 8.6 Hz, 1H), 6.30 (s, 1H), 4.80 (dtd, J = 11.5, 7.7, 3.7 Hz, 1H), 4.66-4.61 (m, 1H), 3.63-3.37 (m, 4H). | ESI m/z 468.0 [M + H]⁺ |
| Example 286 | {4-[(3-methyloxetan-3-yl)methyl]piperazin-1-yl}(6-{[5-(trifluoromethyl)pyridin-2-yl]oxy}quinolin-2-yl)methanone | ¹H NMR (400 MHz, DMSO-$d_6$) δ ppm 8.61-8.56 (m, 1H), 8.48 (d, J = 8.4 Hz, 1H), 8.34-8.27 (m, 1H), 8.11 (d, J = 9.0 Hz, 1H), 7.89 (d, J = 2.6 Hz, 1H), 7.74-7.66 (m, 2H), 7.39 (d, J = 8.6 Hz, 1H), 4.36 (d, J = 5.5 Hz, 2H), 4.21-4.13 (m, 2H), 3.69 (t, J = 4.6 Hz, 2H), 3.47-3.41 (m, 2H), 3.34 (m, 2H), 2.43-2.37 (m, 2H), 2.28 (t, J = 4.7 Hz, 2H), 1.33 (s, 3H). | ESI m/z 487.2 [M + H]⁺ |
| Example 287 | [3-(methylsulfonyl)pyrrolidin-1-yl](6-{[5-(trifluoromethyl)pyridin-2-yl]oxy}quinolin-2-yl)methanone | ¹H NMR (400 MHz, DMSO-$d_6$) δ ppm 8.62-8.57 (m, 1H), 8.50 (dd, J = 8.6, 4.6 Hz, 1H), 8.31 (dd, J = 8.6, 2.6 Hz, 1H), 8.16 (t, J = 9.0 Hz, 1H), 7.93-7.86 (m, 2H), 7.73 (ddd, J = 9.0, 3.9, 2.6 Hz, 1H), 7.43-7.37 (m, 1H), 4.27-4.14 (m, 1H), 4.08-3.92 (m, 2H), 3.86-3.65 (m, 2H), 3.11 and 3.03 (2s, 3H), 2.41-2.29 (m, 2H). | ESI m/z 466.1 [M + H]⁺ |
| Example 288 | 2-[(6-{[5-(trifluoromethyl)pyridin-2- | ¹H NMR (400 MHz, DMSO-$d_6$ rotamers) δ ppm 1.38-1.55 (m, 0.5H), 1.60-1.80 (m, 0.5H), 1.96-2.09 (m, 0.5H), 2.12-2.38 (m, | DCI m/z 457.0 [M + H]⁺ |

| Example Number | Name | ¹H NMR | MS |
|---|---|---|---|
| | yl]oxy}quinolin-2-yl)carbonyl]hexahydropyrrolo[1,2-a]pyrazin-6(2H)-one | 2.5H), 2.61-3.15 (m, 3H), 3.52-3.75 (m, 1H), 3.84 (dd, J = 30.3, 12.3 Hz, 1H), 3.99 (t, J = 11.7 Hz, 1H), 4.60 (d, J = 12.1 Hz, 0.5H), 4.70 (d, J = 12.1 Hz, 0.5H), 7.40 (d, J = 8.7 Hz, 1H), 7.62-7.81 (m, 2H), 7.90 (d, J = 2.6 Hz, 1H), 8.13 (d, J = 9.1 Hz, 1H), 8.31 (dd, J = 8.7, 2.6 Hz, 1H), 8.50 (d, J = 8.3 Hz, 1H), 8.59 (s, 1H) | |
| Example 289 | ethyl 4-[(6-{[5-(trifluoromethyl)pyridin-2-yl]oxy}quinolin-2-yl)carbonyl]piperazine-1-carboxylate | ¹H NMR (400 MHz, DMSO-d₆) δ ppm 8.59-8.60 (m, 1H), 8.50 (d, J = 8.5 Hz, 1H), 8.31 (dd, J = 8.7, 2.6 Hz, 1H), 8.12 (d, J = 9.2 Hz, 1H), 7.90 (d, J = 2.4 Hz, 1H), 7.71-7.75 (m, 2H), 7.40 (d, J = 8.9 Hz, 1H), 4.07 (q, J = 7.0 Hz, 2H), 3.71-3.74 (m, 4H), 3.51-3.55 (m, 4H), 3.42-3.44 (m, 2H), 1.20 (t, J = 7.0 Hz, 3H). | MS (ESI) m/z 475.1 [M + H]⁺ |
| Example 290 | cyclopropyl{4-[(6-{[5-(trifluoromethyl)pyridin-2-yl]oxy}quinolin-2-yl)carbonyl]piperazin-1-yl}methanone | ¹H NMR (400 MHz, DMSO-d₆) δ ppm 8.59-8.60 (m, 1H), 8.50 (d, J = 8.5 Hz, 8.31 (dd, J = 8.7, 2.6 Hz, 1H), 1H), 8.12 (d, J = 9.2 Hz, 1H), 7.90 (d, J = 2.4 Hz, 7.71-7.76 (m, 2H), 1H), 7.40 (d, J = 8.9 Hz, 1H), 3.52-3.85 (m, 8H), 1.94-2.04 (m, 1H), 0.73-0.78 (m, 4H). | MS (ESI) m/z 471.1 [M + H]⁺ |
| Example 291 | (4-cyclohexylpiperazin-1-yl)(6-{[5-(trifluoromethyl)pyridin-2-yl]oxy}quinolin-2-yl)methanone | ¹H NMR (500 MHz, DMSO-d₆) δ ppm 8.58-8.59 (m, 1H), 8.48 (d, J = 8.5 Hz, 1H), 8.30 (dd, J = 8.7, 2.6 Hz, 1H), 8.11 (d, J = 9.2 Hz, 1H), 7.89 (d, J = 2.8 Hz, 1H), 7.68-7.72 (m, 2H), 7.39 (d, J = 8.5 Hz, 1H), 3.66-3.68 (m, 2H), 3.40-3.42 (m, 2H), 2.64-2.67 (m, 2H), 2.53-2.56 (m, 2H), 1.67-1.72 (m, 1H), 0.42-0.46 (m, 2H), 0.32-0.36 (m, 2H). | MS (ESI) m/z 485.1 [M + H]⁺ |
| Example 292 | (3-fluoro-4-hydroxypyrrolidin-1-yl)(6-{[5-(trifluoromethyl)pyridin-2-yl]oxy}quinolin-2-yl)methanone | ¹H NMR (400 MHz, DMSO-d₆) δ ppm 8.60 (s, 1H), 8.50 (d, J = 8.7 Hz, 1H), 8.31 (dd, J = 8.7, 2.5 Hz, 1H), 8.17 (dd, J = 9.1, 5.0 Hz, 1H), 7.97-7.86 (m, 1H), 7.74 (dd, J = 9.3, 2.6 Hz, 1H), 7.40 (d, J = 8.7 Hz, 1H), 5.67 and 5.58 (2br s, 1H), 5.10 and 4.99 (2d, J = 7.9 Hz, 1H), 4.30-3.66 (m, 5H). | ESI m/z 422.1 [M + H]⁺ |
| Example 293 | isobutyl 4-[(6-{[5-(trifluoromethyl)pyridin-2-yl]oxy}quinolin-2-yl)carbonyl]piperazine-1-carboxylate | ¹H NMR (400 MHz, DMSO-d₆) δ ppm 8.59-8.60 (m, 1H). 8.50 (d, J = 8.2 Hz, 1H), 8.31 (dd, J = 8.6, 2.4 Hz, 1H), 8.12 (d, J = 9.2 Hz, 1H), 7.90 (d, J = 2.4 Hz, 1H), 7.71-7.75 (m, 2H), 7.40 (d, J = 8.9 Hz, 1H), 3.82 (d, J = 6.7 Hz, 2H), 3.72-3.74 (m, 2H), 3.51-3.54 (m, 4H), 3.43-3.45 (m, 2H), 1.85-1.91 (m, 1H), 0.90 (d, J = 6.1 Hz, 6H). | MS (ESI) m/z 503.1 [M + H]⁺ |
| Example 294 | (4-ethylpiperazin-1-yl)(6-{[5-(trifluoromethyl)pyridin-2-yl]oxy}quinolin-2-yl)methanone | ¹H NMR (500 MHz, DMSO-d₆) δ ppm 8.58-8.59 (m, 1H), 8.48 (d, J = 8.6 Hz, 1H), 8.30 (dd, J = 8.7, 2.6 Hz, 1H), 8.11 (d, J = 9.2 Hz, 1H), 7.89 (d, J = 2.4 Hz, 1H), 7.68-7.72 (m, 2H), 7.39 (d, J = 8.9 Hz, 1H), 3.70-3.73 (m, 2H), 3.44-3.47 (m, 2H), 2.47-2.49 (m, 2H), 2.35-2.38 (m, 4H), 1.87 (s, 3H), 1.01(t, J = 7.2 Hz, 3H). | MS (ESI) m/z 431.1 [M + H]⁺ |
| Example 295 | (6-{[3-bromo-5-(trifluoromethyl)pyridin-2-yl]oxy}quinolin-2-yl)(piperazin-1-yl)methanone | ¹H NMR (400 MHz, DMSO-d₆) δ ppm 8.73 (d, J = 2.1 Hz, 1H), 8.56-8.52 (m, 1H), 8.48 (d, J = 8.5 Hz, 1H), 8.11 (d, J = 9.1 Hz, 1H), 7.92 (d, J = 2.6 Hz, 1H), 7.74 (dd, J = 9.1, 2.6 Hz, 1H), 7.70 (d, J = 8.5 Hz, 1H), 3.69-3.63 (m, 2H), 3.42-3.37 (m, 2H), 2.88-2.82 (m, 2H), 2.76-2.68 (m, 2H). | MS (ESI) m/z 481.0 [M + H]⁺ |
| Example 296 | morpholin-4-yl(6-{[5-(trifluoromethyl)pyridin-2-yl]oxy}quinolin-2-yl)methanone | ¹H NMR (500 MHz, DMSO-d₆) δ ppm 8.58-8.59 (m, 1H). 8.49 (d, J = 8.5 Hz, 1H), 8.30 (dd, J = 8.9, 2.4 Hz, 1H), 8.11 (d, J = 9.2 Hz, 1H), 7.89 (d, J = 2.4 Hz, 1H), 7.70-7.74 (m, 2H), 7.39 (d, J = 8.5 Hz, 1H), 3.71-3.73 (m, 4H), 3.59-3.61 (m, 2H), 3.51-3.53 (m, 2H). | MS (ESI) m/z 404.1 [M + H]⁺ |
| Example 297 | piperidin-1-yl(6-{[5-(trifluoromethyl)pyridin-2-yl]oxy}quinolin-2-yl)methanone | ¹H NMR (500 MHz, DMSO-d₆) δ ppm 8.58-8.59 (m, 1H), 8.47 (d, J = 8.5 Hz, 1H), 8.30 (dd, J = 8.7, 2.6 Hz, 1H), 8.10 (d, J = 9.2 Hz, 1H), 7.88 (d, J = 2.4 Hz, 1H), 7.70 (dd, J = 9.0, 2.6 Hz, 1H), 7.66 (d, J = 8.5 Hz, 1H), 7.39 (d, J = 8.5 Hz, 1H), 3.66-3.69 (m, 2H), 3.36-3.37 (m, 2H), 1.62-1.66 (m, 4H), 1.50-1.53 (m, 1H). | MS (ESI) m/z 402.2 [M + H]⁺ |
| Example 298 | [4-(2, 2-difluoroethyl)piperazin-1-yl](6-{[5- | ¹H NMR (500 MHz, DMSO-d₆) δ ppm 8.59-8.60 (m, 1H), 8.48 (d, J = 8.2 Hz, 1H), 8.30 (dd, J = 8.5, 2.1 Hz, 1H), 8.11 (d, J = 9.2 Hz, 1H), | MS (ESI) m/z |

| Example Number | Name | ¹H NMR | MS |
|---|---|---|---|
| | (trifluoromethyl)pyridin-2-yl]oxy}quinolin-2-yl)methanone | 7.89 (d, J = 2.8 Hz, 1H), 7.69-7.73 (m, 2H), 7.39 (d, J = 8.5 Hz, 1H), 6.17 (tt, J = 55.7, 4.3 Hz, 1H), 3.71-3.73 (m, 2H), 3.47-3.49 (m, 2H), 2.81 (td, J = 15.7, 4.3 Hz, 2H), 2.66-2.69 (m, 2H), 2.55-2.57 (m, 2H). | 467.1 [M + H]⁺ |
| Example 299 | morpholin-4-yl{4-[(6-{[5-(trifluoromethyl)pyridin-2-yl]oxy}quinolin-2-yl)carbonyl]piperazin-1-yl}methanone | ¹H NMR (400 MHz, DMSO-d₆) δ ppm 8.58-8.59 (m, 1H), 8.49 (d, J = 8.2 Hz, 1H), 8.31 (dd, J = 9.2, 2.7 Hz, 1H), 8.12 (d, J = 9.2 Hz, 1H), 7.90 (d, J = 2.7 Hz, 1H), 7.71-7.74 (m, 2H), 7.39 (d, J = 8.9 Hz, 1H), 3.72-3.75 (m, 2H), 3.55-3.58 (m, 4H), 3.49-3.52 (m, 2H), 3.31-3.34 (m, 2H), 3.20-3.22 (m, 2H), 3.16-3.18 (m, 4H). | MS (ESI) m/z 516.0 [M + H]⁺ |
| Example 300 | [(2S,4R)-4-hydroxy-2-(hydroxymethyl)pyrrolidin-1-yl](6-{[5-(trifluoromethyl)pyridin-2-yl]oxy}quinolin-2-yl)methanone | ¹H NMR (400 MHz, DMSO-d₆) δ ppm 8.62-8.58 (m, 1H), 8.47 (dd, J = 8.5, 3.0 Hz, 1H), 8.31 (dd, J = 8.7, 2.6 Hz, 1H), 8.13 (dd, J = 9.1, 5.9 Hz, 1H), 7.89 (t, J = 2.9 Hz, 1H), 7.85 (d, J = 8.5 Hz, 1H), 7.79-7.68 (m, 1H), 7.40 (d, J = 8.7 Hz, 1H), 5.03-4.23 (m, 4H), 3.80-3.49 (m, 3H), 3.25-3.03 (m, 1H), 2.18-1.88 (m, 2H). | ESI m/z 434.1 [M + H]⁺ |
| Example 301 | [(3R)-3-fluoropyrrolidin-1-yl](6-{[5-(trifluoromethoxy)pyridin-2-yl]oxy}quinolin-2-yl)methanone | ¹H NMR (400 MHz, DMSO-d₆) δ ppm 8.47 (d, J = 8.5 Hz, 1H), 8.29 (d, J = 2.9 Hz, 1H), 8.14 (dd, J = 9.1, 5.0 Hz, 1H), 8.04 (dd, J = 8.9, 2.8 Hz, 1H), 7.92-7.86 (m, 1H), 7.85 (d, J = 2.6 Hz, 1H), 7.70 (dd, J = 9.3, 2.9 Hz, 1H), 7.34 (d, J = 8.9 Hz, 1H), 5.52-5.29 (m, 1H), 4.16-3.56 (m, 4H), 2.30-2.03 (m, 2H). | MS (ESI) m/z 422.1 [M + H]+ |
| Example 302 | N-(trans-3-hydroxycyclobutyl)-6-{[5-(trifluoromethyl)pyridin-2-yl]oxy}quinoline-2-carboxamide | ¹H NMR (400 MHz, DMSO-d₆) δ ppm 9.00 (d, J = 7.6 Hz, 1H), 8.64-8.59 (m, 1H), 8.52 (d, J = 8.5 Hz, 1H), 8.31 (dd, J = 8.7, 2.6 Hz, 1H), 8.23 (d, J = 9.1 Hz, 1H), 8.14 (d, J = 8.4 Hz, 1H), 7.92 (d, J = 2.6 Hz, 1H), 7.76 (dd, J = 9.1, 2.6 Hz, 1H), 7.40 (d, J = 8.6 Hz, 1H), 5.04 (d, J = 5.0 Hz, 1H), 4.65-4.52 (m, 1H), 4.40-4.30 (m, 1H), 2.44 (m, 2H), 2.26-2.15 (m, 2H). | ESI m/z 404.1 [M + H]⁺ |
| Example 303 | [trans-3,4-dihydroxypyrrolidin-1-yl](6-{[5-(trifluoromethyl)pyridin-2-yl]oxy}quinolin-2-yl)methanone | ¹H NMR (500 MHz, DMSO-d₆) δ ppm 8.60 (s, 1H), 8.48 (d, J = 8.5 Hz, 1H), 8.31 (m, 1H), 8.13 (m, 1H), 7.92-7.84 (m, 2H), 7.72 (m, 1H), 7.39 (m, 1H), 5.24 (d, J = 3.0 Hz, 1H), 5.15 (bs, 1H), 4.04-3.97 (m, 3H), 3.74-3.58 (m, 2H), 3.52 (d, J = 12.8 Hz, 1H). | ESI m/z 420.1 [M + H]⁺ |
| Example 304 | [(2R,3S)-3-hydroxy-2-(hydroxymethyl)pyrrolidin-1-yl](6-{[5-(trifluoromethyl)pyridin-2-yl]oxy}quinolin-2-yl)methanone | ¹H NMR (400 MHz, DMSO-d₆) δ ppm 8.62-8.57 (m, 1H), 8.47 (d, J = 8.5 Hz, 1H), 8.31 (dd, J = 8.7, 2.6 Hz, 1H), 8.14 (dd, J = 9.1, 6.4 Hz, 1H), 7.92-7.87 (m, 1H), 7.81 (d, J = 8.5, 3.3 Hz, 1H), 7.72 (ddd, J = 9.2, 7.0, 2.4 Hz, 1H), 7.40 (dd, J = 8.7, 2.5 Hz, 1H), 5.03-4.81 (m, 2H), 4.33-4.26 (m, 1H), 4.10 (m, 1H), 3.90-3.38 (m, 3H), 3.25-3.11 (m, 1H), 2.20-2.04 (m, 1H), 1.85-1.72 (m, 1H). | ESI m/z 434.1 [M + H]⁺ |
| Example 305 | [trans-3-hydroxy-4-methoxypyrrolidin-1-yl](6-{[5-(trifluoromethyl)pyridin-2-yl]oxy}quinolin-2-yl)methanone | ¹H NMR (400 MHz, DMSO-d₆) δ ppm 8.60 (d, J = 0.8 Hz, 1H), 8.48 (d, J = 8.6 Hz, 1H), 8.31 (dd, J = 8.7, 2.5 Hz, 1H), 8.16 (dd, J = 9.1, 6.3 Hz, 1H), 7.93-7.84 (m, 2H), 7.73 (dd, J = 9.1, 2.6 Hz, 1H), 7.40 (d, J = 8.7 Hz, 1H), 5.32 (m, 1H), 4.20 (m, 1H), 4.00-3.47 (m, 5H), 3.34 and 3.26 (2s, 3H). | ESI m/z 434.1 [M + H]⁺ |
| Example 306 | [trans-3-hydroxy-4-methylpyrrolidin-1-yl](6-{[5-(trifluoromethyl)pyridin-2-yl]oxy}quinolin-2-yl)methanone | ¹H NMR (400 MHz, DMSO-d₆) δ ppm 8.60 (d, J = 2.3 Hz, 1H), 8.47 (d, J = 8.5 Hz, 1H), 8.31 (dd, J = 8.7, 2.6 Hz, 1H), 8.14 (d, J = 9.1 Hz, 1H), 7.96-7.81 (m, 2H), 7.72 (dt, J = 9.1, 2.6 Hz, 1H), 7.40 (dd, J = 8.7, 1.2 Hz, 1H), 5.15 (dd, J = 25.0, 4.2 Hz, 1H), 4.00-3.77 (m, 3H), 3.59 and 3.40 (2m, 1H), 3.37 and 3.22 (2m, 1H), 2.08 (m, 1H), 1.04 and 0.93 (2d, J = 6.9 Hz, 3H). | ESI m/z 418.1 [M + H]⁺ |
| Example 307 | [cis-3,5-bis(hydroxymethyl)piperidin-1-yl](6-{[5-(trifluoromethyl)pyridin-2-yl]oxy}quinolin-2-yl)methanone | ¹H NMR (400 MHz, DMSO-d₆) δ ppm 8.63-8.58 (m, 1H), 8.47 (d, J = 8.4 Hz, 1H), 8.30 (dd, J = 8.7, 2.6 Hz, 1H), 8.11 (d, J = 9.1 Hz, 1H), 7.89 (d, J = 2.6 Hz, 1H), 7.71 (dd, J = 9.0, 2.6 Hz, 1H), 7.66 (d, J = 8.4 Hz, 1H), 7.40 (d, J = 8.6 Hz, 1H), 4.79-4.58 (m, 2H), 4.40 (t, J = 5.2 Hz, 1H), 3.87-3.79 (m, 1H), 3.45-3.38 | ESI m/z 462.2 [M + H]⁺ |

| Example Number | Name | ¹H NMR | MS |
|---|---|---|---|
| | | (m, 1H), 3.28-3.19 (m, 1H), 3.07 (m, 1H), 2.72-2.62 (m, 1H), 2.39 (t, J = 12.1 Hz, 1H), 1.77-1.69 (m, 2H), 0.96-0.82 (m, 1H). | |
| Example 308 | [4-(pyridin-2-ylmethyl)piperazin-1-yl](6-{[5-(trifluoromethyl)pyridin-2-yl]oxy}quinolin-2-yl)methanone | ¹H NMR (400 MHz, DMSO-d₆) δ ppm 2.43-2.49 (m, 2H), 2.53-2.62 (m, 2H), 3.46-3.57 (m, 2H), 3.66 (s, 2H), 3.71-3.81 (m, 2H), 7.19-7.32 (m, 1H), 7.39 (d, J = 8.7 Hz, 1H), 7.48 (d, J = 7.8 Hz, 1H), 7.64-7.74 (m, 2H), 7.78 (td, J = 7.7, 1.6 Hz, 1H), 7.89 (t, J = 4.9 Hz, 1H), 8.10 (d, J = 9.1 Hz, 1H), 8.30 (dd, J = 8.7, 2.6 Hz, 1H), 8.49 (dd, J = 9.7, 6.6 Hz, 2H), 8.59 (s, 1H) | DCI m/z 494.0 [M + H]⁺ |
| Example 309 | 3,3-dimethyl-1-{4-[(6-{[5-(trifluoromethyl)pyridin-2-yl]oxy}quinolin-2-yl)carbonyl]piperazin-1-yl}butan-1-one | ¹H NMR (400 MHz, DMSO-d, ) δ ppm 8.59-8.60 (m, 1H). 8.50 (d, J = 8.5 Hz, 1H), 8.31 (dd, J = 8.5, 2.4 Hz, 1H), 8.12 (d, J = 9.2 Hz, 1H), 7.90 (d, J = 2.4 Hz, 1H), 7.71-7.76 (m, 2H), 7.39 (d, J = 8.9 Hz, 1H), 3.64-3.71 (m, 4H), 3.49-3.56 (m, 4H), 2.27 (s, 2H), 0.99 (s, 9H). | MS (ESI) m/z 501.1 [M + H]⁺ |
| Example 310 | [(3R)-3-aminopyrrolidin-1-yl](6-{[5-(trifluoromethyl)pyridin-2-yl]oxy}quinolin-2-yl)methanone | ¹H NMR (400 MHz, DMSO-d₆) δ ppm 8.60 (s, 1H), 8.47 (d, J = 8.6 Hz, 1H), 8.30 (dd, J = 8.7, 2.5 Hz, 1H), 8.13 (dd, J = 9.1, 4.6 Hz, 1H), 7.89-7.88 (m, 1H), 7.84 (dd, J = 8.5, 2.3 Hz, 1H), 7.71 (ddd, J = 9.1, 2.2, 2.2 Hz, 1H), 7.39 (d, J = 8.7 Hz, 1H), 3.80-3.25 (m, 2H) 2.05-1.93 (m, 1H), 1.72-1.61 (m, 1H) | MS (ESI) m/z 403.2 [M + H]⁺ |
| Example 311 | (6-{[5-(trifluoromethyl)pyridin-2-yl]oxy}quinolin-2-yl)[4-(3, 3, 3-trifluoropropyl)piperazin-1-yl]methanone | ¹H NMR (400 MHz, DMSO-d₆) δ ppm 8.58-8.59 (m, 1H). 8.48 (d, J = 8.6 Hz, 1H), 8.30 (dd, J = 8.7, 2.6 Hz, 1H), 8.11 (d, J = 9.2 Hz, 1H), 7.89 (d, J = 2.4 Hz, 1H), 7.69-7.73 (m, 2H), 7.39 (d, J = 8.9 Hz, 1H), 3.70-3.73 (m, 2H), 3.46-3.48 (m, 2H), 2.43-2.61 (m, 8H). | MS (ESI) m/z 499.1 [M + H]⁺ |
| Example 312 | (3, 3-difluoropiperidin-1-yl)(6-{[5-(trifluoromethyl)pyridin-2-yl]oxy}quinolin-2-yl)methanone | ¹H NMR (400 MHz, DMSO-d₆, rotamers) δ ppm 1.65-1.85 (m, 2H), 2.05-2.25 (m, 2H), 3.47-3.60 (m, 1H), 3.71-3.82 (m, 1H), 3.88-4.14 (m, 2H), 7.40 (d, J = 8.7 Hz, 1H), 7.66-7.79 (m, 2H), 7.91 (d, J = 2.1 Hz, 1H), 8.12 (d, J = 9.1 Hz, 1H), 8.31 (dd, J = 8.7, 2.5 Hz, 1H), 8.51 (dd, J = 8.5, 4.2 Hz, 1H) | DCI m/z 438.0 [M + H]⁺ |
| Example 313 | [(5S,7S)-7-hydroxy-1-azaspiro[4.4]non-1-yl](6-{[5-(trifluoromethyl)pyridin-2-yl]oxy}quinolin-2-yl)methanone | ¹H NMR (400 MHz, DMSO-d₆) δ ppm 1.50-1.68 (m, 2H), 1.69-1.87 (m, 3H), 1.94-2.28 (m, 3H), 2.40-2.51 (m, 1H), 2.64-2.81 (m, 1H), 3.55-3.69 (m, 2H), 4.36-4.73 (m, 2H), 7.44 (d, J = 8.7 Hz, 1H), 7.71-7.81 (m, 2H), 7.93 (t, J = 4.4 Hz, 1H), 8.16 (dd, J = 16.2, 10.5 Hz, 1H), 8.30-8.41 (m, 1H), 8.51 (t, J = 9.3 Hz, 1H), 8.66 (t, J = 9.0 Hz, 1H) | DCI m/z 458.0 M + H]⁺ |
| Example 314 | [3-(azetidin-1-yl)pyrrolidin-1-yl](6-{[5-(trifluoromethyl)pyridin-2-yl]oxy}quinolin-2-yl)methanone | ¹H NMR (400 MHz, DMSO-d₆) δ ppm 1.59-2.06 (m, 4H), 2.80-3.09 (m, 3H), 3.09-3.19 (m, 2H), 3.36-3.90 (m, 4H), 7.38 (t, J = 13.9 Hz, 1H), 7.71 (dt, J = 9.0, 4.5 Hz, 1H), 7.79-7.92 (m, 2H), 8.11 (dt, J = 20.0, 10.2 Hz, 1H), 8.30 (dd, J = 8.8, 2.4 Hz, 1H), 8.47 (dd, J = 8.5, 2.1 Hz, 1H), 8.52-8.65 (m, 1H) | DCI m/z 443.0 [M + H]⁺ |
| Example 315 | [4-(l, 3-oxazol-4-ylmethyl)piperazin-1-yl](6-{[5-(trifluoromethyl)pyridin-2-yl]oxy}quinolin-2-yl)methanone | ¹H NMR (400 MHz, DMSO-d₆) δ ppm 2.34-2.48 (m, 2H), 2.55 (dd, J = 12.0, 7.2 Hz, 2H), 3.40-3.55 (m, 4H), 3.66-3.83 (m, 2H), 7.39 (d, J = 8.7 Hz, 1H), 7.70 (dd, J = 12.9, 5.7 Hz, 2H), 7.89 (d, J = 2.6 Hz, 1H), 8.00 (s, 1H), 8.06-8.17 (m, 1H), 8.26-8.36 (m, 2H), 8.47 (d, J = 8.6 Hz, 1H), 8.59 (s, 1H) | DCI m/z 484.0 [M + H]⁺ |
| Example 316 | [3-(morpholin-4-yl)pyrrolidin-1-yl](6-{[5-(trifluoromethyl)pyridin-2-yl]oxy}quinolin-2-yl)methanone | ¹H NMR (400 MHz, DMSO-d₆, rotamers) δ ppm 1.69-1.88 (m, 1H), 2.03-2.22 (m, 1H), 2.25-2.49 (m, 4H), 2.74-3.00 (m, 1H), 3.45-3.68 (m, 5.4H), 3.89 (m, J = 45.7, 15.3, 14.5, 6.2 Hz, 2.7H), 7.39 (d, J = 8.7 Hz, 1H), 7.71 (dd, J = 9.1, 2.6 Hz, 1H), 7.87 (dd, J = 15.3, 5.6 Hz, 2H), 8.14 (dd, J = 9.1, 5.8 Hz, 1H), 8.30 (dd, J = 8.7, 2.6 Hz, 1H), 8.47 (d, J = 8.6 Hz, 1H), 8.59 (s, 1H) | DCI m/z 473.0 [M + H]⁺ |

| Example Number | Name | ¹H NMR | MS |
|---|---|---|---|
| Example 317 | N-(2-sulfamoylethyl)-6-{[5-(trifluoromethyl)pyridin-2-yl]oxy}quinoline-2-carboxamide | ¹H NMR (400 MHz, DMSO-d$_6$) δ ppm 3.31-3.45 (m, 2H), 3.80 (dd, J = 13.5, 6.5 Hz, 2H), 7.01 (s, 2H), 7.40 (t, J = 9.2 Hz, 1H), 7.68-7.84 (m, 1H), 7.94 (d, J = 2.6 Hz, 1H), 8.18 (dd, J = 8.8, 6.2 Hz, 2H), 8.55 (d, J = 8.6 Hz, 1H), 8.63 (d, J = 14.3 Hz, 1H), 9.17 (t, J = 6.0 Hz, 1H) | DCI m/z 441.0 [M + H]$^+$ |
| Example 318 | (4-fluoropiperidin-1-yl)(6-{[5-(trifluoromethyl)pyridin-2-yl]oxy}quinolin-2-yl)methanone | ¹H NMR (400 MHz, DMSO-d$_6$) δ ppm 1.66-2.18 (m, 4H), 3.36-3.49 (m, 1H), 3.49-3.64 (m, 1H), 3.70-3.84 (m, 2H), 4.82-4.96 (m, 1H), 4.96-5.12 (m, 1H), 7.38 (dd, J = 10.9, 5.5 Hz, 1H), 7.60-7.77 (m, 2H), 7.88 (dd, J = 7.7, 2.7 Hz, 1H), 8.04-8.17 (m, 1H), 8.25-8.37 (m, 1H), 8.42-8.53 (m, 1H), 8.54-8.67 (m, 1H) | DCI m/z 420.0 [M + H]$^+$ |
| Example 319 | [(3R)-3-(piperidin-1-yl)pyrrolidin-1-yl](6-{[5-(trifluoromethyl)pyridin-2-yl]oxy}quinolin-2-yl)methanone | ¹H NMR (400 MHz, DMSO-d$_6$) δ ppm 8.59-8.60 (m, 1H). 8.46 (d, J = 8.6 Hz, 1H), 8.30 (dd, J = 8.7, 2.6 Hz, 1H), 8.12-8.15 (m, 1H), 7.89 (d, J = 2.4 Hz, 1H), 7.83-7.85 (m, 1H), 7.70-7.73 (m, 1H), 7.38-7.41 (m, 1H), 3.86-3.98 (m, 2H), 3.71-3.79 (m, 1H), 3.45-3.58 (m, 1H), 3.24-3.29 (m, 1H), 2.77-2.88 (m, 1H), 2.39-2.45 (m, 2H), 2.23-2.27 (m, 1H), 2.06-2.17 (m, 1H), 1.68-1.80 (m, 1H), 1.34-1.55 (m, 6H). | MS (ESI) m/z 471.2 [M + H]$^+$ |
| Example 320 | piperazin-1-yl(6-{[5-(trifluoromethyl)-1,3,4-thiadiazol-2-yl]oxy}quinolin-2-yl)methanone | ¹H NMR (400 MHz, DMSO-d$_6$) δ ppm 8.55 (d, J = 8.2 Hz, 1H), 8.24 (d, J = 2.8 Hz, 1H), 8.21 (d, J = 9.2 Hz, 1H), 7.95 (dd, J = 9.3, 2.9 Hz, 1H), 7.74 (d, J = 8.5 Hz, 1H), 3.63-3.65 (m, 2H), 3.33-3.35 (m, 2H), 2.80-2.82 (m, 2H), 2.67-2.69 (m, 2H), 1.90 (s, 3H). | MS (ESI) m/z 410.1 [M + H]$^+$ |
| Example 321 | N-isopropyl-4-[(6-{[5-(trifluoromethyl)pyridin-2-yl]oxy}quinolin-2-yl)carbonyl]piperazine-2-carboxamide | ¹H NMR (400 MHz, DMSO-d$_6$, rotamers) δ ppm 8.62-8.56 (m, 1H), 8.48 (d, J = 8.4 Hz, 1H), 8.30 (dt, J = 8.7, 2.4 Hz, 1H), 8.11 (dd, J = 9.1, 6.0 Hz, 1H), 7.89 (t, J = 2.2 Hz, 1H), 7.78-7.65 (m, 2.5H), 7.53 (d, J = 7.9 Hz, 0.5H), 7.39 (d, J = 8.7 Hz, 1H), 4.48 (dd, J = 12.5, 2.7 Hz, 0.5H), 4.06-3.97 (m, 0.5H), 3.96-3.83 (m, 0.5H), 3.81-3.67 (m, 1H), 3.58 (d, J = 13.2 Hz, 0.5H), 3.24-3.07 (m, 2H), 3.02-2.81 (m, 1.5H), 2.80-2.62 (m, 1.5H), 1.10 (dd, J = 6.6, 2.4 Hz, 3H), 1.00 (dd, J = 16.8, 6.6 Hz, 3H). | MS (ESI) m/z 488.1 [M + H]$^+$ |
| Example 322 | N-methyl-4-[(6-{[5-(trifluoromethyl)pyridin-2-yl]oxy}quinolin-2-yl)carbonyl]piperazine-2-carboxamide | ¹H NMR (400 MHz, DMSO-d$_6$, rotamers) δ ppm 8.62-8.57 (m, 1H), 8.48 (d, J = 8.6 Hz, 1H), 8.32-8.27 (m, 1H), 8.11 (dd, J = 9.1, 4.2 Hz, 1H), 7.93-7.87 (m, 1.5H), 7.81-7.74 (m, 0.5H), 7.74-7.67 (m, 2H), 7.40 (d, J = 8.8 Hz, 1H), 4.55-4.47 (m, 0.5H), 4.12-4.02 (m, 0.5H), 3.73 (d, J = 10.4 Hz, 0.5H), 3.59 (d, J = 13.1 Hz, 0.5H), 3.30-3.21 (m, 2H), 3.20-3.08 (m, 1H), 3.02-2.94 (m, 0.5H), 2.92-2.80 (m, 1.5H), 2.64 (d, J = 4.7 Hz, 1.5H), 2.52 (d, J = 4.7 Hz, 1.5H). | MS (ESI) m/z 460.1 [M + H]$^+$ |
| Example 323 | rac-[(3R,4S)-3,4-dihydroxy-2,5-dimethylpyrrolidin-1-yl](6-{[5-(trifluoromethyl)pyridin-2-yl]oxy}quinolin-2-yl)methanone | ¹H NMR (400 MHz, DMSO-d$_6$) δ ppm 8.60 (bs, 1H), 8.48 (dd, J = 8.5, 2.4 Hz, 1H), 8.31 (dd, J = 8.7, 2.6 Hz, 1H), 8.14 (d, J = 9.2 Hz, 1H), 7.89 (d, J = 2.6 Hz, 1H), 7.80-7.67 (m, 2H), 7.40 (d, J = 8.7 Hz, 1H), 5.02-4.88 (m, 2H), 4.73 and 4.58 (2m, 1H), 4.33 and 4.23 (2m, 1H), 4.12 and 3.93 (2m, 1H), 3.80 and 3.74 (2m, 1H), 1.38 and 1.27 (2d, J = 6.7 Hz, 3H), 0.74 and 0.69 (2d, J = 6.7 Hz, 3H). | ESI m/z 448.1 [M + H]$^+$ |
| Example 324 | [cis-3,4-dimethoxypyrrolidin-1-yl](6-{[5-(trifluoromethyl)pyridin-2-yl]oxy}quinolin-2-yl)methanone | ¹H NMR (400 MHz, DMSO-d$_6$) δ ppm 8.59 (bs, 1H), 8.51-8.45 (m, 1H), 8.31 (dd, J = 8.7, 2.6 Hz, 1H), 8.15 (d, J = 9.0 Hz, 1H), 7.92-7.84 (m, 2H), 7.72 (dd, J = 9.0, 2.6 Hz, 1H), 7.43-7.34 (m, 1H), 4.08-3.92 (m, 3H), 3.85-3.76 (m, 1H), 3.70 (dd, J = 12.6, 5.5 Hz, 1H), 3.62-3.55 (m, 1H), 3.38 (s, 3H), 3.30 (s, 3H). | ESI m/z 448.1 [M + H]$^+$ |
| Example 325 | (3S)-1-[(6-{[5-(trifluoromethyl)pyridin-2-yl]oxy}quinolin-2-yl)carbonyl]piperidine-3-carboxamide | ¹H NMR (400 MHz, DMSO-d$_6$, rotamers) δ ppm 1.40-1.75 (m, 2.6H), 1.88 (dd, J = 53.5, 13.0 Hz, 1.4H), 2.30-2.49 (m, 1H), 2.97 (ddd, J = 34.9, 23.4, 12.3 Hz, 1.56H), 3.20 (dt, J = 15.6, 7.8 Hz, 0.5H), 3.67 (dt, J = 37.3, 18.7 Hz, 1H), 4.37 (d, J = 12.6 Hz, 0.5H), 4.55 (d, J = | DCI m/z 445.0 [M + H]$^+$ |

-continued

| Example Number | Name | ¹H NMR | MS |
|---|---|---|---|
| | | 13.0 Hz, 0.5H), 6.82 (s, 0.5H), 6.94 (s, 0.5H), 7.29-7.53 (m, 2H), 7.70 (ddd, J = 20.1, 11.4, 5.8 Hz, 2H), 7.89 (d, J = 2.6 Hz, 1H), 8.12 (dd, J = 11.3, 9.2 Hz, 1H), 8.30 (dt, J = 8.6, 2.6 Hz, 1H), 8.48 (dd, J = 8.4, 2.0 Hz, 1H), 8.59 (dd, J = 2.8, 1.8 Hz, 1H) | |
| Example 326 | N-(2-hydroxyethyl)-6-{[5-(trifluoromethyl)pyridin-2-yl]oxy}quinoline-2-carboxamide | ¹H NMR (400 MHz, DMSO-d$_6$) δ ppm 8.83 (t, J = 5.8 Hz, 1H), 8.61-8.62 (m, 1H), 8.54 (d, J = 8.5 Hz, 1H), 8.31 (dd, J = 8.7, 2.6 Hz, 1H), 8.11-8.22 (m, 2H), 7.93 (d, J = 2.5 Hz, 1H), 7.76 (dd, J = 9.2, 2.8 Hz, 1H), 7.41 (d, J = 8.5 Hz, 1H), 4.86 (t, 5.3 Hz, 1H), 3.58-3.62 (m, 2H), 3.45-3.49 (m, 2H). | MS (ESI) m/z 378.1 [M + H]⁺ |
| Example 327 | N-(tetrahydro-2H-pyran-4-yl)-6-{[5-(trifluoromethyl)pyridin-2-yl]oxy}quinoline-2-carboxamide | ¹H NMR (400 MHz, DMSO-d$_6$) δ ppm 8.77 (d, J = 8.2 Hz, 1H), 8.61-8.62 (m, 1H), 8.53 (d, J = 8.2 Hz, 1H), 8.31 (dd, J = 8.7, 2.6 Hz, 1H), 8.24 (d, J = 9.2 Hz, 1H), 8.18 (d, J = 8.5 Hz, 1H), 7.93 (d, J = 2.8 Hz, 1H), 7.76 (dd, J = 9.0, 2.6 Hz, 1H), 7.41 (d, J = 8.9 Hz, 1H), 4.05-4.15 (m, 1H), 3.90-3.93 (m, 2H), 3.40-3.46 (m, 2H), 1.71-1.81 (m, 4H). | MS (ESI) m/z 418.1 [M + H]⁺ |
| Example 328 | 6-{[2-(piperazin-1-ylcarbonyl)quinolin-6-yl]oxy}nicotinonitrile | ¹H NMR (400 MHz, DMSO-d$_6$) δ ppm 8.67 (d, J = 2.4 Hz, 1H), 8.47 (d, J = 8.2 Hz, 1H), 8.39 (dd, J = 8.7, 2.3 Hz, 1H), 8.11 (d, J = 9.2 Hz, 1H), 7.88 (d, J = 2.4 Hz, 1H), 7.64-7.73 (m, 2H), 7.38 (d, J = 8.5 Hz, 1H), 3.63-3.65 (m, 2H), 3.34-3.36 (m, 2H), 2.79-2.82 (m, 2H), 2.67-2.69 (m, 2H), 1.85 (s, 3H). | MS (ESI) m/z 360.1 [M + H]⁺ |
| Example 329 | 7-[(6-{[5-(trifluoromethyl)pyridin-2-yl]oxy}quinolin-2-yl)carbonyl]hexahydro[1,3]oxazolo[3,4-a]pyrazin-3-one | ¹H NMR (400 MHz, DMSO-d$_6$) δ ppm 2.85-3.05 (m, 1 H) 3.12-3.27 (m, 2 H) 3.58-4.19 (m, 4 H) 4.28-4.56 (m, 1 H) 4.57-4.84 (m, 1 H) 7.45 (d, J = 8.85 Hz, 1 H) 7.74-7.84 (m, 2 H) 7.96 (t, J = 2.29 Hz, 1 H) 8.19 (d, J = 9.16 Hz, 1 H) 8.36 (dd, J = 8.85, 2.44 Hz, 1 H) 8.56 (dd, J = 8.54, 2.14 Hz, 1 H) 8.61-8.69 (m, 1 H) | MS (ESI) m/z 459.0 [M + H]⁺ |
| Example 330 | (4,4-difluoropiperidin-1-yl)(6-{[5-(trifluoromethyl)pyridin-2-yl]oxy}quinolin-2-yl)methanone | ¹H NMR (400 MHz, DMSO-d$_6$) δ ppm 2.01-2.23 (m, 4H), 3.61 (dd, J = 18.3, 12.7 Hz, 2H), 3.78-3.89 (m, 2H), 7.39 (d, J = 8.7 Hz, 1H), 7.65-7.82 (m, 2H), 7.90 (d, J = 2.6 Hz, 1H), 8.12 (d, J = 9.1 Hz, 1H), 8.30 (dd, J = 8.7, 2.6 Hz, 1H), 8.50 (d, J = 8.5 Hz, 1H), 8.56-8.63 (m, 1H) | DCI m/z 438.0 [M + H]⁺ |
| Example 331 | N-[(3R)-pyrrolidin-3-yl]-6-{[5-(trifluoromethyl)pyridin-2-yl]oxy}quinoline-2-carboxamide | ¹H NMR (400 MHz, DMSO-d$_6$) δ ppm 8.61-8.62 (m, 1H), 8.56 (d, J = 8.5 Hz, 1H), 8.32 (dd, J = 8.7, 2.6 Hz, 1H), 8.23 (d, J = 9.2 Hz, 1H), 8.18 (d, J = 8.6 Hz, 1H), 7.95 (d, J = 2.4 Hz, 1H), 7.78 (dd, J = 9.2, 2.8 Hz, 1H), 7.41 (d, J = 8.9 Hz, 1H), 4.66-4.74 (m, 1H), 3.41-3.53 (m, 2H), 3.22-3.37 (m, 2H), 2.26-2.35 (m, 1H), 2.08-2.17 (m, 1H). | MS (ESI) m/z 403.1 [M + H]⁺ |
| Example 332 | (6-{[5-(trifluoromethyl)pyridin-2-yl]oxy}quinolin-2-yl){4-[(3,3,3-trifluoropropyl)sulfonyl]piperazin-1-yl}methanone | ¹H NMR (400 MHz, DMSO-d$_6$) δ ppm 2.60-2.86 (m, 2H), 3.32-3.50 (m, 6H), 3.56-3.70 (m, 2H), 3.73-3.89 (m, 2H), 7.40 (d, J = 8.6 Hz, 1H), 7.67-7.82 (m, 2H), 7.91 (d, J = 2.6 Hz, 1H), 8.13 (d, J = 9.1 Hz, 1H), 8.31 (dd, J = 8.7, 2.6 Hz, 1H), 8.51 (d, J = 8.4 Hz, 1H), 8.59 (dd, J = 1.6, 0.8 Hz, 1H) | DCI m/z 563.0 [M + H]⁺ |
| Example 333 | (8aR)-7-[(6-{[5-(trifluoromethyl)pyridin-2-yl]oxy}quinolin-2-yl)carbonyl]hexahydro[1,3]oxazolo[3,4-a]pyrazin-3-one | ¹H NMR (400 MHz, DMSO-d$_6$, rotamers) δ ppm 2.90 (dt, J = 21.4, 8.2 Hz, 1H), 3.04-3.24 (m, 2H), 3.57 (t, J = 10.8 Hz, 0.5H), 3.76 (dd, J = 13.3, 3.3 Hz, 0.5H), 3.86 (dd, J = 8.9, 5.4 Hz, 1H), 3.91-4.16 (m, 2H), 4.28 (t, J = 8.5 Hz, 0.5H), 4.46 (t, J = 8.6 Hz, 0.5H), 4.57 (d, J = 12.8 Hz, 0.5H), 4.72 (dd, J = 12.6, 3.3 Hz, 0.5H), 7.40 (d, J = 8.7 Hz, 1H), 7.74 (ddd, J = 9.2, 6.9, 3.2 Hz, 2H), 7.90 (t, J = 2.4 Hz, 1H), 8.13 (d, J = 9.1 Hz, 1H), 8.31 (dd, J = 8.7, 2.5 Hz, 1H), 8.51 (dd, J = 8.5, 2.2 Hz, 1H), 8.59 (s, 1H) | DCI m/z 459.0 [M + H]⁺ |

-continued

| Example Number | Name | ¹H NMR | MS |
|---|---|---|---|
| Example 334 | N-(3-hydroxy-3-methylbutyl)-6-{[5-(trifluoromethyl)pyridin-2-yl]oxy}quinoline-2-carboxamide | ¹H NMR (400 MHz, DMSO-$d_6$) δ ppm 8.99 (t, J = 5.7 Hz, 1H), 8.61 (d, J = 3.0 Hz, 1H), 8.53 (d, J = 8.5 Hz, 1H), 8.31 (dd, J = 8.7, 2.6 Hz, 1H), 8.20-8.13 (m, 2H), 7.92 (d, J = 2.6 Hz, 1H), 7.75 (dd, J = 9.1, 2.6 Hz, 1H), 7.40 (d, J = 8.6 Hz, 1H), 4.47 (s, 1H), 3.52-3.43 (m, 2H), 1.71 (t, J = 7.4 Hz, 2H), 1.18 (s, 6H). | MS (ESI) m/z 420.0 [M + H]⁺ |
| Example 335 | N-[(2R)-pyrrolidin-2-ylmethyl]-6-{[5-(trifluoromethyl)pyridin-2-yl]oxy}quinoline-2-carboxamide | ¹H NMR (400 MHz, DMSO-$d_6$) δ ppm 8.81 (t, J = 5.8 Hz, 1H), 8.61 (d, J = 3.1 Hz, 1H), 8.54 (d, J = 8.5 Hz, 1H), 8.31 (dd, J = 8.7, 2.6 Hz, 1H), 8.23-8.16 (m, 2H), 7.93 (d, J = 2.6 Hz, 1H), 7.75 (dd, J = 9.1, 2.6 Hz, 1H), 7.40 (d, J = 8.7 Hz, 1H), 3.46-3.36 (m, 2H), 3.25-3.08 (m, 2H), 3.11-2.71 (m, 2H), 1.95-1.52 (m, 3H), 1.47-1.21 (m, 1H). | MS (ESI) m/z 417.1 [M + H]⁺ |
| Example 336 | N-[(1-hydroxycyclobutyl)methyl]-6-{[5-(trifluoromethyl)pyridin-2-yl]oxy}quinoline-2-carboxamide | ¹H NMR (400 MHz, DMSO-$d_6$) δ ppm 8.63-8.53 (m, 3H), 8.31 (dd, J = 8.7, 2.6 Hz, 1H), 8.25-8.18 (m, 2H), 7.94 (d, J = 2.6 Hz, 1H), 7.76 (dd, J = 9.1, 2.7 Hz, 1H), 7.41 (d, J = 8.7 Hz, 1H), 5.46 (s, 1H), 3.54 (d, J = 6.0 Hz, 2H), 2.20-1.90 (m, 4H), 1.78-1.44 (m, 2H). | MS (ESI) m/z 418.0 [M + H]⁺ |
| Example 337 | N-[2-(2-oxopyrrolidin-1-yl)ethyl]-6-{[5-(trifluoromethyl)pyridin-2-yl]oxy}quinoline-2-carboxamide | ¹H NMR (400 MHz, DMSO-$d_6$) δ ppm 9.01 (t, J = 6.0 Hz, 1H), 8.60-8.61 (m, 1H), 8.53 (d, J = 8.6 Hz, 1H), 8.31 (dd, J = 8.7, 2.6 Hz, 1H), 8.15-8.19 (m, 2H), 7.93 (d, J = 2.4 Hz, 1H), 7.76 (dd, J = 9.2, 2.4 Hz, 1H), 7.40 (d, J = 8.9 Hz, 1H), 3.42-3.53 (m, 6H), 2.15-2.19 (m, 2H), 1.87-1.94 (m, 2H). | MS (ESI) m/z 445.1 [M + H]⁺ |
| Example 338 | N-(2-aminoethyl)-6-{[5-(trifluoromethyl)pyridin-2-yl]oxy}quinoline-2-carboxamide | ¹H NMR (400 MHz, DMSO-$d_6$) δ ppm 8.95 (t, J = 5.9 Hz, 1H), 8.62-8.59 (m, 1H), 8.53 (d, J = 8.6 Hz, 1H), 8.31 (dd, J = 8.7, 2.6 Hz, 1H), 8.19 (dd, J = 8.8, 6.9 Hz, 2H), 7.93 (d, J = 2.6 Hz, 1H), 7.75 (dd, J = 9.1, 2.6 Hz, 1H), 7.40 (d, J = 8.8 Hz, 1H), 3.43 (q, J = 6.3 Hz, 2H), 2.82 (t, J = 6.4 Hz, 2H). | MS (ESI) m/z 377.0 [M + H]⁺ |
| Example 339 | [2-(hydroxymethyl)morpholin-4-yl](6-{[5-(trifluoromethyl)pyridin-2-yl]oxy}quinolin-2-yl)methanone | 1H NMR (400 MHz, DMSO-$d_6$) δ ppm 2.97-3.09 (m, 1 H) 3.19-3.29 (m, 1 H) 3.37-3.62 (m, 4 H) 3.67-4.03 (m, 2 H) 4.33-4.58 (m, 1 H) 4.63-4.92 (m, 1 H) 7.39 (d, J = 8.24 Hz, 1 H) 7.67-7.76 (m, 2 H) 7.90 (d, J = 2.44 Hz, 1 H) 8.12 (d, J = 8.85 Hz, 1 H) 8.30 (dd, J = 8.70, 2.59 Hz, 1 H) 8.49 (d, J = 8.54 Hz, 1 H) 8.59 (s, 1 H) | MS (ESI) m/z 434.0 [M + H]⁺ |
| Example 340 | [2-(fluoromethyl)morpholin-4-yl](6-{[5-(trifluoromethyl)pyridin-2-yl]oxy}quinolin-2-yl)methanone | 1H NMR (500 MHz, DMSO-$d_6$) δ ppm 2.85-3.11 (m, 1 H) 3.15-3.30 (m, 1 H) 3.52-3.66 (m, 1 H) 3.71-3.90 (m, 3 H) 4.32-4.65 (m, 3 H) 7.40 (d, J = 8.54 Hz, 1 H) 7.69-7.78 (m, 2 H) 7.90 (d, J = 2.44 Hz, 1 H) 8.12 (d, J = 9.16 Hz, 1 H) 8.31 (dd, J = 8.85, 2.44 Hz, 1 H) 8.50 (d, J = 8.54 Hz, 1 H) 8.59 (s, 1 H) | MS (ESI) m/z 436.0 [M + H]⁺ |
| Example 341 | (1-hydroxy-7-azaspiro[3.5]non-7-yl)(6-{[5-(trifluoromethyl)pyridin-2-yl]oxy}quinolin-2-yl)methanone | 1H NMR (500 MHz, DMSO-$d_6$) δ ppm 1.19-1.36 (m, 2 H) 1.45-1.68 (m, 4 H) 1.70-1.86 (m, 2 H) 2.05-2.18 (m, 1 H) 3.22-3.30 (m, 1 H) 3.37-3.50 (m, 1 H) 3.75-3.89 (m, 1 H) 3.91-4.15 (m, 1 H) 4.97 (dd, J = 10.38, 5.80 Hz, 1 H) 7.39 (dd, J = 8.70, 2.29 Hz, 1 H) 7.65 (d, J = 8.54 Hz, 1 H) 7.68-7.73 (m, 1 H) 7.84-7.95 (m, 1 H) 8.04-8.18 (m, 1 H) 8.26-8.37 (m, 1 H) 8.47 (dd, J = 8.39, 4.12 Hz, 1 H) 8.59 (s, 1 H) | MS (ESI) m/z 458.0 [M + H]⁺ |
| Example 342 | 6-[(6-{[5-(trifluoromethyl)pyridin-2-yl]oxy}quinolin-2-yl)carbonyl]-5,6,7,8-tetrahydropyrido[4,3-d]pyrimidin-4(3H)-one | 1H NMR (400 MHz, DMSO-$d_6$) δ ppm 2.70-2.83 (m, 2 H) 3.72 (t, J = 5.65 Hz, 1 H) 3.97 (t, J = 5.80 Hz, 1 H) 4.35 (s, 1 H) 4.53 (s, 1 H) 7.40 (d, J = 8.54 Hz, 1 H) 7.69-7.81 (m, 2 H) 7.89-7.94 (m, 1 H) 8.04-8.18 (m, 2 H) 8.26-8.34 (m, 1 H) 8.51 (dd, J = 8.55, 4.27 Hz, 1 H) 8.60 (d, J = 6.41 Hz, 1 H) 12.48 (s, 1 H) | MS (ESI) m/z 468.0 [M + H]⁺ |
| Example 343 | 4-[(6-{[5-(trifluoromethyl)pyridin-2-yl]oxy}quinolin-2-yl)carbonyl]-1,4-diazepan-2-one | 1H NMR (400 MHz, DMSO-$d_6$) δ ppm 1.78-1.96 (m, 2 H) 3.22-3.29 (m, 2 H) 3.59 (t, J = 5.65 Hz, 1 H) 3.85 (t, J = 5.80 Hz, 1 H) 4.22 (s, 1 H) 4.31 (s, 1 H) 7.36-7.45 (m, 1 H) 7.61-7.76 (m, 3 H) 7.90 (d, J = 2.75 Hz, 1 H) 8.10 (t, J = 9.77 Hz, 1 H) 8.30 (dd, J = 8.70, 1.98 Hz, 1 H) 8.43-8.53 (m, 1 H) 8.56-8.64 (m, 1 H) | MS (ESI) m/z 431.0 [M + H]⁺ |

| Example Number | Name | ¹H NMR | MS |
|---|---|---|---|
| Example 344 | N-(2,2,2-trifluoroethyl)-6-{[5-(trifluoromethyl)pyridin-2-yl]oxy}quinoline-2-carboxamide | 1H NMR (400 MHz, DMSO-$d_6$) δ ppm 4.09-4.27 (m, 2 H) 7.42 (d, J = 8.85 Hz, 1 H) 7.79 (dd, J = 9.16, 2.44 Hz, 1 H) 7.96 (d, J = 2.75 Hz, 1 H) 8.22 (dd, J = 13.12, 8.85 Hz, 2 H) 8.32 (dd, J = 8.70, 2.59 Hz, 1 H) 8.55-8.65 (m, 2 H) 9.46 (t, J = 6.71 Hz, 1 H) | MS (ESI) m/z 416.0 [M + H]⁺ |
| Example 345 | (2-hydroxy-6-azaspiro[3.4]oct-6-yl)(6-{[5-(trifluoromethyl)pyridin-2-yl]oxy}quinolin-2-yl)methanone | 1H NMR (400 MHz, DMSO-$d_6$) δ ppm 1.74-1.98 (m, 4 H) 2.14-2.37 (m, 2 H) 3.47-3.61 (m, 2 H) 3.66 (d, J = 4.27 Hz, 1 H) 3.70-3.81 (m, 1 H) 3.95-4.25 (m, 1 H) 4.92-5.09 (m, 1 H) 7.39 (d, J = 8.54 Hz, 1 H) 7.67-7.75 (m, 1 H) 7.80-7.91 (m, 2 H) 8.14 (dd, J = 9.16, 3.66 Hz, 1 H) 8.30 (d, J = 8.85 Hz, 1 H) 8.46 (dd, J = 8.54, 3.97 Hz, 1 H) 8.59 (s, 1 H) | MS (ESI) m/z 444.0 [M + H]⁺ |
| Example 346 | N-(2-fluoroethyl)-6-{[5-(trifluoromethyl)pyridin-2-yl]oxy}quinoline-2-carboxamide | 1H NMR (400 MHz, DMSO-$d_6$) δ ppm 3.61-3.81 (m, 2 H) 4.57 (t, J = 5.19 Hz, 1 H) 4.69 (t, J = 5.19 Hz, 1 H) 7.41 (d, J = 8.85 Hz, 1 H) 7.77 (dd, J = 9.16, 2.44 Hz, 1 H) 7.94 (d, J = 2.44 Hz, 1 H) 8.20 (t, J = 9.31 Hz, 2 H) 8.31 (dd, J = 8.85, 2.44 Hz, 1 H) 8.55 (d, J = 8.24 Hz, 1 H) 8.61 (s, 1 H) 9.07 (t, J = 5.95 Hz, 1 H) | MS (ESI) m/z 380.0 [M + H]⁺ |
| Example 347 | N-(2,2-difluoroethyl)-6-{[5-(trifluoromethyl)pyridin-2-yl]oxy}quinoline-2-carboxamide | 1H NMR (400 MHz, DMSO-$d_6$) δ ppm 3.71-3.90 (m, 2 H) 6.01-6.41 (m, 1 H) 7.41 (d, J = 8.54 Hz, 1 H) 7.78 (dd, J = 9.16, 2.75 Hz, 1 H) 7.95 (d, J = 2.44 Hz, 1 H) 8.21 (t, J = 9.00 Hz, 2 H) 8.32 (dd, J = 8.70, 2.59 Hz, 1 H) 8.57 (d, J = 8.54 Hz, 1 H) 8.62 (s, 1 H) 9.21 (t, J = 6.26 Hz, 1 H) | MS (ESI) m/z 398.0 [M + H]⁺ |
| Example 348 | [(3S,4S)-3-hydroxy-4-(methylsulfanyl)pyrrolidin-1-yl](6-{[5-(trifluoromethyl)pyridin-2-yl]oxy}quinolin-2-yl)methanone. | ¹H NMR (400 MHz, DMSO-$d_6$) δ ppm 8.63-8.57 (m, 1H), 8.49 (d, J = 8.5 Hz, 1H), 8.31 (dd, J = 8.7, 2.6 Hz, 1H), 8.16 (d, J = 9.1 Hz, 1H), 7.93-7.85 (m, 2H), 7.73 (dd, J = 9.0, 2.6 Hz, 1H), 7.40 (d, J = 8.6 Hz, 1H), 5.56-5.43 (m, 1H), 4.31-3.97 (m, 2H), 3.89-3.46 (m, 3H), 3.28-3.18 (m, 1H), 2.19 and 2.11 (2s, 3H). | ESI m/z 450.1 [M + H]⁺ |
| Example 349 | N-(1,1-dioxidotetrahydro-2H-thiopyran-3-yl)-6-{[5-(trifluoromethyl)pyridin-2-yl]oxy}quinoline-2-carboxamide | ¹H NMR (400 MHz, DMSO-$d_6$) δ ppm 9.21-9.10 (m, 1H), 8.64-8.59 (m, 1H), 8.59-8.50 (m, 1H), 8.35-8.29 (m, 1H), 8.23-8.16 (m, 2H), 7.94 (t, J = 3.8 Hz, 1H), 7.85-7.71 (m, 1H), 7.46-7.36 (m, 1H), 4.54-4.41 (m, 1H), 3.42-3.26 (m, 2H), 3.22-3.01 (m, 2H), 2.17-2.04 (m, 1H), 2.03-1.72 (m, 3H). | ESI m/z 466.1 [M + H]⁺ |
| Example 350 | [cis-3,4-dihydroxypiperidin-1-yl](6-{[5-(trifluoromethyl)pyridin-2-yl]oxy}quinolin-2-yl)methanone | ¹H NMR (400 MHz, DMSO-$d_6$) δ ppm 8.58 (s, 1H), 8.47 (d, J = 8.6 Hz, 1H), 8.30 (dd, J = 8.7, 2.5 Hz, 1H), 8.10 (d, J = 9.1 Hz, 1H), 7.88 (d, J = 2.6 Hz, 1H), 7.69 (ddd, J = 20.6, 11.0, 5.6 Hz, 2H), 7.39 (d, J = 8.7 Hz, 1H), 4.86 and 4.67 (2d, J = 4.7 Hz, 1H), 4.63 (m, 1H), 3.90-3.37 (m, 6H), 1.83-1.55 (m, 2H). | ESI m/z 434.1 [M + H]⁺ |
| Example 351 | [trans-3-hydroxy-4-(methylsulfonyl)pyrrolidin-1-yl](6-{[5-(trifluoromethyl)pyridin-2-yl]oxy}quinolin-2-yl)methanone | ¹H NMR (400 MHz, DMSO-$d_6$) δ ppm 8.60 (bs, 1H), 8.50 (dd, J = 8.6, 3.9 Hz, 1H), 8.31 (dd, J = 8.7, 2.7 Hz, 1H), 8.16 (t, J = 9.0 Hz, 1H), 7.94-7.88 (m, 2H), 7.74 (dt, J = 9.0, 2.4 Hz, 1H), 7.40 (d, J = 8.6 Hz, 1H), 5.95-5.84 (m, 1H), 4.71-4.59 (m, 1H), 4.39-3.56 (m, 5H), 3.14 and 3.08 (2s, 3H). | ESI m/z 482.1 [M + H]⁺ |
| Example 352 | 1,4-dioxa-7-azaspiro[4.4]non-7-yl(6-{[5-(trifluoromethyl)pyridin-2-yl]oxy}quinolin-2-yl)methanone | ¹H NMR (400 MHz, DMSO-$d_6$) δ ppm 8.59 (bs, 1H), 8.48 (d, J = 8.5 Hz, 1H), 8.30 (dd, J = 8.7, 2.6 Hz, 1H), 8.15 (dd, J = 9.1, 3.1 Hz, 1H), 7.92-7.83 (m, 2H), 7.72 (dd, J = 9.0, 2.6 Hz, 1H), 7.40 (d, J = 8.6 Hz, 1H), 4.01-3.84 (m, 6H), 3.69 (t, J = 7.5 Hz, 1H), 3.61 (s, 1H), 2.13-2.05 (m, 2H). | ESI m/z 446.1 [M + H]⁺ |
| Example 353 | [4-(methoxyimino)piperidin-1-yl](6-{[5-(trifluoromethyl)pyridin-2-yl]oxy}quinolin-2-yl)methanone | ¹H NMR (400 MHz, Benzene-$d_6$) δ 8.27-8.16 (m, 1H), 7.98 (dd, J = 9.3, 5.6 Hz, 1H), 7.71 (dd, J = 8.5, 1.8 Hz, 1H), 7.47 (dd, J = 8.5, 2.5 Hz, 1H), 7.30-7.18 (m, 3H), 6.48 (d, J = 8.6 Hz, 1H), 3.80 (d, J = 5.9 Hz, 3H), 3.71 (dt, J = 14.8, 6.1 Hz, 2H), 3.44 (dt, J = 19.8, 6.0 Hz, 2H), 2.69 (t, J = 6.0 Hz, 1H), 2.55 (t, J = 6.2 Hz, 2H), 2.40-2.33 (m, 1H), 2.31-2.20 (m, 1H). | ESI m/z 445.0 [M + H]⁺ |
| Example 354 | (2-hydroxy-7-azaspiro[3.5]non-7- | 1H NMR (400 MHz, DMSO-$d_6$) δ ppm 1.44-1.55 (m, 2 H) 1.55-1.68 (m, 4 H) 2.12-2.25 | MS (ESI) |

| Example Number | Name | ¹H NMR | MS |
|---|---|---|---|
| | yl)(6-{5-(trifluoromethyl)pyridin-2-yl]oxy}quinolin-2-yl)methanone | (m, 2 H) 3.22-3.32 (m, 2 H) 3.55-3.68 (m, 2 H) 4.00-4.19 (m, 1 H) 4.91-4.98 (m, 1 H) 7.39 (d, J = 8.54 Hz, 1 H) 7.61-7.74 (m, 2 H) 7.88 (d, J = 2.44 Hz, 1 H) 8.09 (d, J = 8.85 Hz, 1 H) 8.30 (dd, J = 8.70, 2.59 Hz, 1 H) 8.46 (d, J = 8.54 Hz, 1 H) 8.59 (s, 1 H) | m/z 458.0 [M + H]⁺ |
| Example 355 | 6-{5-(trifluoromethyl)pyridin-2-yl]oxy}-N-(3,3,3-trifluoropropyl)quinoline-2-carboxamide | 1H NMR (500 MHz, DMSO-d₆) δ ppm 2.58-2.72 (m, 2 H) 3.63 (q, J = 6.71 Hz, 2 H) 7.41 (d, J = 8.85 Hz, 1 H) 7.77 (dd, J = 9.16, 2.75 Hz, 1 H) 7.94 (d, J = 2.44 Hz, 1 H) 8.19 (d, J = 8.85, 4.88 Hz, 2 H) 8.32 (dd, J = 8.70, 2.59 Hz, 1 H) 8.55 (d, J = 8.24 Hz, 1 H) 8.61 (s, 1 H) 9.15 (t, J = 6.10 Hz, 1 H) | MS (ESI) m/z 430.0 [M + H]⁺ |
| Example 356 | [(7S,8aR)-7-fluorohexahydropyrrolo[1,2-a]pyrazin-2(1H)-yl](6-{5-(trifluoromethyl)pyridin-2-yl]oxy}quinolin-2-yl)methanone | 1H NMR (400 MHz, DMSO-d₆) δ ppm 1.47-2.13 (m, 2 H) 2.24-2.44 (m, 3 H) 2.57-3.00 (m, 2 H) 3.01-3.24 (m, 1 H) 3.48-3.61 (m, 1 H) 3.80 (dd, J = 60.27, 12.66 Hz, 1 H) 4.63 (dd, J = 62.71, 12.66 Hz, 1 H) 5.08-5.38 (m, 1 H) 7.39 (d, J = 8.54 Hz, 1 H) 7.66-7.75 (m, 2 H) 7.89 (d, J = 2.44 Hz, 1 H) 8.11 (d, J = 9.16 Hz, 1 H) 8.30 (dd, J = 8.85, 2.44 Hz, 1 H) 8.49 (d, J = 8.55 Hz, 1 H) 8.58 (s, 1 H) | MS (ESI) m/z 461.0 [M + H]⁺ |
| Example 357 | [(3R,7S,8aR)-7-fluoro-3-methylhexahydropyrrolo[1,2-a]pyrazin-2(1H)-yl](6-{5-(trifluoromethyl)pyridin-2-yl]oxy}quinolin-2-yl)methanone | 1H NMR (500 MHz, DMSO-d₆) δ ppm 1.32 (t, J = 7.02 Hz, 3 H) 1.51-2.13 (m, 2 H) 2.16-2.31 (m, 2 H) 2.32-2.46 (m, 1 H) 2.71-2.81 (m, 1 H) 2.91-3.06 (m, 1 H) 3.47-3.58 (m, 1 H) 3.67-3.98 (m, 1 H) 4.59-4.89 (m, 1 H) 5.13-5.37 (m, 1 H) 7.39 (d, J = 8.85 Hz, 1 H) 7.64-7.74 (m, 2 H) 7.89 (t, J = 2.14 Hz, 1 H) 8.11 (dd, J = 9.00, 6.87 Hz, 1 H) 8.30 (dd, J = 8.85, 2.44 Hz, 1 H) 8.48 (dd, J = 8.39, 5.34 Hz, 1 H) 8.58 (s, 1 H) | MS (ESI) m/z 475.0 [M + H]⁺ |
| Example 358 | [(3R,8aR)-7,7-difluoro-3-methylhexahydropyrrolo[1,2-a]pyrazin-2(1H)-yl](6-{5-(trifluoromethyl)pyridin-2-yl]oxy}quinolin-2-yl)methanone | 1H NMR (500 MHz, DMSO-d₆) δ ppm 1.37 (dd, J = 6.87, 3.81 Hz, 3 H) 1.80-2.14 (m, 1 H) 2.18-2.44 (m, 3 H) 2.45-2.59 (m, 1 H) 2.72-3.21 (m, 2 H) 3.35-3.44 (m, 1 H) 3.69-4.02 (m, 1 H) 4.57-4.91 (m, 1 H) 7.39 (d, J = 8.54 Hz, 1 H) 7.65-7.74 (m, 2 H) 7.87-7.91 (m, 1 H) 8.12 (t, J = 8.54 Hz, 1 H) 8.31 (dd, J = 8.54, 2.44 Hz, 1 H) 8.45-8.52 (m, 1 H) 8.58 (s, 1 H) | MS (ESI) m/z 493.0 [M + H]⁺ |
| Example 359 | [(7S,8aS)-7-fluorohexahydropyrrolo[1,2-a]pyrazin-2(1H)-yl](6-{5-(trifluoromethyl)pyridin-2-yl]oxy}quinolin-2-yl)methanone | 1H NMR (500 MHz, DMSO-d₆) δ ppm 1.30-1.67 (m, 1 H) 1.95-2.48 (m, 4 H) 2.70-3.06 (m, 2 H) 3.09-3.29 (m, 2 H) 3.80 (dd, J = 60.12, 12.82 Hz, 1 H) 4.64 (dd, J = 63.02, 12.66 Hz, 1 H) 5.07-5.31 (m, 1 H) 7.39 (d, J = 8.54 Hz, 1 H) 7.66-7.74 (m, 2 H) 7.89 (d, J = 2.44 Hz, 1 H) 8.11 (dd, J = 9.16, 3.05 Hz, 1 H) 8.30 (dd, J = 8.54, 2.44 Hz, 1 H) 8.48 (dd, J = 8.55, 1.83 Hz, 1 H) 8.59 (s, 1 H) | MS (ESI) m/z 461.0 [M + H]⁺ |
| Example 360 | 1,4,6,7-tetrahydro-5H-imidazo[4,5-c]pyridin-5-yl(6-{5-(trifluoromethyl)pyridin-2-yl]oxy}quinolin-2-yl)methanone | 1H NMR (400 MHz, DMSO-d₆) δ ppm 2.61-2.83 (m, 2 H) 3.68 (t, J = 5.65 Hz, 2 H) 4.03 (t, J = 5.49 Hz, 1 H) 4.42-4.79 (m, 2 H) 7.40 (d, J = 8.54 Hz, 1 H) 7.45-7.59 (m, 1 H) 7.68-7.77 (m, 2 H) 7.91 (d, J = 2.44 Hz, 1 H) 8.14 (d, J = 9.16 Hz, 1 H) 8.31 (dd, J = 8.55, 2.44 Hz, 1 H) 8.50 (t, J = 7.78 Hz, 1 H) 8.60 (s, 1 H) 11.92 (s, 1 H) | MS (ESI) m/z 440.0 [M + H]⁺ |
| Example 361 | N-[(4-benzylmorpholin-3-yl)methyl]-6-{5-(trifluoromethyl)pyridin-2-yl]oxy}quinoline-2-carboxamide | ¹H NMR (500 MHz, CDCl₃) δ ppm 8.82 (bs, 1H), 8.46 (bs, 1H), 8.38-8.20 (m, 3H), 7.99 (dd, J = 8.7, 2.4 Hz, 1H), 7.68 (d, J = 2.5 Hz, 1H), 7.63 (dd, J = 9.1, 2.5 Hz, 1H), 7.54-7.49 (m, 2H), 7.34 (t, J = 7.4 Hz, 2H), 7.16 (d, J = 8.6 Hz, 1H), 4.30-4.1 (m, 1H), 3.94-3.86 (m, 1H), 3.81-3.74 (m, 2H), 3.69-3.59 (m, 2H), 3.48-3.27 (m, 1H), 2.94-2.73 (m, 2H), 2.41-2.15 (m, 1H), 1.42-1.23 (m, 2H), 1.25-0.76 (m, 3H). | MS (ESI) m/z 523.2 [M + H]⁺ |
| Example 362 | N-[(4-hydroxytetrahydro-2H-pyran-4-yl)methyl]-6-{5-(trifluoromethyl)pyridin-2-yl]oxy}quinoline-2-carboxamide | ¹H NMR (500 MHz, CDCl₃) δ ppm 8.82 (bs, 1H), 8.46 (bs, 1H), 8.38-8.20 (m, 3H), 7.99 (dd, J = 8.7, 2.4 Hz, 1H), 7.68 (d, J = 2.5 Hz, 1H), 7.63 (dd, J = 9.1, 2.5 Hz, 1H), 7.54-7.49 (m, 2H), 7.34 (t, J = 7.4 Hz, 2H), 7.16 (d, J = 8.6 Hz, 1H), 4.30-4.2 1 (m, 1H), 3.94-3.86 (m, 1H), 3.81-3.74 (m, 2H), 3.69-3.59 (m, 2H), 3.48-3.27 (m, 1H), 2.94-2.73 (m, 2H), | MS (ESI) m/z 448.0 [M + H]⁺ |

| Example Number | Name | ¹H NMR | MS |
|---|---|---|---|
| | | 2.41-2.15 (m, 1H), 1.42-1.23 (m, 2H), 1.25-0.76 (m, 3H). | |
| Example 363 | N-[(2S)-pyrrolidin-2-ylmethyl]-6-{[5-(trifluoromethyl)pyridin-2-yl]oxy}quinoline-2-carboxamide | ¹H NMR (400 MHz, CDCl₃) δ ppm 9.19 (s, 1H), 8.40 (s, 1H), 8.28 (d, J = 9.2 Hz, 1H), 8.17 (q, J = 8.7 Hz, 2H), 7.95 (d, J = 8.8 Hz, 1H), 7.56 (d, J = 2.2 Hz, 1H), 7.45 (d, J = 9.0 Hz, 1H), 7.09 (d, J = 8.6 Hz, 1H), 3.77 (s, 3H), 3.21 (s, 2H), 2.03 (s, 2H), 1.84 (s, 2H), 1.68 (s, 1H). | MS (ESI) m/z 417.1 [M + H]⁺ |
| Example 364 | N-[2-(3,3-dimethylazetidin-1-yl)ethyl]-6-{[5-(trifluoromethyl)pyridin-2-yl]oxy}quinoline-2-carboxamide | ¹H NMR (400 MHz, DMSO-d₆) δ ppm 8.89 (t, J = 6.1 Hz, 1H), 8.60-8.61 (m, 1H), 8.52 (d, J = 8.5 Hz, 1H), 8.31 (dd, = 8.7, 2.6 Hz, 1H), 8.13-8.19 (m, 2H), 7.91 (d, J = 2.4 Hz, 1H), 7.73 (dd, J = 9.2, 2.4 Hz, 1H), 7.39 (d, J = 8.9 Hz, 1H), 3.37-3.40 (m, 2H), 3.13 (s, 4H), 2.76-2.79 (m, 2H), 1.20 (s, 6H). | MS (ESI) m/z 445.1 [M + H]⁺ |
| Example 365 | N-[2-(thiomorpholin-4-yl)ethyl]-6-{[5-(trifluoromethyl)pyridin-2-yl]oxy}quinoline-2-carboxamide | ¹H NMR (400 MHz, DMSO-d₆) δ ppm 8.88 (t, J = 5.8 Hz, 1H), 8.60-8.61 (m, 1H), 8.54 (d, J = 8.5 Hz, 1H), 8.31 (dd, J = 8.9, 2.4 Hz, 1H), 8.17-8.20 (m, 2H), 7.93 (d, J = 2.4 Hz, 1H), 7.76 (dd, J = 9.2, 2.4 Hz, 1H), 7.41 (d, J = 8.9 Hz, 1H), 3.47-3.51 (m, 2H), 2.73-2.75 (m, 4H), 2.62-2.64 (m, 4H), 2.59 (t, J = 2.6 Hz, 2H). | MS (ESI) m/z 463.1 [M + H]⁺ |
| Example 366 | N-allyl-N-methyl-6-{[5-(trifluoromethyl)pyridin-2-yl]oxy}quinoline-2-carboxamide | ¹H NMR (500 MHz, CDCl₃) δ ppm 8.45 (bs, 1H), 8.28-8.11 (m, 2H), 7.97 (dd, J = 8.7, 2.4 Hz, 1H), 7.75 (dd, J = 8.4, 5.0 Hz, 1H), 7.62 (t, J = 2.9 Hz, 1H), 7.57 (dt, J = 9.1, 2.8 Hz, 1H), 7.14 (d, J = 8.6 Hz, 1H), 6.01-5.88 (m, 1H), 5.37-5.26 (m, 1H), 5.23-5.15 (m, 1H), 4.25 (d, J = 6.1 Hz, 1H), 4.12 (d, J = 5.8 Hz, 1H), 3.17-3.10 (m, 3H). | MS (ESI) m/z 388.1 [M + H]⁺ |
| Example 367 | 1-[(6-{[5-(trifluoromethyl)pyridin-2-yl]oxy}quinolin-2-yl)carbonyl]azetidine-3-carbonitrile | ¹H NMR (400 MHz, DMSO-d₆) δ ppm 8.62-8.58 (m, 1H), 8.51 (d, J = 8.6 Hz, 1H), 8.31 (dd, J = 8.7, 2.6 Hz, 1H), 8.19 (d, J = 9.1 Hz, 1H), 8.07 (d, J = 8.5 Hz, 1H), 7.91 (d, J = 2.6 Hz, 1H), 7.75 (dd, J = 9.0, 2.6 Hz, 1H), 7.40 (d, J = 8.7 Hz, 1H), 5.08 (t, J = 9.6 Hz, 1H), 4.98 (dd, J = 10.3, 6.1 Hz, 1H), 4.44 (t, J = 9.6 Hz, 1H), 4.30 (dd, J = 10.0, 6.0 Hz, 1H), 3.99-3.87 (m, 1H). | ESI m/z 399.1 [M + H]⁺ |
| Example 368 | [cis-3-hydroxy-4-(methoxymethoxy)pyrrolidin-1-yl](6-{[5-(trifluoromethyl)pyridin-2-yl]oxy}quinolin-2-yl)methanone | ¹H NMR (400 MHz, DMSO-d₆) δ ppm 8.59 (bs, 1H), 8.48 (d, J = 8.5 Hz, 1H), 8.30 (dd, J = 8.7, 2.6 Hz, 1H), 8.14 (d, J = 9.1 Hz, 1H), 7.90 (d, J = 2.7 Hz, 1H), 7.87 (d, J = 8.5 Hz, 1H), 7.73 (dd, J = 9.0, 2.6 Hz, 1H), 7.40 (d, J = 8.7 Hz, 1H), 5.10 (dd, J = 11.5, 4.8 Hz, 1H), 4.79-4.66 (m, 2H), 4.32-3.45 (m, 6H), 3.34 and 3.25 (2s, 3H). | ESI m/z 464.1 [M + H]⁺ |
| Example 369 | N-[(1-hydroxycyclopropyl)methyl]-6-{[5-(trifluoromethyl)pyridin-2-yl]oxy}quinoline-2-carboxamide | ¹H NMR (400 MHz, CDCl₃) δ ppm 8.88 (t, J = 5.9 Hz, 1H), 8.48-8.42 (m, 1H), 8.40-8.15 (m, 3H), 8.02-7.94 (m, 1H), 7.65 (dd, J = 6.1, 2.6 Hz, 1H), 7.58 (ddd, J = 10.4, 9.1, 2.6 Hz, 1H), 7.14 (dd, J = 8.6, 4.7 Hz, 1H), 4.13 (d, J = 6.0 Hz, 1H), 1.42-1.01 (m, 4H), 1.02-0.77 (m, 2H). | MS (ESI) m/z 404.1 [M + H]⁺ |
| Example 370 | 1-[(6-{[5-(trifluoromethyl)pyridin-2-yl]oxy}quinolin-2-yl)carbonyl]azetidin-3-one | ¹H NMR (400 MHz, DMSO-d₆) δ ppm 8.60 (dd, J = 2.7, 1.3 Hz, 1H), 8.53 (d, J = 8.5 Hz, 1H), 8.31 (dd, J = 8.6, 2.6 Hz, 1H), 8.20 (d, J = 9.0 Hz, 1H), 8.16 (d, J = 8.5 Hz, 1H), 7.92 (d, J = 2.6 Hz, 1H), 7.75 (dd, J = 9.1, 2.6 Hz, 1H), 7.41 (d, J = 8.6 Hz, 1H), 5.55-5.50 (m, 2H), 5.02-4.97 (m, 2H). | ESI m/z 386.0 [M − H]⁻ |
| Example 371 | N-(4-hydroxytetrahydrofuran-3-yl)-6-{[5-(trifluoromethyl)pyridin-2-yl]oxy}quinoline-2-carboxamide | ¹H NMR (400 MHz, DMSO-d₆) δ ppm 8.79 (d, J = 7.4 Hz, 1H), 8.64-8.59 (m, 1H), 8.54 (d, J = 8.5 Hz, 1H), 8.35-8.28 (m, 1H), 8.23 (d, J = 9.1 Hz, 1H), 8.17 (d, J = 8.5 Hz, 1H), 7.93 (d, J = 2.6 Hz, 1H), 7.76 (dd, J = 9.1, 2.6 Hz, 1H), 7.40 (d, J = 8.6 Hz, 1H), 5.37 (d, J = 3.4 Hz, 1H), 4.36 (m, 1H), 4.26 (m, 1H), 4.08-3.96 (m, 2H), 3.74 (dd, J = 9.0, 3.8 Hz, 1H), 3.57 (dd, J = 9.3, 2.7 Hz, 1H). | ESI m/z 420.1 [M + H]⁺ |

| Example Number | Name | ¹H NMR | MS |
|---|---|---|---|
| Example 372 | 5-{[2-(piperazin-1-ylcarbonyl)quinolin-6-yl]oxy}pyrazine-2-carbonitrile | ¹H NMR (400 MHz, DMSO-d₆) δ ppm 8.97 (br s, 2H), 8.87 (d, J = 1.2 Hz, 1H), 8.82 (d, J = 1.5 Hz, 1H), 8.54 (d, J = 8.2 Hz, 1H), 8.16 (d, J = 9.2 Hz, 1H), 8.00 (d, J = 2.4 Hz, 1H), 7.79-7.82 (m, 2H), 3.91-3.93 (m, 2H), 3.78-3.80 (m, 2H), 3.27-3.30 (m, 2H), 3.16-3.20 (m, 2H). | MS (ESI) m/z 361.1 [M + H]⁺ |
| Example 373 | [cis-2,2-dimethyltetrahydro-5H-[1,3]dioxolo[4,5-c]pyrrol-5-yl](6-{[5-(trifluoromethyl)pyridin-2-yl]oxy}quinolin-2-yl)methanone | ¹H NMR (400 MHz, DMSO-d₆) δ ppm 8.60 (dd, J = 2.7, 1.3 Hz, 1H), 8.53 (d, J = 8.5 Hz, 1H), 8.31 (dd, J = 8.6, 2.6 Hz, 1H), 8.20 (d, J = 9.0 Hz, 1H), 8.16 (d, J = 8.5 Hz, 1H), 7.92 (d, J = 2.6 Hz, 1H), 7.75 (dd, J = 9.1, 2.6 Hz, 1H), 7.41 (d, J = 8.6 Hz, 1H), 5.55-5.50 (m, 2H), 5.02-4.97 (m, 2H). | ESI m/z 386.0 [M − H]⁻ |
| Example 374 | {2-[(dimethylamino)methyl]morpholin-4-yl}(6-{[5-(trifluoromethyl)pyridin-2-yl]oxy}quinolin-2-yl)methanone | ¹H NMR (400 MHz, DMSO-d₆) δ ppm 8.79 (d, J = 7.4 Hz, 1H), 8.64-8.59 (m, 1H), 8.54 (d, J = 8.5 Hz, 1H), 8.35-8.28 (m, 1H), 8.23 (d, J = 9.1 Hz, 1H), 8.17 (d, J = 8.5 Hz, 1H), 7.93 (d, J = 2.6 Hz, 1H), 7.76 (dd, J = 9.1, 2.6 Hz, 1H), 7.40 (d, J = 8.6 Hz, 1H), 5.37 (d, J = 3.4 Hz, 1H), 4.36 (m, 1H), 4.26 (m, 1H), 4.08-3.96 (m, 2H), 3.74 (dd, J = 9.0, 3.8 Hz, 1H), 3.57 (dd, J = 9.3, 2.7 Hz, 1H). | ESI m/z 420.1 [M + H]⁺ |
| Example 375 | 1-[(6-{[5-(trifluoromethyl)pyridin-2-yl]oxy}quinolin-2-yl)carbonyl]piperidin-4-one | ¹H NMR (400 MHz, DMSO-d₆) δ ppm 2.48 (t, J = 6.2 Hz, 2H), 2.56 (t, J = 6.4 Hz, 2H), 3.79 (t, J = 6.2 Hz, 2H), 3.92-4.07 (m, 2H), 7.40 (d, J = 8.8 Hz, 1H), 7.68-7.85 (m, 2H), 7.89 (dd, J = 14.4, 5.3 Hz, 1H), 8.13 (d, J = 9.1 Hz, 1H), 8.31 (dd, J = 8.7, 2.5 Hz, 1H), 8.50 (t, J = 9.3 Hz, 1H), 8.55-8.65 (m, 1H) | DCI m/z 416.0 [M + H]⁺ |
| Example 376 | N,N-di(tetrahydro-2H-pyran-4-yl)-6-{[5-(trifluoromethyl)pyridin-2-yl]oxy}quinoline-2-carboxamide | ¹H NMR (400 MHz, CDCl₃) δ 8.45 (s, 1H), 8.23 (d, 1H, 8.6 Hz), 8.1 (d, 1H, J = 8.9 Hz), 7.98 (dd, 1H, J = 6.3, 2.5 Hz), 7.68 (d, 1H, 8.5 Hz), 7.63 (d, 1H, J = 2.5), 7.57 (dd, 1H, J = 6.5, 2.5 Hz), 7.15 (d, 1H, 8.5 Hz), 4.00-4.10 (m), 3.45 (m), 3.05-3.20 (m) | DCI m/z 502.1 [M + H]⁺ |
| Example 377 | {4-[(1S,4S)-2-oxa-5-azabicyclo[2.2.1]hept-5-yl]piperidin-1-yl}(6-{[5-(trifluoromethyl)pyridin-2-yl]oxy}quinolin-2-yl)methanone | ¹H NMR (500 MHz, DMSO-d₆) δ ppm 1.36 (dt, J = 19.3, 6.3 Hz, 2H), 1.60 (t, J = 7.8 Hz, 1H), 1.72 (dd, J = 30.0, 11.3 Hz, 1H), 1.90 (t, J = 15.6 Hz, 1H), 2.32 (dd, J = 23.0, 9.6 Hz, 1H), 2.65 (s, 1H), 2.93 (dd, J = 24.4, 8.7 Hz, 1H), 3.15 (dd, J = 24.0, 12.0 Hz, 2H), 3.49 (dd, J = 19.0, 7.1 Hz, 1H), 3.64 (dd, J = 33.2, 20.1 Hz, 2H), 3.88 (dd, J = 19.5, 7.6 Hz, 1H), 4.31 (t, J = 11.6 Hz, 2H), 7.39 (d, J = 8.7 Hz, 1H), 7.60-7.75 (m, 2H), 7.88 (d, J = 2.4 Hz, 1H), 8.10 (dd, J = 9.1, 3.0 Hz, 1H), 8.30 (dd, J = 8.7, 2.3 Hz, 1H), 8.47 (d, J = 8.5 Hz, 1H), 8.59 (s, 1H) | DCI m/z 499.0 [M + H]⁺ |
| Example 378 | {4-[(1R,4R)-2-oxa-5-azabicyclo[2.2.1]hept-5-yl]piperidin-1-yl}(6-{[5-(trifluoromethyl)pyridin-2-yl]oxy}quinolin-2-yl)methanone | ¹H NMR (400 MHz, DMSO-d₆) δ ppm 1.38 (dd, J = 19.7, 12.8 Hz, 2H), 1.53-1.83 (m, 3H), 1.90 (t, J = 13.7 Hz, 1H), 2.32 (dd, J = 18.4, 9.6 Hz, 1H), 2.65 (t, J = 9.2 Hz, 1H), 2.93 (dd, J = 19.5, 8.6 Hz, 1H), 3.15 (dd, J = 21.9, 10.9 Hz, 2H), 3.49 (dd, J = 15.2, 7.2 Hz, 1H), 3.58-3.73 (m, 2H), 3.88 (dd, J = 15.6, 7.6 Hz, 1H), 4.29 (d, J = 14.6 Hz, 2H), 7.39 (d, J = 8.7 Hz, 1H), 7.63-7.77 (m, 2H), 7.88 (d, J = 2.6 Hz, 1H), 8.10 (dd, J = 9.1, 2.3 Hz, 1H), 8.30 (dd, J = 8.7, 2.5 Hz, 1H), 8.47 (d, J = 8.5 Hz, 1H), 8.60 (d, J = 13.0 Hz, 1H) | DCI m/z 499.0 [M + H]⁺ |
| Example 379 | N,N-bis(2-methoxyethyl)-6-{[5-(trifluoromethyl)pyridin-2-yl]oxy}quinoline-2-carboxamide | ¹H NMR (400 MHz, CDCl₃) δ ppm 8.45 (s, 1H), 8.20 (d, 1H). 8.14 (d, 1H, J = 9.7 Hz), 7.76 (dd, 1H), 7.6 (d, 1H), 7.55 (dd, 1H), 7.15 (d, 1H), 3.86 (t, 2H), 3.81 (t, 2H), 3.745 (t, 2H), 3.63 (t, 2H), 3.42 (s, 3H), 3.26 (s, 3H) | DCI m/z 450.1 [M + H]⁺ |
| Example 380 | N-[1-(hydroxymethyl)cyclopropyl]-6-{[5-(trifluoromethyl)pyridin-2-yl]oxy}quinoline-2-carboxamide | ¹H NMR (400 MHz, DMSO-d₆) δ ppm 0.77-0.93 (m, 4H), 3.58 (d, J = 5.7 Hz, 2H), 4.81 (t, J = 5.7 Hz, 1H), 7.40 (d, J = 8.6 Hz, 1H), 7.75 (dd, J = 9.1, 2.6 Hz, 1H), 7.92 (d, J = 2.6 Hz, 1H), 8.18 (dd, J = 17.9, 8.8 Hz, 2H), 8.31 (dd, J = 8.7, 2.5 Hz, 1H), 8.53 (d, J = 8.6 Hz, 1H), 8.58-8.66 (m, 1H), 8.89 (s, 1H) | DCI m/z 404.0 [M + H]⁺ |

| Example Number | Name | ¹H NMR | MS |
|---|---|---|---|
| Example 381 | [4-(tetrahydrofuran-3-ylsulfonyl)piperazin-1-yl](6-{[5-(trifluoromethyl)pyridin-2-yl]oxy}quinolin-2-yl)methanone | ¹H NMR (400 MHz, DMSO-$d_6$/$D_2O$, 90° C.) δ ppm 8.53 (s, 1H), 8.46 (d, J = 8.5 Hz, 1H), 8.22 (dd, J = 8.7, 2.5 Hz, 1H), 8.13 (d, J = 9.1 Hz, 1H), 7.82 (d, J = 2.6 Hz, 1H), 7.72 (d, J = 8.5 Hz, 1H), 7.68 (dd, J = 9.1, 2.7 Hz, 1H), 7.33 (d, J = 8.7 Hz, 1H), 4.08-3.81 (m, 4H), 3.80-3.57 (m, 5H), 3.38 (s, 4H), 2.34-2.22 (m, 1H), 2.22-2.07 (m, 1H). | MS (APCI) m/z 537.0 [M + H]⁺ |
| Example 382 | methyl ({4-[(6-{[5-(trifluoromethyl)pyridin-2-yl]oxy}quinolin-2-yl)carbonyl]piperazin-1-yl}sulfonyl)acetate | ¹H NMR (400 MHz, DMSO-$d_6$/$D_2O$, 90° C.) δ ppm 8.53 (s, 1H), 8.47 (d, J = 8.5 Hz, 1H), 8.22 (dd, J = 8.8, 2.5 Hz, 1H), 8.13 (d, J = 9.1 Hz, 1H), 7.83 (d, J = 2.6 Hz, 1H), 7.72 (dd, J = 8.5, 2.6 Hz, 1H), 7.69 (dd, J = 9.1, 2.7 Hz, 1H), 7.33 (d, J = 8.7 Hz, 1H), 4.26 (s, 2H), 3.75 (d, J = 6.2 Hz, 7H), 3.49 (s, 1H), 3.39 (s, 3H). | MS (APCI) m/z 539.0 [M + H]⁺ |
| Example 383 | [4-(tetrahydro-2H-pyran-4-ylsulfonyl)piperazin-1-yl](6-{[5-(trifluoromethyl)pyridin-2-yl]oxy}quinolin-2-yl)methanone | ¹H NMR (400 MHz, DMSO-$d_6$/$D_2O$, 90° C.) δ ppm 8.53 (s, 1H), 8.46 (d, J = 8.5 Hz, 1H), 8.22 (dd, J = 8.7, 2.6 Hz, 1H), 8.12 (d, J = 9.1 Hz, 1H), 7.82 (d, J = 2.6 Hz, 1H), 7.75-7.64 (m, 2H), 7.33 (d, J = 8.7 Hz, 1H), 3.94 (dd, J = 11.8, 2.9 Hz, 2H), 3.71 (s, 4H), 3.51-3.33 (m, 7H), 1.99-1.85 (m, 2H), 1.69 (qd, J = 11.9, 4.7 Hz, 2H). | MS (APCI) m/z 551.0 [M + H]⁺ |
| Example 384 | (4-{[1-(2-methoxyethyl)-1H-pyrazol-4-yl]sulfonyl}piperazin-1-yl)(6-{[5-(trifluoromethyl)pyridin-2-yl]oxy}quinolin-2-yl)methanone | ¹H NMR (400 MHz, DMSO-$d_6$/$D_2O$, 90° C.) δ ppm 8.52 (dd, J = 1.6, 0.8 Hz, 1H), 8.44 (d, J = 8.4 Hz, 1H), 8.25-8.20 (m, 2H), 8.08 (d, J = 9.1 Hz, 1H), 7.83-7.78 (m, 2H), 7.70-7.63 (m, 2H), 7.32 (d, J = 8.6 Hz, 1H), 4.35 (t, J = 5.3 Hz, 2H), 3.81-3.65 (m, 6H), 3.25 (s, 3H), 3.07 (s, 4H). | MS (APCI) m/z 591.0 [M + H]⁺ |
| Example 385 | {4-[(tetrahydrofuran-3-ylmethyl)sulfonyl]piperazin-1-yl}(6-{[5-(trifluoromethyl)pyridin-2-yl]oxy}quinolin-2-yl)methanone | ¹H NMR (400 MHz, DMSO-$d_6$/$D_2O$, 90° C.) δ ppm 8.56-8.50 (m, 1H), 8.46 (d, J = 8.5 Hz, 1H), 8.22 (dd, J = 8.7, 2.6 Hz, 1H), 8.13 (d, J = 9.1 Hz, 1H), 7.82 (d, J = 2.6 Hz, 1H), 7.72 (d, J = 8.5 Hz, 1H), 7.68 (dd, J = 9.1, 2.6 Hz, 1H), 7.33 (d, J = 8.6 Hz, 1H), 3.87 (dd, J = 8.6, 7.2 Hz, 1H), 3.82-3.60 (m, 6H), 3.45 (dd, J = 8.6, 6.8 Hz, 1H), 3.34 (s, 4H), 3.20 (dd, J = 7.0, 5.6 Hz, 2H), 2.68-2.55 (m, 1H), 2.19-2.08 (m, 1H), 1.77-1.64 (m, 1H). | MS (APCI) m/z 551.0 [M + H]⁺ |
| Example 386 | {4-[(1,1-dioxidotetrahydrothiophen-3-yl)sulfonyl]piperazin-1-yl}(6-{[5-(trifluoromethyl)pyridin-2-yl]oxy}quinolin-2-yl)methanone | ¹H NMR (400 MHz, DMSO-$d_6$/$D_2O$, 90° C.) δ ppm 8.53 (s, 1H), 8.47 (d, J = 8.5 Hz, 1H), 8.22 (dd, J = 8.7, 2.7 Hz, 1H), 8.13 (d, J = 9.1 Hz, 1H), 7.83 (d, J = 2.6 Hz, 1H), 7.72 (d, J = 8.5 Hz, 1H), 7.69 (dd, J = 9.1, 2.7 Hz, 1H), 7.33 (d, J = 8.6 Hz, 1H), 4.28 (dd, J = 9.0, 7.0 Hz, 1H), 3.74 (s, 4H), 3.59 (dd, J = 13.7, 8.9 Hz, 1H), 3.43 (s, 4H), 3.36-3.29 (m, 1H), 3.23-3.13 (m, 2H), 2.64-2.54 (m, 1H), 2.41-2.27 (m, 1H). | MS (APCI) m/z 584.9 [M + H]⁺ |
| Example 387 | {4-[(1-methyl-1H-pyrazol-4-yl)sulfonyl]piperazin-1-yl}(6-{[5-(trifluoromethyl)pyridin-2-yl]oxy}quinolin-2-yl)methanone | ¹H NMR (400 MHz, DMSO-$d_6$/$D_2O$, 90° C.) δ ppm 8.52 (d, J = 0.9 Hz, 1H), 8.44 (d, J = 8.4 Hz, 1H), 8.25-8.19 (m, 2H), 8.09 (d, J = 9.1 Hz, 1H), 7.81 (d, J = 2.6 Hz, 1H), 7.76 (s, 1H), 7.67 (dd, J = 8.9, 2.7 Hz, 2H), 7.32 (d, J = 8.7 Hz, 1H), 3.92 (s, 3H), 3.74 (s, 4H), 3.06 (s, 4H). | MS (APCI) m/z 547.0 [M + H]⁺ |
| Example 388 | N-[4-methyl-5-({4-[(6-{[5-(trifluoromethyl)pyridin-2-yl]oxy}quinolin-2-yl)carbonyl]piperazin-1-yl}sulfonyl)-1,3-thiazol-2-yl]acetamide | ¹H NMR (400 MHz, DMSO-$d_6$/$D_2O$, 90° C.) δ ppm 8.52 (s, 1H), 8.44 (d, J = 8.5 Hz, 1H), 8.22 (dd, J = 8.7, 2.5 Hz, 1H), 8.08 (d, J = 9.1 Hz, 1H), 7.81 (d, J = 2.6 Hz, 1H), 7.71-7.63 (m, 2H), 7.32 (d, J = 8.7 Hz, 1H), 3.76 (s, 4H), 3.22 (s, 4H), 2.50 (s, 3H), 2.19 (s, 3H). | MS (APCI) m/z 621.0 [M + H]⁺ |

-continued

| Example Number | Name | ¹H NMR | MS |
|---|---|---|---|
| Example 389 | N-[5-({4-[(6-{[5-(trifluoromethyl)pyridin-2-yl]oxy}quinolin-2-yl)carbonyl]piperazin-1-yl}sulfonyl)-1,3-thiazol-2-yl]acetamide | ¹H NMR (400 MHz, DMSO-$d_6$/$D_2O$, 90° C.) δ ppm 8.53 (s, 1H), 8.43 (d, J = 8.5 Hz, 1H), 8.22 (dd, J = 8.7, 2.7 Hz, 1H), 8.08 (d, J = 9.1 Hz, 1H), 7.95 (s, 1H), 7.81 (d, J = 2.6 Hz, 1H), 7.71-7.61 (m, 2H), 7.32 (d, J = 8.7 Hz, 1H), 3.77 (s, 4H), 3.19 (s, 4H), 2.22 (s, 3H). | MS (APCI) m/z 606.9 [M + H]⁺ |
| Example 390 | {4-[(1,5-dimethyl-1H-pyrazol-4-yl)sulfonyl]piperazin-1-yl}(6-{[5-(trifluoromethyl)pyridin-2-yl]oxy}quinolin-2-yl)methanone | ¹H NMR (400 MHz, DMSO-$d_6$/$D_2O$, 90° C.) δ ppm 8.55-8.50 (m, 1H), 8.44 (d, J = 8.6 Hz, 1H), 8.22 (dd, J = 8.7, 2.6 Hz, 1H), 8.09 (d, J = 9.1 Hz, 1H), 7.81 (d, J = 2.6 Hz, 1H), 7.70-7.64 (m, 3H), 7.32 (d, J = 8.7 Hz, 1H), 3.80 (s, 3H), 3.73 (s, 4H), 3.07 (s, 4H), 2.44 (s, 3H). | MS (APCI) m/z 561.0 [M + H]⁺ |
| Example 391 | N-[(3S)-tetrahydrofuran-3-yl]-6-{[5-(trifluoromethyl)pyridin-2-yl]oxy}quinoline-2-carboxamide | ¹H NMR (400 MHz, DMSO-$d_6$) δ ppm 8.88 (d, J = 7.0 Hz, 1H), 8.61-8.62 (m, 1H), 8.54 (d, J = 8.5 Hz, 1H), 8.31 (dd, J = 8.7, 2.6 Hz, 1H), 8.24 (d, J = 9.2 Hz, 1H), 8.16 (d, J = 8.6 Hz, 1H), 7.92 (d, J = 2.8 Hz, 1H), 7.76 (dd, J = 9.2, 2.8 Hz, 1H), 7.40 (d, J = 8.5 Hz, 1H), 4.53-4.60 (m, 1H), 3.85-3.96 (m, 2H), 3.69-3.79 (m, 2H), 2.20-2.28 (m, 1H), 2.02-2.10 (m, 1H). | MS (ESI) m/z 404.1 [M + H]⁺ |
| Example 392 | N-(2-methoxyethyl)-N-methyl-6-{[5-(trifluoromethyl)pyridin-2-yl]oxy}quinoline-2-carboxamide | ¹H NMR (400 MHz, DMSO-$d_6$) 1:1 rotamers δ ppm 8.59-8.60 (m, 1H), 8.45-8.49 (m, 1H), 8.30 (dd, J = 8.7, 2.6 Hz, 1H), 8.09-8.14 (m, 1H), 7.87-7.89 (m, 1H), 7.65-7.72 (m, 2H), 7.39 (d, J = 8.9 Hz, 1H), 3.69-3.71(m, 1H), 3.57-3.64 (m, 2H), 3.49-3.52 (m, 1H), 3.33 (s, 1.5H), 3.13 (s, 1.5H), 3.09 (s, 1.5H), 3.04 (s, 1.5H). | MS (ESI) m/z 406.1 [M + H]⁺ |
| Example 393 | N-[(3R)-tetrahydrofuran-3-yl]-6-{[5-(trifluoromethyl)pyridin-2-yl]oxy}quinoline-2-carboxamide | ¹H NMR (400 MHz, DMSO-$d_6$) δ ppm 8.88 (d, J = 7.0 Hz, 1H), 8.61-8.62 (m, 1H), 8.54 (d, J = 8.5 Hz, 1H), 8.31 (dd, J = 8.7, 2.6 Hz, 1H), 8.24 (d, J = 9.2 Hz, 1H), 8.16 (d, J = 8.6 Hz, 1H), 7.92 (d, J = 2.8 Hz, 1H), 7.76 (dd, J = 9.2, 2.8 Hz, 1H), 7.40 (d, J = 8.5 Hz, 1H), 4.53-4.60 (m, 1H), 3.85-3.96 (m, 2H), 3.69-3.79 (m, 2H), 2.20-2.28 (m, 1H), 2.02-2.10 (m, 1H). | MS (ESI) m/z 404.1 [M + H]⁺ |
| Example 394 | N-[(2S)-tetrahydrofuran-2-ylmethyl]-6-{[5-(trifluoromethyl)pyridin-2-yl]oxy}quinoline-2-carboxamide | ¹H NMR (400 MHz, DMSO-$d_6$) δ ppm 8.80 (t, J = 6.1 Hz, 1H). 8.61-8.62 (m, 1H), 8.54 (d, J = 8.5 Hz, 1H), 8.31 (dd, J = 8.5, 2.4 Hz, 1H), 8.18-8.22 (m, 2H), 7.93 (d, J = 2.4 Hz, 1H), 7.76 (dd, J = 9.2, 2.4 Hz, 1H), 7.41 (d, J = 8.9 Hz, 1H), 4.04-4.10 (m, 1H), 3.80-3.85 (m, 1H), 3.64-3.70 (m, 1H), 3.37-3.52 (m, 2H), 1.77-1.99 (m, 3H), 1.59-1.69 (m, 1H). | MS (ESI) m/z 418.1 [M + H]⁺ |
| Example 395 | [(3R,5R)-3,5-dihydroxypiperidin-1-yl](6-{[5-(trifluoromethyl)pyridin-2-yl]oxy}quinolin-2-yl)methanone | ¹H NMR (400 MHz, DMSO-$d_6$) δ ppm 8.61-8.56 (m, 1H), 8.46 (d, J = 8.5 Hz, 1H), 8.30 (dd, J = 8.7, 2.6 Hz, 1H), 8.09 (d, J = 9.0 Hz, 1H), 7.88 (d, J = 2.6 Hz, 1H), 7.74-7.62 (m, 2H), 7.39 (d, J = 8.6 Hz, 1H), 4.93 (d, J = 4.2 Hz, 1H), 4.72 (d, J = 3.5 Hz, 1H), 4.03 (dd, J = 12.4, 3.8 Hz, 1H), 3.98-3.86 (m, 1H), 3.85-3.78 (m, 1H), 3.38 (d, J = 3.9 Hz, 2H), 3.15 (dd, J = 12.2, 7.9 Hz, 1H), 1.86-1.76 (m, 1H), 1.61 (m, 1H). | ESI m/z 434.1 [M + H]⁺ |
| Example 396 | (3-methoxyazetidin-1-yl)(6-{[5-(trifluoromethyl)pyridin-2-yl]oxy}quinolin-2-yl)methanone | ¹H NMR (500 MHz, DMSO-$d_6$) δ ppm 8.62-8.58 (m, 1H), 8.49 (d, J = 8.5 Hz, 1H), 8.31 (dd, J = 8.7, 2.6 Hz, 1H), 8.17 (d, J = 9.1 Hz, 1H), 8.05 (d, J = 8.5 Hz, 1H), 7.90 (d, J = 2.6 Hz, 1H), 7.73 (dd, J = 9.0, 2.6 Hz, 1H), 7.40 (d, J = 8.7 Hz, 1H), 4.96-4.89 (m, 1H), 4.55 (dd, J = 11.0, 2.5 Hz, 1H), 4.36-4.27 (m, 2H), 4.07-3.90 (m, 1H), 3.27 (s, 3H). | ESI m/z 404.1 [M + H]⁺ |
| Example 397 | N-(trans-3-methoxycyclobutyl)-6-{[5-(trifluoromethyl)pyridin-2-yl]oxy}quinoline-2-carboxamide | ¹H NMR (500 MHz, DMSO-$d_6$) δ ppm 9.12 (d, J = 7.7 Hz, 1H), 8.64-8.59 (m, 1H), 8.52 (d, J = 8.5 Hz, 1H), 8.31 (dd, J = 8.7, 2.6 Hz, 1H), 8.24 (d, J = 9.1 Hz, 1H), 8.14 (d, J = 8.5 Hz, 1H), 7.92 (d, J = 2.6 Hz, 1H), 7.76 (dd, J = 9.1, 2.6 Hz, 1H), 7.41 (d, J = 8.6 Hz, 1H), 4.63-4.51 (m, 1H), 4.08-4.01 (m, 1H), 3.18 (s, 3H), 2.46-2.39 (m, 2H), 2.38-2.26 (m, 2H). | ESI m/z 418.1 [M + H]⁺ |

-continued

| Example Number | Name | ¹H NMR | MS |
|---|---|---|---|
| Example 398 | N-(4-hydroxy-1,1-dioxidotetrahydro-thiophen-3-yl)-N-methyl-6-{[5-(trifluoromethyl)pyridin-2-yl]oxy}quinoline-2-carboxamide | ¹H NMR (500 MHz, DMSO-$d_6$) δ ppm 8.59 (bs, 1H), 8.51 (d, J = 8.5 Hz, 1H), 8.31 (dd, J = 8.7, 2.6 Hz, 1H), 8.13 (d, J = 7.9 Hz, 1H), 7.90 (d, J = 2.6 Hz, 1H), 7.76-7.68 (m, 2H), 7.40 (d, J = 8.7 Hz, 1H), 6.19-6.05 (m, 1H), 5.17 and 4.73 (2m, 1H), 4.96 and 4.80 (2m, 1H), 4.82-4.71 (m, 1H), 3.68-3.44 (m, 2H), 3.27 (m, 1H), 3.16 and 3.04 (2s, 3H). | ESI m/z 482.0 [M + H]⁺ |
| Example 399 | N-(oxetan-3-yl)-6-{[5-(trifluoromethyl)pyridin-2-yl]oxy}quinoline-2-carboxamide | ¹H NMR (500 MHz, DMSO-$d_6$) δ ppm 9.58 (d, J = 6.9 Hz, 1H), 8.64-8.59 (m, 1H), 8.54 (d, J = 8.5 Hz, 1H), 8.32 (dd, J = 8.7, 2.6 Hz, 1H), 8.25 (d, J = 9.1 Hz, 1H), 8.14 (d, J = 8.4 Hz, 1H), 7.93 (d, J = 2.6 Hz, 1H), 7.78 (dd, J = 9.1, 2.6 Hz, 1H), 7.41 (d, J = 8.6 Hz, 1H), 5.11 (m, 1H), 4.82-4.73 (m, 4H). | ESI m/z 390.1 [M + H]⁺ |
| Example 400 | N-(tetrahydro-2H-thiopyran-4-yl)-6-{[5-(trifluoromethyl)pyridin-2-yl]oxy}quinoline-2-carboxamide | ¹H NMR (500 MHz, DMSO-$d_6$) δ ppm 8.79 (d, J = 8.5 Hz, 1H), 8.64-8.59 (m, 1H), 8.53 (d, J = 8.5 Hz, 1H), 8.31 (dd, J = 8.6, 2.7 Hz, 1H), 8.23 (d, J = 9.0 Hz, 1H), 8.16 (d, J = 8.5 Hz, 1H), 7.92 (d, J = 2.7 Hz, 1H), 7.75 (dd, J = 9.1, 2.7 Hz, 1H), 7.40 (d, J = 8.7 Hz, 1H), 3.96-3.85 (m, 1H), 2.82-2.73 (m, 2H), 2.72-2.64 (m, 2H), 2.17-2.09 (m, 2H), 1.89-1.77 (m, 2H). | ESI m/z 434.1 [M + H]⁺ |
| Example 401 | N-[(1S,2R)-2-hydroxycyclopentyl]-6-{[5-(trifluoromethyl)pyridin-2-yl]oxy}quinoline-2-carboxamide | ¹H NMR (500 MHz, CDCl₃) δ ppm 8.50 (d, J = 7.8 Hz, 1H), 8.45 (d, J = 0.5 Hz, 1H), 8.28 (d, J = 8.5 Hz, 1H), 8.21 (d, J = 8.5 Hz, 1H), 8.16 (d, J = 9.1 Hz, 1H), 7.97 (dd, J = 8.6, 2.5 Hz, 1H), 7.62 (d, J = 2.5 Hz, 1H), 7.57 (dd, J = 9.1, 2.6 Hz, 1H), 7.14 (d, J = 8.6 Hz, 1H), 4.45-4.29 (m, 2H), 2.21-2.11 (m, 1H), 2.09-1.92 (m, 2H), 1.88-1.78 (m, 2H), 1.73-1.63 (m, 1H). | MS (ESI) m/z 418.1 [M + H]⁺ |
| Example 402 | 4-[(6-{[5-(trifluoromethyl)pyridin-2-yl]oxy}quinolin-2-yl)carbonyl]piperazine-2-carboxamide | ¹H NMR (400 MHz, DMSO-$d_6$, rotamers) δ ppm 2.55-3.02 (m, 3.5H), 3.06-3.28 (m, 2H), 3.57 (d, J = 13.3 Hz, 0.5H), 3.73 (dd, J = 12.8, 2.9 Hz, 0.5H), 3.95-4.14 (m, 1H), 4.50 (dd, J = 12.5, 3.0 Hz, 0.5H), 7.11-7.26 (m, 1.56H), 7.39 (d, J = 8.6 Hz, 1.42H), 7.64-7.76 (m, 2H), 7.89 (t, J = 2.3 Hz, 1H), 8.11 (dd, J = 9.1, 5.2 Hz, 1H), 8.30 (dt, J = 8.7, 2.6 Hz, 1H), 8.48 (d, J = 8.5 Hz, 1H), 8.61 (t, J = 9.8 Hz, 1H) | DCI m/z 446.0 [M + H]⁺ |
| Example 403 | (4-aminopiperidin-1-yl)(6-{[5-(trifluoromethyl)pyridin-2-yl]oxy}quinolin-2-yl)methanone | ¹H NMR (400 MHz, DMSO-$d_6$) δ ppm 1.19-1.41 (m, 2H), 1.66 (dd, J = 21.1, 7.3 Hz, 1H), 1.83 (dd, J = 26.9, 17.6 Hz, 1H), 2.77-3.15 (m, 5H), 3.59-3.74 (m, 1H), 4.37 (d, J = 13.0 Hz, 1H), 7.39 (d, J = 8.7 Hz, 1H), 7.59-7.76 (m, 2H), 7.89 (d, J = 2.6 Hz, 1H), 8.11 (t, J = 7.6 Hz, 1H), 8.30 (dd, J = 8.7, 2.5 Hz, 1H), 8.48 (dd, J = 8.3, 4.5 Hz, 1H), 8.59 (s, 1H) | DCI m/z 417.0 M + H]⁺ |
| Example 404 | (3,3-difluoropyrrolidin-1-yl)(6-{[5-(trifluoromethyl)pyridin-2-yl]oxy}quinolin-2-yl)methanone | ¹H NMR (500 MHz, DMSO-$d_6$, rotamers) δ ppm 8.61-8.57 (m, 1H), 8.50 (dd, J = 8.5, 2.7 Hz, 1H), 8.31 (dd, J = 8.7, 2.5 Hz, 1H), 8.20 (d, J = 9.1 Hz, 0.5H), 8.16 (d, J = 9.1 Hz, 0.5H), 7.97 (d, J = 8.5 Hz, 0.5H), 7.92-7.89 (m, 1.5H), 7.74 (dd, J = 9.1, 2.6 Hz, 1H), 7.40 (d, J = 8.6 Hz, 1H), 4.40 (t, J = 13.1 Hz, 1H), 4.11 (t, J = 7.4 Hz, 1H), 4.01 (t, J = 13.3 Hz, 1H), 3.83 (t, J = 7.6 Hz, 1H), 2.57-2.45 (m, 2H). | MS (ESI) m/z 424.1 [M + H]⁺ |
| Example 405 | (3,3-dimethylpyrrolidin-1-yl)(6-{[5-(trifluoromethyl)pyridin-2-yl]oxy}quinolin-2-yl)methanone | ¹H NMR (500 MHz, DMSO-$d_6$) δ ppm 8.60-8.56 (m, 1H), 8.46 (d, J = 8.6 Hz, 1H), 8.30 (dd, J = 8.7, 2.5 Hz, 1H), 8.13 (dd, J = 9.0, 7.3 Hz, 1H), 7.88 (d, J = 2.6 Hz, 1H), 7.84 (dd, J = 9.6, 8.6 Hz, 1H), 7.70 (dd, J = 9.1, 2.6 Hz, 1H), 7.39 (d, J = 8.7 Hz, 1H), 3.84 (t, J = 7.1 Hz, 1H), 3.65 (t, J = 7.2 Hz, 1H), 3.46 (s, 1H), 3.35 (s, 1H), 1.75-1.68 (m, 2H), 1.13 (s, 3H), 1.03 (s, 3H). | MS (ESI) m/z 416.2 [M + H]⁺ |

| Example Number | Name | ¹H NMR | MS |
|---|---|---|---|
| Example 406 | (6-fluoro-1,4-diazepan-1-yl)(6-{[5-(trifluoromethyl)pyridin-2-yl]oxy}quinolin-2-yl)methanone | ¹H NMR (400 MHz, CDCl₃) δ ppm 8.45 (bs, 1H), 8.24 (d, J = 8.6 Hz, 1H), 8.14 (dd, J = 9.1, 2.9 Hz, 1H), 7.99 (dd, J = 8.6, 2.5 Hz, 1H), 7.80 (dd, J = 14.7, 8.5 Hz, 1H), 7.64 (t, J = 2.2 Hz, 1H), 7.58 (dd, J = 9.1, 2.4 Hz, 1H), 7.16 (d, J = 8.6 Hz, 1H), 5.23-4.95 (m, 1H), 4.54-4.19 (m, 1H), 4.17-3.71 (m, 2H), 3.64-2.95 (m, 6H). | MS (ESI) m/z 435.1 [M + H]⁺ |
| Example 407 | (6-hydroxy-1,4-diazepan-1-yl)(6-{[5-(trifluoromethyl)pyridin-2-yl]oxy}quinolin-2-yl)methanone | ¹H NMR (400 MHz, CDCl₃) δ ppm 8.44 (s, 1H), 8.26 (dd, J = 23.9, 8.6 Hz, 1H), 8.14 (d, J = 9.1 Hz, 1H), 7.99 (dd, J = 8.6, 2.5 Hz, 1H), 7.86 (dd, J = 25.6, 8.5 Hz, 1H), 7.79-7.54 (m, 2H), 7.16 (dd, J = 8.6, 4.4 Hz, 1H), 4.62-4.32 (m, 2H), 4.31-4.11 (m, 2H), 3.87 (dddd, J = 25.4, 20.2, 14.4, 7.2 Hz, 1H), 3.57-3.08 (m, 6H). | MS (ESI) m/z 433.1 [M + H]⁺ |
| Example 408 | N-{1-[(6-{[5-(trifluoromethyl)pyridin-2-yl]oxy}quinolin-2-yl)carbonyl]piperidin-4-yl}methanesulfonamide | ¹H NMR (400 MHz, DMSO-d₆, rotamers) δ ppm 1.50 (td, J = 14.4, 3.9 Hz, 2H), 1.84 (d, J = 10.1 Hz, 1H), 2.00 (d, J = 9.3 Hz, 1H), 2.95 (s, 3H), 2.99-3.13 (m, 1H), 3.18 (dd, J = 24.1, 13.0 Hz, 1H), 3.40-3.59 (m, 1H), 3.71 (d, J = 13.8 Hz, 1H), 4.39 (d, J = 13.1 Hz, 1H), 7.21 (d, J = 7.4 Hz, 1H), 7.39 (d, J = 8.7 Hz, 1H), 7.62-7.80 (m, 2H), 7.89 (d, J = 2.6 Hz, 1H), 8.10 (d, J = 9.1 Hz, 1H), 8.30 (dd, J = 8.7, 2.5 Hz, 1H), 8.48 (d, J = 8.5 Hz, 1H), 8.59 (s, 1H) | DCI m/z 495.0 M + H]⁺ |
| Example 409 | N-[(2R)-tetrahydrofuran-2-ylmethyl]-6-{[5-(trifluoromethyl)pyridin-2-yl]oxy}quinoline-2-carboxamide | ¹H NMR (400 MHz, DMSO-d₆) δ ppm 8.80 (t, J = 6.1 Hz, 1H). 8.61-8.62 (m, 1H), 8.54 (d, J = 8.5 Hz, 1H), 8.31 (dd, J = 8.5, 2.4 Hz, 1H), 8.18-8.22 (m, 2H), 7.93 (d, J = 2.4 Hz, 1H), 7.76 (dd, J = 9.2, 2.4 Hz, 1H), 7.41 (d, J = 8.9 Hz, 1H), 4.04-4.10 (m, 1H), 3.80-3.85 (m, 1H), 3.64-3.70 (m, 1H), 3.37-3.52 (m, 2H), 1.77-1.99 (m, 3H), 1.59-1.69 (m, 1H). | MS (ESI) m/z 418.1 [M + H]⁺ |
| Example 410 | N-[(2S)-2-hydroxypropyl]-6-{[5-(trifluoromethyl)pyridin-2-yl]oxy}quinoline-2-carboxamide | ¹H NMR (400 MHz, DMSO-d₆) δ ppm 8.76 (t, J = 6.0 Hz, 1H). 8.61-8.62 (m, 1H), 8.55 (d, J = 8.5 Hz, 1H), 8.31 (dd, J = 8.7, 2.6 Hz, 1H), 8.18-8.22 (m, 2H), 7.93 (d, J = 2.8 Hz, 1H), 7.76 (dd, J = 9.0, 2.6 Hz, 1H), 7.41 (d, J = 8.9 Hz, 1H), 4.91 (br s, 1H), 3.83-3.91 (m, 1H), 3.40-3.47 (m, 1H), 3.23-3.30 (m, 1H), 1.12 (d, J = 6.1 Hz, 3H). | MS (ESI) m/z 392.1 [M + H]⁺ |
| Example 411 | N-methyl-N-(tetrahydro-2H-pyran-4-yl)-6-{[5-(trifluoromethyl)pyridin-2-yl]oxy}quinoline-2-carboxamide | ¹H NMR (400 MHz, DMSO-d₆) 1:1 rotamers δ ppm 8.59-8.60 (m, 1H), 8.46-8.49 (m, 1H), 8.29-8.32 (m, 1H), 8.13 (d, J = 9.2 Hz, 0.5H), 8.07 (d, J = 9.2 Hz, 0.5H), 7.88-7.90 (m, 1H), 7.65-7.73 (m, 2H), 7.38-7.41 (m, 1H), 4.61-4.69 (m, 0.5H), 3.96-4.00 (m, 1H), 3.79-3.86 (m, 1.5H), 3.45-3.50 (m, 1H), 3.05-3.11 (m, 1H), 2.97 (s, 1.5H), 2.86 (s, 1.5H), 1.63-1.95 (m, 4H). | MS (ESI) m/z 417.1 [M + H]⁺ |
| Example 412 | N-[(3-hydroxyoxetan-3-yl)methyl]-6-{[5-(trifluoromethyl)pyridin-2-yl]oxy}quinoline-2-carboxamide | ¹H NMR (400 MHz, DMSO-d₆) δ ppm 8.91 (t, J = 6.3 Hz, 1H), 8.61-8.62 (m, 1H), 8.56 (d, J = 8.5 Hz, 1H), 8.32 (dd, J = 8.9, 2.4 Hz, 1H), 8.21-8.23 (m, 2H), 7.94 (d, J = 2.4 Hz, 1H), 7.77 (dd, J = 9.2, 2.8 Hz, 1H), 7.41 (d, J = 8.5 Hz, 1H), 6.10 (br s, 1H), 4.50 (d, J = 6.7 Hz, 2H), 4.45 (d, J = 6.4 Hz, 2H), 3.74 (d, J = 6.4 Hz, 2H). | MS (ESI) m/z 420.1 [M + H]⁺ |
| Example 413 | N-[2-(dimethylamino)-2-oxoethyl]-N-methyl-6-{[5-(trifluoromethyl)pyridin-2-yl]oxy}quinoline-2-carboxamide | ¹H NMR (400 MHz, CDCl₃) δ ppm 8.45 (bs, 1H), 8.28-8.04 (m, 2H), 8.04-7.77 (m, 2H), 7.68-7.51 (m, 2H), 7.15 (dd, J = 8.6, 5.3 Hz, 1H), 4.51 (d, J = 82.7 Hz, 2H), 3.25 (d, J = 8.6 Hz, 3H), 2.99 (dd, J = 66.7, 25.6 Hz, 6H). | MS (ESI) m/z 433.1 [M + H]⁺ |

-continued

| Example Number | Name | ¹H NMR | MS |
|---|---|---|---|
| Example 414 | (6-{[5-(trifluoromethyl)pyridin-2-yl]oxy}quinolin-2-yl)[3-(trifluoromethyl)pyrrolidin-1-yl]methanone | ¹H NMR (400 MHz, DMSO-d$_6$) δ ppm 8.60-8.56 (m, 1H), 8.49 (dd, J = 8.5, 2.9 Hz, 1H), 8.30 (dd, J = 8.7, 2.6 Hz, 1H), 8.14 (dd, J = 9.1, 3.3 Hz, 1H), 7.92-7.87 (m, 2H), 7.72 (dd, J = 9.1, 2.6 Hz, 1H), 7.39 (dd, J = 8.6, 0.4 Hz, 1H), 4.14 (dd, J = 12.0, 8.1 Hz, 0.5H), 4.00-3.86 (m, 2H), 3.82-3.74 (m, 0.5H), 3.72-3.61 (m, 1H), 3.42-3.32 (m, 1H), 2.30-2.19 (m, 1H), 2.12-2.00 (m, 1H). | MS (ESI) m/z 456.1 [M + H]⁺ |
| Example 415 | (3,4-difluoropyrrolidin-1-yl)(6-{[5-(trifluoromethyl)pyridin-2-yl]oxy}quinolin-2-yl)methanone | ¹H NMR (400 MHz, DMSO-d$_6$) δ ppm 8.61-8.58 (m, 1H), 8.50 (d, J = 8.4 Hz, 1H), 8.31 (dd, J = 8.7, 2.6 Hz, 1H), 8.18 (d, J = 9.1 Hz, 1H), 7.94 (d, J = 8.5 Hz, 1H), 7.91 (d, J = 2.6 Hz, 1H), 7.74 (dd, J = 9.1, 2.6 Hz, 1H), 7.40 (d, J = 8.7 Hz, 1H), 5.56-5.25 (m, 2H), 4.38-4.24 (m, 1H), 4.18-3.92 (m, 2H), 3.85-3.71 (m, 1H). | MS (ESI) m/z 424.1 [M + H]⁺ |
| Example 416 | N-(6-oxopiperidin-3-yl)-6-{[5-(trifluoromethyl)pyridin-2-yl]oxy}quinoline-2-carboxamide | ¹H NMR (500 MHz, DMSO-d$_6$) δ ppm 8.84 (d, J = 8.0 Hz, 1H), 8.62-8.59 (m, 1H), 8.54 (d, J = 8.6 Hz, 1H), 8.31 (dd, J = 8.7, 2.5 Hz, 1H), 8.23 (d, J = 9.1 Hz, 1H), 8.17 (d, J = 8.5 Hz, 1H), 7.93 (d, J = 2.6 Hz, 1H), 7.76 (dd, J = 9.1, 2.6 Hz, 1H), 7.52-7.48 (m, 1H), 7.40 (d, J = 8.7 Hz, 1H), 4.31-4.22 (m, 1H), 3.41-3.24 (m, 2H), 2.38-2.27 (m, 2H), 2.11-1.93 (m, 2H). | MS (ESI) m/z 431.1 [M + H]⁺ |
| Example 417 | (6,6-difluoro-1,4-diazepan-1-yl)(6-{[5-(trifluoromethyl)pyridin-2-yl]oxy}quinolin-2-yl)methanone | ¹H NMR (400 MHz, DMSO-d$_6$) δ ppm 8.59 (s, 1H), 8.50 (dd, J = 8.5, 2.8 Hz, 1H), 8.31 (dd, J = 8.7, 2.5 Hz, 1H), 8.12 (d, J = 9.1 Hz, 1H), 7.90 (d, J = 2.5 Hz, 1H), 7.78-7.68 (m, 2H), 7.40 (dd, J = 8.7, 3.1 Hz, 1H), 4.30 (t, J = 12.9 Hz, 1H), 4.20 (t, J = 13.1 Hz, 1H), 3.78 (t, J = 5.0 Hz, 1H), 3.49 (t, J = 4.8 Hz, 1H), 3.24-3.12 (m, 1H), 3.04 (dd, .7 = 25.5, 11.4 Hz, 1H), 2.87 (s, 1H), 1.34-1.07 (m, 1H), 0.89-0.80 (m, 1H). | MS (ESI) m/z 453.1 [M + H]⁺ |
| Example 418 | 5,8-diazaspiro[3.5]non-8-yl(6-{[5-(trifluoromethyl)pyridin-2-yl]oxy}quinolin-2-yl)methanone | ¹H NMR (500 MHz, DMSO-d$_6$) δ ppm 8.62-8.57 (m, 1H), 8.48 (dd, J = 11.0, 8.5 Hz, 1H), 8.31 (ddd, J = 8.6, 2.6, 2.6 Hz, 1H), 8.09 (dd, J = 14.7, 9.1 Hz, 1H), 7.90 (dd, J = 8.1, 2.6 Hz, 1H), 7.77-7.64 (m, 2H), 7.40 (dd, J = 13.4, 5.2 Hz, 1H) 3.63 (s, 1H), 3.62-3.55 (m, 1H), 3.36-3.31 (m, 2H), 2.75-2.73 (m, 1H), 2.65-2.58 (m, 1H), 2.04-1.92 (m, 2H), 1.87-1.57 (m, 4H), 1.42-1.29 (m, 1H) | MS (ESI) m/z 443.1 [M + H]⁺ |
| Example 419 | N-(1,1-dioxidotetrahydrothiophen-3-yl)-N-methyl-6-{[5-(trifluoromethyl)pyridin-2-yl]oxy}quinoline-2-carboxamide | ¹H NMR (500 MHz, DMSO-d$_6$) 0.7:0.3 rotamers δ ppm 8.59-8.60 (m, 1H), 8.49-8.51 (m, 1H), 8.30-8.32 (m, 1H), 8.13-8.16 (m, 1H), 7.90-7.91 (m, 1H), 7.71-7.76 (m, 2H), 7.39-7.41 (m, 1H), 5.30-5.37 (m, 0.3H), 4.81-4.88 (m, 0.7H), 3.36-3.53 (m, 2.3H), 3.24-3.29 (m, 1H), 3.04-3.08 (m, 0.7H), 3.02 (m, 2.1H), 2.97 (m, 0.9H), 2.30-2.46 (m, 2H). | MS (ESI) m/z 466.1 [M + H]⁺ |
| Example 420 | N-(tetrahydrothiophen-3-yl)-6-{[5-(trifluoromethyl)pyridin-2-yl]oxy}quinoline-2-carboxamide | ¹H NMR (400 MHz, DMSO-d$_6$) δ ppm 8.85 (d, J = 7.6 Hz, 1H), 8.61-8.62 (m, 1H), 8.54 (d, J = 8.5 Hz, 1H), 8.32 (dd, J = 8.7, 2.6 Hz, 1H), 8.23 (d, J = 9.2 Hz, 1H), 8.18 (d, J = 8.6 Hz, 1H), 7.93 (d, J = 2.4 Hz, 1H), 7.76 (dd, J = 9.2, 2.8 Hz, 1H), 7.41 (d, J = 8.9 Hz, 1H), 4.59-4.65 (m, 1H), 3.05-3.08 (m, 1H), 3.89-3.94 (m, 3H), 2.16-2.20 (m, 2H). | MS (ESI) m/z 420.1 [M + H]⁺ |
| Example 421 | N-[2-(2-oxoimidazolidin-1-yl)ethyl]-6-{[5-(trifluoromethyl)pyridin-2-yl]oxy}quinoline-2-carboxamide | ¹H NMR (400 MHz, DMSO-d$_6$) δ ppm 8.99 (t, J = 6.1 Hz, 1H), 8.60-8.61 (m, 1H), 8.53 (d, J = 8.5 Hz, 1H), 8.31 (dd, J = 8.7, 2.6 Hz, 1H), 8.16-8.19 (m, 2H), 7.93 (d, J = 2.8 Hz, 1H), 7.76 (dd, J = 9.0, 2.6 Hz, 1H), 7.40 (d, J = 8.9 Hz, 1H), 6.28 (s, 1H), 3.42-3.52 (m, 4H), 3.29-3.33 (m, 2H), 3.20-3.24 (m, 2H). | MS (ESI) m/z 446.1 [M + H]⁺ |
| Example 422 | N-[2-(pyridin-2-ylamino)ethyl]-6-{[5-(trifluoromethyl)pyridin-2-yl]oxy}quinoline-2-carboxamide | ¹H NMR (400 MHz, DMSO-d$_6$) δ ppm 9.23 (t, J = 5.5 Hz, 1H), 8.60-8.61 (m, 1H), 8.53 (d, J = 8.6 Hz, 1H), 8.31 (dd, J = 8.7, 2.6 Hz, 1H), 8.17-8.20 (m, 2H), 8.04 (d, J = 4.9 Hz, 1H), 7.92 (d, J = 2.4 Hz, 1H), 7.76 (dd, J = 9.0, 2.6 Hz, 1H), 7.36-7.42 (m, 2H), 6.74 (t, J = 5.2 Hz, 1H), 6.48-6.52 (m, 2H), 3.49-3.58 (m, 4H). | MS (ESI) m/z 454.1 [M + H]⁺ |

| Example Number | Name | ¹H NMR | MS |
|---|---|---|---|
| Example 423 | N-[2-(1H-imidazol-1-yl)ethyl]-6-{[5-(trifluoromethyl)pyridin-2-yl]oxy}quinoline-2-carboxamide | ¹H NMR (400 MHz, DMSO-$d_6$) δ ppm 9.05 (t, J = 6.0 Hz, 1H), 8.60-8.61 (m, 1H), 8.54 (d, J = 8.5 Hz, 1H), 8.31 (dd, J = 8.9, 2.4 Hz, 1H), 8.14-8.19 (m, 2H), 7.93 (d, J = 2.4 Hz, 1H), 7.76 (dd, J = 9.2, 2.4 Hz, 1H), 7.62 (s, 1H), 7.41 (d, J = 8.5 Hz, 1H), 7.19 (s, 1H), 6.87 (s, 1H), 4.26 (t, J = 6.3 Hz, 1H), 3.72 (q, J = 6.1 Hz, 2H). | MS (ESI) m/z 428.1 [M + H]⁺ |
| Example 424 | N-(azetidin-2-ylmethyl)-6-{[5-(trifluoromethyl)pyridin-2-yl]oxy}quinoline-2-carboxamide | ¹H NMR (400 MHz, DMSO-$d_6$) δ ppm 9.30 (t, J = 6.1 Hz, 1H), 8.60-8.61 (m, 1H), 8.57 (d, J = 8.5 Hz, 1H), 8.33 (dd, J = 8.9, 2.4 Hz, 1H), 8.19-8.22 (m, 2H), 7.96 (d, J = 2.8 Hz, 1H), 7.79 (dd, J = 9.2, 2.8 Hz, 1H), 7.42 (d, J = 8.5 Hz, 1H), 4.57-4.64 (m, 1H),), 3.72-3.95 (m, 4H), 2.3 1-2.48 (m, 2H). | MS (ESI) m/z 403.1 [M + H]⁺ |
| Example 425 | N-[(3R,4R)-4-hydroxy-1,1-dioxidotetrahydrothiophen-3-yl]-6-{[5-(trifluoromethyl)pyridin-2-yl]oxy}quinoline-2-carboxamide | ¹H NMR (400 MHz, DMSO-$d_6$) δ ppm 8.88 (d, J = 8.1 Hz, 1H), 8.62 (d, J = 3.0 Hz, 1H), 8.58 (d, J = 8.5 Hz, 1H), 8.32 (dd, J = 8.7, 2.6 Hz, 1H), 8.25-8.19 (m, 2H), 7.95 (d, J = 2.6 Hz, 1H), 7.78 (dd, J = 9.1, 2.7 Hz, 1H), 7.41 (d, J = 8.6 Hz, 1H), 6.29 (s, 1H), 4.86-4.75 (m, 1H), 4.66-4.60 (m, 1H), 3.61-3.27 (m, 4H). | ESI m/z 468.0 [M + H]⁺ |
| Example 426 | N-(3-hydroxy-3-methylcyclobutyl)-6-{[5-(trifluoromethyl)pyridin-2-yl]oxy}quinoline-2-carboxamide | ¹H NMR (500 MHz, DMSO-$d_6$) δ ppm 8.86 (d, J = 7.8 Hz, 1H), 8.61 (d, J = 2.5 Hz, 1H), 8.52 (d, J = 8.5 Hz, 1H), 8.31 (dd, J = 8.7, 2.6 Hz, 1H), 8.22 (d, J = 9.1 Hz, 1H), 8.14 (d, J = 8.4 Hz, 1H), 7.92 (d, J = 2.6 Hz, 1H), 7.76 (dd, J = 9.0, 2.6 Hz, 1H), 7.41 (d, J = 8.6 Hz, 1H), 5.00 (s, 1H), 4.13-3.99 (m, 1H), 2.42-2.33 (m, 2H), 2.27-2.20 (m, 2H), 1.29 (s, 3H). | ESI m/z 418.0 [M + H]⁺ |
| Example 427 | [3-(2-methoxyethoxy)azetidin-1-yl](6-{[5-(trifluoromethyl)pyridin-2-yl]oxy}quinolin-2-yl)methanone | ¹H NMR (400 MHz, DMSO-$d_6$) δ ppm 8.63 (bs, 1H), 8.36 (d, J = 8.5 Hz, 1H), 8.14 (dd, J = 8.7, 2.6 Hz, 1H), 8.04-7.96 (m, 2H), 7.51-7.43 (m, 2H), 7.15 (d, J = 8.7 Hz, 1H), 5.59-5.50 (m, 1H), 5.22-5.14 (m, 1H), 4.79-4.70 (m, 1H), 4.62-4.54 (m, 1H), 4.30-4.24 (m, 2H), 4.18-4.10 (m, 1H), 3.78-3.71 (m, 2H). | ESI m/z 448.0 [M + H]⁺ |
| Example 428 | N-{1-[(6-{[5-(trifluoromethyl)pyridin-2-yl]oxy}quinolin-2-yl)carbonyl]azetidin-3-yl}methanesulfonamide | ¹H NMR (400 MHz, DMSO-$d_6$) δ ppm 8.62-8.57 (m, 1H), 8.50 (d, J = 8.5 Hz, 1H), 8.31 (dd, J = 8.7, 2.6 Hz, 1H), 8.17 (d, J = 9.0 Hz, 1H), 8.07 (d, J = 8.5 Hz, 1H), 7.96-7.88 (m, 2H), 7.74 (dd, J = 9.0, 2.7 Hz, 1H), 7.40 (d, J = 8.6 Hz, 1H), 5.07 (dd, J = 10.7, 7.8 Hz, 1H), 4.62 (dd, J = 10.8, 5.4 Hz, 1H), 4.50-4.42 (m, 1H), 4.38-4.27 (m, 1H), 4.03 (dd, J = 10.5, 5.2 Hz, 1H), 2.95 (s, 3H). | ESI m/z 467.1 [M + H]⁺ |
| Example 429 | (6-{[5-(difluoromethyl)pyridin-2-yl]oxy}quinolin-2-yl)[3-(morpholin-4-yl)azetidin-1-yl]methanone | ¹H NMR (500 MHz, DMSO-$d_6$) δ ppm 8.47 (d, J = 8.6 Hz, 1H), 8.42-8.36 (m, 1H), 8.16 (d, J = 9.1 Hz, 1H), 8.13 (dd, J = 8.6, 2.2 Hz, 1H), 8.03 (d, J = 8.5 Hz, 1H), 7.85 (d, J = 2.6 Hz, 1H), 7.69 (dd, J = 9.1, 2.6 Hz, 1H), 7.32 (d, J = 8.6 Hz, 1H), 7.12 (t, J = 55.3 Hz, 1H), 4.76 (dd, J = 10.2, 7.2 Hz, 1H), 4.55 (dd, J = 10.6, 4.8 Hz, 1H), 4.15 (dd, J = 10.1, 7.4 Hz, 1H), 3.96 (dd, J = 10.5, 4.8 Hz, 1H), 3.65-3.56 (m, 4H), 3.23-3.15 (m, 1H), 2.37 (br s, 4H). | MS (ESI) m/z 441.1 [M + H]⁺ |
| Example 430 | [2-(difluoromethyl)piperazin-1-yl](6-{[5-(difluoromethyl)pyridin-2-yl]oxy}quinolin-2-yl)methanone | ¹H NMR (400 MHz, DMSO-$d_6$, rotamers) δ ppm 8.49 (d, J = 8.5 Hz, 1H), 8.41-8.36 (m, 1H), 8.17-8.07 (m, 2H), 7.86 (d, J = 2.6 Hz, 1H), 7.75-7.63 (m, 2H), 7.32 (d, J = 8.6 Hz, 1H), 7.12 (t, J = 55.3 Hz, 1H), 6.55 (tdd, J = 57.1, 29.3, 6.7 Hz, 1H), 4.84-4.72 (m, 0.5H), 4.44-4.26 (m, 1H), 3.57 (d, J = 13.1 Hz, 0.5H), 3.38-3.34 (m, 0.5H), 3.16 (d, J = 13.2 Hz, 0.5H), 3.12-2.92 (m, 2H), 2.89-2.53 (m, 3H). | MS (ESI) m/z 435.1 [M + H]⁺ |
| Example 431 | piperazin-1-yl(6-{[5-(trifluoromethoxy)pyridin-2-yl]oxy}quinolin-2-yl)methanone | 1H NMR (300 MHz, DMSO-d6): 8.46 (d, J = 8.5 Hz, 1H), 8.29 (d, J = 2.8 Hz, 1H), 8.09 (d, J = 9.2 Hz, 1H), 8.03 (dd, J = 8.7, 2.6 Hz, 1H), 7.83 (d, J = 2.8 Hz, 1H), 7.65-7.69 (m, 2H), 7.33 (d, J = 8.9 Hz, 1H), 3.62-3.65 (m, 2H), 3.37-3.40 (m, 2H), 2.79-2.82 (m, 2H), 2.67-3.69 (m, 2H). | (APCI) m/z 418.9 [M + H]+ |
| Example 432 | N-(3-oxocyclobutyl)-6-{[5-(trifluoromethyl)pyr- | ¹H NMR (500 MHz, DMSO-$d_6$) δ ppm 3.42 (t, J = 8.0 Hz, 4H), 4.64-4.78 (m, 1H), 7.41 (d, J = 8.7 Hz, 1H), 7.77 (dd, J = 9.1, 2.6 Hz, 1H), | DCI m/z 402.0 M + H]⁺ |

| Example Number | Name | ¹H NMR | MS |
|---|---|---|---|
| | idin-2-yl]oxy}quinoline-2-carboxamide | 7.94 (d, J = 2.6 Hz, 1H), 8.20 (dd, J = 21.7, 8.8 Hz, 2H), 8.32 (dd, J = 8.7, 2.5 Hz, 1H), 8.54 (d, J = 8.5 Hz, 1H), 8.59-8.65 (m, 1H), 9.52 (d, J = 7.6 Hz, 1H) | |
| Example 433 | N-[3-(morpholin-4-yl)cyclobutyl]-6-{[5-(trifluoromethyl)pyridin-2-yl]oxy}quinoline-2-carboxamide | ¹H NMR (400 MHz, DMSO-d₆) δ ppm 2.06 (qd, J = 8.8, 2.4 Hz, 2H), 2.30 (s, 4H), 2.37-2.46 (m, 2H), 3.54-3.64 (m, 4H), 4.16-4.33 (m, 1H), 7.40 (d, J = 8.6 Hz, 1H), 7.76 (dd, J = 9.1, 2.6 Hz, 1H), 7.92 (d, J = 2.6 Hz, 1H), 8.13 (d, J = 8.5 Hz, 1H), 8.22 (d, J = 9.1 Hz, 1H), 8.31 (dd, J = 8.7, 2.5 Hz, 1H), 8.52 (d, J = 8.6 Hz, 1H), 8.61 (d, J = 1.5 Hz, 1H), 9.03 (d, J = 8.3 Hz, 1H) | DCI m/z 473.0 M + H⁺ |
| Example 434 | 6-{[5-(difluoromethyl)pyridin-2-yl]oxy}-N-(2-hydroxy-2-methylpropyl)quinoline-2-carboxamide | ¹H NMR (400 MHz, DMSO-d₆) δ ppm 1.17 (d, J = 6.1 Hz, 7H), 3.37 (d, J = 6.2 Hz, 2H), 4.76 (s, 1H), 7.13 (t, J = 55.3 Hz, 1H), 7.33 (d, J = 8.6 Hz, 1H), 7.73 (dd, J = 9.1, 2.6 Hz, 1H), 7.90 (d, J = 2.6 Hz, 1H), 8.17 (ddd, J = 10.6, 8.9, 2.8 Hz, 3H), 8.41 (d, J = 1.3 Hz, 1H), 8.55 (d, J = 8.6 Hz, 1H), 8.63 (t, J = 6.1 Hz, 1H) | DCI m/z 388.0 M + H⁺ |
| Example 435 | (6-{[5-(difluoromethyl)pyridin-2-yl]oxy}quinolin-2-yl)[4-(morpholin-4-yl)piperidin-1-yl]methanone | ¹H NMR (400 MHz, DMSO-d₆) δ ppm 1.44 (qd, J = 12.2, 4.2 Hz, 2H), 1.73 (d, J = 12.2 Hz, 1H), 1.92 (d, J = 12.3 Hz, 1H), 2.48-2.56 (m, 5H), 2.90 (td, J = 12.7, 2.6 Hz, 1H), 3.09 (t, J = 11.5 Hz, 1H), 3.50-3.64 (m, 4H), 3.74 (d, J = 13.4 Hz, 1H), 4.53 (d, J = 13.2 Hz, 1H), 7.12 (t, J = 55.3 Hz, 1H), 7.32 (d, J = 8.6 Hz, 1H), 7.68 (dd, J = 8.7, 3.6 Hz, 2H), 7.84 (d, J = 2.6 Hz, 1H), 8.05-8.18 (m, 2H), 8.39 (d, J = 1.5 Hz, 1H), 8.46 (d, J = 8.5 Hz, 1H). | DCI m/z 469.0 M + H⁺ |
| Example 436 | 6-{[5-(difluoromethyl)pyridin-2-yl]oxy}-N-(2,2,2-trifluoroethyl)quinoline-2-carboxamide | ¹H NMR (500 MHz, DMSO-d₆) δ ppm 9.46 (t, J = 6.6 Hz, 1H), 8.57 (d, J = 8.6 Hz, 1H), 8.43-8.39 (m, 1H), 8.22 (d, J = 9.1 Hz, 1H), 8.19 (d, J = 8.5 Hz, 1H), 8.14 (dd, J = 8.5, 2.3 Hz, 1H), 7.91 (d, J = 2.6 Hz, 1H), 7.76 (dd, J = 9.2, 2.7 Hz, 1H), 7.34 (d, J = 8.6 Hz, 1H), 7.13 (t, J = 55.3 Hz, 1H), 4.23-4.10 (m, 2H). | |
| Example 437 | N-(4,4-difluorocyclohexyl)-6-{[5-(difluoromethyl)pyridin-2-yl]oxy}quinoline-2-carboxamide | ¹H NMR (500 MHz, DMSO-d₆) δ ppm 1.69-2.18 (m, 8H), 3.97-4.14 (m, 1H), 7.13 (t, J = 55.3 Hz, 1H), 7.33 (d, J = 8.6 Hz, 1H), 7.73 (dd, J = 9.1, 2.7 Hz, 1H), 7.88 (d, J = 2.6 Hz, 1H), 8.14 (dd, J = 12.4, 5.4 Hz, 2H), 8.21 (d, J = 9.1 Hz, 1H), 8.41 (d, J = 1.4 Hz, 1H), 8.52 (d, J = 8.5 Hz, 1H), 8.81 (d, J = 8.4 Hz, 1H) | DCI m/z 434.0 M + H⁺ |
| Example 438 | N-{(3R)-1-[(6-{[5-(trifluoromethyl)pyridin-2-yl]oxy}quinolin-2-yl)carbonyl]pyrrolidin-3-yl}acetamide | ¹H NMR (400 MHz, DMSO-d₆) δ ppm 8.59 (s, 1H), 8.48 (d, J = 8.6 Hz, 1H), 8.34-8.27 (m, 1H), 8.22-8.11 (m, 2H), 7.90-7.86 (m, 2H), 7.72 (dd, J = 9.1, 2.6 Hz, 1H), 7.39 (d, J = 8.7 Hz, 1H), 4.33-4.21 (m, 1H), 4.01-3.43 (m, 4H), 2.16-2.06 (m, 1H), 1.88-1.78 (m, 4H) | MS (ESI) m/z 445.1 [M + H]⁺ |
| Example 439 | N-{(3R)-1-[(6-{[5-(trifluoromethyl)pyridin-2-yl]oxy}quinolin-2-yl)carbonyl]pyrrolidin-3-yl}cyclopropanecarboxamide | ¹H NMR (500 MHz, DMSO-d₆) δ ppm 8.60 (s, 1H), 8.48 (d, J = 8.5 Hz, 1H), 8.45-8.35 (m, 1H), 8.31 (dd, J = 8.7, 2.8, 2.8 Hz, 1H), 8.13 (dd, J = 12.7, 9.1 Hz, 1H), 7.92-7.85 (m, 2H), 7.72 (ddd, J = 9.1, 2.5, 2.5 Hz, 1H), 7.40 (dd, J = 8.7, 2.6 Hz, 1H), 4.41-4.21 (m, 1H), 4.03-3.42 (m, 4H), 2.23-2.04 (m, 1H), 1.95-1.80 (m, 1H), 1.67-1.46 (m, 1H), 0.80-0.52 (m, 4H) | MS (ESI) m/z 471.1 [M + H]⁺ |
| Example 440 | (6-{[5-(difluoromethyl)pyridin-2-yl]oxy}quinolin-2-yl)[(3R)-3-(hydroxymethyl)piperazin-1-yl]methanone | ¹H NMR (400 MHz, DMSO-d₆) δ ppm 2.66-3.06 (m, 4H), 3.07-3.29 (m, 3H), 3.76 (d, J = 13.7 Hz, 0.5H), 3.83 (t, J = 12.4 Hz, 0.5H), 4.43 (d, J = 12.9 Hz, 0.5H), 4.54 (d, J = 12.8 Hz, 0.5H), 4.91 (d, J = 88.7 Hz, 1H), 7.12 (t, J = 55.3 Hz, 1H), 7.32 (d, J = 8.6 Hz, 1H), 7.63-7.77 (m, 2H), 7.85 (d, J = 2.6 Hz, 1H), 8.04-8.19 (m, 2H), 8.39 (s, 1H), 8.49 (t, J = 8.2 Hz, 1H) | DCI m/z 415.0 M + H⁺ |
| Example 441 | 6-{[5-(difluoromethyl)pyridin-2-yl]oxy}-N-[2-(dimethylamino)-2-oxoethyl]quinoline-2-carboxamide | ¹H NMR (400 MHz, DMSO-d₆) δ ppm 8.94 (t, J = 5.1 Hz, 1H), 8.56 (d, J = 8.6 Hz, 1H), 8.43 (t, J = 8.6 Hz, 1H), 8.19 (dd, J = 8.8, 1.7 Hz, 2H), 8.13 (dt, J = 8.2, 4.1 Hz, 1H), 7.90 (d, J = 2.6 Hz, 1H), 7.74 (dd, J = 9.1, 2.6 Hz, 1H), 7.34 (d, J = 8.6 Hz, 1H), 7.13 (t, J = 55.3 Hz, 1H), 4.24 (t, J = 7.2 Hz, 2H), 3.04 (s, 3H), 2.91 (s, 3H). | MS (ESI) m/z 401.0 [M + H]⁺ |

| Example Number | Name | ¹H NMR | MS |
|---|---|---|---|
| Example 442 | N-{2-[(2-methoxyethyl)amino]-2-oxoethyl}-N-methyl-6-{[5-(trifluoromethyl)pyridin-2-yl]oxy}quinoline-2-carboxamide | ¹H NMR (400 MHz, DMSO-$d_6$/$D_2O$) δ ppm 8.55 (s, 1H), 8.46 (d, J = 8.5 Hz, 1H), 8.25 (dd, J = 8.7, 2.5 Hz, 1H), 8.14 (d, J = 9.1 Hz, 1H), 7.83 (d, J = 2.2 Hz, 1H), 7.77-7.64 (m, 2H), 7.35 (d, J = 8.7 Hz, 1H), 4.20 (s, 2H), 3.46-3.18 (m, 7H), 3.10 (s, 3H). | MS (ESI) m/z 463.3 [M + H]⁺ |
| Example 443 | N-[2-(morpholin-4-yl)-2-oxoethyl]-6-{[5-(trifluoromethyl)pyridin-2-yl]oxy}quinoline-2-carboxamide | ¹H NMR (400 MHz, DMSO-$d_6$/$D_2O$) δ ppm 8.61-8.50 (m, 2H), 8.30-8.16 (m, 3H), 7.89 (d, J = 2.6 Hz, 1H), 7.75 (dd, J = 9.2, 2.7 Hz, 1H), 7.37 (d, J = 8.7 Hz, 1H), 4.31 (s, 2H), 3.71-3.61 (m, 4H), 3.59-3.51 (m, 4H). | MS (ESI) m/z 461.2 [M + H]⁺ |
| Example 444 | N-[3-(morpholin-4-yl)-3-oxopropyl]-6-{[5-(trifluoromethyl)pyridin-2-yl]oxy}quinoline-2-carboxamide | ¹H NMR (400 MHz, DMSO-$d_6$/$D_2O$) δ ppm 8.57 (s, 1H), 8.51 (t, J = 9.6 Hz, 1H), 8.25 (dd, J = 8.7, 2.6 Hz, 1H), 8.20 (dd, J = 12.8, 8.9 Hz, 2H), 7.86 (t, J = 6.6 Hz, 1H), 7.73 (dd, J = 9.1, 2.6 Hz, 1H), 7.36 (d, J = 8.7 Hz, 1H), 3.68 (t, J = 6.8 Hz, 2H), 3.64-3.57 (m, 4H), 3.55-3.47 (m, 4H), 2.72 (t, J = 6.7 Hz, 2H). | MS (ESI) m/z 475.3 [M + H]⁺ |
| Example 445 | N-[3-oxo-3-(pyrrolidin-1-yl)propyl]-6-{[5-(trifluoromethyl)pyridin-2-yl]oxy}quinoline-2-carboxamide | ¹H NMR (400 MHz, DMSO-$d_6$/$D_2O$) δ ppm 8.59-8.50 (m, 2H), 8.29-8.15 (m, 3H), 7.87 (d, J = 2.6 Hz, 1H), 7.73 (dd, J = 9.1, 2.6 Hz, 1H), 7.36 (d, J = 8.6 Hz, 1H), 3.67 (t, J = 6.7 Hz, 2H), 3.41 (dt, J = 35.1, 6.7 Hz, 4H), 2.65 (t, J = 6.7 Hz, 2H), 1.86 (dt, J = 13.2, 7.0 Hz, 4H). | MS (ESI) m/z 459.3 [M + H]⁺ |
| Example 446 | N-[2-(diethylamino)-2-oxoethyl]-6-{[5-(trifluoromethyl)pyridin-2-yl]oxy}quinoline-2-carboxamide | ¹H NMR (400 MHz, DMSO-$d_6$/$D_2O$) δ ppm 8.62-8.49 (m, 2H), 8.31-8.16 (m, 3H), 7.88 (d, J = 2.6 Hz, 1H), 7.75 (dd, J = 9.1, 2.6 Hz, 1H), 7.37 (d, J = 8.7 Hz, 1H), 4.28 (s, 2H), 3.41 (q, J = 7.1 Hz, 4H), 1.18 (s, 6H). | MS (ESI) m/z 447.2 [M + H]⁺ |
| Example 447 | N-[2-oxo-2-(piperidin-1-yl)ethyl]-6-{[5-(trifluoromethyl)pyridin-2-yl]oxy}quinoline-2-carboxamide | ¹H NMR (400 MHz, DMSO-$d_6$/$D_2O$) δ ppm 8.62-8.49 (m, 2H), 8.31-8.16 (m, 3H), 7.88 (d, J = 2.6 Hz, 1H), 7.75 (dd, J = 9.1, 2.6 Hz, 1H), 7.37 (d, J = 8.6 Hz, 1H), 4.28 (s, 2H), 3.51 (d, J = 5.4 Hz, 4H), 1.65 (d, J = 4.6 Hz, 2H), 1.57 (s, 4H). | MS (ESI) m/z 459.3 [M + H]⁺ |
| Example 448 | N-(1-methyl-5-oxopyrrolidin-3-yl)-6-{[5-(trifluoromethyl)pyridin-2-yl]oxy}quinoline-2-carboxamide | ¹H NMR (400 MHz, DMSO-$d_6$/$D_2O$) δ ppm 8.29 (s, 1H), 8.25 (d, J = 8.5 Hz, 1H), 7.98 (d, J = 9.3 Hz, 2H), 7.89 (d, J = 8.5 Hz, 1H), 7.60 (d, J = 2.6 Hz, 1H), 7.46 (dd, J = 9.2, 2.6 Hz, 1H), 7.09 (d, J = 8.7 Hz, 1H), 4.41 (ddd, J = 13.4, 8.2, 5.2 Hz, 1H), 3.52 (dd, J = 10.2, 7.7 Hz, 1H), 3.20 (dd, J = 10.2, 4.8 Hz, 1H), 2.54 (s, 3H), 2.47 (dd, J = 17.0, 8.8 Hz, 1H), 2.33-2.20 (m, 1H). | MS (ESI) m/z 431.2 [M + H]⁺ |
| Example 449 | N-[3-oxo-3-(piperidin-1-yl)propyl]-6-{[5-(trifluoromethyl)pyridin-2-yl]oxy}quinoline-2-carboxamide | ¹H NMR (400 MHz, DMSO-$d_6$/$D_2O$) δ ppm 8.56 (s, 1H), 8.52 (d, J = 8.5 Hz, 1H), 8.25 (dd, J = 8.7, 2.5 Hz, 1H), 8.20 (dd, J = 12.1, 8.8 Hz, 2H), 7.87 (d, J = 2.6 Hz, 1H), 7.73 (dd, J = 9.1, 2.6 Hz, 1H), 7.36 (d, J = 8.6 Hz, 1H), 3.66 (t, J = 6.8 Hz, 2H), 3.54-3.41 (m, 4H), 2.70 (t, J = 6.8 Hz, 2H), 1.67-1.56 (m, 2H), 1.51 (s, 4H). | MS (ESI) m/z 473.3 [M + H]⁺ |
| Example 450 | 1-methyl-4-[(6-{[5-(trifluoromethyl)pyridin-2-yl]oxy}quinolin-2-yl)carbonyl]piperazin-2-one | ¹H NMR (400 MHz, DMSO-$d_6$/$D_2O$) δ ppm 8.59-8.51 (m, 1H), 8.50-8.44 (m, 1H), 8.28-8.19 (m, 1H), 8.17-8.10 (m, 1H), 7.86-7.81 (m, 1H), 7.79-7.74 (m, 1H), 7.73-7.65 (m, 1H), 7.38-7.30 (m, 1H), 4.27 (s, 2H), 3.99-3.80 (m, 2H), 3.52-3.41 (m, 2H), 2.92 (s, 3H). | MS (ESI) m/z 431.2 [M + H]⁺ |
| Example 451 | N,N-dimethyl-1-[(6-{[5-(trifluoromethyl)pyridin-2-yl]oxy}quinolin-2-yl)carbonyl]-L-prolinamide | ¹H NMR (400 MHz, DMSO-$d_6$/$D_2O$) δ ppm 8.54 (s, 1H), 8.48-8.34 (m, 1H), 8.23 (dd, J = 8.7, 2.5 Hz, 1H), 8.18-7.98 (m, 1H), 7.91-7.76 (m, 2H), 7.68 (dd, J = 9.1, 2.5 Hz, 1H), 7.32 (d, J = 8.7 Hz, 1H), 5.66-4.99 (m, 1H), 3.94-3.68 (m, 2H), 2.74 (d, J = 130.6 Hz, 6H), 2.46-2.22 (m, 1H), 2.07-1.75 (m, 3H). | MS (ESI) m/z 459.3 [M + H]⁺ |
| Example 452 | N-[2-(cyclopropylamino)-2-oxoethyl]-N- | ¹H NMR (400 MHz, DMSO-$d_6$/$D_2O$) δ ppm 8.54-8.50 (m, 1H), 8.41 (d, J = 8.5 Hz, 1H), 8.19 (dd, J = 8.6, 2.6 Hz, 1H), 8.08 (d, J = 9.1 | MS (ESI) m/z |

| Example Number | Name | ¹H NMR | MS |
|---|---|---|---|
| | methyl-6-{[5-(trifluoromethyl)pyridin-2-yl]oxy}quinoline-2-carboxamide | Hz, 1H), 7.78 (d, J = 2.6 Hz, 1H), 7.73-7.63 (m, 2H), 7.30 (d, J = 8.6 Hz, 1H), 4.17-4.12 (m, 2H), 3.08 (d, J = 4.1 Hz, 3H), 2.64 (s, 1H), 0.66-0.59 (m, 2H), 0.55-0.33 (m, 2H). | 445.2 [M + H]⁺ |
| Example 453 | N-[3-(diethylamino)-3-oxopropyl]-6-{[5-(trifluoromethyl)pyridin-2-yl]oxy}quinoline-2-carboxamide | ¹H NMR (400 MHz, DMSO-d₆/D₂O) δ ppm 8.54 (d, J = 0.8 Hz, 1H), 8.51 (dd, J = 8.4, 4.2 Hz, 1H), 8.28-8.21 (m, 1H), 8.20-8.13 (m, 2H), 7.84 (d, J = 2.6 Hz, 1H), 7.71 (dd, J = 9.1, 2.6 Hz, 1H), 7.37-7.31 (m, 1H), 3.65 (t, J = 6.8 Hz, 2H), 3.33 (dt, J = 9.1, 4.5 Hz, 4H), 2.67 (t, J = 6.8 Hz, 2H), 1.23-0.95 (m, 6H). | MS (ESI) m/z 461.3 [M + H]⁺ |
| Example 454 | N-[2-(isopropylamino)-2-oxoethyl]-N-methyl-6-{[5-(trifluoromethyl)pyridin-2-yl]oxy}quinoline-2-carboxamide | ¹H NMR (400 MHz, DMSO-d₆/D₂O) δ ppm 8.56-8.50 (m, 1H), 8.49-8.35 (m, 1H), 8.26-8.17 (m, 1H), 8.16-8.03 (m, 1H), 7.85-7.77 (m, 1H), 7.75-7.63 (m, 2H), 7.38-7.29 (m, 1H), 4.12 (s, 2H), 4.02-3.72 (m, 1H), 3.08 (d, J = 8.8 Hz, 3H), 1.27-0.88 (m, 6H). | MS (ESI) m/z 447.3 [M + H]⁺ |
| Example 455 | 1-[(6-{[5-(difluoromethyl)pyridin-2-yl]oxy}quinolin-2-yl)carbonyl]-N-methyl-L-prolinamide | ¹H NMR (400 MHz, DMSO-d₆/D₂O) δ ppm 8.38 (s, 2H), 8.09 (d, J = 8.4 Hz, 2H), 7.83 (d, J = 9.0 Hz, 1H), 7.75 (s, 1H), 7.64 (d, J = 9.4 Hz, 1H), 7.26 (d, J = 8.5 Hz, 1H), 7.04 (t, J = 55.5 Hz, 1H), 3.75 (s, 2H), 2.66 (s, 1H), 2.42 (s, 2H), 2.21 (s, 1H), 2.02-1.80 (m, 4H). | MS (ESI) m/z 427.2 [M + H]⁺ |
| Example 456 | 6-{[5-(difluoromethyl)pyridin-2-yl]oxy}-N-[2-oxo-2-(pyrrolidin-1-yl)ethyl]quinoline-2-carboxamide | ¹H NMR (400 MHz, DMSO-d₆/D₂O) δ ppm 8.51 (d, J = 8.5 Hz, 1H), 8.39 (s, 1H), 8.19 (dd, J = 14.5, 8.8 Hz, 2H), 8.10 (d, J = 8.5 Hz, 1H), 7.82 (d, J = 2.6 Hz, 1H), 7.70 (dd, J = 9.1, 2.6 Hz, 1H), 7.28 (d, J = 8.5 Hz, 1H), 7.04 (t, J = 55.5 Hz, 1H), 4.19 (s, 2H), 3.56-3.34 (m, 4H), 2.03-1.75 (m, 4H). | MS (ESI) m/z 427.2 [M + H]⁺ |
| Example 457 | 6-{[5-(difluoromethyl)pyridin-2-yl]oxy}-N-{2-[(2-methoxyethyl)amino]-2-oxoethyl}-N-methylquinoline-2-carboxamide | ¹H NMR (400 MHz, DMSO-d₆/D₂O) δ ppm 8.42 (s, 1H), 8.37 (s, 1H), 8.08 (d, J = 8.5 Hz, 2H), 7.77 (s, 1H), 7.70 (d, J = 8.5 Hz, 1H), 7.65 (dd, J = 9.1, 2.5 Hz, 1H), 7.26 (d, J = 8.6 Hz, 1H), 7.04 (t, J = 55.5 Hz, 1H), 4.17 (s, 2H), 3.28 (s, 7H), 3.08 (s, 3H). | MS (ESI) m/z 445.3 [M + H]⁺ |
| Example 458 | 6-{[5-(difluoromethyl)pyridin-2-yl]oxy}-N-[2-(morpholin-4-yl)-2-oxoethyl]quinoline-2-carboxamide | ¹H NMR (400 MHz, DMSO-d₆/D₂O) δ ppm 8.52 (d, J = 8.5 Hz, 1H), 8.39 (s, 1H), 8.18 (dd, J = 14.6, 8.8 Hz, 2H), 8.10 (d, J = 8.8 Hz, 1H), 7.82 (d, J = 2.6 Hz, 1H), 7.70 (dd, J = 9.2, 2.6 Hz, 1H), 7.28 (d, J = 8.5 Hz, 1H), 7.04 (t, J = 55.4 Hz, 1H), 4.28 (s, 2H), 3.69-3.60 (m, 4H), 3.56-3.49 (m, 4H). | MS (ESI) m/z 443.2 [M + H]⁺ |
| Example 459 | 6-{[5-(difluoromethyl)pyridin-2-yl]oxy}-N-[3-(morpholin-4-yl)-3-oxopropyl]quinoline-2-carboxamide | ¹H NMR (400 MHz, DMSO-d₆/D₂O) δ ppm 8.49 (d, J = 8.5 Hz, 1H), 8.38 (s, 1H), 8.16 (dd, J = 11.6, 8.9 Hz, 2H), 8.09 (d, J = 8.7 Hz, 1H), 7.80 (d, J = 2.7 Hz, 1H), 7.68 (dd, J = 9.1, 2.6 Hz, 1H), 7.27 (d, J = 8.7 Hz, 1H), 7.04 (t, J = 55.6 Hz, 1H), 3.65 (t, J = 6.8 Hz, 2H), 3.61-3.54 (m, 4H), 3.53-3.44 (m, 4H), 2.69 (t, J = 6.7 Hz, 2H). | MS (ESI) m/z 457.3 [M + H]⁺ |
| Example 460 | 6-{[5-(difluoromethyl)pyridin-2-yl]oxy}-N-[3-oxo-3-(pyrrolidin-1-yl)propyl]quinoline-2-carboxamide | ¹H NMR (400 MHz, DMSO-d₆/D₂O) δ ppm 8.49 (d, J = 8.6 Hz, 1H), 8.38 (s, 1H), 8.16 (dd, J = 12.6, 8.8 Hz, 2H), 8.09 (d, J = 8.6 Hz, 1H), 7.80 (d, J = 2.6 Hz, 1H), 7.68 (dd, J = 9.1, 2.6 Hz, 1H), 7.27 (d, J = 8.6 Hz, 1H), 7.04 (t, J = 55.5 Hz, 1H), 3.64 (t, J = 6.7 Hz, 2H), 3.39 (dt, J = 34.8, 6.5 Hz, 4H), 2.62 (t, J = 6.7 Hz, 2H), 1.83 (dt, J = 38.2, 6.6 Hz, 4H). | MS (ESI) m/z 441.3 [M + H]⁺ |
| Example 461 | N-[2-(diethylamino)-2-oxoethyl]-6-{[5-(difluoromethyl)pyridin-2-yl]oxy}quinoline-2-carboxamide | ¹H NMR (400 MHz, DMSO-d₆/D₂O) δ ppm 8.51 (d, J = 8.5 Hz, 1H), 8.39 (d, J = 1.4 Hz, 1H), 8.19 (dd, J = 14.0, 8.8 Hz, 2H), 8.09 (dd, J = 8.5, 2.3 Hz, 1H), 7.82 (d, J = 2.6 Hz, 1H), 7.70 (dd, J = 9.1, 2.7 Hz, 1H), 7.28 (d, J = 8.6 Hz, 1H), 7.04 (t, J = 55.5 Hz, 1H), 4.26 (s, 2H), 3.38 (q, J = 7.1 Hz, 4H), 1.16 (s, 6H). | MS (ESI) m/z 429.2 [M + H]⁺ |
| Example 462 | 6-{[5-(difluoromethyl)pyridin-2-yl]oxy}-N-(1-methyl-5-oxopyrrolidin-3- | ¹H NMR (400 MHz, DMSO-d₆/D₂O) δ ppm 8.49 (d, J = 8.5 Hz, 1H), 8.38 (s, 1H), 8.22 (d, J = 9.2 Hz, 1H), 8.13 (d, J = 8.5 Hz, 1H), 8.10 (d, J = 8.6 Hz, 1H), 7.80 (d, J = 2.6 Hz, 1H), 7.69 (dd, J = 9.2, 2.6 Hz, 1H), 7.27 (d, J = 8.6 | MS (ESI) m/z 413.2 [M + H]⁺ |

| Example Number | Name | ¹H NMR | MS |
|---|---|---|---|
| | yl)quinoline-2-carboxamide | Hz, 1H), 7.04 (t, J = 55.5 Hz, 1H), 4.66 (ddd, J = 13.5, 8.2, 5.4 Hz, 1H), 3.77 (dd, J = 10.1, 7.7 Hz, 1H), 3.44 (dd, J = 10.2, 4.8 Hz, 1H), 2.79 (s, 3H), 2.71 (dd, J = 17.0, 8.8 Hz, 1H), 2.56-2.47 (m, 1H). | |
| Example 463 | 6-{5-(difluoromethyl)pyridin-2-yl]oxy}-N-[3-oxo-3-(piperidin-1-yl)propyl]quinoline-2-carboxamide | ¹H NMR (400 MHz, DMSO-d₆/D₂O) δ ppm 8.49 (d, J = 8.5 Hz, 1H), 8.38 (s, 1H), 8.16 (dd, J = 10.9, 8.9 Hz, 2H), 8.09 (d, J = 8.7 Hz, 1H), 7.80 (d, J = 2.6 Hz, 1H), 7.68 (dd, J = 9.2, 2.6 Hz, 1H), 7.27 (d, J = 8.5 Hz, 1H), 7.04 (t, J = 55.4 Hz, 1H), 3.64 (t, J = 6.8 Hz, 2H), 3.45 (d, J = 5.2 Hz, 4H), 2.67 (t, J = 6.8 Hz, 2H), 1.58 (d, J = 4.5 Hz, 2H), 1.48 (s, 4H). | MS (ESI) m/z 455.3 [M + H]⁺ |
| Example 464 | 4-[(6-{5-(difluoromethyl)pyridin-2-yl]oxy}quinolin-2-yl)carbonyl]-1-methylpiperazin-2-one | ¹H NMR (400 MHz, DMSO-d₆/D₂O) δ ppm 8.47 (d, J = 8.5 Hz, 1H), 8.38 (s, 1H), 8.11 (dd, J = 15.5, 7.8 Hz, 2H), 7.79 (d, J = 2.6 Hz, 1H), 7.75 (d, J = 8.5 Hz, 1H), 7.67 (dd, J = 9.2, 2.6 Hz, 1H), 7.27 (d, J = 8.5 Hz, 1H), 7.04 (t, J = 55.5 Hz, 1H), 4.27 (s, 2H), 3.91 (s, 2H), 3.47 (t, J = 5.5 Hz, 2H), 2.92 (s, 3H). | MS (ESI) m/z 413.3 [M + H]⁺ |
| Example 465 | 1-[(6-{5-(difluoromethyl)pyridin-2-yl]oxy}quinolin-2-yl)carbonyl]-N,N-dimethyl-L-prolinamide | ¹H NMR (400 MHz, DMSO-d₆/D₂O) δ ppm 8.48-8.32 (m, 2H), 8.18-7.95 (m, 2H), 7.91-7.72 (m, 2H), 7.65 (d, J = 9.0 Hz, 1H), 7.26 (d, J = 8.5 Hz, 1H), 7.04 (t, J = 55.4 Hz, 1H), 5.66-4.97 (m, 1H), 3.95-3.82 (m, 1H), 3.75 (d, J = 4.4 Hz, 1H), 2.72 (d, J = 145.7 Hz, 8H), 1.91 (d, J = 6.5 Hz, 2H). | MS (ESI) m/z 441.3 [M + H]⁺ |
| Example 466 | N-[2-(cyclopropylamino)-2-oxoethyl]-6-{5-(difluoromethyl)pyridin-2-yl]oxy}-N-methylquinoline-2-carboxamide | ¹H NMR (400 MHz, DMSO-d₆/D₂O) δ ppm 8.50-8.32 (m, 2H), 8.18-7.98 (m, 2H), 7.77 (s, 1H), 7.73-7.59 (m, 2H), 7.26 (d, J = 8.8 Hz, 1H), 7.04 (t, J = 55.4 Hz, 1H), 4.11 (s, 2H), 3.07 (s, 3H), 2.68 (s, 1H), 0.76-0.20 (m, 4H). | MS (ESI) m/z 427.2 [M + H]⁺ |
| Example 467 | N-[3-(diethylamino)-3-oxopropyl]-6-{5-(difluoromethyl)pyridin-2-yl]oxy}quinoline-2-carboxamide | ¹H NMR (400 MHz, DMSO-d₆/D₂O) δ ppm 8.49 (d, J = 8.5 Hz, 1H), 8.38 (s, 1H), 8.16 (t, J = 8.8 Hz, 2H), 8.12-8.06 (m, 1H), 7.80 (d, J = 2.6 Hz, 1H), 7.68 (dd, J = 9.1, 2.6 Hz, 1H), 7.27 (d, J = 8.5 Hz, 1H), 7.04 (t, J = 55.5 Hz, 1H), 3.65 (t, J = 6.8 Hz, 2H), 3.33 (q, J = 7.1 Hz, 4H), 2.67 (t, J = 6.8 Hz, 2H), 1.09 (s, 6H). | MS (ESI) m/z 443.3 [M + H]⁺ |
| Example 468 | 6-{5-(difluoromethyl)pyridin-2-yl]oxy}-N-[2-(isopropylamino)-2-oxoethyl]-N-methylquinoline-2-carboxamide | ¹H NMR (400 MHz, DMSO-d₆/D₂O) δ ppm 8.49-8.32 (m, 2H), 8.15-8.00 (m, 2H), 7.77 (s, 1H), 7.72-7.60 (m, 2H), 7.26 (d, J = 8.5 Hz, 1H), 7.04 (t, J = 55.5 Hz, 1H), 4.12 (s, 2H), 4.00-3.70 (m, 1H), 3.07 (s, 3H), 1.06 (d, J = 46.2 Hz, 6H). | MS (ESI) m/z 429.2 [M + H]⁺ |
| Example 469 | N-[2-(2-oxopiperazin-1-yl)ethyl]-6-{5-(trifluoromethyl)pyridin-2-yl]oxy}quinoline-2-carboxamide | ¹H NMR (400 MHz, DMSO-d₆) δ ppm 8.92 (t, J = 6.0 Hz, 1H), 8.61-8.62 (m, 1H), 8.54 (d, J = 8.5 Hz, 1H), 8.31 (dd, J = 8.5, 2.4 Hz, 1H), 8.17-8.20 (m, 2H), 7.93 (d, J = 2.4 Hz, 1H), 7.75-7.77 (m, 2H), 7.41 (d, J = 8.5 Hz, 1H), 3.52 (q, J = 6.4 Hz, 1H), 3.16-3.18 (m, 2H), 3.04 (s, 2H), 2.62-2.66 (m, 4H). | MS (ESI) m/z 460.1 [M + H]⁺ |
| Example 470 | N-(azetidin-3-ylmethyl)-6-{5-(trifluoromethyl)pyridin-2-yl]oxy}quinoline-2-carboxamide | ¹H NMR (400 MHz, DMSO-d₆) δ ppm 9.27 (t, J = 6.3 Hz, 1H), 8.60-8.61 (m, 1H), 8.55 (d, J = 8.8 Hz, 1H), 8.32 (dd, J = 8.9, 2.4 Hz, 1H), 8.18-8.22 (m, 2H), 7.94 (d, J = 2.8 Hz, 1H), 7.77 (dd, J = 9.0, 2.6 Hz, 1H), 7.41 (d, J = 8.9 Hz, 1H), 3.97-4.04 (m, 2H), 3.85-3.92 (m, 2H), 3.60 (t, J = 6.4 Hz, 2H), 3.07-3.18 (m, 1H). | MS (ESI) m/z 403.1 [M + H]⁺ |
| Example 471 | N-(2-hydroxy-2-methylpropyl)-6-{6-(trifluoromethyl)pyridin-3-yl]oxy}quinoline-2-carboxamide | ¹H NMR (400 MHz, CDCl₃) δ ppm 9.60-9.35 (m, 1H), 9.00-8.82 (m, 1H), 8.67-8.60 (m, 1H), 8.60-8.46 (m, 2H), 7.87-7.73 (m, 2H), 7.67-7.54 (m, 1H), 7.50-7.39 (m, 1H), 3.69-3.57 (m, 2H), 1.37 (s, 6H). | MS (ESI) m/z 406.0 [M + H]⁺ |
| Example 472 | 4-{4-[(6-{5-(trifluoromethyl)pyridin-2-yl]oxy}quinolin-2-yl)carbonyl]piperazin-1-yl}butanenitrile | ¹H NMR (400 MHz, DMSO-d₆) δ ppm 8.59 (d, J = 3.1 Hz, 1H), 8.48 (d, J = 8.5 Hz, 1H), 8.30 (dd, J = 8.7, 2.6 Hz, 1H), 8.11 (d, J = 9.1 Hz, 1H), 7.89 (d, J = 2.6 Hz, 1H), 7.74-7.66 (m, 2H), 7.39 (d, J = 8.7 Hz, 1H), 3.72 (t, J = 4.6 Hz, 2H), 3.46 (t, J = 4.5 Hz, 2H), 2.53-2.36 (m, 8H), 1.75 (p, J = 7.0 Hz, 2H). | ESI m/z 470.1 [M + H]⁺ |

-continued

| Example Number | Name | ¹H NMR | MS |
|---|---|---|---|
| Example 473 | 3-{4-[(6-{[5-(trifluoromethyl)pyridin-2-yl]oxy}quinolin-2-yl)carbonyl]piperazin-1-yl}propanenitrile | ¹H NMR (400 MHz, DMSO-d$_6$) δ ppm 8.61-8.57 (m, 1H), 8.48 (d, J = 8.5 Hz, 1H), 8.30 (dd, J = 8.7, 2.5 Hz, 1H), 8.11 (d, J = 9.1 Hz, 1H), 7.89 (d, J = 2.6 Hz, 1H), 7.75-7.66 (m, 2H), 7.39 (d, J = 8.7 Hz, 1H), 3.73 (t, J = 4.6 Hz, 2H), 3.48 (t, J = 4.6 Hz, 2H), 2.74-2.45 (m, 8H). | ESI m/z 456.1 [M + H]$^+$ |
| Example 474 | 1-[(6-{[5-(trifluoromethyl)pyridin-2-yl]oxy}quinolin-2-yl)carbonyl]piperidine-4-carbonitrile | ¹H NMR (400 MHz, DMSO-d$_6$) δ ppm 8.59 (bs, 1H), 8.49 (d, J = 8.4 Hz, 1H), 8.30 (dd, J = 8.7, 2.6 Hz, 1H), 8.11 (d, J = 9.0 Hz, 1H), 7.89 (d, J = 2.6 Hz, 1H), 7.73 (s, 1H), 7.71 (s, 1H), 7.39 (d, J = 8.7 Hz, 1H), 4.07-3.97 (m, 1H), 3.65-3.55 (m, 1H), 3.53-3.43 (m, 1H), 3.37 (m, 1H), 3.26-3.14 (m, 1H), 2.10-1.97 (m, 1H), 1.98-1.86 (m, 1H), 1.88-1.72 (m, 2H). | ESI m/z 427.1 [M + H]$^+$ |
| Example 475 | 6-{[5-(difluoromethyl)pyridin-2-yl]oxy}-N-(oxetan-3-yl)quinoline-2-carboxamide | ¹H NMR (500 MHz, DMSO-d$_6$) δ ppm 9.58 (d, J = 6.9 Hz, 1H), 8.53 (d, J = 8.5 Hz, 1H), 8.43-8.39 (m, 1H), 8.24 (d, J = 9.1 Hz, 1H), 8.17-8.11 (m, 2H), 7.89 (d, J = 2.6 Hz, 1H), 7.75 (dd, J = 9.1, 2.7 Hz, 1H), 7.34 (d, J = 8.5 Hz, 1H), 5.11 (h, J = 7.1 Hz, 1H), 4.82-4.73 (m, 4H). | ESI m/z 372.1 [M + H]$^+$ |
| Example 476 | 5,8-dioxa-2-azaspiro[3.4]oct-2-yl(6-{[5-(trifluoromethyl)pyridin-2-yl]oxy}quinolin-2-yl)methanone | ¹H NMR (400 MHz, DMSO-d$_6$) δ ppm 8.60 (d, J = 2.9 Hz, 1H), 8.50 (d, J = 8.5 Hz, 1H), 8.31 (dd, J = 8.7, 2.6 Hz, 1H), 8.18 (d, J = 9.0 Hz, 1H), 8.08 (d, J = 8.5 Hz, 1H), 7.90 (d, J = 2.6 Hz, 1H), 7.73 (dd, J = 9.0, 2.7 Hz, 1H), 7.40 (d, J = 8.6 Hz, 1H), 4.86 (bs, 2H), 4.26 (bs, 2H), 4.00-3.96 (m, 4H). | ESI m/z 432.1 [M + H]$^+$ |
| Example 477 | 6-{[5-(difluoromethyl)pyridin-2-yl]oxy}-N-[(3S,4S)-4-hydroxy-1,1-dioxidotetrahydrothiophen-3-yl]quinoline-2-carboxamide | ¹H NMR (500 MHz, DMSO-d$_6$) δ ppm 8.88 (d, J = 8.1 Hz, 1H), 8.57 (d, J = 8.5 Hz, 1H), 8.44-8.39 (m, 1H), 8.21 (s, 1H), 8.20 (s, 1H), 8.15 (dd, J = 8.5, 2.3 Hz, 1H), 7.91 (d, J = 2.6 Hz, 1H), 7.75 (dd, J = 9.1, 2.6 Hz, 1H), 7.34 (d, J = 8.5 Hz, 1H), 7.13 (t, J = 55.3 Hz, 1H), 6.30 (s, 1H), 4.85-4.75 (m, 1H), 4.66-4.61 (m, 1H), 3.61-3.46 (m, 2H), 3.42-3.30 (m, 2H). | ESI m/z 450.0 [M + H]$^+$ |
| Example 478 | tetrahydro-5H-[1,3]dioxolo[4,5-c]pyrrol-5-yl(6-{[5-(trifluoromethyl)pyridin-2-yl]oxy}quinolin-2-yl)methanone | ¹H NMR (500 MHz, DMSO-d$_6$) δ ppm 8.60 (bs, 1H), 8.49 (d, J = 8.5 Hz, 1H), 8.31 (dd, J = 8.7, 2.6 Hz, 1H), 8.15 (d, J = 9.0 Hz, 1H), 7.90 (d, J = 2.6 Hz, 1H), 7.86 (d, J = 8.4 Hz, 1H), 7.73 (dd, J = 9.0, 2.6 Hz, 1H), 7.40 (d, J = 8.6 Hz, 1H), 5.06 (s, 1H), 4.82-4.73 (m, 2H), 4.76-4.69 (m, 1H), 4.11-4.07 (m, 1H), 4.08-4.00 (m, 1H), 3.89 (dd, J = 13.3, 5.2 Hz, 1H), 3.60 (dd, J = 13.8, 5.5 Hz, 1H). | ESI m/z 432.1 [M + H]$^+$ |
| Example 479 | (6-{[5-(difluoromethyl)pyridin-2-yl]oxy}quinolin-2-yl)[3-(methylsulfonyl)azetidin-1-yl]methanone | ¹H NMR (500 MHz, DMSO-d$_6$) δ ppm 8.51 (d, J = 8.5 Hz, 1H), 8.42-8.38 (m, 1H), 8.21 (d, J = 9.1 Hz, 1H), 8.14 (dd, J = 8.7, 2.4 Hz, 1H), 8.08 (d, J = 8.5 Hz, 1H), 7.87 (d, J = 2.6 Hz, 1H), 7.73 (dd, J = 9.0, 2.6 Hz, 1H), 7.33 (d, J = 8.5 Hz, 1H), 7.12 (t, J = 55.3 Hz, 1H), 5.09 (dd, J = 11.7, 6.9 Hz, 1H), 4.99 (dd, J = 11.5, 3.9 Hz, 1H), 4.47-4.38 (m, 2H), 4.37-4.27 (m, 1H), 3.10 (s, 3H). | ESI m/z 434.0 [M + H]$^+$ |
| Example 480 | N-methyl-N-(oxetan-3-yl)-6-{[5-(trifluoromethyl)pyridin-2-yl]oxy}quinoline-2-carboxamide | ¹H NMR (500 MHz, DMSO-d$_6$) δ ppm 8.59 (bs, 1H), 8.49 (dd, J = 8.5, 5.5 Hz, 1H), 8.31 (dd, J = 8.7, 2.5 Hz, 1H), 8.12 (dd, J = 19.2, 9.1 Hz, 1H), 7.90 (d, J = 2.6 Hz, 1H), 7.77-7.65 (m, 2H), 7.40 (d, J = 8.7 Hz, 1H), 5.41 and 5.13 (2m, 1H), 4.78 and 4.63 (2t, J = 7.3 Hz, 4H), 3.28 and 3.11 (2s, 3H). | ESI m/z 404.1 [M + H]$^+$ |
| Example 481 | 6-{[5-(difluoromethyl)pyridin-2-yl]oxy}-N-(1-oxidotetrahydro-2H-thiopyran-4-yl)quinoline-2-carboxamide | ¹H NMR (500 MHz, DMSO-d$_6$) δ ppm 9.03-8.81 (m, 1H), 8.52 (d, J = 8.5 Hz, 1H), 8.41 (bs, 1H), 8.22 (dd, J = 9.1, 3.5 Hz, 1H), 8.18-8.11 (m, 2H), 7.88 (d, J = 2.6 Hz, 1H), 7.73 (dd, J = 9.1, 2.7 Hz, 1H), 7.33 (d, J = 8.5 Hz, 1H), 7.13 (t, J = 55.3 Hz, 1H), 4.34-4.04 (m, 1H), 3.41-3.11 (m, 1H), 3.01-2.78 (m, 3H), 2.43-1.80 (m, 4H). | ESI m/z 432.1 [M + H]$^+$ |

| Example Number | Name | ¹H NMR | MS |
|---|---|---|---|
| Example 482 | N-(oxetan-3-ylmethyl)-6-{[5-(trifluoromethyl)pyridin-2-yl]oxy}quinoline-2-carboxamide | ¹H NMR (400 MHz, DMSO-$d_6$) δ ppm 9.16 (t, J = 6.1 Hz, 1H), 8.61-8.62 (m, 1H), 8.53 (d, J = 8.5 Hz, 1H), 8.31 (dd, J = 8.7, 2.6 Hz, 1H), 8.17-8.21 (m, 2H), 7.93 (d, J = 2.8 Hz, 1H), 7.76 (dd, J = 9.2, 2.8 Hz, 1H), 7.40 (d, J = 8.5 Hz, 1H), 4.64-4.67 (m, 2H), 4.40-4.43 (m, 2H), 3.65-3.68 (m, 2H), 3.22-3.30 (m, 1H). | MS (ESI) m/z 404.1 [M + H]⁺ |
| Example 483 | 4-[(6-{[5-(trifluoromethyl)pyridin-2-yl]oxy}quinolin-2-yl)carbonyl]piperazine-2-carbonitrile | ¹H NMR (500 MHz, DMSO-$d_6$, rotamers) δ ppm 8.59 (s, 1H), 8.51 (dd, J = 8.5, 3.1 Hz, 1H), 8.30 (dd, J = 8.7, 2.4 Hz, 1H), 8.12 (dd, J = 9.1, 5.5 Hz, 1H), 7.92-7.88 (m, 1H), 7.75-7.67 (m, 2H), 7.39 (d, J = 8.7 Hz, 1H), 4.51 (d, J = 13.2 Hz, 0.5H), 4.38 (d, J = 12.8 Hz, 0.5H), 4.33-4.30 (m, 0.5H), 4.10-4.00 (m, 1H), 3.73 (d, J = 13.2 Hz, 0.5H), 3.54-3.46 (m, 1.5H), 3.30-3.18 (m, 1H), 3.08-2.99 (m, 0.5H), 2.97-2.81 (m, 1.5H), 2.79-2.71 (m, 0.5H). | MS (ESI) m/z 428.0 [M + H]⁺ |
| Example 484 | 6-(4-cyanophenoxy)-N-(2-oxopiperidin-4-yl)quinoline-2-carboxamide | ¹H NMR (400 MHz, DMSO-$d_6$) δ ppm 8.87 (d, J = 8.1 Hz, 1H), 8.51 (d, J = 8.6 Hz, 1H), 8.25 (d, J = 9.1 Hz, 1H), 8.15 (d, J = 8.5 Hz, 1H), 7.92 (d, J = 8.7 Hz, 2H), 7.75-7.73 (m, 1H), 7.72-7.68 (m, 1H), 7.58 (s, 1H), 7.30 (d, J = 8.7 Hz, 2H), 4.35-4.21 (m, 1H), 3.26-3.17 (m, 2H), 2.55-2.44 (m, 2H), 2.03-1.81 (m, 2H). | MS (ESI) m/z 387.0 [M + H]⁺ |
| Example 485 | N-(3,3-difluorocyclopentyl)-6-{[5-(trifluoromethyl)pyridin-2-yl]oxy}quinoline-2-carboxamide | ¹H NMR (500 MHz, DMSO-$d_6$) δ ppm 1.94-2.04 (m, 1H), 2.05-2.24 (m, 2H), 2.25-2.57 (m, 3H), 4.46-4.64 (m, 1H), 7.41 (d, J = 8.7 Hz, 1H), 7.72-7.82 (m, 1H), 7.93 (t, J = 4.2 Hz, 1H), 8.15 (dd, J = 14.7, 8.5 Hz, 1H), 8.23 (d, J = 9.1 Hz, 1H), 8.27-8.37 (m, 1H), 8.53 (t, J = 9.0 Hz, 1H), 8.61 (d, J = 7.4 Hz, 1H), 9.03-9.12 (m, 1H) | DCI m/z 438.0 M + H]⁺ |
| Example 486 | N-(3,3-difluorocyclopentyl)-6-{[5-(difluoromethyl)pyridin-2-yl]oxy}quinoline-2-carboxamide | ¹H NMR (500 MHz, DMSO-$d_6$) δ ppm 1.99 (ddd, J = 12.0, 10.3, 5.9 Hz, 1H), 2.06-2.24 (m, 2H), 2.23-2.43 (m, 2H), 2.45-2.58 (m, 1H), 4.43-4.64 (m, 1H), 7.13 (t, J = 55.3 Hz, 1H), 7.34 (d, J = 8.6 Hz, 1H), 7.73 (dd, J = 9.1, 2.6 Hz, 1H), 7.89 (d, J = 2.6 Hz, 1H), 8.15 (t, J = 7.5 Hz, 2H), 8.21 (d, J = 9.1 Hz, 1H), 8.41 (s, 1H), 8.53 (d, J = 8.6 Hz, 1H), 9.07 (d, J = 8.1 Hz, 1H) | DCI m/z 420.0 [M + H]⁺ |
| Example 487 | [3-fluoro-3-(methoxymethyl)pyrrolidin-1-yl](6-{[5-(trifluoromethyl)pyridin-2-yl]oxy}quinolin-2-yl)methanone | ¹H NMR (400 MHz, DMSO-$d_6$, 90° C.) δ ppm 8.58-8.40 (m, 2H), 8.22 (dd, J = 8.7, 2.6 Hz, 1H), 8.15 (d, J = 9.2 Hz, 1H), 7.91-7.78 (m, 2H), 7.68 (dd, J = 9.1, 2.7 Hz, 1H), 7.33 (d, J = 8.8 Hz, 1H), 4.08-3.58 (m, 6H), 3.37 (d, J = 28.6 Hz, 3H), 2.27-2.06 (m, 2H). | MS (APCI) m/z 450.2 [M + H]⁺ |
| Example 488 | [3-(ethoxymethyl)-3-fluoropyrrolidin-1-yl](6-{[5-(trifluoromethyl)pyridin-2-yl]oxy}quinolin-2-yl)methanone | ¹H NMR (400 MHz, DMSO-$d_6$, 90° C.) δ ppm 8.58-8.40 (m, 2H), 8.22 (dd, J = 8.7, 2.6 Hz, 1H), 8.15 (d, J = 8.7 Hz, 1H), 7.91-7.78 (m, 2H), 7.68 (dd, J = 9.2, 2.6 Hz, 1H), 7.33 (d, J = 8.7 Hz, 1H), 4.09-3.48 (m, 8H), 2.18 (ddd, J = 28.4, 11.7, 7.0 Hz, 2H), 1.14 (dt, J = 26.5, 6.8 Hz, 3H). | MS (APCI) m/z 464.3 [M + H]⁺ |
| Example 489 | {3-fluoro-3-[(pyridin-4-yloxy)methyl]pyrrolidin-1-yl}(6-{[5-(trifluoromethyl)pyridin-2-yl]oxy}quinolin-2-yl)methanone | ¹H NMR (400 MHz, DMSO-$d_6$, 90° C.) δ ppm 8.53 (s, 4H), 8.47 (d, J = 8.5 Hz, 1H), 8.23 (dd, J = 8.8, 2.6 Hz, 1H), 8.15 (s, 1H), 7.89 (s, 1H), 7.83 (d, J = 2.6 Hz, 1H), 7.69 (dd, J = 9.1, 2.6 Hz, 1H), 7.40 (s, 1H), 7.34 (d, J = 8.6 Hz, 2H), 4.69 (d, J = 23.7 Hz, 2H), 4.04 (s, 4H), 2.43-2.27 (m, 3H). | MS (APCI) m/z 513.2 [M + H]⁺ |
| Example 490 | {3-fluoro-3-[(pyridin-3-yloxy)methyl]pyrrolidin-1-yl}(6-{[5-(trifluoromethyl)pyridin-2-yl]oxy}quinolin-2-yl)methanone | ¹H NMR (400 MHz, DMSO-$d_6$, 90° C.) δ ppm 8.53 (s, 1H), 8.50-8.30 (m, 2H), 8.22 (dd, J = 8.7, 2.7 Hz, 2H), 8.14 (d, J = 13.2 Hz, 1H), 7.89 (s, 1H), 7.83 (d, J = 2.6 Hz, 1H), 7.69 (dd, J = 9.1, 2.7 Hz, 1H), 7.62-7.36 (m, 2H), 7.33 (d, J = 8.7 Hz, 1H), 4.57-4.38 (m, 2H), 4.12 (d, J = 85.5 Hz, 4H), 2.35 (d, J = 14.8 Hz, 2H). | MS (APCI) m/z 513.2 [M + H]⁺ |
| Example 491 | [3-fluoro-3-(phenoxymethyl)pyrrolidin-1-yl](6-{[5- | ¹H NMR (400 MHz, DMSO-$d_6$, 90° C.) δ ppm 8.58-8.41 (m, 2H), 8.22 (dd, J = 8.7, 2.6 Hz, 1H), 8.15 (dd, J = 17.3, 9.1 Hz, 1H), 7.88 (d, J = | MS (APCI) m/z |

| Example Number | Name | ¹H NMR | MS |
|---|---|---|---|
| | (trifluoromethyl)pyridin-2-yl]oxy}quinolin-2-yl)methanone | 8.6 Hz, 1H), 7.83 (d, J = 2.6 Hz, 1H), 7.69 (dd, J = 9.1, 2.6 Hz, 1H), 7.31 (dd, J = 16.0, 8.5 Hz, 3H), 7.08-6.92 (m, 3H), 4.45-3.74 (m, 6H), 2.40-2.21 (m, 2H). | 512.2 [M + H]⁺ |
| Example 492 | benzyl({4-fluoro-1-[(6-{[5-(trifluoromethyl)pyridin-2-yl]oxy}quinolin-2-yl)carbonyl]pyrrolidin-3-yl}methyl)carbamate | ¹H NMR (400 MHz, DMSO-d₆, 90° C.) δ ppm 8.53 (s, 1H), 8.45 (d, J = 8.5 Hz, 1H), 8.22 (dd, J = 8.7, 2.6 Hz, 1H), 8.14 (dd, J = 9.3, 5.6 Hz, 1H), 7.93-7.78 (m, 2H), 7.73-7.63 (m, 1H), 7.40-7.23 (m, 5H), 5.27 (dd, J = 53.9, 16.2 Hz, 1H), 5.04 (d, J = 28.8 Hz, 1H), 4.31-3.30 (m, 5H), 3.20 (dd, J = 13.7, 7.8 Hz, 1H), 2.72-2.54 (m, 1H). | MS (APCI) m/z 569.2 [M + H]⁺ |
| Example 493 | {3-fluoro-3-[(2-methoxyethoxy)methyl]pyrrolidin-1-yl}(6-{[5-(trifluoromethyl)pyridin-2-yl]oxy}quinolin-2-yl)methanone | ¹H NMR (400 MHz, DMSO-d₆, 90° C.) δ ppm 8.58-8.36 (m, 2H), 8.22 (d, J = 8.6, 2.6 Hz, 1H), 8.15 (s, 1H), 7.91-7.78 (m, 2H), 7.68 (dd, J = 9.1, 2.7 Hz, 1H), 7.33 (d, J = 8.7 Hz, 1H), 4.12-3.41 (m, 9H), 3.30 (s, 1H), 3.23 (s, 3H), 2.27-2.09 (m, 2H). | MS (APCI) m/z 494.2 [M + H]⁺ |
| Example 494 | 2-oxa-6-azaspiro[3.4]oct-6-yl(6-{[5-(trifluoromethyl)pyridin-2-yl]oxy}quinolin-2-yl)methanone | ¹H NMR (400 MHz, DMSO-d₆, 90° C.) δ ppm 8.57-8.48 (m, 1H), 8.44 (d, J = 8.5 Hz, 1H), 8.22 (dd, J = 8.8, 2.5 Hz, 1H), 8.14 (d, J = 13.4 Hz, 1H), 7.87-7.77 (m, 2H), 7.68 (dd, J = 9.3, 3.6 Hz, 1H), 7.33 (d, J = 8.7 Hz, 1H), 4.95-4.32 (m, 4H), 4.04-3.39 (m, 4H), 2.23 (t, J = 7.1 Hz, 2H). | MS (APCI) m/z 430.2 [M + H]⁺ |
| Example 495 | [(2R,4S)-4-fluoro-2-(hydroxymethyl)pyrrolidin-1-yl](6-{[5-(trifluoromethyl)pyridin-2-yl]oxy}quinolin-2-yl)methanone | ¹H NMR (400 MHz, DMSO-d₆, 90° C.) δ ppm 8.61-8.50 (m, 1H), 8.46 (d, J = 8.5 Hz, 1H), 8.22 (dd, J = 8.7, 2.5 Hz, 1H), 8.14 (d, J = 9.1 Hz, 1H), 7.82 (d, J = 2.7 Hz, 1H), 7.69 (dd, J = 9.1, 2.6 Hz, 1H), 7.33 (d, J = 8.7 Hz, 1H), 5.31 (d, J = 54.0 Hz, 1H), 5.01-3.50 (m, 4H), 2.31 (d, J = 29.3 Hz, 2H). | MS (APCI) m/z 436.2 [M + H]⁺ |
| Example 496 | [(2R)-4,4-difluoro-2-(hydroxymethyl)pyrrolidin-1-yl](6-{[5-(trifluoromethyl)pyridin-2-yl]oxy}quinolin-2-yl)methanone | ¹H NMR (400 MHz, DMSO-d₆, 90° C.) δ ppm 8.53 (d, J = 2.5 Hz, 1H), 8.47 (d, J = 8.5 Hz, 1H), 8.22 (dd, J = 8.7, 2.7 Hz, 1H), 8.17 (d, J = 9.2 Hz, 1H), 7.88 (d, J = 8.3 Hz, 1H), 7.83 (d, J = 2.6 Hz, 1H), 7.69 (dd, J = 9.1, 2.6 Hz, 1H), 7.34 (d, J = 8.8 Hz, 1H), 5.05-3.35 (m, 5H), 2.76-2.52 (m, 2H). | MS (APCI) m/z 454.2 [M + H]⁺ |
| Example 497 | [(2S)-4,4-difluoro-2-(hydroxymethyl)pyrrolidin-1-yl](6-{[5-(trifluoromethyl)pyridin-2-yl]oxy}quinolin-2-yl)methanone | ¹H NMR (400 MHz, DMSO-d₆, 90° C.) δ ppm 8.62-8.51 (m, 1H), 8.47 (d, J = 8.6 Hz, 1H), 8.23 (dd, J = 8.8, 2.6 Hz, 1H), 8.17 (d, J = 9.2 Hz, 1H), 7.90 (dd, J = 17.9, 8.5 Hz, 1H), 7.83 (d, J = 2.6 Hz, 1H), 7.69 (dd, J = 9.1, 2.6 Hz, 1H), 7.34 (d, J = 8.8 Hz, 1H), 5.09-3.34 (m, 5H), 2.95-2.54 (m, 2H). | MS (APCI) m/z 454.2 [M + H]⁺ |
| Example 498 | 1-(3-methoxyphenyl)-4-[(6-{[5-(trifluoromethyl)pyridin-2-yl]oxy}quinolin-2-yl)carbonyl]piperazin-2-one | 1H NMR (500 MHz, DMSO-d₆) δ ppm 3.76 (d, J = 3.36 Hz, 3 H) 3.78-3.91 (m, 2 H) 3.96-4.12 (m, 2 H) 4.47 (d, J = 19.84 Hz, 2 H) 6.82-6.91 (m, 1 H) 6.91-7.03 (m, 2 H) 7.28-7.35 (m, 1 H) 7.40 (dd, J = 8.54, 2.75 Hz, 1 H) 7.67-7.78 (m, 1 H) 7.85 (dd, J = 12.82, 8.54, 1 H) 7.90-7.96 (m, 1 H) 8.16 (d, J = 9.16 Hz, 1 H) 8.31 (dd, J = 8.85, 2.44 Hz, 1 H) 8.53 (d, J = 8.54 Hz, 1 H) 8.59 (s, 1 H) | MS (ESI) m/z 523.0 [M + H]⁺ |
| Example 499 | N-(thietan-3-yl)-6-{[5-(trifluoromethyl)pyridin-2-yl]oxy}quinoline-2-carboxamide | ¹H NMR (500 MHz, DMSO-d₆) δ ppm 9.58 (d, J = 8.4 Hz, 1H), 8.62 (d, J = 2.4 Hz, 1H), 8.53 (d, J = 8.5 Hz, 1H), 8.32 (dd, J = 8.7, 2.6 Hz, 1H), 8.23 (d, J = 9.1 Hz, 1H), 8.15 (d, J = 8.4 Hz, 1H), 7.93 (d, J = 2.6 Hz, 1H), 7.77 (dd, J = 9.1, 2.6 Hz, 1H), 7.41 (d, J = 8.7 Hz, 1H), 5.38-5.26 (m, 1H), 3.76 (t, J = 8.9 Hz, 2H), 3.28-3.21 (m, 2H). | ESI m/z 406.0 [M + H]⁺ |
| Example 500 | N-{3-[(2-methylphenyl)amino]-3-oxopropyl}-6-{[5-(trifluoromethyl)pyridin-2-yl]oxy}quinoline-2-carboxamide | 1H NMR (500 MHz, DMSO-d₆) δ ppm 2.17 (s, 3 H) 2.73 (t, J = 6.71 Hz, 2 H) 3.70 (q, J = 6.61 Hz, 2 H) 7.07 (t, J = 7.32 Hz, 1 H) 7.11-7.22 (m, 2 H) 7.40 (t, J = 8.24 Hz, 2 H) 7.76 (dd, J = 9.16, 2.44 Hz, 1 H) 7.93 (d, J = 2.75 Hz, 1 H) 8.13-8.23 (m, 2 H) 8.31 (dd, J = 8.54, 2.44 Hz, 1 H) 8.55 (d, J = 8.54 Hz, 1 H) 8.61 (s, 1 H) 8.99 (t, J = 5.80 Hz, 1 H) 9.40 (s, 1 H) | MS (ESI) m/z 495.0 [M + H]⁺ |
| Example 501 | N-[(2S)-1-(dimethylamino)-1-oxo-3-phenylpropan- | 1H NMR (500 MHz, DMSO-d₆) δ ppm 2.84 (s, 3 H) 2.94 (s, 3 H) 3.05-3.16 (m, 2 H) 5.20-5.28 (m, 1 H) 7.18-7.30 (m, 5 H) 7.41 (d, | MS (ESI) m/z |

| Example Number | Name | ¹H NMR | MS |
|---|---|---|---|
| | 2-yl]-6-{[5-(trifluoromethyl)pyridin-2-yl]oxy}quinoline-2-carboxamide | J = 8.55 Hz, 1 H) 7.77 (dd, J = 9.16, 2.44 Hz, 1 H) 7.93 (d, J = 2.44 Hz, 1 H) 8.13 (d, J = 8.54 Hz, 1 H) 8.22 (d, J = 9.16 Hz, 1 H) 8.32 (dd, J = 8.85, 2.44 Hz, 1 H) 8.54 (d, J = 8.85 Hz, 1 H) 8.61 (s, 1 H) 8.86 (d, J = 8.24 Hz, 1 H) | 509.0 [M + H]⁺ |
| Example 502 | N-[1-(2-methoxyphenyl)-5-oxopyrrolidin-3-yl]-6-{[5-(trifluoromethyl)pyridin-2-yl]oxy}quinoline-2-carboxamide | 1H NMR (400 MHz, DMSO-d₆) δ ppm 2.70-2.91 (m, 2 H) 3.77 (dd, J = 9.61, 5.04 Hz, 1 H) 3.83 (s, 3 H) 4.02 (dd, J = 9.77, 7.32 Hz, 1 H) 4.77-4.89 (m, 1 H) 6.99 (t, J = 7.48 Hz, 1 H) 7.13 (d, J = 8.24 Hz, 1 H) 7.32 (t, J = 7.02 Hz, 2 H) 7.41 (d, J = 8.85 Hz, 1 H) 7.78 (dd, J = 9.16, 2.44 Hz, 1 H) 7.94 (d, J = 2.44 Hz, 1 H) 8.19 (d, J = 8.55 Hz, 1 H) 8.25 (d, J = 9.16 Hz, 1 H) 8.32 (dd, J = 8.70, 2.59 Hz, 1 H) 8.55 (d, J = 8.85 Hz, 1 H) 8.62 (s, 1 H) 9.29 (d, J = 7.32 Hz, 1 H) | MS (ESI) m/z 523.0 [M + H]⁺ |
| Example 503 | N-(1-oxidothietan-3-yl)-6-{[5-(trifluoromethyl)pyridin-2-yl]oxy}quinoline-2-carboxamide | ¹H NMR (500 MHz, DMSO-d₆) δ ppm 9.56 (m, 1H), 8.62 (bs, 1H), 8.55 (d, J = 8.5 Hz, 1H), 8.32 (dd, J = 8.7, 2.6 Hz, 1H), 8.23 (d, J = 9.1 Hz, 1H), 8.17 (d, J = 8.3 Hz, 1H), 7.94 (d, J = 2.6 Hz, 1H), 7.81-7.75 (m, 1H), 7.41 (d, J = 8.7 Hz, 1H), 5.43 and 4.50 (2m, 1H), 4.08-3.79 (m, 2H), 3.63-3.36 (m, 2H). | ESI m/z 422.0 [M + H]⁺ |
| Example 504 | N-(1,1-dioxidothietan-3-yl)-6-{[5-(trifluoromethyl)pyridin-2-yl]oxy}quinoline-2-carboxamide | ¹H NMR (400 MHz, DMSO-d₆) δ ppm 9.61 (d, J = 6.1 Hz, 1H), 8.62 (d, J = 2.4 Hz, 1H), 8.56 (d, J = 8.5 Hz, 1H), 8.32 (dd, J = 8.7, 2.6 Hz, 1H), 8.23 (d, J = 9.1 Hz, 1H), 8.16 (d, J = 8.4 Hz, 1H), 7.95 (d, J = 2.6 Hz, 1H), 7.79 (dd, J = 9.1, 2.7 Hz, 1H), 7.41 (d, J = 8.6 Hz, 1H), 4.78-4.65 (m, 1H), 4.63-4.49 (m, 4H). | ESI m/z 438.1 [M + H]⁺ |
| Example 505 | 6-oxa-1-azaspiro[3.3]hept-1-yl(6-{[5-(trifluoromethyl)pyridin-2-yl]oxy}quinolin-2-yl)methanone | ¹H NMR (400 MHz, DMSO-d₆) δ ppm 8.60 (m, 1H), 8.49 (m, 1H), 8.28 (m, 1H), 8.11 (m, 2H), 7.91 (m, 1H), 7.72 (m, 1H), 7.39 (m, 1H), 5.36 (m, 2H), 4.61 (m, 4H), 2.66 (m, 2H). | ESI m/z 416.0 [M + H]⁺ |
| Example 506 | 1-{1-[(6-{[5-(trifluoromethyl)pyridin-2-yl]oxy}quinolin-2-yl)carbonyl]azetidin-3-yl}ethanone | ¹H NMR (400 MHz, DMSO-d₆) δ ppm 8.62-8.58 (m, 1H), 8.49 (d, J = 8.5 Hz, 1H), 8.31 (dd, J = 8.7, 2.6 Hz, 1H), 8.17 (d, J = 9.1 Hz, 1H), 8.05 (d, J = 8.5 Hz, 1H), 7.90 (d, J = 2.6 Hz, 1H), 7.73 (dd, J = 9.1, 2.7 Hz, 1H), 7.40 (d, J = 8.7 Hz, 1H), 4.90 (t, J = 9.7 Hz, 1H), 4.79 (dd, J = 10.3, 6.0 Hz, 1H), 4.29-4.16 (m, 2H), 3.81-3.69 (m, 1H), 2.20 (s, 3H). | ESI m/z 416.1 [M + H]⁺ |
| Example 507 | (3-fluoroazetidin-1-yl)(6-{[5-(trifluoromethyl)pyridin-2-yl]oxy}quinolin-2-yl)methanone | ¹H NMR (500 MHz, DMSO-d₆) δ ppm 8.60 (bs, 1H), 8.50 (d, J = 8.5 Hz, 1H), 8.31 (dd, J = 8.7, 2.6 Hz, 1H), 8.18 (d, J = 9.0 Hz, 1H), 8.08 (d, J = 8.5 Hz, 1H), 7.91 (d, J = 2.6 Hz, 1H), 7.74 (dd, J = 9.0, 2.6 Hz, 1H), 7.40 (d, J = 8.6 Hz, 1H), 5.56 and 5.46 (2m, 1H), 5.08 (dddd, J = 22.4, 12.2, 5.8, 2.0 Hz, 1H), 4.89-4.78 (m, 1H), 4.49 (dddd, J = 21.6, 12.0, 6.0, 1.9 Hz, 1H), 4.25-4.13 (m, 1H). | ESI m/z 392.1 [M + H]⁺ |
| Example 508 | (3,3-difluoroazetidin-1-yl)(6-{[5-(trifluoromethyl)pyridin-2-yl]oxy}quinolin-2-yl)methanone | ¹H NMR (500 MHz, DMSO-d₆) δ ppm 8.60 (bs, 1H), 8.53 (d, J = 8.5 Hz, 1H), 8.31 (dd, J = 8.7, 2.6 Hz, 1H), 8.22 (d, J = 9.0 Hz, 1H), 8.11 (d, J = 8.5 Hz, 1H), 7.92 (d, J = 2.6 Hz, 1H), 7.76 (dd, J = 9.0, 2.6 Hz, 1H), 7.41 (d, J = 8.6 Hz, 1H), 5.26-5.17 (m, 2H), 4.63-4.54 (m, 2H). | ESI m/z 410.0 [M + H]⁺ |
| Example 509 | (4R)-4-fluoro-N,N-dimethyl-1-[(6-{[5-(trifluoromethyl)pyridin-2-yl]oxy}quinolin-2-yl)carbonyl]-L-prolinamide | ¹H NMR (400 MHz, DMSO-d₆, 90° C.) δ ppm 8.57-8.34 (m, 2H), 8.25-8.02 (m, 2H), 7.97-7.74 (m, 2H), 7.74-7.59 (m, 1H), 7.30 (d, J = 8.7 Hz, 1H), 5.89-5.12 (m, 1H), 4.07 (d, J = 72.2 Hz, 1H), 3.07 (s, 6H), 2.90-2.58 (m, 3H), 2.44-2.03 (m, 1H). | MS (APCI) m/z 477.1 [M + H]⁺ |
| Example 510 | [4-(1,3-oxazol-2-ylmethyl)piperazin-1-yl](6-{[5-(trifluoromethyl)pyridin-2-yl]oxy}quinolin-2-yl)methanone | ¹H NMR (400 MHz, DMSO-d₆) δ ppm 2.37 (s, 3H), 2.40-2.46 (m, 2H), 2.52-2.59 (m, 2H), 3.35-3.56 (m, 4H), 3.61-3.79 (m, 2H), 7.39 (d, J = 8.7 Hz, 1H), 7.65-7.75 (m, 2H), 7.76-7.94 (m, 2H), 8.11 (t, J = 7.7 Hz, 1H), 8.30 (dd, J = 8.7, 2.4 Hz, 1H), 8.48 (t, J = 7.3 Hz, 1H), 8.58 (s, 1H) | DCI m/z 484.0 M + H]⁺ |

| Example Number | Name | ¹H NMR | MS |
|---|---|---|---|
| Example 511 | N-(4,4-difluorocyclohexyl)-6-{6-(trifluoromethyl)pyridin-3-yl]oxy}quinoline-2-carboxamide | ¹H NMR (400 MHz, DMSO-$d_6$) δ ppm 8.80 (d, J = 8.6 Hz, 1H). 8.71 (d, J = 2.4 Hz, 1H), 8.51 (d, J = 8.6 Hz, 1H), 8.25 (d, J = 10.1 Hz, 1H), 8.15 (d, J = 8.5 Hz, 1H), 7.99 (d, J = 8.5 Hz, 1H), 7.76-7.82 (m, 3H), 4.03-4.10 (m, 1H), 1.76-2.09 (m, 8H). | MS (ESI) m/z 452.1 [M + H]⁺ |
| Example 512 | N-[(4S)-2-oxopiperidin-4-yl]-6-{[5-(trifluoromethyl)pyridin-2-yl]oxy}quinoline-2-carboxamide | ¹H NMR (500 MHz, DMSO-d6) δ 8.89 (d, J = 8.1 Hz, 1H), 8.63-8.60 (m, 1H), 8.54 (d, J = 8.6 Hz, 1H), 8.31 (dd, J = 8.7, 2.5 Hz, 1H), 8.23 (d, J = 9.1 Hz, 1H), 8.17 (d, J = 8.5 Hz, 1H), 7.93 (d, J = 2.6 Hz, 1H), 7.76 (dd, J = 9.1, 2.6 Hz, 1H), 7.60 (s, 1H), 7.40 (d, J = 8.8 Hz, 1H), 4.34-4.24 (m, 1H), 3.26-3.20 (m, 2H), 2.55-2.42 (m, 2H), 2.04-1.96 (m, 1H), 1.95-1.83 (m, 1H). | (ESI) m/z 431.0 [M + H]⁺ |
| Example 513 | N-[2-oxo-2-(pyrrolidin-1-yl)ethyl]-6-{[6-(trifluoromethyl)pyridin-3-yl]oxy}quinoline-2-carboxamide | ¹H NMR (400 MHz, DMSO-$d_6$/D$_2$O) δ ppm 8.62 (d, J = 2.7 Hz, 1H), 8.50 (d, J = 8.5 Hz, 1H), 8.24 (d, J = 10.1 Hz, 1H), 8.17 (d, J = 8.5 Hz, 1H), 7.71-7.77 (m, 3H), 4.18 (s, 2H), 3.37-3.53 (m, 4H), 1.80-1.99 (m, 4H). | MS (ESI) m/z 445.2 [M + H]⁺ |
| Example 514 | N-{2-[(2-methoxyethyl)amino]-2-oxoethyl}-N-methyl-6-{[6-(trifluoromethyl)pyridin-3-yl]oxy}quinoline-2-carboxamide | ¹H NMR (400 MHz, DMSO-$d_6$/D$_2$O) δ ppm 8.60 (d, J = 2.7 Hz, 1H), 8.41 (d, J = 7.9 Hz, 1H), 8.13 (d, J = 8.2 Hz, 1H), 7.92 (d, J = 8.5 Hz, 1H), 7.67-7.74 (m, 4H), 4.17 (s, 2H), 3.19-3.32 (m, 7H), 3.08 (s, 3H). | MS (ESI) m/z 463.2 [M + H]⁺ |
| Example 515 | N-[3-(morpholin-4-yl)-3-oxopropyl]-6-{[6-(trifluoromethyl)pyridin-3-yl]oxy}quinoline-2-carboxamide | ¹H NMR (400 MHz, DMSO-$d_6$/D$_2$O) δ ppm 8.61 (d, J = 2.7 Hz, 1H), 8.48 (d, J = 8.5 Hz, 1H), 8.22 (d, J = 9.8 Hz, 1H), 8.15 (d, J = 8.5 Hz, 1H), 7.92 (d, J = 8.5 Hz, 1H), 7.70-7.76 (m, 3H), 3.65 (t, J = 6.7 Hz, 2H), 3.57-3.59 (m, 4H), 3.47-3.50 (m, 4H), 2.69 (t, J = 6.7 Hz, 2H). | MS (ESI) m/z 475.3 [M + H]⁺ |
| Example 516 | N-[3-oxo-3-(pyrrolidin-1-yl)propyl]-6-{[6-(trifluoromethyl)pyridin-3-yl]oxy}quinoline-2-carboxamide | ¹H NMR (400 MHz, DMSO-$d_6$/D$_2$O) δ ppm 8.61 (d, J = 3.1 Hz, 1H), 8.48 (d, J = 8.5 Hz, 1H), 8.22 (d, J = 9.8 Hz, 1H), 8.15 (d, J = 8.5 Hz, 1H), 7.92 (d, J = 8.5 Hz, 1H), 7.70-7.76 (m, 3H), 3.64 (t, J = 6.7 Hz, 2H), 333-3.45 (m, 4H), 2.69 (t, J = 6.7 Hz, 2H), 1.77-1.91 (m, 4H). | MS (ESI) m/z 459.3 [M + H]⁺ |
| Example 517 | N-[2-(diethylamino)-2-oxoethyl]-6-{[6-(trifluoromethyl)pyridin-3-yl]oxy}quinoline-2-carboxamide | ¹H NMR (400 MHz, DMSO-$d_6$/D$_2$O) δ ppm 8.62 (d, J = 3.1 Hz, 1H), 8.50 (d, J = 8.5 Hz, 1H), 8.24 (d, J = 10.1 Hz, 1H), 8.17 (d, J = 8.5 Hz, 1H), 7.92 (d, J = 8.5 Hz, 1H), 7.71-7.77 (m, 3H), 4.26 (s, 2H), 3.38 (q, J = 7.0 Hz, 4H), 1.16 (t, J = 7.0 Hz, 6H). | MS (ESI) m/z 447.2 [M + H]⁺ |
| Example 518 | N-[2-oxo-2-(piperidin-1-yl)ethyl]-6-{[6-(trifluoromethyl)pyridin-3-yl]oxy}quinoline-2-carboxamide | ¹H NMR (400 MHz, DMSO-$d_6$/D$_2$O) δ ppm 8.62 (d, J = 2.7 Hz, 1H), 8.50 (d, J = 8.5 Hz, 1H), 8.24 (d, J = 10.1 Hz, 1H), 8.17 (d, J = 8.5 Hz, 1H), 7.92 (d, J = 8.5 Hz, 1H), 7.71-7.77 (m, 3H), 4.25 (s, 2H), 3.46-3.49 (m, 4H), 1.50-1.66 (m, 6H). | MS (ESI) m/z 459.3 [M + H]⁺ |
| Example 519 | N-(1-methyl-5-oxopyrrolidin-3-yl)-6-{[6-(trifluoromethyl)pyridin-3-yl]oxy}quinoline-2-carboxamide | ¹H NMR (400 MHz, DMSO-$d_6$/D$_2$O) δ ppm 8.61 (d, J = 2.7 Hz, 1H), 8.48 (d, J = 8.5 Hz, 1H), 8.26 (d, J = 9.8 Hz, 1H), 8.13 (d, J = 8.5 Hz, 1H), 7.92 (d, J = 8.5 Hz, 1H), 7.70-7.77 (m, 3H), 4.62-4.69 (m, 1H), 3.77 (dd, J = 10.1, 7.6 Hz, 1H), 3.44 (dd, J = 10.2, 4.7 Hz, 1H), 2.79 (s, 3H), 2.71 (dd, J = 17.1, 8.9 Hz, 1H), 2.47-2.54 (m, 1H). | MS (ESI) m/z 431.2 [M + H]⁺ |
| Example 520 | N-[3-oxo-3-(piperidin-1-yl)propyl]-6-{[6-(trifluoromethyl)pyridin-3-yl]oxy}quinoline-2-carboxamide | ¹H NMR (400 MHz, DMSO-$d_6$/D$_2$O) δ ppm 8.61 (d, J = 2.7 Hz, 1H), 8.48 (d, J = 8.9 Hz, 1H), 8.21 (d, J = 10.1 Hz, 1H), 8.15 (d, J = 8.5 Hz, 1H), 7.92 (d, J = 8.9 Hz, 1H), 7.69-7.76 (m, 3H), 3.63 (t, J = 6.7 Hz, 2H), 3.43-3.46 (m, 4H), 2.67 (t, J = 6.7 Hz, 2H), 1.56-1.61 (m, 2H), 1.44-1.53 (m, 4H). | MS (ESI) m/z 473.3 [M + H]⁺ |
| Example 521 | N-[(4R)-2-oxopiperidin-4-yl]-6-{[5- | ¹H NMR (500 MHz, DMSO-$d_6$) δ ppm 8.89 (d, J = 8.1 Hz, 1H), 8.63-8.60 (m, 1H), 8.54 (d, J = 8.6 Hz, 1H), 8.31 (dd, J = 8.7, 2.5 Hz, 1H), | (ESI) m/z 431.0 |

-continued

| Example Number | Name | ¹H NMR | MS |
|---|---|---|---|
| | (trifluoromethyl)pyridin-2-yl]oxy}quinoline-2-carboxamide | 8.23 (d, J = 9.1 Hz, 1H), 8.17 (d, J = 8.5 Hz, 1H), 7.93 (d, J = 2.6 Hz, 1H), 7.76 (dd, J = 9.1, 2.6 Hz, 1H), 7.60 (s, 1H), 7.40 (d, J = 8.8 Hz, 1H), 4.34-4.24 (m, 1H), 3.26-3.20 (m, 2H), 2.55-2.42 (m, 2H), 2.04-1.96 (m, 1H), 1.95-1.83 (m, 1H). | [M + H]⁺ |
| Example 522 | N-[2-(cyclopropylamino)-2-oxoethyl]-N-methyl-6-{[6-(trifluoromethyl)pyridin-3-yl]oxy}quinoline-2-carboxamide | ¹H NMR (400 MHz, DMSO-d₆/D₂O) δ ppm 8.60 (d, J = 2.4 Hz, 1H), 8.41 (d, J = 8.9 Hz, 1H), 8.12 (d, J = 8.5 Hz, 1H), 7.92 (d, J = 8.5 Hz, 1H), 7.67-7.74 (m, 4H), 4.12 (s, 2H), 3.07 (s, 3H), 2.59-2.69 (m, 1H), 0.31-0.67 (m, 4H). | MS (ESI) m/z 445.2 [M + H]⁺ |
| Example 523 | N-(1-ethyl-5-oxopyrrolidin-3-yl)-6-{[6-(trifluoromethyl)pyridin-3-yl]oxy}quinoline-2-carboxamide | ¹H NMR (400 MHz, DMSO-d₆/D₂O) δ ppm 8.61 (d, J = 2.7 Hz, 1H), 8.48 (d, J = 8.5 Hz, 1H), 8.25 (d, J = 10.1 Hz, 1H), 8.13 (d, J = 8.2 Hz, 1H), 7.92 (d, J = 8.5 Hz, 1H), 7.70-7.77 (m, 3H), 4.63-4.69 (m, 1H), 3.78 (dd, J = 10.1, 7.6 Hz, 1H), 3.44 (dd, J = 10.1, 4.9 Hz, 1H), 3.29 (q, J = 7.2 Hz, 2H), 2.73 (dd, J = 8.9, 16.8 Hz, 1H), 2.56 (dd, J = 6.1, 16.8 Hz, 1H), 1.09 (t, J = 7.2 Hz, 2H). | MS (ESI) m/z 445.2 [M + H]⁺ |
| Example 524 | N-[3-(diethylamino)-3-oxopropyl]-6-{[6-(trifluoromethyl)pyridin-3-yl]oxy}quinoline-2-carboxamide | ¹H NMR (400 MHz, DMSO-d₆/D₂O) δ ppm 8.61 (d, J = 2.7 Hz, 1H), 8.48 (d, J = 8.5 Hz, 1H), 8.21 (d, J = 10.1 Hz, 1H), 8.15 (d, J = 8.5 Hz, 1H), 7.92 (d, J = 8.5 Hz, 1H), 7.69-7.76 (m, 3H), 3.64 (t, J = 6.9 Hz, 2H), 3.33 (q, J = 7.0 Hz, 4H), 3.29 (q, J = 7.2 Hz, 2H), 2.67 (t, J = 6.7 Hz, 2H), 1.09 (brs, 6H). | MS (ESI) m/z 461.3 [M + H]⁺ |
| Example 525 | N-[2-(isopropylamino)-2-oxoethyl]-N-methyl-6-{[6-(trifluoromethyl)pyridin-3-yl]oxy}quinoline-2-carboxamide | ¹H NMR (400 MHz, DMSO-d₆/D₂O) δ ppm 8.60 (d, J = 2.7 Hz, 1H), 8.41 (d, J = 8.5 Hz, 1H), 8.12 (d, J = 8.5 Hz, 1H), 7.91 (d, J = 8.5 Hz, 1H), 7.66-7.74 (m, 4H), 4.12 (s, 2H), 3.76-3.94 (m, 1H), 3.07 (s, 3H), 1.00-1.10 (m, 6H). | MS (ESI) m/z 447.2 [M + H]⁺ |
| Example 526 | [4-(morpholin-4-yl)piperidin-1-yl](6-{[6-(trifluoromethyl)pyridin-3-yl]oxy}quinolin-2-yl)methanone | ¹H NMR (500 MHz, DMSO-d₆) δ ppm 8.70 (d, J = 2.8 Hz, 1H), 8.45 (d, J = 8.2 Hz, 1H), 8.14 (d, J = 9.2 Hz, 1H), 7.96 (d, J = 8.9 Hz, 1H), 7.72-7.78 (m, 3H), 7.67 (d, J = 8.5 Hz, 1H), 4.51-4.57 (m, 1H), 3.71-3.74 (m, 1H), 3.56-3.58 (m, 4H), 3.06-3.11 (m, 1H), 2.87-2.93 (m, 1H), 2.44-2.48 (m, 5H), 1.91-1.93 (m, 1H), 1.85 (s, 3H), 1.72-1.76 (m, 1H), 1.40-1.48 (m, 2H). | MS (ESI) m/z 487.1 [M + H]⁺ |
| Example 527 | N-methyl-6-{[5-(trifluoromethyl)pyridin-2-yl]oxy}quinoline-2-carboxamide | ¹H NMR (400 MHz, DMSO-d₆) δ ppm 8.95-8.84 (m, 1H), 8.61 (s, 1H), 8.53 (d, J = 8.6 Hz, 1H), 8.31 (dd, J = 8.7, 2.5 Hz, 1H), 8.17 (dd, J = 8.8, 3.5 Hz, 2H), 7.92 (d, J = 2.6 Hz, 1H), 7.75 (dd, J = 9.1, 2.6 Hz, 1H), 7.40 (d, J = 8.7 Hz, 1H), 2.91 (d, J = 4.8 Hz, 3H). | MS (ESI) m/z 348.1 [M + H]⁺ |
| Example 528 | meso-[(1R,5S,6s)-6-amino-3-azabicyclo[3.1.0]hex-3-yl](6-{[6-(trifluoromethyl)pyridin-3-yl]oxy}quinolin-2-yl)methanone | ¹H NMR (500 MHz, CDCl₃) δ ppm 8.60-8.53 (m, 1H), 8.19-8.10 (m, 2H), 7.93-7.87 (m, 1H), 7.75-7.67 (m, 1H), 7.57-7.51 (m, 1H), 7.50-7.44 (m, 1H), 7.43-7.36 (m, 1H), 4.30-4.16 (m, 1H), 4.14-4.00 (m, 3H), 3.75-3.65 (m, 1H), 0.97-0.82 (m, 2H). | MS (ESI) m/z 415.0 [M + H]⁺ |
| Example 529 | N-methyl-N-(1-methyl-2-oxopiperidin-4-yl)-6-{[5-(trifluoromethyl)pyridin-2-yl]oxy}quinoline-2-carboxamide | ¹H NMR (500 MHz, DMSO-d₆, rotamers) δ ppm 8.60-8.56 (m, 1H), 8.47 (dd, J = 8.5, 4.3 Hz, 1H), 8.30 (dd, J = 8.7, 2.4 Hz, 1H), 8.13 (d, J = 9.1 Hz, 0.4H), 8.06 (d, J = 9.1 Hz, 0.6H), 7.90-7.87 (m, 1H), 7.73-7.67 (m, 2H), 7.39 (d, J = 8.7 Hz, 1H), 4.84-4.74 (m, 0.4H), 4.07-3.98 (m, 0.6H), 3.48-3.38 (m, 0.4H), 3.38-3.34 (m, 0.6H), 3.23-3.17 (m, 0.4H), 3.08 (td, J = 12.0, 4.5 Hz, 0.6H), 2.98 (s, 2H), 2.88 (s, 1H), 2.85 (s, 1H), 2.69 (s, 2H), 2.66-2.52 (m, 1.6H), 2.45-2.35 (m, 0.4H), 2.18-1.95 (m, 2H). | MS (ESI) m/z 459.0 [M + H]⁺ |
| Example 530 | N-[(3R)-2-oxotetrahydrofuran-3-yl]-6-{[5-(trifluoromethyl)pyr- | 1H NMR (500 MHz, DMSO-d₆) δ ppm 2.42-2.57 (m, 2 H) 4.27-4.38 (m, 1 H) 4.41-4.50 (m, 1 H) 4.86-4.99 (m, 1 H) 7.42 (d, J = 8.85 Hz, 1 H) 7.78 (dd, J = 9.16, 2.75 Hz, 1 H) 7.95 | MS (ESI) m/z 418.0 |

| Example Number | Name | ¹H NMR | MS |
|---|---|---|---|
| | idin-2-yl]oxy}quinoline-2-carboxamide | (d, J = 2.75 Hz, 1 H) 8.20 (dd, J = 11.60, 8.85 Hz, 2 H) 8.32 (dd, J = 8.54, 2.44 Hz, 1 H) 8.57 (d, J = 8.54 Hz, 1 H) 8.62 (s, 1 H) 9.49 (d, J = 8.54 Hz, 1 H) | [M + H]⁺ |
| Example 531 | {4-[(2-methyl-1,3-oxazol-4-yl)methyl]piperazin-1-yl}(6-{[5-(trifluoromethyl)pyridin-2-yl]oxy}quinolin-2-yl)methanone | ¹H NMR (400 MHz, DMSO-d₆) δ ppm 2.31-2.46 (m, 4H), 2.52-2.59 (m, 2H), 3.35-3.56 (m, 3H), 3.61-3.79 (m, 2H), 7.39 (d, J = 8.7 Hz, 1H), 7.65-7.75 (m, 2H), 7.76-7.94 (m, 2H), 8.11 (t, J = 7.7 Hz, 1H), 8.30 (dd, J = 8.7, 2.4 Hz, 1H), 8.48 (t, J = 7.3 Hz, 1H), 8.58 (s, 1H) | DCI m/z 498.0 [M + H]⁺ |
| Example 532 | 6-oxa-2-azaspiro[3.4]oct-2-yl(6-{[5-(trifluoromethyl)pyridin-2-yl]oxy}quinolin-2-yl)methanone | ¹H NMR (400 MHz, DMSO-d₆) δ ppm 8.62-8.57 (m, 1H), 8.49 (d, J = 8.5 Hz, 1H), 8.31 (dd, J = 8.7, 2.6 Hz, 1H), 8.16 (d, J = 9.1 Hz, 1H), 8.07 (d, J = 8.5 Hz, 1H), 7.89 (d, J = 2.6 Hz, 1H), 7.73 (dd, J = 9.0, 2.7 Hz, 1H), 7.40 (d, J = 8.7 Hz, 1H), 4.75 (bs, 2H), 4.12 (bs, 2H), 3.85 (s, 2H), 3.75 (t, J = 7.0 Hz, 2H), 2.19 (t, J = 6.9 Hz, 2H). | ESI m/z 430.2 [M + H]⁺ |
| Example 533 | 6-oxa-2-azaspiro[3.5]non-2-yl(6-{[5-(trifluoromethyl)pyridin-2-yl]oxy}quinolin-2-yl)methanone | ¹H NMR (400 MHz, DMSO-d₆) δ ppm 8.62-8.58 (m, 1H), 8.48 (d, J = 8.6 Hz, 1H), 8.31 (dd, J = 8.7, 2.6 Hz, 1H), 8.17 (d, J = 9.1 Hz, 1H), 8.07 (d, J = 8.5 Hz, 1H), 7.89 (d, J = 2.6 Hz, 1H), 7.72 (dd, J = 9.1, 2.7 Hz, 1H), 7.40 (d, J = 8.7 Hz, 1H), 4.48 (m, 2H), 3.87-3.75 (m, 2H), 3.65 (bs, 2H), 3.53 (t, J = 5.0 Hz, 2H), 1.85 (t, J = 5.7 Hz, 2H), 1.59-1.50 (m, 2H). | ESI m/z 444.1 [M + H]⁺ |
| Example 534 | [3-(methylsulfonyl)azetidin-1-yl](6-{[6-(trifluoromethyl)pyridin-3-yl]oxy}quinolin-2-yl)methanone | ¹H NMR (400 MHz, DMSO-d₆) δ ppm 8.71 (d, J = 2.8 Hz, 1H), 8.50 (d, J = 8.5 Hz, 1H), 8.25 (d, J = 9.9 Hz, 1H), 8.08 (d, J = 8.5 Hz, 1H), 7.98 (d, J = 8.6 Hz, 1H), 7.83-7.75 (m, 3H), 5.13-5.02 (m, 1H), 4.98 (dd, J = 11.5, 3.9 Hz, 1H), 4.48-4.37 (m, 2H), 4.37-4.26 (m, 1H), 3.10 (s, 3H). | ESI m/z 452.1 [M + H]⁺ |
| Example 535 | N-(1,1-dioxidotetrahydro-2H-thiopyran-4-yl)-6-{[6-(trifluoromethyl)pyridin-3-yl]oxy}quinoline-2-carboxamide | ¹H NMR (500 MHz, DMSO-d₆) δ ppm 9.01 (d, J = 8.4 Hz, 1H), 8.71 (d, J = 2.7 Hz, 1H), 8.51 (d, J = 8.5 Hz, 1H), 8.25 (d, J = 9.9 Hz, 1H), 8.14 (d, J = 8.5 Hz, 1H), 7.99 (d, J = 8.6 Hz, 1H), 7.84-7.74 (m, 3H), 4.34-4.23 (m, 1H), 3.43-3.36 (m, 2H), 3.16-3.08 (m, 2H), 2.34-2.20 (m, 2H), 2.18-2.10 (m, 2H). | ESI m/z 466.1 [M + H]⁺ |
| Example 536 | N-(oxetan-3-yl)-6-{[6-(trifluoromethyl)pyridin-3-yl]oxy}quinoline-2-carboxamide | ¹H NMR (400 MHz, DMSO-d₆) δ ppm 9.57 (d, J = 6.9 Hz, 1H), 8.72 (d, J = 2.8 Hz, 1H), 8.51 (d, J = 8.5 Hz, 1H), 8.30-8.24 (m, 1H), 8.13 (d, J = 8.5 Hz, 1H), 7.99 (d, J = 8.6 Hz, 1H), 7.85-7.76 (m, 3H), 5.17-5.04 (m, 1H), 4.82-4.72 (m, 4H). | ESI m/z 390.1 [M + H]⁺ |
| Example 537 | N-[(3R,4S)-4-hydroxy-1,1-dioxidotetrahydrothiophen-3-yl]-6-{[6-(trifluoromethyl)pyridin-3-yl]oxy}quinoline-2-carboxamide | ¹H NMR (400 MHz, DMSO-d₆) δ ppm 8.87 (d, J = 8.1 Hz, 1H), 8.72 (d, J = 2.8 Hz, 1H), 8.55 (d, J = 8.5 Hz, 1H), 8.27-8.16 (m, 2H), 7.99 (d, J = 8.6 Hz, 1H), 7.86-7.74 (m, 3H), 6.29 (s, 1H), 4.79 (dtd, J = 11.5, 7.7, 3.7 Hz, 1H), 4.62 (bs, 1H), 3.63-3.33 (m, 4H). | ESI m/z 468.1 [M + H]⁺ |
| Example 538 | N-[(3S,4S)-4-hydroxy-1,1-dioxidotetrahydrothiophen-3-yl]-6-{[6-(trifluoromethyl)pyridin-3-yl]oxy}quinoline-2-carboxamide | ¹H NMR (400 MHz, DMSO-d₆) δ ppm 8.87 (d, J = 8.1 Hz, 1H), 8.72 (d, J = 2.8 Hz, 1H), 8.55 (d, J = 8.5 Hz, 1H), 8.27-8.11 (m, 2H), 7.99 (d, J = 8.6 Hz, 1H), 7.86-7.76 (m, 3H), 6.28 (s, 1H), 4.85-4.74 (m, 1H), 4.62 (bs, 1H), 3.61-3.31 (m, 4H). | ESI m/z 468.0 [M + H]⁺ |
| Example 539 | 2,5-dihydro-1H-pyrrol-1-yl(6-{[6-(trifluoromethyl)pyridin-3-yl]oxy}quinolin-2-yl)methanone | ¹H NMR (400 MHz, DMSO-d₆) δ ppm 8.70 (m, 1H), 8.47 (d, J = 8.5 Hz, 1H), 8.20 (d, J = 8.9 Hz, 1H), 7.97 (d, J = 8.6 Hz, 1H), 7.92 (d, J = 8.5 Hz, 1H), 7.83-7.72 (m, 3H), 6.02-5.96 (m, 1H), 5.98-5.91 (m, 1H), 4.69-4.63 (m, 2H), 4.42-4.36 (m, 2H). | ESI m/z 386.1 [M + H]⁺ |
| Example 540 | [4-(3,3-difluoroazetidin-1-yl)piperidin-1-yl](6-{[5- | ¹H NMR (400 MHz, DMSO-d₆) δ ppm 8.58-8.59 (m, 1H), 8.47 (d, J = 8.6 Hz, 1H), 8.30 (dd, J = 8.7, 2.6 Hz, 1H), 8.10 (d, J = 9.2 Hz, 1H), 7.88 (d, J = 2.8 Hz, 1H), 7.67-7.72 (m, 2H), | MS (ESI) m/z 493.1 |

-continued

| Example Number | Name | ¹H NMR | MS |
|---|---|---|---|
| | (trifluoromethyl)pyridin-2-yl]oxy}quinolin-2-yl)methanone | 7.39 (d, J = 8.5 Hz, 1H), 4.15-4.20 (m, 1H), 3.55-3.65 (m, 5H), 3.13-3.26 (m, 2H), 2.48-2.50 (m, 1H), 1.78-1.82 (m, 1H), 1.65-1.67 (m, 1H), 1.23-1.35 (m, 2H). | [M + H]⁺ |
| Example 541 | N-(2-methoxy-2-methylpropyl)-6-{[5-(trifluoromethyl)pyridin-2-yl]oxy}quinoline-2-carboxamide | ¹H NMR (400 MHz, DMSO-d₆) δ ppm 8.61-8.62 (m, 1H), 8.56 (d, J = 8.6 Hz, 1H), 8.52 (t, J = 6.3 Hz, 1H), 8.31 (dd, J = 8.7, 2.6 Hz, 1H), 8.19-8.23 (m, 2H), 7.94 (d, J = 2.4 Hz, 1H), 7.76 (dd, J = 9.2, 2.4 Hz, 1H), 7.41 (d, J = 8.5 Hz, 1H), 3.46 (d, J = 6.4 Hz, 1H), 3.21 (s, 3H), 1.17 (s, 6H). | MS (ESI) m/z 420.1 [M + H]⁺ |
| Example 542 | [(8aS)-7,7-difluorohexahydropyrrolo[1,2-a]pyrazin-2(1H)-yl](6-{[5-(difluoromethyl)pyridin-2-yl]oxy}quinolin-2-yl)methanone | 1H NMR (400 MHz, DMSO-d₆) δ ppm 1.73-2.14 (m, 1 H) 2.18-2.46 (m, 2 H) 2.53-2.80 (m, 2 H) 2.84-3.13 (m, 2 H) 3.15-3.30 (m, 1 H) 3.37-3.50 (m, 1 H) 3.85 (dd, J = 51.57, 12.82 Hz, 1 H) 4.64 (dd, J = 48.83, 12.82 Hz, 1 H) 7.12 (t, J = 55.24 Hz, 1 H) 7.32 (d, J = 8.54 Hz, 1 H) 7.64-7.73 (m, 2 H) 7.85 (d, J = 2.44 Hz, 1 H) 8.06-8.16 (m, 2 H) 8.38 (s, 1 H) 8.48 (d, J = 8.54 Hz, 1 H) | MS (ESI) m/z 461.0 [M + H]⁺ |
| Example 543 | [(3R)-3-ethylpiperazin-1-yl](6-{[6-(trifluoromethyl)pyridin-3-yl]oxy}quinolin-2-yl)methanone | ¹H NMR (400 MHz, DMSO-d₆, rotamers) δ ppm 0.74 (t, J = 7.5 Hz, 1.4H), 0.95 (t, J = 7.5 Hz, 1.6H), 1.08-1.33 (m, 1.6 H), 1.34-1.52 (m, 1.4H), 2.55-2.94 (m, 3H), 2.95-3.17 (m, 1H), 3.52-3.77 (m, 1H), 4.39 (dd, J = 26.4, 11.0 Hz, 1H), 7.62-7.82 (m, 4H), 7.95 (dd, J = 16.4, 8.2 Hz, 1H), 8.13 (dd, J = 9.0, 4.4 Hz, 1H), 8.46 (d, J = 8.5 Hz, 1H), 8.70 (t, J = 2.9 Hz, 1H) | DCI m/z 431.0 [M + H]⁺ |
| Example 544 | [(3R)-3-(hydroxymethyl)piperazin-1-yl](6-{[6-(trifluoromethyl)pyridin-3-yl]oxy}quinolin-2-yl)methanone | ¹H NMR (400 MHz, DMSO-d₆, rotamers) δ ppm 2.40 (s, 1H), 2.62 (ddt, J = 28.5, 22.7, 9.7 Hz, 2.5H), 2.74-2.94 (m, 1.5H), 2.95-3.19 (m, 1.5H), 3.25 (dt, J = 10.7, 5.4 Hz, 0.5H), 3.35-3.46 (m, 1H), 3.58 (d, J = 13.3 Hz, 0.5H), 3.69 (d, J = 11.8 Hz, 0.5H), 4.36 (d, J = 12.5 Hz, 0.5H), 4.51 (dd, J = 14.2, 8.9 Hz, 1H), 4.74 (t, J = 5.5 Hz, 0.5H), 7.67 (dd, J = 8.5, 2.4 Hz, 1H), 7.71-7.81 (m, 3H), 7.96 (d, J = 8.7 Hz, 1H), 8.14 (d, J = 9.1 Hz, 1H), 8.45 (d, J = 8.5 Hz, 1H), 8.70 (dd, J = 4.3, 3.0 Hz, 1H) | DCI m/z 433.0 [M + H]⁺ |
| Example 545 | [(3S)-3-(hydroxymethyl)piperazin-1-yl](6-{[6-(trifluoromethyl)pyridin-3-yl]oxy}quinolin-2-yl)methanone | ¹H NMR (400 MHz, DMSO-d₆, rotamers) δ ppm 2.40 (s, 1H), 2.62 (ddt, J = 28.5, 22.7, 9.7 Hz, 2.5H), 2.74-2.94 (m, 1.5H), 2.95-3.19 (m, 1.5H), 3.25 (dt, J = 10.7, 5.4 Hz, 0.5H), 3.35-3.46 (m, 1H), 3.58 (d, J = 13.3 Hz, 0.5H), 3.69 (d, J = 11.8 Hz, 0.5H), 4.36 (d, J = 12.5 Hz, 0.5H), 4.51 (dd, J = 14.2, 8.9 Hz, 1H), 4.74 (t, J = 5.5 Hz, 0.5H), 7.67 (dd, J = 8.5, 2.4 Hz, 1H), 7.71-7.81 (m, 3H), 7.96 (d, J = 8.7 Hz, 1H), 8.14 (d, J = 9.1 Hz, 1H), 8.45 (d, J = 8.5 Hz, 1H), 8.70 (dd, J = 4.3, 3.0 Hz, 1H) | DCI m/z 433.0 [M + H]⁺ |
| Example 546 | [cis-3,4-dihydroxypyrrolidin-1-yl](6-{[6-(trifluoromethyl)pyridin-3-yl]oxy}quinolin-2-yl)methanone | ¹R NMR (400 MHz, DMSO-d₆) δ ppm 8.71 (d, J = 2.8 Hz, 1H), 8.45 (d, J = 8.5 Hz, 1H), 8.16 (d, J = 8.9 Hz, 1H), 7.96 (d, J = 8.6 Hz, 1H), 7.84 (d, J = 8.5 Hz, 1H), 7.81-7.71 (m, 3H), 5.03-4.92 (m, 2H), 4.12 (d, J = 3.4 Hz, 1H), 4.11-3.98 (m, 1H), 3.89 (dd, J = 11.4, 5.7 Hz, 1H), 3.71-3.58 (m, 2H), 3.44 (m, 1H). | ESI m/z 420.1 [M + H]⁺ |
| Example 547 | N-[2-(trifluoromethoxy)ethyl]-6-{[5-(trifluoromethyl)pyridin-2-yl]oxy}quinoline-2-carboxamide | ¹H NMR (400 MHz, DMSO-d₆) δ ppm 9.14 (t, J = 6.0 Hz, 1H), 8.64-8.59 (m, 1H), 8.55 (d, J = 8.5 Hz, 1H), 8.35-8.28 (m, 1H), 8.24-8.16 (m, 2H), 7.94 (d, J = 2.6 Hz, 1H), 7.77 (dd, J = 9.1, 2.6 Hz, 1H), 7.41 (d, J = 8.6 Hz, 1H), 4.29 (t, J = 5.6 Hz, 2H), 3.71 (q, J = 5.7 Hz, 2H). | ESI m/z 446.1 [M + H]⁺ |
| Example 548 | [(3R)-3-fluoropyrrolidin-1-yl](6-{[6-(trifluoromethyl)pyridin-3-yl]oxy}quinolin-2-yl)methanone | ¹H NMR (400 MHz, DMSO-d₆ 1:1 rotamers) δ ppm 8.71 (d, J = 2.4 Hz, 1H), 8.47 (d, J = 8.5 Hz, 1H), 8.20 (d, J = 9.2 Hz, 0.5H), 8.17 (d, J = 9.2 Hz, 0.5H), 7.97 (d, J = 8.5 Hz, 1H), 7.87-7.92 (m, 1H), 7.74-7.80 (m, 3H), 5.46-5.49 (m, 0.5H), 5.33-5.36 (m, 0.5H), 3.59-4.12 (m, 4H), 2.04-2.27 (m, 2H). | MS (ESI) m/z 406.1 [M + H]⁺ |

-continued

| Example Number | Name | ¹H NMR | MS |
|---|---|---|---|
| Example 549 | [(3S)-3-methylpiperazin-1-yl](6-{[6-(trifluoromethyl)pyridin-3-yl]oxy}quinolin-2-yl)methanone | ¹H NMR (400 MHz, DMSO-d$_6$) 1:1 rotamers δ ppm 8.69-8.70 (m, 1H), 8.45 (d, J = 8.5 Hz, 1H), 8.13 (d, J = 9.2 Hz, 1H), 7.97 (d, J = 8.9 Hz, 1H), 7.71-7.77 (m, 2H), 7.67 (d, J = 8.5 Hz, 1H), 4.36-4.39 (m, 1H), 3.54-3.58 (m, 1H), 2.97-3.09 (m, 1H), 2.60-2.87 (m, 4H), 1.05 (d, J = 6.4 Hz, 1.5H), 0.84 (d, J = 5.8 Hz, 1.5H). | MS (ESI) m/z 417.1 [M + H]⁺ |
| Example 550 | [(3S)-3-fluoropyrrolidin-1-yl](6-{[6-(trifluoromethyl)pyridin-3-yl]oxy}quinolin-2-yl)methanone | ¹H NMR (400 MHz, DMSO-d$_6$) 1:1 rotamers δ ppm 8.71 (d, J = 2.4 Hz, 1H), 8.47 (d, J = 8.5 Hz, 1H), 8.20 (d, J = 9.2 Hz, 0.5H), 8.17 (d, J = 9.2 Hz, 0.5H), 7.97 (d, J = 8.5 Hz, 1H), 7.87-7.92 (m, 1H), 7.74-7.80 (m, 3H), 5.46-5.49 (m, 0.5H), 5.33-5.36 (m, 0.5H), 3.59-4.12 (m, 4H), 2.04-2.27 (m, 2H). | MS (ESI) m/z 406.1 [M + H]⁺ |
| Example 551 | N-(3,3,3-trifluoro-2-hydroxypropyl)-6-{[6-(trifluoromethyl)pyridin-3-yl]oxy}quinoline-2-carboxamide | ¹H NMR (400 MHz, DMSO-d$_6$) δ ppm 9.00 (t, J = 6.1 Hz, 1H), 8.72 (d, J = 2.8 Hz, 1H), 8.54 (d, J = 8.2 Hz, 1H), 8.21-8.24 (m, 1H), 8.18 (d, J = 8.2 Hz, 1H), 7.99 (d, J = 8.5 Hz, 1H), 7.77-7.83 (m, 3H), 6.57 (s, 1H), 4.28-4.37 (m, 1H), 3.68-3.74 (m, 1H), 3.49-3.56 (m, 1H). | MS (ESI) m/z 446.0 [M + H]⁺ |
| Example 552 | (3,5-dimethylpiperazin-1-yl)(6-{[5-(trifluoromethyl)pyridin-2-yl]oxy}quinolin-2-yl)methanone | ¹H NMR (400 MHz, DMSO-d$_6$) δ ppm 0.84 (d, J = 6.2 Hz, 3H), 1.06 (d, J = 6.2 Hz, 3H), 2.35 (dd, J = 12.2, 10.9 Hz, 2H), 2.57-2.70 (m, 1H), 2.76 (ddt, J = 8.6, 6.0, 4.4 Hz, 2H), 3.57 (d, J = 12.0 Hz, 1H), 4.37-4.53 (m, 1H), 7.40 (d, J = 8.7 Hz, 1H), 7.63-7.75 (m, 2H), 7.89 (d, J = 2.6 Hz, 1H), 8.10 (d, J = 9.1 Hz, 1H), 8.30 (dd, J = 8.7, 2.5 Hz, 1H), 8.47 (d, J = 8.4 Hz, 1H), 8.59 (dd, J = 1.5, 0.8 Hz, 1H) | DCI m/z 431.0 [M + H]⁺ |
| Example 553 | [(3S)-3-ethylpiperazin-1-yl](6-{[6-(trifluoromethyl)pyridin-3-yl]oxy}quinolin-2-yl)methanone | ¹H NMR (400 MHz, DMSO-d$_6$, rotamers) δ ppm 0.74 (t, J = 7.5 Hz, 1.4H), 0.95 (t, J = 7.5 Hz, 1.6H), 1.08-1.32 (m, 1H), 1.33-1.50 (m, 1H), 2.25-2.43 (m, 1H), 2.56-2.93 (m, 3H), 2.93-3.16 (m, 1H), 3.48-3.62 (m, 0.6H), 3.64-3.77 (m, 0.4H), 4.30-4.49 (m, 1H), 7.62-7.82 (m, 4H), 7.92-8.01 (m, 1H), 8.06-8.20 (m, 1H), 8.45 (d, J = 8.4 Hz, 1H), 8.70 (t, J = 3.1 Hz, 1H) | DCI m/z 431.0 [M + H]⁺ |
| Example 554 | [3-(morpholin-4-yl)azetidin-1-yl](6-{[6-(trifluoromethyl)pyridin-3-yl]oxy}quinolin-2-yl)methanone | ¹H NMR (500 MHz, DMSO-d$_6$ rotamers) δ ppm 2.37 (s, 4H), 3.13-3.26 (m, 1H), 3.62 (t, J = 4.3 Hz, 4H), 3.88-4.00 (m, 1H), 4.15 (dd, J = 10.1, 7.5 Hz, 1H), 4.56 (dd, J = 10.6, 4.9 Hz, 1H), 4.77 (dd, J = 10.3, 7.2 Hz, 1H), 7.70-7.85 (m, 3H), 7.98 (dd, J = 13.1, 8.9 Hz, 1H), 8.04 (d, J = 8.6 Hz, 1H), 8.21 (d, J = 8.7 Hz, 1H), 8.47 (d, J = 8.6 Hz, 1H), 8.70 (d, J = 2.7 Hz, 1H) | DCI m/z 459.0 [M + H]⁺ |
| Example 555 | N-(3,3-difluorocyclobutyl)-6-{[6-(trifluoromethyl)pyridin-3-yl]oxy}quinoline-2-carboxamide | ¹H NMR (500 MHz, DMSO-d$_6$) δ ppm 2.83-3.07 (m, 4H), 4.31-4.48 (m, 1H), 7.74-7.88 (m, 3H), 7.95-8.02 (m, 1H), 8.14 (d, J = 8.5 Hz, 1H), 8.21-8.29 (m, 1H), 8.52 (d, J = 8.6 Hz, 1H), 8.72 (d, J = 2.6 Hz, 1H), 9.41 (d, J = 7.5 Hz, 1H) | DCI m/z 424.0 [M + H]⁺ |
| Example 556 | N-(3-oxocyclobutyl)-6-{[6-(trifluoromethyl)pyridin-3-yl]oxy}quinoline-2-carboxamide | ¹H NMR (500 MHz, DMSO-d$_6$) δ ppm 3.40 (t, J = 7.2 Hz, 4H), 4.71 (h, J = 7.2 Hz, 1H), 7.74-7.87 (m, 3H), 7.98 (t, J = 10.8 Hz, 1H), 8.17 (d, J = 8.5 Hz, 1H), 8.24 (dd, J = 14.2, 6.7 Hz, 1H), 8.52 (d, J = 8.5 Hz, 1H), 8.72 (d, J = 2.6 Hz, 1H), 9.51 (d, J = 7.6 Hz, 1H) | DCI m/z 402.0 [M + H]⁺ |
| Example 557 | [3-(piperazin-1-yl)azetidin-1-yl](6-{[5-(trifluoromethyl)pyridin-2-yl]oxy}quinolin-2-yl)methanone | ¹H NMR (400 MHz, DMSO-d$_6$) δ ppm 8.61-8.57 (m, 1H), 8.48 (d, J = 8.4 Hz, 1H), 8.30 (dd, J = 8.7, 2.5 Hz, 1H), 8.18 (d, J = 9.1 Hz, 1H), 8.04 (d, J = 8.5 Hz, 1H), 7.89 (d, J = 2.6 Hz, 1H), 7.72 (dd, J = 9.1, 2.6 Hz, 1H), 7.39 (d, J = 8.7 Hz, 1H), 4.75 (dd, J = 10.1, 7.3 Hz, 1H), 4.52 (dd, J = 10.6, 5.1 Hz, 1H), 4.13 (dd, J = 10.0, 7.6 Hz, 1H), 3.93 (dd, J = 10.4, 5.0 Hz, 1H), 3.18-3.10 (m, 1H), 2.76-2.66 (m, 4H), 2.27 (br s, 4H). | MS (ESI) m/z 458.2 [M + H]⁺ |
| Example 558 | 4,7-diazaspiro[2.5]oct-7-yl(6-{[5-(difluoromethyl)pyridin-2-yl]oxy}quinolin- | ¹H NMR (500 MHz, CDCl$_3$) δ ppm 8.29 (s, 1H), 8.22 (t, J = 7.9 Hz, 1H), 8.14 (dd, J = 25.1, 9.1 Hz, 1H), 7.92 (dd, J = 8.5, 1.6 Hz, 1H), 7.75 (dd, J = 8.4, 5.1 Hz, 1H), 7.62 (dd, J = 5.6, 2.4 Hz, 1H), 7.57 (ddd, J = 8.9, 6.0, 2.5 | MS (ESI) m/z 411.1 [M + H]⁺ |

-continued

| Example Number | Name | ¹H NMR | MS |
|---|---|---|---|
| | 2-yl)methanone | Hz, 1H), 7.14 (dd, J = 8.5, 3.3 Hz, 1H), 6.69 (t, J = 55.9 Hz, 1H), 3.94-3.85 (m, 1H), 3.79-3.68 (m, 2H), 3.56 (s, 1H), 3.18-3.09 (m, 1H), 3.07-2.98 (m, 1H), 0.82-0.46 (m, 4H). | |
| Example 559 | N-{2-[(3R)-3-hydroxypyrrolidin-1-yl]-2-oxoethyl}-6-{[5-(trifluoromethyl)pyridin-2-yl]oxy}quinoline-2-carboxamide | 1H NMR (400 MHz, DMSO-d₆/D₂O) δ ppm 8.59-8.47 (m, 2H), 8.29-8.12 (m, 3H), 7.86 (d, J = 2.6 Hz, 1H), 7.73 (dd, J = 9.1, 2.7 Hz, 1H), 7.34 (d, J = 8.7 Hz, 1H), 4.45-4.27 (m, 1H), 4.24-4.12 (m, 4H), 3.67-3.39 (m, 2H), 2.09-1.77 (m, 2H). | MS (APCI) m/z 461.1 [M + H]⁺ |
| Example 560 | N-{2-[(3S)-3-hydroxypyrrolidin-1-yl]-2-oxoethyl}-6-{[5-(trifluoromethyl)pyridin-2-yl]oxy}quinoline-2-carboxamide | ¹H NMR (400 MHz, DMSO-d₆/D₂O) δ ppm 8.59-8.47 (m, 2H), 8.28-8.12 (m, 3H), 7.86 (d, J = 2.6 Hz, 1H), 7.73 (dd, J = 9.1, 2.7 Hz, 1H), 7.34 (d, J = 8.7 Hz, 1H), 4.36 (d, J = 36.6 Hz, 1H), 4.18 (d, J = 15.8 Hz, 2H), 3.68-3.32 (m, 4H), 2.09-1.76 (m, 2H). | MS (APCI) m/z 461.1 [M + H]⁺ |
| Example 561 | N-[2-(3-hydroxy-3-methylpyrrolidin-1-yl)-2-oxoethyl]-6-{[5-(trifluoromethyl)pyridin-2-yl]oxy}quinoline-2-carboxamide | ¹H NMR (400 MHz, DMSO-d₆/D₂O) δ ppm 8.59-8.47 (m, 2H), 8.29-8.12 (m, 3H), 7.86 (d, J = 2.6 Hz, 1H), 7.73 (dd, J = 9.1, 2.6 Hz, 1H), 7.34 (d, J = 8.7 Hz, 1H), 4.28-4.08 (m, 2H), 3.71-3.37 (m, 3H), 3.20 (d, J = 12.1 Hz, 1H), 2.00-1.70 (m, 2H), 1.35 (d, J = 7.3 Hz, 3H). | MS (APCI) m/z 475.1 [M + H]⁺ |
| Example 562 | N-{2-[(3S,4S)-3,4-dihydroxypyrrolidin-1-yl]-2-oxoethyl}-6-{[5-(trifluoromethyl)pyridin-2-yl]oxy}quinoline-2-carboxamide | ¹H NMR (400 MHz, DMSO-d₆/D₂O) δ ppm 8.59-8.48 (m, 2H), 8.28-8.13 (m, 3H), 7.86 (d, J = 2.6 Hz, 1H), 7.73 (dd, J = 9.1, 2.7 Hz, 1H), 7.35 (d, J = 8.7 Hz, 1H), 4.18 (d, J = 1.6 Hz, 2H), 4.08 (s, 1H), 3.99 (s, 1H), 3.79-3.67 (m, 1H), 3.60-3.47 (m, 1H), 3.46-3.36 (m, 2H). | MS (APCI) m/z 477.1 [M + H]⁺ |
| Example 563 | N-{2-[(3R,4R)-3,4-dihydroxypyrrolidin-1-yl]-2-oxoethyl}-6-{[5-(trifluoromethyl)pyridin-2-yl]oxy}quinoline-2-carboxamide | ¹H NMR (400 MHz, DMSO-d₆/D₂O) δ ppm 8.59-8.47 (m, 2H), 8.29-8.12 (m, 3H), 7.86 (d, J = 2.6 Hz, 1H), 7.73 (dd, J = 9.1, 2.6 Hz, 1H), 7.34 (d, J = 8.7 Hz, 1H), 4.18 (d, J = 1.7 Hz, 2H), 4.08 (s, 1H), 3.99 (s, 1H), 3.79-3.67 (m, 1H), 3.60-3.47 (m, 1H), 3.46-3.36 (m, 2H). | MS (APCI) m/z 477.1 [M + H]⁺ |
| Example 564 | N-{2-[(2S,4R)-4-hydroxy-2-(hydroxymethyl)pyrrolidin-1-yl]-2-oxoethyl}-6-{[5-(trifluoromethyl)pyridin-2-yl]oxy}quinoline-2-carboxamide | ¹H NMR (400 MHz, DMSO-d₆/D₂O) δ ppm 8.58-8.50 (m, 2H), 8.26-8.15 (m, 3H), 7.86 (d, J = 2.6 Hz, 1H), 7.73 (dd, J = 9.1, 2.6 Hz, 1H), 7.35 (d, J = 8.7 Hz, 1H), 4.46-4.06 (m, 4H), 3.68-3.36 (m, 4H), 2.11-1.98 (m, 1H), 1.98-1.82 (m, 1H). | MS (APCI) m/z 491.1 [M + H]⁺ |
| Example 565 | N-[2-(3,3-difluoropyrrolidin-1-yl)-2-oxoethyl]-6-{[5-(trifluoromethyl)pyridin-2-yl]oxy}quinoline-2-carboxamide | ¹H NMR (400 MHz, DMSO-d₆/D₂O) δ ppm 8.59-8.48 (m, 2H), 8.28-8.12 (m, 3H), 7.86 (d, J = 2.6 Hz, 1H), 7.73 (dd, J = 9.1, 2.7 Hz, 1H), 7.35 (d, J = 8.7 Hz, 1H), 4.22 (s, 2H), 4.01 (s, 1H), 3.89-3.54 (m, 3H), 2.49-2.33 (m, 2H). | MS (APCI) m/z 481.0 [M + H]⁺ |
| Example 566 | N-[2-(3-hydroxyazetidin-1-yl)-2-oxoethyl]-6-{[5-(trifluoromethyl)pyridin-2-yl]oxy}quinoline-2-carboxamide | ¹H NMR (400 MHz, DMSO-d₆/D₂O) δ ppm 8.59-8.47 (m, 2H), 8.29-8.11 (m, 3H), 7.86 (d, J = 2.6 Hz, 1H), 7.72 (dd, J = 9.1, 2.7 Hz, 1H), 7.34 (d, J = 8.6 Hz, 1H), 4.60-4.47 (m, 1H), 4.19 (s, 2H), 4.03 (s, 2H), 3.99-3.54 (m, 2H). | MS (APCI) m/z 447.1 [M + H]⁺ |
| Example 567 | N-[2-(3-hydroxy-3-methylazetidin-1-yl)-2-oxoethyl]-6-{[5-(trifluoromethyl)pyridin-2-yl]oxy}quinoline-2-carboxamide | ¹H NMR (400 MHz, DMSO-d₆/D₂O) δ ppm 8.59-8.47 (m, 2H), 8.29-8.11 (m, 3H), 7.86 (d, J = 2.6 Hz, 1H), 7.72 (dd, J = 9.1, 2.7 Hz, 1H), 7.34 (d, J = 8.7 Hz, 1H), 4.20-3.94 (m, 4H), 3.94-3.68 (m, 2H), 1.43 (s, 3H). | MS (APCI) m/z 461.1 [M + H]⁺ |

| Example Number | Name | ¹H NMR | MS |
|---|---|---|---|
| Example 568 | N-[2-(1,1-dioxido-1,3-thiazolidin-3-yl)-2-oxoethyl]-6-{[5-(trifluoromethyl)pyridin-2-yl]oxy}quinoline-2-carboxamide | ¹H NMR (400 MHz, DMSO-$d_6$/$D_2O$) δ ppm 8.59-8.48 (m, 2H), 8.29-8.12 (m, 3H), 7.86 (d, J = 2.6 Hz, 1H), 7.73 (dd, J = 9.1, 2.7 Hz, 1H), 7.35 (d, J = 8.7 Hz, 1H), 4.66 (s, 2H), 4.31 (s, 2H), 4.07 (s, 2H), 3.47 (s, 2H). | MS (APCI) m/z 495.0 [M + H]⁺ |
| Example 569 | N-[2-(3-methoxyazetidin-1-yl)-2-oxoethyl]-6-{[5-(trifluoromethyl)pyridin-2-yl]oxy}quinoline-2-carboxamide | ¹H NMR (400 MHz, DMSO-$d_6$/$D_2O$) δ ppm 8.59-8.48 (m, 2H), 8.27-8.11 (m, 3H), 7.86 (d, J = 2.6 Hz, 1H), 7.72 (dd, J = 9.1, 2.7 Hz, 1H), 7.34 (d, J = 8.7 Hz, 1H), 4.41-4.24 (m, 2H), 4.24-3.61 (m, 5H), 3.25 (s, 3H). | MS (APCI) m/z 461.1 [M + H]⁺ |
| Example 570 | N-{2-[(2R)-2-(hydroxymethyl)pyrrolidin-1-yl]-2-oxoethyl}-6-{[5-(trifluoromethyl)pyridin-2-yl]oxy}quinoline-2-carboxamide | ¹H NMR (400 MHz, DMSO-$d_6$/$D_2O$) δ ppm 8.59-8.47 (m, 2H), 8.29-8.12 (m, 3H), 7.86 (d, J = 2.6 Hz, 1H), 7.73 (dd, J = 9.1, 2.7 Hz, 1H), 7.35 (d, J = 8.7 Hz, 1H), 4.37-4.11 (m, 2H), 4.06 (s, 1H), 3.58-3.39 (m, 4H), 2.02-1.81 (m, 4H). | MS (APCI) m/z 475.1 [M + H]⁺ |
| Example 571 | N-[2-(azetidin-1-yl)-2-oxoethyl]-6-{[5-(trifluoromethyl)pyridin-2-yl]oxy}quinoline-2-carboxamide | ¹H NMR (400 MHz, DMSO-$d_6$/$D_2O$) δ ppm 8.59-8.47 (m, 2H), 8.29-8.11 (m, 3H), 7.86 (d, J = 2.5 Hz, 1H), 7.72 (dd, J = 9.1, 2.6 Hz, 1H), 7.34 (d, J = 8.7 Hz, 1H), 4.36-4.08 (m, 2H), 4.08-3.92 (m, 3H), 2.36-2.20 (m, 2H). | MS (APCI) m/z 431.1 [M + H]⁺ |
| Example 572 | N-[2-oxo-2-(3-oxopyrrolidin-1-yl)ethyl]-6-{[5-(trifluoromethyl)pyridin-2-yl]oxy}quinoline-2-carboxamide | ¹H NMR (400 MHz, DMSO-$d_6$/$D_2O$) δ ppm 8.59-8.48 (m, 2H), 8.27-8.13 (m, 3H), 7.86 (d, J = 2.6 Hz, 1H), 7.73 (dd, J = 9.2, 2.6 Hz, 1H), 7.35 (d, J = 8.7 Hz, 1H), 4.26 (s, 2H), 4.12-3.67 (m, 4H), 2.69 (s, 2H). | MS (APCI) m/z 459.1 [M + H]⁺ |
| Example 573 | N-[2-(3-fluoropyrrolidin-1-yl)-2-oxoethyl]-6-{[5-(trifluoromethyl)pyridin-2-yl]oxy}quinoline-2-carboxamide | ¹H NMR (400 MHz, DMSO-$d_6$/$D_2O$) δ ppm 8.59-8.48 (m, 2H), 8.28-8.14 (m, 3H), 7.86 (d, J = 2.6 Hz, 1H), 7.73 (dd, J = 9.2, 2.7 Hz, 1H), 7.35 (d, J = 8.7 Hz, 1H), 5.53-5.23 (m, 1H), 4.29-4.14 (m, 2H), 3.88-3.39 (m, 4H), 2.39-1.97 (m, 2H). | MS (APCI) m/z 463.1 [M + H]⁺ |
| Example 574 | N-[3-(morpholin-4-yl)cyclobutyl]-6-{[6-(trifluoromethyl)pyridin-3-yl]oxy}quinoline-2-carboxamide | ¹H NMR (400 MHz, DMSO-$d_6$) δ ppm 1.97-2.14 (m, 2H), 2.30 (s, 4H), 2.35-2.46 (m, 2H), 3.54-3.65 (m, 4H), 4.15-4.31 (m, 1H), 7.74-7.85 (m, 3H), 7.98 (d, J = 8.7 Hz, 1H), 8.12 (d, J = 8.5 Hz, 1H), 8.20-8.29 (m, 1H), 8.49 (d, J = 8.5 Hz, 1H), 8.71 (d, J = 2.7 Hz, 1H), 9.02 (d, J = 8.4 Hz, 1H) | DCI m/z 473.0 [M + H]⁺ |
| Example 575 | (6-{[5-(difluoromethyl)pyridin-2-yl]oxy}quinolin-2-yl)[(3R)-3-fluoropyrrolidin-1-yl]methanone | ¹H NMR (500 MHz, DMSO-$d_6$) δ ppm 2.01-2.32 (m, 2H), 3.56-4.19 (m, 4H), 5.36 (d, J = 15.9 Hz, 0.5H), 5.46 (d, J = 15.6 Hz, 0.5H), 7.13 (t, J = 55.3 Hz, 1H), 7.33 (d, J = 8.6 Hz, 1H), 7.70 (dd, J = 9.1, 2.0 Hz, 1H), 7.81-7.95 (m, 2H), 8.15 (t, J = 7.9 Hz, 2H), 8.40 (s, 1H), 8.48 (d, J = 8.6 Hz, 1H) | DCI m/z 388.0 [M + H]⁺ |
| Example 576 | (6-{[5-(difluoromethyl)pyridin-2-yl]oxy}quinolin-2-yl)[(3S)-3-fluoropyrrolidin-1-yl]methanone | ¹H NMR (500 MHz, DMSO-$d_6$) δ ppm 2.01-2.32 (m, 2H), 3.56-4.19 (m, 4H), 5.36 (d, J = 15.9 Hz, 0.5H), 5.46 (d, J = 15.6 Hz, 0.5H), 7.13 (t, J = 55.3 Hz, 1H), 7.33 (d, J = 8.6 Hz, 1H), 7.70 (dd, J = 9.1, 2.0 Hz, 1H), 7.81-7.95 (m, 2H), 8.15 (t, J = 7.9 Hz, 2H), 8.40 (s, 1H), 8.48 (d, J = 8.6 Hz, 1H) | DCI m/z 388.0 [M + H]⁺ |
| Example 577 | N-(methylsulfonyl)-6-{[5-(trifluoromethyl)pyridin-2-yl]oxy}quinoline-2-carboxamide | ¹H NMR (400 MHz, DMSO-$d_6$) δ ppm 2.95 (s, 3H), 7.39 (t, J = 9.7 Hz, 1H), 7.67 (dd, J = 9.1, 2.7 Hz, 1H), 7.83 (d, J = 2.6 Hz, 1H), 8.19 (t, J = 7.9 Hz, 1H), 8.25-8.42 (m, 3H), 8.60 (dd, J = 1.6, 0.8 Hz, 1H) | DCI m/z 412.0 [M + H]⁺ |

| Example Number | Name | ¹H NMR | MS |
|---|---|---|---|
| Example 578 | N-(3-hydroxy-3-methylcyclobutyl)-6-{[6-(trifluoromethyl)pyridin-3-yl]oxy}quinoline-2-carboxamide | ¹H NMR (400 MHz, DMSO-$d_6$) δ ppm 1.29 (s, 3H), 2.16-2.30 (m, 2H), 2.30-2.44 (m, 2H), 4.00-4.16 (m, 1H), 4.99 (s, 1H), 7.75-7.88 (m, 3H), 7.98 (d, J = 8.7 Hz, 1H), 8.13 (d, J = 8.5 Hz, 1H), 8.22-8.29 (m, 1H), 8.50 (d, J = 8.5 Hz, 1H), 8.71 (d, J = 2.7 Hz, 1H), 8.85 (d, J = 7.9 Hz, 1H) | DCI m/z 418.0 [M + H]⁺ |
| Example 579 | N-[1-(dimethylamino)-1-oxopropan-2-yl]-6-{[5-(trifluoromethyl)pyridin-2-yl]oxy}quinoline-2-carboxamide | ¹H NMR (400 MHz, CDCl₃) δ ppm 9.08-9.01 (m, 1H), 8.46 (d, J = 3.0 Hz, 1H), 8.32-8.19 (m, 3H), 7.97 (dd, J = 8.6, 2.5 Hz, 1H), 7.64 (d, J = 2.6 Hz, 1H), 7.57 (dd, J = 9.1, 2.6 Hz, 1H), 7.14 (d, J = 8.6 Hz, 1H), 5.25-5.13 (m, 1H), 3.17 (s, 3H), 3.04 (s, 3H), 1.52 (d, J = 6.8 Hz, 3H). | MS (ESI) m/z 433.0 [M + H]⁺ |
| Example 580 | N-(3,3-difluorocyclobutyl)-6-{[5-(difluoromethyl)pyridin-2-yl]oxy}quinoline-2-carboxamide | ¹H NMR (400 MHz, DMSO-$d_6$) δ ppm 2.86-3.09 (m, 4H), 4.32-4.52 (m, 1H), 7.13 (t, J = 55.3 Hz, 1H), 7.34 (d, J = 8.6 Hz, 1H), 7.74 (dd, J = 9.1, 2.7 Hz, 1H), 7.89 (d, J = 2.6 Hz, 1H), 8.08-8.19 (m, 2H), 8.22 (d, J = 9.1 Hz, 1H), 8.41 (d, J = 1.7 Hz, 1H), 8.53 (d, J = 8.4 Hz, 1H), 9.40 (d, J = 7.5 Hz, 1H) | DCI m/z 406.0 [M + H]⁺ |
| Example 581 | [(3R)-3-hydroxypiperidin-1-yl](6-{[5-(trifluoromethyl)pyridin-2-yl]oxy}quinolin-2-yl)methanone | ¹H NMR (400 MHz, DMSO-$d_6$) δ ppm 8.59 (dd, J = 1.7, 0.8 Hz, 1H), 8.47 (dd, J = 8.5, 2.2 Hz, 1H), 8.30 (dd, J = 8.7, 2.6 Hz, 1H), 8.10 (dd, J = 9.1, 4.4 Hz, 1H), 7.89 (dd, J = 2.5, 2.5 Hz, 1H), 7.76-7.63 (m, 2H), 7.39 (d, J = 8.7 Hz, 1H), 5.04-4.81 (m, 1H), 4.29-3.90 (m, 1H), 3.66-3.44 (m, 2H), 3.30-2.88 (m, 2H), 1.97-1.58 (m, 2H), 1.58-1.36 (m, 2H) | MS (ESI) m/z 418.1 [M + H]⁺ |
| Example 582 | [(3S)-3-hydroxypiperidin-1-yl](6-{[5-(trifluoromethyl)pyridin-2-yl]oxy}quinolin-2-yl)methanone | ¹H NMR (400 MHz, DMSO-$d_6$) δ ppm 8.59 (dd, J = 1.5, 0.7 Hz, 1H), 8.47 (dd, J = 8.5, 2.4 Hz, 1H), 8.30 (dd, J = 8.7, 2.6 Hz, 1H), 8.11 (dd, J = 9.1, 4.6 Hz, 1H), 7.89 (dd, J = 2.5, 2.5 Hz, 1H), 7.76-7.63 (m, 2H), 7.39 (d, J = 8.8 Hz, 1H), 5.06-4.81 (m, 1H), 4.32-3.90 (m, 1H), 3.66-3.44 (m, 2H), 3.30-2.88 (m, 2H), 1.97-1.58 (m, 2H), 1.54-1.39 (m, 2H) | MS (ESI) m/z 418.1 [M + H]⁺ |
| Example 583 | [(3R,4R)-4-amino-3-fluoropiperidin-1-yl](6-{[5-(trifluoromethyl)pyridin-2-yl]oxy}quinolin-2-yl)methanone | ¹H NMR (400 MHz, CDCl₃) δ ppm 8.44 (bs, 1H), 8.23 (dd, J = 8.5, 2.8 Hz, 1H), 8.15 (t, J = 8.4 Hz, 1H), 7.97 (dd, J = 8.6, 2.5 Hz, 1H), 7.76 (dd, J = 11.5, 8.4 Hz, 1H), 7.63 (bs, 1H), 7.62-7.54 (m, 1H), 7.15 (d, J = 8.6 Hz, 1H), 5.03-4.09 (m, 3H), 3.37-2.96 (m, 3H), 1.71-1.56 (m, 1H), 0.91-0.80 (m, 1H). | MS (ESI) m/z 435.1 [M + H]⁺ |
| Example 584 | N-[(3R,4R)-3-fluoropiperidin-4-yl]-6-{[5-(trifluoromethyl)pyridin-2-yl]oxy}quinoline-2-carboxamide | ¹H NMR (500 MHz, CDCl₃) δ ppm 8.45 (bs, 1H), 8.37-8.30 (m, 2H), 8.28 (d, J = 8.5 Hz, 1H), 8.19 (d, J = 9.1 Hz, 1H), 7.98 (dd, J = 8.7, 2.4 Hz, 1H), 7.66 (d, J = 2.5 Hz, 1H), 7.60 (dd, J = 9.1, 2.5 Hz, 1H), 7.15 (d, J = 8.6 Hz, 1H), 4.67-4.49 (m, 1H), 4.39-4.27 (m, 1H), 3.49-3.40 (m, 1H), 3.14-3.06 (m, 1H), 2.92-2.75 (m, 2H), 2.32-2.23 (m, 1H), 1.69 (qd, J = 10.6, 4.0 Hz, 1H). | MS (ESI) m/z 435.1 [M + H]⁺ |
| Example 585 | (6-{[5-(difluoromethyl)pyridin-2-yl]oxy}quinolin-2-yl)[(3S)3-(hydroxymethyl)piperazin-1-yl]methanone | ¹H NMR (400 MHz, DMSO-$d_6$) δ ppm 2.66-3.06 (m, 4H), 3.07-3.29 (m, 3H), 3.76 (d, J = 13.7 Hz, 0.5H), 3.83 (t, J = 12.4 Hz, 0.5H), 4.43 (d, J = 12.9 Hz, 0.5H), 4.54 (d, J = 12.8 Hz, 0.5H), 4.91 (d, J = 88.7 Hz, 1H), 7.12 (t, J = 55.3 Hz, 1H), 7.32 (d, J = 8.6 Hz, 1H), 7.63-7.77 (m, 2H), 7.85 (d, J = 2.6 Hz, 1H), 8.04-8.19 (m, 2H), 8.39 (s, 1H), 8.49 (t, J = 8.2 Hz, 1H) | DCI m/z 415.0 [M + H]⁺ |
| Example 586 | {3-[(3S)-3-fluoropyrrolidin-1-yl]azetidin-1-yl}(6-{[5-(trifluoromethyl)pyridin-2-yl]oxy}quinolin-2-yl)methanone | ¹H NMR (400 MHz, DMSO-$d_6$, rotamers) δ ppm 8.61-8.57 (m, 1H), 8.48 (d, J = 8.5 Hz, 1H), 8.30 (dd, J = 8.7, 2.6 Hz, 1H), 8.18 (dd, J = 9.1, 2.7 Hz, 1H), 8.04 (d, J = 8.6 Hz, 1H), 7.89 (d, J = 2.6 Hz, 1H), 7.73 (dd, J = 9.1, 2.7 Hz, 1H), 7.39 (d, J = 8.7 Hz, 1H), 5.35-5.25 (m, 0.5H), 5.20-5.11 (m, 0.5H), 4.80 (dd, J = 10.2, 7.5 Hz, 1H), 4.61-4.53 (m, 1H), 4.19 (dd, J = 10.1, 7.4 Hz, 1H), 4.02-3.93 (m, 1H), 3.49-3.40 (m, 1H), 2.94-2.78 (m, 2H), 2.72 (dd, J = 11.5, 4.9 Hz, 0.5H), 2.64 (dd, J = 11.5, 4.9 Hz, 0.5H), 2.44-2.35 (m, 1H), 2.24-2.07 (m, 1H), 2.00-1.83 (m, 1H). | MS (ESI) m/z 461.1 [M + H]⁺ |

| Example Number | Name | ¹H NMR | MS |
|---|---|---|---|
| Example 587 | N-(1-methyl-2-oxopyrrolidin-3-yl)-6-{[5-(trifluoromethyl)pyridin-2-yl]oxy}quinoline-2-carboxamide | ¹H NMR (400 MHz, CDCl$_3$) δ ppm 8.69 (d, J = 5.8 Hz, 1H), 8.46 (d, J = 3.0 Hz, 1H), 8.27 (q, J = 8.5 Hz, 2H), 8.17 (d, J = 9.1 Hz, 1H), 7.98 (dd, J = 8.6, 2.5 Hz, 1H), 7.65 (d, J = 2.5 Hz, 1H), 7.57 (dd, J = 9.1, 2.5 Hz, 1H), 7.14 (d, J = 8.6 Hz, 1H), 4.66 (dd, J = 15.4, 9.1 Hz, 1H), 3.54-3.37 (m, 2H), 2.98 (s, 3H), 2.91-2.78 (m, 1H), 2.08 (dq, J = 12.7, 9.6 Hz, 1H). | MS (ESI) m/z 431.1 [M + H]⁺ |
| Example 588 | [(3R)-3-methoxypyrrolidin-1-yl](6-{[5-(trifluoromethyl)pyridin-2-yl]oxy}quinolin-2-yl)methanone | ¹H NMR (400 MHz, DMSO-d$_6$) δ ppm 8.59 (s, 1H), 8.47 (dd, J = 8.5, 1.9 Hz, 1H), 8.30 (dd, J = 8.7, 2.5 Hz, 1H), 8.14 (d, J = 9.1 Hz, 1H), 7.91-7.89 (m, 1H), 7.86 (dd, J = 8.5, 5.5 Hz, 1H), 7.72 (ddd, J = 9.1, 2.3, 2.3 Hz, 1H), 7.40 (d, J = 8.7 Hz, 1H), 4.08-3.97 (m, 1H), 3.95-3.77 (m, 2H), 3.72-3.52 (m, 2H), 3.30-3.21 (m, 3H), 2.10-1.92 (m, 2H) | MS (ESI) m/z 418.1 [M + H]⁺ |
| Example 589 | [(3S)-3-methoxypyrrolidin-1-yl](6-{[5-(trifluoromethyl)pyridin-2-yl]oxy}quinolin-2-yl)methanone | ¹H NMR (400 MHz, DMSO-d$_6$) δ ppm 8.59 (s, 1H), 8.47 (dd, J = 8.5, 1.0 Hz, 1H), 8.30 (dd, J = 8.7, 2.5 Hz, 1H), 8.14 (d, J = 9.1 Hz, 1H), 7.91-7.88 (m, 1H), 7.86 (dd, J = 8.5, 5.5 Hz, 1H), 7.72 (ddd, J = 9.1, 2.3, 2.3 Hz, 1H), 7.40 (d, J = 8.7 Hz, 1H), 4.08-3.97 (m, 1H), 3.95-3.77 (m, 2H), 3.72-3.52 (m, 2H), 3.30-3.21 (m, 3H), 2.10-1.92 (m, 2H) | MS (ESI) m/z 418.1 [M + H]⁺ |
| Example 590 | N-(2-methoxypropyl)-6-{[5-(trifluoromethyl)pyridin-2-yl]oxy}quinoline-2-carboxamide | ¹H NMR (400 MHz, DMSO-d$_6$) δ ppm 8.78 (t, J = 6.1 Hz, 1H), 8.60-8.61 (m, 1H), 8.55 (d, J = 8.5 Hz, 1H), 8.31 (dd, J = 8.7, 2.6 Hz, 1H), 8.18-8.22 (m, 2H), 7.93 (d, J = 2.8 Hz, 1H), 7.76 (dd, J = 9.2, 2.4 Hz, 1H), 7.40 (d, J = 8.5 Hz, 1H), 3.55-3.62 (m, 1H), 3.36-3.50 (m, 2H), 3.31 (s, 3H), 1.13 (d, J = 6.1 Hz, 3H). | MS (ESI) m/z 406.1 [M + H]⁺ |
| Example 591 | N-[(1-methoxycyclobutyl)methyl]-6-{[5-(trifluoromethyl)pyridin-2-yl]oxy}quinoline-2-carboxamide | ¹H NMR (400 MHz, DMSO-d$_6$) δ ppm 8.61-8.62 (m, 1H), 8.52-8.57 (m, 2H), 8.31 (dd, J = 8.7, 2.6 Hz, 1H), 8.20-8.23 (m, 2H), 7.94 (d, J = 2.4 Hz, 1H), 7.75 (dd, J = 9.2, 2.8 Hz, 1H), 7.40 (d, J = 8.9 Hz, 1H), 3.66 (d, J = 6.1 Hz, 2H), 3.20 (s, 3H), 2.04-2.12 (m, 2H), 1.92-1.98 (m, 2H), 1.60-1.75 (m, 2H). | MS (ESI) m/z 432.1 [M + H]⁺ |
| Example 592 | 6-{[5-(difluoromethyl)pyridin-2-yl]oxy}-N-(3-oxocyclobutyl)quinoline-2-carboxamide | ¹H NMR (400 MHz, DMSO-d$_6$) δ ppm 3.41 (d, J = 7.1 Hz, 4H), 4.63-4.81 (m, 1H), 7.13 (t, J = 55.3 Hz, 1H), 7.34 (d, J = 8.6 Hz, 1H), 7.74 (dd, J = 9.1, 2.6 Hz, 1H), 7.89 (d, J = 2.6 Hz, 1H), 8.17 (ddd, J = 13.3, 10.9, 5.8 Hz, 3H), 8.41 (d, J = 1.6 Hz, 1H), 8.54 (d, J = 8.5 Hz, 1H), 9.51 (d, J = 7.6 Hz, 1H) | DCI m/z 384.0 [M + H]⁺ |
| Example 593 | [(3S)-3-(methoxymethyl)piperazin-1-yl](6-{[5-(trifluoromethyl)pyridin-2-yl]oxy}quinolin-2-yl)methanone | ¹H NMR (400 MHz, DMSO-d$_6$, rotamers) δ ppm 2.56-3.26 (m, 8H), 3.32 (d, J = 10.9 Hz, 3H), 3.64 (dd, J = 27.4, 11.9 Hz, 3H), 4.34 (d, J = 12.6 Hz,, 0.5H), 4.42-4.52 (d, J = 12.6 Hz, 0.5H), 7.39 (dd, J = 8.7, 3.7 Hz, 1H), 7.63-7.77 (m, 2H), 7.89 (t, J = 2.2 Hz, 1H), 8.11 (dd, J = 9.1, 2.0 Hz, 1H), 8.30 (dd, J = 8.7, 2.2 Hz, 1H), 8.48 (d, J = 8.5 Hz, 1H), 8.59 (s, 1H) | DCI m/z 447.0 [M + H]⁺ |
| Example 594 | [3-(difluoromethyl)piperazin-1-yl](6-{[5-(trifluoromethyl)pyridin-2-yl]oxy}quinolin-2-yl)methanone | ¹H NMR (500 MHz, CDCl$_3$) δ ppm 8.45 (d, J = 3.9 Hz, 1H), 8.24 (d, J = 8.5 Hz, 1H), 8.16 (d, J = 9.1 Hz, 1H), 7.98 (dd, J = 8.6, 2.5 Hz, 1H), 7.79 (dd, J = 20.5, 8.5 Hz, 1H), 7.64 (d, J = 2.5 Hz, 1H), 7.58 (dd, J = 9.1, 2.6 Hz, 1H), 7.15 (d, J = 8.6 Hz, 1H), 5.76 (tdd, J = 56.1, 13.8, 4.5 Hz, 1H), 4.64 (dd, J = 117.7, 13.1 Hz, 1H), 4.21 (dd, J = 114.0, 11.4 Hz, 1H), 3.41-3.16 (m, 3H), 3.11-2.89 (m, 1H). | MS (ESI) m/z 453.1 [M + H]⁺ |
| Example 595 | N-(3-cyanopropyl)-6-{[5-(trifluoromethyl)pyridin-2-yl]oxy}quinoline-2-carboxamide | ¹H NMR (400 MHz, DMSO-d$_6$) δ ppm 9.09 (t, J = 6.2 Hz, 1H), 8.61 (s, 1H), 8.53 (d, J = 8.4 Hz, 1H), 8.31 (dd, J = 8.7, 2.6 Hz, 1H), 8.18 (t, J = 9.2 Hz, 2H), 7.93 (d, J = 2.6 Hz, 1H), 7.76 (dd, J = 9.1, 2.6 Hz, 1H), 7.40 (d, J = 8.7 Hz, 1H), 3.46 (dd, J = 13.2, 6.7 Hz, 2H), 2.53 (m, 2H), 2.01-1.84 (m, 2H). | ESI m/z 401.2 [M + H]⁺ |

| Example Number | Name | ¹H NMR | MS |
| --- | --- | --- | --- |
| Example 596 | N-cyclobutyl-6-{[5-(trifluoromethyl)pyridin-2-yl]oxy}quinoline-2-carboxamide | ¹H NMR (500 MHz, DMSO-d₆) δ ppm 9.03 (d, J = 8.4 Hz, 1H), 8.63-8.59 (m, 1H), 8.52 (d, J = 8.4 Hz, 1H), 8.31 (dd, J = 8.7, 2.5 Hz, 1H), 8.23 (d, J = 9.1 Hz, 1H), 8.14 (d, J = 8.5 Hz, 1H), 7.92 (d, J = 2.6 Hz, 1H), 7.75 (dd, J = 9.1, 2.6 Hz, 1H), 7.40 (d, J = 8.7 Hz, 1H), 4.57-4.46 (m, 1H), 2.28-2.20 (m, 4H), 1.75-1.65 (m, 2H). | MS (ESI) m/z 388.1 [M + H]⁺ |
| Example 597 | azetidin-1-yl(6-{[5-(trifluoromethyl)pyridin-2-yl]oxy}quinolin-2-yl)methanone | ¹H NMR (400 MHz, DMSO-d₆) δ ppm 8.61-8.56 (m, 1H), 8.47 (d, J = 8.5 Hz, 1H), 8.30 (dd, J = 8.8, 2.5 Hz, 1H), 8.13 (d, J = 9.1 Hz, 1H), 8.03 (d, J = 8.5 Hz, 1H), 7.88 (d, J = 2.6 Hz, 1H), 7.71 (dd, J = 9.1, 2.7 Hz, 1H), 7.39 (d, J = 8.6 Hz, 1H), 4.79-4.70 (m, 2H), 4.18-4.09 (m, 2H), 2.39-2.28 (m, 2H). | MS (ESI) m/z 374.1 [M + H]⁺ |
| Example 598 | [2-(trifluoromethyl)piperazin-1-yl](6-{[5-(trifluoromethyl)pyridin-2-yl]oxy}quinolin-2-yl)methanone | ¹H NMR (400 MHz, DMSO-d₆, rotamers) δ ppm 8.58 (s, 1H), 8.52 (d, J = 8.5 Hz, 1H), 8.30 (dd, J = 8.8, 2.5 Hz, 1H), 8.17-8.09 (m, 1H), 7.91 (d, J = 2.6 Hz, 1H), 7.79-7.69 (m, 2H), 7.43-7.37 (m, 1H), 5.26-5.08 (m, 1H), 4.34 (d, J = 14.0 Hz, 0.4H), 3.59 (d, J = 12.6 Hz, 0.6H), 3.24 (d, J = 13.8 Hz, 0.6H), 3.15-2.91 (m, 2H), 2.87-2.55 (m, 2.4H). | MS (ESI) m/z 471.1 [M + H]⁺ |
| Example 599 | N-(3-methoxypropyl)-6-{[5-(trifluoromethyl)pyridin-2-yl]oxy}quinoline-2-carboxamide | ¹H NMR (500 MHz, DMSO-d₆) δ ppm 8.98 (t, J = 5.9 Hz, 1H), 8.61 (dd, J = 1.6, 0.7 Hz, 1H), 8.53 (d, J = 8.4 Hz, 1H), 8.31 (dd, J = 8.7, 2.5 Hz, 1H), 8.18 (t, J = 9.0 Hz, 2H), 7.93 (d, J = 2.6 Hz, 1H), 7.75 (dd, J = 9.1, 2.7 Hz, 1H), 7.40 (d, J = 8.7 Hz, 1H), 3.49-3.38 (m, 4H), 3.28 (s, 3H), 1.84 (p, J = 6.5 Hz, 2H). | |
| Example 600 | N-(thietan-3-ylmethyl)-6-{[5-(trifluoromethyl)pyridin-2-yl]oxy}quinoline-2-carboxamide | ¹H NMR (400 MHz, DMSO-d₆) δ ppm 9.11 (t, J = 6.1 Hz, 1H), 8.61 (d, J = 3.0 Hz, 1H), 8.53 (d, J = 8.5 Hz, 1H), 8.31 (dd, J = 8.7, 2.6 Hz, 1H), 8.23-8.14 (m, 2H), 7.93 (d, J = 2.6 Hz, 1H), 7.76 (dd, J = 9.1, 2.6 Hz, 1H), 7.40 (d, J = 8.6 Hz, 1H), 3.61-3.42 (m, 3H), 3.19 (t, J = 8.6 Hz, 2H), 3.05 (dd, J = 9.1, 6.4 Hz, 2H). | |
| Example 601 | N-[(1-oxidothietan-3-yl)methyl]-6-{[5-(trifluoromethyl)pyridin-2-yl]oxy}quinoline-2-carboxamide | ¹H NMR (400 MHz, DMSO-d₆) δ ppm 9.29-9.17 (m, 1H), 8.61 (dd, J = 2.6, 1.3 Hz, 1H), 8.54 (d, J = 8.5 Hz, 1H), 8.35-8.28 (m, 1H), 8.24-8.15 (m, 2H), 7.94 (d, J = 2.6 Hz, 1H), 7.76 (dd, J = 9.1, 2.6 Hz, 1H), 7.41 (d, J = 8.6 Hz, 1H), 3.72-3.50 (m, J = 6.2 Hz, 4H), 3.26-2.94 (m, 3H). | |
| Example 602 | N-[(1,1-dioxidothietan-3-yl)methyl]-6-{[5-(trifluoromethyl)pyridin-2-yl]oxy}quinoline-2-carboxamide | ¹H NMR (500 MHz, DMSO-d₆) δ ppm 9.36 (t, J = 6.2 Hz, 1H), 8.64-8.59 (m, 1H), 8.54 (d, J = 8.5 Hz, 1H), 8.32 (dd, J = 8.7, 2.6 Hz, 1H), 8.19 (t, J = 8.4 Hz, 2H), 7.94 (d, J = 2.6 Hz, 1H), 7.77 (dd, J = 9.0, 2.6 Hz, 1H), 7.41 (d, J = 8.6 Hz, 1H), 4.32-4.23 (m, 2H), 4.10-3.99 (m, 2H), 3.64 (t, J = 6.7 Hz, 2H), 2.93-2.82 (m, 1H). | |
| Example 603 | [(2R)-2-(difluoromethyl)piperazin-1-yl](6-{[5-(trifluoromethyl)pyridin-2-yl]oxy}quinolin-2-yl)methanone | ¹H NMR (500 MHz, DMSO-d₆, rotamers) δ ppm 8.59 (s, 1H), 8.50 (d, J = 8.5 Hz, 1H), 8.30 (dd, J = 8.7, 2.5 Hz, 1H), 8.12 (t, J = 8.9 Hz, 1H), 7.90 (d, J = 2.6 Hz, 1H), 7.74-7.71 (m, 1H), 7.69 (dd, J = 8.5, 7.0 Hz, 1H), 7.40 (dd, J = 8.7, 3.7 Hz, 1H), 6.55 (tdd, J = 57.0, 37.5, 6.7 Hz, 1H), 4.82-4.74 (m, 0.5H), 4.43-4.34 (m, 0.5H), 4.35-4.27 (m, 0.5H), 3.56 (d, J = 13.3 Hz, 0.5H), 3.39-3.34 (m, 0.5H), 3.16 (d, J = 13.1 Hz, 0.5H), 3.09-2.93 (m, 2H), 2.87-2.77 (m, 1H), 2.76-2.68 (m, 0.5H), 2.63-2.55 (m, 1.5H). | MS (ESI) m/z 453.1 [M + H]⁺ |
| Example 604 | N-(3-fluorocyclobutyl)-6-{[5-(trifluoromethyl)pyridin-2-yl]oxy}quinoline-2-carboxamide | ¹H NMR (400 MHz, DMSO-d₆, rotamers) δ ppm 2.51-2.83 (m, 4H), 4.08 (dt, J = 16.0, 8.1 Hz, 0.4H), 4.60-4.88 (m, 0.8H), 4.97 (p, J = 6.9 Hz, 0.2H), 5.27 (tt, J = 6.4, 3.2 Hz, 0.3H), 5.41 (tt, J = 6.2, 3.2 Hz, 0.3H), 7.41 (d, J = 8.7 Hz, 1H), 7.72-7.81 (m, 1H), 7.92 (d, J = 2.6 Hz, 1H), 8.15 (dd, J = 8.5, 2.4 Hz, 1H), 8.23 (d, J = 9.1 Hz, 1H), 8.31 (dd, J = 8.7, 2.5 Hz, 1H), 8.53 (d, J = 8.5 Hz, 1H), 8.61 (s, 1H), 9.23 (d, J = 7.4 Hz, 1H) | DCI m/z 406.0 [M + H]⁺ |

| Example Number | Name | ¹H NMR | MS |
|---|---|---|---|
| Example 605 | N-[2-(2-oxo-1,3-oxazolidin-3-yl)ethyl]-6-{[5-(trifluoromethyl)pyridin-2-yl]oxy}quinoline-2-carboxamide | ¹H NMR (400 MHz, DMSO-$d_6$) δ ppm 9.08 (t, J = 6.1 Hz, 1H), 8.61 (d, J = 2.8 Hz, 1H), 8.54 (d, J = 8.5 Hz, 1H), 8.31 (dd, J = 8.7, 2.6 Hz, 1H), 8.22-8.14 (m, 2H), 7.93 (d, J = 2.6 Hz, 1H), 7.76 (dd, J = 9.1, 2.6 Hz, 1H), 7.40 (d, J = 8.6 Hz, 1H), 4.24 (d, J = 15.8 Hz, 2H), 3.66 (t, J = 7.9 Hz, 2H), 3.55 (q, J = 6.0 Hz, 2H), 3.42 (t, J = 6.0 Hz, 2H). | ESI m/z 447.1 [M + H]⁺ |
| Example 606 | N-[2-(pyridin-2-yl)ethyl]-6-{[5-(trifluoromethyl)pyridin-2-yl]oxy}quinoline-2-carboxamide | ¹H NMR (400 MHz, DMSO-$d_6$) δ ppm 9.12 (t, J = 6.0 Hz, 1H), 8.63-8.58 (m, 1H), 8.58-8.50 (m, 2H), 8.31 (dd, J = 8.6, 2.6 Hz, 1H), 8.21-8.14 (m, 2H), 7.92 (d, J = 2.6 Hz, 1H), 7.78-7.68 (m, 2H), 7.40 (d, J = 8.6 Hz, 1H), 7.33 (d, J = 7.8 Hz, 1H), 7.25 (ddd, J = 7.5, 4.8, 1.2 Hz, 1H), 3.75 (q, J = 6.8 Hz, 2H), 3.09 (t, J = 7.2 Hz, 2H). | ESI m/z 439.1 [M + H]⁺ |
| Example 607 | N-[3-(pyridin-2-yl)propyl]-6-{[5-(trifluoromethyl)pyridin-2-yl]oxy}quinoline-2-carboxamide | ¹H NMR (400 MHz, DMSO-$d_6$) δ ppm 8.99 (t, J = 6.1 Hz, 1H), 8.63-8.59 (m, 1H), 8.55-8.46 (m, 2H), 8.34-8.28 (m, 1H), 8.23-8.14 (m, 2H), 7.92 (d, J = 2.6 Hz, 1H), 7.76 (dd, J = 9.1, 2.6 Hz, 1H), 7.69 (td, J = 7.6, 1.9 Hz, 1H), 7.40 (d, J = 8.6 Hz, 1H), 7.31 (d, J = 7.8 Hz, 1H), 7.19 (ddd, J = 7.4, 4.8, 1.2 Hz, 1H), 3.43 (q, J = 6.7 Hz, 2H), 2.82 (t, J = 7.6 Hz, 2H), 2.07-1.94 (m, 2H). | ESI m/z 453.1 [M + H]⁺ |
| Example 608 | N-[3-(2-oxopyrrolidin-1-yl)propyl]-6-{[5-(trifluoromethyl)pyridin-2-yl]oxy}quinoline-2-carboxamide | ¹H NMR (400 MHz, DMSO-$d_6$) δ ppm 9.03-8.96 (m, 1H), 8.61 (dt, J = 2.2, 1.1 Hz, 1H), 8.53 (d, J = 8.5 Hz, 1H), 8.34-8.28 (m, 1H), 8.21-8.14 (m, 2H), 7.93 (d, J = 2.6 Hz, 1H), 7.76 (dd, J = 9.1, 2.6 Hz, 1H), 7.40 (d, J = 8.6 Hz, 1H), 3.39-3.24 (m, 6H), 2.24 (t, J = 8.0 Hz, 2H), 2.00-1.88 (m, 2H), 1.83-1.72 (m, 2H). | ESI m/z 459.1 [M + H]⁺ |
| Example 609 | N-[(5-oxopyrrolidin-3-yl)methyl]-6-{[5-(trifluoromethyl)pyridin-2-yl]oxy}quinoline-2-carboxamide | ¹H NMR (500 MHz, DMSO-$d_6$) δ ppm 9.14 (t, J = 6.2 Hz, 1H), 8.61 (d, J = 3.0 Hz, 1H), 8.53 (d, J = 8.5 Hz, 1H), 8.31 (dd, J = 8.7, 2.6 Hz, 1H), 8.21 (d, J = 9.1 Hz, 1H), 8.17 (d, J = 8.4 Hz, 1H), 7.93 (d, J = 2.6 Hz, 1H), 7.76 (dd, J = 9.0, 2.6 Hz, 1H), 7.51 (s, 1H), 7.40 (d, J = 8.6 Hz, 1H), 3.49-3.36 (m, 3H), 3.08 (dd, J = 9.7, 4.8 Hz, 1H), 2.81-2.71 (m, 1H), 2.27 (dd, J = 16.6, 8.8 Hz, 1H), 2.06-1.94 (m, 1H). | ESI m/z 431.1 [M + H]⁺ |
| Example 610 | N-(3-acetamido-2-methylpropyl)-6-{[5-(trifluoromethyl)pyridin-2-yl]oxy}quinoline-2-carboxamide | ¹H NMR (500 MHz, DMSO-$d_6$) δ ppm 9.02 (t, J = 6.4 Hz, 1H), 8.61 (d, J = 3.0 Hz, 1H), 8.53 (d, J = 8.5 Hz, 1H), 8.31 (dd, J = 8.7, 2.6 Hz, 1H), 8.18 (t, J = 8.2 Hz, 2H), 7.95-7.87 (m, 2H), 7.76 (dd, J = 9.0, 2.6 Hz, 1H), 7.40 (d, J = 8.6 Hz, 1H), 3.26 (m, 2H), 3.02 (m, 2H), 1.92 (m, 1H), 1.85 (s, 3H), 0.88 (d, J = 6.8 Hz, 3H). | ESI m/z 447.1 [M + H]⁺ |
| Example 611 | N-methyl-N-[2-(methylsulfonyl)ethyl]-6-{[5-(trifluoromethyl)pyridin-2-yl]oxy}quinoline-2-carboxamide | ¹H NMR (500 MHz, DMSO-$d_6$) δ ppm 8.63-8.57 (m, 1H), 8.49 (d, J = 8.5 Hz, 1H), 8.31 (dd, J = 8.7, 2.6 Hz, 1H), 8.15 (d, J = 9.1 Hz, 1H), 7.90 (d, J = 2.6 Hz, 1H), 7.81-7.66 (m, 2H), 7.40 (dd, J = 8.7, 2.4 Hz, 1H), 3.94 (t, J = 7.1 Hz, 1H), 3.89-3.82 (m, 1H), 3.81-3.74 (m, 1H), 3.56 (t, J = 7.1 Hz, 1H), 3.12 (m, 2H), 3.10 and 3.12 (2s, 3H), 3.07 and 2.97 (2s, 3H). | ESI m/z 454.1 [M + H]⁺ |
| Example 612 | N-[4-(methylsulfonyl)butyl]-6-{[5-(trifluoromethyl)pyridin-2-yl]oxy}quinoline-2-carboxamide | ¹H NMR (400 MHz, DMSO-$d_6$) δ ppm 9.01 (t, J = 6.1 Hz, 1H), 8.61 (d, J = 3.1 Hz, 1H), 8.53 (d, J = 8.5 Hz, 1H), 8.31 (dd, J = 8.7, 2.6 Hz, 1H), 8.23-8.15 (m, 2H), 7.93 (d, J = 2.6 Hz, 1H), 7.90-7.72 (m, 1H), 7.40 (d, J = 8.7 Hz, 1H), 3.42 (m, 2H), 3.22-3.11 (m, 2H), 2.95 (s, 3H), 1.84-1.59 (m, 4H). | ESI m/z 468.1 [M + H]⁺ |
| Example 613 | N-(3-acetamidopropyl)-6-{[5-(trifluoromethyl)pyridin-2-yl]oxy}quinoline-2-carboxamide | ¹H NMR (500 MHz, DMSO-$d_6$) δ ppm 8.99 (t, J = 6.1 Hz, 1H), 8.64-8.59 (m, 1H), 8.53 (d, J = 8.5 Hz, 1H), 8.31 (dd, J = 8.7, 2.6 Hz, 1H), 8.22-8.14 (m, 2H), 7.95-7.86 (m, 2H), 7.76 (dd, J = 9.0, 2.6 Hz, 1H), 7.41 (d, J = 8.7 Hz, 1H), 3.37 (m, 2H), 3.19-3.07 (m, 2H), 1.82 (s, 3H), 1.70 (m, 2H). | ESI m/z 433.1 [M + H]⁺ |
| Example 614 | 1-[(6-{[5-(trifluoromethyl)pyridin-2-yl]oxy}quinolin-2-yl)carbonyl]hexahydro- | ¹H NMR (500 MHz, DMSO-$d_6$) δ ppm 8.61-8.57 (m, 1H), 8.51 (d, J = 8.5 Hz, 1H), 8.31 (dd, J = 8.7, 2.6 Hz, 1H), 8.15 (d, J = 9.1 Hz, 1H), 7.91 (d, J = 2.6 Hz, 1H), 7.84-7.77 (m, 1H), 7.73 (dd, J = 9.0, 2.6 Hz, 1H), 7.40 (d, J = | ESI m/z 457.1 [M + H]⁺ |

| Example Number | Name | ¹H NMR | MS |
|---|---|---|---|
| | pyrrolo[1,2-a]pyrimidin-6(2H)-one | 8.7 Hz, 1H), 5.62 (bs, 1H), 4.00-3.64 (m, 2H), 3.23 (m, 1H), 3.05-2.96 (m, 1H), 2.57 (m, 1H), 2.39-2.32 (m, 2H), 2.10-1.96 (m, 2H), 1.86-1.80 (m, 1H). | |
| Example 615 | N-[2-(1,1-dioxidothietan-3-yl)ethyl]-6-{[5-(trifluoromethyl)pyridin-2-yl]oxy}quinoline-2-carboxamide | ¹H NMR (500 MHz, DMSO-$d_6$) δ ppm 9.06 (t, J = 6.2 Hz, 1H), 8.63-8.59 (m, 1H), 8.53 (d, J = 8.5 Hz, 1H), 8.32 (dd, J = 8.7, 2.6 Hz, 1H), 8.23-8.15 (m, 2H), 7.93 (d, J = 2.6 Hz, 1H), 7.76 (dd, J = 9.0, 2.6 Hz, 1H), 7.41 (d, J = 8.6 Hz, 1H), 4.32-4.21 (m, 2H), 3.96-3.85 (m, 2H), 3.38 (m, 2H), 2.54 (m, 1H), 1.94 (q, J = 7.0 Hz, 2H). | ESI m/z 466.1 [M + H]⁺ |
| Example 616 | N-methyl-N-(2,2,2-trifluoroethyl)-6-{[5-(trifluoromethyl)pyridin-2-yl]oxy}quinoline-2-carboxamide | ¹H NMR (500 MHz, DMSO-$d_6$, rotamers) δ ppm 8.62-8.57 (m, 1H), 8.54-8.49 (m, 1H), 8.31 (dd, J = 8.7, 2.5 Hz, 1H), 8.14 (dd, J = 19.7, 9.1 Hz, 1H), 7.91 (d, J = 2.6 Hz, 1H), 7.80 (d, J = 8.5 Hz, 0.4H), 7.77-7.71 (m, 1.6H), 7.40 (dd, J = 8.7, 4.1 Hz, 1H), 4.78 (q, J = 9.4 Hz, 1H), 4.46 (q, J = 9.7 Hz, 1H), 3.20 (s, 1H), 3.17 (s, 2H). | MS (ESI) m/z 430.0 [M + H]⁺ |
| Example 617 | 6-{[5-(difluoromethyl)pyridin-2-yl]oxy}-N3-fluorocyclobutyl)quinoline-2-carboxamide | ¹H NMR (500 MHz, DMSO-$d_6$) δ ppm 2.51-2.81 (m, 4H), 4.02-4.14 (m, 0.5H), 4.65-4.77 (m, 0.5H), 4.84 (p, J = 6.9 Hz, 0.25H), 4.96 (p, J = 6.8 Hz, 0.25H), 5.28 (tt, J = 6.2, 3.1 Hz, 0.25H), 5.40 (tt, J = 6.2, 3.2 Hz, 0.25H), 7.13 (t, J = 55.3 Hz, 1H), 7.33 (d, J = 8.6 Hz, 1H), 7.69-7.77 (m, 1H), 7.88 (d, J = 2.6 Hz, 1H), 8.14 (dd, J = 8.5, 2.9 Hz, 2H), 8.22 (d, J = 9.1 Hz, 1H), 8.41 (d, J = 1.4 Hz, 1H), 8.52 (dd, J = 8.6, 1.6 Hz, 1H), 9.19-9.27 (m, 1H) | DCI m/z 388.0 [M + H]⁺ |
| Example 618 | [4-fluoro-4-(methoxymethyl)piperidin-1-yl](6-{[5-(trifluoromethyl)pyridin-2-yl]oxy}quinolin-2-yl)methanone | ¹H NMR (500 MHz, DMSO-$d_6$) δ ppm 1.67-1.88 (m, 3H), 1.93 (t, J = 11.8 Hz, 1H), 3.17 (td, J = 12.8, 3.2 Hz, 1H), 3.27-3.36 (m, 4H), 3.42-3.52 (m, 2H), 3.68 (d, J = 13.9 Hz, 1H), 4.39 (d, J = 13.2 Hz, 1H), 7.39 (d, J = 8.7 Hz, 1H), 7.71 (dd, J = 8.8, 2.3 Hz, 2H), 7.89 (d, J = 2.7 Hz, 1H), 8.11 (d, J = 9.1 Hz, 1H), 8.30 (dd, J = 8.7, 2.5 Hz, 1H), 8.49 (d, J = 8.4 Hz, 1H), 8.59 (dd, J = 1.5, 0.7 Hz, 1H) | DCI m/z 464.0 [M + H]⁺ |
| Example 619 | [3-(2, 2-difluoroethoxy)azetidin-1-yl](6-{[5-(trifluoromethyl)pyridin-2-yl]oxy}quinolin-2-yl)methanone | ¹H NMR (500 MHz, DMSO-$d_6$) δ ppm 3.77 (td, J = 15.3, 3.6 Hz, 2H), 3.98 (ddd, J = 11.3, 3.7, 1.4 Hz, 1H), 4.36 (ddd, J = 11.1, 6.5, 1.4 Hz, 1H), 4.49-4.58 (m, 1H), 4.58-4.66 (m, 1H), 4.95 (ddd, J = 11.1, 6.2, 1.3 Hz, 1H), 6.21 (tt, J = 54.8, 3.6 Hz, 1H), 7.40 (d, J = 8.7 Hz, 1H), 7.74 (dd, J = 9.1, 2.6 Hz, 1H), 7.90 (d, J = 2.6 Hz, 1H), 8.06 (d, J = 8.5 Hz, 1H), 8.17 (d, J = 9.1 Hz, 1H), 8.31 (dd, J = 8.7, 2.5 Hz, 1H), 8.49 (d, J = 8.5 Hz, 1H), 8.60 (dd, J = 1.5, 0.7 Hz, 1H) | DCI m/z 454.0 [M + H]⁺ |
| Example 620 | 1,1-dimethyl-4-[(6-{[5-(trifluoromethyl)pyridin-2-yl]oxy}quinolin-2-yl)carbonyl]piperazin-1-ium iodide | ¹H NMR (400 MHz, DMSO-$d_6$) δ ppm 3.41-3.52 (m, 2H), 3.52-3.65 (m, 2H), 4.03 (ddd, J = 20.3, 12.0, 3.6 Hz, 4H), 4.80-5.19 (m, 6H), 7.41 (d, J = 8.7 Hz, 1H), 7.70-7.83 (m, 2H), 7.93 (d, J = 2.6 Hz, 1H), 8.12 (t, J = 7.1 Hz, 1H), 8.32 (dd, J = 8.7, 2.5 Hz, 1H), 8.55 (dd, J = 16.8, 8.2 Hz, 2H) | DCI m/z 559.0 [M + H]⁺ |
| Example 621 | {3-[(2,2,2-trifluoroethyl)amino]azetidin-1-yl}(6-{[5-(trifluoromethyl)pyridin-2-yl]oxy}quinolin-2-yl)methanone | ¹H NMR (500 MHz, DMSO-$d_6$) δ ppm 8.61-8.58 (m, 1H), 8.48 (d, J = 8.5 Hz, 1H), 8.30 (dd, J = 8.7, 2.5 Hz, 1H), 8.14 (d, J = 9.1 Hz, 1H), 8.05 (d, J = 8.5 Hz, 1H), 7.89 (d, J = 2.6 Hz, 1H), 7.73 (dd, J = 9.1, 2.6 Hz, 1H), 7.40 (d, J = 8.7 Hz, 1H), 4.90-4.84 (m, 1H), 4.43 (dd, J = 10.6, 5.2 Hz, 1H), 4.27 (dd, J = 9.7, 8.1 Hz, 1H), 3.88-3.82 (m, 1H), 3.80-3.71 (m, 1H), 3.30-3.26 (m, 2H). | MS (ESI) m/z 471.1 [M + H]⁺ |
| Example 622 | N-(2,2-difluoroethyl)-N-methyl-6-{[5-(trifluoromethyl)pyridin-2-yl]oxy}quinoline-2-carboxamide | ¹H NMR (500 MHz, DMSO-$d_6$, rotamers) δ ppm 8.61-8.56 (m, 1H), 8.50 (dd, J = 8.5, 2.2 Hz, 1H), 8.30 (dd, J = 8.7, 2.5 Hz, 1H), 8.14 (dd, J = 9.1, 3.4 Hz, 1H), 7.91-7.88 (m, 1H), 7.77 (d, J = 8.5 Hz, 0.5H), 7.75-7.70 (m, 1.5H), 7.40 (d, J = 8.7 Hz, 1H), 6.62-6.21 (m, 1H), 4.08-3.94 (m, 2H), 3.16 (s, 1.5H), 3.13 (s, 1.5H). | MS (ESI) m/z 412.0 [M + H]⁺ |

| Example Number | Name | $^1$H NMR | MS |
|---|---|---|---|
| Example 623 | 7-oxa-2-azaspiro[3.5]non-2-yl(6-{[5-(trifluoromethyl)pyridin-2-yl]oxy}quinolin-2-yl)methanone | $^1$H NMR (400 MHz, DMSO-d$_6$) δ ppm 1.69-1.84 (m, 4H), 3.47-3.63 (m, 4H), 3.89 (s, 2H), 4.50 (s, 2H), 7.40 (d, J = 8.7 Hz, 1H), 7.73 (dd, J = 9.1, 2.6 Hz, 1H), 7.89 (d, J = 2.6 Hz, 1H), 8.06 (d, J = 8.6 Hz, 1H), 8.18 (d, J = 9.1 Hz, 1H), 8.31 (dd, J = 8.7, 2.5 Hz, 1H), 8.48 (d, J = 8.6 Hz, 1H), 8.60 (d, J = 0.8 Hz, 1H) | DCI m/z 444.0 [M + H]$^+$ |

Determination of Biological Activity

Abbreviations: CC2-DMPE for N-(6-chloro-7-hydroxycoumarin-3-carbonyl)-dimyristoylphosphatidylethanolamine; DiSBAC$_2$(3) for bis(1,3-diethylthiobarbiturate)trimethine oxonol; DMEM for Dulbecco's Modified Eagle Media; EGTA for ethylene glycol tetraacetic acid; FBS for Fetal Bovine Serum; FLIPR® for Fluorometric Imaging Plate Reader; FRET for Fluorescence Resonance Energy Transfer; HI FBS for Heat-Inactivated Fetal Bovine Serum; HBSS for Hank's Balanced Salt Solution; HEPES for N-2-Hydroxy-EthylPiperazine-N'-2-Ethane Sulfonic acid; K-aspartate for potassium aspartate; MEM for Minimal Essential Media; MgATP for magnesium adenosine triphosphate; and VABSC-1 for Voltage Assay Background Suppression Compound.

FRET-Based Membrane Potential Assays.

Recombinant, Human Sodium Channel, Na$_v$ 1.7.

Two days prior to the experiment, frozen HEK293 cells stably expressing recombinant human Na$_v$ 1.7 were quickly thawed and plated at 25,000 cells/well in growth medium [DMEM (Invitrogen #11965) with 10% HI FBS (Invitrogen #10082), 2 mM glutamine, 100 units/mL penicillin, 0.1 mg/mL streptomycin (PSG, Sigma #G1146), and 500 µg/mL Geneticin (Invitrogen #10131)] in black-walled, clear-bottom 384-well poly-D-lysine-coated assay plates (Greiner Bio-One, Frickenhausen, Germany) and incubated in a humidified 5% CO$_2$ incubator at 37° C. On the day of the assay, medium was removed by aspiration, and cells were washed with assay buffer [HBSS (Invitrogen, Carlsbad, Calif.) containing 20 mM HEPES (Invitrogen, Carlsbad, Calif.)]. After washing, 30 µL assay buffer containing the fluorescent voltage-sensor probe CC2-DMPE (Invitrogen, Carlsbad, Calif.) at 20 µM and 0.01% pluronic F-127 (Invitrogen, Carlsbad, Calif.) was added to the cells. Cells were incubated for 40 minutes at room temperature in the dark. Following the incubation, the cells were washed and 30 µL assay buffer containing 2.5 µM DiSBAC$_2$(3) substrate (Invitrogen, Carlsbad, Calif.) and 0.5 mM VABSC-1 (Invitrogen, Carlsbad, Calif.) was added to the cells. The cells were incubated for 90 minutes at room temperature in the dark. Fluorescence readings were made using a FLIPR®$^{TETRA}$ (Molecular Devices, Sunnyvale Calif.) equipped with voltage-sensor probe optics. At the start of each experiment the optimal (EC$_{80}$) concentration of depolarizing agent (veratridine) was determined by testing a dilution curve of assay buffer containing veratridine (Sigma-Aldrich, St. Louis, Mo.) and 1 mg/mL scorpion venom (SVqq, from Leiurus quinquestriatus; Sigma-Aldrich, St. Louis, Mo.). Compounds were dissolved in dimethyl sulfoxide, and 8-point, 1:3 dilution concentration-response curves were prepared in duplicate in dimethyl sulfoxide, followed by preparation of 0.8 uL/well daughter plates of the dilutions. Test compounds in the daughter plate were diluted to (~3×) solutions in assay buffer immediately before assaying. Using the FLIPR®$^{TETRA}$, 20 µL of the (3×) compound solutions were first added to the cells, then 20 µL of depolarizing solution (3×EC$_{80}$ veratridine+SVqq) were added 3 minutes later to activate the channel. Changes in fluorescence were measured at wavelengths of 440-480 nm and 565-625 nm over the course of the experimental run. Membrane depolarization was expressed as a ratio of the maximum $F_{440\text{-}480\ nm}/F_{565\text{-}625\ nm}$ reading above average baseline $F_{440\text{-}480\ nm}/F_{565\text{-}625\ nm}$ reading. IC$_{50}$ values were calculated from curve fits of the ratio data using a four-parameter logistic Hill equation (Accelrys Assay Explorer 3.3 Client, Accelrys, San Diego, Calif.) with percent inhibition plotted against compound concentration.

Data reported in Table 1.

Recombinant, Human Sodium Channel, Na$_v$ 1.8.

Two days prior to the experiment, frozen HEK293 cells stably expressing recombinant human Na$_v$ 1.8 (Essen, Ann Arbor, Mich.) were quickly thawed and plated at 22,500 cells/well in growth medium [MEM (Invitrogen #11095) with 10% FBS (Invitrogen #10082), 1 mM sodium pyruvate (Invitrogen, #C11360), 10 units/mL penicillin/10 U/mL streptomycin/29.2 µg/mL glutamine ((PSG 1%, Invitrogen #10378), 400 µg/mL zeocin (Invitrogen #R250) in black-walled, clear-bottom 384-well poly-D-lysine-coated assay plates (Greiner Bio-One, Frickenhausen, Germany) and incubated in a humidified 5% CO$_2$ incubator at 37° C. On the day of the assay, medium was removed by aspiration, and cells were washed with assay buffer [HBSS (Invitrogen, Carlsbad, Calif.) containing 20 mM HEPES (Invitrogen, Carlsbad, Calif.)]. After washing, 30 µL assay buffer containing the fluorescent voltage-sensor probe CC2-DMPE (Invitrogen, Carlsbad, Calif.) at 20 M and 0.01% pluronic F-127 (Invitrogen, Carlsbad, Calif.) was added to the cells. Cells were incubated for 40 minutes at room temperature in the dark. Following the incubation, the cells were washed and 30 µL assay buffer containing 2.5 M DiSBAC$_2$(3) substrate (Invitrogen, Carlsbad, Calif.) and 0.5 mM VABSC-1 (Invitrogen, Carlsbad, Calif.) was added to the cells. The cells were incubated for 60 minutes at room temperature in the dark. Fluorescence readings were made using a FLIPR®$^{TETRA}$ (Molecular Devices, Sunnyvale Calif.) equipped with voltage-sensor probe optics. The depolarizing agent, veratridine (Sigma-Aldrich, St. Louis, Mo.), was made up at 3× concentrations in assay buffer containing 1 mg/mL scorpion venom (SVqq, from Leiurus quinquestriatus; Sigma-Aldrich, St. Louis, Mo.). The assay agonist/opener concentration was determined each day using a 6-point veratridine concentration curve in duplicate, tested with three concentrations of tetracaine (0.1, 0.06, 0.01 µM all in 0.03% dimethyl sulfoxide) and 0.03% dimethyl sulfoxide control in assay buffer. The concentration of veratridine chosen for the assay, the "$EC_{80}$", was where the assay achieved maximum signal with the dimethyl sulfoxide control, minimal inhibition with 0.01 μM tetracaine, ~50% inhibition with 0.06 μM tetracaine, and >50% inhibition with 0.1 μM tetracaine. Compounds were dissolved in dimethyl sulfoxide, and 8-point, 1:3 dilution concentration-response curves were prepared in duplicate in dimethyl sulfoxide, followed by preparation of 0.8 μL/well daughter plates of the dilutions. Test compounds in the daughter plate were diluted to (~3×) solutions in assay buffer immediately before assaying. Using the FLIPR®$^{TETRA}$, 20 μL of the (3×) compound solutions were first added to the cells, then 20 μL of depolarizing solution (3×$EC_{80}$ veratridine+SVqq) were added 3 minutes later to activate the channel. Changes in fluorescence were measured at wavelengths of 440-480 nm and 565-625 nm over the course of the experimental run. Membrane depolarization was expressed as a ratio of the maximum $F_{440-480\ nm}/F_{565-625\ nm}$ reading above average baseline $F_{440-480\ nm}/F_{565-625\ nm}$ reading. $IC_{50}$ values were calculated from curve fits of the ratio data using a four-parameter logistic Hill equation (Accelrys Assay Explorer 3.3 Client, Accelrys, San Diego, Calif.) with percent inhibition plotted against compound concentration.

Data reported in Table 1.

TABLE 1

FRET-Based membrane potential assays for human sodium channels, $Na_v1.7$ and $Na_v1.8$.

| Example | FRET-Membrane Potential Nav1.7 $IC_{50}$ (μM) | FRET-Membrane Potential Nav1.8 $IC_{50}$ (μM) |
|---|---|---|
| 1 | 0.911 | 1.55 |
| 2 | 0.504 | 0.648 |
| 3 | 1.45 | |
| 4 | 0.856 | |
| 5 | 0.262 | |
| 6 | 2.93 | 4.61 |
| 7 | 1.7 | |
| 8 | 0.232 | |
| 9 | 2.08 | |
| 10 | 4.6 | 2.53 |
| 11 | 1.61 | 1.69 |
| 12 | 0.348 | |
| 13 | 0.454 | |
| 14 | 2.37 | 15.1 |
| 15 | 1.09 | |
| 16 | 0.406 | |
| 17 | 3.12 | |
| 18 | 2.2 | 5.34 |
| 19 | 1.26 | 3.96 |
| 20 | 10.5 | 3.23 |
| 21 | 0.529 | |
| 22 | 1.98 | 3.54 |
| 23 | 1.45 | >20.0 |
| 24 | 1.58 | |
| 25 | 1.75 | 3.83 |
| 26 | 1.99 | |
| 27 | 1.1 | |
| 28 | 3.06 | 4.22 |
| 29 | 0.79 | |
| 30 | 0.793 | |
| 31 | 0.619 | 1.86 |
| 32 | 0.535 | |
| 33 | 0.471 | 0.74 |
| 34 | 0.841 | |
| 35 | 1.27 | |
| 36 | 0.727 | 1.42 |
| 37 | 0.392 | |
| 38 | 0.311 | |
| 39 | 0.735 | |
| 40 | 0.285 | |
| 41 | 1.27 | |
| 42 | 1.79 | |
| 43 | 3.06 | |
| 44 | 1.67 | 0.937 |
| 45 | 0.325 | 0.468 |
| 46 | 0.344 | 0.501 |
| 47 | 1.42 | 0.334 |
| 48 | 4.43 | 0.774 |
| 49 | 2.27 | 0.702 |
| 50 | 12.2 | |
| 51 | 2.25 | 4.06 |
| 52 | 2.98 | 3.85 |
| 53 | 3.26 | 11.0 |
| 54 | 0.409 | |
| 55 | 0.594 | 2.08 |
| 56 | 3.01 | 1.49 |
| 57 | 3.19 | 0.87 |
| 58 | 1.03 | 2.84 |
| 59 | 1.7 | 1.53 |
| 60 | 1.26 | |
| 61 | 0.556 | 1.14 |
| 62 | 0.50 | 0.12 |
| 63 | 0.976 | 1.16 |
| 64 | 0.382 | 0.491 |
| 65 | 2.25 | 4.23 |
| 66 | 0.883 | 1.18 |
| 67 | 1.28 | 1.75 |
| 68 | 1.21 | 1.89 |
| 69 | 0.895 | 2.32 |
| 70 | 1.25 | 0.821 |
| 71 | 1.81 | 1.64 |
| 72 | 2.73 | 3.84 |
| 73 | 1.44 | 1.7 |
| 74 | 0.863 | 1.88 |
| 75 | 0.944 | |
| 76 | >20.0 | |
| 77 | >20.0 | |
| 78 | >20.0 | |
| 79 | >20.0 | |
| 80 | >20.0 | |
| 81 | 1.87 | |
| 82 | 0.222 | |
| 83 | >20.0 | |
| 84 | >20.0 | |
| 85 | 0.238 | |
| 86 | 1.74 | |
| 87 | 1.23 | |
| 88 | >20.0 | |
| 89 | 1.52 | |
| 90 | 0.368 | |
| 91 | 3.25 | |
| 92 | 9.83 | |
| 93 | 1.55 | |
| 94 | 5.25 | |
| 95 | 4.87 | |
| 96 | 0.329 | |
| 97 | 0.842 | |
| 98 | 0.885 | |
| 99 | 5.05 | |
| 100 | 0.221 | |
| 101 | >20.0 | |
| 102 | >20.0 | |
| 103 | >20.0 | |
| 104 | >20.0 | |
| 105 | 7.25 | |
| 106 | 2.42 | |
| 107 | 4.12 | |
| 108 | 2.41 | |
| 109 | 0.66 | |
| 110 | 1.96 | |
| 111 | >20.0 | |
| 112 | 1.48 | |
| 113 | 0.741 | |
| 114 | 0.56 | |
| 115 | 11.2 | |
| 116 | 1.03 | |
| 117 | 2.23 | |

TABLE 1-continued

FRET-Based membrane potential assays for human sodium channels, $Na_v1.7$ and $Na_v1.8$.

| Example | FRET-Membrane Potential Nav1.7 IC$_{50}$ (μM) | FRET-Membrane Potential Nav1.8 IC$_{50}$ (μM) |
|---|---|---|
| 118 | 2.27 | |
| 119 | 0.819 | |
| 120 | 2.04 | |
| 121 | 1.66 | |
| 122 | 2.49 | |
| 123 | 6.55 | |
| 124 | 2.14 | |
| 125 | 3.46 | |
| 126 | 8.76 | |
| 127 | 4.07 | |
| 128 | 2.85 | |
| 129 | 2.58 | |
| 130 | 2.05 | |
| 131 | 1.15 | |
| 132 | 2.7 | |
| 133 | 1.17 | |
| 134 | 2.32 | |
| 135 | 0.688 | |
| 136 | 0.533 | |
| 137 | 8.24 | |
| 138 | 2.47 | |
| 139 | >20.0 | |
| 140 | 0.559 | |
| 141 | >20.0 | |
| 142 | 0.766 | |
| 143 | 1.08 | |
| 144 | 0.832 | |
| 145 | 3.09 | |
| 146 | 8.03 | |
| 147 | 4.28 | |
| 148 | 12.1 | |
| 149 | 0.981 | |
| 150 | 2.28 | |
| 151 | 0.792 | |
| 152 | 2.07 | |
| 153 | 3.3 | |
| 154 | 2.32 | |
| 155 | 5.38 | |
| 156 | >20.0 | |
| 157 | >20.0 | |
| 158 | >20.0 | |
| 159 | 0.73 | |
| 160 | 0.71 | |
| 161 | >20.0 | |
| 162 | >20.0 | |
| 163 | >20.0 | |
| 164 | 12.7 | |
| 165 | >20.0 | |
| 166 | 11.1 | |
| 167 | 2.91 | |
| 168 | >20.0 | |
| 169 | 17.2 | |
| 170 | 8.87 | |
| 171 | 7.95 | |
| 172 | 10.5 | |
| 173 | 0.833 | |
| 174 | 0.294 | |
| 175 | 0.206 | |
| 176 | 8.77 | |
| 177 | 2.68 | |
| 178 | 0.523 | |
| 179 | 0.684 | |
| 180 | 0.675 | |
| 181 | 3.47 | |
| 182 | 0.69 | |
| 183 | >20.0 | |
| 184 | 0.923 | |
| 185 | >20.0 | |
| 186 | 3.97 | |
| 187 | >20.0 | |
| 188 | 9.53 | |
| 189 | 15.1 | |
| 190 | 12.1 | |
| 191 | >20.0 | |
| 192 | 17.7 | |
| 193 | 4.25 | |
| 194 | 2.55 | |
| 195 | 7.6 | |
| 196 | 4.93 | |
| 197 | 2.72 | |
| 198 | 2.21 | |
| 199 | 2.55 | |
| 200 | >20.0 | |
| 201 | >20.0 | |
| 202 | 0.911 | |
| 203 | >20.0 | |
| 204 | 1.63 | |
| 205 | 3.17 | |
| 206 | >20.0 | |
| 207 | 3.65 | |
| 208 | 3.05 | |
| 209 | 8.86 | |
| 210 | >20.0 | |
| 211 | 1.93 | |
| 212 | >20.0 | |
| 213 | 9.4 | |
| 214 | >20.0 | |
| 215 | 0.81 | |
| 216 | 1.67 | |
| 217 | 1.04 | |
| 218 | >20.0 | |
| 219 | 2.56 | |
| 220 | 2.0 | |
| 221 | 2.79 | |
| 222 | 2.15 | |
| 223 | 2.79 | |
| 224 | >20.0 | |
| 225 | >20.0 | |
| 226 | >20.0 | |
| 227 | 2.94 | |
| 228 | 1.15 | |
| 229 | 7.12 | |
| 230 | 0.259 | |
| 231 | 0.783 | |
| 232 | 17.4 | |
| 233 | 0.586 | |
| 234 | 2.87 | |
| 235 | 2.36 | |
| 236 | 1.01 | |
| 237 | 3.07 | |
| 238 | 1.54 | |
| 239 | >20.0 | |
| 240 | 2.01 | |
| 241 | 1.85 | |
| 242 | >20.0 | |
| 243 | >20.0 | |
| 244 | >20.0 | |
| 245 | 4.63 | |
| 246 | 19.8 | |
| 247 | 13.3 | |
| 248 | 17.3 | |
| 249 | 0.902 | |
| 250 | 1.39 | |
| 251 | 1.59 | |
| 252 | >20.0 | |
| 253 | >20.0 | |
| 254 | 13.8 | |
| 255 | 12.1 | |
| 256 | 16.4 | |
| 257 | 10.6 | |
| 258 | 6.13 | |
| 259 | 2.06 | |
| 260 | 1.04 | |
| 261 | 6.31 | |
| 262 | 2.09 | |
| 263 | 0.402 | |
| 264 | 3.21 | |
| 265 | 3.45 | |

TABLE 1-continued

FRET-Based membrane potential assays for human sodium channels, $Na_v1.7$ and $Na_v1.8$.

| Example | FRET-Membrane Potential Nav1.7 IC$_{50}$ (μM) | FRET-Membrane Potential Nav1.8 IC$_{50}$ (μM) |
|---|---|---|
| 266 | 5.76 | |
| 267 | 10.2 | |
| 268 | 2.98 | |
| 269 | 3.07 | |
| 270 | 3.08 | |
| 271 | 11.2 | |
| 272 | 2.99 | |
| 273 | 0.488 | |
| 274 | 0.304 | |
| 275 | 11.4 | |
| 276 | 3.1 | |
| 277 | 3.09 | |
| 278 | 3.72 | |
| 279 | 5.68 | |
| 280 | 0.605 | |
| 281 | 1.28 | |
| 282 | 8.52 | |
| 283 | 10.9 | |
| 284 | 8.59 | |
| 285 | 0.774 | |
| 286 | 11.4 | |
| 287 | 2.81 | |
| 288 | 7.88 | |
| 289 | 3.91 | |
| 290 | 9.86 | |
| 291 | 13.7 | |
| 292 | 3.26 | |
| 293 | 3.32 | |
| 294 | 1.4 | |
| 295 | 3.2 | |
| 296 | 12.4 | |
| 297 | 7.99 | |
| 298 | 12.3 | |
| 299 | >20.0 | |
| 300 | >20.0 | |
| 301 | 3.12 | 1.4 |
| 302 | 3.49 | |
| 303 | 5.68 | |
| 304 | >20.0 | |
| 305 | 13.6 | |
| 306 | 14.8 | |
| 307 | 14.6 | |
| 308 | 3.07 | |
| 309 | 3.57 | |
| 310 | 0.665 | |
| 311 | 3.11 | |
| 312 | 6.93 | |
| 313 | 14.0 | |
| 314 | 0.218 | |
| 315 | 6.12 | |
| 316 | 12.0 | |
| 317 | 3.01 | |
| 318 | 7.41 | |
| 319 | 0.285 | |
| 320 | 17.1 | |
| 321 | 8.07 | |
| 322 | 12.0 | |
| 323 | >20.0 | |
| 324 | 5.01 | |
| 325 | 8.58 | |
| 326 | 3.15 | |
| 327 | 0.557 | |
| 328 | >20.0 | |
| 329 | 9.28 | |
| 330 | 2.95 | |
| 331 | 2.64 | |
| 332 | 10.1 | |
| 333 | >20.0 | |
| 334 | 3.44 | |
| 335 | 0.573 | |
| 336 | 0.439 | |
| 337 | 1.66 | |
| 338 | 0.984 | |
| 339 | 14.4 | |
| 340 | 2.9 | |
| 341 | 4.23 | |
| 342 | 3.38 | |
| 343 | >20.0 | |
| 344 | 2.1 | 0.67 |
| 345 | 9.15 | |
| 346 | 2.5 | |
| 347 | 2.63 | |
| 348 | 3.9 | |
| 349 | 3.25 | |
| 350 | >20.0 | |
| 351 | 3.6 | |
| 352 | 3.28 | |
| 353 | 3.63 | |
| 354 | 12.4 | |
| 355 | 1.27 | |
| 356 | 3.36 | |
| 357 | 2.72 | |
| 358 | 1.31 | |
| 359 | 4.71 | |
| 360 | 1.09 | |
| 361 | 2.88 | |
| 362 | 1.0 | |
| 363 | 1.19 | |
| 364 | 0.37 | |
| 365 | 0.356 | |
| 366 | 3.18 | |
| 367 | 2.53 | |
| 368 | 1.25 | |
| 369 | 15.2 | |
| 370 | 3.39 | |
| 371 | 1.46 | |
| 372 | >20.0 | |
| 373 | 3.7 | |
| 374 | 0.97 | |
| 375 | 13.2 | |
| 376 | 3.06 | |
| 377 | 3.32 | |
| 378 | 2.23 | |
| 379 | 3.39 | |
| 380 | 3.0 | |
| 381 | 3.41 | |
| 382 | 1.82 | |
| 383 | >20.0 | |
| 384 | 1.93 | |
| 385 | 2.33 | |
| 386 | >20.0 | |
| 387 | 2.48 | |
| 388 | >20.0 | |
| 389 | 9.22 | |
| 390 | 2.34 | |
| 391 | 0.687 | |
| 392 | 7.96 | |
| 393 | 0.399 | |
| 394 | 0.443 | |
| 395 | >20.0 | |
| 396 | 1.94 | |
| 397 | 0.896 | |
| 398 | 6.11 | |
| 399 | 0.375 | |
| 400 | 1.22 | |
| 401 | 0.40 | |
| 402 | 9.07 | |
| 403 | 9.67 | |
| 404 | 1.95 | |
| 405 | 1.4 | |
| 406 | 1.06 | |
| 407 | 3.81 | |
| 408 | >20.0 | |
| 409 | 0.403 | |
| 410 | 0.557 | |
| 411 | 14.1 | |
| 412 | 0.513 | |
| 413 | 12.4 | |

TABLE 1-continued

FRET-Based membrane potential assays for human sodium channels, Na$_v$1.7 and Na$_v$1.8.

| Example | FRET-Membrane Potential Nav1.7 IC$_{50}$ (µM) | FRET-Membrane Potential Nav1.8 IC$_{50}$ (µM) |
|---|---|---|
| 414 | 5.02 | |
| 415 | 1.61 | |
| 416 | 0.70 | |
| 417 | 11.5 | 2.75 |
| 418 | 0.539 | |
| 419 | 11.9 | |
| 420 | 2.43 | |
| 421 | 1.06 | |
| 422 | 0.617 | |
| 423 | 0.83 | |
| 424 | 1.31 | |
| 425 | 9.09 | |
| 426 | 0.972 | |
| 427 | >20.0 | |
| 428 | 10.3 | |
| 429 | 13.8 | |
| 430 | 3.45 | |
| 431 | 1.06 | 0.382 |
| 432 | 2.87 | |
| 433 | 0.442 | |
| 434 | 5.58 | |
| 435 | 12.6 | |
| 436 | 1.74 | 3.42 |
| 437 | 3.17 | |
| 438 | 12.5 | |
| 439 | 5.86 | |
| 440 | 12.6 | |
| 441 | 1.15 | |
| 442 | 5.52 | |
| 443 | 0.703 | |
| 444 | 1.4 | |
| 445 | 0.268 | |
| 446 | 0.166 | |
| 447 | 0.69 | |
| 448 | 0.371 | |
| 449 | 0.789 | |
| 450 | 3.58 | |
| 451 | 5.23 | |
| 452 | 3.21 | |
| 453 | 0.405 | |
| 454 | 3.14 | |
| 455 | >20.0 | |
| 456 | 0.886 | |
| 457 | >20.0 | |
| 458 | 1.19 | |
| 459 | 8.69 | |
| 460 | 2.4 | |
| 461 | 0.354 | |
| 462 | 0.947 | |
| 463 | 1.12 | |
| 464 | >20.0 | |
| 465 | >20.0 | |
| 466 | 9.41 | |
| 467 | 0.521 | |
| 468 | 13.8 | |
| 469 | 1.71 | |
| 470 | 6.6 | |
| 471 | 2.4 | |
| 472 | 7.76 | |
| 473 | 16.2 | |
| 474 | 9.1 | |
| 475 | 1.96 | |
| 476 | 3.92 | |
| 477 | 5.51 | |
| 478 | 5.94 | |
| 479 | 3.19 | |
| 480 | 19.9 | |
| 481 | 2.63 | |
| 482 | 0.569 | |
| 483 | 3.61 | |
| 484 | 0.879 | |
| 485 | 3.14 | |
| 486 | 2.54 | |
| 487 | 0.919 | |
| 488 | 0.526 | |
| 489 | 1.1 | |
| 490 | 1.42 | |
| 491 | 4.99 | |
| 492 | 0.858 | |
| 493 | 0.802 | |
| 494 | 9.32 | |
| 495 | 1.69 | |
| 496 | 2.91 | |
| 497 | 3.43 | |
| 498 | 0.923 | |
| 499 | 0.938 | |
| 500 | 0.293 | |
| 501 | 0.734 | |
| 502 | 0.429 | |
| 503 | 0.586 | |
| 504 | 0.593 | |
| 505 | 4.94 | 2.3 |
| 506 | 0.781 | |
| 507 | 2.18 | |
| 508 | 3.65 | |
| 509 | 2.64 | |
| 510 | 7.29 | |
| 511 | 1.98 | |
| 512 | 0.983 | 0.213 |
| 513 | 0.911 | |
| 514 | 12.9 | |
| 515 | 4.25 | |
| 516 | 2.0 | |
| 517 | 0.37 | |
| 518 | 0.998 | |
| 519 | 1.16 | |
| 520 | 0.945 | |
| 521 | 2.63 | 1.1 |
| 522 | 10.7 | |
| 523 | 0.356 | |
| 524 | 1.08 | |
| 525 | 6.65 | |
| 526 | 3.09 | |
| 527 | 5.91 | |
| 528 | 2.92 | |
| 529 | 10.3 | >20.0 |
| 530 | 0.911 | |
| 531 | 3.57 | |
| 532 | 2.77 | |
| 533 | 2.4 | |
| 534 | 1.97 | |
| 535 | >20.0 | |
| 536 | 1.15 | |
| 537 | 2.71 | |
| 538 | 3.16 | |
| 539 | >20.0 | |
| 540 | 4.03 | |
| 541 | 1.19 | |
| 542 | 14.5 | |
| 543 | 0.398 | |
| 544 | 3.45 | |
| 545 | 3.7 | |
| 546 | 10.1 | |
| 547 | 3.29 | |
| 548 | 4.05 | |
| 549 | 2.49 | |
| 550 | 10.7 | |
| 551 | 2.77 | |
| 552 | 0.615 | |
| 553 | 0.949 | |
| 554 | 14.1 | |
| 555 | 2.7 | |
| 556 | 2.81 | |
| 557 | 16.7 | |
| 558 | 4.49 | |
| 559 | 3.02 | |
| 560 | 2.87 | |
| 561 | 3.47 | |

TABLE 1-continued

FRET-Based membrane potential assays for human sodium channels, Na$_v$1.7 and Na$_v$1.8.

| Example | FRET-Membrane Potential Nav1.7 IC$_{50}$ (μM) | FRET-Membrane Potential Nav1.8 IC$_{50}$ (μM) |
|---|---|---|
| 562 | >20.0 | |
| 563 | >20.0 | |
| 564 | 16.6 | |
| 565 | 3.43 | |
| 566 | 2.37 | |
| 567 | 3.28 | |
| 568 | 3.26 | |
| 569 | 1.21 | |
| 570 | 0.977 | |
| 571 | 0.448 | |
| 572 | 2.7 | |
| 573 | 0.987 | |
| 574 | 0.295 | |
| 575 | 12.1 | |
| 576 | 10.1 | |
| 577 | 10.1 | |
| 578 | 1.07 | |
| 579 | 1.69 | |
| 580 | 1.56 | 1.14 |
| 581 | 12.6 | |
| 582 | 10.3 | |
| 583 | 0.96 | |
| 584 | 0.304 | |
| 585 | >20.0 | |
| 586 | 1.8 | |
| 587 | 1.02 | |
| 588 | 3.64 | |
| 589 | 4.07 | |
| 590 | 1.0 | |
| 591 | 0.737 | |
| 592 | 3.44 | |
| 593 | 0.238 | |
| 594 | 7.59 | |
| 595 | 1.13 | |
| 596 | 1.76 | |
| 597 | 3.29 | |
| 598 | 2.98 | |
| 599 | 1.59 | |
| 600 | 1.76 | |
| 601 | 2.51 | |
| 602 | 1.07 | |
| 603 | 1.95 | 3.67 |
| 604 | 3.01 | |
| 605 | 2.88 | |
| 606 | 0.856 | |
| 607 | 0.91 | |
| 608 | 2.7 | |
| 609 | 4.5 | |
| 610 | 2.76 | |
| 611 | 4.99 | |
| 612 | 2.93 | |
| 613 | 2.21 | |
| 614 | 12.2 | |
| 615 | 2.32 | |
| 616 | 2.63 | |
| 617 | 2.78 | |
| 618 | 2.69 | |
| 619 | 2.88 | 2.91 |
| 620 | >20.0 | >20.0 |
| 621 | 2.69 | 1.65 |
| 622 | 5.4 | 2.28 |
| 623 | 4.91 | 3.7 |

Osteoarthritic (OA) Pain Induced by Sodium Monoiodoacetate (MIA)

Pain behavior was assessed by measurement of hind limb grip force (GF) in adult osteoarthritic rats. Male Sprague Dawley rats, obtained from Charles River Laboratories, (Wilmington, Mass.), weighing 150-175 g, were injected in the unilateral knee join with a single intra-articular injection of sodium monoiodoacetate (MIA, 3 mg/rat). All rats were tested at 20 days following MIA injection. A behavioral measure of activity-induced pain was carried out. Measurements of the peak hind limb grip force were conducted by recording the maximum compressive force (CFmax), in grams of force, exerted on a hind limb strain gauge setup, in a commercially available grip force measurement system (Columbus Instruments, Columbus, Ohio).

During testing, each rat was gently restrained by grasping it around its rib cage and then allowed to grasp the wire mesh frame attached to the strain gauge. The experimenter then moved the animal in a rostral-to-caudal direction until the grip was broken. Each rat was sequentially tested twice at an approximately 2-3 minute interval to obtain a raw mean grip force (CFmax). This raw mean grip force data was in turn converted to a maximum hindlimb cumulative compressive force (CFmax), as the grams of force/kg of body weight, for each animal.

For evaluating the compound effects, the hind limb grip force was conducted 20 days following the intra-articular injection of MIA. A group of age-matched naïve (not injected with MIA) animals was added as a comparator to the drug-dosed groups. The vehicle control response for each group of MIA-treated animals was defined as the 0% response (0% effect), whereas the naïve control group was defined as the normal response and as 100% effect. The % effect for each dose group was expressed as % return of response to normalcy, compared to the naïve group. A percent maximal possible effect (% MPE) of testing compound was calculated according to the formula: (Treatment CFmax−Vehicle CFmax)/Vehicle CFmax]×100). Higher % effect numbers indicate increased relief from the pain in the model, with 100% indicating a return to the level of response seen in normal (non-osteoarthritic) animals. All experiments evaluating drug effects in this model were conducted in a randomized blinded fashion.

The animals were housed in Association for Assessment and Accreditation of Laboratory Animal Care (AAALAC) approved facilities at AbbVie Inc. in a temperature-regulated environment under a controlled 12-hour light-dark cycle, with lights on at 6:00 a.m. Food and water were available ad libitum at all times except during testing. All testing was done following procedures outlined in protocols approved by AbbVie Inc.'s Institutional Animal Care and Use Committee.

Data reported in Table 2.

Rat Spinal Nerve Ligation (SNL) Model of Neuropathic Pain.

A model of spinal nerve ligation-induced (SNL model) neuropathic pain as originally described by Kim and Chung (Kim, S. H. and J. M. Chung, 1992, Pain 50, 355) was used to test a compound of the present application. The male Sprague Dawley rats (Charles River Laboratories, Wilmington, Mass.), weighing 150-175 g at the time of surgery, were placed under isoflurane anesthesia and a 1.5 cm incision was made dorsal to the lumbosacral plexus. The paraspinal muscles (left side) were separated from the spinous processes, the left L5 and L6 spinal nerves isolated, and tightly ligated with 5-0 silk suture distal to the dorsal root ganglion. Care was taken to avoid ligating the L4 spinal nerve. Following spinal nerve ligation, a minimum of 7 days of recovery and no more than 3 weeks was allowed prior to the behavioral testing (mechanical sensitivity). Only rats with threshold scores ≤4.5 g were considered allodynic and utilized in pharmacological experiments.

Mechanical sensitivity was measured using calibrated von Frey filaments (Stoelting, Wood Dale, Ill.). Paw withdrawal threshold (PWT) was determined by using the Dixon's up-down method (Dixon, W. J., 1980, Ann. Rev. Pharmacol.

Toxicol., 20, 441). Rats were placed into inverted individual plastic containers (20×12.5×20 cm) on top of a suspended wire mesh with a 1 cm² grid to provide access to the ventral side of the hind paws, and acclimated to the test chambers for 20 minutes. The von Frey filaments were presented perpendicularly to the plantar surface of the selected hind paw, and then held in this position for approximately 8 seconds with enough force to cause a slight bend in the filament. Positive responses included an abrupt withdrawal of the hind paw from the stimulus, or flinching behavior immediately following removal of the stimulus. A 50% withdrawal threshold was determined using an up-down procedure (Dixon, 1980). A percent maximal possible effect (% MPE) of testing compound was calculated according to the formula: (Log [compound−treated threshold]−Log [vehicle−treated threshold])/(Log [maximum threshold]−Log [vehicle-treated threshold])×100%, where the maximum threshold was equal to 15 g.

The animals were housed in Association for Assessment and Accreditation of Laboratory Animal Care (AAALAC) approved facilities at AbbVie Inc. in a temperature-regulated environment under a controlled 12-hour light-dark cycle, with lights on at 6:00 a.m. Food and water were available ad libitum at all times except during testing. All testing was done following procedures outlined in protocols approved by AbbVie Inc.s' Institutional Animal Care and Use Committee.

Data reported in Table 2.

TABLE 2

In vivo data for MIA-OA and SNL pain assays.

| Example | OA Dose (mg/kg) | OA MPE (%) | SNL Dose (mg/kg) | SNL MPE (%) |
|---|---|---|---|---|
| 1 | 30 | 64 | 100 | 49 |
| 2 | 30 | 85 | 100 | 54 |
| 3 | 30 | 46 | | |
| 4 | 30 | 60 | 100 | 56 |
| 5 | 30 | 27 | | |
| 6 | 10 | 72 | 100 | 27 |
| 7 | 30 | 51 | | |
| 8 | 30 | 91 | | |
| 9 | 10 | 68 | | |
| 10 | 30 | 48 | 100 | 35 |
| 11 | 10 | 72 | 100 | 34 |
| 12 | 10 | 79 | | |
| 13 | 10 | 44 | | |
| 14 | 30 | 81 | 100 | 44 |
| 15 | 10 | 52 | | |
| 16 | 10 | 57 | | |
| 17 | 10 | 19 | | |
| 18 | 10 | 23 | | |
| 19 | 30 | 64 | | |
| 20 | 10 | 24 | | |
| 21 | 10 | 35 | | |
| 22 | 30 | 73 | 100 | 72 |
| 23 | 30 | 83 | | |
| 24 | 10 | 62 | | |
| 25 | 30 | 102 | | |
| 26 | 10 | 67 | | |
| 27 | 10 | 49 | | |
| 28 | 10 | 16 | | |
| 29 | 10 | 20 | | |
| 30 | 10 | 66 | | |
| 31 | 30 | 94 | 100 | 64 |
| 32 | 10 | 23 | | |
| 33 | 30 | 61 | 100 | 50 |
| 34 | 10 | 41 | | |
| 35 | 10 | 79 | 100 | 74 |
| 36 | 10 | 55 | | |
| 37 | 10 | 29 | | |
| 38 | 10 | 30 | | |
| 39 | 30 | 43 | | |
| 40 | 10 | 59 | | |
| 41 | 10 | 67 | | |
| 42 | 10 | 64 | | |
| 43 | 10 | 71 | | |
| 44 | 10 | 42 | | |
| 45 | 30 | 17 | | |
| 46 | 30 | 98 | | |
| 47 | 10 | 30 | | |
| 48 | 10 | 41 | | |
| 49 | 30 | 58 | | |
| 50 | 30 | 81 | 100 | 94 |
| 51 | 30 | 52 | 100 | 90 |
| 52 | 30 | 86 | 100 | 81 |
| 53 | 30 | 70 | | |
| 54 | 10 | 21 | | |
| 55 | 10 | 42 | | |
| 56 | 10 | 43 | | |
| 57 | 30 | 53 | | |
| 58 | 30 | 64 | | |
| 59 | 30 | 83 | 100 | 84 |
| 60 | 10 | 23 | | |
| 61 | 10 | 61 | | |
| 62 | 10 | −1 | | |
| 63 | 10 | 15 | | |
| 64 | 10 | 29 | | |
| 65 | 30 | 63 | | |
| 66 | 30 | 52 | | |
| 67 | 10 | 43 | | |
| 68 | 10 | 52 | | |
| 69 | 10 | 2 | | |
| 70 | 10 | 23 | | |
| 71 | 10 | 33 | | |
| 72 | 30 | 11 | | |
| 73 | 30 | 66 | | |
| 74 | 30 | 69 | | |
| 301 | 30 | 58 | | |
| 344 | 30 | 59 | 100 | 76 |
| 431 | 30 | 73 | | |
| 436 | 30 | 51 | | |
| 441 | 10 | 22 | | |
| 483 | 10 | 55 | | |
| 505 | 30 | 52 | | |
| 616 | 30 | 28 | | |
| 619 | 30 | 53 | | |

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed is:

1. A compound of formula (I):

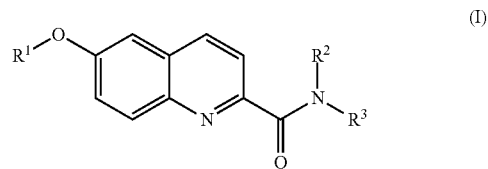

or a pharmaceutically acceptable salt, ester, amide, or radiolabelled form thereof, wherein:

$R^1$ is selected from the group consisting of phenyl and monocyclic 5- or 6-membered heteroaryl, wherein the phenyl or 5- or 6-membered heteroaryl is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, halogen, cyano, —$NO_2$, —$OR^{1a}$, —$OC(O)R^{1a}$, —$OC(O)N(R^b)(R^{3a})$, —$SR^{1a}$, —$S(O)R^{2a}$, —$S(O)_2R^{2a}$, —$S(O)_2N(R^b)(R^{3a})$, —$C(O)R^{1a}$, —$C(O)OR^{1a}$, —$C(O)N(R^b)(R^{3a})$, —$N(R^b)(R^{3a})$, —$N(R^a)C(O)R^{1a}$, —$N(R^a)C(O)O(R^{1a})$, —$N(R^a)C(O)N(R^b)(R^{3a})$, —$(CR^{4a}R^{5a})_m$—$NO_2$, —$N(R^b)S(O)_2(R^{2a})$, —$(CR^{4a}R^{5a})_m$—$OR^{1a}$, —$(CR^{4a}R^{5a})_m$—$OC(O)R^{1a}$, —$(CR^{4a}R^{5a})_m$—$OC(O)N(R^b)(R^{3a})$, —$(CR^{4a}R^{5a})_m$—$SR^{1a}$, —$(CR^{4a}R^{5a})_m$—$S(O)R^{2a}$, —$(CR^{4a}R^{5a})_m$—$S(O)_2R^{2a}$, —$(CR^{4a}R^{5a})_m$—$S(O)_2N(R^b)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^a)(R^{3a})$, —$(CR^{4a}R^{5a})_m$—$N(R^b)(R^{3a})$, —$(CR^{4a}R^{5a})_m$—$N(R^a)C(O)R^{1a}$, —$(CR^{4a}R^{5a})_m$—$N(R^a)C(O)O(R^{1a})$, —$(CR^{4a}R^{5a})_m$—$N(R^a)C(O)N(R^b)(R^{3a})$, —$(CR^{4a}R^{5a})_m$—$N(R^b)S(O)_2(R^{2a})$, cyano-$C_1$-$C_6$-alkyl, and halo-$C_1$-$C_6$-alkyl;

$R^a$ and $R^b$, at each occurrence, are each independently hydrogen, $C_1$-$C_6$-alkyl, or halo-$C_1$-$C_6$-alkyl;

$R^{1a}$ and $R^{3a}$, at each occurrence, are each independently hydrogen, $C_1$-$C_6$-alkyl, or halo-$C_1$-$C_6$-alkyl;

$R^{2a}$, at each occurrence, is independently $C_1$-$C_6$-alkyl or halo-$C_1$-$C_6$-alkyl;

$R^{4a}$ and $R^{5a}$, at each occurrence, are each independently hydrogen, halogen, $C_1$-$C_6$-alkyl, or halo-$C_1$-$C_6$-alkyl;

m, at each occurrence, is independently 1, 2, 3, 4, or 5;

$R^2$ is selected from the group consisting of hydrogen, $C_1$-$C_6$-alkyl, $C_1$-$C_6$-alkoxy-$C_1$-$C_6$-alkyl, and -$G^2$;

$R^3$ is selected from the group consisting of hydrogen, $C_1$-$C_6$-alkyl, $C_2$-$C_6$-alkenyl, $C_2$-$C_6$-alkynyl, —$(CR^{4b}R^{5b})_n$—$NO_2$, —$(CR^{4b}R^{5b})_n$—$OR^{1b}$, —$CH[(CR^{4b}R^{5b})_n$—$OR^{1b}]_2$, —$(CR^{4b}R^{5b})_n$—$OC(O)R^{1b}$, —$(CR^{4b}R^{5b})_n$—$OC(O)N(R^b)(R^{3b})$, —$(CR^{4b}R^{5b})_n$—$SR^{1b}$, —$(CR^{4b}R^{5b})_n$—$S(O)_2R^{2b}$, —$(CR^{4b}R^{5b})_n$—$S(O)_2N(R^b)(R^{3b})$, —$(CR^{4b}R^{5b})_n$—$C(O)R^{1b}$, —$(CR^{4b}R^{5b})_n$—$C(O)OR^{1b}$, —$(CR^{4b}R^{5b})_n$—$C(O)N(R^b)(R^{3b})$, —$(CR^{4b}R^{5b})_n$—$C(O)N(R^b)(—(CR^{4b}R^{5b})_n$—$OR^{1b})$, —$(CR^{4b}R^{5b})_n$—$C(O)N(R^b)(G^4)$, —$(CR^{4b}R^{5b})_n$—$C(O)N(R^b)(G^3)$, —$(CR^{4b}R^{5b})_n$—$C(O)G^4$, —$(CR^{4b}R^{5b})_n$—$N(R^b)(R^{3b})$, —$(CR^{4b}R^{5b})_n$—$N(R^b)(G^3)$, —$(CR^{4b}R^{5b})_n$—$N(R^a)C(O)R^{1b}$, —$(CR^{4b}R^{5b})_n$—$N(R^b)S(O)_2R^{2b}$, —$S(O)_2R^{2b}$, —$(CR^{4b}R^{5b})_n$—$N(R^a)C(O)O(R^{1b})$, —$(CR^{4b}R^{5b})_n$—$N(R^a)C(O)N(R^b)(R^{3b})$, -$G^2$, —$(CR^{4b}R^{5b})_n$-$G^4$, -$G^2$-$G^6$, -$G^1$, —$(CR^{4b}R^{5b})_n$-$G^3$, —$CH[C(O)N(R^b)(R^{3b})][—(CR^{4b}R^{5b})_n$-$G^3]$, cyano-$C_1$-$C_6$-alkyl, and halo-$C_1$-$C_6$-alkyl;

$R^{1b}$ and $R^{3b}$, at each occurrence, are each independently hydrogen, $C_1$-$C_6$-alkyl, or halo-$C_1$-$C_6$-alkyl;

$R^{2b}$, at each occurrence, is independently $C_1$-$C_6$-alkyl or halo-$C_1$-$C_6$-alkyl;

$R^{4b}$ and $R^{5b}$, at each occurrence, are each independently hydrogen, halogen, $C_1$-$C_6$-alkyl, or halo-$C_1$-$C_6$-alkyl;

n, at each occurrence, is independently 1, 2, 3, 4, or 5;

$G^1$ and $G^3$ are each independently aryl or heteroaryl; wherein $G^1$ and $G^3$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, —$N(R^c)_2$, —$N(R^c)C(O)R^c$, —$OR^c$, —$C(O)R^c$, —$C(O)OR^c$, —$C(O)N(R^c)_2$, —$SO_2R^d$, and —$SO_2N(R^c)_2$;

$G^2$, $G^4$ and $G^6$ are each independently 3-6-membered-cycloalkyl, 3-6-membered-cycloalkenyl, or 4-10-membered-heterocycle; wherein $G^2$, $G^4$ and $G^6$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, benzyl, cyano, hydroxy-$C_1$-$C_6$-alkyl, halogen, nitro, oxo, —$N(R^c)_2$, —$N(R^c)C(O)R^c$, —$OR^c$, —$C(O)R^c$, —$C(O)OR^c$, —$C(O)N(R^c)_2$, —$SO_2R^d$, —$SO_2N(R^c)_2$, and phenyl, wherein phenyl and the phenyl ring of benzyl are optionally substituted with 1, 2, 3, or 4 $C_1$-$C_6$-alkyl, halogen, or $C_1$-$C_6$-alkoxy;

$R^c$ at each occurrence, is independently hydrogen, $C_1$-$C_6$-alkyl, aryl, cycloalkyl, cycloalkyl-$C_1$-$C_6$-alkyl, or halo-$C_1$-$C_6$-alkyl; wherein said aryl, the aryl of aryl-$C_1$-$C_6$-alkyl, the cycloalkyl, and the cycloalkyl of cycloalkyl-$C_1$-$C_6$-alkyl are independently unsubstituted or substituted with 1, 2 3, 4, or 5 substituents independently selected from the group consisting of $C_1$-$C_6$-alkyl, halo-$C_1$-$C_6$-alkyl, and halogen;

$R^d$ is $C_1$-$C_6$-alkyl or halo-$C_1$-$C_6$-alkyl; or $R^2$, $R^3$ and the nitrogen atom to which they are attached form a 4-8-membered-monocyclic heterocycle, 6-11-membered-bicyclic heterocycle, 10-12-membered-tricyclic heterocycle, 7-11-membered-spirocyclic heterocycle or 8-11-membered-bicyclic heteroaryl comprised of a monocyclic heterocycle fused to a monocyclic heteroaryl, wherein said 4-8-membered monocyclic heterocycle, said 6-11-membered-bicyclic heterocycle, said, 10-12-membered-tricyclic heterocycle, said 7-11-membered-spirocyclic heterocycle and said 8-11-membered-bicyclic heteroaryl are unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, halogen, cyano, —$NO_2$, —$OR^{1c}$, —O—$(CR^{4c}R^{5c})_p$—$OR^{1c}$, —$OG^{13}$, —$OC(O)R^{1c}$, —$OC(O)N(R^b)(R^{3c})$, —$S(O)R^{2c}$, —$S(O)_2R^{2c}$, —$S(O)_2G^{13}$, —$S(O)_2G^{14}$, —$S(O)_2N(R^b)(R^{3c})$, —$S(O)_2$—$(CR^{4c}R^{5c})_p C(O)OR^{1c}$, —$S(O)_2$—$(CR^{4c}R^{5c})_p G^{14}$, —$C(O)R^{1c}$, —$C(O)G^{14}$, —$C(O)OR^{1c}$, —$C(O)N(R^b)(R^{3c})$, —$N(R^b)(R^{3c})$, —$N(R^c)C(O)R^{1c}$, —$N(R^a)C(O)G^{14}$, —$N(R^a)C(O)O(R^{1c})$, —$N(R^a)C(O)N(R^b)(R^{3c})$, —$(CR^{4c}R^{5c})_p$—$NO_2$, —$N(R^b)S(O)_2(R^{2c})$, —$N(R^b)S(O)_2(G^{13})$, —$(CR^{4c}R^{5c})_p$—$OR^{1c}$, —$(CR^{4c}R^{5c})_p$—O—$(CR^{4c}R^{5c})_p$—$OR^{1c}$, —$(CR^{4c}R^{5c})_p$—$OC(O)R^{1c}$, —$(CR^{4c}R^{5c})_p$—$OC(O)N(R^b)(R^{3c})$, —$(CR^{4c}R^{5c})_p$—$SR^{1c}$, —$(CR^{4c}R^{5c})_p$—$S(O)R^{2c}$, —$(CR^{4c}R^{5c})_p$—$S(O)_2R^{2c}$, —$(CR^{4c}R^{5c})_p$—$S(O)_2N(R^b)(R^{3c})$, —$(CR^{4c}R^{5c})_p$—$C(O)R^{1c}$, —$(CR^{4c}R^{5c})_p$—$C(O)OR^{1c}$, —$(CR^{4c}R^{5c})_p$—$C(O)N(R^a)(R^{3c})$, —$(CR^{4c}R^{5c})_p$—$N(R^b)(R^{3c})$, —$(CR^{4c}R^{5c})_p$—$N(R^a)C(O)R^{1c}$, —$(CR^{4c}R^{5c})_p$—$N(R^a)C(O)O(R^{1c})$, —$(CR^{4c}R^{5c})_p$—$N(R^a)C(O)(CH_2G^{13})$, —$(CR^{4c}R^{5c})_p$—$N(R^a)C(O)N(R^b)(R^{3c})$, —$(CR^{4c}R^{5c})_p$—$N(R^b)S(O)_2(R^{2c})$, -$G^{11}$, —$(CR^{4c}R^{5c})_p$-$G^{13}$, —$(CR^{4c}R^{5c})_p$—$OG^{13}$, -$G^{12}$, —$(CR^{4c}R^{5c})_p$-$G^{14}$, cyano-$C_1$-$C_6$-alkyl, oxo, $C^1$-$C^6$-alkoxyimino and halo-$C_1$-$C_6$-alkyl;

$R^{1c}$ and $R^{3c}$, at each occurrence, are each independently hydrogen, $C_1$-$C_6$-alkyl, or halo-$C_1$-$C_6$-alkyl;

$R^{2c}$, at each occurrence, is independently $C_1$-$C_6$-alkyl or halo-$C_1$-$C_6$-alkyl;

$R^{4c}$ and $R^{5c}$, at each occurrence, are each independently hydrogen, halogen, $C_1$-$C_6$-alkyl, or halo-$C_1$-$C_6$-alkyl;

p, at each occurrence, is independently 1, 2, 3, 4, or 5;

$G^{11}$ and $G^{13}$ are each independently phenyl or 5-6-membered-heteroaryl; wherein $G^{11}$ and $G^{13}$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, $C_1$-$C_6$-alkoxy-$C_1$-$C_6$-alkyl, halo-$C_1$-$C_6$-alkyl, halogen, nitro, —N($R^e$)$_2$, —N($R^e$)C(O)$R^e$, —O$R^e$, —C(O)$R^e$, —C(O)O$R^e$, —C(O)N($R^e$)$_2$, —SO$_2R^f$, and —SO$_2$N($R^e$)$_2$;

$G^{12}$, and $G^{14}$ are each independently 3-6-membered-cycloalkyl, 3-6-membered-cycloalkenyl, or 4-10-membered-heterocycle, wherein $G^{12}$ and $G^{14}$ are each independently unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, benzyl, cyano, halo-$C_1$-$C_6$-alkyl, hydroxy-$C_1$-$C_6$-alkyl, halogen, nitro, oxo, —N($R^e$)$_2$, —N($R^e$)C(O)$R^e$, —N($R^e$)S(O)$_2R^f$, —C(O)$R^e$, —C(O)O$R^e$, —C(O)N($R^e$)$_2$, —SO$_2R^f$, —SO$_2$N($R^e$)$_2$, and phenyl, wherein phenyl and the phenyl ring of benzyl are optionally substituted with $C_1$-$C_6$-alkyl, halogen, or $C_1$-$C_6$-alkoxy;

$R^e$ at each occurrence, is independently hydrogen, $C_1$-$C_6$-alkyl, aryl, aryl-$C_1$-$C_6$-alkyl, cycloalkyl, cycloalkyl-$C_1$-$C_6$-alkyl, or halo-$C_1$-$C_6$-alkyl; wherein said aryl, the aryl of aryl-$C_1$-$C_6$-alkyl, the cycloalkyl, and the cycloalkyl of cycloalkyl-$C_1$-$C_6$-alkyl are independently unsubstituted or substituted with 1, 2 3, 4, or 5 substituents independently selected from the group consisting of $C_1$-$C_6$-alkyl, halo-$C_1$-$C_6$-alkyl, and halogen; and $R^f$ is $C_1$-$C_6$-alkyl or halo-$C_1$-$C_6$-alkyl, wherein when $R^1$ is phenyl, the phenyl is unsubstituted or substituted with 1, 2, 3, or 4 substituents selected from the group consisting of $C_1$-$C_6$-alkyl, halogen, cyano, —S(O)$_2R^{2a}$, —S(O)$_2$N($R^b$)($R^{3a}$), —C(O)$R^{1a}$, —(C$R^{4a}R^{5a}$)$_m$—O$R^{1a}$, and halo-$C_1$-$C_6$-alkyl;

$R^{4a}$ and $R^{5a}$, at each occurrence, are each independently hydrogen, $C_1$-$C_6$-alkyl, or halo-$C_1$-$C_6$-alkyl; and m, at each occurrence, is independently 1, 2, or 3.

2. The compound of claim 1, wherein, $R^1$ is a 6-membered heteroaryl, wherein the 6-membered heteroaryl is unsubstituted or substituted with 1, 2, 3, or 4 halo-$C_1$-$C_6$-alkyl substituents.

3. The compound of claim 2, wherein, $R^2$, $R^3$ and the nitrogen atom to which they are attached form a 4-8-membered-monocyclic heterocycle, wherein said 4-8-membered monocyclic heterocycle is unsubstituted or substituted with 1, 2, 3, 4, or 5 halogen substituents.

4. The compound of claim 3, wherein, $R^1$ is 5-(trifluoromethyl)pyridin-2-yl; and $R^2$, $R^3$ and the nitrogen atom to which they are attached form a pyrrolidine, wherein said pyrrolidine is unsubstituted or substituted with 1, 2, or 3 halogen substituents.

5. A pharmaceutical composition comprising a therapeutically effective amount of a compound of claim 1 in combination with a pharmaceutically acceptable carrier.

6. A method of selectively modulating the effects of pain in a mammal comprising administering an effective amount of a compound of claim 1.

7. The method according to claim 6, wherein the pain is selected from the group consisting of osteoarthritis pain, joint pain, knee pain, neuropathic pain, post-surgical pain, low back pain, diabetic neuropathy, pain during surgery, cancer pain, chemotherapy induced pain, headaches, cluster headache, tension headache, migraine pain, trigeminal neuralgia, shingles pain, post-herpetic neuralgia, carpal tunnel syndrome, inflammatory pain, pain from rheumatoid arthritis, colitis, pain of interstitial cystitis, visceral pain, pain from kidney stone, pain from gallstone, angina, fibromyalgia, chronic pain syndrome, thalamic pain syndrome, pain from stroke, phantom limb pain, sunburn, radiculopathy, complex regional pain syndrome, HIV sensory neuropathy, central neuropathic pain syndromes, multiple sclerosis pain, Parkinson disease pain, spinal cord injury pain, menstrual pain, toothache, pain from bone metastasis, pain from endometriosis, pain from uterine fibroids, nociceptive pain, hyperalgesia, temporomandibular joint pain, inherited erythromelalgia (IEM), and paroxysmal extreme pain disorder (PEPD).

8. [(3R)-3-fluoropyrrolidin-1-yl](6-{[5-(trifluoromethyl)pyridin-2-yl]oxy}quinolin-2-yl)methanone, or a pharmaceutically acceptable salt, ester, amide, or radiolabelled form thereof.

9. A pharmaceutical composition comprising a therapeutically effective amount of the compound of claim 8, or a pharmaceutically acceptable salt, ester, amide, or radiolabelled form thereof, in combination with a pharmaceutically acceptable carrier.

10. A method of selectively modulating the effects of pain in a mammal comprising administering an effective amount of the compound of claim 8, or a pharmaceutically acceptable salt, ester, amide, or radiolabelled form thereof.

11. The method according to claim 10, wherein the pain is selected from the group consisting of osteoarthritis pain, joint pain, knee pain, neuropathic pain, post-surgical pain, low back pain, diabetic neuropathy, pain during surgery, cancer pain, chemotherapy induced pain, headaches, cluster headache, tension headache, migraine pain, trigeminal neuralgia, shingles pain, post-herpetic neuralgia, carpal tunnel syndrome, inflammatory pain, pain from rheumatoid arthritis, colitis, pain of interstitial cystitis, visceral pain, pain from kidney stone, pain from gallstone, angina, fibromyalgia, chronic pain syndrome, thalamic pain syndrome, pain from stroke, phantom limb pain, sunburn, radiculopathy, complex regional pain syndrome, HIV sensory neuropathy, central neuropathic pain syndromes, multiple sclerosis pain, Parkinson disease pain, spinal cord injury pain, menstrual pain, toothache, pain from bone metastasis, pain from endometriosis, pain from uterine fibroids, nociceptive pain, hyperalgesia, temporomandibular joint pain, inherited erythromelalgia (IEM), and paroxysmal extreme pain disorder (PEPD).

* * * * *